US012077526B2

(12) United States Patent
Howard et al.

(10) Patent No.: US 12,077,526 B2
(45) Date of Patent: Sep. 3, 2024

(54) ISOINDOLINONE INHIBITORS OF THE MDM2-P53 INTERACTION AND PROCESS FOR MAKING THEM

(71) Applicants: ASTEX THERAPEUTICS LIMITED, Cambridge (GB); CANCER RESEARCH TECHNOLOGY LIMITED, London (GB)

(72) Inventors: Steven Howard, Cambridge (GB); Benjamin David Cons, Cambridge (GB); Jeffrey David St. Denis, Cambridge (GB); Rhian Sara Holvey, Cambridge (GB); Guillaume François Parra, Ste. Eulalie (FR); Kim Louise Hirst, Saffron Walden (GB); Isabelle Anne Lemasson, Cambridge (GB); David John Nash, Saffron Walden (GB); James Daniel Osborne, Cambridge (GB); Jonas Calleja Priede, Cambridge (GB); Nicholas Paul Richards, Haverhill (GB); Aaron Michael Dumas, Stevenage (GB); Brian Christopher Bishop, Harlow (GB); David Parry-Jones, Welwyn Garden (GB); Meenakshi Sundaram Shanmugham, London (GB); Darren James Dixon, Oxford (GB); Matthew James Gaunt, Cambridge (GB)

(73) Assignees: ASTEX THERAPEUTICS LIMITED, Cambridge (GB); CANCER RESEARCH TECHNOLOGY LIMITED, London (GB)

( * ) Notice: Subject to any disclaimer, the term of this patent is extended or adjusted under 35 U.S.C. 154(b) by 0 days.

(21) Appl. No.: 18/159,452

(22) Filed: Jan. 25, 2023

(65) Prior Publication Data

US 2023/0278989 A1    Sep. 7, 2023

Related U.S. Application Data

(62) Division of application No. 16/498,207, filed as application No. PCT/GB2018/050845 on Mar. 28, 2018, now Pat. No. 11,603,367.

(30) Foreign Application Priority Data

Mar. 28, 2017   (GB) ..................................... 1704965

(51) Int. Cl.
C07D 405/06      (2006.01)
(52) U.S. Cl.
CPC ........ *C07D 405/06* (2013.01); *C07B 2200/13* (2013.01)
(58) Field of Classification Search
None
See application file for complete search history.

(56) References Cited

U.S. PATENT DOCUMENTS

| 3,466,298 A | 9/1969 | Sulkowski et al. |
| 3,763,178 A | 10/1973 | Sulkowski et al. |
| 3,898,232 A | 8/1975 | Cotrel et al. |
| 4,001,271 A | 1/1977 | Cotrel et al. |
| 4,200,759 A | 4/1980 | Dickinson |
| 4,244,966 A | 1/1981 | Lippman et al. |
| 4,312,809 A | 1/1982 | Haugwitz |
| 4,331,600 A | 5/1982 | Golec, Jr. et al. |
| 4,505,921 A | 3/1985 | Beregi et al. |
| 6,344,468 B1 | 2/2002 | Schindler et al. |
| 8,258,175 B2 | 9/2012 | Willems et al. |
| 8,618,158 B2 | 12/2013 | Golding et al. |
| 9,358,222 B2 | 6/2016 | Golding et al. |
| 10,414,726 B2 | 9/2019 | Golding et al. |
| 10,526,311 B2 | 1/2020 | Chessari et al. |
| 10,544,132 B2 | 1/2020 | Chessari et al. |
| 10,981,898 B2 | 4/2021 | Chessari et al. |
| 11,236,047 B2 | 2/2022 | Chessari et al. |
| 11,261,171 B1 | 3/2022 | Chessari et al. |
| 11,603,367 B2 | 3/2023 | Howard et al. |
| 2005/0004207 A1 | 1/2005 | Straub et al. |
| 2006/0264473 A1 | 11/2006 | Khazak et al. |
| 2012/0264738 A1 | 10/2012 | Sugimoto et al. |
| 2014/0194486 A1 | 7/2014 | Golding et al. |
| 2016/0355478 A1 | 12/2016 | Golding et al. |
| 2018/0118684 A1 | 5/2018 | Golding et al. |
| 2019/0016708 A1 | 1/2019 | Chessari et al. |
| 2019/0055215 A1 | 2/2019 | Chessari et al. |

(Continued)

FOREIGN PATENT DOCUMENTS

| CH | 374071 | 12/1963 |
| DE | 2313227 | 9/1973 |

(Continued)

OTHER PUBLICATIONS

Great Britain Search Report for GB1704965.1, dated Jan. 15, 2018, 5 pp.
International Search Report for PCT/GB2018/050845, dated Jun. 11, 2018, 16 pp.
Prodrug [online, wikipedia], [retrieved on Mar. 11, 2007], Retrieved from the internet, URL http://en.wikipedia.org/wiki/Prodrugs.
Lala, P.K., et al., Role of nitric oxide in tumor progression: Lessons from experimental tumors, Cancer and Metastasis Reviews, vol. 17, No. 1, pp. 91-106 (1998).

(Continued)

*Primary Examiner* — Joseph R Kosack
(74) *Attorney, Agent, or Firm* — Heslin Rothenberg Farley & Mesiti P.C.

(57) ABSTRACT

The invention relates to processes for preparing isoindolin-1-one derivatives, and in particular processes for preparing (2S,3S)-3-(4-chlorophenyl)-3-[(1R)-1-(4-chlorophenyl)-7-fluoro-5-[(1S)-1-hydroxy-1-(oxan-4-yl)propyl]-1-methoxy-3-oxo-2,3-dihydro-1H-isoindol-2-yl]-2-methylpropanoic acid. The invention also relates to crystalline forms of the compound (2S,3S)-3-(4-chlorophenyl)-3-[(1R)-1-(4-chlorophenyl)-7-fluoro-5-[(1S)-1-hydroxy-1-(oxan-4-yl)propyl]-1-methoxy-3-oxo-2,3-dihydro-1H-isoindol-2-yl]-2-methylpropanoic acid and its salts.

22 Claims, 2 Drawing Sheets

(56) References Cited

U.S. PATENT DOCUMENTS

| | | | |
|---|---|---|---|
| 2020/0040403 | A1 | 2/2020 | Stanford et al. |
| 2020/0079761 | A1 | 3/2020 | Chessari et al. |
| 2020/0207711 | A1 | 7/2020 | Chessari et al. |
| 2021/0101887 | A1 | 4/2021 | Howard et al. |
| 2021/0276984 | A1 | 9/2021 | Chessari et al. |
| 2022/0106287 | A1 | 4/2022 | Chessari et al. |
| 2023/0313313 | A1 | 10/2023 | Ferrari et al. |
| 2023/0338337 | A1 | 10/2023 | Ferrari et al. |

FOREIGN PATENT DOCUMENTS

| | | | |
|---|---|---|---|
| EP | 0461079 | A2 | 12/1991 |
| EP | 1199306 | A1 | 4/2002 |
| EP | 1566378 | A1 | 8/2005 |
| EP | 2108642 | A1 | 10/2009 |
| GB | 1325065 | | 8/1973 |
| GB | 1601701 | | 11/1981 |
| JP | 2000506163 | A | 5/2000 |
| JP | 2004217591 | | 8/2004 |
| JP | 2005255660 | A | 9/2005 |
| JP | 2011/526260 | A | 10/2011 |
| KR | 2013/0088577 | A | 8/2013 |
| WO | 97/32846 | A1 | 9/1997 |
| WO | 99/42444 | A1 | 8/1999 |
| WO | 01/32928 | A2 | 5/2001 |
| WO | 03/051359 | A1 | 6/2003 |
| WO | 03/101450 | A1 | 12/2003 |
| WO | 2005/021532 | A1 | 3/2005 |
| WO | 2005/095341 | A1 | 10/2005 |
| WO | 2006/020879 | A1 | 2/2006 |
| WO | 2006/024837 | A1 | 3/2006 |
| WO | 2006/091646 | A2 | 8/2006 |
| WO | 2007/021309 | A1 | 2/2007 |
| WO | 2008/024892 | A2 | 2/2008 |
| WO | 2008/117061 | A2 | 10/2008 |
| WO | 2008/151184 | A1 | 12/2008 |
| WO | 2009/156735 | A2 | 12/2009 |
| WO | 2010/031713 | A1 | 3/2010 |
| WO | 2011/060049 | A2 | 5/2011 |
| WO | 2011/076786 | A1 | 6/2011 |
| WO | 2011/098398 | A1 | 8/2011 |
| WO | 2011/153509 | A1 | 12/2011 |
| WO | 2012/175487 | A1 | 12/2012 |
| WO | 2012/175520 | A1 | 12/2012 |
| WO | 2013/033176 | A1 | 3/2013 |
| WO | 2013/111105 | A1 | 8/2013 |
| WO | 2013/120835 | A1 | 8/2013 |
| WO | 2014/070948 | A1 | 5/2014 |
| WO | 2014/134355 | A1 | 9/2014 |
| WO | 2015/000945 | A1 | 1/2015 |
| WO | 2015/108175 | A1 | 7/2015 |
| WO | 2015/161032 | A1 | 10/2015 |
| WO | 2016/056673 | A1 | 4/2016 |
| WO | 2016/059241 | A2 | 4/2016 |
| WO | 2017/004538 | A1 | 1/2017 |
| WO | 2017/055859 | A1 | 4/2017 |
| WO | 2017/055860 | A1 | 4/2017 |
| WO | 2017/068412 | A1 | 4/2017 |
| WO | 2017/087607 | A1 | 5/2017 |
| WO | 2018/178679 | A1 | 10/2018 |
| WO | 2020/169073 | A1 | 8/2020 |
| WO | 2021/130682 | A2 | 7/2021 |
| WO | 2022/043930 | A2 | 3/2022 |
| WO | 2022/185260 | A1 | 9/2022 |

OTHER PUBLICATIONS

Golub, T.R., et al., Molecular Classification of Cancer: Class Discovery and Class Prediction by Gene Expression Monitoring, Science, vol. 286, pp. 531-537 (1999).
Cancer [online, medline], [retrieved on Jul. 6, 2007], Retrieved from the internet, URL http://www.nlm.nih.gov/medlineplus/cancer.html.
Cancer [online, wikipedia], [retrieved on Jul. 6, 2007], Retrieved from the internet, URL http://en.wikipedia.org/wiki/Cancer.
Bartfeld, H.D., et al., 3-Oxo-Isoindole, Tetrahedron Letters, No. 10, pp. 757-760 (1970).
Caplus 95:150329 record for Lencbergs, I., et al., 3-Hydroxy-3-(α-aminobenzyl)-2-substituted 1-isoindolinones, Latvijas PSR Zinatnu Akademijas Vestis, Kimijas Serija (1981), (3), 335-40.
Rebek, Jr., J., et al., Olefin Epoxidation with α-Substituted Hydroperoxides, J. Am. Chem. Soc., vol. 102, pp. 5602-5605 (1980).
Griffiths, J., et al., Model Studies for Damage to Nucleic Acids Mediated by Thiyl Radicals, Tetrahedron, vol. 48, No. 26, pp. 5543-5556 (1992).
Park, J.S., et al., Noble 2-[3(Cyclopentyloxy)-4-Methoxyphenyl]-1-Isoindolinone Derivatives. Part I; Synthesis and SAR Studies for the Inhibition of TNF-α Production, Arch. Pharma. Res., vol. 24, No. 5, pp. 367-370 (2001).
Ito, Y., et al., Solid-State and Solution Photolyses of Tetracyanobenzene with Benzyl Cyanlides or Benzyl Alcohols, Tetrahedron, vol. 56, pp. 7139-7152 (2000).
Mvekananda Bhatt, M., et al., Aspects of Tautomerism. Part V. † Solvent, Substituent, and Steric Effects on the Ring-Chain Tautomerism of o-Benzoylbenzamides, Journal of the Chemical Society, Perkin Transactions II, pp. 1160-1166 (1973).
Topliss, J.G., et al., Antihypertensive Agents. III. 3-Hydroxy-3-phenylphthalimidines, Journal of Medicinal Chemistry, vol. 7, pp. 453-456 (1964).
Charlesworth, E.H., et al., Fluoranthene studies. III. A synthesis of 3-bromo-6-nitrofluorenone, Canadian Journal of Chemistry, vol. 46, No. 3, pp. 463-465 (1968).
STN 1972:419475 (CAPLUS) record for Valters, R., et al., Ring-chain transformations involving the carbonyl group. XI. Acid chlorides and amides of 2-benzoyl-3-,4-, 5-, and 6-nitrobenzoic acids, Rizh. Politekh. Inst., Riga, USSR, Latvijas PSR Zinatnu Akademijas Vestis, Kimijas Serija, vol. 1, pp. 61-65 (1972).
Yang et al., "Practical Proline-Catalyzed Asymmetric Mannich Reaction of Aldehydes with N-Boc-Imines," Nature Protocols, vol. 2, No. 8, 2007, pp. 1937-1942.
Körmendy, K., Über Reaktionen In Polyaminsynthesen Mit Phthaliminoakjylhaloiden, I., Acta Chimica Academiae Scientiarum Hungaricae, pp. 255-264 (1958).
Inaba, M., et al., Reversal of Resistance to Vincristine in P388 Leukemia by Various Polycyclic Clinical Drugs, with a Special Emphasis on Quinacrine, Cancer Research, vol. 48, No. 8, pp. 2064-2067 (1988).
Croisy-Delcey, M., et al., Dipheyl Quinolines and Isoquinolines: Synthesis and Primary Biological Evaluation, Bioorganic and Medicinal Chemistry, vol. 8, pp. 2629-2641 (2000).
Kitching, M.S., et al., Synthesis of 3-Alkoxy- and 3-Alkylamino-2-alkyl-3-arylisoindolinones, Synlett, vol. 81, pp. 997-999 (1999).
Nikitin, K. V., et al., Synthesis of 5-alkyl- and 5-aryl-1,5-dihydro-2H-pyrrol-2-ones via coupling of 5-chloro-1,5-dihydro-2H-pyrrol-2-ones with organometallic compounds, Can. J. Chem., vol. 78, pp. 1285-1288 (2000).
Truitt, P., et al., 3-Phenylphthalimidines, New Compounds, J. Med. Chem., vol. 8, pp. 731-732 (1965).
Liebl, R., et al., Notiz zur Synthese von 3-[Aklyl(aryl)thio]isoindolinonen aus 2-Formylbenzoesäure-methylester, Liebigs Ann. Chem., pp. 1093-1094 (1985).
Usov, V.A., et al., Formation of Isoquinolones and Isoindolones in the Oxidation of 2-Aryl-1-phenylamino-3-phenyliminoindenes, Chemistry of Heterocyclic Compounds (Khimiya Geterotsiklicheskikh Soedinenil), vol. 5, No. 4, pp. 474-477 (1969).
Ahmed, M., et al., Preparation of Some Isoindolo[2,1-f]phenanthridine Derivatives, J. Chem. Soc., Perkins Trans. 1, pp. 601-605 (1977).
Beanlands, D.S., et al., Therapeutic Trial Of A New Oral Diuretic, Canadian Medical Association Journal, vol. 84, pp. 91-95 (1961).
Chene, P., et al., A Small Synthetic Peptide, which Inhibits the p53-hdm2 Interaction, Stimulates the p53 Pathway in Tumour Cell Lines, J. Molecular Biology, vol. 299, pp. 245-253 (2000).
Donehower, L.A., et al., Mice deficient for p53 are developmentally normal but susceptible to spontaneous tumours, Nature, vol. 356, pp. 215-221 (1992).

(56) References Cited

OTHER PUBLICATIONS

Epsztajn, J., et al., Application of Organolithium and Related Reagents in Synthesis. Part 23: Synthetic Strategies Based on ortho-Aromatic Metallation. Synthesis of 4b-Arylisoindolo[2,1-α]quinolone derivatives, Tetrahedron, vol. 56 pp. 4837-4844 (2000).
Ghosh, M., et al., Overexpression of Mdm2 and MdmX Fusion Proteins Alters p53 Mediated Transactivation, Ubiquitination, and Degradation, American Chemical Society, Biochemistry, vol. 42, pp. 2291-2299 (2003).
Lane, D.P., p53, guardian of the genome, Nature, vol. 358, pp. 15-16 (1992).
Levine, A.J., p53, the Cellular Gatekeeper for Growth and Division, Cell, vol. 88, pp. 323-331 (1997).
Oliner, J.D., et al., Amplification of a gene encoding a p53-associated protein in human sarcomas, Nature, vol. 358, pp. 80-83 (1992).
Schon, O., et al., Molecular Mechanism of the Interaction between MDM2 and p53, Journal of Molecular Biology, vol. 323, pp. 491-501 (2002).
Toledo, F., et al., Regulating the p53 pathway: in vitro hypotheses, in vivo veritas, Nature Reviews Cancer, vol. 6, pp. 909-923 (2006).
Vassilev, L.T., et al., In Vivo Activation of the p53 Pathway by Small-Molecule Antagonists of MDM2, Science, vol. 303, pp. 844-848 (2004).
Golik, U., The Synthesis of some 2,4-Benzodiazepin-1-ones, Potent C.N.S. Agents (I), Journal of Heterocyclic Chemistry, vol. 12, No. 5, pp. 903-908 (1975).
Hardcastle, I.R., et al., Small-Molecule Inhibitors of the MDM2-p53 Protein-Protein Interaction Based on an Isoindolinone Scaffold, Journal of Medicinal Chemistry (2006), 49(21), 6209-6221.
Suzuki, T., et al., Novel Chemoselective Desulfurization of γ-Phenylthio-Substituted Aromatic Lactams: Application to the Synthesis of Isoindolobenzazepine Alkaloid, Lennoxamine, *Synlett*, No. 20, pp. 3407-3410 (2006).
Ying, H., et al., The Docking Based 3D-QSAR Studies on Isoindolinone Derived Inhibitors of p53-MDM2 Binding, Letters in Drug Design & Discovery, vol. 11, pp. 50-58 (2014).
Mondal, C., et al., Comparative validated molecular modeling of p53-HDM2 inhibitors as antiproliferative agents, European Journal of Medicinal Chemistry, vol. 90, pp. 860-875 (2015).
Dong, X., et al., QSAR Models for isoindolinone-based p53-MDM2 Interaction Inhibitors Using Linear and Non-linear Statistical Methods, Chem Biol Drug Des, vol. 79, pp. 691-702 (2012).
Watson, A.F., et al., MDM2-p53 protein-protein interactions inhibitors: A-ring substituted isoindolinones, Bioorganic & Medicinal Chemistry Letters, vol. 21, pp. 5916-5919 (2011).
Riedinger, C., et al., Understanding Small-Molecule Binding to MDM2: Insights into Structural Effects of Isoindolinone Inhibitors from NMR Spectroscopy, Chem Biol Drug Des, vol. 77, pp. 301-308 (2011).
Hardcastle, I.R., et al., "Isoindolinone Inhibitors of the Murine Double Minute 2 (MDM2)-p53 Protein-Protein Interaction: Structure-Activity Studies Leading to Improved Potency", Journal of Medicinal Chemistry, vol. 54, pp. 1233-1243 (2011).
Grigoreva, T.A., et al., "Proapoptotic modification of substituted isoindolinones as MDM2-p53 inhibitors", *Bioorganic & Medicinal Chemistry Letters*, vol. 27, pp. 5197-5202 (2017).
Riedinger, C., et al., "Analysis of Chemical Shift Changes Reveals the Binding Modes of Isoindolinone Inhibitors of the MDM2-p53 Interaction", *Journal of the American Chemical Society*, vol. 130, No. 47, pp. 16038-16044 (2008).
Esfandiari, Armen et al., "Chemical Inhibition of Wild-Type p53-Induced Phosphatase 1 (WIP1/PPM1D) by GSK2830371 Potentiates the Sensitivity to MDM2 Inhibitors in a p53-Dependent Manner," Molecular Cancer Therapeutics, Feb. 1, 2016, pp. 379-391.
Zhang, Xiaoling et al., "Degradation of MDM2 by the Interaction Between Berberine and DAXX Leads to Potent Apoptosis in MDM2-Overexpressing Cancer Cells," Cancer Research, Therapeutics, Targets and Chemical Biology, Oct. 8, 2010, pp. 9895-9904.

Encyclopedic Dictionary of Chemistry, Moscow, Soviet Encyclopedia, 1983, pp. 130-131.
Khimicheskaya entsiklopediya (Chemical Encyclopedia), vol. 1, Bol'shaya Rossiyskaya Entsiklopediya, Moscow, 1998.
Nag., S. et al., "Targeting MDM2-p53 Interaction for Cancer Therapy: Are We There Yet?," Curr Med Chem. 2014, 21(5), pp. 553-574.
Dyson, G., May P. "Chemistry of Synthetic Drugs", Moscow, Publishing house "Mir", 1964, pp. 12-19.
Belikov, V.G. "Farmatsevticheskaya khimiya" (English: "Pharmaceutical Chemistry"), Chapter 2.2., Moscow, Publishing house "Vysshaya shkola", 1993, pp. 43-47.
Belikov V. G., "Farmacevtičeskaâ himiâ (Pharmaceutical chemistry)", Chapter 2.6, M.: MEDpress-inform, 2007, pp. 27-29.
Petrovskij, B. V., "Bol'šaâ medicinskaâènciklopediâ (Big encyclopedia of medicine)", 1981, vol. 16, p. 452-463.
Durnov, L. A., Goldobenko, G. V., „Detskaâ onkologiâ (Pediatric oncology), Moscow: "Medicina", 2002, p. 139.
"Malaâ medicinskaâènciklopediâ (Small encyclopedia of medicine)", vol. 5, Moscow: "Medicina", 1996, p. 90-96.
Maškovskij M. D., "Lekarstvennye sredstva (Medicaments)", 14th edition, vol. 1, 2011, p. 11.
Žulenko, V. N., Gorškov, G. I. "Farmakologiâ (English: "Pharmacology")", 2008, pp. 34-35.
Harkevič, D. A., "Farmakologiâ (English: "Pharmacology")", 10th edition, 2010, pp. 72-74.
Uy et al., Phase 1 study of the MDM2 antagonist RO6839921 in patients with acute myeloid leukemia, Investigational New Drugs, 2020, vol. 38, pp. 1430-1441.
Kojima et al., MDM2 antagonists induce p53-dependent apoptosis in AML: implications for leukemia therapy, Blood, 2005, vol. 106(9), pp. 3150-3159.
Iorio et al., A Landscape of Pharmacogenomic Interactions in Cancer, 2016, Cell 166, 740-754.
Ji et al., p53 Rescue through HDM2 Antagonism Suppresses Melanoma Growth and Potentiates MEK Inhibition, Journal of Investigative Dermatology (2012) vol. 132, 356-364.
Crane et al., Nutlin-3a: A Potential Therapeutic Opportunity for TP53 Wild-Type Ovarian Carcinomas, PLOS ONE 10(8): e0135101 2015.
Tagawa et al., Molecular Therapy, vol. 24, Supplement 1, Abstract 211., 2016, Combination of Forced Transduction of P53 and an Agent That Blocks MDM2-p53 Interactions Produces Synergistic Cytotoxicity on Mesothelioma Defective of the INK4A/ARF Region.
Tagawa et al., Human Gene Therapy, vol. 26 (10), Abstracts supplement, abstract: P014, 2016, Inhibited interaction between p53 and Mdm2 enhances p53-mediated cytotoxic activities on INK4A/ARF defective mesothelioma.
Kitagawa et al., Skp2 Suppresses p53-Dependent Apoptosis by Inhibiting p300, Molecular Cell 29, 217-231, 2008.
Knijnenburg et al., 2018, Cell Reports 23, 239-254.
Chander, et al., Skp2B attenuates p53 function by inhibiting prohibitin, EMBO reports vol. 11, No. 3, 2010.
Zhao et al., Implications of Genetic and Epigenetic Alterations of CDKN2A (p16$^{INK4a}$) in Cancer, EBioMedicine 8 (2016) 30-39.
Huang et al., Drugging the undruggables: exploring the ubiquitin system for drug development; Cell Res, 26, 4, 2016, 484-498.
Liu et al., "Targeting IFN/STAT1 Pathway as a Promising Strategy to Overcome Radioresistance", Oncotargets and Therapy, vol. 13, 2020, pp. 6037-6050.
Nguyen et al., "Reviving the guardian of the genome: Small molecule activators of p53 ", Pharmacology & Therapeutics, vol. 178, 2017, pp. 92-108.
Kojima et al., "Pharmacological activation of wild-type p53 in the therapy of leukemia" Experiment AL Hematalogy, vol. 44, 2016, pp. 791-798.
Zanjirband et al., "Pre-clinical efficacy and synergistic potential of the MDM2-p53 antagonists, Nutlin-3 and RG7388, as single agents and in combined treatment with cisplatin in ovarian cancer", Oncotarget, vol. 7, 2016, pp. 40115-40134.
Jeay et al., "A distinct p53 target gene set predicts for response to the selective p53 HDM2 inhibitor NVP-CGM097", Elife, 2015, pp. 1-23.

(56) References Cited

OTHER PUBLICATIONS

Kobayashi et al., "Nutlin-3A Suppresses poly (ADP-ribose) polymerase 1 by mechanisms different from conventional PARP1 suppressors in a human breast cancer cell line", Oncotarget 2020, vol. 11, No. 1B, pp. 1653-1665.

Zanjirband et al., "Combination treatment with rucaparib (Rubraca) and MDM2 inhibitors, Nutlin-3 and RG7388, has synergistic and dose reduction potential in ovarian cancer", Oncotarget 2017, vol. 8, No. 41, pp. 69779-69796.

Pokrovskij V. I. [ed.]: "Malaâ medizinskaâ enziklopediâ [Concise medical encyclopedia]", Moscow: "Medizina", 1996, vol. 4, p. 84-85.

Momand, J. et al., "The MDM2 gene amplification database", Nucleic Acids Research. 1998, vol. 26, pp. 3453-3459.

Mohammad, Ramzi M., et al. "An MDM2 Antagonist (MI-319) Restores P53 functions and Increases the Life Span of Orally Treated Follicular Lymphoma Bearing Animals." Molecular Cancer, vol. 8, No. 1, Dec. 2009, p. 115. BioMed Central, 2009.

Andreef, Michael, et al. A multi-centre, open-label, Phase I Study of Single Agent RG7112, A First In Class P53-MDM2 Antagonist Blood, vol. 116, No. 21, Nov. 2010, p. 657 (year: 2010).

Lakoma, A. et al., "The MDM2 small-molecule inhibitor RG7388 leads to potent tumor inhibition in P53 Wild-Type Neuroblastoma." Cell Death Discovery, vol. 1 no. 1, Aug. 2015, pp. 1-9.

Lu, Min and Ronald Hoffman, "P53 as a Target in Myeloproliferative Neoplasms" Oncotarget, vol. 3, No. 10, Oct. 2012, pp. 1052-1053, Year 2012.

Ferrari et al., U.S. Appl. No. 18/548,522, filed Aug. 31, 2023.

ISOINDOLINONE INHIBITORS OF THE MDM2-P53 INTERACTION AND PROCESS FOR MAKING THEM

This application is a divisional of a U.S. application Ser. No. 16/498,207, which is a national stage entry of International Application No. PCT/GB2018/050845 filed on Mar. 28, 2018, which published as WO 2018/178691 on Oct. 4, 2018, which claims priority to United Kingdom Application No. GB 1704965.1, filed on Mar. 28, 2017. The entire contents of WO 2018/178691 are hereby incorporated by reference herein.

FIELD OF THE INVENTION

The invention relates to processes for preparing isoindolin-1-one derivatives, and in particular processes for preparing (2S,3S)-3-(4-chlorophenyl)-3-[(1R)-1-(4-chlorophenyl)-7-fluoro-5-[(1S)-1-hydroxy-1-(oxan-4-yl)propyl]-1-methoxy-3-oxo-2,3-dihydro-1H-isoindol-2-yl]-2-methylpropanoic acid and crystalline forms of the compound (2S,3S)-3-(4-chlorophenyl)-3-[(1R)-1-(4-chlorophenyl)-7-fluoro-5-[(1S)-1-hydroxy-1-(oxan-4-yl)propyl]-1-methoxy-3-oxo-2,3-dihydro-1H-isoindol-2-yl]-2-methylpropanoic acid and its salts.

BACKGROUND OF THE INVENTION

Isoindoline compounds are disclosed in our earlier international patent applications PCT/GB2016/053042 and PCT/GB2016/053041 filed 29 Sep. 2016 claiming priority from United Kingdom patent application numbers 1517216.6 and 1517217.4 filed 29 Sep. 2015, the contents of all of which are incorporated herein by reference in their entirety. In particular, the compound (2S,3S)-3-(4-chlorophenyl)-3-[(1R)-1-(4-chlorophenyl)-7-fluoro-5-[(1S)-1-hydroxy-1-(oxan-4-yl)propyl]-1-methoxy-3-oxo-2,3-dihydro-1H-isoindol-2-yl]-2-methylpropanoic acid is disclosed in our earlier international patent application PCT/GB2016/053042.

The transformation-related protein 53 (TP53) gene encodes a 53 KDa protein—p53. The tumour suppressor protein p53 reacts to cellular stresses, such as hypoxia, DNA damage and oncogenic activation, via a number of post-translational modifications including phosphorylation, acetylation and methylation, and acts as a signalling node in the diverse pathways that become activated. p53 has additional roles in other physiological processes, including autophagy, cell adhesion, cell metabolism, fertility, and stem cell aging and development. Phosphorylation of p53, resulting from activation of kinases including ATM, CHK1 and 2, and DNA-PK, results in a stabilised and transcriptionally active form of the protein, thus producing a range of gene products. The responses to p53 activation include apoptosis, survival, cell-cycle arrest, DNA-repair, angiogenesis, invasion and autoregulation. The specific combination of which, in concert with the cell's genetic background, gives rise to the observed cellular effect i.e. apoptosis, cell-cycle arrest or senescence. For tumour cells, the apoptotic pathway may be favoured due to the loss of tumour suppressor proteins and associated cell cycle checkpoint controls, coupled with oncogenic stress.

Under conditions of stress such as hypoxia and DNA damage it is known that the cellular level of the protein p53 increases. p53 is known to initiate transcription of a number of genes which govern progression through the cell cycle, the initiation of DNA repair and programmed cell death. This provides a mechanism for the tumour suppressor role of p53 evidenced through genetic studies.

The activity of p53 is negatively and tightly regulated by a binding interaction with the MDM2 protein, the transcription of which is itself directly regulated by p53. p53 is inactivated when its transactivation domain is bound by the MDM2 protein. Once inactivated the functions of p53 are repressed and the p53-MDM2 complex becomes a target for ubiquitinylation.

In normal cells the balance between active p53 and inactive MDM2-bound p53 is maintained in an autoregulatory negative feedback loop. That is to say that p53 can activate MDM2 expression, which in turn leads to the repression of p53.

It has been found that inactivation of p53 by mutation is common in around half of all common adult sporadic cancers. Furthermore, in around 10% of tumours, gene amplification and over-expression of MDM2 results in the loss of functional p53, thereby allowing malignant transformation and uncontrolled tumour growth.

Inactivation of p53 by a range of mechanisms is a frequent causal event in the development and progression of cancer. These include inactivation by mutation, targeting by oncogenic viruses and, in a significant proportion of cases, amplification and/or an elevated rate of transcription of the MDM2 gene resulting in overexpression or increased activation of the MDM2 protein. Gene amplification of MDM2 giving rise to overexpression of MDM2 protein has been observed in tumour samples taken from common sporadic cancers. Overall, around 10% of tumours had MDM2 amplification, with the highest incidence found in hepatocellular carcinoma (44%), lung (15%), sarcomas and osteosarcomas (28%), and Hodgkin disease (67%) (Danovi et al., Mol. Cell. Biol. 2004, 24, 5835-5843, Toledo et al., Nat Rev Cancer 2006, 6, 909-923, Gembarska et al., Nat Med 2012, 18, 1239-1247). Normally, transcriptional activation of MDM2 by activated p53 results in increased MDM2 protein levels, forming a negative feedback loop. The essential nature of p53 regulation by MDM2 and MDMX is demonstrated by gene knockout mouse models. MDM2−/− knockout mice are embryonically lethal around the time of implantation. Lethality is rescued in the double knockout for Mdm2 and Trp53. MDM2 inhibits the activity of p53 directly, by binding to and occluding the p53 transactivation domain, and by promoting the proteosomal destruction of the complex, through its E3-ubiquitin ligase activity. In addition, MDM2 is a transcriptional target of p53, and so the two proteins are linked in an autoregulatory feedback loop, ensuring that p53 activation is transient.

The induction of the p14ARF protein, the alternate reading frame (ARF) product of the p16INK4a locus, is also a mechanism of negatively regulating the p53-MDM2 interaction. p14ARF directly interacts with MDM2 and leads to up-regulation of p53 transcriptional response. Loss of p14ARF by a homozygous mutation in the CDKN2A (INK4A) gene will lead to elevated levels in MDM2 and, therefore, loss of p53 function and cell cycle control.

Although MDMX shows strong amino acid sequence and structural homology to MDM2, neither protein can substitute for loss of the other; MDMX null mice die in utero, whereas MDM2 knockout is lethal during early embryogenesis, however both can be rescued by p53 knockout, demonstrating p53-dependence of the lethality. MDMX also binds p53 and inhibits p53-dependent transcription, but unlike MDM2 it is not transcriptionally activated by p53 and so does not form the same autoregulatory loop. Furthermore, MDMX has neither E3 ubiquitin ligase activity nor a nuclear localisation signal, however it is believed to contribute to p53 degradation by forming heterodimers with MDM2 and contributing to MDM2 stabilisation.

The therapeutic rationale for MDM2-p53 inhibition is that a potent inhibitor of the protein-protein interaction will liberate p53 from the repressive control of MDM2, and activate p53 mediated cell death in the tumour. In tumours, selectivity is envisioned to result from p53 sensing preexisting DNA-damage or oncogenic activation signals that had previously been blocked by the action of MDM2 at normal or overexpressed levels. In normal cells, p53 activation is anticipated to result in activation of non-apoptotic pathways and if anything a protective growth inhibition response. In addition due to the non-genotoxic mechanism of action for MDM2-p53 inhibitors they are suitable for the treatment of cancer in particular in the pediatric population.

About 50% of cancers harbour cells in which TP53, the gene that encodes for p53, is mutated resulting in a loss of the protein's tumour suppressor function and sometimes even in p53 protein versions that gain novel oncogenic functions.

Cancers where there is a high level of MDM2 amplification include liposarcoma (88%), soft tissue sarcoma (20%), osteosarcoma (16%) oesophageal cancer (13%), and certain paediatric malignancies including B-cell malignancies.

The present invention describes a novel series of compounds which selectively inhibit the MDM2-p53 interaction and which have anticancer activity.

SUMMARY OF THE INVENTION

The invention provides novel processes for preparing 1-methoxyisoindolines, and in particular (2S,3S)-3-(4-chlorophenyl)-3-[(1R)-1-(4-chlorophenyl)-7-fluoro-5-[(1S)-1-hydroxy-1-(oxan-4-yl)propyl]-1-methoxy-3-oxo-2,3-dihydro-1H-isoindol-2-yl]-2-methylpropanoic acid, and intermediates useful in the synthesis of that compound. The invention also provides novel crystalline forms of the compound (2S,3S)-3-(4-chlorophenyl)-3-[(1R)-1-(4-chlorophenyl)-7-fluoro-5-[(1S)-1-hydroxy-1-(oxan-4-yl)propyl]-1-methoxy-3-oxo-2,3-dihydro-1H-isoindol-2-yl]-2-methylpropanoic acid and its salts.

In a first aspect, the invention a process for preparing a 1-methoxyisoindoline of formula (1°):

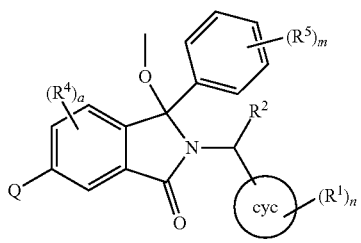

(1°)

or a tautomer or a solvate or a salt thereof, the process comprising taking a compound of the formula (2°)

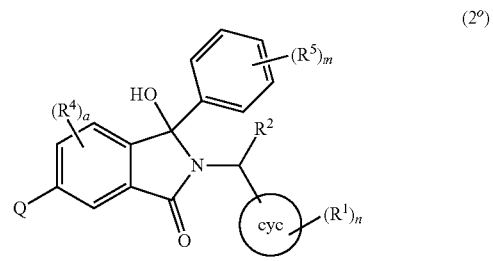

(2°)

wherein cyc is phenyl or a heterocyclic group Het which is pyridinyl, pyrimidinyl, pyrazinyl or pyridazinyl, or an N-oxide thereof;

$R^1$ is independently selected from hydroxy, halogen, nitro, nitrile, $C_{1-4}$alkyl, halo$C_{1-4}$alkyl, hydroxy$C_{1-4}$alkyl, $C_{2-6}$alkenyl, $C_{1-4}$alkoxy, halo$C_{1-4}$alkoxy, $C_{2-4}$alkynyl, —$O_{0,1}$—$(CR^xR^y)_v$—$CO_2H$, —$(CR^xR^y)_v$—$CO_2C_{1-4}$alkyl, —$(CR^xR^y)_v$—$CON(C_{1-4}$alkyl$)_2$, —$P(=O)(R^x)_2$, —$S(O)_d$—$R^x$, —$S(O)_d$-heterocyclic group with 3 to 6 ring members and —$S(O)_d$—$N(R^8)_2$, wherein when cyc is Het then $R^1$ is attached to a carbon atom;

$R^2$ is selected from hydrogen, $C_{1-4}$alkyl, $C_{2-6}$alkenyl, hydroxy$C_{1-4}$alkyl, —$(CR^xR^y)_u$—$CO_2H$, —$(CR^xR^y)_u$—$CONR^xR^y$, —$(CR^xR^y)_u$—$CO_2R^{10}$ wherein $R^{10}$ is selected from $C_{1-7}$ alkyl, $C_{1-7}$ alkenyl, $C_{1-7}$ haloalkyl, tri$C_{1-7}$ alkylsilyl-$C_{1-7}$alkyl, $C_{5-20}$ aryl and $C_{5-20}$ aryl-$C_{1-7}$ alkyl;

$R^4$ and $R^5$ are independently selected from halogen, nitrile, $C_{1-4}$ alkyl, halo$C_{1-4}$alkyl, $C_{1-4}$alkoxy and halo$C_{1-4}$alkoxy;

Q is selected from —$C(OH)R^6R^7$, —$C(=O)R^7$, halogen (e.g. —F, —Cl, —Br, —I) and —OTf;

$R^6$ and $R^7$ are independently selected from hydrogen, $C_{1-6}$alkyl, halo$C_{1-6}$alkyl, $C_{2-6}$alkenyl, $C_{2-6}$alkynyl, hydroxy, hydroxy$C_{1-6}$alkyl, —$COOC_{1-6}$alkyl, —$(CH_2)_j$—$O$—$C_{1-6}$alkyl, —$(CH_2)_j$—$O$-(hydroxy$C_{1-6}$alkyl), —$C_{1-6}$alkyl-$NR^xR^y$, —$(CR^xR^y)_p$—$CONR^xR^y$, —$(CR^xR^y)_p$—$NR^xCOR^y$, —$(CR^xR^y)_p$—$O$—$CH_2$—$CONR^xR^y$, heterocyclic group with 3 to 7 ring members, —$CH_2$-heterocyclic group with 3 to 7 ring members, —$CH_2$—$O$-heterocyclic group with 3 to 7 ring members, —$CH_2$—$NH$-heterocyclic group with 3 to 7 ring members, —$CH_2$—$N(C_{1-6}$alkyl)-heterocyclic group with 3 to 7 ring members, —$C(=O)NH$-heterocyclic group with 3 to 7 ring members, $C_{3-8}$cycloalkyl, —$CH_2$—$C_{3-8}$cycloalkyl, —$CH_2$—$O$—$C_{3-8}$cycloalkyl, and $C_{3-8}$cycloalkenyl, wherein said cycloalkyl, cycloalkenyl or heterocyclic groups may be optionally substituted by one or more $R^z$ groups, and wherein in each instance the heterocyclic group comprises one or more (e.g. 1, 2, or 3) heteroatoms selected from N, O, S and oxidised forms thereof;

or, when Q is —$C(OH)R^6R^7$, the $R^6$ and $R^7$ groups, together with the carbon atom to which they are attached, can join to form a $C_{3-6}$cycloalkyl or heterocyclyl group with 3 to 6 ring members, wherein the heterocyclic group comprises one or more (e.g. 1, 2, or 3) heteroatoms selected from N, O, S and oxidised forms thereof, and wherein said $C_{3-8}$cycloalkyl and heterocyclyl groups may be optionally substituted by one or more $R^z$ groups;

$R^8$ is selected from hydrogen, $C_{1-6}$alkyl, halo$C_{1-6}$alkyl, hydroxy$C_{1-6}$alkyl, —$(CH_2)_k$—$O$—$C_{1-6}$alkyl, —$(CH_2)_k$—$O$-(hydroxy$C_{1-6}$alkyl), hydroxy$C_{1-6}$alkoxy, —(CH$_2$)$_k$—CO$_2$C$_{1-6}$alkyl, —(CH$_2$)$_k$—CO$_2$H, —C$_{1-6}$alkyl-N(H)$_e$(C$_{1-4}$alkyl)$_{2-e}$, —(CH$_2$)$_j$—C$_{3-8}$cycloalkyl and —(CH$_2$)$_j$—C$_{3-8}$cycloalkenyl;

R$^x$ and R$^y$ are independently selected from hydrogen, halogen, nitro, nitrile, C$_{1-6}$alkyl, haloC$_{1-6}$alkyl, C$_{2-6}$alkenyl, C$_{2-6}$alkynyl, hydroxy, hydroxyC$_{1-6}$alkyl, C$_{1-6}$alkoxy, —(CH$_2$)$_k$—O—C$_{1-6}$alkyl, hydroxyC$_{1-6}$alkoxy, —COOC$_{1-6}$alkyl, —N(H)$_e$(C$_{1-4}$alkyl)$_{2-e}$, —C$_{1-6}$alkyl-N(H)$_e$(C$_{1-4}$alkyl)$_{2-e}$, —(CH$_2$)$_k$—C(═O)N(H)$_e$(C$_{1-4}$alkyl)$_{2-e}$, C$_{3-8}$cycloalkyl and C$_{3-8}$cycloalkenyl;

or the R$^x$ and R$^y$ groups, together with the carbon or nitrogen atom to which they are attached, can join to form a C$_{3-6}$cycloalkyl or saturated heterocyclyl group with 3 to 6 ring members which may be optionally fused to an aromatic heterocyclyl group of 3 to 5 ring members;

or when on a carbon atom the R$^x$ and R$^y$ groups can join together to form a ═CH$_2$ group; R$^z$ is independently selected from halogen, nitro, nitrile, C$_{1-6}$alkyl, haloC$_{1-6}$alkyl, C$_{2-6}$alkenyl, C$_{2-6}$alkynyl, ═O, hydroxy, hydroxyC$_{1-6}$alkyl, C$_{1-6}$alkoxy, —(CH$_2$)$_k$—O—C$_{1-6}$alkyl, hydroxyC$_{1-6}$alkoxy, —C(═O)C$_{1-6}$alkyl, —C(═O)C$_{1-6}$alkyl-OH, —C(═O)C$_{1-6}$alkyl-N(H)$_e$(C$_{1-4}$alkyl)$_{2-e}$, —C(═O)N(H)$_e$(C$_{1-4}$alkyl)$_{2-e}$, —(CH$_2$)$_r$CO$_2$C$_{1-6}$alkyl, —(CH$_2$)$_r$CO$_2$H, —N(H)$_e$(C$_{1-4}$alkyl)$_{2-e}$, —C$_{1-6}$alkyl-N(H)$_e$(C$_{1-4}$alkyl)$_{2-e}$, heterocyclyl group with 3 to 6 ring members, heterocyclyl group with 3 to 6 ring members substituted by —C(═O)C$_{1-4}$alkyl, heterocyclyl group with 3 to 6 ring members substituted by —C(═O)OC$_{1-4}$alkyl, heterocyclyl group with 3 to 6 ring members substituted by —C(═O)N(H)$_e$(C$_{1-4}$alkyl)$_{2-e}$, —C(═O)heterocyclyl group with 3 to 6 ring members, C$_{3-8}$cycloalkyl and C$_{3-8}$cycloalkenyl, wherein if R$^7$ is pyridine then R$^z$ is other then —NH$_2$;

a, j, d, e, n, r and p are independently selected from 0, 1 and 2;

k and m are independently selected from 1 and 2;

u is selected from 0, 1, 2 and 3; and v and w are independently selected from 0 and 1;

and reacting the compound of formula (2°) with a methylating agent in the presence of a base.

In a second aspect, the invention provides a process for preparing a 1-methoxyisoindoline which is (2S,3S)-3-(4-chlorophenyl)-3-[(1R)-1-(4-chlorophenyl)-7-fluoro-5-[(1S)-1-hydroxy-1-(oxan-4-yl)propyl]-1-methoxy-3-oxo-2,3-dihydro-1H-isoindol-2-yl]-2-methylpropanoic acid (3'):

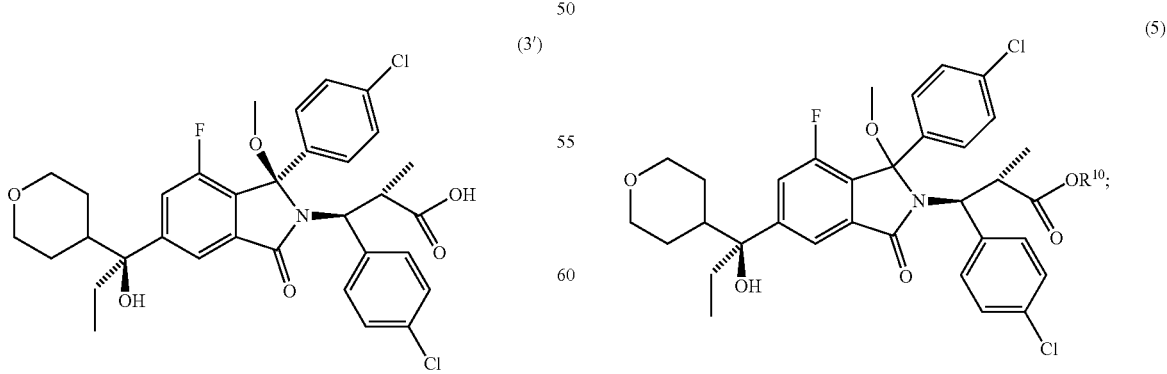

or a tautomer or a solvate or a pharmaceutically acceptable salt thereof, the process comprising the process according to the first aspect of the invention.

In a third aspect, the invention provides a process for preparing a 1-methoxyisoindoline which is (2S,3S)-3-(4-chlorophenyl)-3-[1-(4-chlorophenyl)-7-fluoro-5-[(1S)-1-hydroxy-1-(oxan-4-yl)propyl]-1-methoxy-3-oxo-2,3-dihydro-1H-isoindol-2-yl]-2-methylpropanoic acid:

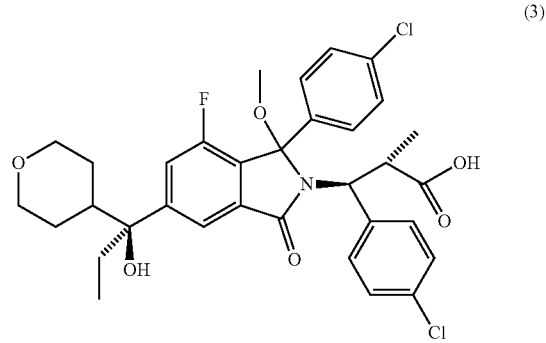 [SMILES: CC[C@@](O)(c1cc(F)c2c(c1)C(=O)N([C@H](c1ccc(Cl)cc1)[C@H](C)C(=O)O)C2(OC)c1ccc(Cl)cc1)C1CCOCC1]

(3)

or a tautomer or a solvate or a pharmaceutically acceptable salt thereof, the process comprising:

(i) taking a compound of the formula (4)

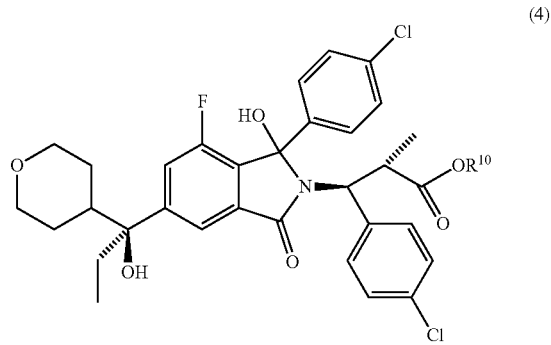

(4)

wherein R$^{10}$ is selected from C$_{1-7}$ alkyl, C$_{1-7}$ alkeneyl, C$_{1-7}$ haloalkyl, triC$_{1-7}$ alkylsilyl-C$_{1-7}$alkyl, C$_{5-20}$ aryl and C$_{5-20}$ aryl-C$_{1-7}$ alkyl;

and reacting the compound of formula (4) with a methylating agent in the presence of a base to give a compound of formula (5):

(5)

and (ii) then a de-esterification step to convert the group R$^{10}$ to hydrogen and provide (2S,3S)-3-(4-chlorophenyl)-

3-[1-(4-chlorophenyl)-7-fluoro-5-[(1S)-1-hydroxy-1-(oxan-4-yl)propyl]-1-methoxy-3-oxo-2,3-dihydro-1H-isoindol-2-yl]-2-methylpropanoic acid (3):

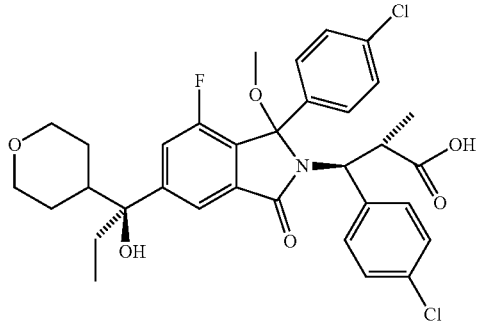

(3)

or a tautomer or a solvate or a pharmaceutically acceptable salt thereof; and (iii) optionally, a further step in which the compound of formula (3) is resolved to increase the proportion of the stereoisomer which is (2S,3S)-3-(4-chlorophenyl)-3-[(1R)-1-(4-chlorophenyl)-7-fluoro-5-[(1S)-1-hydroxy-1-(oxan-4-yl)propyl]-1-methoxy-3-oxo-2,3-dihydro-1H-isoindol-2-yl]-2-methylpropanoic acid of formula (3')

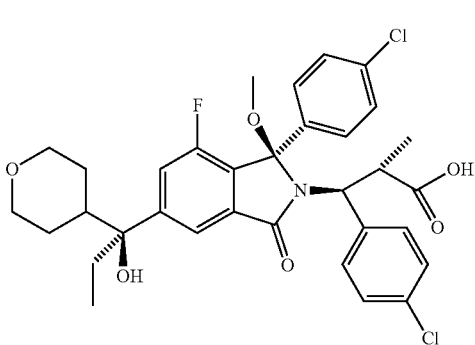

(3')

or a tautomer or a solvate or a pharmaceutically acceptable salt thereof.

In a fourth aspect, the invention provides a process for preparing an amine of formula (7):

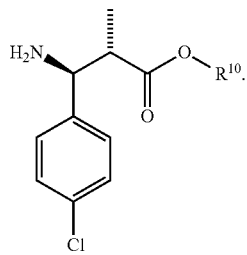

(7)

the process starting from an aldehyde of formula (12):

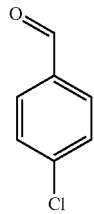

(12)

the process comprising the steps of:
(i) reacting the aldehyde of formula (12) with H$_2$NBoc and PhSO$_2$Na to give a compound of formula (13):

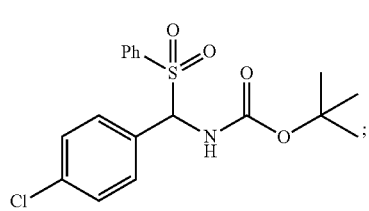

(13)

(ii) an elimination reaction on the compound of formula (13) in the presence of a base to give an imine of formula (14):

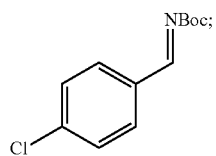

(14)

(iii) an imino-aldol reaction catalysed by (S)-proline between imine (14) and propan-2-al to give an aldehyde of formula (15):

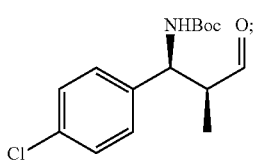

(15)

(iii) oxidation of aldehyde (15) to provide acid (16):

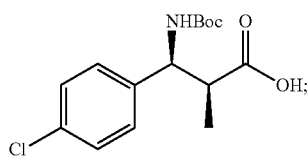

(16)

(iii) conversion of acid (16) to provide ester (17):

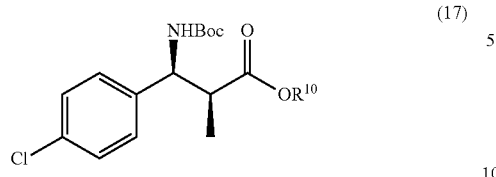

(iv) and then removal of the Boc protecting group to give the amine of formula (7).

In a fifth aspect, the invention provides a process for preparing a 1-methoxyisoindoline which is (2S,3S)-3-(4-chlorophenyl)-3-[1-(4-chlorophenyl)-7-fluoro-5-[(1S)-1-hydroxy-1-(oxan-4-yl)propyl]-1-methoxy-3-oxo-2,3-dihydro-1H-isoindol-2-yl]-2-methylpropanoic acid (3):

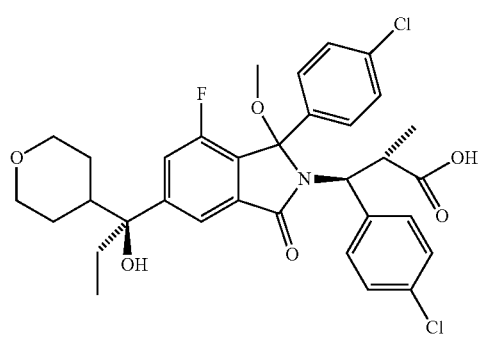

or a tautomer or a solvate or a pharmaceutically acceptable salt thereof,
the process comprising the step of de-esterifying a compound of the formula:

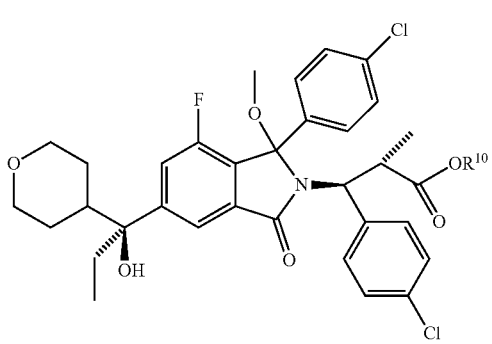

wherein $R^{10}$ is selected from $C_{1-7}$ alkyl, $C_{1-7}$ haloalkyl, tri$C_{1-7}$ alkylsilyl-$C_{1-7}$alkyl, $C_{5-20}$ aryl and $C_{5-20}$ aryl-$C_{1-7}$ alkyl;
to provide (2S,3S)-3-(4-chlorophenyl)-3-[1-(4-chlorophenyl)-7-fluoro-5-[(1S)-1-hydroxy-1-(oxan-4-yl)propyl]-1-methoxy-3-oxo-2,3-dihydro-1H-isoindol-2-yl]-2-methylpropanoic acid or a tautomer or a solvate or a pharmaceutically acceptable salt thereof; and
optionally, a further step in which the compound of formula (3) is resolved to increase the proportion of the stereoisomer which is (2S,3S)-3-(4-chlorophenyl)-3-[(1R)-1-(4-chlorophenyl)-7-fluoro-5-[(1S)-1-hydroxy-1-(oxan-4-yl)propyl]-1-methoxy-3-oxo-2,3-dihydro-1H-isoindol-2-yl]-2-methylpropanoic acid of formula (3')

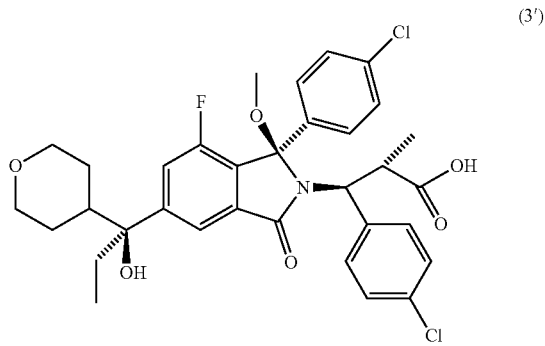 [SMILES: CC[C@@](O)(c1cc(F)c2c(c1)C(=O)N([C@H](c1ccc(Cl)cc1)[C@H](C)C(=O)O)[C@@]2(OC)c1ccc(Cl)cc1)C1CCOCC1]

or a tautomer or a solvate or a pharmaceutically acceptable salt thereof.

In a sixth aspect, the invention provides a process for preparing a 1-methoxyisoindoline which is (2S,3S)-3-(4-chlorophenyl)-3-[1-(4-chlorophenyl)-7-fluoro-5-[(1S)-1-hydroxy-1-(oxan-4-yl)propyl]-1-methoxy-3-oxo-2,3-dihydro-1H-isoindol-2-yl]-2-methylpropanoic acid (3):

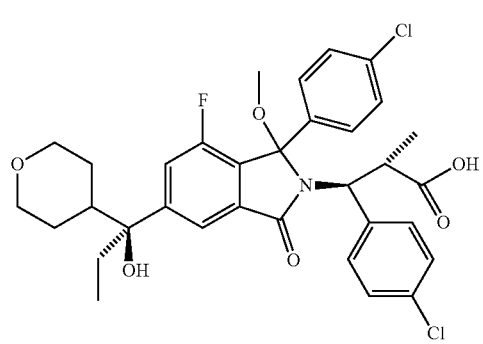

or a tautomer or a solvate or a pharmaceutically acceptable salt thereof,
the process comprising the step of, in any order:
(i) de-esterifying a compound of the formula (4"):

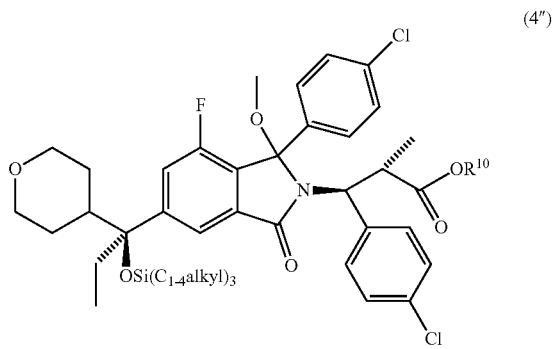

wherein $R^{10}$ is selected from $C_{1-7}$ alkyl, $C_{1-7}$ haloalkyl, tri$C_{1-7}$ alkylsilyl-$C_{1-7}$alkyl, $C_{5-20}$ aryl and $C_{5-20}$ aryl-$C_{1-7}$ alkyl; and (ii) removing the —Si(C₁₋₄alkyl)₃ protecting group from the alcohol to provide (2S,3S)-3-(4-chlorophenyl)-3-[(1-(4-chlorophenyl)-7-fluoro-5-[(1S)-1-hydroxy-1-(oxan-4-yl)propyl]-1-methoxy-3-oxo-2,3-dihydro-1H-isoindol-2-yl]-2-methylpropanoic acid or a tautomer or a solvate or a pharmaceutically acceptable salt thereof; and optionally, a further step in which the compound of formula (3) is resolved to increase the proportion of the stereoisomer which is (2S,3S)-3-(4-chlorophenyl)-3-[(1R)-1-(4-chlorophenyl)-7-fluoro-5-[(1S)-1-hydroxy-1-(oxan-4-yl)propyl]-1-methoxy-3-oxo-2,3-dihydro-1H-isoindol-2-yl]-2-methylpropanoic acid of formula (3')

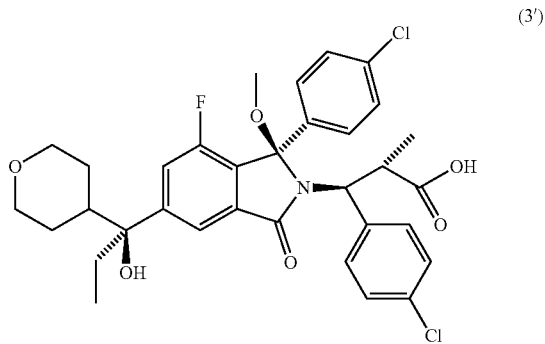 [SMILES: CC[C@@](O)(c1cc(F)c2c(c1)C(=O)N([C@H](c1ccc(Cl)cc1)[C@H](C)C(=O)O)[C@@]2(OC)c1ccc(Cl)cc1)C1CCOCC1]

(3')

or a tautomer or a solvate or a pharmaceutically acceptable salt thereof.

In a seventh aspect, the invention provides a novel compound which is compound (4'), (4"), (5), (18), (19), (21), (22), (23), (24), (25), (26a), (26b) or (27) as defined herein.

In an eighth aspect, the invention provides a crystalline form of (2S,3S)-3-(4-chlorophenyl)-3-[(1R)-1-(4-chlorophenyl)-7-fluoro-5-[(1S)-1-hydroxy-1-(oxan-4-yl)propyl]-1-methoxy-3-oxo-2,3-dihydro-1H-isoindol-2-yl]-2-methylpropanoic acid having:

(a) an X-ray powder diffraction pattern characterised by peaks at diffraction angles 15.1, 15.5, 15.8 and 22.3 degrees 2θ (±0.2 degrees 2θ); or (b) interplanar spacings of 3.99, 5.62, 5.71 and 5.87 Å.

In a ninth aspect, the invention provides a crystalline form of (2S,3S)-3-(4-chlorophenyl)-3-[(1R)-1-(4-chlorophenyl)-7-fluoro-5-[(1S)-1-hydroxy-1-(oxan-4-yl)propyl]-1-methoxy-3-oxo-2,3-dihydro-1H-isoindol-2-yl]-2-methylpropanoic acid which exhibits an exothermic peak at 266-267° C. (e.g. 266.61° C.) when subjected to DSC.

Definitions

Unless the context indicates otherwise, references to any compounds herein in all sections of this document (including the uses, methods and other aspects of the invention) include references to all other sub-formula, sub-groups, embodiments and examples as defined herein.

"Potency" is a measure of drug activity expressed in terms of the amount required to produce an effect of given intensity. A highly potent drug evokes a larger response at low concentrations. Potency is proportional to affinity and efficacy. Affinity is the ability of the drug to bind to a receptor. Efficacy is the relationship between receptor occupancy and the ability to initiate a response at the molecular, cellular, tissue or system level.

The term "antagonist" refers to a type of receptor ligand or drug that blocks or dampens agonist-mediated biological responses. Antagonists have affinity but no agonistic efficacy for their cognate receptors, and binding will disrupt the interaction and inhibit the function of any ligand (e.g. endogenous ligands or substrates, an agonist or inverse agonist) at receptors. The antagonism may arise directly or indirectly, and may be mediated by any mechanism and at any physiological level. As a result, antagonism of ligands may under different circumstances manifest itself in functionally different ways. Antagonists mediate their effects by binding to the active site or to allosteric sites on receptors, or they may interact at unique binding sites not normally involved in the biological regulation of the receptor's activity. Antagonist activity may be reversible or irreversible depending on the longevity of the antagonist-receptor complex, which, in turn, depends on the nature of antagonist receptor binding.

As used herein, the term "mediated", as used e.g. in conjunction with MDM2/p53 as described herein (and applied for example to various physiological processes, diseases, states, conditions, therapies, treatments or interventions) is intended to operate limitatively so that the various processes, diseases, states, conditions, treatments and interventions to which the term is applied are those in which the protein plays a biological role. In cases where the term is applied to a disease, state or condition, the biological role played by the protein may be direct or indirect and may be necessary and/or sufficient for the manifestation of the symptoms of the disease, state or condition (or its aetiology or progression). Thus, the protein function (and in particular aberrant levels of function, e.g. over- or under-expression) need not necessarily be the proximal cause of the disease, state or condition: rather, it is contemplated that the mediated diseases, states or conditions include those having multifactorial aetiologies and complex progressions in which the protein in question is only partially involved. In cases where the term is applied to treatment, prophylaxis or intervention, the role played by the protein may be direct or indirect and may be necessary and/or sufficient for the operation of the treatment, prophylaxis or outcome of the intervention. Thus, a disease state or condition mediated by a protein includes the development of resistance to any particular cancer drug or treatment.

The term "treatment" as used herein in the context of treating a condition i.e. state, disorder or disease, pertains generally to treatment and therapy, whether for a human or an animal (e.g. in veterinary applications), in which some desired therapeutic effect is achieved, for example, the inhibition of the progress of the condition, and includes a reduction in the rate of progress, a halt in the rate of progress, amelioration of the condition, diminishment or alleviation of at least one symptom associated or caused by the condition being treated and cure of the condition. For example, treatment can be diminishment of one or several symptoms of a disorder or complete eradication of a disorder.

The term "prophylaxis" (i.e. use of a compound as prophylactic measure) as used herein in the context of treating a condition i.e. state, disorder or disease, pertains generally to the prophylaxis or prevention, whether for a human or an animal (e.g. in veterinary applications), in which some desired preventative effect is achieved, for example, in preventing occurrence of a disease or guarding from a disease. Prophylaxis includes complete and total blocking of all symptoms of a disorder for an indefinite period of time, the mere slowing of the onset of one or several symptoms of the disease, or making the disease less likely to occur.

References to the prophylaxis or treatment of a disease state or condition such as cancer include within their scope alleviating or reducing the incidence e.g. of cancer.

The combinations of the invention may produce a therapeutically efficacious effect relative to the therapeutic effect of the individual compounds/agents when administered separately.

The term 'efficacious' includes advantageous effects such as additivity, synergism, reduced side effects, reduced toxicity, increased time to disease progression, increased time of survival, sensitization or resensitization of one agent to another, or improved response rate. Advantageously, an efficacious effect may allow for lower doses of each or either component to be administered to a patient, thereby decreasing the toxicity of chemotherapy, whilst producing and/or maintaining the same therapeutic effect. A "synergistic" effect in the present context refers to a therapeutic effect produced by the combination which is larger than the sum of the therapeutic effects of the agents of the combination when presented individually. An "additive" effect in the present context refers to a therapeutic effect produced by the combination which is larger than the therapeutic effect of any of the agents of the combination when presented individually. The term "response rate" as used herein refers, in the case of a solid tumour, to the extent of reduction in the size of the tumour at a given time point, for example 12 weeks. Thus, for example, a 50% response rate means a reduction in tumour size of 50%. References herein to a "clinical response" refer to response rates of 50% or greater. A "partial response" is defined herein as being a response rate of less than 50%.

As used herein, the term "combination", as applied to two or more compounds and/or agents, is intended to define material in which the two or more agents are associated. The terms "combined" and "combining" in this context are to be interpreted accordingly.

The association of the two or more compounds/agents in a combination may be physical or non-physical. Examples of physically associated combined compounds/agents include:

compositions (e.g. unitary formulations) comprising the two or more compounds/agents in admixture (for example within the same unit dose);

compositions comprising material in which the two or more compounds/agents are chemically/physicochemically linked (for example by crosslinking, molecular agglomeration or binding to a common vehicle moiety);

compositions comprising material in which the two or more compounds/agents are chemically/physicochemically co-packaged (for example, disposed on or within lipid vesicles, particles (e.g. micro- or nanoparticles) or emulsion droplets);

pharmaceutical kits, pharmaceutical packs or patient packs in which the two or more compounds/agents are co-packaged or co-presented (e.g. as part of an array of unit doses);

Examples of non-physically associated combined compounds/agents include:

material (e.g. a non-unitary formulation) comprising at least one of the two or more compounds/agents together with instructions for the extemporaneous association of the at least one compound to form a physical association of the two or more compounds/agents;

material (e.g. a non-unitary formulation) comprising at least one of the two or more compounds/agents together with instructions for combination therapy with the two or more compounds/agents;

material comprising at least one of the two or more compounds/agents together with instructions for administration to a patient population in which the other(s) of the two or more compounds/agents have been (or are being) administered;

material comprising at least one of the two or more compounds/agents in an amount or in a form which is specifically adapted for use in combination with the other(s) of the two or more compounds/agents.

As used herein, the term "combination therapy" is intended to define therapies which comprise the use of a combination of two or more compounds/agents (as defined above). Thus, references to "combination therapy", "combinations" and the use of compounds/agents "in combination" in this application may refer to compounds/agents that are administered as part of the same overall treatment regimen. As such, the posology of each of the two or more compounds/agents may differ: each may be administered at the same time or at different times. It will therefore be appreciated that the compounds/agents of the combination may be administered sequentially (e.g. before or after) or simultaneously, either in the same pharmaceutical formulation (i.e. together), or in different pharmaceutical formulations (i.e. separately). Simultaneously in the same formulation is as a unitary formulation whereas simultaneously in different pharmaceutical formulations is non-unitary. The posologies of each of the two or more compounds/agents in a combination therapy may also differ with respect to the route of administration.

As used herein, the term "pharmaceutical kit" defines an array of one or more unit doses of a pharmaceutical composition together with dosing means (e.g. measuring device) and/or delivery means (e.g. inhaler or syringe), optionally all contained within common outer packaging. In pharmaceutical kits comprising a combination of two or more compounds/agents, the individual compounds/agents may unitary or non-unitary formulations. The unit dose(s) may be contained within a blister pack. The pharmaceutical kit may optionally further comprise instructions for use.

As used herein, the term "pharmaceutical pack" defines an array of one or more unit doses of a pharmaceutical composition, optionally contained within common outer packaging. In pharmaceutical packs comprising a combination of two or more compounds/agents, the individual compounds/agents may unitary or non-unitary formulations. The unit dose(s) may be contained within a blister pack. The pharmaceutical pack may optionally further comprise instructions for use.

The term 'optionally substituted' as used herein refers to a group which may be unsubstituted or substituted by a substituent as herein defined.

The prefix "$C_{x-y}$" (where x and y are integers) as used herein refers to the number of carbon atoms in a given group. Thus, a $C_{1-6}$ alkyl group contains from 1 to 6 carbon atoms, a $C_{3-6}$ cycloalkyl group contains from 3 to 6 carbon atoms, a $C_{1-4}$ alkoxy group contains from 1 to 4 carbon atoms, and so on.

The term 'halo' or 'halogen' as used herein refers to fluorine, chlorine, bromine or iodine, in particular fluorine or chlorine.

Each and every hydrogen in the compound (such as in an alkyl group or where referred to as hydrogen) includes all isotopes of hydrogen, in particular $^1H$ and $^2H$ (deuterium).

The term 'oxo' as used herein refers to the group =O.

The term '$C_{1-4}$alkyl' as used herein as a group or part of a group refers to a linear or branched saturated hydrocarbon group containing from 1 to 4 carbon atoms respectively. Examples of such groups include methyl, ethyl, n-propyl, isopropyl, n-butyl, isobutyl, sec-butyl, tert butyl and the like.

The term '$C_{2-4}$alkenyl' or '$C_{2-6}$alkenyl' as used herein as a group or part of a group refers to a linear or branched hydrocarbon group containing from 2 to 4, or 2 to 6 carbon atoms, respectively, and containing a carbon carbon double bond. Examples of such groups include $C_{3-4}$alkenyl or $C_{3-6}$alkenyl groups, such as ethenyl (vinyl), 1-propenyl, 2-propenyl (allyl), isopropenyl, butenyl, buta-1,4-dienyl, pentenyl, and hexenyl.

The term '$C_{2-4}$alkynyl' or '$C_{2-6}$alkynyl' as used herein as a group or part of a group refers to a linear or branched hydrocarbon group having from 2 to 4 or 2 to 6 carbon atoms, respectively, and containing a carbon carbon triple bond. Examples of such groups include $C_{3-4}$alkynyl or $C_{3-6}$alkynyl groups such as ethynyl and 2 propynyl (propargyl) groups.

The term '$C_{1-4}$alkoxy' as used herein as a group or part of a group refers to an —O—$C_{1-4}$alkyl group wherein $C_{1-4}$alkyl is as defined herein. Examples of such groups include methoxy, ethoxy, propoxy, butoxy, and the like.

The term '$C_{3-6}$cycloalkyl' as used herein refers to a saturated monocyclic hydrocarbon ring of 3 to 6 carbon atoms. Examples of such groups include cyclopropyl, cyclobutyl, cyclopentyl or cyclohexyl and the like.

The term '$C_{3-6}$cycloalkenyl' as used herein refers to a partially saturated monocyclic hydrocarbon ring of 3 to 6 carbon atoms having one or more (usually one) carbon carbon double bond(s). Examples of such groups include cyclopentenyl, cyclohexenyl, and cyclohexadienyl.

The term 'hydroxy$C_{1-4}$alkyl' as used herein as a group or part of a group refers to a $C_{1-4}$alkyl group as defined herein wherein one or more (e.g. 1, 2 or 3) than one hydrogen atom is replaced with a hydroxyl group. The term 'hydroxy$C_{1-4}$alkyl' therefore includes monohydroxy$C_{1-4}$ alkyl, and also polyhydroxy$C_{1-4}$ alkyl. There may be one, two, three or more hydrogen atoms replaced with a hydroxyl group, so the hydroxy$C_{1-4}$alkyl may have one, two, three or more hydroxyl groups. Examples of such groups include hydroxymethyl, hydroxyethyl, hydroxypropyl and the like.

The term 'halo$C_{1-4}$alkyl' as used herein as a group or part of a group refers to a $C_{1-4}$alkyl group as defined herein wherein one or more (e.g. 1, 2 or 3) than one hydrogen atom is replaced with a halogen. The term 'halo$C_{1-4}$alkyl' therefore includes monohalo$C_{1-4}$alkyl and also polyhalo$C_{1-4}$alkyl.

There may be one, two, three or more hydrogen atoms replaced with a halogen, so the halo$C_{1-4}$alkyl may have one, two, three or more halogens. Examples of such groups include fluoroethyl, fluoromethyl, difluoromethyl, trifluoromethyl or trifluoroethyl and the like.

The term 'halo$C_{1-4}$alkoxy' as used herein as a group or part of a group refers to a —O—$C_{1-4}$alkyl group as defined herein wherein one or more (e.g. 1, 2 or 3) than one hydrogen atom is replaced with a halogen. The terms 'halo$C_{1-4}$alkoxy' therefore include monohalo$C_{1-4}$alkoxy, and also polyhalo$C_{1-4}$alkoxy. There may be one, two, three or more hydrogen atoms replaced with a halogen, so the halo$C_{1-4}$alkoxy may have one, two, three or more halogens. Examples of such groups include fluoroethyloxy, difluoromethoxy or trifluoromethoxy and the like.

The term "heterocyclyl group" as used herein shall, unless the context indicates otherwise, include both aromatic and non-aromatic ring systems. Thus, for example, the term "heterocyclyl group" include within their scope aromatic, non-aromatic, unsaturated, partially saturated and saturated heterocyclyl ring systems. In general, unless the context indicates otherwise, such groups may be monocyclic or bicyclic (including fused, spiro and bridged bicyclic groups) and may contain, for example, 3 to 12 ring members, more usually 5 to 10 ring members. Reference to 4 to 7 ring members includes 4, 5, 6 or 7 atoms in the ring and reference to 4 to 6 ring members include 4, 5, or 6 atoms in the ring. Examples of monocyclic groups are groups containing 3, 4, 5, 6, 7 and 8 ring members, more usually 3 to 7, or 4 to 7 and preferably 5, 6 or 7 ring members, more preferably 5 or 6 ring members. Examples of bicyclic groups are those containing 8, 9, 10, 11 and 12 ring members, and more usually 9 or 10 ring members. The heterocyclyl groups can be heteroaryl groups having from 5 to 12 ring members, more usually from 5 to 10 ring members. Where reference is made herein to a heterocyclyl group, the heterocyclyl ring can, unless the context indicates otherwise, be optionally substituted i.e. unsubstituted or substituted, by one or more (e.g. 1, 2, 3, or 4 in particular one or two) substituents as defined herein.

The heterocyclyl group can be, for example, a five membered or six membered monocyclic ring or a bicyclic structure formed from fused five and six membered rings or two fused six membered rings, or two fused five membered rings. Each ring may contain up to five heteroatoms particularly selected from nitrogen, sulfur and oxygen and oxidised forms of nitrogen or sulfur. Particularly the heterocyclyl ring will contain up to 4 heteroatoms, more particularly up to 3 heteroatoms, more usually up to 2, for example a single heteroatom. In one embodiment, the heterocyclyl ring will contain one or two heteroatoms selected from N, O, S and oxidised forms of N or S. In one embodiment, the heterocyclyl ring contains at least one ring nitrogen atom. The nitrogen atoms in the heterocyclyl rings can be basic, as in the case of an imidazole or pyridine, or essentially non-basic as in the case of an indole or pyrrole nitrogen. In general the number of basic nitrogen atoms present in the heterocyclyl group, including any amino group substituents of the ring, will be less than five.

The heterocyclyl groups can be attached via a carbon atom or a heteroatom (e.g. nitrogen). Equally the heterocyclyl groups can be substituted on a carbon atom or on a heteroatom (e.g. nitrogen).

Examples of five membered aromatic heterocyclyl groups include but are not limited to pyrrolyl, furanyl, thienyl, imidazolyl, furazanyl, oxazolyl, oxadiazolyl, oxatriazolyl, isoxazolyl, thiazolyl, thiadiazolyl, isothiazolyl, pyrazolyl, triazolyl and tetrazolyl groups.

Examples of six membered aromatic heterocyclic groups include but are not limited to pyridinyl, pyrazinyl, pyridazinyl, pyrimidinyl and triazinyl.

The term "heteroaryl" is used herein to denote a heterocyclyl group having aromatic character. The term "heteroaryl" embraces polycyclic (e.g. bicyclic) ring systems wherein one or more rings are non-aromatic, provided that at least one ring is aromatic. In such polycyclic systems, the group may be attached by the aromatic ring, or by a non-aromatic ring.

Examples of heteroaryl groups are monocyclic and bicyclic groups containing from five to twelve ring members, and more usually from five to ten ring members.

Examples of five membered heteroaryl groups include but are not limited to pyrrole, furan, thiophene, imidazole, furazan, oxazole, oxadiazole, oxatriazole, isoxazole, thiazole, thiadiazole, isothiazole, pyrazole, triazole and tetrazole groups.

Examples of six membered heteroaryl groups include but are not limited to pyridine, pyrazine, pyridazine, pyrimidine and triazine.

A bicyclic heteroaryl group may be, for example, a group selected from:
a) a benzene ring fused to a 5- or 6-membered ring containing 1, 2 or 3 ring heteroatoms;
b) a pyridine ring fused to a 5- or 6-membered ring containing 0, 1, 2 or 3 ring heteroatoms;
c) a pyrimidine ring fused to a 5- or 6-membered ring containing 0, 1 or 2 ring heteroatoms;
d) a pyrrole ring fused to a 5- or 6-membered ring containing 0, 1, 2 or 3 ring heteroatoms;
e) a pyrazole ring fused to a 5- or 6-membered ring containing 0, 1 or 2 ring heteroatoms;
f) an imidazole ring fused to a 5- or 6-membered ring containing 0, 1 or 2 ring heteroatoms;
g) an oxazole ring fused to a 5- or 6-membered ring containing 0, 1 or 2 ring heteroatoms;
h) an isoxazole ring fused to a 5- or 6-membered ring containing 0, 1 or 2 ring heteroatoms;
i) a thiazole ring fused to a 5- or 6-membered ring containing 0, 1 or 2 ring heteroatoms;
j) an isothiazole ring fused to a 5- or 6-membered ring containing 0, 1 or 2 ring heteroatoms;
k) a thiophene ring fused to a 5- or 6-membered ring containing 0, 1, 2 or 3 ring heteroatoms;
l) a furan ring fused to a 5- or 6-membered ring containing 0, 1, 2 or 3 ring heteroatoms;
m) a cyclohexyl ring fused to a 5- or 6-membered ring containing 1, 2 or 3 ring heteroatoms; and
n) a cyclopentyl ring fused to a 5- or 6-membered ring containing 1, 2 or 3 ring heteroatoms.

Particular examples of bicyclic heteroaryl groups containing a five membered ring fused to another five membered ring include but are not limited to imidazothiazole (e.g. imidazo[2,1-b]thiazole) and imidazoimidazole (e.g. imidazo [1,2-a]imidazole).

Particular examples of bicyclic heteroaryl groups containing a six membered ring fused to a five membered ring include but are not limited to benzofuran, benzothiophene, benzimidazole, benzoxazole, isobenzoxazole, benzisoxazole, benzothiazole, benzisothiazole, isobenzofuran, indole, isoindole, indolizine, indoline, isoindoline, purine (e.g., adenine, guanine), indazole, pyrazolopyrimidine (e.g. pyrazolo[1,5-a]pyrimidine), triazolopyrimidine (e.g. [1,2,4]triazolo[1,5-a]pyrimidine), benzodioxole, imidazopyridine and pyrazolopyridine (e.g. pyrazolo[1,5-a]pyridine) groups.

Particular examples of bicyclic heteroaryl groups containing two fused six membered rings include but are not limited to quinoline, isoquinoline, chroman, thiochroman, isochroman, chromene, isochromene, benzodioxan, quinolizine, benzoxazine, pyridopyridine, quinoxaline, quinazoline, cinnoline, phthalazine, naphthyridine and pteridine groups.

Examples of polycyclic heteroaryl groups containing an aromatic ring and a non-aromatic ring include, tetrahydroisoquinoline, tetrahydroquinoline, dihydrobenzthiophene, dihydrobenzofuran, 2,3-dihydro-benzo[1,4]dioxine, benzo[1,3]dioxole, 4,5,6,7-tetrahydrobenzofuran, tetrahydrotriazolopyrazine (e.g. 5,6,7,8-tetrahydro-[1,2,4]triazolo[4,3-a]pyrazine), chroman, thiochroman, isochroman, chromene, isochromene, benzodioxan, benzoxazine, benzodiazepine, and indoline groups.

A nitrogen-containing heteroaryl ring must contain at least one ring nitrogen atom. The nitrogen-containing heteroaryl ring can be N-linked or C-linked. Each ring may, in addition, contain up to about four other heteroatoms particularly selected from nitrogen, sulfur and oxygen. Particularly the heteroaryl ring will contain up to 3 heteroatoms, for example 1, 2 or 3, more usually up to 2 nitrogens, for example a single nitrogen. The nitrogen atoms in the heteroaryl rings can be basic, as in the case of an imidazole or pyridine, or essentially non-basic as in the case of an indole or pyrrole nitrogen. In general the number of basic nitrogen atoms present in the heteroaryl group, including any amino group substituents of the ring, will be less than five.

Examples of nitrogen-containing heteroaryl groups include, but are not limited to, monocyclic groups such as pyridyl, pyrrolyl, imidazolyl, oxazolyl, oxadiazolyl, thiadiazolyl, oxatriazolyl, isoxazolyl, thiazolyl, isothiazolyl, furazanyl, pyrazolyl, pyrazinyl, pyrimidinyl, pyridazinyl, triazinyl, triazolyl (e.g., 1,2,3-triazolyl, 1,2,4-triazolyl), tetrazolyl, and bicyclic groups such as quinolinyl, isoquinolinyl, benzimidazolyl, benzoxazolyl, benzisoxazole, benzothiazolyl and benzisothiazole, indolyl, 3H-indolyl, isoindolyl, indolizinyl, isoindolinyl, purinyl (e.g., adenine [6-aminopurine], guanine [2-amino-6-hydroxypurine]), indazolyl, quinolizinyl, benzoxazinyl, benzodiazepinyl, pyridopyridinyl, quinoxalinyl, quinazolinyl, cinnolinyl, phthalazinyl, naphthyridinyl and pteridinyl.

Examples of nitrogen-containing polycyclic heteroaryl groups containing an aromatic ring and a non-aromatic ring include tetrahydroisoquinolinyl, tetrahydroquinolinyl, and indolinyl.

The term "non-aromatic" embraces, unless the context indicates otherwise, unsaturated ring systems without aromatic character, partially saturated and saturated heterocyclyl ring systems. The terms "unsaturated" and "partially saturated" refer to rings wherein the ring structure(s) contains atoms sharing more than one valence bond i.e. the ring contains at least one multiple bond e.g. a C=C, C≡C or N=C bond. The term "saturated" refers to rings where there are no multiple bonds between ring atoms. Saturated heterocyclyl groups include piperidinyl, morpholinyl, and thiomorpholinyl. Partially saturated heterocyclyl groups include pyrazolinyl, for example pyrazolin-2-yl and pyrazolin-3-yl.

Examples of non-aromatic heterocyclyl groups are groups having from 3 to 12 ring members, more usually 5 to 10 ring members. Such groups can be monocyclic or bicyclic, for example, have 3 to 7 ring members in particular 4 to 6 ring members. Such groups particularly have from 1 to 5 or 1 to 4 heteroatom ring members (more usually 1, 2, or 3 heteroatom ring members), usually selected from nitrogen, oxygen and sulfur and oxidised forms thereof. The heterocyclyl groups can contain, for example, cyclic ether moieties (e.g. as in tetrahydrofuran and dioxane), cyclic thioether moieties (e.g. as in tetrahydrothiophene and dithiane), cyclic amine moieties (e.g. as in pyrrolidine), cyclic amide moieties (e.g. as in pyrrolidone), cyclic thioamides, cyclic thioesters, cyclic ureas (e.g. as in imidazolidin-2-one) cyclic ester moieties (e.g. as in butyrolactone), cyclic sulfones (e.g. as in sulfolane and sulfolene), cyclic sulfoxides, cyclic sulfonamides and combinations thereof (e.g. thiomorpholine).

Particular examples include morpholinyl, piperidinyl (e.g. piperidin-1-yl, piperidin-2-yl, piperidin-3-yl and piperidin-4-yl), piperidinonyl, pyrrolidinyl (e.g. pyrrolidin-1-yl, pyrrolidin-2-yl and pyrrolidin-3-yl), pyrrolidonyl, azetidinyl, pyranyl (2H-pyran or 4H-pyran), dihydrothienyl, dihydropyranyl, dihydrofuranyl, dihydrothiazolyl, tetrahydrofuranyl, tetrahydrothienyl, dioxanyl, oxanyl (also known as tetrahydropyranyl) (e.g. oxan-4-yl), imidazolinyl, imidazolidinonyl, oxazolinyl, thiazolinyl, pyrazolin-2-yl, pyrazolidinyl, piperazinonyl, piperazinyl, and N-alkyl piperazines such as N-methyl piperazinyl. In general, typical non-aromatic heterocyclyl groups include saturated groups such as piperidinyl, pyrrolidinyl, azetidinyl, morpholinyl, piperazinyl and N-alkyl piperazines such as N-methyl piperazinyl.

The terms "oxan" and "oxanyl" as used herein refer to the group:

which may also be referred to as "tetrahydropyran" or "tetrahydropyranyl".

In a nitrogen-containing non-aromatic heterocyclyl ring the ring must contain at least one ring nitrogen atom. The nitrogen-containing heterocyclyl ring can be N-linked or C-linked. The heterocylic groups can contain, for example, cyclic amine moieties (e.g. as in pyrrolidinyl), cyclic amides (such as a pyrrolidinonyl, piperidinonyl or caprolactamyl), cyclic sulfonamides (such as an isothiazolidinyl 1,1-dioxide, [1,2]thiazinanyl 1,1-dioxide or [1,2]thiazepanyl 1,1-dioxide) and combinations thereof.

Particular examples of nitrogen-containing non-aromatic heterocyclyl groups include aziridinyl, morpholinyl, thiomorpholinyl, piperidinyl (e.g. piperidin-1-yl, piperidin-2yl, piperidin-3-yl and piperidin-4-yl), pyrrolidinyl; (e.g. pyrrolidin-1-yl, pyrrolidin-2-yl and pyrrolidin-3-yl), pyrrolidonyl, dihydrothiazolyl, imidazolinyl, imidazolidinonyl, oxazolinyl, thiazolinyl, 6H-1,2,5-thiadiazinyl, pyrazolin-2-yl, pyrazolin-3-yl, pyrazolidinyl, piperazinyl, and N-alkyl piperazines such as N-methyl piperazinyl.

The heterocyclyl groups can be polycyclic fused ring systems or bridged ring systems such as the oxa- and aza analogues of bicycloalkanes, tricycloalkanes (e.g. adamantane and oxa-adamantane). For an explanation of the distinction between fused and bridged ring systems, see Advanced Organic Chemistry, by Jerry March, 4th Edition, Wiley Interscience, pages 131-133, 1992.

Where, in a definition of a cyclic group or ring, it is stated that the cyclic group contains a certain number of heteroatom ring members, e.g. as in the phrase "a 5 or 6 membered ring containing 0, 1 or 2 nitrogen ring members", this is to be taken as meaning that apart from the certain number of heteroatom ring members specified, the remaining ring members are carbon atoms.

The compound of formula (1°) may contain saturated cyclic groups that can be joined to the rest of the molecule by one or more bonds. When the cyclic group is joined to the rest of the molecule by two or more bonds, these bonds (or two of these bonds) can be made to the same atom (usually a carbon atom) of the ring or different atoms of the ring. Where the bonds are made to the same atom of the ring, this results in a cyclic group with a single atom (usually a quaternary carbon) bound to two groups. In other words, when the compound of formula (1°) includes a cyclic group that group may either be linked to the rest of the molecule by a bond or the cyclic group and the rest of the molecule can have an atom in common e.g. a spiro compound.

The heterocyclyl group can each be unsubstituted or substituted by one or more (e.g. 1, 2 or 3) substituent groups. For example, heterocyclyl or carbocyclyl groups can be unsubstituted or substituted by 1, 2, 3 or 4 substituents and particularly it is unsubstituted or has 1, 2 or 3 substituents as defined herein. Where the cyclic group is saturated there may be 2 substituents joined to the same carbon (where the substituents are the same so called geminal or 'gem' disubstitution).

A combination of substituents is permissible only if such as combination results in a stable or chemically feasible compound (i.e. one that is not substantially altered when kept at 40° C. or less for at least a week).

The various functional groups and substituents making up the compounds of the invention are particularly chosen such that the molecular weight of the compound of the invention does not exceed 1000. More usually, the molecular weight of the compound will be less than 750, for example less than 700, or less than 650, or less than 600, or less than 550. More particularly, the molecular weight is less than 525 and, for example, is 500 or less.

DETAILED DESCRIPTION OF THE INVENTION

The 1-methoxyisoindolines

The invention provides process for preparing compounds of formula (1°):

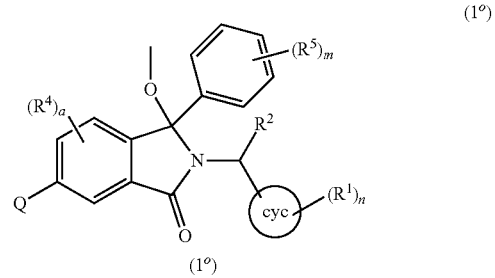

(1°)

or a tautomer or a solvate or a pharmaceutically acceptable salt thereof, wherein $R^1$, $R^2$, $R^4$, $R^5$, Q, a, m and n are as defined herein.

The compounds of the formula (1°) have a chiral centre, marked below with a "*":

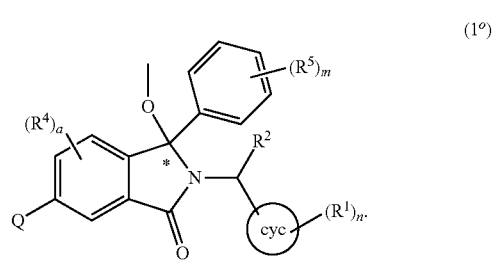

(1°)

The compounds of formula (1°) include a stereocentre at the position indicated (referred to herein as (3)) and are chiral non-racemic.

In particular, the compounds of formula (1°) are compounds of the formula (1°') and have the stereochemistry shown by the hashed and solid wedged bonds:

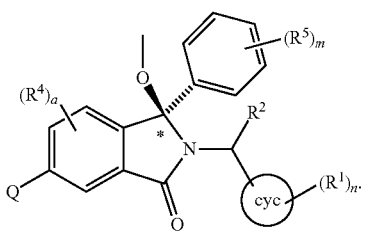

(1°′)

Typically, at least 55% (e.g. at least 60%, 65%, 70%, 75%, 80%, 85%, 90% or 95%) of the compound of the formula (1°) is present as the shown stereoisomer. In one general embodiment, 97% (e.g. 99%) or more (e.g. substantially all) of the total amount of the compound of the formula (1°) may be present as a single stereoisomer.

The compounds may also include one or more further chiral centres (e.g. in the —$CR^6R^7OH$ group and/or in the —$CHR^2$ group).

Typically, the compound of formula (1°) has an enantiomeric excess of at least 10% (e.g. at least 20%, 40%, 60%, 80%, 85%, 90% or 95%). In one general embodiment, the compound of formula (1°) has an enantiomeric excess of 97% (e.g. 99%) or more.

In one embodiment, the process is for making a compound of formula (1°), (1), (4'), (5), (18), (19), (21), (22), (23), (24), (25), (26a), (26b) or (27) with at least 10% (e.g. at least 20%, 40%, 60%, 80%, 85%, 90% or 95%) stereoisomeric purity.

For the purposes of this section the isoindolin-1-one ring is numbered as followed:

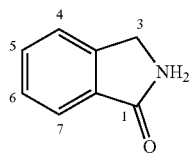

Compounds are named in accordance with protocols utilized by chemical naming software packages.

Cyc

The group cyc can be:
(i) phenyl; or
(ii) a heterocyclic group Het which is pyridinyl, pyrimidinyl, pyrazinyl or pyridazinyl, or an N-oxide thereof.

Compounds Wherein Cyc is Phenyl

In one embodiment, cyc is phenyl, and the invention provides a process for preparing a 1-methoxyisoindoline of formula (1):

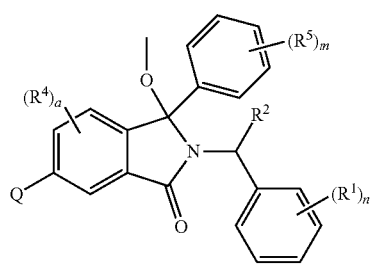

(1)

or a tautomer or a solvate or a salt thereof,
the process comprising taking a compound of the formula (2)

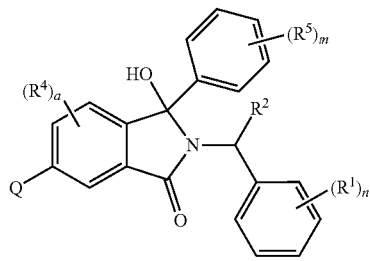

(2)

wherein $R^1$ is independently selected from hydroxy, halogen, nitro, nitrile, $C_{1-4}$alkyl, halo$C_{1-4}$alkyl, hydroxy$C_{1-4}$ alkyl, $C_{2-5}$alkenyl, $C_{1-4}$alkoxy, halo$C_{1-4}$ alkoxy, $C_{2-4}$alkynyl, —$O_{0,1}$—$(CR^xR^y)_v$—$CO_2H$, —$(CR^xR^y)_v$—$CO_2C_{1-4}$alkyl, —$(CR^xR^y)_v$—$CON(C_{1-4}$alkyl)$_2$, —$P(=O)(R^x)_2$, —$S(O)_d$—$R^x$, —$S(O)_d$-heterocyclic group with 3 to 6 ring members and —$S(O)_d$—$N(R^8)_2$;

$R^2$ is selected from hydrogen, $C_{1-4}$alkyl, $C_{2-6}$alkenyl, hydroxy$C_{1-4}$alkyl, —$(CR^xR^y)_u$—$CO_2H$, —$(CR^xR^y)_u$—$CONR^xR^y$, —$(CR^xR^y)_u$—$CO_2R^{10}$ wherein $R^{10}$ is selected from $C_{1-7}$ alkyl, $C_{1-7}$ haloalkyl, tri$C_{1-7}$ alkylsilyl-$C_{1-7}$alkyl, $C_{5-20}$ aryl and $C_{5-20}$ aryl-$C_{1-7}$ alkyl;

$R^4$ and $R^5$ are independently selected from halogen, nitrile, $C_{1-4}$ alkyl, halo$C_{1-4}$alkyl, $C_{1-4}$alkoxy and halo$C_{1-4}$alkoxy;

Q is selected from —$C(OH)R^6R^7$, —$C(=O)R^7$, halogen (e.g. —F, —Cl, —Br, —I) and —OTf;

$R^6$ and $R^7$ are independently selected from hydrogen, $C_{1-6}$alkyl, halo$C_{1-6}$alkyl, $C_{2-6}$alkenyl, $C_{2-6}$alkynyl, hydroxy, hydroxy$C_{1-6}$alkyl, —$COOC_{1-6}$alkyl, —$(CH_2)_j$—$O$—$C_{1-6}$alkyl, —$(CH_2)_j$—$O$-(hydroxy$C_{1-6}$ alkyl), —$C_{1-6}$alkyl-$NR^xR^y$, —$(CR^xR^y)_p$—$CONR^xR^y$, —$(CR^xR^y)_p$—$NR^xCOR^y$, —$(CR^xR^y)_p$—$O$—$CH_2$—$CONR^xR^y$, heterocyclic group with 3 to 7 ring members, —$CH_2$-heterocyclic group with 3 to 7 ring members, —$CH_2$—$O$-heterocyclic group with 3 to 7 ring members, —$CH_2$—$NH$-heterocyclic group with 3 to 7 ring members, —$CH_2$—$N(C_{1-6}$alkyl)-heterocyclic group with 3 to 7 ring members, —$C(=O)NH$-heterocyclic group with 3 to 7 ring members, $C_{3-8}$cycloalkyl, —$CH_2$—$C_{3-8}$cycloalkyl, —$CH_2$—$O$—$C_{3-8}$cycloalkyl, and $C_{3-8}$cycloalkenyl, wherein said cycloalkyl, cycloalkenyl or heterocyclic groups may be optionally substituted by one or more $R^z$ groups, and wherein in each instance the heterocyclic group comprises one or more (e.g. 1, 2, or 3) heteroatoms selected from N, O, S and oxidised forms thereof;

or, when Q is —$C(OH)R^6R^7$, the $R^6$ and $R^7$ groups, together with the carbon atom to which they are attached, can join to form a $C_{3-6}$cycloalkyl or heterocyclyl group with 3 to 6 ring members, wherein the heterocyclic group comprises one or more (e.g. 1, 2, or 3) heteroatoms selected from N, O, S and oxidised forms thereof, and wherein said $C_{3-6}$cycloalkyl and heterocyclyl groups may be optionally substituted by one or more $R^z$ groups;

$R^8$ is selected from hydrogen, $C_{1-6}$alkyl, halo$C_{1-6}$alkyl, hydroxy$C_{1-6}$alkyl, —$(CH_2)_k$—$O$—$C_{1-6}$alkyl, —$(CH_2)_k$—$O$-(hydroxy$C_{1-6}$alkyl), hydroxy$C_{1-6}$alkoxy, —(CH$_2$)$_k$—CO$_2$C$_{1-6}$alkyl, —(CH$_2$)$_k$—CO$_2$H, —C$_{1-6}$ alkyl-N(H)$_e$(C$_{1-4}$alkyl)$_{2-e}$, —(CH$_2$)$_j$—C$_{3-8}$cycloalkyl and —(CH$_2$)$_j$—C$_{3-6}$cycloalkenyl;

R$^x$ and R$^y$ are independently selected from hydrogen, halogen, nitro, nitrile, C$_{1-6}$alkyl, haloC$_{1-6}$alkyl, C$_{2-6}$alkenyl, C$_{2-6}$alkynyl, hydroxy, hydroxyC$_{1-6}$alkyl, C$_{1-6}$alkoxy, —(CH$_2$)$_k$—O—C$_{1-6}$alkyl, hydroxyC$_{1-6}$alkoxy, —COOC$_{1-6}$alkyl, —N(H)$_e$(C$_{1-4}$alkyl)$_{2-e}$, —C$_{1-6}$ alkyl-N(H)$_e$(C$_{1-4}$alkyl)$_{2-e}$, —(CH$_2$)$_k$—C(=O)N(H)$_e$(C$_{1-4}$alkyl)$_{2-e}$, C$_{3-8}$cycloalkyl and C$_{3-8}$cycloalkenyl;

or the R$^x$ and R$^y$ groups, together with the carbon or nitrogen atom to which they are attached, can join to form a C$_{3-6}$cycloalkyl or saturated heterocyclyl group with 3 to 6 ring members which may be optionally fused to an aromatic heterocyclyl group of 3 to 5 ring members;

or when on a carbon atom the R$^x$ and R$^y$ groups can join together to form a =CH$_2$ group; R$^z$ is independently selected from halogen, nitro, nitrile, C$_{1-6}$alkyl, haloC$_{1-6}$alkyl, C$_{2-6}$alkenyl, C$_{2-6}$alkynyl, =O, hydroxy, hydroxyC$_{1-6}$alkyl, C$_{1-6}$alkoxy, —(CH$_2$)$_k$—O—C$_{1-6}$alkyl, hydroxyC$_{1-6}$alkoxy, —C(=O)C$_{1-6}$alkyl, —C(=O)C$_{1-6}$alkyl-OH, —C(=O)C$_{1-6}$alkyl-N(H)$_e$(C$_{1-4}$alkyl)$_{2-e}$, —C(=O)N(H)$_e$(C$_{1-4}$alkyl)$_{2-e}$, —(CH$_2$)$_r$CO$_2$C$_{1-6}$alkyl, —(CH$_2$)$_r$CO$_2$H, —N(H)$_e$(C$_{1-4}$alkyl)$_{2-e}$, —C$_{1-6}$alkyl-N(H)$_e$(C$_{1-4}$alkyl)$_{2-e}$, heterocyclyl group with 3 to 6 ring members, heterocyclyl group with 3 to 6 ring members substituted by —C(=O)C$_{1-4}$alkyl, heterocyclyl group with 3 to 6 ring members substituted by —C(=O)OC$_{1-4}$alkyl, heterocyclyl group with 3 to 6 ring members substituted by —C(=O)N(H)$_e$(C$_{1-4}$alkyl)$_{2-e}$, —C(=O)heterocyclyl group with 3 to 6 ring members, C$_{3-8}$cycloalkyl and C$_{3-8}$cycloalkenyl, wherein if R$^7$ is pyridine then R$^z$ is other then —NH$_2$;

a, j, d, e, n, r and p are independently selected from 0, 1 and 2;

k and m are independently selected from 1 and 2;

u is selected from 0, 1, 2 and 3; and v and w are independently selected from 0 and 1;

and reacting the compound of formula (2) with a methylating agent in the presence of a base.

R$^1$ and n

R$^1$ is the substituent(s) on the phenyl group bonded to —CHR$^2$—.

n is 0, 1, 2 or 3. In other words, the phenyl group bonded to —CHR$^2$— group may have 0, 1, 2 or 3 substituents R$^1$.

In one embodiment n is 1, 2 or 3. In one embodiment n is 1 or 2. In another embodiment n is 1.

When n is 2 or 3 (i.e. the phenyl group bonded to —CHR$^2$— group is substituted with more than one R$^1$) the substituents R$^1$ may be the same or different (i.e. are independently selected from the definitions of R$^1$).

R$^1$ may be attached at the ortho (or o-), meta (or m-) or para (or p-) position of the phenyl group, wherein the position is defined relative to the point of attachment of the phenyl group to the group —CHR$^2$—.

R$^1$ is independently selected from hydroxy, halogen, nitro, nitrile, C$_{1-4}$alkyl, haloC$_{1-4}$alkyl, hydroxyC$_{1-4}$alkyl, C$_{2-6}$alkenyl, C$_{1-4}$alkoxy, haloC$_{1-4}$alkoxy, C$_{2-4}$alkynyl, —O$_{0,1}$—(CR$^x$R$^y$)$_v$—CO$_2$H, —(CR$^x$R$^y$)$_v$—CO$_2$C$_{1-4}$alkyl, —(CH$_2$)—CON(C$_{1-4}$alkyl)$_2$, —P(=O)(R$^x$)$_2$, —S(O)$_d$—R$^x$, —S(O)$_d$-heterocyclic group with 3 to 6 ring members and —S(O)$_d$—N(R$^8$)$_2$.

R$^1$ is independently selected from hydroxy, halogen, nitro, nitrile, C$_{1-4}$alkyl, haloC$_{1-4}$alkyl, hydroxyC$_{1-4}$alkyl, C$_{2-6}$alkenyl, C$_{1-4}$alkoxy, haloC$_{1-4}$alkoxy, C$_{2-4}$alkynyl, —O$_{0,1}$—(CH$_2$)—CO$_2$H, —(CH$_2$)—CO$_2$C$_{1-4}$alkyl, —(CH$_2$)—CON(C$_{1-4}$alkyl)$_2$, —P(=O)(R$^x$)$_2$, —S(O)$_d$—R$^x$, —S(O)$_d$-heterocyclic group with 3 to 6 ring members and —S(O)$_d$—N(R$^8$)$_2$.

R$^1$ is independently selected from hydroxy, halogen, nitro, nitrile, C$_{1-4}$alkyl, haloC$_{1-4}$alkyl, hydroxyC$_{1-4}$alkyl, C$_{2-6}$alkenyl, C$_{1-4}$alkoxy, haloC$_{1-4}$alkoxy, C$_{2-4}$alkynyl, —(CH$_2$)—CO$_2$H, —(CH$_2$)—CO$_2$C$_{1-4}$alkyl, —(CH$_2$)$_v$—CON(C$_{1-4}$alkyl)$_2$, —P(=O)(R$^x$)$_2$, —S(O)$_d$—R$^x$, —S(O)$_d$-heterocyclic group with 3 to 6 ring members and —S(O)$_d$—N(R$^8$)$_2$.

In one embodiment, R$^1$ is independently selected from halogen, hydroxy, nitrile, C$_{1-4}$alkyl, C$_{2-4}$alkynyl, or C$_{1-4}$alkoxy, for example R$^1$ is independently selected from chloro, hydroxy, nitrile, methyl or methoxy.

In one embodiment R$^1$ is independently selected from halogen (e.g. chloro), C$_{1-4}$alkyl (e.g. methyl), C$_{1-4}$alkoxy (e.g. methoxy), —O$_{0,1}$—(CR$^x$R$^y$)$_v$—CO$_2$H (e.g. —CO$_2$H, —(CH$_2$)—CO$_2$H, —(C(CH$_3$)$_2$)—CO$_2$H, or —O(CH$_2$)—CO$_2$H) or —S(O)$_d$—R$^x$ (e.g. SO$_2$CH$_3$).

In one embodiment R$^1$ is O$_{0,1}$—(CR$^x$R$^y$)$_v$—CO$_2$H in particular —CO$_2$H, —(CH$_2$)—CO$_2$H, —(C(CH$_3$)$_2$)—CO$_2$H, or —O(CH$_2$)—CO$_2$H), such as —(C(CH$_3$)$_2$)—CO$_2$H.

In one embodiment, R$^1$ is chloro or nitrile, in particular chloro.

In one embodiment, R$^1$ is nitro (e.g. p-NO$_2$).

In one embodiment, R$^1$ is nitro at the ortho or meta position.

In one embodiment, R$^1$ is independently selected from hydroxy, halogen, nitrile, C$_{1-4}$alkyl, haloC$_{1-4}$alkyl, hydroxyC$_{1-4}$alkyl, C$_{2-6}$alkenyl, C$_{1-4}$alkoxy, haloC$_{1-4}$alkoxy, C$_{2-4}$alkynyl, —(CH$_2$)—CO$_2$H, —(CH$_2$)$_v$—CO$_2$C$_{1-4}$alkyl, —(CH$_2$) CON(C$_{1-4}$alkyl)$_2$, —P(=O)(R$^x$)$_2$, —S(O)$_d$—C$_{1-6}$alkyl, —S(O)$_d$-heterocyclic group with 3 to 6 ring members and —S(O)$_d$—N(R$^8$)$_2$.

In another embodiment, n is 1 and R$^1$ is chloro or nitrile.

In another embodiment, n is 1 and R$^1$ is chloro.

In another embodiment, n is 1 and R$^1$ is nitrile.

In one embodiment, one of the R$^1$ groups or the R$^1$ group (where n=1) is at the para-position (i.e. para to the point of attachment of the phenyl ring). In one embodiment n is 1 and R$^1$ is p-chloro or p-nitrile.

In one embodiment, n is 1 and R$^1$ is halogen (e.g. Cl or F), nitrile, C$_{1-4}$alkoxy (e.g. —OCH$_3$) or C$_{1-4}$alkyl (e.g. —CH$_3$).

In one embodiment, R$^1$ is —S(O)$_d$—C$_{1-6}$alkyl, or —S(O)$_d$-heterocyclic group with 3 to 6 ring members and —S(O)$_d$—N(R$^8$)$_2$. In one embodiment, R$^1$ is —S—C$_{1-6}$alkyl, —S(O)—C$_{1-6}$alkyl, —S(O)$_2$—C$_{1-6}$alkyl, —S(O)$_d$-heterocyclic group with 3 to 6 ring members or —S(O)$_d$—N(C$_{1-6}$alkyl)$_2$.

In another embodiment, R$^1$ is —S—CH$_3$, —S(O)—CH$_3$, —S(O)$_2$—CH$_3$, or —S(O)$_2$-morpholinyl. In another embodiment, one or more R$^1$ is —SO$_2$CH$_3$, or —SO$_2$-heterocyclic group with 6 ring members e.g. —SO$_2$-(morpholinyl), in particular —SO$_2$-(1-morpholinyl).

In one embodiment, R$^1$ is o-(—S(O)$_d$—C$_{1-4}$alkyl) or o-(—S(O)$_d$-heterocyclic group with 3 to 6 ring members). In one embodiment, R$^1$ is o-S—C$_{1-4}$alkyl, o-(—S(O)$_d$—C$_{1-4}$ alkyl) or o-(—S(O)$_d$-heterocyclic group with 3 to 6 ring members). In one embodiment, R$^1$ is o-(—S(O)$_2$—CH$_3$)

In one embodiment, R$^1$ is —(CH$_2$)$_u$—CO$_2$H. In one embodiment, R$^1$ is —CO$_2$H. In one embodiment, R$^1$ is —(CH$_2$)$_u$—CO$_2$H at the meta or para position. In one embodiment, R$^1$ is —(CH$_2$)$_u$—CO$_2$H at the ortho position.

In one embodiment, R$^1$ is independently selected from hydroxy, halogen, nitrile, C$_{1-4}$alkyl, haloC$_{1-4}$alkyl, hydroxyC$_{1-4}$alkyl, C$_{2-6}$alkenyl, C$_{1-4}$alkoxy, haloC$_{1-4}$alkoxy, C$_{2-4}$alkynyl, —(CH$_2$)$_v$—CO$_2$C$_{1-4}$alkyl, —(CH$_2$))CON(C$_{1-4}$alkyl)$_2$, —P(=O)(R$^x$)$_2$, —S(O)$_d$—C$_{1-6}$alkyl, —S(O)$_d$-heterocyclic group with 3 to 6 ring members and —S(O)$_d$—N(R$^8$)$_2$.

In one embodiment, n is 2. In one embodiment when n is 2, the phenyl group is substituted with (i) o-(—S(O)$_d$—C$_{1-4}$alkyl) or o-(—S(O)$_d$-heterocyclic group with 3 to 6 ring members) and (ii) halogen (e.g. Cl or F), nitrile, or C$_{1-4}$ alkyl, in particular chloro, nitrile or methyl.

In one embodiment, n is 2 and R$^1$ is (i) —SO$_2$CH$_3$ and (ii) chloro.

In one embodiment n is 2 and R$^1$ is (i) —SO$_2$CH$_3$ and (ii) chloro, nitrile or methyl.

In one embodiment, n is 2 and R$^1$ is (i) —CO$_2$H and (ii) chloro.

In one embodiment n is 2 and R$^1$ is (i) —CO$_2$H and (ii) chloro, or nitrile.

In one embodiment, when n is 2, the phenyl group bonded to —CHR$^2$— is substituted with (i) hydroxyl and (ii) halogen (e.g. Cl or F), or nitrile, in particular chloro, or nitrile.

In one embodiment, the phenyl group bonded to —CHR$^2$— and R$^1$ form a group:

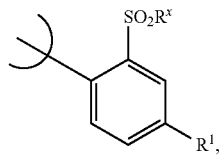

wherein in particular, R$^1$ is halogen (for example chloro), nitrile or C$_{1-4}$alkyl (for example —CH$_3$) and R$^x$ is C$_{1-4}$alkyl (for example —CH$_3$).

In one embodiment, the phenyl group bonded to —CHR$^2$— and R$^1$ form a group:

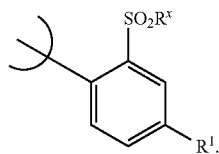

wherein in particular, R$^1$ is C$_{1-4}$alkyl (for example —CH$_3$) and R$^x$ is C$_{1-4}$alkyl (for example —CH$_3$).

In one embodiment when n is 2, the phenyl group is substituted with (i) o-OH or o-CH$_2$OH and (ii) halogen (e.g. Cl or F), nitrile, or C$_{1-4}$ alkyl, in particular chloro, or nitrile. In one embodiment, when n is 2, the phenyl group is substituted with (i) hydroxy and (ii) halogen (e.g. Cl or F) or nitrile, in particular chloro or nitrile. In one embodiment, when n is 2, the phenyl group is substituted with (i) o-hydroxy and (ii) p-Cl or p-CN (e.g. p-Cl).

In one embodiment, n is 2 and R$^1$ is fluorine (e.g. at the ortho and para positions of the phenyl group).

In one embodiment, R$^1$ is halogen (e.g. Cl or F), C$_{1-4}$alkynyl (e.g. —C≡CH), nitrile, —(CH$_2$)$_v$COOH (e.g. —COOH) or SO$_2$C$_{1-4}$alkyl (e.g. SO$_2$CH$_3$) and n is 1 or 2.

In one embodiment, R$^1$ is halogen (e.g. Cl), C$_{1-4}$alkynyl (e.g. —C≡CH), nitrile, hydroxyC$_{1-4}$alkyl (e.g. CH$_2$OH), —(CH$_2$)$_v$COOH (e.g. —COOH), —S(O)$_d$—C$_{1-4}$alkyl (e.g. SCH$_3$, SOCH$_3$, or SO$_2$CH$_3$), —SO$_2$-(1-morpholinyl) or —P(=O)(R$^x$)$_2$, (e.g. —P(=O)(CH$_3$)$_2$).

In one embodiment, n is 1 and R$^1$ is Cl (e.g. p-Cl), CN (e.g. p-CN), or C$_{2-4}$alkynyl (e.g. p-Cl alkynyl), or n is 2 and (i) R$^1$ is p-Cl, o-CH$_2$OH; (ii) p-CN, o-CH$_2$OH; or (iii) p-Cl, o-COOH, (iv) p-Cl, o-SCH$_3$, (v) p-Cl, o-S(O)CH$_3$, (vi) p-Cl, o-SO$_2$CH$_3$, (vii) p-Cl, o-SO$_2$-(1-morpholinyl), or (viii) p-Cl, o-P(O)(CH$_3$)$_2$.

In one embodiment, n is 1 and R$^1$ is Cl (e.g. p-Cl), CN (e.g. p-CN), or C$_{2-4}$alkynyl (e.g. p-Cl alkynyl).

In one embodiment, n is 2 and (i) R$^1$ is p-Cl, o-CH$_2$OH; (ii) p-CN, o-CH$_2$OH; or (iii) p-Cl, o-COOH, (iv) p-Cl, o-SCH$_3$, (v) p-Cl, o-S(O)CH$_3$, (vi) p-Cl, o-SO$_2$CH$_3$, (vii) p-Cl, o-SO$_2$-(1-morpholinyl), or (viii) p-Cl, o-P(O)(CH$_3$)$_2$.

In one embodiment n is 1 and R$^1$ is —Cl, —CN or —OMe (e.g. p-Cl, p-CN or p-OMe). In one embodiment n is 1 and R$^1$ is —Cl or —CN (e.g. p-Cl or p-CN).

In one embodiment, n is 2. When n is 2, typically the phenyl group is substituted at the o- and p-positions. In particular, n is 2 and R$^1$ is substituted by a p-chloro and either o-(—S(O)$_d$—C$_{1-4}$alkyl) or o-(—S(O)$_d$-heterocyclic group with 3 to 6 ring members).

In one embodiment, n is 2 and R$^1$ is o-CO$_2$H and p-chloro.
In one embodiment, n is 2 and R$^1$ is o-CO$_2$H and p-nitrile.
In one embodiment, n is 2 and R$^1$ is o-CH$_2$OH and p-chloro.
In one embodiment, n is 2 and R$^1$ is o-CH$_2$OH and p-nitrile.
In one embodiment, n is 2 and R$^1$ is o-OH and p-chloro.
In one embodiment, n is 2 and R$^1$ is o-OH and p-nitrile.
In one embodiment, n is 2 and R$^1$ is o-SO$_2$CH$_3$ and p-chloro.
In one embodiment n is 2 and R$^1$ is —SO$_2$-(1-morpholinyl) and p-chloro.

In one embodiment, R$^1$ is —O$_{0,1}$(CR$^x$R$^y$)$_v$COOH (e.g. —COOH, —CH$_2$COOH, —OCH$_2$COOH or —C(CH$_3$)$_2$COOH In one embodiment, n is 2 and R$^1$ is p-Cl and o-O$_{0,1}$(CR$^x$R$^y$)$_v$COOH (e.g. —COOH, —CH$_2$COOH, —OCH$_2$COOH or —C(CH$_3$)$_2$COOH).

In one embodiment, R$^1$ is halogen (e.g. Cl), hydroxyalkyl (e.g. —CH$_2$OH), C$_{1-4}$alkynyl (e.g. —C≡CH), nitrile, —O$_{0,1}$(CR$^x$R$^y$)$_v$COOH (e.g. —COOH, —CH$_2$COOH, —OCH$_2$COOH or —C(CH$_3$)$_2$COOH) or —SO$_2$C$_{1-4}$alkyl (e.g. —SO$_2$CH$_3$) and n is 1 or 2.

In one embodiment, R$^1$ is halogen (e.g. Cl), hydroxyalkyl (e.g. —CH$_2$OH), C$_{1-4}$alkynyl (e.g. —C≡CH), nitrile, —(CH$_2$)$_v$COOH (e.g. —COOH) or —SO$_2$C$_{1-4}$alkyl (e.g. —SO$_2$CH$_3$) and n is 1 or 2.

In one embodiment, R$^1$ is independently selected from hydroxy, halogen, nitrile, C$_{1-4}$alkyl, haloC$_{1-4}$alkyl, hydroxyC$_{1-4}$alkyl, C$_{2-6}$alkenyl, C$_{1-4}$alkoxy, haloC$_{1-4}$alkoxy, C$_{2-4}$alkynyl, —(CH$_2$)$_v$—CO$_2$H, —O$_{0,1}$—(CR$^x$R$^y$)$_v$—CO$_2$C$_{1-4}$alkyl (e.g. —(CH$_2$)$_v$—CO$_2$C$_{1-4}$alkyl), —(CH$_2$)$_v$—CON(C$_{1-4}$alkyl)$_2$, —P(=O)(R$^x$)$_2$, —S(O)$_d$—C$_{1-6}$alkyl, —S(O)$_d$-heterocyclic group with 3 to 6 ring members and —S(O)$_d$—N(R$^8$)$_2$.

In one embodiment wherein n is 2, and one R$^1$ is —O$_{0,1}$—(CR$^x$R$^y$)$_v$—CO$_2$C$_{1-4}$alkyl, o-(—S(O)$_d$—C$_{1-4}$alkyl) or o-(—S(O)$_d$-heterocyclic group with 3 to 6 ring members) and one R$^1$ is halogen (e.g. Cl or F), nitrile, or C$_{1-4}$ alkyl, in particular chloro, nitrile or methyl.

In one embodiment wherein n is 2, and one R$^1$ is o-(—S(O)$_d$—C$_{1-4}$alkyl) or o-(—S(O)$_d$-heterocyclic group with 3 to 6 ring members) and one R$^1$ is halogen (e.g. Cl or F), nitrile, or C$_{1-4}$ alkyl, in particular chloro, nitrile or methyl.

In one embodiment wherein n is 2, and one $R^1$ is $-O_{0,1}$—$(CR^xR^y)_v$—$CO_2C_{1-4}$alkyl, and one $R^1$ is halogen (e.g. Cl or F), nitrile, or $C_{1-4}$ alkyl, in particular chloro, nitrile or methyl, such as chloro.

$R^2$ $R^2$ is selected from hydrogen, $C_{1-4}$ alkyl, $C_{2-6}$alkenyl, hydroxy$C_{1-4}$alkyl, —$(CR^xR^y)_u$—$CO_2H$, —$(CR^xR^y)_u$—$CONR^xR^y$, —$(CR^xR^y)_u$—$CO_2R^{10}$ wherein $R^{10}$ is selected from $C_{1-7}$ alkyl, $C_{1-7}$ alkeneyl, $C_{1-7}$ haloalkyl, tri$C_{1-7}$ alkylsilyl-$C_{1-7}$alkyl, $C_{5-20}$ aryl and $C_{5-20}$ aryl-$C_{1-7}$ alkyl.

In one embodiment, $R^2$ is selected from —$(CR^xR^y)_u$—$CO_2R^{10}$ and $R^{10}$ is an acid protecting group.

In one embodiment, $R^2$ is selected from —$(CR^xR^y)_u$—$CO_2R^{10}$ and $R^{10}$ is selected from $C_{1-7}$ alkyl, $C_{1-7}$ alkeneyl, $C_{1-7}$ haloalkyl, tri$C_{1-7}$ alkylsilyl-$C_{1-7}$alkyl, $C_{5-20}$ aryl and $C_{5-20}$ aryl-$C_{1-7}$ alkyl.

In one embodiment, $R^2$ is selected from

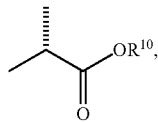

wherein $R^{10}$ is selected from $C_{1-7}$ alkyl, $C_{1-7}$ alkeneyl, $C_{1-7}$ haloalkyl, tri$C_{1-7}$ alkylsilyl-$C_{1-7}$alkyl, $C_{5-20}$ aryl and $C_{5-20}$ aryl-$C_{1-7}$ alkyl.

In one embodiment, $R^2$ is selected from

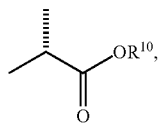

wherein $R^{10}$ is an acid protecting group.

In particular, $R^2$ is selected from —$(CR^xR^y)_u$—$CO_2R^{10}$ wherein $R^{10}$ is selected from $C_{1-7}$ alkyl, $C_{1-7}$ alkeneyl $C_{1-7}$ haloalkyl, tri$C_{1-7}$ alkylsilyl-$C_{1-7}$alkyl, $C_{5-20}$ aryl and $C_{5-20}$ aryl-$C_{1-7}$ alkyl.

In one embodiment, $R^{10}$ is $C_{1-7}$ alkyl, for example $C_{1-4}$ alkyl (e.g. methyl, t-butyl).

In one embodiment, $R^{10}$ is $C_{1-7}$ alkeneyl, for example $C_{1-4}$ alkeneyl (e.g. —$CH_2CH$=$CH_2$).

In one embodiment, $R^{10}$ is $C_{1-7}$ trihaloalkyl, for example $C_{1-4}$ trihaloalkyl (e.g. —$CF_3$, —$CCl_{13}$).

In one embodiment, $R^{10}$ is tri$C_{1-7}$ alkylsilyl-$C_{1-7}$alkyl (e.g —$CH_2CH_2Si(CH_3)_3$).

In one embodiment, $R^{10}$ is selected from $C_{5-20}$ aryl-$C_{1-7}$ alkyl (e.g., benzyl, nitrobenzyl, para-methoxybenzyl).

In one embodiment, $R^{10}$ is selected from $C_{5-20}$ aryl (e.g. phenyl).

In one embodiment, $R^{10}$ is selected from methyl, t-butyl, —$CH_2CH$=$CH_2$, —$CF_3$, —$CCl_3$, —$CH_2CH_2Si(CH_3)_3$, phenyl, benzyl, nitrobenzyl, para-methoxybenzyl.

In one embodiment, $R^{10}$ is selected from —$CH_2CH$=$CH_2$, —$CH_2CH_2Si(CH_3)_3$, and phenyl.

In one embodiment, $R^2$ is selected from

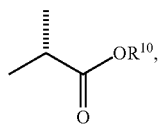

wherein $R^{10}$ is selected from —$CH_2CH$=$CH_2$, —$CH_2CH_2Si(CH_3)_3$, and phenyl.

In one embodiment u is selected from 0, 1, or 2. In one embodiment u is selected from 0 or 1.

In one embodiment, $R^2$ is selected from hydrogen, $C_{1-4}$ alkyl, $C_{2-6}$alkenyl, hydroxy$C_{1-4}$alkyl and —$(CR^xR^y)_u$—$CO_2H$. In one embodiment, $R^2$ is selected from hydrogen, $C_{1-4}$ alkyl, hydroxy$C_{1-4}$alkyl and —$(CR^xR^y)_u$—$CO_2H$. In one embodiment, $R^2$ is selected from hydrogen, $C_{1-4}$ alkyl, $C_{2-6}$alkenyl, and hydroxy$C_{1-4}$alkyl. In another embodiment $R^2$ is selected from hydrogen and —$(CH_2)_u$—$CO_2H$ (e.g. —$CH_2$—$CO_2H$).

In one embodiment, $R^2$ is hydrogen, $C_{1-4}$ alkyl (e.g. —$CH_3$), hydroxy$C_{1-4}$alkyl (e.g. $CH_2OH$) or —$(CH_2)_u$COOH (e.g. —COOH, —$CH_2$COOH, —$CH_2CH_2$—$CO_2H$, —$(CH(CH_3))$—$CO_2H$ or —$(C(CH_3)_2$—$CO_2H$, such as —COOH, —$CH_2$COOH, —$CH_2CH_2$—$CO_2H$, or —$(CH(CH_3))$—$CO_2H$).

In one embodiment, $R^2$ is selected from hydrogen, $C_{1-4}$ alkyl, $C_{2-6}$alkenyl, and hydroxy$C_{1-4}$alkyl.

In one embodiment, $R^2$ is hydrogen, $C_{1-4}$ alkyl (e.g. —$CH_3$), hydroxy$C_{1-4}$alkyl (e.g. $CH_2OH$) or —$(CH_2)_u$COOH (e.g. —$CH_2$COOH). In one embodiment, $R^2$ is selected from hydrogen, —$CH_3$, —$CH_2OH$, and —$CH_2CO_2H$.

In one embodiment, $R^2$ is selected from hydrogen, —$CH_3$, —$CH_2OH$, —CH=$CH_2$ and —$CH(OH)CH_2OH$.

In one embodiment, $R^2$ is selected from hydrogen, —$CH_3$, —$CH_2OH$, and —$CH_2CO_2H$.

In one embodiment, $R^2$ is hydrogen or $C_{1-4}$alkyl (e.g. —$CH_3$ or —$CH_2CH_3$).

In one embodiment, $R^2$ is selected from hydrogen, —$CH_3$ and —$CH_2CH_3$. In one embodiment, $R^2$ is selected from hydrogen and methyl.

In one embodiment, $R^2$ is selected from hydrogen and —$(R^xR^y)_u$—$CO_2H$ (e.g. —COOH, —$CH_2$COOH, —$CH_2CH_2$—$CO_2H$, —$(CH(CH_3))$—$CO_2H$ and —$(C(CH_3)_2$—$CO_2H$).

In one embodiment, $R^2$ is —$(R^xR^y)_u$COOH (e.g. —$CH_2$COOH, —$CH_2CH_2$—$CO_2H$, —$(CH(CH_3))$—$CO_2H$ (e.g.

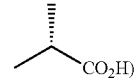

or —$(C(CH_3)_2$—$CO_2H$).

In one embodiment, $R^2$ is hydrogen, $C_{1-4}$ alkyl (e.g. —$CH_3$) or —$(CH_2)_u$COOH (e.g. —$CH_2$COOH, —$CH_2CH_2$—$CO_2H$ or —$(CH(CH_3))$—$CO_2H$).

In one embodiment, $R^2$ is hydrogen, $C_{1-4}$ alkyl (e.g. —$CH_3$) or —$(CH_2)_u$COOH (e.g. —$CH_2$COOH).

In one embodiment, $R^2$ is —$(CR^xR^y)_u$—$CO_2H$ (e.g. —$CH_2$—$CO_2H$).

In another embodiment, $R^2$ is selected from —$(CH(CH_3))$—$CO_2H$ and —$(C(CH_3)_2$—$CO_2H$) (e.g.

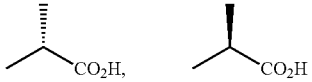

or —$(C(CH_3)_2$—$CO_2H$.

When $R^2$ is other than hydrogen, the compound of formula (1) can exist as at least two diastereoisomers:

Diasteroisomer 1A

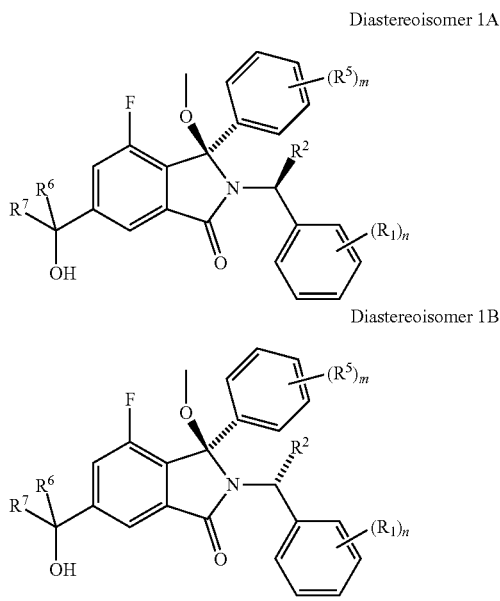

Diasteroisomer 1B

For the avoidance of doubt, the general formula (1°) and all subformulae cover both individual diastereoisomers and mixtures of the diastereoisomers which are related as epimers at the —CHR$^2$— group. In one embodiment the compound of formula I is diastereoisomer 1A or a tautomer or a solvate or a pharmaceutically acceptable salt thereof. In one embodiment the compound of formula I is diastereoisomer 1B or a tautomer or a solvate or a pharmaceutically acceptable salt thereof.

In one embodiment, the compound is diastereoisomer 1A and R$^2$ is selected from:
i. C$_{1-4}$ alkyl, C$_{2-6}$alkenyl, hydroxyC$_{1-4}$alkyl, —(R$^x$R$^y$)$_u$—CO$_2$H (e.g. —COOH, —CH$_2$COOH, —CH$_2$CH$_2$—CO$_2$H, —(CH(CH$_3$))—CO$_2$H and —(C(CH$_3$)$_2$—CO$_2$H), —(CH$_2$)$_u$—CO$_2$C$_{1-4}$alkyl, and —(CH$_2$)$_u$—CONR$^x$R$^y$; or
ii. C$_{1-4}$alkyl, C$_{2-6}$alkenyl, and hydroxyC$_{1-4}$alkyl.

In one embodiment, the compound is diastereoisomer 1A and R$^2$ is selected from:
i. C$_{1-4}$ alkyl, C$_{2-6}$alkenyl, hydroxyC$_{1-4}$alkyl, —(CH$_2$)$_u$—CO$_2$H, —(CH$_2$)$_u$—CO$_2$C$_{1-4}$alkyl, and —(CH$_2$)$_u$—CONR$^x$R$^y$; or
ii. C$_{1-4}$alkyl, C$_{2-6}$alkenyl, and hydroxyC$_{1-4}$alkyl.

In another embodiment R$^2$ is selected from hydrogen and —(R$^x$R$^y$)$_u$—CO$_2$H (e.g. —COOH, —CH$_2$COOH, —CH$_2$CH$_2$—CO$_2$H, —(CH(CH$_3$))—CO$_2$H and —(C(CH$_3$)$_2$—CO$_2$H), In another embodiment R$^2$ is selected from hydrogen and —(CH$_2$)$_u$—CO$_2$H (e.g. —CH$_2$—CO$_2$H).

In one embodiment, the compound is diastereoisomer 1A and R$^2$ is selected from:
i. —CH$_3$, —CH$_2$OH, —CH=CH$_2$ and —CH(OH)CH$_2$OH; or
ii. C$_{1-4}$ alkyl (e.g. —CH$_3$ or —CH$_2$CH$_3$); or
iii. —CH$_3$ and —CH$_2$CH$_3$.

In one embodiment, the compound is diastereoisomer 1B and R$^2$ is selected from:
i. C$_{1-4}$ alkyl, C$_{2-6}$alkenyl, hydroxyC$_{1-4}$alkyl, —(R$^x$R$^y$)$_u$—CO$_2$H (e.g. —COOH, —CH$_2$COOH, —CH$_2$CH$_2$—CO$_2$H, —(CH(CH$_3$))—CO$_2$H and —(C(CH$_3$)$_2$—CO$_2$H), —(CH$_2$)$_u$—CO$_2$C$_{1-4}$alkyl, and —(CH$_2$)$_u$—CONR$^x$R$^y$; or
ii. C$_{1-4}$alkyl, C$_{2-6}$alkenyl, and hydroxyC$_{1-4}$alkyl.

In one embodiment, the compound is diastereoisomer 1B and R$^2$ is selected from:
i. C$_{1-4}$ alkyl, C$_{2-6}$alkenyl, hydroxyC$_{1-4}$alkyl, —(CH$_2$)$_u$—CO$_2$H, —(CH$_2$)$_u$—CO$_2$C$_{1-4}$alkyl, and —(CH$_2$)$_u$—CONR$^x$R$^y$; or
ii. C$_{1-4}$alkyl, C$_{2-6}$alkenyl, and hydroxyC$_{1-4}$alkyl.

In another embodiment R$^2$ is selected from hydrogen and —(CH$_2$)$_u$—CO$_2$H (e.g. —CH$_2$—CO$_2$H).

In one embodiment, the compound is diastereoisomer 1B and R$^2$ is selected from:
i. —CH$_3$, —CH$_2$OH, —CH=CH$_2$ and —CH(OH)CH$_2$OH; or
ii. C$_{1-4}$ alkyl (e.g. —CH$_3$ or —CH$_2$CH$_3$); or
iii. —CH$_3$ and —CH$_2$CH$_3$.

In another embodiment R$^2$ is selected from hydrogen and —(R$^x$R$^y$)$_u$—CO$_2$H (e.g. —COOH, —CH$_2$COOH, —CH$_2$CH$_2$—CO$_2$H, —(CH(CH$_3$))—CO$_2$H and —(C(CH$_3$)$_2$—CO$_2$H), In one embodiment R$^2$ is selected from C$_{1-4}$ alkyl, hydroxyC$_{1-4}$alkyl, —(CH$_2$)$_u$—CO$_2$H, —(CH$_2$)$_u$—CO$_2$C$_{1-4}$alkyl, and —(CH$_2$)$_w$—CONR$^x$R$^y$ (in particular —CH$_2$—CO$_2$H) and the compound is diastereoisomer 1A.

In one embodiment R$^2$ is selected from C$_{1-4}$ alkyl, hydroxyC$_{1-4}$alkyl, —(CH$_2$)$_u$—CO$_2$H, —(CH$_2$)$_u$—CO$_2$C$_{1-4}$alkyl, and —(CH$_2$)$_u$—CONR$^x$R$^y$ (in particular —CH$_2$—CO$_2$H) and the compound is diastereoisomer 1B.

In one embodiment R$^2$ is hydroxyC$_{1-4}$alkyl (e.g. —CH$_2$OH) and the compound is diastereoisomer 1A.

In one embodiment R$^2$ is —(CH$_2$)$_u$—CO$_2$H (e.g. —CH$_2$—CO$_2$H) and the compound is diastereoisomer 1A.

In one embodiment R$^2$ and the hydrogen on the carbon to which it is attached are $^2$H (i.e. deuterium).

R$^4$ and a a is 0, 1, 2 or 3. In other words, the phenyl group of the isoindolin-1-one may have 0, 1, 2 or 3 substituents R$^4$.

In one embodiment a is 0 or 1. In another embodiment a is 0. In another embodiment a is 1.

When a is 2 or 3 (i.e. the phenyl group of the isoindolin-1-one is substituted with more than one R$^4$) the substituents R$^4$ may be the same or different (i.e. are independently selected from the definitions of R$^4$).

In one embodiment, a is 1 and the substituent R$^4$ is at the 4-position of the isoindolin-1-one, and the compound of formula (1°) is a compound of formula (Ir) or a tautomer or a solvate or a pharmaceutically acceptable salt thereof:

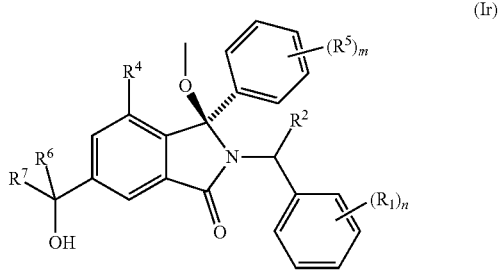

(Ir)

R$^4$ is independently selected from halogen, nitrile, C$_{1-4}$ alkyl, haloC$_{1-4}$alkyl, C$_{1-4}$alkoxy and haloC$_{1-4}$alkoxy.

In one embodiment, R$^4$ is halogen. In one embodiment, R$^4$ is fluoro or chloro. In another embodiment, R$^4$ is fluoro.

In one embodiment, a is 1, the substituent R$^4$ is at the 4-position of the isoindolin-1-one, and R$^4$ is F and the compound of formula (1°) is a compound of formula (Is) or a tautomer or a solvate or a pharmaceutically acceptable salt thereof:

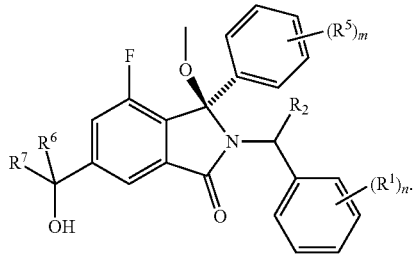
(Is)

In one embodiment, a is 0, and the compound of formula (1°) is a compound of formula (It) or a tautomer or a solvate or a pharmaceutically acceptable salt thereof:

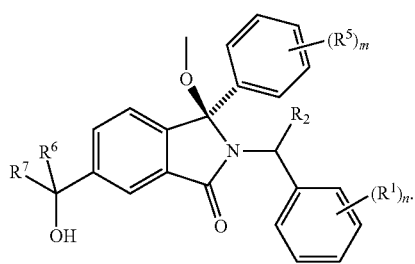
(It)

In one embodiment, $R^4$ is $C_{1-4}$ alkyl (e.g. —$CH_3$), or halogen (e.g. F or Cl) and a is 1.

In one embodiment, a is 0 and $R^4$ is absent (i.e. hydrogen).

In one embodiment a is 0 or 1 and $R^4$ is halogen (e.g. fluorine).

$R^5$ and m m is 1 or 2. In other words, the phenyl group may have 1 or 2 substituents $R^5$.

In one embodiment, m is 1 and the phenyl group has one substituent.

$R^5$ may be attached at the ortho (or o-), meta (or m-) or para (or p-) position of the phenyl group, wherein the position is defined relative to the point of attachment of the phenyl group to the 3-position of the isoindolin-1-one ring.

When m is 2 (i.e. the phenyl group is substituted with more than one $R^5$) the substituents $R^5$ may be the same or different (i.e. are independently selected from the definitions of $R^5$).

In one embodiment, m is 1 and the substituent $R^4$ is at the p-position of the phenyl group, and the compound of formula (1°) is a compound of formula (Iu) or a tautomer or a solvate or a pharmaceutically acceptable salt thereof:

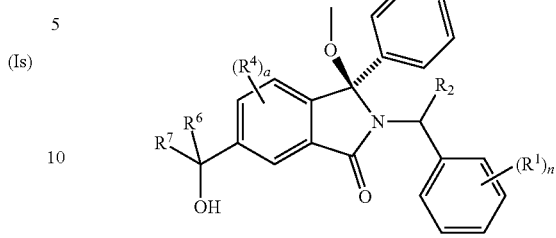
(Iu)

$R^5$ is independently selected from halogen, nitrile, $C_{1-4}$ alkyl, halo$C_{1-4}$alkyl, $C_{1-4}$alkoxy and halo$C_{1-4}$alkoxy.

In one embodiment, $R^5$ is halogen, $C_{1-4}$ alkyl, halo$C_{1-4}$ alkyl or $C_{1-4}$alkoxy. In another embodiment $R^5$ is halogen (e.g. chloro).

In one embodiment, $R^5$ is halogen (e.g. Cl or F), $C_{1-4}$ alkyl (e.g. —$CH_2CH_3$), nitrile, halo$C_{1-4}$alkyl (e.g. —$CF_3$, or —$CF_2CH_3$), or halo$C_{1-4}$alkoxy (e.g. —$OCF_3$), and m is 1 or 2.

In one embodiment, m is 1 and $R^5$ is selected from halogen, nitrile, $C_{1-4}$ alkyl, halo$C_{1-4}$alkyl, $C_{1-4}$alkoxy and halo$C_{1-4}$alkoxy.

In one embodiment, m=1 and $R^5$ is —Cl (e.g. p-Cl), —F (e.g. 4-F), —CN (e.g. p-CN), —$CF_3$ (e.g. p-$CF_3$), —$OCF_3$ (e.g. p-$OCF_3$), $CF_2CH_3$ (e.g. p-$CF_2CH_3$) or —$CH_2CH_3$ (e.g. p-$CH_2CH_3$), or m=2 and $R^5$ is p-F or m-F.

In one embodiment, m=1 and $R^5$ is —Cl (e.g. p-Cl)

Q

Q is selected from —C(OH)$R^6R^7$, —C(=O)$R^7$, halogen (e.g. —F, —Cl, —Br, —I) and OTf.

In one embodiment, Q is —C(OH)$R^6R^7$.

In one embodiment, Q is —C(=O)$R^7$.

In one embodiment, Q is a leaving group, for example a leaving group suitable for use in a palladium coupling reaction, such as halogen (e.g. —F, —Cl, —Br, —I) or OTf.

In one embodiment, Q is halogen (e.g. —F, —Cl, —Br, —I).

In one embodiment, Q is OTf.

$R^6$ and $R^7$ $R^6$ and $R^7$ are independently selected from hydrogen, $C_{1-6}$alkyl, halo$C_{1-6}$alkyl, $C_{2-6}$alkenyl, $C_{2-6}$alkynyl, hydroxy, hydroxy$C_{1-6}$alkyl, —COO$C_{1-6}$alkyl, —$(CH_2)_j$—O—$C_{1-6}$alkyl, —$(CH_2)_j$—O-(hydroxy$C_{1-6}$ alkyl), —$C_{1-6}$alkyl-N$R^xR^y$, —$(CR^xR^y)_p$—CON$R^xR^y$, —$(CR^xR^y)_p$—N$R^x$CO$R^y$, —$(CR^xR^y)_p$—O—$CH_2$—CON$R^xR^y$, heterocyclic group with 3 to 7 ring members, —$CH_2$-heterocyclic group with 3 to 7 ring members, —$CH_2$—O-heterocyclic group with 3 to 7 ring members, —$CH_2$—NH-heterocyclic group with 3 to 7 ring members, —$CH_2$—N($C_{1-6}$alkyl)-heterocyclic group with 3 to 7 ring members, —C(=O)NH-heterocyclic group with 3 to 7 ring members, $C_{3-8}$cycloalkyl, —$CH_2$—$C_{3-8}$cycloalkyl, —$CH_2$—O—$C_{3-8}$cycloalkyl, and $C_{3-8}$cycloalkenyl, wherein said cycloalkyl, cycloalkenyl or heterocyclic groups may be optionally substituted by one or more $R^z$ groups, and wherein in each instance the heterocyclic group comprises one or more (e.g. 1, 2, or 3) heteroatoms selected from N, O, S and oxidised forms thereof;

or, when Q is —C(OH)$R^6R^7$, the $R^6$ and $R^7$ groups, together with the carbon atom to which they are attached, can join to form a $C_{3-6}$cycloalkyl or heterocyclyl group with 3 to 6 ring members, wherein the heterocyclic group comprises one or more (e.g. 1, 2, or 3) heteroatoms selected from N, O, S and oxidised forms thereof, and wherein said $C_{3-6}$cycloalkyl and heterocyclyl groups may be optionally substituted by one or more $R^z$ groups;

$R^x$ and $R^y$ are independently selected from hydrogen, halogen, nitro, nitrile, $C_{1-6}$alkyl, halo$C_{1-6}$alkyl, $C_{2-6}$alkenyl, $C_{2-6}$alkynyl, hydroxy, hydroxy$C_{1-6}$alkyl, $C_{1-6}$alkoxy, —(CH$_2$)$_k$—O—$C_{1-6}$alkyl, hydroxy$C_{1-6}$alkoxy, —COO$C_{1-6}$alkyl, —N(H)$_e$($C_{1-4}$alkyl)$_{2-e}$, —$C_{1-6}$alkyl-N(H)$_e$($C_{1-4}$alkyl)$_{2-e}$, —(CH$_2$)$_k$—C(=O)N(H)$_e$($C_{1-4}$alkyl)$_{2-e}$, $C_{3-8}$cycloalkyl and $C_{3-8}$cycloalkenyl;

or, when Q is —C(OH)R$^6$R$^7$, the R$^x$ and R$^y$ groups, together with the carbon or nitrogen atom to which they are attached, can join to form a $C_{3-6}$cycloalkyl or saturated heterocyclyl group with 3 to 6 ring members which may be optionally fused to an aromatic heterocyclyl group of 3 to 5 ring members; or when on a carbon atom the R$^x$ and R$^y$ groups can join together to form a =CH$_2$ group;

$R^z$ is independently selected from halogen, nitro, nitrile, $C_{1-6}$alkyl, halo$C_{1-6}$alkyl, $C_{2-6}$alkenyl, $C_{2-6}$alkynyl, =O, hydroxy, hydroxy$C_{1-6}$alkyl, $C_{1-6}$alkoxy, —(CH$_2$)$_k$—O—$C_{1-6}$alkyl, hydroxy$C_{1-6}$alkoxy, —C(=O)$C_{1-6}$alkyl, —C(=O)$C_{1-6}$alkyl-OH, —C(=O)$C_{1-6}$alkyl-N(H)$_e$ ($C_{1-4}$alkyl)$_{2-e}$, —C(=O)N(H)$_e$($C_{1-4}$alkyl)$_{2-e}$, —(CH$_2$)$_r$CO$_2$$C_{1-6}$alkyl, —(CH$_2$)$_r$CO$_2$H, —N(H)$_e$($C_{1-4}$alkyl)$_{2-e}$, —$C_{1-6}$alkyl-N(H)$_e$($C_{1-4}$alkyl)$_{2-e}$, heterocyclyl group with 3 to 6 ring members, heterocyclyl group with 3 to 6 ring members substituted by —C(=O)$C_{1-4}$alkyl, heterocyclyl group with 3 to 6 ring members substituted by —C(=O)O$C_{1-4}$alkyl, heterocyclyl group with 3 to 6 ring members substituted by —C(=O)N(H)$_e$($C_{1-4}$alkyl)$_{2-e}$, —C(=O)heterocyclyl group with 3 to 6 ring members, $C_{3-8}$cycloalkyl and $C_{3-8}$cycloalkenyl, wherein if R$^7$ is pyridine then R$^z$ is other then —NH$_2$;

j, e, r and p are independently selected from 0, 1 and 2; and k is selected from 1 and 2.

In one embodiment, R$^6$ and R$^7$ are independently selected from hydrogen, $C_{1-6}$alkyl, halo$C_{1-6}$alkyl, $C_{2-6}$alkenyl, $C_{2-6}$alkynyl, hydroxy, hydroxy$C_{1-6}$alkyl, —COO$C_{1-6}$alkyl, —(CH$_2$)$_j$—O—$C_{1-6}$alkyl, —(CH$_2$)—O-(hydroxy$C_{1-6}$alkyl), —$C_{1-6}$alkyl-NR$^x$R$^y$, —(CR$^x$R$^y$)$_p$—CONR$^x$R$^y$, —(CR$^x$R$^y$)$_p$—NR$^x$COR$^y$, —(CR$^x$R$^y$)$_p$—O—CH$_2$—CONR$^x$R$^y$, heterocyclic group with 3 to 7 ring members, —CH$_2$-heterocyclic group with 3 to 7 ring members, —CH$_2$—O-heterocyclic group with 3 to 7 ring members, —CH$_2$—NH-heterocyclic group with 3 to 7 ring members, —CH$_2$—N($C_{1-6}$alkyl)-heterocyclic group with 3 to 7 ring members, —C(=O)NH-heterocyclic group with 3 to 7 ring members, $C_{3-8}$cycloalkyl, —CH$_2$—$C_{3-8}$cycloalkyl, —CH$_2$—O—$C_{3-8}$cycloalkyl, and $C_{3-8}$cycloalkenyl, wherein said cycloalkyl, cycloalkenyl or heterocyclic groups may be optionally substituted by one or more R$^z$ groups, and wherein in each instance the heterocyclic group comprises one or more (e.g. 1, 2, or 3) heteroatoms selected from N, O, S and oxidised forms thereof;

In one embodiment R$^7$ is a cycloalkyl, cycloalkenyl or heterocyclic group optionally substituted by one or more R$^z$ selected from $C_{1-6}$alkyl (e.g. methyl), $C_{1-6}$alkoxy (e.g. methoxy) and —C(=O)$C_{1-6}$alkyl (e.g. —C(=O)CH$_3$).

In one embodiment R$^7$ is a cycloalkyl or cycloalkenyl group optionally substituted by one or more R$^z$ groups wherein R$^z$ is hydroxy.

R$^6$ and R$^7$ may be the same or different.

When R$^6$ and R$^7$ are different, the compound of formula (1°) can exist as at least two diastereoisomers:

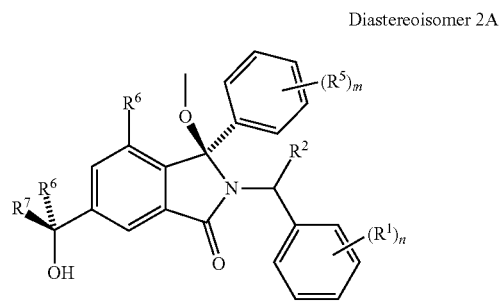

Diastereoisomer 2A

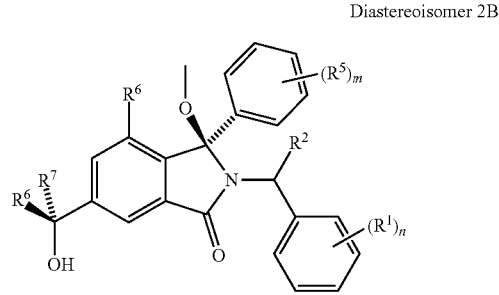

Diastereoisomer 2B

For the avoidance of doubt, the general formula (1°) and all subformulae cover both individual diastereoisomers and mixtures of the diastereoisomers which are related as epimers at the —CR$^6$R$^7$OH group.

In one embodiment of the compound of formula (1°) R$^6$ and R$^7$ are different and the compound is diastereoisomer 2A or a tautomer or a solvate or a pharmaceutically acceptable salt thereof.

In one embodiment of the compound of formula (1°) R$^6$ and R$^7$ are different and the compound is diastereoisomer 2B or a tautomer or a solvate or a pharmaceutically acceptable salt thereof.

In one embodiment, R$^6$ is methyl and the compound of formula (1°) is a compound of formula (Iv) or a tautomer or a solvate or a pharmaceutically acceptable salt thereof:

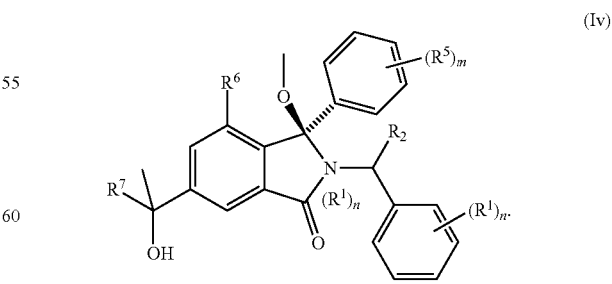

(Iv)

In one embodiment, R$^6$ is ethyl and the compound of formula (1°) is a compound of formula (Iv') or a tautomer or a solvate or a pharmaceutically acceptable salt thereof:

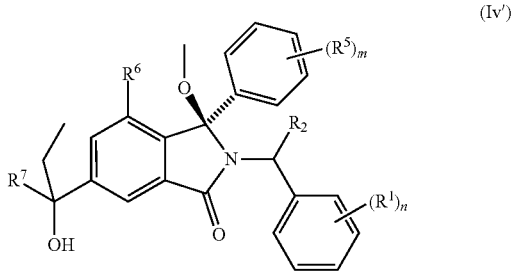

(Iv')

In one embodiment, R[7] is selected from $C_{1-6}$alkyl or halo$C_{1-6}$alkyl. In one embodiment R[7] is a $C_{3-6}$cycloalkyl (e.g. cyclopropyl, cyclobutyl or cyclohexyl) optionally substituted by one or more R[z] groups (e.g. —OH).

In one embodiment, R[7] is selected from $C_{1-6}$alkyl, hydroxy$C_{1-6}$alkyl, —(CH$_2$)$_f$—O—$C_{1-6}$alkyl, —(CH$_2$)$_f$—O—(hydroxy$C_{1-6}$alkyl), —$C_{1-6}$alkyl-NR[x]R[y] (e.g. —$C_{1-6}$alkyl-N(H)$_e$($C_{1-4}$alkyl)$_{2-e}$), —(CR[x]R[y])$_p$—NR[x]COR[y], heterocyclic group with 3 to 7 ring members, —CH$_2$-heterocyclic group with 3 to 7 ring members, —CH$_2$—NH-heterocyclic group with 3 to 7 ring members, —CH$_2$—N($C_{1-6}$alkyl)-heterocyclic group with 3 to 7 ring members, —C(=O)NH-heterocyclic group with 3 to 7 ring members, $C_{3-8}$cycloalkyl, and —CH$_2$—$C_{3-8}$cycloalkyl, wherein said cycloalkyl or heterocyclic groups may be optionally substituted by one or more R[z] groups, and wherein in each instance the heterocyclic group comprises one or more (e.g. 1, 2, or 3) heteroatoms selected from N, O, S and oxidised forms thereof.

In one embodiment, R[7] is selected from $C_{1-6}$alkyl, hydroxy$C_{1-6}$alkyl, —(CH$_2$)$_f$—O—$C_{1-6}$alkyl, —(CH$_2$)—O—(hydroxy$C_{1-6}$alkyl), —$C_{1-6}$alkyl-N(H)$_e$($C_{1-4}$alkyl)$_{2-e}$), heterocyclic group with 3 to 7 ring members, —CH$_2$-heterocyclic group with 3 to 7 ring members, —C(=O)NH-heterocyclic group with 3 to 7 ring members, $C_{3-8}$cycloalkyl, and —CH$_2$—$C_{3-8}$cycloalkyl, wherein said cycloalkyl or heterocyclic groups may be optionally substituted by one or more R[z] groups, and wherein in each instance the heterocyclic group comprises one or more (e.g. 1, 2, or 3) heteroatoms selected from N, O, S and oxidised forms thereof.

In one embodiment, R[7] is selected from heterocyclic group with 3 to 7 ring members, —CH$_2$-heterocyclic group with 3 to 7 ring members, —C(=O)NH-heterocyclic group with 3 to 7 ring members, $C_{3-8}$cycloalkyl, and —CH$_2$—$C_{3-8}$cycloalkyl, wherein said cycloalkyl or heterocyclic groups may be optionally substituted by one or more R[z] groups, and wherein in each instance the heterocyclic group comprises one or more (e.g. 1, 2, or 3) heteroatoms selected from N, O, S and oxidised forms thereof.

In one embodiment, R[7] is selected from heterocyclic group with 3 to 7 ring members and —CH$_2$-heterocyclic group with 3 to 7 ring members, wherein said heterocyclic groups may be optionally substituted by one or more R[z] groups, and wherein in each instance the heterocyclic group comprises one or more (e.g. 1, or 2) heteroatoms selected from N, O, S and oxidised forms thereof.

In embodiment, the heterocyclic group is saturated. In one embodiment, R[7] is saturated heterocyclic group with 3 to 6 ring members or —CH$_2$-(saturated heterocyclic group with 3 to 6 ring members) such as wherein the heterocyclic group is selected from oxetanyl, oxanyl, piperidinyl, piperazinyl, morpholinyl, pyrrolidinyl, imidazolinyl, azetidinyl, thiomorpolinyl, such as oxanyl, piperdinyl or piperazinyl.

In one embodiment, R[7] is selected from saturated heterocyclic group with 3 to 6 ring members and —CH$_2$-saturated heterocyclic group with 3 to 6 ring members, wherein said heterocyclic groups may be optionally substituted by one or more R[z] groups, and wherein in each instance the heterocyclic group comprises one or more (e.g. 1, 2, or 3) heteroatoms selected from N, O, S. In one embodiment, R[7] is selected from a nitrogen containing saturated heterocyclic group with 3 to 6 ring member and —CH$_2$-(nitrogen containing saturated heterocyclic group with 3 to 6 ring members), wherein said heterocyclic groups may be optionally substituted by one or more R[z] groups, and wherein the heterocyclic group may optionally contain one or more (e.g. 1, 2, or 3) additional heteroatoms selected from N, O, S.

In one embodiment, R[7] is nitrogen containing saturated heterocyclic group with 3 to 7 ring members or —CH$_2$-(nitrogen containing saturated heterocyclic group with 3 to 7 ring members), wherein said nitrogen containing saturated heterocyclic groups may be optionally substituted by one or more R[z] groups and wherein the nitrogen containing saturated heterocyclic group may optionally contain one or more (e.g. 1, 2, or 3) additional heteroatoms selected from N, O, S. In one embodiment the nitrogen containing saturated heterocyclic group with 3 to 7 ring members (such as 3 to 6 ring members) is selected from piperidinyl, piperazinyl, morpholinyl, pyrrolidinyl, imidazolinyl, azetidinyl, thiomorpolinyl, such as piperdinyl or piperazinyl.

In one embodiment, R[7] is nitrogen containing aromatic heterocyclic group with 3 to 6 ring members or —CH$_2$-(nitrogen containing aromatic heterocyclic group with 3 to 6 ring members), wherein said heterocyclic groups may be optionally substituted by one or more R[z] groups and wherein the heterocyclic group may optionally contain one or more (e.g. 1, 2, or 3) additional heteroatoms selected from N, O, S.

In another embodiment, R[7] is nitrogen containing aromatic heterocyclic group with 3 to 6 ring members, wherein said heterocyclic group may be unsubstituted or substituted by one or more R[z] groups, for example selected from halogen (e.g. fluorine), $C_{1-6}$alkyl (e.g. methyl), $C_{1-6}$alkoxy (e.g. methoxy), and —C(=O)$C_{1-6}$alkyl (e.g. —C(=O)CH$_3$).

In one embodiment, R[7] is oxygen containing aromatic heterocyclic group with 3 to 6 ring members or —CH$_2$-(oxygen containing aromatic heterocyclic group with 3 to 6 ring members), wherein said heterocyclic groups may be optionally substituted by one or more R[z] groups and wherein the heterocyclic group may optionally contain one or more (e.g. 1, 2, or 3) additional heteroatoms selected from N, O, S.

In another embodiment, R[7] is oxygen containing aromatic heterocyclic group with 3 to 6 ring members, wherein said heterocyclic group may be unsubstituted or substituted by one or more R[z] groups, for example R[z] groups selected from halogen (e.g. fluorine), $C_{1-6}$alkyl (e.g. methyl), $C_{1-6}$alkoxy (e.g. methoxy), and —C(=O)$C_{1-6}$alkyl (e.g. —C(=O)CH$_3$).

In one embodiment R[7] is selected from heterocyclyl groups containing 5 or 6 ring members optionally substituted by one or more R[z].

In one embodiment R[7] is selected from aromatic heterocyclyl groups containing 5 ring members optionally substituted by one or more R[z]. In one embodiment R[7] is selected from an aromatic nitrogen containing (e.g. diaza) heeterocyclyl group containing 5 ring members optionally substituted by one or more R[z]. In one embodiment R[7] is pyrazolyl (e.g. pyrazol-4-yl or pyrazol-3-yl).

In one embodiment $R^7$ is selected from a saturated heteterocyclyl group containing 6 ring members optionally substituted by one or more $R^z$. In one embodiment $R^7$ is selected from a saturated oxygen or nitrogen containing heteterocyclyl group containing 6 ring members optionally substituted by one or more $R^z$.

In one embodiment $R^7$ is selected from oxanyl, piperidinyl, pyrazolyl or imidazolyl optionally substituted by one or more $R^z$. In one embodiment $R^7$ is selected from oxanyl, piperidinyl, pyrazolyl or imidazolyl optionally substituted by one or more $R^z$, where $R^z$ is selected from halo (e.g. —F) or $C_{1-4}$alkyl (e.g. methyl).

In one embodiment $R^7$ is selected from oxanyl (also known as tetrahydropyranyl) or piperidinyl optionally substituted by one or more $R^z$. In one embodiment $R^7$ is selected from oxanyl or piperidinyl unsubstituted or substituted by one or more $R^z$, where $R^z$ is selected from halo (e.g. —F) or $C_{1-4}$alkyl (e.g. methyl), in particular halo (e.g. —F).

In one embodiment, $R^7$ is $C_{3-8}$cycloalkyl such as $C_{3-6}$cycloalkyl (e.g. cyclobutyl or cyclohexyl) optionally substituted by one or more $R^z$, for example where $R^z$ is hydroxy. In one embodiment, $R^7$ is cyclohexyl optionally substituted by one or more hydroxy. In one embodiment $R^7$ is cyclohexyl optionally substituted by one or more hydroxyl, in the trans stereochemistry (e.g. trans-4-hydroxycyclohexane).

In one embodiment $R^7$ is selected from —$CH_2$—NH-heterocyclic group with 3 to 7 ring members (e.g. —$CH_2$—NH-oxanyl and —$CH_2$—N($C_{1-6}$alkyl)-heterocyclic group with 3 to 7 ring members (e.g. —$CH_2NCH_3$-(piperidinyl) optionally substituted by one or more $R^z$ groups (e.g. methyl, —$COCH_3$).

In one embodiment, $R^7$ is —$(CR^xR^y)_p$—$CONR^xR^y$ or —C(=O)NH-heterocyclic group with 3 to 7 ring members. In one embodiment, $R^7$ is —C(=O)NH-heterocyclic group with 4 to 6 ring members (e.g. piperidinyl, pyrazolyl, or azetidinyl).

In one embodiment, $R^7$ is —$(CR^xR^y)_p$—$CONR^xR^y$. In one embodiment $R^7$ is —$(CR^xR^y)_p$—$CONH(C_{1-4}alkyl)$, in particular —(CO)$NHCH_3$, —(CO)$NHCH_2CH_3$ or —(CO)$NH(CH(CH_3)_2)$.

In one embodiment $R^7$ is —C(=O)NH-heterocyclic group with 3 to 7 ring members (e.g. —C(=O)NH-piperidinyl, —C(=O)NH-azetidinyl or —C(=O)NH-pyrazolyl) optionally substituted by one or more $R^z$ groups (e.g. methyl, —$COCH_3$).

In one embodiment, $R^7$ is —$C_{1-6}$alkyl-$NR^xR^y$ (e.g. —$C_{1-6}$alkyl-$N(H)_e(C_{1-4}alkyl)_{2-e}$). In one embodiment $R^7$ is —$CH_2NH_2$, —$CH_2NHCH_3$, or —$CH_2N(CH_3)_2$. In one embodiment $R^7$ is —$C_{1-6}$alkyl-$NR^xR^y$ wherein $R^x$ is $C_{3-8}$cycloalkyl. In one embodiment $R^7$ is —$C_{1-2}$alkyl-NH—$C_{3-6}$cycloalkyl (e.g. —$CH_2$—NH-cyclopropyl).

In one embodiment, $R^7$ is —$C_{1-6}$alkyl-$NR^xR^y$ wherein the $R^x$ and $R^y$ groups, together with the nitrogen atom to which they are attached, can join to form a $C_{3-6}$cycloalkyl or heterocyclyl group with 3 to 6 ring members. In one embodiment, $R^x$ and $R^y$ together form a saturated heterocyclyl group with 3 to 6 ring members e.g. piperazinyl.

In one embodiment $R^7$ is —$C_{1-6}$alkyl-$NR^xR^y$, wherein the $R^x$ and $R^y$ groups, together with the nitrogen atom to which they are attached, join to form a $C_{3-6}$cycloalkyl or saturated heterocyclyl group with 3 to 6 ring members which may be optionally fused to an aromatic heterocyclyl group of 3 to 5 ring members. In one embodiment $R^7$ is —$C_{1-6}$alkyl-$NR^xR^y$, wherein the $R^x$ and $R^y$ groups, together with the nitrogen atom to which they are attached, join to form a saturated heterocyclyl group with 3 to 6 ring members which is fused to an aromatic heterocyclyl group of 3 to 5 ring members. $R^z$ is independently selected from halogen, nitro, nitrile, $C_{1-6}$alkyl, halo$C_{1-6}$alkyl, $C_{2-6}$alkenyl, $C_{2-6}$alkynyl, =O, hydroxy, hydroxy$C_{1-6}$alkyl, $C_{1-6}$alkoxy, —$(CH_2)_k$—O—$C_{1-6}$alkyl, hydroxy$C_{1-6}$alkoxy, —C(=O)$C_{1-6}$alkyl, —C(=O)$C_{1-6}$alkyl-OH, —C(=O)$C_{1-6}$alkyl-$N(H)_e(C_{1-4}alkyl)_{2-e}$, —C(=O)$N(H)_e(C_{1-4}alkyl)_{2-e}$, —$(CH_2)_r CO_2 C_{1-6}$alkyl, —$(CH_2)_r$—$CO_2H$, —$N(H)_e(C_{1-4}alkyl)_{2-e}$, —$C_{1-6}$alkyl-$N(H)_e(C_{1-4}alkyl)_{2-e}$, heterocyclyl group with 3 to 6 ring members, heterocyclyl group with 3 to 6 ring members substituted by —C(=O)$C_{1-4}$alkyl, heterocyclyl group with 3 to 6 ring members substituted by —C(=O)$OC_{1-4}$alkyl, heterocyclyl group with 3 to 6 ring members substituted by —C(=O)$N(H)_e(C_{1-4}alkyl)_{2-e}$, —C(=O)heterocyclyl group with 3 to 6 ring members, $C_{3-8}$cycloalkyl and $C_{3-8}$cycloalkenyl.

In one embodiment $R^z$ is independently selected from halogen (e.g. fluorine), $C_{1-6}$alkyl (e.g. methyl), $C_{1-6}$alkoxy (e.g. methoxy), and —C(=O)$C_{1-6}$alkyl (e.g. —C(=O)$CH_3$).

In one embodiment $R^z$ is independently selected from $C_{1-6}$alkyl (e.g. methyl), $C_{1-6}$alkoxy (e.g. methoxy), and —C(=O)$C_{1-6}$alkyl (e.g. —C(=O)$CH_3$).

In one embodiment, $R^7$ is $C_{1-6}$alkyl (e.g. methyl or ethyl), halo$C_{1-6}$alkyl (e.g. trifluoromethyl), $C_{2-6}$alkenyl (e.g. $C_2$alkenyl), hydroxy$C_{1-6}$alkyl (e.g. —$CH_2OH$, —$CH_2CH_2OH$), —$C_{1-6}$alkyl-$NR^xR^y$ (e.g. —$CH_2NH_2$, —$CH_2NHCH_3$, —$CH_2N(CH_3)_2$, or —$CH_2$—NH-cyclopropyl), —$(CR^xR^y)_p$—$CONR^xR^y$(e.g. —(CO)$NHCH_3$, —(CO)$NHCH_2CH_3$, —(CO)$NHCH_2CH_2NH_2$ or —(CO)$NH(CH(CH_3)_2)$, —$(CH_2)_j$—O—$C_{1-6}$alkyl (e.g. —$CH_2OCH_3$, —$CH_2OCH_2CH_3$ or —$CH_2OCD_3$), —$(CR^xR^y)_p$—$NR^xCOR^y$ (e.g. —$CH_2NHCOCH_3$), —$(CR^xR^y)_p$—O—$CH_2$—$CONR^xR^y$(e.g. —$CH_2$—O—$CH_2CON(CH_3)_2$), —$(CH_2)_j$—O-(hydroxy$C_{1-6}$alkyl) (e.g. —$CH_2$—O—$CH_2CH_2OH$,), —C(=O)NH-heterocyclic group with 3 to 7 ring members, $C_{3-8}$cycloalkyl, heterocyclic group with 3 to 7 ring members (e.g. oxanyl), or —$CH_2$-heterocyclic group with 3 to 7 ring members wherein the cycloalkyl or heterocyclic group comprises one or more (e.g. 1, 2, or 3) heteroatoms selected from N, O, S and oxidised forms and may be optionally substituted by one or more $R^z$ groups (for example selected from $C_{1-6}$alkyl (e.g. methyl), $C_{1-6}$alkoxy (e.g. methoxy) and —C(=O)$C_{1-6}$alkyl (e.g. —C(=O)$CH_3$)). In one embodiment, $R^6$ is methyl or ethyl and $R^7$ is $C_{1-6}$alkyl (e.g. methyl), hydroxy$C_{1-6}$alkyl, —$C_{1-6}$alkyl-$NR^xR^y$, —$(CR^xR^y)_p$—$CONR^xR^y$, —$(CH_2)_j$—O—$C_{1-6}$alkyl, —$(CR^xR^y)_p$—$NR^xCOR^y$, —$(CR^xR^y)_p$—O—$CH_2$—$CONR^xR^y$, —$(CH_2)_j$—O-(hydroxy$C_{1-6}$alkyl), heterocyclic group with 3 to 7 ring members (e.g. oxanyl), or —$CH_2$-heterocyclic group with 3 to 7 ring members wherein the heterocyclic group comprises one or more (e.g. 1, 2, or 3) heteroatoms selected from N, O, S and oxidised forms and may be optionally substituted by one or more $R^z$ groups selected from $C_{1-6}$alkyl (e.g. methyl), $C_{1-6}$alkoxy (e.g. methoxy) and —C(=O)$C_{1-6}$alkyl (e.g. —C(=O)$CH_3$).

In one embodiment, $R^6$ is selected from hydrogen, $C_{1-6}$alkyl (e.g. —$CH_3$, —$CH_2CH_3$ or —$CH_2CH_2CH_3$), $C_{2-6}$alkenyl (e.g. —CH=$CH_2$) and halo$C_{1-6}$alkyl (e.g. —$CF_3$).

In one embodiment, $R^6$ is selected from hydrogen or $C_{1-6}$alkyl (e.g. —$CH_3$ or —$CH_2CH_3$).

In one embodiment, $R^7$ is $C_{1-6}$alkyl (e.g. —$CH_3$ or —$CH_2CH_3$), hydroxy$C_{1-6}$alkyl (e.g. —$CH_2OH$), —$C_{1-6}$alkyl-$NR^xR^y$(e.g. —$CH_2N(CH_3)_2$), —$(CR^xR^y)_p$—$CONR^xR^y$ (e.g. —C(=O)$N(CH_3)_2$ or —C(=O)$NHCH_3$ or

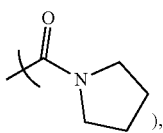),

—(CH$_2$)$_j$—O—C$_{1-6}$alkyl (e.g. —CH$_2$OCH$_3$), C$_{3-8}$cycloalkyl (e.g. cyclobutyl or cyclohexyl), heterocyclic group with 3 to 7 ring members e.g.
(point of attachment represented by dashed bond):

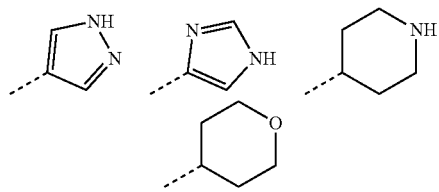

or —CH$_2$-heterocyclic group with 3 to 7 ring members e.g.
(point of attachment represented by dashed bond)

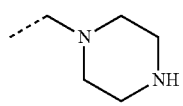

wherein when the moiety R$^7$ comprises a heterocyclic or cycloalkyl group, the heterocyclic group may be optionally substituted by one or more R$^z$ groups selected from C$_{1-6}$alkyl (e.g. methyl), hydroxy, halogen (e.g. fluoro), —C(═O)C$_{1-6}$alkyl (e.g. —C(═O)C(CH$_3$)$_3$), —(CH$_2$)$_r$—CO$_2$H (e.g. —CH$_2$COOH or CH$_2$CH$_2$COOH or —(CH$_2$)$_r$—CO$_2$C$_{1-6}$alkyl (e.g. CH$_2$CH$_2$COOCH$_3$).

In one embodiment, R$^7$ is C$_{1-6}$alkyl (e.g. methyl or ethyl), haloC$_{1-6}$alkyl (e.g. trifluoromethyl), C$_{2-6}$alkenyl (e.g. C$_2$alkenyl), hydroxyC$_{1-6}$alkyl (e.g. —CH$_2$OH, —CH$_2$CH$_2$OH), —C$_{1-6}$alkyl-NR$^x$R$^y$ (e.g. —CH$_2$NH$_2$, —CH$_2$NHCH$_3$, —CH$_2$N(CH$_3$)$_2$, or —CH$_2$—NH-cyclopropyl), —(CR$^x$R$^y$)$_p$—CONR$^x$R$^y$(e.g. —(CO)NHCH$_3$, —(CO)NHCH$_2$CH$_2$NH$_2$ or —(CO)NH(CH(CH$_3$)$_2$), —(CH$_2$)$_j$—O—C$_{1-6}$alkyl (e.g. —CH$_2$OCH$_3$, —CH$_2$OCH$_2$CH$_3$ or —CH$_2$OCD$_3$), —(CR$^x$R$^y$)$_p$—NR$^x$COR$^y$ (e.g. —CH$_2$NHCOCH$_3$), —(CR$^x$R$^y$)$_p$—O—CH$_2$—CONR$^x$R$^y$(e.g. —CH$_2$—O—CH$_2$CON(CH$_3$)$_2$), —(CH$_2$)$_j$—O-(hydroxyC$_{1-6}$alkyl) (e.g. —CH$_2$—O—CH$_2$CH$_2$OH,), —C(═O)NH-heterocyclic group with 3 to 7 ring members, C$_{3-6}$cycloalkyl, heterocyclic group with 3 to 7 ring members (e.g. oxanyl), or —CH$_2$-heterocyclic group with 3 to 7 ring members wherein the cycloalkyl or heterocyclic group comprises one or more (e.g. 1, 2, or 3) heteroatoms selected from N, O, S and oxidised forms and may be optionally substituted by one or more R$^z$ groups (for example selected from C$_{1-6}$alkyl (e.g. methyl), C$_{1-6}$alkoxy (e.g. methoxy) and —C(═O)C$_{1-6}$alkyl (e.g. —C(═O)CH$_3$)). In one embodiment, R$^6$ is methyl or ethyl and R$^7$ is C$_{1-6}$alkyl (e.g. methyl), hydroxyC$_{1-6}$alkyl, —C$_{1-6}$alkyl-NR$^x$R$^y$, —(CR$^x$R$^y$)$_p$—CONR$^x$R$^y$, —(CH$_2$)$_j$—O—C$_{1-6}$alkyl, —(CR$^x$R$^y$)$_p$—NR$^x$COR$^y$, —(CR$^x$R$^y$)$_p$—O—CH$_2$—CONR$^x$R$^y$, —(CH$_2$)$_j$—O-(hydroxyC$_{1-6}$alkyl), heterocyclic group with 3 to 7 ring members (e.g. oxanyl), or —CH$_2$-heterocyclic group with 3 to 7 ring members wherein the heterocyclic group comprises one or more (e.g. 1, 2, or 3) heteroatoms selected from N, O, S and oxidised forms and may be optionally substituted by one or more R$^z$ groups selected from C$_{1-6}$alkyl (e.g. methyl), C$_{1-6}$alkoxy (e.g. methoxy) and —C(═O)C$_{1-6}$alkyl (e.g. —C(═O)CH$_3$).

In one embodiment, R$^6$ is selected from hydrogen or C$_{1-6}$alkyl (e.g. —CH$_3$ or —CH$_2$CH$_3$).

In one embodiment, R$^7$ is C$_{1-6}$alkyl (e.g. —CH$_3$ or —CH$_2$CH$_3$), hydroxyC$_{1-6}$alkyl (e.g. —CH$_2$OH o), —C$_{1-6}$alkyl-NR$^x$R$^y$ (e.g. —CH$_2$N(CH$_3$)$_2$), —(CR$^x$R$^y$)$_p$—CONR$^x$R$^y$(e.g. —C(═O)N(CH$_3$)$_2$ or

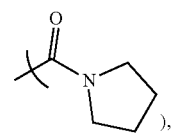), (CH$_2$)$_j$—O—C$_{1-6}$alkyl (e.g. —CH$_2$OCH$_3$), heterocyclic group with 3 to 7 ring members e.g.
(point of attachment represented by dashed bond):

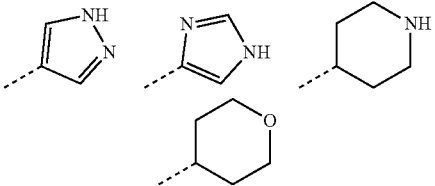

or —CH$_2$-heterocyclic group with 3 to 7 ring members e.g.
(point of attachment represented by dashed bond)

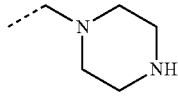

wherein when the moiety R$^7$ comprises a heterocyclic group, the heterocyclic group may be optionally substituted by one or more R$^z$ groups selected from C$_{1-6}$alkyl (e.g. methyl).

In one embodiment of formula (1°) R$^7$ is a heterocyclic group with 3 to 7 ring members optionally substituted by one or more R$^z$ groups e.g.
(point of attachment represented by dashed bond)

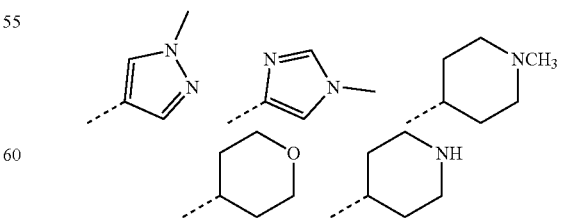

In one embodiment of formula (1°) R$^7$ is a heterocyclic group with 3 to 7 ring members optionally substituted by one or more R$^z$ groups e.g.

(point of attachment represented by dashed bond)

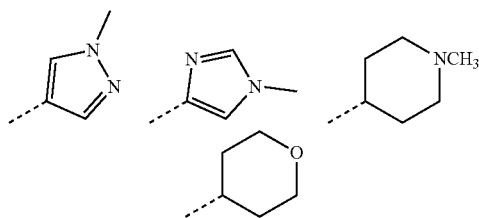

In one embodiment, $R^7$ is a —$CH_2$-heterocyclic group with 3 to 7 ring members optionally substituted by by one or more $R^z$ groups e.g.
(point of attachment represented by dashed bond)

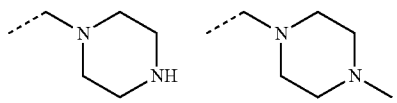

In one embodiment, $R^7$ is selected from:
(point of attachment represented by dashed bond):

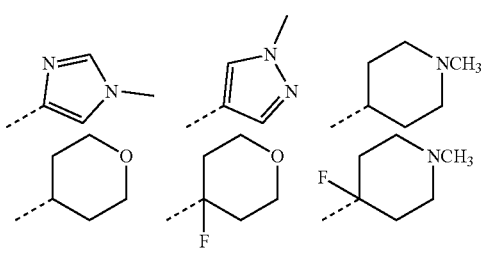

In one embodiment, $R^7$ is selected from:
(point of attachment represented by dashed bond):

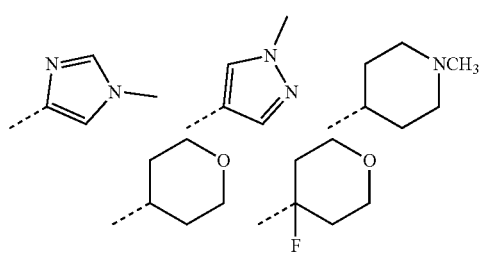

In one embodiment, $R^6$ is hydrogen or $C_{1-6}$alkyl. In one embodiment, $R^6$ is $C_{1-6}$alkyl. In one embodiment, $R^6$ is methyl or ethyl. In one embodiment, $R^6$ is ethyl.

In one embodiment, $R^6$ is $C_{1-6}$alkyl (such as methyl or ethyl e.g. methyl) and $R^7$ is selected from hydroxy$C_{1-6}$alkyl and —$(CH_2)$—O—$C_{1-6}$alkyl, In one embodiment, $R^6$ is methyl and $R^7$ is selected from methyl, —$CH_2$—OH and —$CH_2$—$OCH_3$. In one embodiment $R^6$ is methyl and $R^7$ is methyl, ethyl, or propyl.

In one embodiment, $R^6$ is methyl and $R^7$ is methyl.

In one embodiment, $R^6$ is $C_{1-6}$alkyl or halo$C_{1-6}$alkyl (e.g. methyl, -monofluoromethyl, trifluoromethyl or ethyl).

In one embodiment, $R^6$ is $C_{3-8}$cycloalkyl such as $C_{3-6}$cycloalkyl (e.g. cyclopropyl).

In one embodiment $R^6$ is $C_{1-6}$alkyl (such as methyl or ethyl e.g. ethyl) and $R^7$ is selected from:
(point of attachment represented by dashed bond or bond terminus marked "*")

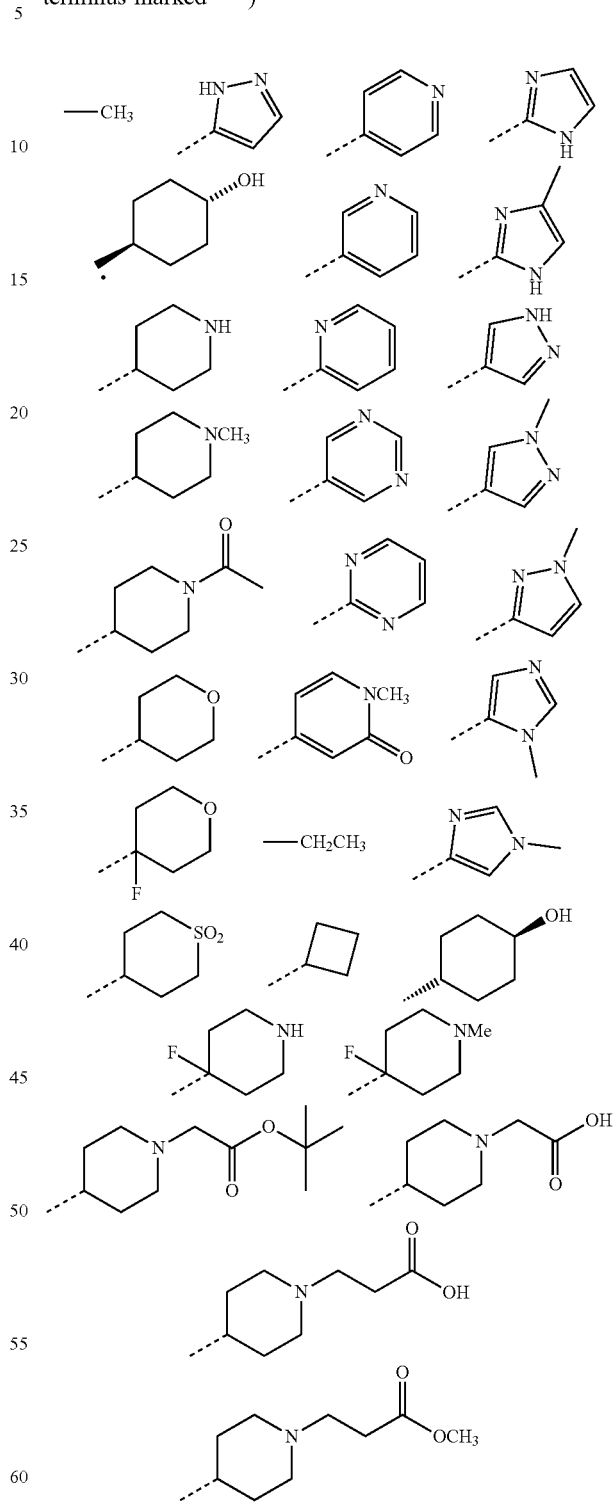

In one embodiment $R^6$ is $C_{1-6}$alkyl (such as methyl or ethyl e.g. ethyl) and $R^7$ is selected from:
(point of attachment represented by dashed bond or bond terminus marked "*")

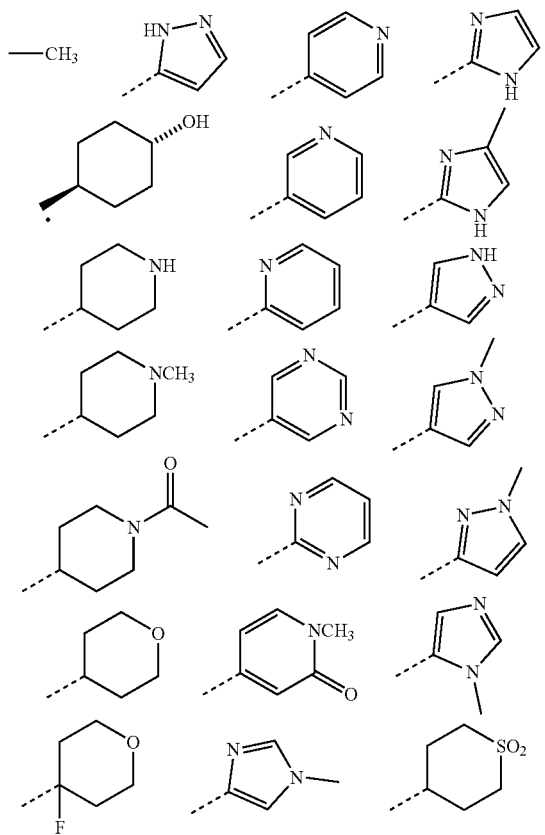

In particular, R⁷ is:
(point of attachment represented by dashed bond):

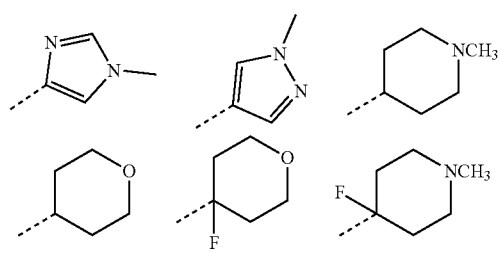

In one embodiment, $R^6$ is $C_{1-6}$alkyl (such as methyl or ethyl e.g. methyl) and $R^7$ is oxanyl, and the compound of formula (1°) is a compound of formula (Iw):

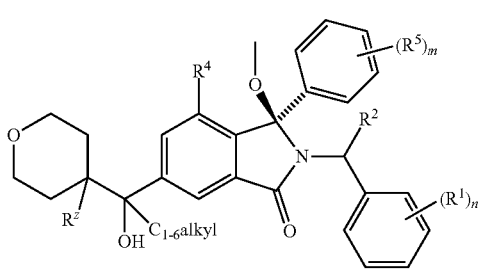

(Iw)

In one embodiment of formula (Iw) $R_z$ is hydrogen or fluorine.

In one embodiment, $R^7$ is imidazolyl and the compound of formula (1°) is a compound of formula (Ix) or a tautomer or a solvate or a pharmaceutically acceptable salt thereof:

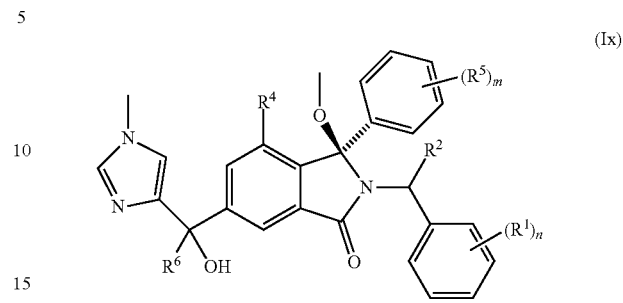

(Ix)

In one embodiment, $R^7$ is N-methyl piperidinyl and the compound of formula (1°) is a compound of formula (Ix') or a tautomer or a solvate or a pharmaceutically acceptable salt thereof:

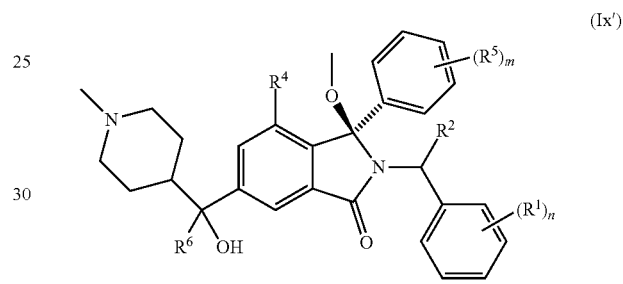

(Ix')

In one embodiment, $R^7$ is 4-fluoro-1-methylpiperidin-4-yl and the compound of formula (1°) is a compound of formula (Ix") or a tautomer or a solvate or a pharmaceutically acceptable salt thereof:

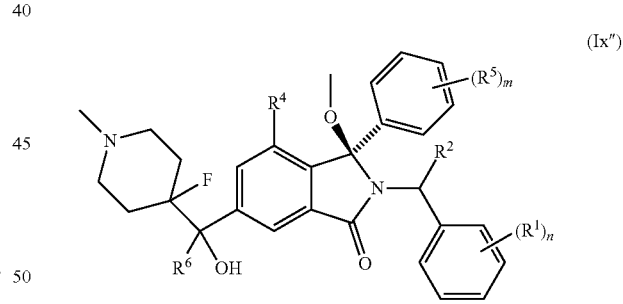

(Ix")

In one embodiment, $R^7$ is pyrazolyl optionally substituted by one or more $R^z$ groups (e.g. methyl). In one embodiment, $R^7$ is N-methylpyrazol-3-yl or N-methylpyrazol-4-yl.

In one embodiment, $R^7$ is selected from methyl, oxanyl, pyrazolyl, imidazolyl, piperidinyl, and cyclohexyl wherein said cycloalkyl and heterocyclic groups are optionally substituted by one or more $R^z$ groups (e.g. methyl, fluorine, or hydroxyl).

In one embodiment, $R^7$ is selected from piperidinyl optionally substituted by one or more $R^z$ groups (e.g. methyl, fluorine, or hydroxyl, in particular methyl and fluorine).

In one embodiment, the compound of formula (1°) is a compound of formula (Ix) and $R^6$ is $C_{1-4}$alkyl.

In one embodiment, $R^6$ is $C_{1-6}$alkyl (e.g. —CH₃, —CH₂CH₃ or —CH₂CH₂CH₃ such as methyl or ethyl e.g.

ethyl) and R⁷ is a heterocyclic group with 3 to 7 ring members optionally substituted by one or more R^z groups.

In one embodiment, R⁶ is $C_{1-6}$alkyl (e.g. —CH₃, —CH₂CH₃ or —CH₂CH₂CH₃ such as methyl or ethyl e.g. ethyl) and R⁷ is imidazolyl optionally substituted by one or more R^z groups (e.g. methyl imidazolyl).

In one embodiment, R⁶ is $C_{1-6}$alkyl (e.g. —CH₃, —CH₂CH₃ or —CH₂CH₂CH₃ such as methyl or ethyl e.g. ethyl) and R⁷ is piperidinyl optionally substituted by one or more R^z groups (e.g. methyl piperidinyl).

In one embodiment, R⁶ is $C_{1-6}$alkyl (e.g. —CH₃, —CH₂CH₃ or —CH₂CH₂CH₃ such as methyl or ethyl e.g. ethyl) and R⁷ is $C_{1-4}$alkyl, hydroxyl$C_{1-4}$alkyl, methoxy$C_{1-4}$alkyl, a heterocyclic group with 5 or 6 ring members or $C_{3-6}$cycloalkyl, wherein the heterocyclic group or $C_{3-6}$cycloalkyl group is optionally substituted by one or more R^z (e.g. methyl, halogen (such as fluorine), C(=O)Me, or —OH).

In one embodiment R⁶ is $C_{1-6}$alkyl (e.g. —CH₃, —CH₂CH₃ or —CH₂CH₂CH₃ such as methyl or ethyl e.g. ethyl) and R⁷ is methyl, ethyl, hydroxylmethyl, hydroxyethyl, methoxymethyl, piperidinyl, oxanyl, imidazolyl, pyrazolyl, cyclobutyl, cyclohexyl, optionally substituted by one or more R^z (e.g. methyl, halogen (such as fluorine), C(=O)Me, or —OH).

In one embodiment, R⁶ and R⁷ are both the same. In one embodiment, R⁶ and R⁷ are both methyl, and the compound of formula (1°) is a compound of formula (Iy) or a tautomer or a solvate or a pharmaceutically acceptable salt thereof:

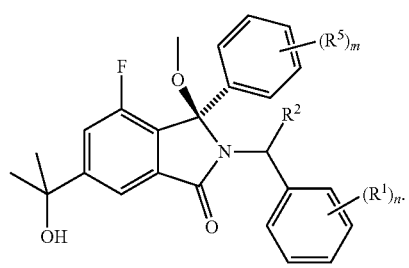

(Iy)

In one embodiment the group —CR⁶R⁷OH is other than —C(CH₃)₂OH.

In one embodiment, R⁷ is selected from the group consisting of:
(point of attachment represented by dashed bond)

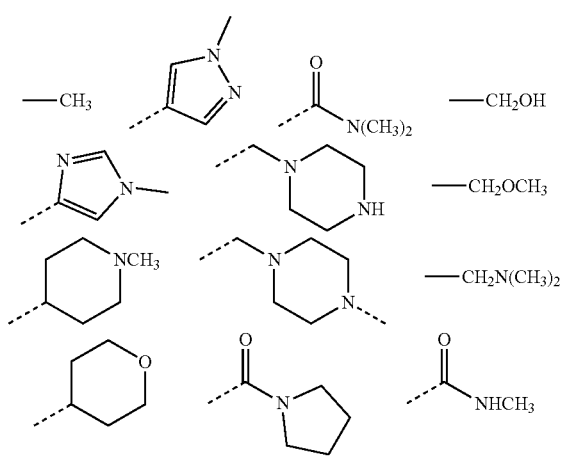

-continued

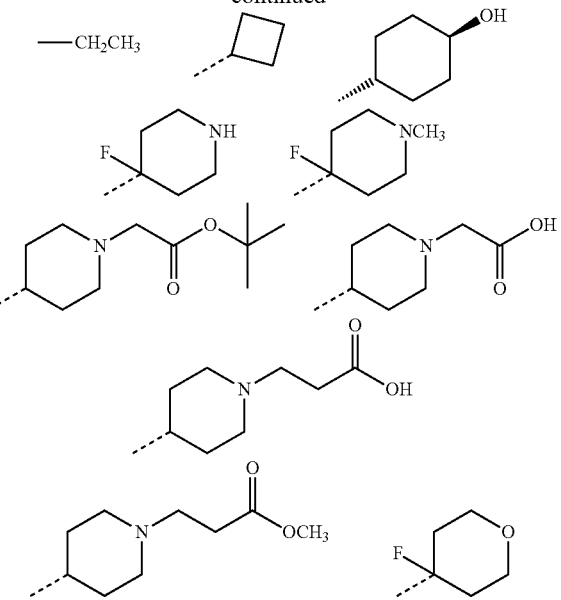

In one embodiment, R⁷ is selected from the group consisting of:
(point of attachment represented by dashed bond)

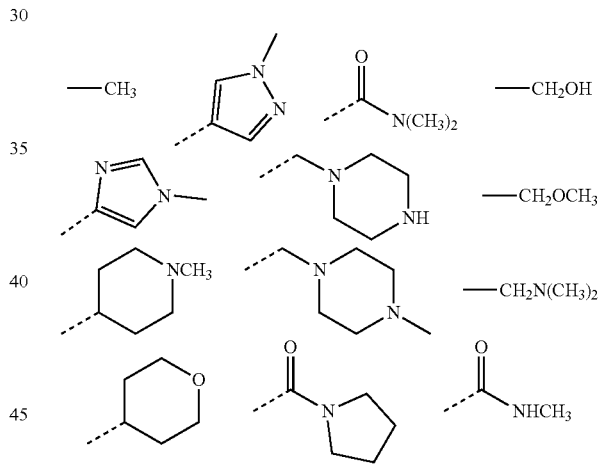

In one embodiment R^z is independently selected from halogen, nitro, nitrile, $C_{1-6}$alkyl, halo$C_{1-6}$alkyl, $C_{2-6}$alkenyl, $C_{2-6}$alkynyl, =O, hydroxy, hydroxy$C_{1-6}$alkyl, $C_{1-6}$alkoxy, —(CH₂)$_k$—O—$C_{1-6}$alkyl, hydroxy$C_{1-6}$alkoxy, —C(=O)$C_{1-6}$alkyl, —C(=O)$C_{1-6}$alkyl-OH, —C(=O)$C_{1-6}$alkyl-N(H)$_e$($C_{1-4}$alkyl)$_{2-e}$, —C(=O)N(H)$_e$($C_{1-4}$alkyl)$_{2-e}$, —(CH₂)$_k$—CO₂$C_{1-6}$alkyl, —(CH₂)$_r$—CO₂H, —NH($C_{1-4}$alkyl), —N($C_{1-4}$alkyl)₂, —$C_{1-6}$alkyl-N(H)$_e$($C_{1-4}$alkyl)$_{2-e}$, heterocyclyl group with 3 to 6 ring members, heterocyclyl group with 3 to 6 ring members substituted by —C(=O)$C_{1-4}$alkyl, heterocyclyl group with 3 to 6 ring members substituted by —C(=O)O$C_{1-4}$alkyl, heterocyclyl group with 3 to 6 ring members substituted by —C(=O)N(H)$_e$($C_{1-4}$alkyl)$_{2-e}$, —C(=O)heterocyclyl group with 3 to 6 ring members, $C_{3-8}$cycloalkyl and $C_{3-8}$cycloalkenyl.

In another embodiment R^z is independently selected from halogen, nitro, nitrile, $C_{1-6}$alkyl, halo$C_{1-6}$alkyl, $C_{2-6}$alkenyl, $C_{2-6}$alkynyl, =O, hydroxy, hydroxy$C_{1-6}$alkyl, $C_{1-6}$alkoxy, —(CH₂)$_k$—O—$C_{1-6}$alkyl, hydroxy$C_{1-6}$alkoxy, —C(=O)

$C_{1-6}$alkyl, —C(=O)$C_{1-6}$alkyl-OH, —C(=O)$C_{1-6}$alkyl-N(H)$_e$($C_{1-4}$alkyl)$_{2-e}$, —C(=O)N(H)$_e$($C_{1-4}$alkyl)$_{2-e}$, —(CH$_2$)$_r$CO$_2$$C_{1-6}$alkyl, —(CH$_2$)$_r$—CO$_2$H, —$C_{1-6}$alkyl-N(H)$_e$($C_{1-4}$alkyl)$_{2-e}$, heterocyclyl group with 3 to 6 ring members, heterocyclyl group with 3 to 6 ring members substituted by —C(=O)$C_{1-4}$alkyl, heterocyclyl group with 3 to 6 ring members substituted by —C(=O)O$C_{1-4}$alkyl, heterocyclyl group with 3 to 6 ring members substituted by —C(=O)N(H)$_e$($C_{1-4}$alkyl)$_{2-e}$, —C(=O)heterocyclyl group with 3 to 6 ring members, $C_{3-8}$cycloalkyl and $C_{3-8}$cycloalkenyl.

In another embodiment when $R^7$ contains a saturated heterocyclic group then $R^z$ is independently selected from halogen, nitro, nitrile, $C_{1-6}$alkyl, halo$C_{1-6}$alkyl, $C_{2-6}$alkenyl, $C_{2-6}$alkynyl, =O, hydroxy, hydroxy$C_{1-6}$alkyl, $C_{1-6}$alkoxy, —(CH$_2$)$_k$—O—$C_{1-6}$alkyl, hydroxy$C_{1-6}$alkoxy, —C(=O)$C_{1-6}$alkyl, —C(=O)$C_{1-6}$alkyl-OH, —C(=O)$C_{1-6}$alkyl-N(H)$_e$($C_{1-4}$alkyl)$_{2-e}$, —C(=O)N(H)$_e$($C_{1-4}$alkyl)$_{2-e}$, —(CH$_2$)$_r$CO$_2$$C_{1-6}$alkyl, —(CH$_2$)$_r$—CO$_2$H, —N(H)$_e$($C_{1-4}$alkyl)$_{2-e}$, —$C_{1-6}$alkyl-N(H)$_e$($C_{1-4}$alkyl)$_{2-e}$, heterocyclyl group with 3 to 6 ring members, heterocyclyl group with 3 to 6 ring members substituted by —C(=O)$C_{1-4}$alkyl, heterocyclyl group with 3 to 6 ring members substituted by —C(=O)O$C_{1-4}$alkyl, heterocyclyl group with 3 to 6 ring members substituted by —C(=O)N(H)$_e$($C_{1-4}$alkyl)$_{2-e}$, —C(=O)heterocyclyl group with 3 to 6 ring members, $C_{3-8}$cycloalkyl and $C_{3-8}$cycloalkenyl.

Subformulae

In one embodiment, the compound of formulae (1°) is a compound of formulae (II) or a tautomer or a solvate or a pharmaceutically acceptable salt thereof:

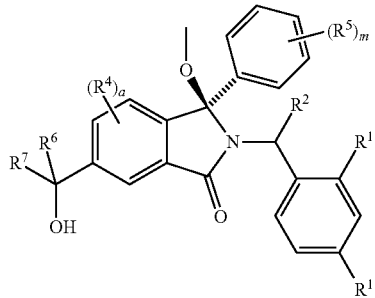

(II)

wherein $R^1$, $R^2$, $R^4$, $R^5$, $R^6$, $R^7$, a, and m are as defined herein.

In one embodiment, $R^1$ is chloro, nitrile, methyl or methoxy. In one embodiment, $R^1$ is hydroxy or hydroxy$C_{1-4}$alkyl (e.g. hydroxyl).

In one embodiment, $R^1$ is O$_{0,1}$(CR$^x$R$^y$)$_v$COOH (e.g. —COOH, —CH$_2$COOH, —OCH$_2$COOH or —C(CH$_3$)$_2$COOH.

In another embodiment, $R^1$ is chloro or nitrile and the compound of formula (II) is a compound of formula (IIa) or (IIb) or a tautomer or a solvate or a pharmaceutically acceptable salt thereof:

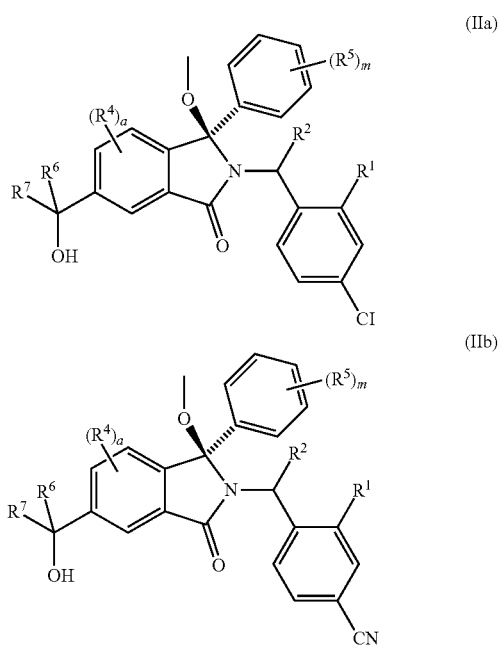

(IIa)

(IIb)

wherein $R^2$, $R^4$, $R^5$, $R^7$, and m are as defined herein. In one embodiment, $R^1$ is —SO$_2$—$R^x$. In particular, $R^x$ is —SO$_2$—$C_{1-4}$alkyl, for example —SO$_2$—CH$_3$ or —SO$_2$-heterocyclic group with 5 to 6 ring members (e.g. —SO$_2$-morpholinyl, typically —SO$_2$-(1-morpholinyl). In another embodiment In one embodiment, $R^1$ is hydroxy or hydroxy$C_{1-4}$alkyl (e.g. —CH$_2$OH or —OH).

In one embodiment, $R^6$ is methyl or ethyl, and the compound of formula (1°) is a compound of formula (IIIa) or (IIIb) or a tautomer or a solvate or a pharmaceutically acceptable salt thereof:

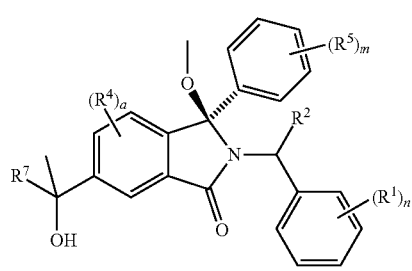

(IIIa)

(IIIb)

wherein $R^1$, $R^2$, $R^4$, $R^5$, $R^7$, a, and m are as defined herein.

In one embodiment, a is 1 and the compound of formula (1°) is a compound of formula (IVa) or a tautomer or a solvate or a pharmaceutically acceptable salt thereof:

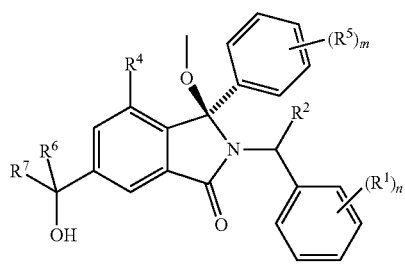

(IVa)

wherein $R^1$, $R^2$, $R^4$, $R^5$, $R^7$, a and m are as defined herein.

In one embodiment, and the compound of formula (1°) is a compound of formula (IVb) or a tautomer or a solvate or a pharmaceutically acceptable salt thereof:

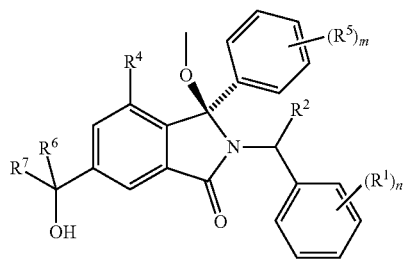

(IVb)

wherein $R^1$, $R^2$, $R^4$, $R^5$, $R^7$, a, and m are as defined herein.

In one embodiment, $R^4$ is F and the compound of formula (IVa) is a compound of formula (V) or a tautomer or a solvate or a pharmaceutically acceptable salt thereof:

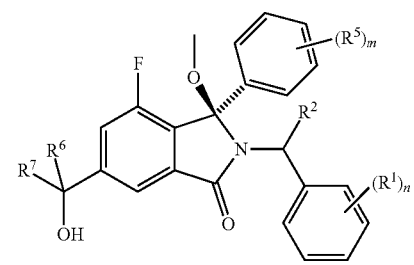

(V)

wherein $R^1$, $R^2$, $R^5$, $R^7$, and m are as defined herein.

In one embodiment, m is 1 and the substituent $R^4$ is at the 4-position of the phenyl group, and the compound of formula (1°) is a compound of formula (VI) or a tautomer or a solvate or a pharmaceutically acceptable salt thereof:

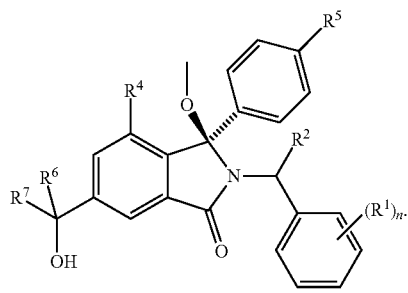

(VI)

In one embodiment, $R^5$ is chloro and the compound of formula (VI) is a compound of formula (VIa) or a tautomer or a solvate or a pharmaceutically acceptable salt thereof:

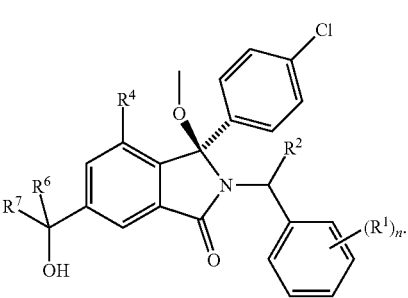

(VIa)

In another embodiment of the subformulae described hereinabove, $R^2$ is selected from hydrogen and —$(R^xR^y)_u$—$CO_2H$ (e.g. —COOH, —$CH_2COOH$, —$CH_2CH_2$—$CO_2H$, —$(CH(CH_3))$—$CO_2H$ and —$(C(CH_3)_2$—$CO_2H)$.

In another embodiment of the subformulae described hereinabove, $R^2$ is selected from —$(CH(CH_3))$—$CO_2H$ and —$(C(CH_3)_2$—$CO_2H)$.

In another embodiment, $R^2$ is selected from —$(CH(CH_3))$—$CO_2H$ and —$(C(CH_3)_2$—$CO_2H)$ (e.g. $CO_2H$ or —$(C(CH_3)_2$—$CO_2H$.

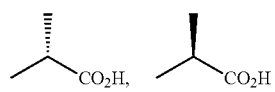

In one embodiment, the invention provides a process for preparing a compound of formula (1°) or a tautomer or a solvate or a pharmaceutically acceptable salt thereof wherein:

$R^1$ is independently selected from hydroxy, halogen, nitro, nitrile, $C_{1-4}$alkyl, halo$C_{1-4}$alkyl, hydroxy$C_{1-4}$alkyl, $C_{2-6}$alkenyl, $C_{1-4}$alkoxy, halo$C_{1-4}$alkoxy, and $C_{2-4}$alkynyl;

$R^2$ is selected from hydrogen, $C_{1-4}$ alkyl, $C_{2-6}$alkenyl, hydroxy$C_{1-4}$alkyl and —$CH_2CO_2H$;

$R^4$ and $R^5$ are independently selected from halogen, nitrile, $C_{1-4}$alkyl, halo$C_{1-4}$alkyl, $C_{1-4}$alkoxy and halo$C_{1-4}$alkoxy;

$R^6$ and $R^7$ are independently selected from hydrogen, $C_{1-6}$alkyl, halo$C_{1-6}$alkyl, $C_{2-6}$alkenyl, $C_{2-6}$alkynyl, hydroxy, hydroxy$C_{1-6}$alkyl, —$COOC_{1-6}$alkyl, heterocyclic group with 3 to 7 ring members, —$CH_2$-heterocyclic group with 3 to 7 ring members, —$CH_2$—O- heterocyclic group with 3 to 7 ring members, —CH$_2$—NH-heterocyclic group with 3 to 7 ring members, —CH$_2$—N(C$_{1-6}$alkyl)-heterocyclic group with 3 to 7 ring members, —C(=O)NH-heterocyclic group with 3 to 7 ring members, C$_{3-8}$cycloalkyl, —CH$_2$—C$_{3-8}$cycloalkyl, —CH$_2$—O—C$_{3-8}$cycloalkyl, and C$_{3-8}$cycloalkenyl, wherein said cycloalkyl, cycloalkenyl or heterocyclic groups may be optionally substituted by one or more R$^z$ groups, and wherein in each instance the heterocyclic group comprises one or more (e.g. 1, 2, or 3) heteroatoms selected from N, O, S and oxidised forms thereof;

R$^x$ and R$^y$ are independently selected from hydrogen, halogen, nitro, nitrile, C$_{1-6}$alkyl, haloC$_{1-6}$alkyl, C$_{2-6}$alkenyl, C$_{2-6}$alkynyl, hydroxy, hydroxyC$_{1-6}$alkyl, C$_{1-6}$alkoxy, —(CH$_2$)$_k$—O—C$_{1-6}$alkyl, hydroxyC$_{1-6}$alkoxy, —COOC$_{1-6}$alkyl, —N(H)$_e$(C$_{1-4}$alkyl)$_{2-e}$, —C$_{1-6}$ alkyl-N(H)$_e$(C$_{1-4}$alkyl)$_{2-e}$, —(CH$_2$)$_k$—C(=O)N(H)$_e$(C$_{1-4}$alkyl)$_{2-e}$ C$_{3-8}$cycloalkyl and C$_{3-8}$cycloalkenyl;

R$^z$ is independently selected from halogen, nitro, nitrile, C$_{1-6}$alkyl, haloC$_{1-6}$alkyl, C$_{2-6}$alkenyl, C$_{2-6}$alkynyl, =O, hydroxy, hydroxyC$_{1-6}$alkyl, C$_{1-6}$alkoxy, —(CH$_2$)$_k$—O—C$_{1-6}$alkyl, hydroxyC$_{1-6}$alkoxy, —C(=O)C$_{1-6}$alkyl, —C(=O)C$_{1-6}$alkyl-OH, —C(=O)C$_{1-6}$alkyl-N(H)$_e$ (C$_{1-4}$alkyl)$_{2-e}$, —C(=O)N(H)$_e$(C$_{1-4}$alkyl)$_{2-e}$, —(CH$_2$)$_r$CO$_2$C$_{1-6}$alkyl, —(CH$_2$)$_r$CO$_2$H, —N(H)$_e$(C$_{1-4}$alkyl)$_{2-e}$, —C$_{1-6}$alkyl-N(H)$_e$(C$_{1-4}$alkyl)$_{2-e}$, heterocyclyl group with 3 to 6 ring members, heterocyclyl group with 3 to 6 ring members substituted by —C(=O)C$_{1-4}$alkyl, heterocyclyl group with 3 to 6 ring members substituted by —C(=O)OC$_{1-4}$alkyl, heterocyclyl group with 3 to 6 ring members substituted by —C(=O)N(H)$_e$(C$_{1-4}$alkyl)$_{2-e}$, —C(=O)heterocyclyl group with 3 to 6 ring members, C$_{3-8}$cycloalkyl and C$_{3-8}$cycloalkenyl;

n, e, r and j are independently selected from 0, 1 and 2;
k and m are independently selected from 1 and 2; and
v and a are independently selected from 0 and 1.

In one embodiment, the invention provides a process for preparing a compound of formula (1°) or a tautomer or a solvate or a pharmaceutically acceptable salt thereof, wherein:

R$^1$ is independently selected from hydroxy, halogen, nitro, nitrile and C$_{1-4}$alkyl;

R$^2$ is selected from hydrogen, C$_{1-4}$ alkyl, C$_{2-6}$alkenyl, hydroxyC$_{1-4}$alkyl and —CH$_2$CO$_2$H;

R$^4$ and R$^5$ are independently selected from halogen, nitrile and C$_{1-4}$ alkyl;

R$^6$ is selected from hydrogen, C$_{1-6}$alkyl, haloC$_{1-6}$alkyl, C$_{2-6}$alkenyl, and C$_{2-6}$alkynyl;

R$^7$ is selected from hydrogen, C$_{1-6}$alkyl, haloC$_{1-6}$alkyl, C$_{2-6}$alkenyl, C$_{2-6}$alkynyl, hydroxy, hydroxyC$_{1-6}$alkyl, —COOC$_{1-6}$alkyl, heterocyclic group with 3 to 7 ring members, —CH$_2$-heterocyclic group with 3 to 7 ring members, —CH$_2$—O-heterocyclic group with 3 to 7 ring members, —CH$_2$—NH-heterocyclic group with 3 to 7 ring members, —CH$_2$—N(C$_{1-6}$alkyl)-heterocyclic group with 3 to 7 ring members, —C(=O)NH-heterocyclic group with 3 to 7 ring members, C$_{3-8}$cycloalkyl, —CH$_2$—C$_{3-8}$cycloalkyl, —CH$_2$—O—C$_{3-8}$cycloalkyl, and C$_{3-8}$cycloalkenyl, wherein said cycloalkyl, cycloalkenyl or heterocyclic groups may be optionally substituted by one or more R$^z$ groups, and wherein in each instance the heterocyclic group comprises one or more (e.g. 1, 2, or 3) heteroatoms selected from N, O, S and oxidised forms thereof;

R$^x$ and R$^y$ are independently selected from hydrogen, halogen, nitro, nitrile, C$_{1-6}$alkyl, haloC$_{1-6}$alkyl, C$_{2-6}$alkenyl, C$_{2-6}$alkynyl, hydroxy, hydroxyC$_{1-6}$alkyl, C$_{1-6}$alkoxy, —(CH$_2$)$_k$—O—C$_{1-6}$alkyl, hydroxyC$_{1-6}$alkoxy, —COOC$_{1-6}$alkyl, —N(H)$_e$(C$_{1-4}$alkyl)$_{2-e}$, —C$_{1-6}$ alkyl-N(H)$_e$(C$_{1-4}$alkyl)$_{2-e}$, —(CH$_2$)$_k$—C(=O)N(H)$_e$(C$_{1-4}$alkyl)$_{2-e}$, C$_{3-8}$cycloalkyl and C$_{3-8}$cycloalkenyl;

R$^z$ is independently selected from halogen, nitro, nitrile, C$_{1-6}$alkyl, haloC$_{1-6}$alkyl, C$_{2-6}$alkenyl, C$_{2-6}$alkynyl, =O, hydroxy, hydroxyC$_{1-6}$alkyl, C$_{1-6}$alkoxy, —(CH$_2$)$_k$—O—C$_{1-6}$alkyl, hydroxyC$_{1-6}$alkoxy, —C(=O)C$_{1-6}$alkyl, —C(=O)C$_{1-6}$alkyl-OH, —C(=O)C$_{1-6}$alkyl-N(H)$_e$ (C$_{1-4}$alkyl)$_{2-e}$, —C(=O)N(H)$_e$(C$_{1-4}$alkyl)$_{2-e}$, —(CH$_2$)$_r$CO$_2$C$_{1-6}$alkyl, —(CH$_2$)$_r$CO$_2$H, —N(H)$_e$(C$_{1-4}$alkyl)$_{2-e}$, —C$_{1-6}$alkyl-N(H)$_e$(C$_{1-4}$alkyl)$_{2-e}$, heterocyclyl group with 3 to 6 ring members, heterocyclyl group with 3 to 6 ring members substituted by —C(=O)C$_{1-4}$alkyl, heterocyclyl group with 3 to 6 ring members substituted by —C(=O)OC$_{1-4}$alkyl, heterocyclyl group with 3 to 6 ring members substituted by —C(=O)N(H)$_e$(C$_{1-4}$alkyl)$_{2-e}$, —C(=O)heterocyclyl group with 3 to 6 ring members, C$_{3-8}$cycloalkyl and C$_{3-8}$cycloalkenyl;

n, e, r and j are independently selected from 0, 1 and 2;
k and m are independently selected from 1 and 2; and
v and a are independently selected from 0 and 1.

In one embodiment, the invention provides a process for preparing a compound of formula (1°) or a tautomer or a solvate or a pharmaceutically acceptable salt thereof, wherein:

R$^1$ is independently selected from hydroxy, halogen, nitro, nitrile and C$_{1-4}$alkyl;

R$^2$ is selected from hydrogen, C$_{1-4}$ alkyl, C$_{2-6}$alkenyl, hydroxyC$_{1-4}$alkyl and —CH$_2$CO$_2$H;

R$^4$ and R$^5$ are independently selected from halogen, nitrile and C$_{1-4}$ alkyl;

R$^5$ is selected from hydrogen and C$_{1-6}$alkyl;

R$^7$ is selected from heterocyclic group with 3 to 7 ring members, —CH$_2$-heterocyclic group with 3 to 7 ring members, C$_{3-8}$cycloalkyl, and —CH$_2$—C$_{3-8}$cycloalkyl, wherein said cycloalkyl or heterocyclic groups may be optionally substituted by one or more R$^z$ groups, and wherein in each instance the heterocyclic group comprises one or more (e.g. 1, 2, or 3) heteroatoms selected from N, O, S and oxidised forms thereof;

R$^x$ and R$^y$ are independently selected from hydrogen and C$_{1-6}$alkyl;

R$^z$ is independently selected from halogen, nitro, nitrile, C$_{1-6}$alkyl, haloC$_{1-6}$alkyl, C$_{2-6}$alkenyl, hydroxy, hydroxyC$_{1-6}$alkyl, C$_{1-6}$alkoxy, —C(=O)C$_{1-6}$alkyl, and —N(H)$_e$(C$_{1-4}$alkyl)$_{2-e}$;

n and e are independently selected from 0, 1 and 2
m is selected from 1 and 2; and
a is selected from 0 and 1.

In one embodiment, the invention provides a process for preparing a process for preparing a compound of formula (1°) or a tautomer or a solvate or a pharmaceutically acceptable salt thereof, wherein:

R$^1$ is independently selected from halogen, hydroxy and nitrile;

R$^2$ is selected from hydrogen, C$_{1-4}$ alkyl and —CH$_2$CO$_2$H;

R$^4$ and R$^5$ are independently selected from halogen;

R$^6$ is selected from hydrogen and C$_{1-6}$alkyl;

R$^7$ is selected from heterocyclic group with 3 to 7 ring members, —CH$_2$-heterocyclic group with 3 to 7 ring members, $C_{3-8}$cycloalkyl, and —$CH_2$—$C_{3-8}$cycloalkyl, wherein said cycloalkyl, cycloalkenyl or heterocyclic groups may be optionally substituted by one or more $R^z$ groups, and wherein in each instance the heterocyclic group comprises one or more (e.g. 1, 2, or 3) heteroatoms selected from N, O, S and oxidised forms thereof;

$R^x$ and $R^y$ are independently selected from hydrogen and $C_{1-6}$alkyl;

$R^z$ is independently selected from halogen, nitro, nitrile, and $C_{1-6}$alkyl;

n is 1 and m is 1; and a is selected from 0 and 1.

In one embodiment, the invention provides a process for preparing a compound of formula (1°) or a tautomer or a solvate or a pharmaceutically acceptable salt thereof, wherein:

$R^1$ is independently selected from halogen, hydroxy and nitrile;

$R^2$ is selected from hydrogen, $C_{1-4}$ alkyl and —$CH_2CO_2H$;

$R^4$ and $R^5$ are independently selected from halogen;

$R^6$ is selected from hydrogen and $C_{1-6}$alkyl;

$R^7$ is a heterocyclic group with 3 to 7 ring members optionally substituted by one or more $R^z$ groups;

$R^x$ and $R^y$ are independently selected from hydrogen and $C_{1-6}$alkyl;

$R^z$ is independently selected from halogen and $C_{1-6}$alkyl; and n is, 1 and m is 1; and a is 1.

In one embodiment, the invention provides a process for preparing a compound of formula (1°) or a tautomer or a solvate or a pharmaceutically acceptable salt thereof, wherein:

$R^1$ is halogen (e.g. Cl), $C_{1-4}$alkynyl (e.g. —C≡CH), nitrile, hydroxy$C_{1-4}$alkyl (e.g. $CH_2OH$), —$O_{0,1}$(CR$^x$R$^y$)$_v$COOH (e.g. —COOH, —$CH_2$COOH, —OCH$_2$COOH or —C(CH$_3$)$_2$COOH, —S(O)$_d$—C$_{1-4}$alkyl (e.g. SCH$_3$, SOCH$_3$, or SO$_2$CH$_3$), —SO$_2$-(1-morpholinyl) or —P(=O)(R$^x$)$_2$, (e.g. —P(=O)(CH$_3$)$_2$);

n is 1 or 2;

$R^2$ is hydrogen, $C_{1-4}$ alkyl (e.g. —CH$_3$), hydroxy$C_{1-4}$alkyl (e.g. CH$_2$OH) or —(CH$_2$)$_u$COOH (e.g. —CH$_2$COOH, —CH$_2$CH$_2$—CO$_2$H or —(CH(CH$_3$))—CO$_2$H);

$R^4$ is halogen (e.g. F);

a is 0 or 1;

$R^5$ is halogen (e.g. Cl);

m is 1;

$R^6$ is hydrogen or $C_{1-6}$alkyl (e.g. —CH$_3$ or —CH$_2$CH$_3$);

$R^7$ is $C_{1-6}$alkyl (e.g. —CH$_3$ or —CH$_2$CH$_3$), hydroxy$C_{1-6}$alkyl (e.g. —CH$_2$OH), —$C_{1-6}$alkyl-NR$^x$R$^y$ (e.g. —CH$_2$N(CH$_3$)$_2$), —(CR$^x$R$^y$)$_p$—CONR$^x$R$^y$(e.g. —C(=O)N(CH$_3$)$_2$ or —C(=O)NHCH$_3$) or

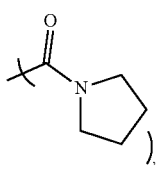

—(CH$_2$)$_j$—O—$C_{1-6}$alkyl (e.g. —CH$_2$OCH$_3$), $C_{3-8}$cycloalkyl (e.g. cyclobutyl or cyclohexyl), heterocyclic group with 3 to 7 ring members e.g.

(point of attachment represented by dashed bond)

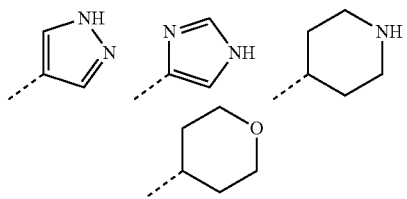

or —CH$_2$-heterocyclic group with 3 to 7 ring members e.g. (point of attachment represented by dashed bond)

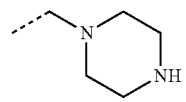

wherein when the moiety $R^7$ comprises a heterocyclic or cycloalkyl group, the heterocyclic group may be optionally substituted by one or more $R^z$ groups selected from $C_{1-6}$alkyl (e.g. methyl), hydroxy, halogen (e.g. fluoro), —C(=O)C$_{1-6}$alkyl (e.g. —C(=O)C(CH$_3$)$_3$), —(CH$_2$)$_r$—CO$_2$H (e.g. —CH$_2$COOH or CH$_2$CH$_2$COOH or —(CH$_2$)$_r$—CO$_2$C$_{1-6}$alkyl (e.g. CH$_2$CH$_2$COOCH$_3$).

In one embodiment, the invention provides a process for preparing a compound of formula (1°) or a tautomer or a solvate or a pharmaceutically acceptable salt thereof, wherein:

$R^1$ is halogen (e.g. Cl), $C_{1-4}$alkynyl (e.g. —C≡CH), nitrile, hydroxy$C_{1-4}$alkyl (e.g. CH$_2$OH), —(CH$_2$)$_v$COOH (e.g. —COOH), —S(O)$_d$—C$_{1-4}$alkyl (e.g. SCH$_3$, SOCH$_3$, or SO$_2$CH$_3$), —SO$_2$-(1-morpholinyl) or —P(=O)(R$^x$)$_2$, (e.g. —P(=O)(CH$_3$)$_2$);

n is 1 or 2;

$R^2$ is hydrogen, $C_{1-4}$ alkyl (e.g. —CH$_3$), hydroxy$C_{1-4}$alkyl (e.g. CH$_2$OH) or —(CH$_2$)$_u$COOH (e.g. —CH$_2$COOH);

$R^4$ is halogen (e.g. F);

a is 0 or 1;

$R^5$ is halogen (e.g. Cl);

m is 1;

$R^6$ is hydrogen or $C_{1-6}$alkyl (e.g. —CH$_3$ or —CH$_2$CH$_3$);

$R^7$ is $C_{1-6}$alkyl (e.g. —CH$_3$), hydroxy$C_{1-6}$alkyl (e.g. —CH$_2$OH), —(CH$_2$)$_j$—O—$C_{1-6}$alkyl (e.g. —CH$_2$OCH$_3$), —$C_{1-6}$alkyl-NR$^x$R$^y$ (e.g. —CH$_2$N(CH$_3$)$_2$), —(CR$^x$R$^y$)$_p$—CONR$^x$R$^y$(e.g. —C(=O)N(CH$_3$)$_2$ or —C(=O)NHCH$_3$) or

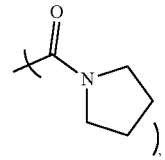

heterocyclic group with 3 to 7 ring members e.g. (point of attachment represented by dashed bond)

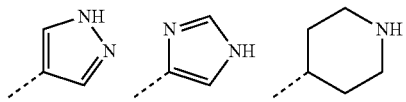

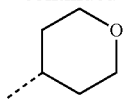

or —CH$_2$-heterocyclic group with 3 to 7 ring members e.g.
(point of attachment represented by dashed bond)

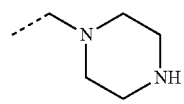

wherein when R$^7$ comprises a heterocyclic group, the heterocyclic group may be optionally substituted by one or more R$^z$ groups selected from C$_{1-6}$alkyl (e.g. methyl).

In one embodiment of formula (I) R$^7$ is a heterocyclic group with 3 to 7 ring members e.g.

(point of attachment represented by dashed bond)

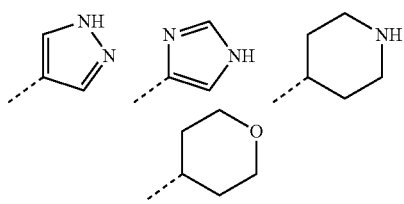

In one embodiment of formula wherein when R$^7$ comprises a heterocyclic group, the heterocyclic group may be R$^7$ is a heterocyclic group with 3 to 7 ring members optionally substituted by one or more R$^z$ groups e.g.

(point of attachment represented by dashed bond)

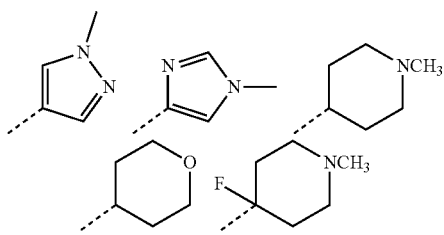

or a —CH$_2$-heterocyclic group with 3 to 7 ring members optionally substituted by one or more R$^z$ groups e.g.

(point of attachment represented by dashed bond)

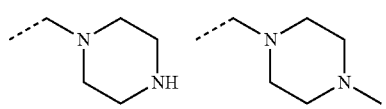

In one embodiment of formula wherein when R$^7$ comprises a heterocyclic group, the heterocyclic group may be R$^7$ is a heterocyclic group with 3 to 7 ring members optionally substituted by one or more R$^z$ groups e.g.

(point of attachment represented by dashed bond)

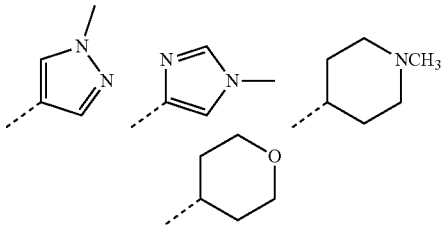

or a —CH$_2$-heterocyclic group with 3 to 7 ring members optionally substituted by one or more R$^z$ groups e.g.
(point of attachment represented by dashed bond)

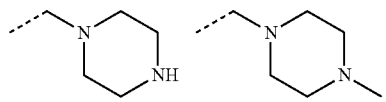

In one embodiment, the invention provides a process for preparing a compound of formula (1°) or a tautomer or a solvate or a pharmaceutically acceptable salt thereof, wherein:
R$^1$ is —Cl, —CN, —OH or —OCH$_3$;
n is 1;
R$^2$ is hydrogen;
a is 0 or 1 and R$^4$ is halogen (e.g. fluorine);
R$^5$ is halogen (e.g. Cl);
m is 1;
R$^6$ is C$_{1-4}$alkyl (e.g. methyl or ethyl);
R$^7$ is C$_{1-4}$alkyl (e.g. methyl or ethyl), hydroxylC$_{1-4}$alkyl (e.g. hydroxylmethyl or hydroxyethyl), methoxyC$_{1-4}$alkyl (e.g. methoxymethyl), a heterocyclic group with 5 or 6 ring members (e.g. piperidinyl, oxanyl, imidazolyl or pyrazolyl) or C$_{3-6}$cycloalkyl (e.g. cyclobutyl or cyclohexyl) wherein said heterocyclic group with 5 or 6 ring members and C$_{3-6}$cycloalkyl groups may be optionally substituted with one or two R$^z$ groups independently selected from methyl, halogen (such as fluorine), —C(=O)Me, and —OH.

In one embodiment, the invention provides a process for preparing a compound of formula (1°) or a tautomer or a solvate or a pharmaceutically acceptable salt thereof, wherein:
R$^1$ is —Cl, —CN, —OH or —OCH$_3$;
n is 1;
R$^2$ is hydrogen or —(CH$_2$)$_u$—CO$_2$H wherein u is independently selected from 0 and 1;
a is 0 or 1 and R$^4$ is halogen (e.g. fluorine);
R$^5$ is halogen (e.g. Cl);
m is 1;
R$^6$ is C$_{1-4}$alkyl (e.g. methyl or ethyl);
R$^7$ is C$_{1-4}$alkyl (e.g. methyl or ethyl), hydroxylC$_{1-4}$alkyl (e.g. hydroxylmethyl or hydroxyethyl), methoxyC$_{1-4}$alkyl (e.g. methoxymethyl), a heterocyclic group with 5 or 6 ring members (e.g. piperidinyl, oxanyl, imidazolyl or pyrazolyl) or C$_{3-6}$cycloalkyl (e.g. cyclobutyl or cyclohexyl);
wherein said heterocyclic group with 5 or 6 ring members and C$_{3-6}$cycloalkyl groups may be optionally substituted with one or two R$^z$ groups independently selected from methyl, halogen (such as fluorine), —C(=O)Me, and —OH.

In one embodiment, the invention provides a process for preparing a compound of formula (1°) or a tautomer or a solvate or a pharmaceutically acceptable salt thereof, wherein:
- $R^1$ is halogen (e.g. Cl) or nitrile;
- n is 1;
- $R^2$ is hydrogen or —$(CH_2)_u$COOH (e.g. —$CH_2$COOH);
- $R^4$ is halogen (e.g. F);
- a is 0 or 1;
- $R^5$ is halogen (e.g. Cl);
- m is 1;
- $R^6$ is hydrogen or $C_{1-6}$alkyl (e.g. —$CH_3$ or —$CH_2CH_3$);
- $R^7$ is $C_{1-4}$alkyl (e.g. methyl), hydroxyl$C_{1-4}$alkyl (e.g. hydroxylmethyl), methoxy$C_{1-4}$alkyl (e.g. methoxymethyl), a heterocyclic group with 5 or 6 ring members (e.g. piperidinyl, oxanyl, imidazolyl or pyrazolyl));
- wherein said heterocyclic group with 5 or 6 ring members may be optionally substituted with one or two $R^z$ groups independently selected from $C_{1-4}$alkyl (e.g. methyl).

In one embodiment, the invention provides a process for preparing a compound of formula (1°) or a tautomer or a solvate or a pharmaceutically acceptable salt thereof, wherein:
- $R^1$ is halogen (e.g. Cl), nitrile, $O_{0,1}(CR^xR^y)_v$COOH (e.g. —COOH, —$CH_2$COOH, —$OCH_2$COOH or —$C(CH_3)_2$COOH;
- n is 1 or 2;
- $R^2$ is selected from hydrogen and —$(R^xR^y)_u$—$CO_2H$ (e.g. —COOH, —$CH_2$COOH, —$CH_2CH_2$—$CO_2H$, —(CH($CH_3$))—$CO_2H$ and —$(C(CH_3)_2$—$CO_2H)$.
- $R^4$ is halogen (e.g. F);
- $R^5$ is halogen (e.g. Cl);
- m is 1;
- $R^6$ is hydrogen or $C_{1-6}$alkyl (e.g. —$CH_3$ or —$CH_2CH_3$);
- $R^7$ is $C_{1-4}$alkyl (e.g. methyl), hydroxyl$C_{1-4}$alkyl (e.g. hydroxylmethyl), methoxy$C_{1-4}$alkyl (e.g. methoxymethyl), a heterocyclic group with 5 or 6 ring members (e.g. piperidinyl, oxanyl, imidazolyl or pyrazolyl));
- wherein said heterocyclic group with 5 or 6 ring members may be optionally substituted with one or two $R^z$ groups independently selected from $C_{1-4}$alkyl (e.g. methyl).

For the avoidance of doubt, it is to be understood that each general and specific embodiment and example for one substituent may be combined with each general and specific embodiment and example for one or more, in particular all, other substituents as defined herein and that all such embodiments are embraced by this application.

Compounds Wherein Cyc is Het.

In one embodiment, cyc is Het, and the invention provides a process for preparing a 1-methoxyisoindoline of formula (1$^x$):

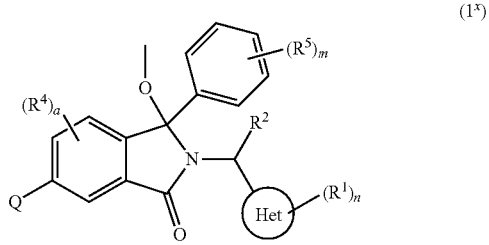

(1$^x$)

or a tautomer or a solvate or a salt thereof, the process comprising taking a compound of the formula (2$^y$)

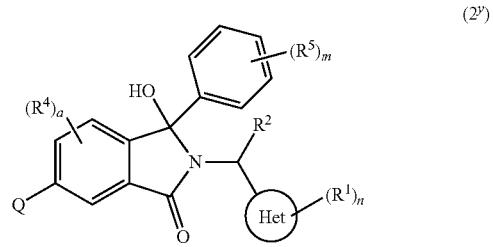

(2$^y$)

wherein Het which is pyridinyl, pyrimidinyl, pyrazinyl or pyridazinyl, or an N-oxide thereof;
- $R^1$ is attached to a carbon atom and is independently selected from hydroxy, halogen, nitro, nitrile, $C_{1-4}$alkyl, halo$C_{1-4}$alkyl, hydroxy$C_{1-4}$alkyl, $C_{2-6}$alkenyl, $C_{1-4}$alkoxy, halo$C_{1-4}$alkoxy, $C_{2-4}$alkynyl, —$O_{0,1}$—$(CR^xR^y)_v$—$CO_2H$, —$(CR^xR^y)_v$—$CO_2C_{1-4}$alkyl, —$(CR^xR^y)_v$—$CON(C_{1-4}$alkyl$)_2$, —$P(=O)(R^x)_2$, —$S(O)_d$—$R^x$, —$S(O)_d$-heterocyclic group with 3 to 6 ring members and —$S(O)_d$—$N(R^8)_2$;
- wherein $R^1$ is independently selected from hydroxy, halogen, nitro, nitrile, $C_{1-4}$alkyl, halo$C_{1-4}$alkyl, hydroxy$C_{1-4}$alkyl, $C_{2-6}$alkenyl, $C_{1-4}$alkoxy, halo$C_{1-4}$alkoxy, $C_{2-4}$alkynyl, —$O_{0,1}$—$(CR^xR^y)_v$—$CO_2H$, —$(CR^xR^y)_v$—$CO_2C_{1-4}$alkyl, —$(CR^xR^y)_v$—$CON(C_{1-4}$alkyl$)_2$, —$P(=O)(R^x)_2$, —$S(O)_d$—$R^x$, —$S(O)_d$-heterocyclic group with 3 to 6 ring members and —$S(O)_d$—$N(R^8)_2$;
- $R^2$ is selected from hydrogen, $C_{1-4}$ alkyl, $C_{2-6}$alkenyl, hydroxy$C_{1-4}$alkyl, —$(CR^xR^y)_u$—$CO_2H$, —$(CR^xR^y)_u$—$CONR^xR^y$, —$(CR^xR^y)_u$—$CO_2R^{10}$ wherein $R^{10}$ is selected from $C_{1-7}$ alkyl, $C_{1-7}$ haloalkyl, tri$C_{1-7}$ alkylsilyl-$C_{1-7}$alkyl, $C_{5-20}$ aryl and $C_{5-20}$ aryl-$C_{1-7}$ alkyl;
- $R^4$ and $R^5$ are independently selected from halogen, nitrile, $C_{1-4}$ alkyl, halo$C_{1-4}$alkyl, $C_{1-4}$alkoxy and halo$C_{1-4}$alkoxy;
- Q is selected from —$C(OH)R^6R^7$, —$C(=O)R^7$, halogen (e.g. —F, —Cl, —Br, —I) and —OTf;
- $R^6$ and $R^7$ are independently selected from hydrogen, $C_{1-6}$alkyl, halo$C_{1-6}$alkyl, $C_{2-6}$alkenyl, $C_{2-6}$alkynyl, hydroxy, hydroxy$C_{1-6}$alkyl, —COO$C_{1-6}$alkyl, —$(CH_2)_j$—O—$C_{1-6}$alkyl, —$(CH_2)_j$—O-(hydroxy$C_{1-6}$alkyl), —$C_{1-6}$alkyl-$NR^xR^y$, —$(CR^xR^y)_p$—$CONR^xR^y$, —$(CR^xR^y)_p$—$NR^xCOR^y$, —$(CR^xR^y)_p$—O—$CH_2$—$CONR^xR^y$, heterocyclic group with 3 to 7 ring members, —$CH_2$-heterocyclic group with 3 to 7 ring members, —$CH_2$—O-heterocyclic group with 3 to 7 ring members, —$CH_2$—NH-heterocyclic group with 3 to 7 ring members, —$CH_2$—$N(C_{1-6}$alkyl)-heterocyclic group with 3 to 7 ring members, —$C(=O)$NH-heterocyclic group with 3 to 7 ring members, $C_{3-8}$cycloalkyl, —$CH_2$—$C_{3-8}$cycloalkyl, —$CH_2$—O—$C_{3-8}$cycloalkyl, and $C_{3-8}$cycloalkenyl, wherein said cycloalkyl, cycloalkenyl or heterocyclic groups may be optionally substituted by one or more $R^z$ groups, and wherein in each instance the heterocyclic group comprises one or more (e.g. 1, 2, or 3) heteroatoms selected from N, O, S and oxidised forms thereof;
- or, when Q is —$C(OH)R^6R^7$, the $R^6$ and $R^7$ groups, together with the carbon atom to which they are attached, can join to form a $C_{3-6}$cycloalkyl or heterocyclyl group with 3 to 6 ring members, wherein the heterocyclic group comprises one or more (e.g. 1, 2, or 3) heteroatoms selected from N, O, S and oxidised forms thereof, and wherein said $C_{3-8}$cycloalkyl and heterocyclyl groups may be optionally substituted by one or more $R^z$ groups;

$R^8$ is selected from hydrogen, $C_{1-6}$alkyl, halo$C_{1-6}$alkyl, hydroxy$C_{1-6}$alkyl, —$(CH_2)_k$—O—$C_{1-6}$alkyl, —$(CH_2)_k$—O-(hydroxy$C_{1-6}$alkyl), hydroxy$C_{1-6}$alkoxy, —$(CH_2)_k$—$CO_2C_{1-6}$alkyl, —$(CH_2)_k$—$CO_2H$, —$C_{1-6}$alkyl-$N(H)_e(C_{1-4}$alkyl$)_{2-e}$, —$(CH_2)_j$—$C_{3-8}$cycloalkyl and —$(CH_2)_j$—$C_{3-8}$cycloalkenyl;

$R^x$ and $R^y$ are independently selected from hydrogen, halogen, nitro, nitrile, $C_{1-6}$alkyl, halo$C_{1-6}$alkyl, $C_{2-6}$alkenyl, $C_{2-6}$alkynyl, hydroxy, hydroxy$C_{1-6}$alkyl, $C_{1-6}$alkoxy, —$(CH_2)_k$—O—$C_{1-6}$alkyl, hydroxy$C_{1-6}$alkoxy, —$COOC_{1-6}$alkyl, —$N(H)_e(C_{1-4}$alkyl$)_{2-e}$, —$C_{1-6}$alkyl-$N(H)_e(C_{1-4}$alkyl$)_{2-e}$, —$(CH_2)_k$—$C(=O)N(H)_e(C_{1-4}$alkyl$)_{2-e}$, $C_{3-8}$cycloalkyl and $C_{3-8}$cycloalkenyl;

or the $R^x$ and $R^y$ groups, together with the carbon or nitrogen atom to which they are attached, can join to form a $C_{3-6}$cycloalkyl or saturated heterocyclyl group with 3 to 6 ring members which may be optionally fused to an aromatic heterocyclyl group of 3 to 5 ring members;

or when on a carbon atom the $R^x$ and $R^y$ groups can join together to form a =$CH_2$ group; $R^z$ is independently selected from halogen, nitro, nitrile, $C_{1-6}$alkyl, halo$C_{1-6}$alkyl, $C_{2-6}$alkenyl, $C_{2-6}$alkynyl, =O, hydroxy, hydroxy$C_{1-6}$alkyl, $C_{1-6}$alkoxy, —$(CH_2)_k$—O—$C_{1-6}$alkyl, hydroxy$C_{1-6}$alkoxy, —$C(=O)C_{1-6}$alkyl, —$C(=O)C_{1-6}$alkyl-OH, —$C(=O)C_{1-6}$alkyl-$N(H)_e(C_{1-4}$alkyl$)_{2-e}$, —$C(=O)N(H)_e(C_{1-4}$alkyl$)_{2-e}$, —$(CH_2)_r$-$CO_2C_{1-6}$alkyl, —$(CH_2)_r$$CO_2H$, —$N(H)_e(C_{1-4}$alkyl$)_{2-e}$, —$C_{1-6}$alkyl-$N(H)_e(C_{1-4}$alkyl$)_{2-e}$, heterocyclyl group with 3 to 6 ring members, heterocyclyl group with 3 to 6 ring members substituted by —$C(=O)C_{1-4}$alkyl, heterocyclyl group with 3 to 6 ring members substituted by —$C(=O)OC_{1-4}$alkyl, heterocyclyl group with 3 to 6 ring members substituted by —$C(=O)N(H)_e(C_{1-4}$alkyl$)_{2-e}$, —$C(=O)$heterocyclyl group with 3 to 6 ring members, $C_{3-8}$cycloalkyl and $C_{3-8}$cycloalkenyl, wherein if $R^7$ is pyridine then $R^z$ is other then —$NH_2$;

a, j, d, e, n, r and p are independently selected from 0, 1 and 2;

k and m are independently selected from 1 and 2;

u is selected from 0, 1, 2 and 3; and v and w are independently selected from 0 and 1;

and reacting the compound of formula (2) with a methylating agent in the presence of a base.

Het

Het is pyridinyl, pyrimidinyl, pyrazinyl or pyridazinyl, or an N-oxide thereof.

In one embodiment Het is pyridinyl, pyrimidinyl or pyridazinyl, or an N-oxide thereof.

In one embodiment Het is pyridinyl or pyrimidinyl, or an N-oxide thereof. In one embodiment Het is pyridinyl or pyrimidinyl. In one embodiment, Het is optionally substituted pyrimidin-2-yl.

In one embodiment, the point of attachment of the Het group is at the 2-position of the Het group and the Het is pyridin-2-yl, pyrimidin-2-yl, or pyridazin-2yl. In other words, the Het ring is attached to the rest of the molecule by a carbon atom adjacent to a nitrogen atom in the Het ring.

In one embodiment, Het is pyridinyl. In particular, Het may be pyridin-2-yl and the compound of formula (1°) is a compound of formula (Ia) or a tautomer or a solvate or a pharmaceutically acceptable salt thereof, or pyridin-3-yl and the compound of formula (1°) is a compound of formula (Ib) or a tautomer or a solvate or a pharmaceutically acceptable salt thereof:

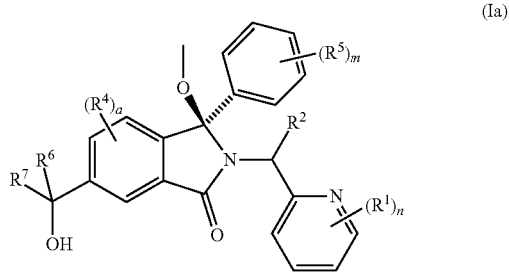

(Ia)

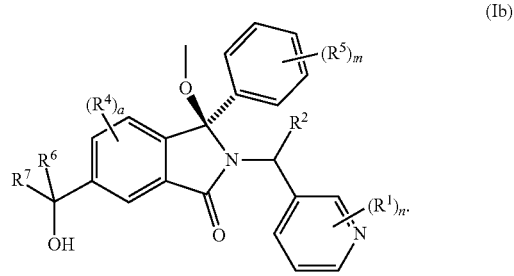

(Ib)

In one embodiment, Het is N-oxide pyridinyl. In particular, Het may be N-oxide pyridin-2-yl and the compound of formula (1°) is a compound of formula (Ia') or a tautomer or a solvate or a pharmaceutically acceptable salt thereof:

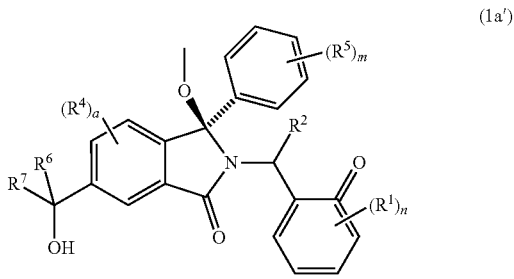

(Ia')

In one embodiment, Het is pyrimidinyl. In particular, Het may be pyrimidin-2-yl and the compound of formula (1°) is a compound of formula (Ic) or a tautomer or a solvate or a pharmaceutically acceptable salt thereof:

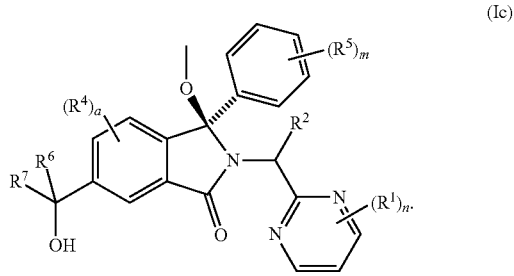

(Ic)

In one embodiment the compound of formula (1°) can be pyridin-2-yl or pyrimidin-2-yl and the compound of formula (1°) is a compound of formula (Id) or a tautomer or a solvate or a pharmaceutically acceptable salt thereof:

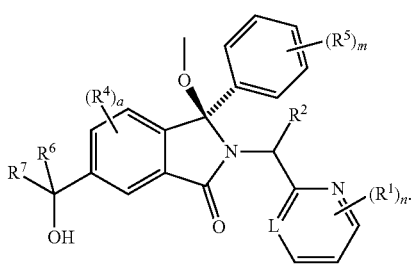

(Id)

wherein L is CR¹, CH or N. In one embodiment of formula (Ic) L is CH or N.

In one embodiment Het is pyrid-2-yl or pyrimidin-2-yl.

In one embodiment, Het is selected from the group consisting of (dashed line represents connection to carbon atom bound to CHR² group):

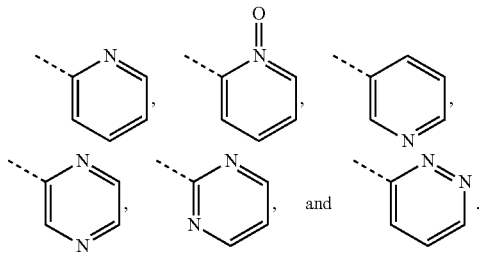

In one embodiment, Het is selected from the group consisting of (dashed line represents connection to carbon atom bound to CHR² group):

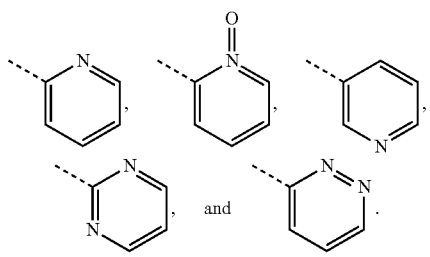

R¹ and n

R¹ is the substituent(s) on the Het group. R¹ is attached to a carbon atom (not a nitrogen atom) of the Het group.

n is 0, 1, 2 or 3. In other words, the Het group may have 0, 1, 2 or 3 substituents R¹.

In one embodiment n is 1, 2 or 3. In one embodiment n is 1 or 2. In another embodiment n is 1.

When n is 2 or 3 (i.e. the Het group is substituted with more than one R¹) the substituents R¹ may be the same or different (i.e. are independently selected from the definitions of R¹).

R¹ may be attached to a carbon atom at the ortho (or o-), meta (or m-) or para (or p-) position of the 6-membered Het group, wherein the position is defined relative to the point of attachment of the 6-membered Het group to the group —CHR²—.

R¹ is independently selected from hydroxy, halogen, nitro, nitrile, $C_{1-4}$alkyl, halo$C_{1-4}$alkyl, hydroxy$C_{1-4}$alkyl, $C_{2-6}$alkenyl, $C_{1-4}$alkoxy, halo$C_{1-4}$alkoxy, $C_{2-4}$alkynyl, —$O_{0,1}$—$(CR^xR^y)_v$—$CO_2H$, —$(CR^xR^y)_v$—$CO_2C_{1-4}$alkyl, —$(CR^xR^y)_v$—$CON(C_{1-4}alkyl)_2$, —$P(=O)(R^x)_2$, —$S(O)_d$—$R^x$, —$S(O)_d$-heterocyclic group with 3 to 6 ring members and —$S(O)_d$—$N(R^8)_2$.

In one embodiment, R¹ is independently selected from hydroxy, halogen, nitro, nitrile, $C_{1-4}$alkyl, halo$C_{1-4}$alkyl, hydroxy$C_{1-4}$alkyl, $C_{2-6}$alkenyl, $C_{1-4}$alkoxy, halo$C_{1-4}$alkoxy, $C_{2-4}$alkynyl, —$(CR^xR^y)_v$—$CO_2H$, —$(CR^xR^y)_v$—$CO_2C_{1-4}$alkyl, —$(CR^xR^y)_v$—$CON(C_{1-4}alkyl)_2$, —$P(=O)(R^x)_2$, —$S(O)_d$—$R^x$, —$S(O)d$-heterocyclic group with 3 to 6 ring members and —$S(O)_d$—$N(R^8)_2$.

In one embodiment, R¹ is attached to a carbon atom and is independently selected from hydroxy, halogen, nitro, nitrile, $C_{1-4}$alkyl, halo$C_{1-4}$alkyl, hydroxy$C_{1-4}$alkyl, $C_{2-6}$alkenyl, $C_{1-4}$alkoxy, halo$C_{1-4}$alkoxy, $C_{2-4}$alkynyl, —$(CR^xR^y)_v$—$CO_2C_{1-4}$alkyl, —$(CR^xR^y)_v$—$CON(C_{1-4}alkyl)_2$, —$P(=O)(R^x)_2$, —$S(O)d$-$R^x$, —$S(O)d$-heterocyclic group with 3 to 6 ring members and —$S(O)_d$—$N(R^8)_2$;

In one embodiment, R¹ is independently selected from halogen, hydroxy, nitrile, $C_{1-4}$alkyl, $C_{2-4}$alkynyl, or $C_{1-4}$alkoxy, for example R¹ is independently selected from fluoro, chloro, hydroxy, nitrile, methyl or methoxy.

In one embodiment R¹ is independently selected from halogen (e.g. chloro), $C_{1-4}$alkyl (e.g. methyl), $C_{1-4}$alkoxy (e.g. methoxy), —$O_{0,1}$—$(CR^xR^y)_v$—$CO_2H$ (e.g. —$CO_2H$, —$(CH_2)$—$CO_2H$, —$(C(CH_3)_2)$—$CO_2H$, or —$O(CH_2)$—$CO_2H$) or —$S(O)_d$—$R^x$ (e.g. $SO_2CH_3$).

In one embodiment R¹ is $O_{0,1}$—$(CR^xR^y)_v$—$CO_2H$ in particular —$CO_2H$, —$(CH_2)$—$CO_2H$, —$(C(CH_3)_2)$—$CO_2H$, or —$O(CH_2)$—$CO_2H$), such as —$(C(CH_3)_2)$—$CO_2H$.

In one embodiment, R¹ is chloro or nitrile, in particular chloro.

In one embodiment, R¹ is nitro (i.e. p-$NO_2$).

In one embodiment, R¹ is nitro at the ortho or meta position.

In another embodiment, n is 1 and R¹ is chloro or nitrile.

In another embodiment, n is 1 and R¹ is chloro.

In another embodiment, n is 1 and R¹ is nitrile.

In one embodiment, one of the R¹ groups or the R¹ group (where n=1) is at the para-position (i.e. para to the point of attachment of the six-membered ring). In one embodiment n is 1 and R¹ is p-chloro or p-nitrile.

In one embodiment, n is 1 and R¹ is halogen (e.g. Cl or F), nitrile, $C_{1-4}$alkoxy (e.g. —$OCH_3$) or $C_{1-4}$alkyl (e.g. $CH_3$).

In one embodiment, n is 2. In one embodiment when n is 2, the Het group is substituted with (i) o-(—$S(O)_d$—$C_{1-4}$alkyl) or o-(—$S(O)_d$-heterocyclic group with 3 to 6 ring members) and (ii) halogen (e.g. Cl or F), nitrile, or $C_{1-4}$alkyl, in particular chloro, nitrile or methyl.

In another embodiment, one or more R¹ is —$SO_2CH_3$, or —$SO_2$-heterocyclic group with 6 ring members e.g. —$SO_2$-(morpholinyl), in particular —$SO_2$-(1-morpholinyl).

In one embodiment, R¹ is o-(—$S(O)_d$—$C_{1-4}$alkyl) or o-(—$S(O)_d$-heterocyclic group with 3 to 6 ring members).

In one embodiment, n is 2 and R¹ is (i) —$SO_2CH_3$ and (ii) chloro.

In one embodiment n is 2 and R¹ is (i) —$SO_2CH_3$ and (ii) chloro, nitrile or methyl.

In one embodiment, Het and R¹ form a group:

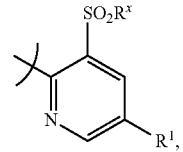

wherein in particular, $R^1$ is halogen (for example chloro), nitrile or $C_{1-4}$alkyl (for example —$CH_3$) and $R^x$ is $C_{1-4}$alkyl (for example —$CH_3$).

In one embodiment, Het and $R^1$ form a group:

wherein in particular, $R^1$ is $C_{1-4}$alkyl (for example —$CH_3$) and $R^x$ is $C_{1-4}$alkyl (for example —$CH_3$).

In one embodiment when n is 2, the Het group is substituted with (i) o-OH or o-$CH_2OH$ and (ii) halogen (e.g. Cl or F), nitrile, or $C_{1-4}$ alkyl, in particular chloro, or nitrile. In one embodiment, when n is 2, the Het group is substituted with (i) hydroxy and (ii) halogen (e.g. Cl or F) or nitrile, in particular chloro or nitrile. In one embodiment, when n is 2, the Het group is substituted with (i) o-hydroxy and (ii) p-Cl or p-CN (e.g. p-Cl).

In one embodiment, n is 2 and $R^1$ is fluorine (e.g. at the ortho and para positions of the Het group).

In one embodiment, $R^1$ is halogen (e.g. Cl or F), $C_{1-4}$alkynyl (e.g. —C≡CH), nitrile, —$(CH_2)_v$COOH (e.g. —COOH) or —$SO_2C_{1-4}$alkyl (e.g. $SO_2CH_3$) and n is 1 or 2.

In one embodiment, n is 1 and $R^1$ is Cl (e.g. p-Cl), CN (e.g. p-CN), F e.g. (p-F), $CH_3$ (e.g. p-$CH_3$), or $OCH_3$ (p-$OCH_3$), or n is 2 and (i) $R^1$ is p-F; o-F, or (ii) p-$CH_3$; o-$OCH_3$; or (iii) p-Cl, o-$SO_2CH_3$ or (iv) p-Cl, o-OH.

In one embodiment, n is 1 and $R^1$ is Cl (e.g. p-Cl), CN (e.g. p-CN), F e.g. (p-F), $CH_3$ (e.g. p-$CH_3$), or $OCH_3$ (p-$OCH_3$).

In one embodiment, n is 2 and (i) $R^1$ is p-F; o-F, or (ii) p-$CH_3$; o-$OCH_3$; or (iii) p-Cl, o-$SO_2CH_3$ or (iv) p-Cl, o-OH.

In one embodiment, n is 2 and $R^1$ is p-Cl and o-OH.

In one embodiment, $R^1$ is —$O_{0,1}(CR^xR^y)_v$COOH (e.g. —COOH, —$CH_2$COOH, —$OCH_2$COOH or —$C(CH_3)_2$COOH).

In one embodiment, n is 2 and $R^1$ is p-Cl and o-$O_{0,1}(CR^xR^y)_v$COOH (e.g. —COOH, —$CH_2$COOH, —$OCH_2$COOH or —$OC(CH_3)_2$COOH).

In one embodiment n is 1 and $R^1$ is —Cl, —CN, —OMe, —$O_{0,1}(CR^xR^y)_v$COOH (e.g. —COOH) or $C_{1-4}$ alkyl (e.g. —$CH_3$) (e.g. p-Cl, p-CN or p-OMe). In one embodiment n is 1 and $R^1$ is —Cl or —CN (e.g. p-Cl or p-CN).

In one embodiment n is 1 and $R^1$ is —Cl, —CN or —OMe (e.g. p-Cl, p-CN or p-OMe). In one embodiment n is 1 and $R^1$ is —Cl or —CN (e.g. p-Cl or p-CN).

In one embodiment, $R^1$ is independently selected from hydroxy, halogen (e.g. chlorine), nitrile, $C_{1-4}$alkyl (e.g. methyl), $C_{1-4}$alkoxy (e.g. methoxy), and —$O_{0,1}$—$(CR^xR^y)_v$—$CO_2H$ (e.g. —$CO_2H$).

In one embodiment $R^1$ is $O_{0,1}$—$(CR^xR^y)_v$—$CO_2H$ in particular —$CO_2H$, —$(CH_2)$—$CO_2H$, —$(C(CH_3)_2)$—$CO_2H$, or —$O(CH_2)$—$CO_2H$), such as —$CO_2H$.

$R^2$ $R^2$ is selected from hydrogen, $C_{1-4}$ alkyl, $C_{2-6}$alkenyl, hydroxy$C_{1-4}$alkyl, —$(CR^xR^y)_u$—$CO_2H$, —$(CR^xR^y)_u$—$CO_2C_{1-4}$alkyl, and —$(CR^xR^y)_u$—$CONR^xR^y$.

In one embodiment u is selected from 0, 1, or 2. In one embodiment u is selected from 0 or 1.

In one embodiment, $R^2$ is selected from hydrogen, $C_{1-4}$ alkyl, $C_{2-6}$alkenyl, hydroxy$C_{1-4}$alkyl and —$(CR^xR^y)_u$—$CO_2H$. In one embodiment, $R^2$ is selected from hydrogen, $C_{1-4}$ alkyl, hydroxy$C_{1-4}$alkyl and —$(CR^xR^y)_u$—$CO_2H$. In one embodiment, $R^2$ is selected from hydrogen, $C_{1-4}$ alkyl, $C_{2-6}$alkenyl, and hydroxy$C_{1-4}$alkyl. In another embodiment $R^2$ is selected from hydrogen and —$(CH_2)_u$—$CO_2H$ (e.g. —$CH_2$—$CO_2H$).

In one embodiment, $R^2$ is hydrogen, $C_{1-4}$ alkyl (e.g. —$CH_3$), hydroxy$C_{1-4}$alkyl (e.g. $CH_2OH$) or —$(CH_2)_u$COOH (e.g. —COOH, —$CH_2$COOH, —$CH_2CH_2$—$CO_2H$, —$(CH(CH_3))$—$CO_2H$ or —$(C(CH_3)_2$—$CO_2H$, such as —COOH, —$CH_2$COOH, —$CH_2CH_2$—$CO_2H$, or —$(CH(CH_3))$—$CO_2H$).

In one embodiment, $R^2$ is selected from hydrogen, $C_{1-4}$ alkyl, $C_{2-6}$alkenyl, and hydroxy$C_{1-4}$alkyl.

In one embodiment, $R^2$ is hydrogen, $C_{1-4}$ alkyl (e.g. —$CH_3$), hydroxy$C_{1-4}$alkyl (e.g. $CH_2OH$) or —$(CH_2)_u$COOH (e.g. —$CH_2$COOH).

In one embodiment, $R^2$ is selected from hydrogen, —$CH_3$, —$CH_2OH$, and —$CH(OH)CH_2OH$.

In one embodiment, $R^2$ is selected from hydrogen, —$CH_3$, —$CH_2OH$, —CH=$CH_2$ and —$CH(OH)CH_2OH$.

In one embodiment, $R^2$ is selected from hydrogen, —$CH_3$, —$CH_2OH$, and —$CH_2CO_2H$.

In one embodiment, $R^2$ is hydrogen or $C_{1-4}$ alkyl (e.g. —$CH_3$ or —$CH_2CH_3$).

In one embodiment, $R^2$ is selected from hydrogen, —$CH_3$ and —$CH_2CH_3$. In one embodiment, $R^2$ is selected from hydrogen and methyl.

In one embodiment, $R^2$ is selected from hydrogen and —$(R^xR^y)_u$—$CO_2H$ (e.g. —COOH, —$CH_2$COOH, —$CH_2CH_2$—$CO_2H$, —$(CH(CH_3))$—$CO_2H$ and —$(C(CH_3)_2$—$CO_2H$).

In one embodiment, $R^2$ is —$(R^xR^y)_u$COOH (e.g. —$CH_2$COOH, —$CH_2CH_2$—$CO_2H$, —$(CH(CH_3))$—$CO_2H$ (e.g.

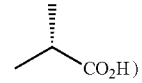

or —$(C(CH_3)_2$—$CO_2H$).

In one embodiment, $R^2$ is hydrogen, $C_{1-4}$ alkyl (e.g. —$CH_3$) or —$(CH_2)_u$COOH (e.g. —$CH_2$COOH, —$CH_2CH_2$—$CO_2H$ or —$(CH(CH_3))$—$CO_2H$).

In one embodiment, $R^2$ is hydrogen, $C_{1-4}$ alkyl (e.g. —$CH_3$) or —$(CH_2)_u$COOH (e.g. —$CH_2$COOH).

In one embodiment, $R^2$ is —$(CR^xR^y)_u$—$CO_2H$ (e.g. —$CH_2$—$CO_2H$).

In another embodiment, $R^2$ is selected from —$(CH(CH_3))$—$CO_2H$ and —$(C(CH_3)_2$—$CO_2H$) (e.g.

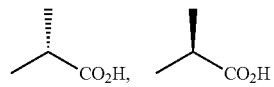

or —$(C(CH_3)_2$—$CO_2H$.

In another embodiment, $R^2$ is hydrogen and the compound of formula (1°) is a compound of formula (Ie) or a tautomer or a solvate or a pharmaceutically acceptable salt thereof:

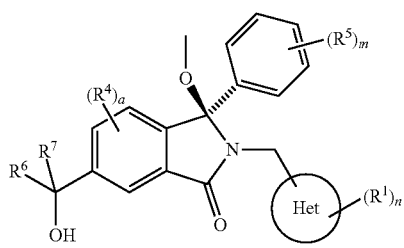

(Ie)

When R² is other than hydrogen, the compound of formula (1°) can exist as at least two diastereoisomers:

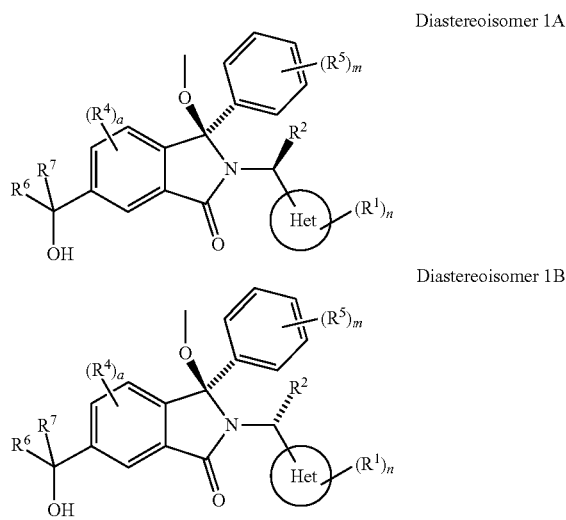

Diastereoisomer 1A

Diastereoisomer 1B

For the avoidance of doubt, the general formula (1°) and all subformulae cover both individual diastereoisomers and mixtures of the diastereoisomers which are related as epimers at the —CHR²— group. In one embodiment the compound of formula I is diastereoisomer 1A or a tautomer or a solvate or a pharmaceutically acceptable salt thereof. In one embodiment the compound of formula I is diastereoisomer 1B or a tautomer or a solvate or a pharmaceutically acceptable salt thereof.

In one embodiment, the compound is diastereoisomer 1A and R² is selected from:
  i. $C_{1-4}$ alkyl, $C_{2-6}$alkenyl, hydroxy$C_{1-4}$alkyl, —($R^xR^y$)$_u$—$CO_2H$ (e.g. —COOH, —$CH_2$COOH, —$CH_2CH_2$—$CO_2H$, —(CH($CH_3$))—$CO_2H$ and —(C($CH_3$)$_2$—$CO_2H$), —($CH_2$)$_u$—$CO_2C_{1-4}$alkyl, and —($CH_2$)$_u$—CONR$^x$R$^y$; or
  ii. $C_{1-4}$alkyl, $C_{2-6}$alkenyl, and hydroxy$C_{1-4}$alkyl.

In one embodiment, the compound is diastereoisomer 1A and R² is selected from:
  i. $C_{1-4}$ alkyl, $C_{2-6}$alkenyl, hydroxy$C_{1-4}$alkyl, —($CH_2$)$_u$—$CO_2H$, —($CH_2$)$_u$—$CO_2C_{1-4}$alkyl, and —($CH_2$)$_u$—CONR$^x$R$^y$; or
  ii. $C_{1-4}$alkyl, $C_{2-6}$alkenyl, and hydroxy$C_{1-4}$alkyl.

In another embodiment R² is selected from hydrogen and —($R^xR^y$)$_u$—$CO_2H$ (e.g. —COOH, —$CH_2$COOH, —$CH_2CH_2$—$CO_2H$, —(CH($CH_3$))—$CO_2H$ and —(C($CH_3$)$_2$ —$CO_2H$), In another embodiment R² is selected from hydrogen and —($CH_2$)$_u$—$CO_2H$ (e.g. —$CH_2$—$CO_2H$).

In one embodiment, the compound is diastereoisomer 1A and R² is selected from:
  iv. —$CH_3$, —$CH_2OH$, —CH=$CH_2$ and —CH(OH)$CH_2$OH; or
  v. $C_{1-4}$ alkyl (e.g. —$CH_3$ or —$CH_2CH_3$); or
  vi. —$CH_3$ and —$CH_2CH_3$.

In one embodiment, the compound is diastereoisomer 1B and R² is selected from:
  i. $C_{1-4}$ alkyl, $C_{2-6}$alkenyl, hydroxy$C_{1-4}$alkyl, —($R^xR^y$)$_u$—$CO_2H$ (e.g. —COOH, —$CH_2$COOH, —$CH_2CH_2$—$CO_2H$, —(CH($CH_3$))—$CO_2H$ and —(C($CH_3$)$_2$—$CO_2H$), —($CH_2$)$_u$—$CO_2C_{1-4}$alkyl, and —($CH_2$)$_u$—CONR$^x$R$^y$; or
  ii. $C_{1-4}$alkyl, $C_{2-6}$alkenyl, and hydroxy$C_{1-4}$alkyl.

In one embodiment, the compound is diastereoisomer 1B and R² is selected from:
  i. $C_{1-4}$ alkyl, $C_{2-6}$alkenyl, hydroxy$C_{1-4}$alkyl, —($CH_2$)$_u$—$CO_2H$, —($CH_2$)$_u$—$CO_2C_{1-4}$alkyl, and —($CH_2$)$_u$—CONR$^x$R$^y$; or
  ii. $C_{1-4}$alkyl, $C_{2-6}$alkenyl, and hydroxy$C_{1-4}$alkyl.

In another embodiment R² is selected from hydrogen and —($CH_2$)$_u$—$CO_2H$ (e.g. —$CH_2$—$CO_2H$).

In one embodiment, the compound is diastereoisomer 1B and R² is selected from:
  iv. —$CH_3$, —$CH_2OH$, —CH=$CH_2$ and —CH(OH)$CH_2$OH; or
  v. $C_{1-4}$ alkyl (e.g. —$CH_3$ or —$CH_2CH_3$); or
  vi. —$CH_3$ and —$CH_2CH_3$.

In another embodiment R² is selected from hydrogen and —($R^xR^y$)$_u$—$CO_2H$ (e.g. —COOH, —$CH_2$COOH, —$CH_2CH_2$—$CO_2H$, —(CH($CH_3$))—$CO_2H$ and —(C($CH_3$)$_2$ —$CO_2H$), In one embodiment R² is selected from $C_{1-4}$ alkyl, hydroxy$C_{1-4}$alkyl, —($CH_2$)$_u$—$CO_2H$, —($CH_2$)$_u$—$CO_2C_{1-4}$ alkyl, and —($CH_2$)$_w$—CONR$^x$R$^y$(in particular —$CH_2$—$CO_2H$) and the compound is diastereoisomer 1A.

In one embodiment R² is selected from $C_{1-4}$ alkyl, hydroxy$C_{1-4}$alkyl, —($CH_2$)$_u$—$CO_2H$, —($CH_2$)$_u$—$CO_2C_{1-4}$ alkyl, and —($CH_2$)$_u$—CONR$^x$R$^y$(in particular —$CH_2$—$CO_2H$) and the compound is diastereoisomer 1B.

In one embodiment R² is hydroxy$C_{1-4}$alkyl (e.g. —$CH_2OH$) and the compound is diastereoisomer 1A.

In one embodiment R² is —($CH_2$)$_u$—$CO_2H$ (e.g. —$CH_2$—$CO_2H$) and the compound is diastereoisomer 1A.

In one embodiment R² and the hydrogen on the carbon to which it is attached are ²H (i.e. deuterium).

R⁴ and a a is 0, 1, 2 or 3. In other words, the phenyl group of the isoindolin-1-one may have 0, 1, 2 or 3 substituents R⁴.

In one embodiment a is 0 or 1. In another embodiment a is 0. In another embodiment a is 1.

When a is 2 or 3 (i.e. the phenyl group of the isoindolin-1-one is substituted with more than one R⁴) the substituents R⁴ may be the same or different (i.e. are independently selected from the definitions of R⁴).

In one embodiment, a is 1 and the substituent R⁴ is at the 4-position of the isoindolin-1-one, and the compound of formula (1°) is a compound of formula (Ir) or a tautomer or a solvate or a pharmaceutically acceptable salt thereof:

(Ir)

$R^4$ is independently selected from halogen, nitrile, $C_{1-4}$alkyl, haloC$_{1-4}$alkyl, $C_{1-4}$alkoxy and haloC$_{1-4}$alkoxy.

In one embodiment, $R^4$ is halogen. In one embodiment, $R^4$ is fluoro or chloro. In another embodiment, $R^4$ is fluoro.

In one embodiment, a is 1, the substituent $R^4$ is at the 4-position of the isoindolin-1-one, and $R^4$ is F and the compound of formula (1°) is a compound of formula (Is) or a tautomer or a solvate or a pharmaceutically acceptable salt thereof:

(Is)

In one embodiment, $R^4$ is $C_{1-4}$ alkyl (e.g. —CH$_3$), or halogen (e.g. F or Cl) and a is 1.

In one embodiment, a is 0 and $R^4$ is absent (i.e. hydrogen).

In one embodiment a is 0 or 1 and $R^4$ is halogen (e.g. fluorine).

$R^5$ and m m is 1 or 2. In other words, the phenyl group may have 1 or 2 substituents $R^5$.

In one embodiment, m is 1 and the phenyl group has one substituent.

$R^5$ may be attached at the ortho (or o-), meta (or m-) or para (or p-) position of the phenyl group, wherein the position is defined relative to the point of attachment of the phenyl group to the 3-position of the isoindolin-1-one ring.

When m is 2 (i.e. the phenyl group is substituted with more than one $R^5$) the substituents $R^5$ may be the same or different (i.e. are independently selected from the definitions of $R^5$).

In one embodiment, m is 1 and the substituent $R^4$ is at the p-position of the phenyl group, and the compound of formula (1°) is a compound of formula (Iu) or a tautomer or a solvate or a pharmaceutically acceptable salt thereof:

(Iu)

$R^5$ is independently selected from halogen, nitrile, $C_{1-4}$ alkyl, haloC$_{1-4}$alkyl, $C_{1-4}$alkoxy and haloC$_{1-4}$alkoxy.

In one embodiment, $R^5$ is halogen, $C_{1-4}$ alkyl, haloC$_{1-4}$ alkyl or $C_{1-4}$alkoxy. In another embodiment $R^5$ is halogen (e.g. chloro).

In one embodiment, $R^5$ is halogen (e.g. Cl or F), $C_{1-4}$ alkyl (e.g. —CH$_2$CH$_3$), nitrile, haloC$_{1-4}$alkyl (e.g. —CF$_3$, or —CF$_2$CH$_3$), or haloC$_{1-4}$alkoxy (e.g. —OCF$_3$), and m is 1 or 2.

In one embodiment, m is 1 and $R^5$ is selected from halogen, nitrile, $C_{1-4}$ alkyl, haloC$_{1-4}$alkyl, $C_{1-4}$alkoxy and haloC$_{1-4}$alkoxy.

In one embodiment, m=1 and $R^5$ is —Cl (e.g. p-Cl), —F (e.g. p-F), —CN (e.g. p-CN), —CF$_3$ (e.g. p-CF$_3$), —OCF$_3$ (e.g. p-OCF$_3$), CF$_2$CH$_3$ (e.g. p-CF$_2$CH$_3$) or —CH$_2$CH$_3$ (e.g. p-CH$_2$CH$_3$), or m=2 and $R^5$ is p-F or m-F.

Q

Q is selected from —C(OH)R$^6$R$^7$, —C(=O)R$^7$, halogen (e.g. —F, —C, —Br, —I) and OTf.

In one embodiment, Q is —C(OH)R$^6$R$^7$.

In one embodiment, Q is —C(=O)R$^7$.

In one embodiment, Q is halogen (e.g. —F, —C, —Br, —I).

In one embodiment, Q is OTf.

$R^6$ and $R^7$ $R^6$ and $R^7$ are independently selected from hydrogen, $C_{1-6}$alkyl, haloC$_{1-6}$alkyl, $C_{2-6}$alkenyl, $C_{2-6}$alkynyl, hydroxy, hydroxyC$_{1-6}$alkyl, —COOC$_{1-6}$alkyl, —(CH$_2$); —O—C$_{1-6}$alkyl, —(CH$_2$); —O-(hydroxyC$_{1-6}$alkyl), —C$_{1-6}$alkyl-NR$^x$R$^y$, —(CR$^x$R$^y$)$_p$—CONR$^x$R$^y$, —(CR$^x$R$^y$)$_p$—NR$^x$COR$^y$, —(CR$^x$R$^y$)$_p$—O—CH$_2$—CONR$^x$R$^y$, heterocyclic group with 3 to 7 ring members, —CH$_2$-heterocyclic group with 3 to 7 ring members, —CH$_2$—O-heterocyclic group with 3 to 7 ring members, —CH$_2$—NH-heterocyclic group with 3 to 7 ring members, —CH$_2$—N(C$_{1-6}$alkyl)-heterocyclic group with 3 to 7 ring members, —C(=O)NH-heterocyclic group with 3 to 7 ring members, $C_{3-8}$cycloalkyl, —CH$_2$—C$_{3-8}$cycloalkyl, —CH$_2$—O—C$_{3-8}$cycloalkyl, and $C_{3-8}$cycloalkenyl, wherein said cycloalkyl, cycloalkenyl or heterocyclic groups may be optionally substituted by one or more $R^z$groups, and wherein in each instance the heterocyclic group comprises one or more (e.g. 1, 2, or 3) heteroatoms selected from N, O, S and oxidised forms thereof;

or the $R^6$ and $R^7$ groups, together with the carbon atom to which they are attached, can join to form a $C_{3-6}$cycloalkyl or heterocyclyl group with 3 to 6 ring members, wherein the heterocyclic group comprises one or more (e.g. 1, 2, or 3) heteroatoms selected from N, O, S and oxidised forms thereof, and wherein said $C_{3-6}$cycloalkyl and heterocyclyl groups may be optionally substituted by one or more $R_z$ groups;

$R^x$ and $R^y$ are independently selected from hydrogen, halogen, nitro, nitrile, $C_{1-6}$alkyl, haloC$_{1-6}$alkyl, $C_{2-6}$alkenyl, $C_{2-6}$alkynyl, hydroxy, hydroxy$C_{1-6}$alkyl, $C_{1-6}$alkoxy, —$(CH_2)_k$—O—$C_{1-6}$alkyl, hydroxy$C_{1-6}$alkoxy, —COO$C_{1-6}$alkyl, —N(H)$_e$($C_{1-4}$alkyl)$_{2-e}$, —$C_{1-6}$ alkyl-N(H)$_e$($C_{1-4}$alkyl)$_{2-e}$, —$(CH_2)_k$—C(=O)N(H)$_e$($C_{1-4}$alkyl)$_{2-e}$, $C_{3-8}$cycloalkyl and $C_{3-8}$cycloalkenyl;

or the $R^x$ and $R^y$ groups, together with the carbon or nitrogen atom to which they are attached, can join to form a $C_{3-6}$cycloalkyl or saturated heterocyclyl group with 3 to 6 ring members which may be optionally fused to an aromatic heterocyclyl group of 3 to 5 ring members;

or when on a carbon atom the $R^x$ and $R^y$ groups can join together to form a =$CH_2$ group;

$R^z$ is independently selected from halogen, nitro, nitrile, $C_{1-6}$alkyl, halo$C_{1-6}$alkyl, $C_{2-6}$alkenyl, $C_{2-6}$alkynyl, =O, hydroxy, hydroxy$C_{1-6}$alkyl, $C_{1-6}$alkoxy, —$(CH_2)_k$—O—$C_{1-6}$alkyl, hydroxy$C_{1-6}$alkoxy, —C(=O)$C_{1-6}$alkyl, —C(=O)$C_{1-6}$alkyl-OH, —C(=O)$C_{1-6}$alkyl-N(H)$_e$ ($C_{1-4}$alkyl)$_{2-e}$, —C(=O)N(H)$_e$($C_{1-4}$alkyl)$_{2-e}$, —$(CH_2)_r$CO$_2$$C_{1-6}$alkyl, —$(CH_2)_r$CO$_2$H, —N(H)$_e$($C_{1-4}$alkyl)$_{2-e}$, —$C_{1-6}$alkyl-N(H)$_e$($C_{1-4}$alkyl)$_{2-e}$, heterocyclyl group with 3 to 6 ring members, heterocyclyl group with 3 to 6 ring members substituted by —C(=O)$C_{1-4}$alkyl, heterocyclyl group with 3 to 6 ring members substituted by —C(=O)O$C_{1-4}$alkyl, heterocyclyl group with 3 to 6 ring members substituted by —C(=O)N(H)$_e$($C_{1-4}$alkyl)$_{2-e}$, —C(=O)heterocyclyl group with 3 to 6 ring members, $C_{3-8}$cycloalkyl and $C_{3-8}$cycloalkenyl, wherein if $R^7$ is pyridine then $R^z$ is other then —$NH_2$;

j, e, r and p are independently selected from 0, 1 and 2; and k is selected from 1 and 2.

In one embodiment, $R^6$ and $R^7$ are independently selected from hydrogen, $C_{1-6}$alkyl, halo$C_{1-6}$alkyl, $C_{2-6}$alkenyl, $C_{2-6}$alkynyl, hydroxy, hydroxy$C_{1-6}$alkyl, —COO$C_{1-6}$alkyl, —$(CH_2)$; —O—$C_{1-6}$alkyl, —$(CH_2)$—O-(hydroxy$C_{1-6}$alkyl), —$C_{1-6}$alkyl-NR$^x$R$^y$, —(CR$^x$R$^y$)$_p$—CONR$^x$R$^y$, —(CR$^x$R$^y$)$_p$—NR$^x$COR$^y$, —(CR$^x$R$^y$)$_p$—O—CH$_2$—CONR$^x$R$^y$, heterocyclic group with 3 to 7 ring members, —CH$_2$-heterocyclic group with 3 to 7 ring members, —CH$_2$—O-heterocyclic group with 3 to 7 ring members, —CH$_2$—NH-heterocyclic group with 3 to 7 ring members, —CH$_2$—N($C_{1-6}$alkyl)-heterocyclic group with 3 to 7 ring members, —C(=O)NH-heterocyclic group with 3 to 7 ring members, $C_{3-8}$cycloalkyl, —CH$_2$—$C_{3-8}$cycloalkyl, —CH$_2$—O—$C_{3-8}$cycloalkyl, and $C_{3-8}$cycloalkenyl, wherein said cycloalkyl, cycloalkenyl or heterocyclic groups may be optionally substituted by one or more $R^z$ groups, and wherein in each instance the heterocyclic group comprises one or more (e.g. 1, 2, or 3) heteroatoms selected from N, O, S and oxidised forms thereof; In one embodiment $R^7$ is a cycloalkyl, cycloalkenyl or heterocyclic group optionally substituted by one or more $R^z$ selected from $C_{1-6}$alkyl (e.g. methyl), $C_{1-6}$alkoxy (e.g. methoxy) and —C(=O)$C_{1-6}$alkyl (e.g. —C(=O)CH$_3$).

In one embodiment $R^7$ is a cycloalkyl or cycloalkenyl group optionally substituted by one or more $R^z$ groups wherein $R^z$ is hydroxy.

$R^6$ and $R^7$ may be the same or different.

When $R^6$ and $R^7$ are different, the compound of formula (1°) can exist as at least two diastereoisomers:

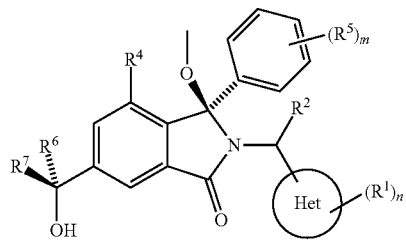

Diastereoisomer 2A

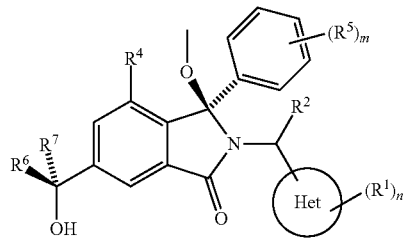

Diastereoisomer 2B

For the avoidance of doubt, the general formula (1°) and all subformulae cover both individual diastereoisomers and mixtures of the diastereoisomers which are related as epimers at the —CR$^6$R$^7$OH group.

In one embodiment of the compound of formula (1°) $R^6$ and $R^7$ are different and the compound is diastereoisomer 2A or a tautomer or a solvate or a pharmaceutically acceptable salt thereof.

In one embodiment of the compound of formula (1°) $R^6$ and $R^7$ are different and the compound is diastereoisomer 2B or a tautomer or a solvate or a pharmaceutically acceptable salt thereof.

In one embodiment, $R^6$ is methyl and the compound of formula (1°) is a compound of formula (Iv) or a tautomer or a solvate or a pharmaceutically acceptable salt thereof:

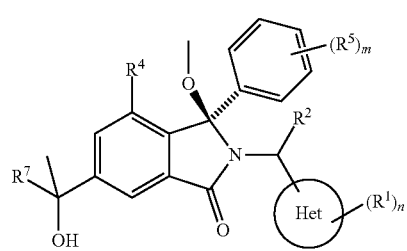

(Iv)

In one embodiment, $R^6$ is ethyl and the compound of formula (1°) is a compound of formula (Iv') or a tautomer or a solvate or a pharmaceutically acceptable salt thereof:

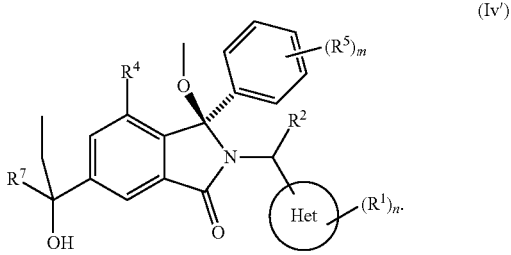

(Iv')

In one embodiment, R⁷ is selected from $C_{1-6}$alkyl or halo$C_{1-6}$alkyl. In one embodiment R⁷ is a $C_{3-6}$cycloalkyl (e.g. cyclopropyl, cyclobutyl or cyclohexyl) optionally substituted by one or more $R^z$ groups (e.g. —OH).

In one embodiment, R⁷ is selected from $C_{1-6}$alkyl, hydroxy$C_{1-6}$alkyl, —$(CH_2)_j$—O—$C_{1-6}$alkyl, —$(CH_2)_j$—O-(hydroxy$C_{1-6}$alkyl), —$C_{1-6}$alkyl-$NR^xR^y$ (e.g. —$C_{1-6}$alkyl-N(H)$_e$($C_{1-4}$alkyl)$_{2-e}$), —$(CR^xR^y)_p$—$NR^xCOR^y$, heterocyclic group with 3 to 7 ring members, —$CH_2$-heterocyclic group with 3 to 7 ring members, —$CH_2$—NH-heterocyclic group with 3 to 7 ring members, —$CH_2$—N($C_{1-6}$alkyl)-heterocyclic group with 3 to 7 ring members, —C(=O)NH-heterocyclic group with 3 to 7 ring members, $C_{3-8}$cycloalkyl, and —$CH_2$—$C_{3-8}$cycloalkyl, wherein said cycloalkyl or heterocyclic groups may be optionally substituted by one or more $R^z$ groups, and wherein in each instance the heterocyclic group comprises one or more (e.g. 1, 2, or 3) heteroatoms selected from N, O, S and oxidised forms thereof.

In one embodiment, R⁷ is selected from $C_{1-6}$alkyl, hydroxy$C_{1-6}$alkyl, —$(CH_2)_j$—O—$C_{1-6}$alkyl, —$(CH_2)$; —O-(hydroxy$C_{1-6}$alkyl), —$C_{1-6}$alkyl-N(H)$_e$($C_{1-4}$alkyl)$_{2-e}$, heterocyclic group with 3 to 7 ring members, —$CH_2$-heterocyclic group with 3 to 7 ring members, —$CH_2$—NH-heterocyclic group with 3 to 7 ring members, —$CH_2$—N($C_{1-6}$alkyl)-heterocyclic group with 3 to 7 ring members, —C(=O)NH-heterocyclic group with 3 to 7 ring members, $C_{3-8}$cycloalkyl, and —$CH_2$—$C_{3-8}$cycloalkyl, wherein said cycloalkyl or heterocyclic groups may be optionally substituted by one or more $R^z$ groups, and wherein in each instance the heterocyclic group comprises one or more (e.g. 1, 2, or 3) heteroatoms selected from N, O, S and oxidised forms thereof.

In one embodiment, R⁷ is selected from heterocyclic group with 3 to 7 ring members, —$CH_2$-heterocyclic group with 3 to 7 ring members, —$CH_2$—NH-heterocyclic group with 3 to 7 ring members, —$CH_2$—N($CH_3$)-heterocyclic group with 3 to 7 ring members, —C(=O)NH-heterocyclic group with 3 to 7 ring members, $C_{3-6}$cycloalkyl, and —$CH_2$—$C_{3-6}$cycloalkyl, wherein said cycloalkyl or heterocyclic groups may be optionally substituted by one or more $R^z$ groups, and wherein in each instance the heterocyclic group comprises one or more (e.g. 1, 2, or 3) heteroatoms selected from N, O, S and oxidised forms thereof.

In one embodiment, R⁷ is selected from heterocyclic group with 3 to 7 ring members and —$CH_2$-heterocyclic group with 3 to 7 ring members, wherein said heterocyclic groups may be optionally substituted by one or more $R^z$ groups, and wherein in each instance the heterocyclic group comprises one or more (e.g. 1, or 2) heteroatoms selected from N, O, S and oxidised forms thereof.

In embodiment, the heterocyclic group is saturated. In one embodiment, R⁷ is saturated heterocyclic group with 3 to 6 ring members or —$CH_2$-(saturated heterocyclic group with 3 to 6 ring members) such as wherein the heterocyclic group is selected from oxetanyl, oxanyl, piperidinyl, piperazinyl, morpholinyl, pyrrolidinyl, imidazolinyl, azetidinyl, thiomorpolinyl, such as oxanyl, piperdinyl or piperazinyl.

In one embodiment, R⁷ is selected from saturated heterocyclic group with 3 to 6 ring members and —$CH_2$-saturated heterocyclic group with 3 to 6 ring members, wherein said heterocyclic groups may be optionally substituted by one or more $R^z$ groups, and wherein in each instance the heterocyclic group comprises one or more (e.g. 1, 2, or 3) heteroatoms selected from N, O, S. In one embodiment, R⁷ is selected from a nitrogen containing saturated heterocyclic group with 3 to 6 ring member and —$CH_2$-(nitrogen containing saturated heterocyclic group with 3 to 6 ring members), wherein said heterocyclic groups may be optionally substituted by one or more $R^z$ groups, and wherein the heterocyclic group may optionally contain one or more (e.g. 1, 2, or 3) additional heteroatoms selected from N, O, S.

In one embodiment, R⁷ is nitrogen containing saturated heterocyclic group with 3 to 7 ring members or —$CH_2$-(nitrogen containing saturated heterocyclic group with 3 to 7 ring members), wherein said nitrogen containing saturated heterocyclic groups may be optionally substituted by one or more $R^z$ groups and wherein the nitrogen containing saturated heterocyclic group may optionally contain one or more (e.g. 1, 2, or 3) additional heteroatoms selected from N, O, S. In one embodiment the nitrogen containing saturated heterocyclic group with 3 to 7 ring members (such as 3 to 6 ring members) is selected from piperidinyl, piperazinyl, morpholinyl, pyrrolidinyl, imidazolinyl, azetidinyl, thiomorpolinyl, such as piperdinyl or piperazinyl.

In one embodiment, R⁷ is nitrogen containing aromatic heterocyclic group with 3 to 6 ring members or —$CH_2$-(nitrogen containing aromatic heterocyclic group with 3 to 6 ring members), wherein said heterocyclic groups may be optionally substituted by one or more $R^z$ groups and wherein the heterocyclic group may optionally contain one or more (e.g. 1, 2, or 3) additional heteroatoms selected from N, O, S.

In another embodiment, R⁷ is nitrogen containing aromatic heterocyclic group with 3 to 6 ring members, wherein said heterocyclic group may be unsubstituted or substituted by one or more $R^z$ groups, for example selected from halogen (e.g. fluorine), $C_{1-6}$alkyl (e.g. methyl), $C_{1-6}$alkoxy (e.g. methoxy), and —C(=O)$C_{1-6}$alkyl (e.g. —C(=O) $CH_3$).

In one embodiment, R⁷ is oxygen containing aromatic heterocyclic group with 3 to 6 ring members or —$CH_2$-(oxygen containing aromatic heterocyclic group with 3 to 6 ring members), wherein said heterocyclic groups may be optionally substituted by one or more $R^z$ groups and wherein the heterocyclic group may optionally contain one or more (e.g. 1, 2, or 3) additional heteroatoms selected from N, O, S.

In another embodiment, R⁷ is oxygen containing aromatic heterocyclic group with 3 to 6 ring members, wherein said heterocyclic group may be unsubstituted or substituted by one or more $R^z$ groups, for example $R^z$ groups selected from halogen (e.g. fluorine), $C_{1-6}$alkyl (e.g. methyl), $C_{1-6}$alkoxy (e.g. methoxy), and —C(=O)$C_{1-6}$alkyl (e.g. —C(=O) $CH_3$).

In one embodiment R⁷ is selected from heterocyclyl groups containing 5 or 6 ring members optionally substituted by one or more $R^z$.

In one embodiment R⁷ is selected from aromatic heterocyclyl groups containing 5 ring members optionally substituted by one or more $R^z$. In one embodiment R⁷ is selected from an aromatic nitrogen containing (e.g. diaza) heteterocyclyl group containing 5 ring members optionally substituted by one or more $R^z$. In one embodiment $R^7$ is pyrazolyl (e.g. pyrazol-4-yl or pyrazol-3-yl).

In one embodiment $R^7$ is selected from a saturated heterocyclyl group containing 6 ring members optionally substituted by one or more $R^z$. In one embodiment $R^7$ is selected from a saturated oxygen or nitrogen containing heteterocyclyl group containing 6 ring members optionally substituted by one or more $R^z$.

In one embodiment $R^7$ is selected from oxanyl, piperidinyl, pyrazolyl or imidazolyl optionally substituted by one or more $R^z$. In one embodiment $R^7$ is selected from oxanyl, piperidinyl, pyrazolyl or imidazolyl optionally substituted by one or more $R^z$, where $R^z$ is selected from halo (e.g. —F) or $C_{1-4}$alkyl (e.g. methyl).

In one embodiment $R^7$ is selected from oxanyl (also known as tetrahydropyranyl) or piperidinyl optionally substituted by one or more $R^z$. In one embodiment $R^7$ is selected from oxanyl or piperidinyl unsubstituted or substituted by one or more $R^z$, where $R^z$ is selected from halo (e.g. —F) or $C_{1-4}$alkyl (e.g. methyl), in particular halo (e.g. —F).

In one embodiment, $R^7$ is $C_{3-8}$cycloalkyl such as $C_{3-6}$cycloalkyl (e.g. cyclobutyl or cyclohexyl) optionally substituted by one or more $R^z$, for example where $R^z$ is hydroxy. In one embodiment, $R^7$ is cyclohexyl optionally substituted by one or more hydroxy. In one embodiment $R^7$ is cyclohexyl optionally substituted by one or more hydroxyl, in the trans stereochemistry (e.g. trans-4-hydroxycyclohexane).

In one embodiment $R^7$ is selected from —$CH_2$—NH-heterocyclic group with 3 to 7 ring members (e.g. —$CH_2$—NH-oxanyl and —$CH_2$—N($C_{1-6}$alkyl)-heterocyclic group with 3 to 7 ring members (e.g. —$CH_2NCH_3$-(piperidinyl) optionally substituted by one or more $R^z$ groups (e.g. methyl, —$COCH_3$).

In one embodiment, $R^7$ is —$(CR^xR^y)_p$—$CONR^xR^y$ or —$C(=O)NH$-heterocyclic group with 3 to 7 ring members. In one embodiment, $R^7$ is —$C(=O)NH$-heterocyclic group with 4 to 6 ring members (e.g. piperidinyl, pyrazolyl, or azetidinyl).

In one embodiment, $R^7$ is —$(CR^xR^y)_p$—$CONR^xR^y$. In one embodiment $R^7$ is —$(CR^xR^y)_p$—$CONH(C_{1-4}$alkyl), in particular —$(CO)NHCH_3$, —$(CO)NHCH_2CH_3$ or —$(CO)NH(CH(CH_3)_2)$.

In one embodiment $R^7$ is —$C(=O)NH$-heterocyclic group with 3 to 7 ring members (e.g. —$C(=O)NH$-piperidinyl, —$C(=O)NH$-azetidinyl or —$C(=O)NH$-pyrazolyl) optionally substituted by one or more $R^z$ groups (e.g. methyl, —$COCH_3$).

In one embodiment, $R^7$ is —$C_{1-6}$alkyl-$NR^xR^y$ (e.g. —$C_{1-6}$alkyl-$N(H)_e(C_{1-4}$alkyl)$_{2-e}$). In one embodiment $R^7$ is —$CH_2NH_2$, —$CH_2NHCH_3$, or —$CH_2N(CH_3)_2$. In one embodiment $R^7$ is —$C_{1-6}$alkyl-$NR^xR^y$ wherein $R^x$ is $C_{3-8}$cycloalkyl. In one embodiment $R^7$ is —$C_{1-2}$alkyl-NH—$C_{3-6}$cycloalkyl (e.g. —$CH_2$—NH-cyclopropyl).

In one embodiment, $R^7$ is —$C_{1-6}$alkyl-$NR^xR^y$ wherein the $R^x$ and $R^y$ groups, together with the nitrogen atom to which they are attached, can join to form a $C_{3-6}$cycloalkyl or heterocyclyl group with 3 to 6 ring members. In one embodiment, $R^x$ and $R^y$ together form a saturated heterocyclyl group with 3 to 6 ring members e.g. piperazinyl.

In one embodiment $R^7$ is —$C_{1-6}$alkyl-$NR^xR^y$, wherein the $R^x$ and $R^y$ groups, together with the nitrogen atom to which they are attached, join to form a $C_{3-8}$cycloalkyl or saturated heterocyclyl group with 3 to 6 ring members which may be optionally fused to an aromatic heterocyclyl group of 3 to 5 ring members. In one embodiment $R^7$ is —$C_{1-6}$alkyl-$NR^xR^y$, wherein the $R^x$ and $R^y$ groups, together with the nitrogen atom to which they are attached, join to form a saturated heterocyclyl group with 3 to 6 ring members which is fused to an aromatic heterocyclyl group of 3 to 5 ring members. $R^z$ is independently selected from halogen, nitro, nitrile, $C_{1-6}$alkyl, halo$C_{1-6}$alkyl, $C_{2-6}$alkenyl, $C_{2-6}$alkynyl, =O, hydroxy, hydroxy$C_{1-6}$alkyl, $C_{1-6}$alkoxy, —$(CH_2)_k$—O—$C_{1-6}$alkyl, hydroxy$C_{1-6}$alkoxy, —$C(=O)C_{1-6}$alkyl, —$C(=O)C_{1-6}$alkyl-OH, —$C(=O)C_{1-6}$alkyl-$N(H)_e(C_{1-4}$alkyl)$_{2-e}$, —$C(=O)N(H)_e(C_{1-4}$alkyl)$_{2-e}$, —$(CH_2)_r$—$CO_2C_{1-6}$alkyl, —$(CH_2)_r$—$CO_2H$, —$N(H)_e(C_{1-4}$alkyl)$_{2-e}$, —$C_{1-6}$alkyl-$N(H)_e(C_{1-4}$alkyl)$_{2-e}$, heterocyclyl group with 3 to 6 ring members, heterocyclyl group with 3 to 6 ring members substituted by —$C(=O)C_{1-4}$alkyl, heterocyclyl group with 3 to 6 ring members substituted by —$C(=O)OC_{1-4}$alkyl, heterocyclyl group with 3 to 6 ring members substituted by —$C(=O)N(H)_e(C_{1-4}$alkyl)$_{2-e}$, —$C(=O)$heterocyclyl with 3 to 6 ring members, $C_{3-8}$cycloalkyl and $C_{3-8}$cycloalkenyl.

In one embodiment $R^z$ is independently selected from halogen (e.g. fluorine), $C_{1-6}$alkyl (e.g. methyl), $C_{1-6}$alkoxy (e.g. methoxy), and —$C(=O)C_{1-6}$alkyl (e.g. —$C(=O)CH_3$).

In one embodiment $R^z$ is independently selected from $C_{1-6}$alkyl (e.g. methyl), $C_{1-6}$alkoxy (e.g. methoxy), and —$C(=O)C_{1-6}$alkyl (e.g. —$C(=O)CH_3$).

In one embodiment, $R^7$ is $C_{1-6}$alkyl (e.g. methyl or ethyl), halo$C_{1-6}$alkyl (e.g. trifluoromethyl), $C_{2-6}$alkenyl (e.g. $C_2$alkenyl), hydroxy$C_{1-6}$alkyl (e.g. —$CH_2OH$, —$CH_2CH_2OH$), —$C_{1-6}$alkyl-$NR^xR^y$ (e.g. —$CH_2NH_2$, —$CH_2NHCH_3$, —$CH_2N(CH_3)_2$, or —$CH_2$—NH-cyclopropyl), —$(CR^xR^y)_p$—$CONR^xR^y$(e.g. —$(CO)NHCH_3$, —$(CO)NHCH_2CH_3$, —$(CO)NHCH_2CH_2NH_2$ or —$(CO)NH(CH(CH_3)_2)$, —$(CH_2)_j$—O—$C_{1-6}$alkyl (e.g. —$CH_2OCH_3$, —$CH_2OCH_2CH_3$ or —$CH_2OCD_3$), —$(CR^xR^y)_p$—$NR^xCOR^y$ (e.g. —$CH_2NHCOCH_3$), —$(CR^xR^y)_p$—O—$CH_2$—$CONR^xR^y$(e.g. —$CH_2$—O—$CH_2CON(CH_3)_2$), —$(CH_2)_j$—O-(hydroxy$C_{1-6}$alkyl) (e.g. —$CH_2$—O—$CH_2CH_2OH$,), —$C(=O)NH$-heterocyclic group with 3 to 7 ring members, $C_{3-8}$cycloalkyl, heterocyclic group with 3 to 7 ring members (e.g. oxanyl), or —$CH_2$-heterocyclic group with 3 to 7 ring members wherein the cycloalkyl or heterocyclic group comprises one or more (e.g. 1, 2, or 3) heteroatoms selected from N, O, S and oxidised forms and may be optionally substituted by one or more $R^z$ groups (for example selected from $C_{1-6}$alkyl (e.g. methyl), $C_{1-6}$alkoxy (e.g. methoxy) and —$C(=O)C_{1-6}$alkyl (e.g. —$C(=O)CH_3$)). In one embodiment, $R^6$ is methyl or ethyl and $R^7$ is $C_{1-6}$alkyl (e.g. methyl), hydroxy$C_{1-6}$alkyl, —$C_{1-6}$alkyl-$NR^xR^y$, —$(CR^xR^y)_p$—$CONR^xR^y$, —$(CH_2)_j$—O—$C_{1-6}$alkyl, —$(CR^xR^y)_p$—$NR^xCOR^y$, —$(CR^xR^y)_p$—O—$CH_2$—$CONR^xR^y$, —$(CH_2)_j$—O-(hydroxy$C_{1-6}$alkyl), heterocyclic group with 3 to 7 ring members (e.g. oxanyl), or —$CH_2$-heterocyclic group with 3 to 7 ring members wherein the heterocyclic group comprises one or more (e.g. 1, 2, or 3) heteroatoms selected from N, O, S and oxidised forms and may be optionally substituted by one or more $R^z$ groups selected from $C_{1-6}$alkyl (e.g. methyl), $C_{1-6}$alkoxy (e.g. methoxy) and —$C(=O)C_{1-6}$alkyl (e.g. —$C(=O)CH_3$).

In one embodiment, $R^6$ is selected from hydrogen, $C_{1-6}$alkyl (e.g. —$CH_3$, —$CH_2CH_3$ or —$CH_2CH_2CH_3$), $C_{2-6}$alkenyl (e.g. —$CH=CH_2$) and halo$C_{1-6}$alkyl (e.g. —$CF_3$).

In one embodiment, $R^6$ is selected from hydrogen, $C_{1-6}$alkyl (e.g. —$CH_3$ or —$CH_2CH_3$), $C_{2-6}$alkenyl (e.g. —$CH=CH_2$) and halo$C_{1-6}$alkyl (e.g. —$CF_3$).

In one embodiment, $R^7$ is $C_{1-6}$alkyl (e.g. —$CH_3$ or —$CH_2CH_3$), $C_{3-8}$cycloalkyl (e.g. cyclopropyl, cyclobutyl or cyclohexyl), $C_{2-6}$alkenyl (e.g. —$CH=CH_2$), halo$C_{1-6}$alkyl (e.g. —$CF_3$), hydroxy$C_{1-6}$alkyl (e.g. —$CH_2OH$ or —CH$_2$CH$_2$OH), —C$_{1-6}$alkyl-NR$^x$R$^y$ (e.g. —CH$_2$NH$_2$, —CH$_2$N(CH$_3$)$_2$, —CH$_2$NHCH$_3$, or —CH$_2$NH(cyclopropyl)), —(CR$^x$R$^y$)$_p$—CONR$^x$R$^y$(e.g. —C(=O)NHCH$_3$, —(CO)NHCH$_2$CH$_3$, —(CO)NHCH$_2$CH$_2$NH$_2$, —C(=O)NH(CH(CH$_3$)$_2$)), or —(CH$_2$)—O—C$_{1-6}$alkyl (e.g. —CH$_2$OCH$_3$, —CH$_2$OCH$_2$CH$_3$ or —CH$_2$OCD$_3$), —(CR$^x$R$^y$)$_p$—NR$^x$COR$^y$ (e.g. —CH$_2$NHC(=O)CH$_3$), —(CR$^x$R$^y$)$_p$—O—CH$_2$—CONR$^x$R$^y$(e.g. —CH$_2$OCH$_2$C(=O)N(CH$_3$)$_2$), —(CH$_2$)$_f$—O-(hydroxyC$_{1-6}$alkyl) (e.g. —CH$_2$OCH$_2$CH$_2$OH), heterocyclic group with 3 to 7 ring members e.g.

(point of attachment represented by dashed bond):

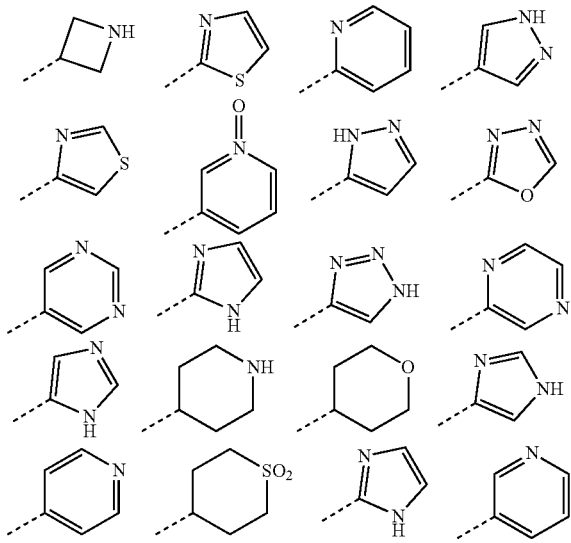

or —CH$_2$-heterocyclic group with 3 to 7 ring members e.g. (point of attachment represented by dashed bond)

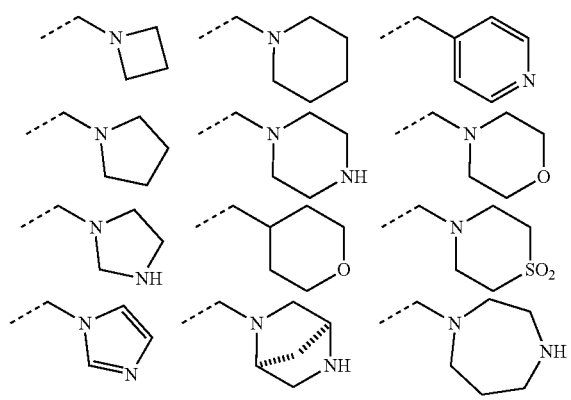

wherein when the moiety R$^7$ comprises a heterocyclic group, the heterocyclic group may be optionally substituted by one or more R$^z$ groups selected from C$_{1-6}$alkyl (e.g. methyl), hydroxyalkyl (e.g. —CH$_2$CH$_2$OH), halogen (e.g. fluoro), =O, C$_{1-6}$alkoxy (e.g. methoxy), —C(=O)C$_{1-6}$alkyl (e.g. —C(=O)CH$_3$), —C(=O)hydroxyC$_{1-6}$alkyl (e.g. —C(=O)CH$_2$OH), heterocyclyl group with 3 to 6 ring members (e.g. oxetanyl or pyrimidinyl), and —S(O)$_d$—C$_{1-4}$alkyl wherein d is selected from 0, 1 and 2 (e.g. —SO$_2$—CH$_3$).

In one embodiment, R$^7$ is C$_{1-6}$alkyl (e.g. —CH$_3$ or —CH$_2$CH$_3$), C$_{3-8}$cycloalkyl (e.g. cyclopropyl, cyclobutyl or cyclohexyl), C$_{2-6}$alkenyl (e.g. —CH=CH$_2$), haloC$_{1-6}$alkyl (e.g. —CF$_3$), hydroxyC$_{1-6}$alkyl (e.g. —CH$_2$OH or —CH$_2$CH$_2$OH), —C$_{1-6}$alkyl-NR$^x$R$^y$(e.g. —CH$_2$NH$_2$, —CH$_2$N(CH$_3$)$_2$, —CH$_2$NHCH$_3$, or —CH$_2$NH(cyclopropyl)), —(CR$^x$R$^y$)$_p$—CONR$^x$R$^y$(e.g. —C(=O)NHCH$_3$, —(CO)NHCH$_2$CH$_3$, —(CO)NHCH$_2$CH$_2$NH$_2$, —C(=O)NH(CH(CH$_3$)$_2$)), or —(CH$_2$); —O—C$_{1-6}$alkyl (e.g. —CH$_2$OCH$_3$, —CH$_2$OCH$_2$CH$_3$ or —CH$_2$OCD$_3$), —(CR$^x$R$^y$)$_p$—NR$^x$COR$^y$ (e.g. —CH$_2$NHC(=O)CH$_3$), —(CR$^x$R$^y$)$_p$—O—CH$_2$—CONR$^x$R$^y$(e.g. —CH$_2$OCH$_2$C(=O)N(CH$_3$)$_2$), —(CH$_2$); —O-(hydroxyC$_{1-6}$alkyl) (e.g. —CH$_2$OCH$_2$CH$_2$OH), heterocyclic group with 3 to 7 ring members e.g.

(point of attachment represented by dashed bond):

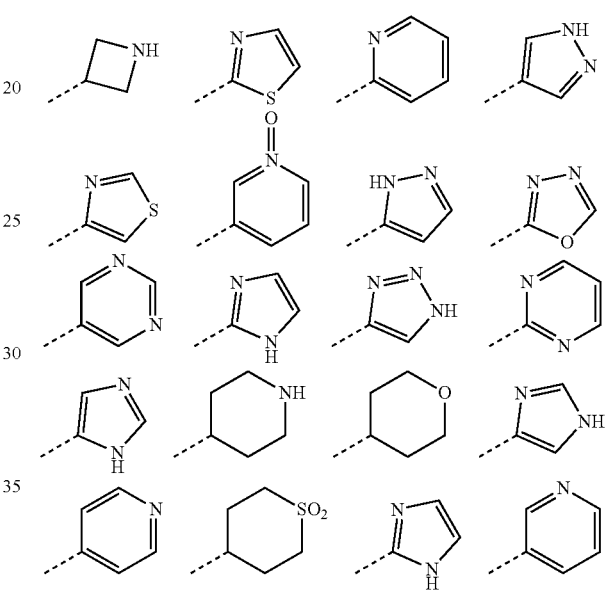

or —CH$_2$-heterocyclic group with 3 to 7 ring members e.g. (point of attachment represented by dashed bond)

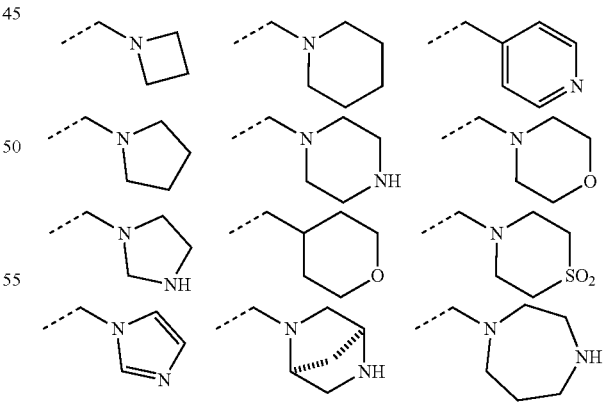

wherein when the moiety R$^7$ comprises a heterocyclic group, the heterocyclic group may be optionally substituted by one or more R$^z$ groups selected from C$_{1-6}$ alkyl (e.g. methyl), halogen (e.g. fluoro), =O, C$_{1-6}$ alkoxy (e.g. methoxy), —C(=O)C$_{1-6}$ alkyl (e.g. —C(=O)CH$_3$), —C(=O)hydroxyC$_{1-6}$ alkyl (e.g. —C(=O)CH$_2$OH), heterocyclyl group with 3 to 6 ring members (e.g. pyrimidinyl), and —S(O)$_d$—C$_{1-4}$alkyl wherein d is selected from 0, 1 and 2 (e.g. —SO$_2$—CH$_3$).

In one embodiment of formula (1°) R$^7$ is a heterocyclic group with 3 to 7 ring members optionally substituted by one or more R$^z$ groups e.g.

(point of attachment represented by dashed bond)

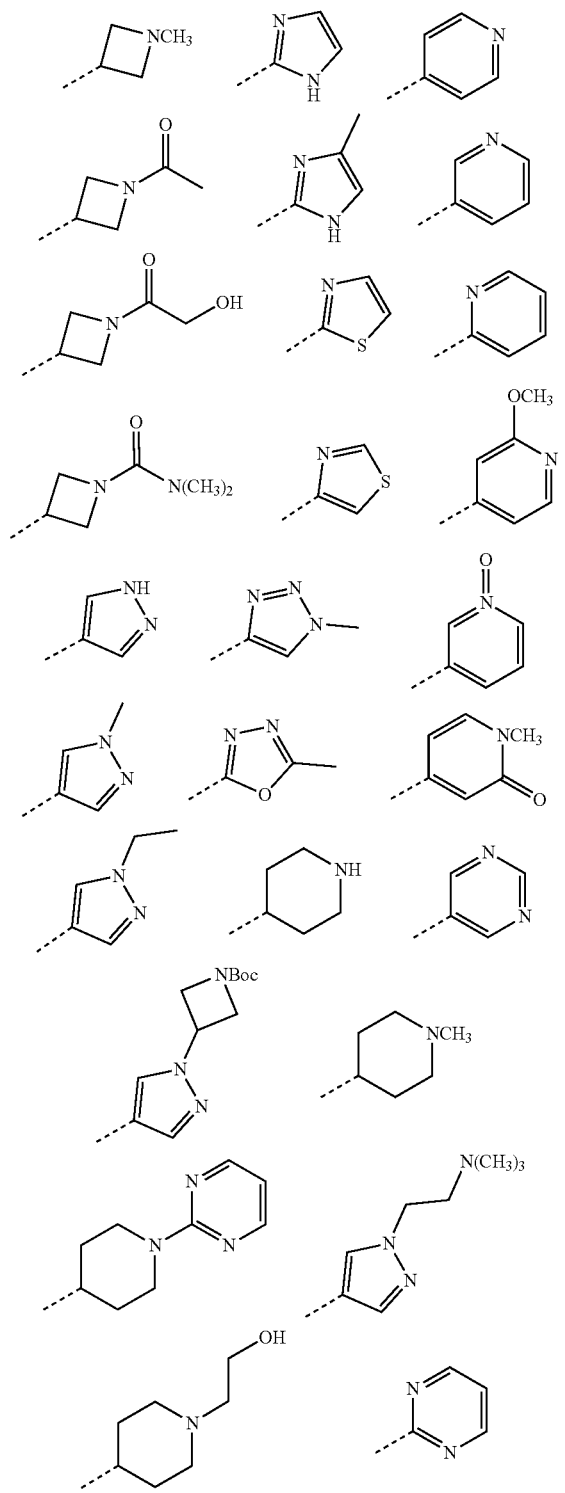

-continued

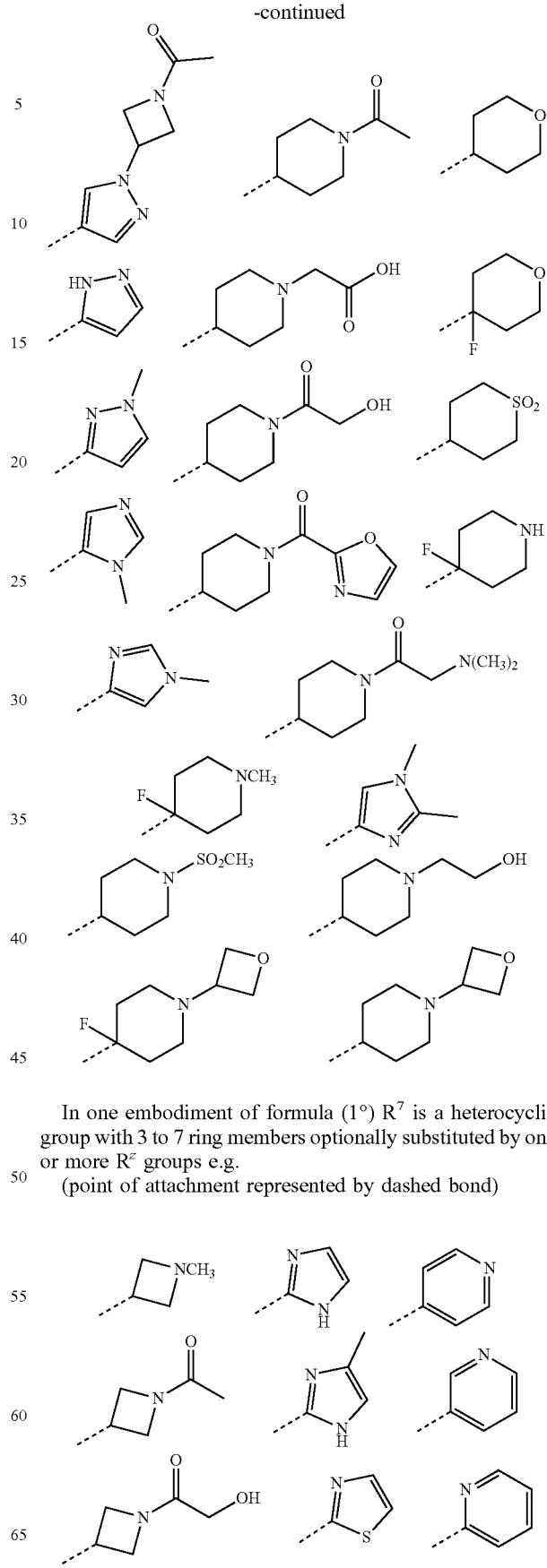

In one embodiment of formula (1°) R$^7$ is a heterocyclic group with 3 to 7 ring members optionally substituted by one or more R$^z$ groups e.g.

(point of attachment represented by dashed bond)

79
-continued
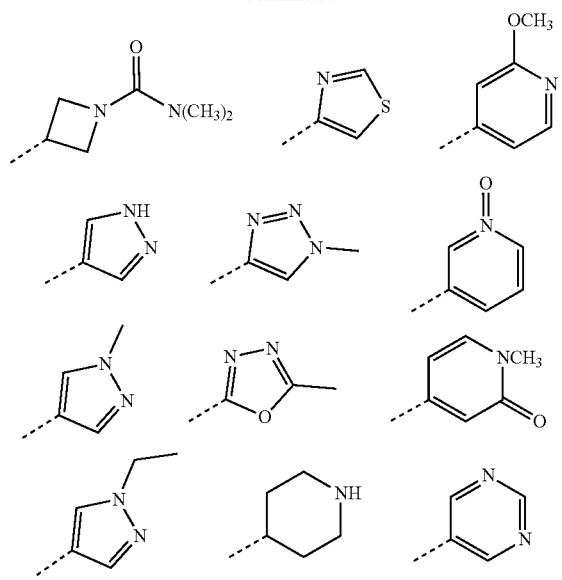
80
-continued
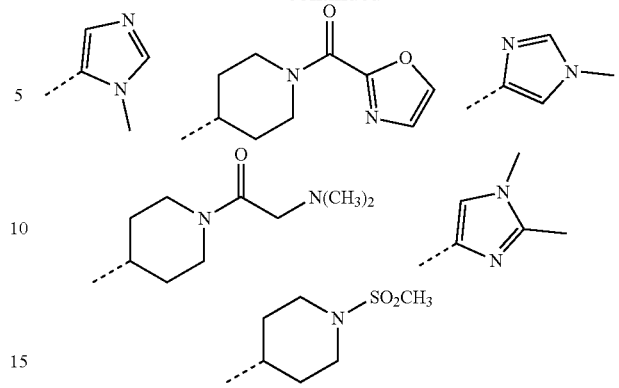
In one embodiment, $R^7$ is a —$CH_2$-heterocyclic group with 3 to 7 ring members optionally substituted by by one or more $R^z$ groups e.g.
(point of attachment represented by dashed bond)
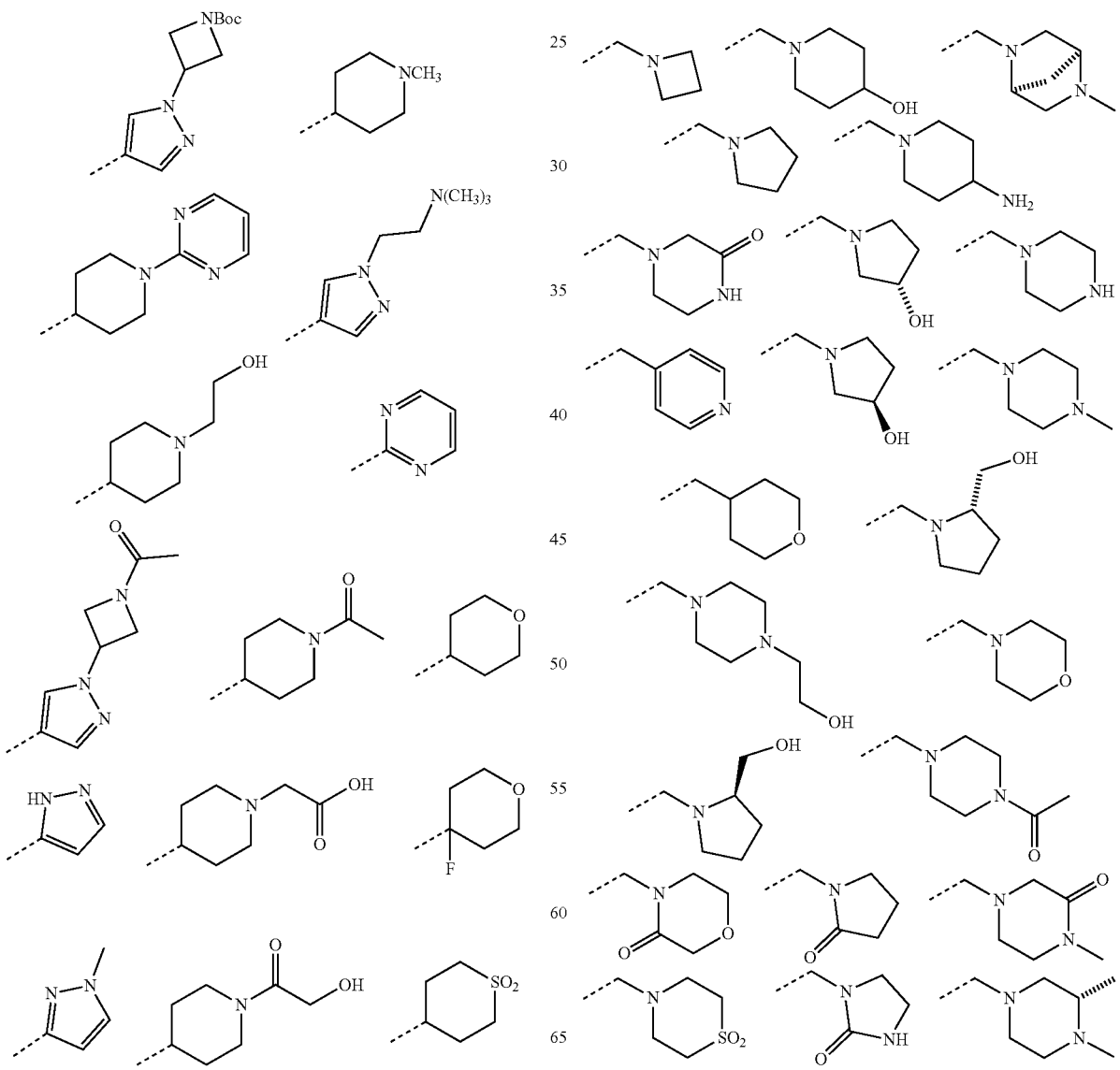

-continued

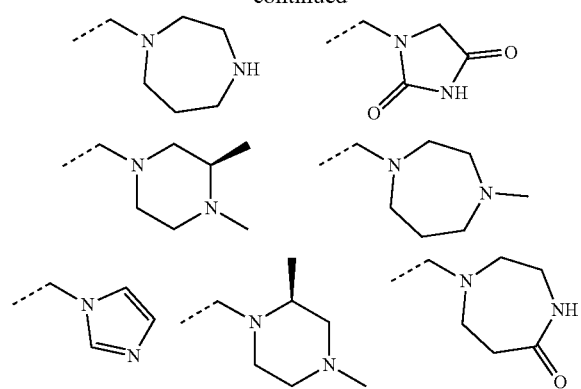

In one embodiment R⁷ is selected from:
(point of attachment represented by dashed bond):

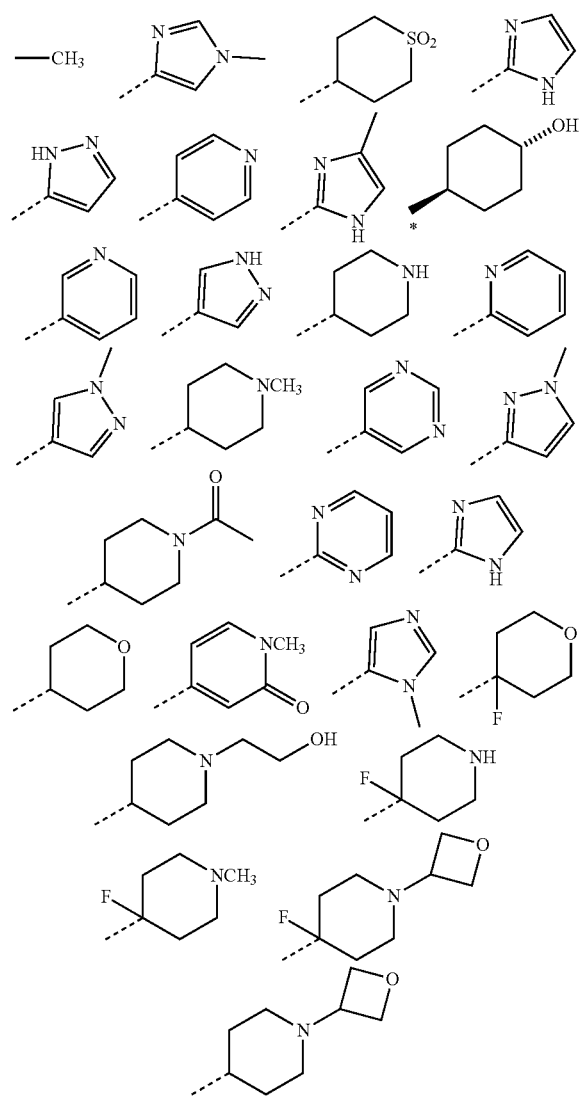

In one embodiment R⁷ is selected from:
(point of attachment represented by dashed bond):

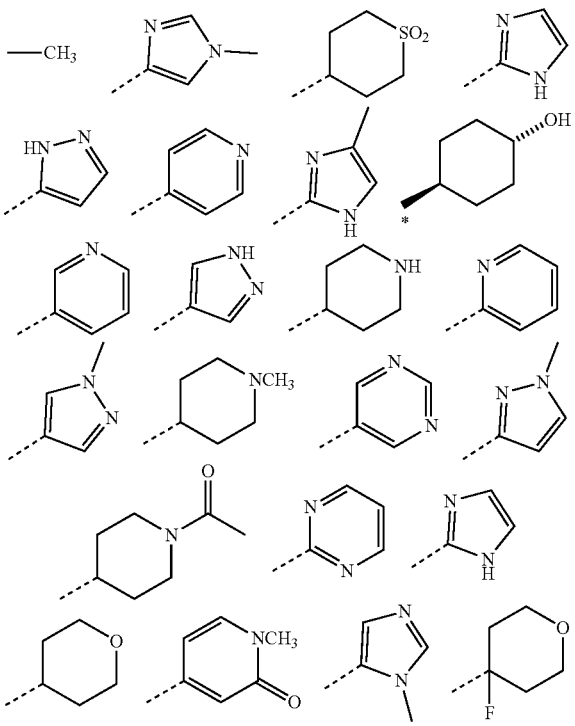

In one embodiment R⁷ is selected from:
(point of attachment represented by dashed bond):

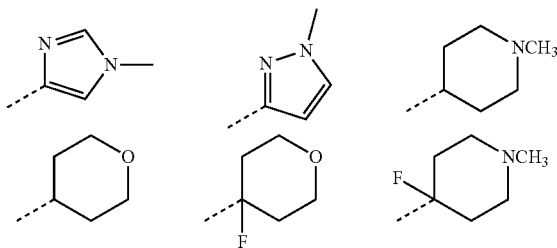

In one embodiment R⁷ is selected from:
(point of attachment represented by dashed bond):

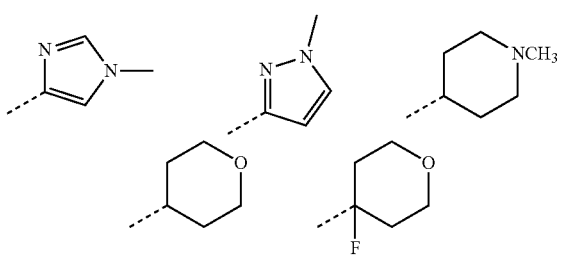

In one embodiment, $R^6$ is hydrogen or $C_{1-6}$alkyl (such as —CH$_3$, —CH$_2$CH$_3$ or —CH$_2$CH$_2$CH$_3$, e.g. —CH$_3$ or —CH$_2$CH$_3$). In one embodiment, $R^6$ is $C_{1-6}$alkyl. In one embodiment, $R^6$ is methyl or ethyl. In one embodiment, $R^6$ is ethyl.

In one embodiment, $R^6$ is $C_{1-6}$alkyl (such as methyl or ethyl e.g. methyl) and $R^7$ is selected from hydroxyC$_{1-6}$alkyl and —(CH$_2$)—O—C$_{1-6}$alkyl, In one embodiment, $R^6$ is methyl and $R^7$ is selected from methyl, —CH$_2$—OH and —CH$_2$—OCH$_3$. In one embodiment $R^6$ is methyl and $R^7$ is methyl, ethyl, or propyl.

In one embodiment $R^6$ is methyl and $R^7$ is methyl.

In one embodiment, $R^6$ is C$_{1-6}$alkyl or haloC$_{1-6}$alkyl (e.g. methyl, monofluoromethyl, trifluoromethyl or ethyl).

In one embodiment, $R^6$ is C$_{3-8}$cycloalkyl such as C$_{3-6}$cycloalkyl (e.g. cyclopropyl).

In one embodiment $R^6$ is C$_{1-6}$alkyl (e.g. —CH$_3$, —CH$_2$CH$_3$ or —CH$_2$CH$_2$CH$_3$ such as methyl or ethyl e.g. ethyl) and $R^7$ is selected from:

(point of attachment represented by dashed bond or bond terminus marked "*")

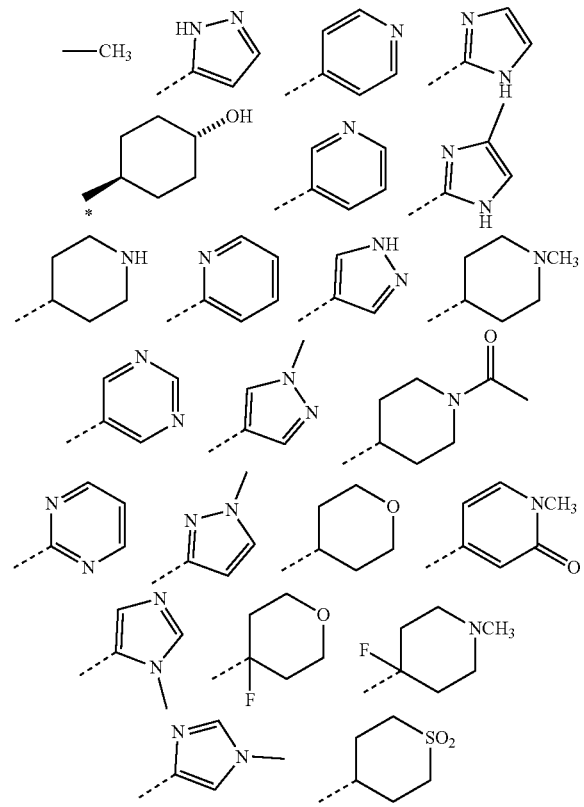

In one embodiment $R^6$ is C$_{1-6}$alkyl (e.g. —CH$_3$, —CH$_2$CH$_3$ or —CH$_2$CH$_2$CH$_3$ such as methyl or ethyl e.g. ethyl) and $R^7$ is selected from:

(point of attachment represented by dashed bond or bond terminus marked "*"):

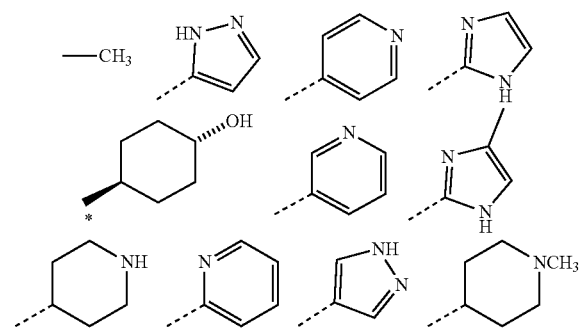

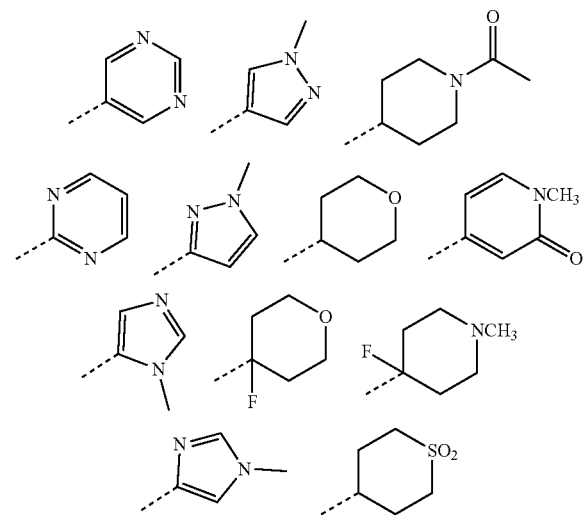

In particular, $R^7$ is:

(point of attachment represented by dashed bond):

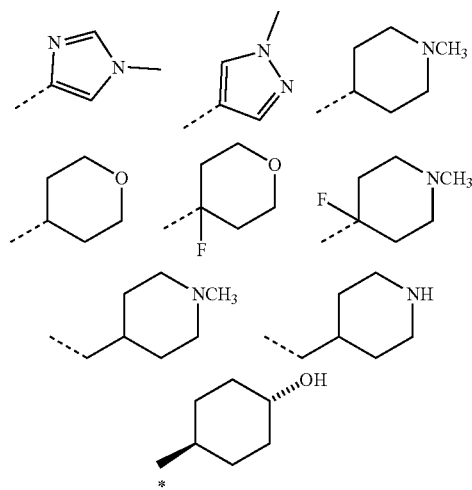

In particular, $R^7$ is:

(point of attachment represented by dashed bond):

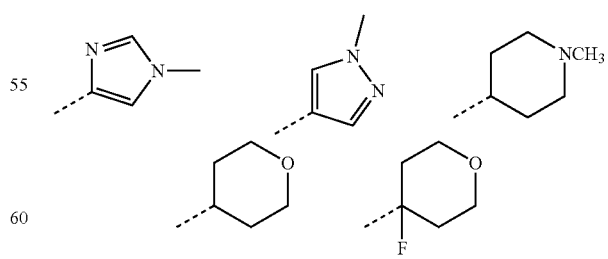

In one embodiment, $R^6$ is C$_{1-6}$alkyl (e.g. —CH$_3$, —CH$_2$CH$_3$ or —CH$_2$CH$_2$CH$_3$) such as methyl or ethyl e.g. methyl) and $R^7$ is oxanyl, and the compound of formula (1°) is a compound of formula (Iw):

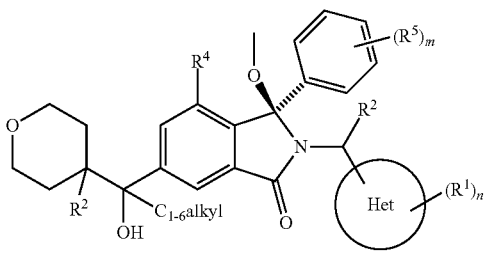

(Iw)

In one embodiment of formula (Iw) $R_z$ is hydrogen or fluorine.

In one embodiment, $R^7$ is imidazolyl and the compound of formula (1°) is a compound of formula (Ix) or a tautomer or a solvate or a pharmaceutically acceptable salt thereof:

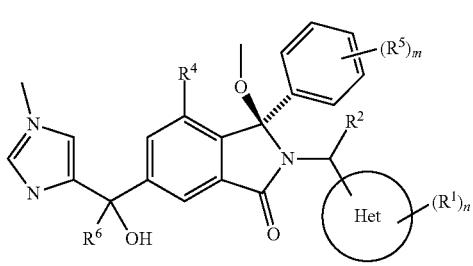

(Ix)

In one embodiment, $R^7$ is N-methyl piperidinyl and the compound of formula (1°) is a compound of formula (Ix') or a tautomer or a solvate or a pharmaceutically acceptable salt thereof:

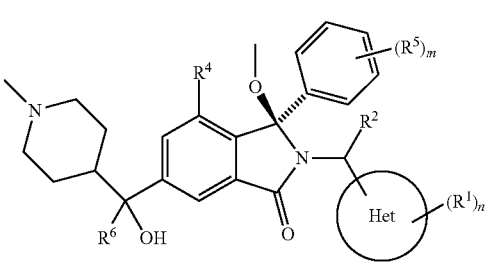

(Ix')

In one embodiment, $R^7$ is 4-fluoro-1-methylpiperidin-4-yl and the compound of formula (1°) is a compound of formula (Ix") or a tautomer or a solvate or a pharmaceutically acceptable salt thereof:

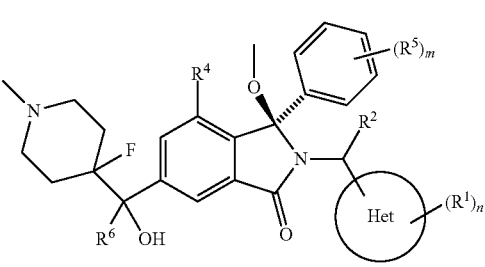

(Ix")

In one embodiment, $R^7$ is pyrazolyl optionally substituted by one or more $R^z$ groups (e.g. methyl). In one embodiment, $R^7$ is N-methylpyrazol-3-yl or N-methylpyrazol-4-yl.

In one embodiment, $R^7$ is selected from methyl, oxanyl, pyrazolyl, imidazolyl, piperidinyl, and cyclohexyl wherein said cycloalkyl and heterocyclic groups are optionally substituted by one or more $R^z$ groups (e.g. methyl, fluorine, or hydroxyl).

In one embodiment, $R^7$ is selected from piperidinyl optionally substituted by one or more $R^z$ groups (e.g. methyl, fluorine, or hydroxyl, in particular methyl and fluorine).

In one embodiment, the compound of formula (1°) is a compound of formula (Ix) and $R^6$ is $C_{1-4}$alkyl.

In one embodiment, $R^6$ is $C_{1-6}$alkyl (e.g. —$CH_3$, —$CH_2CH_3$ or —$CH_2CH_2CH_3$ such as methyl or ethyl e.g. ethyl) and $R^7$ is a heterocyclic group with 3 to 7 ring members optionally substituted by one or more $R^z$ groups.

In one embodiment, $R^6$ is $C_{1-6}$alkyl (e.g. —$CH_3$, —$CH_2CH_3$ or —$CH_2CH_2CH_3$ such as methyl or ethyl e.g. ethyl) and $R^7$ is imidazolyl optionally substituted by one or more $R^z$ groups (e.g. methyl imidazolyl).

In one embodiment, $R^6$ is $C_{1-6}$alkyl (e.g. —$CH_3$, —$CH_2CH_3$ or —$CH_2CH_2CH_3$ such as methyl or ethyl e.g. ethyl) and $R^7$ is piperidinyl optionally substituted by one or more $R^z$ groups (e.g. methyl piperidinyl).

In one embodiment $R^6$ is $C_{1-6}$alkyl (e.g. —$CH_3$, —$CH_2CH_3$ or —$CH_2CH_2CH_3$ such as methyl or ethyl e.g. ethyl) and $R^7$ is $C_{1-4}$alkyl, hydroxyl$C_{1-4}$alkyl, methoxy$C_{1-4}$alkyl, a heterocyclic group with 5 or 6 ring members or $C_{3-6}$cycloalkyl, wherein the heterocyclic group or $C_{3-6}$cycloalkyl group is optionally substituted by one or more $R^z$ (e.g. methyl, halogen (such as fluorine), C(=O)Me, or —OH).

In one embodiment $R^6$ is $C_{1-6}$alkyl (e.g. —$CH_3$, —$CH_2CH_3$ or —$CH_2CH_2CH_3$ such as methyl or ethyl e.g. ethyl) and $R^7$ is methyl, ethyl, hydroxylmethyl, hydroxyethyl, methoxymethyl, piperidinyl, oxanyl, imidazolyl, pyrazolyl, cyclobutyl, cyclohexyl, optionally substituted by one or more $R^z$ (e.g. methyl, halogen (such as fluorine), C(=O)Me, or —OH).

In one embodiment, $R^6$ and $R^7$ are both the same. In one embodiment, $R^6$ and $R^7$ are both methyl, and the compound of formula (1°) is a compound of formula (Iy) or a tautomer or a solvate or a pharmaceutically acceptable salt thereof:

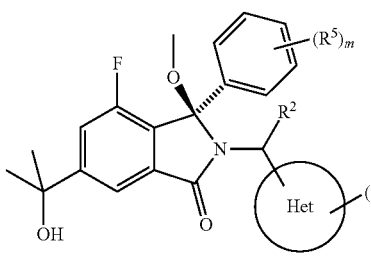

(Iy)

In one embodiment the group —$CR^6R^7OH$ is other than —$C(CH_3)_2OH$.

In one embodiment, $R^7$ is selected from the group consisting of:

(point of attachment represented by dashed bond or bond terminus indicated by "*"):

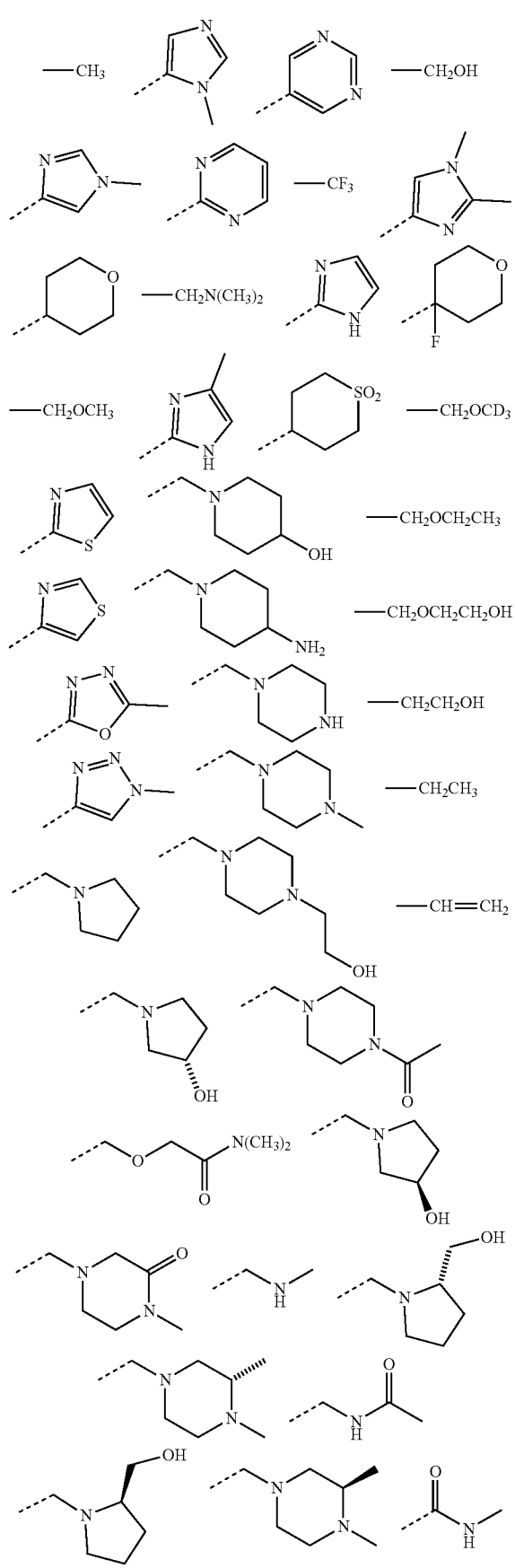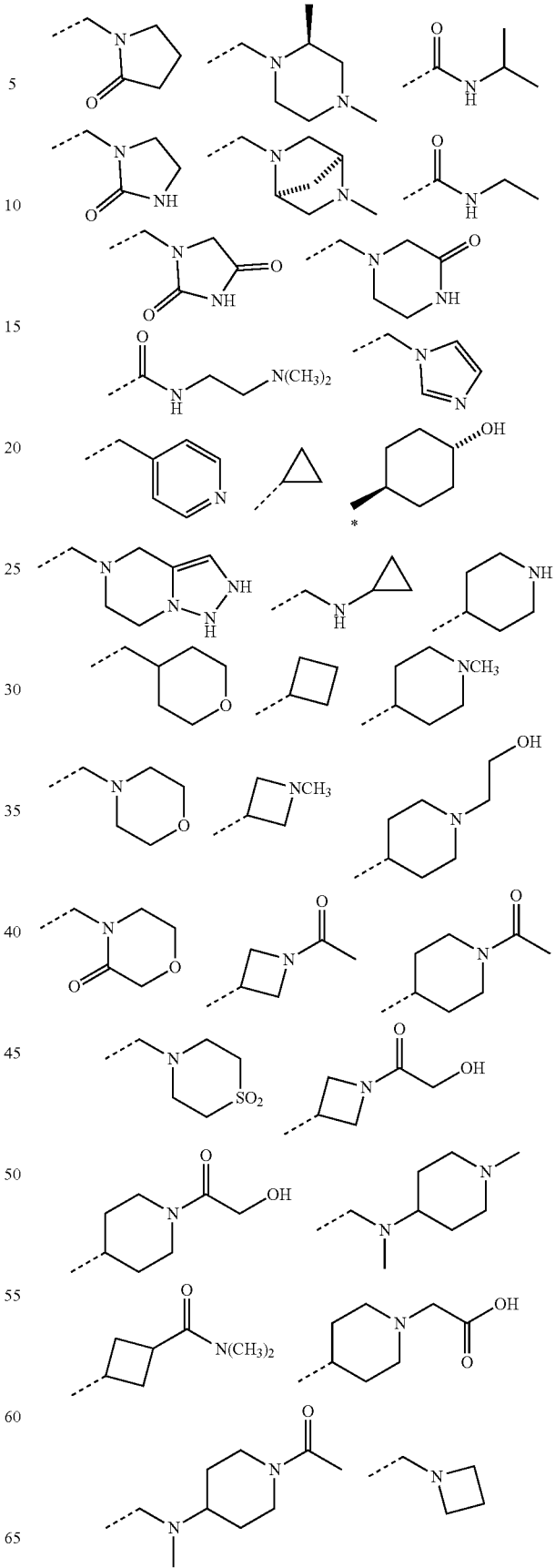

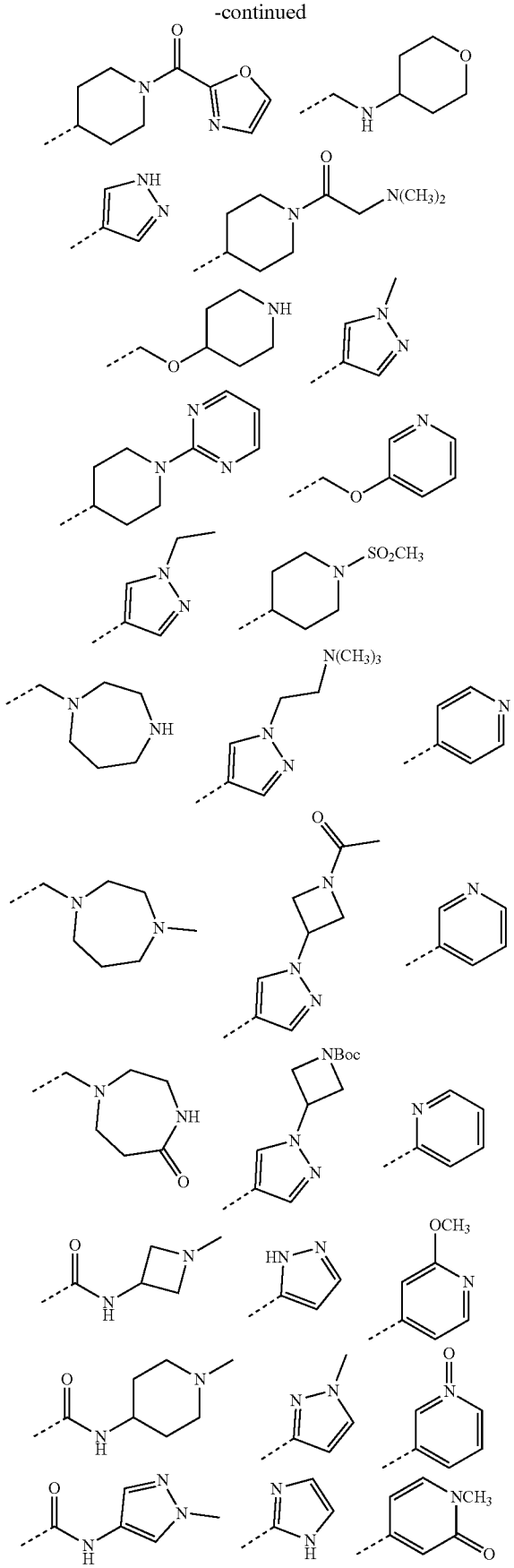
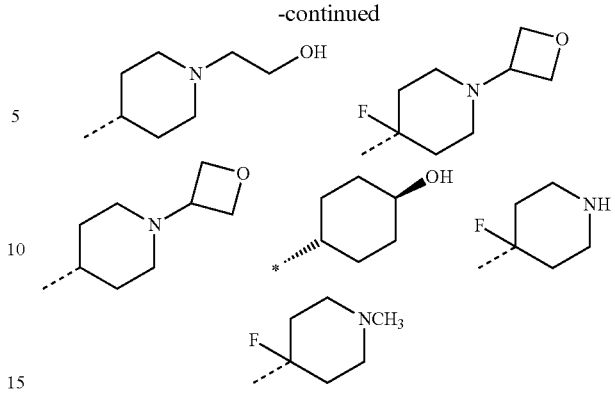

In one embodiment $R^z$ is independently selected from halogen, nitro, nitrile, $C_{1-6}$ alkyl, halo$C_{1-6}$ alkyl, $C_{2-6}$alkenyl, $C_{2-6}$ alkynyl, =O, hydroxy, hydroxy$C_{1-6}$ alkyl, $C_{1-6}$ alkoxy, —(CH$_2$)$_k$—O—C$_{1-6}$ alkyl, hydroxyC$_{1-6}$ alkoxy, —C(=O)C$_{1-6}$ alkyl, —C(=O)C$_{1-6}$ alkyl-OH, —C(=O)C$_{1-6}$ alkyl-N(H)$_e$(C$_{1-6}$alkyl)$_{2-e}$, —C(=O)N(H)$_e$(C$_{1-6}$alkyl)$_{2-e}$, —(CH$_2$)$_k$—CO$_2$C$_{1-6}$ alkyl, —(CH$_2$)$_r$—CO$_2$H, —NH(C$_{1-6}$alkyl), —N(C$_{1-6}$alkyl)$_2$, —C$_{1-6}$ alkyl-N(H)$_e$(C$_{1-6}$alkyl)$_{2-e}$, heterocyclyl group with 3 to 6 ring members, heterocyclyl group with 3 to 6 ring members substituted by —C(=O)C$_{1-6}$alkyl, heterocyclyl group with 3 to 6 ring members substituted by —C(=O)OC$_{1-6}$alkyl, heterocyclyl group with 3 to 6 ring members substituted by —C(=O)N(H)$_e$(C$_{1-6}$alkyl)$_{2-e}$, —C(=O)heterocyclyl group with 3 to 6 ring members, $C_{3-8}$ cycloalkyl and $C_{3-8}$cycloalkenyl.

In another embodiment $R^z$ is independently selected from halogen, nitro, nitrile, $C_{1-6}$alkyl, halo$C_{1-6}$alkyl, $C_{2-6}$alkenyl, $C_{2-6}$alkynyl, =O, hydroxy, hydroxyC$_{1-6}$alkyl, C$_{1-6}$alkoxy, —(CH$_2$)$_k$—O—C$_{1-6}$alkyl, hydroxyC$_{1-6}$alkoxy, —C(=O)C$_{1-6}$alkyl, —C(=O)C$_{1-6}$alkyl-OH, —C(=O)C$_{1-6}$alkyl-N(H)$_e$(C$_{1-4}$alkyl)$_{2-e}$, —C(=O)N(H)$_e$(C$_{1-4}$alkyl)$_{2-e}$, —(CH$_2$)$_r$—CO$_2$C$_{1-6}$alkyl, —(CH$_2$)$_r$—CO$_2$H, —C$_{1-6}$alkyl-N(H)$_e$(C$_{1-4}$ alkyl)$_{2-e}$, heterocyclyl group with 3 to 6 ring members, heterocyclyl group with 3 to 6 ring members substituted by —C(=O)C$_{1-4}$alkyl, heterocyclyl group with 3 to 6 ring members substituted by —C(=O)OC$_{1-4}$alkyl, heterocyclyl group with 3 to 6 ring members substituted by —C(=O)N(H)$_e$(C$_{1-4}$alkyl)$_{2-e}$, —C(=O)heterocyclyl group with 3 to 6 ring members, $C_{3-8}$cycloalkyl and $C_{3-8}$cycloalkenyl.

In another embodiment when $R^7$ contains a saturated heterocyclic group then $R^z$ is independently selected from halogen, nitro, nitrile, C$_{1-6}$alkyl, haloC$_{1-6}$alkyl, C$_{2-6}$alkenyl, C$_{2-6}$alkynyl, =O, hydroxy, hydroxyC$_{1-6}$alkyl, C$_{1-6}$alkoxy, —(CH$_2$)$_k$—O—C$_{1-6}$alkyl, hydroxyC$_{1-6}$alkoxy, —C(=O)C$_{1-6}$alkyl, —C(=O)C$_{1-6}$alkyl-OH, —C(=O)C$_{1-6}$alkyl-N(H)$_e$(C$_{1-4}$alkyl)$_{2-e}$, —C(=O)N(H)$_e$(C$_{1-4}$alkyl)$_{2-e}$, —(CH$_2$)$_r$CO$_2$C$_{1-6}$alkyl, —(CH$_2$)$_r$—CO$_2$H, —N(H)$_e$(C$_{1-4}$alkyl)$_{2-e}$, —C$_{1-6}$alkyl-N(H)$_e$(C$_{1-4}$alkyl)$_{2-e}$, heterocyclyl group with 3 to 6 ring members, heterocyclyl group with 3 to 6 ring members substituted by —C(=O)C$_{1-4}$alkyl, heterocyclyl group with 3 to 6 ring members substituted by —C(=O)OC$_{1-4}$alkyl, heterocyclyl group with 3 to 6 ring members substituted by —C(=O)N(H)$_e$(C$_{1-4}$alkyl)$_{2-e}$, —C(=O)heterocyclyl group with 3 to 6 ring members, $C_{3-8}$cycloalkyl and $C_{3-8}$cycloalkenyl.

Subformulae

In one embodiment, the compound of formulae (1°) is a compound of formulae (II) or a tautomer or a solvate or a pharmaceutically acceptable salt thereof:

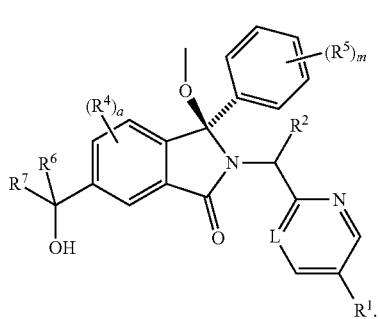
(II)

wherein L is $CR^1$, CH or N and $R^1$, $R^2$, $R^4$, $R^5$, $R^6$, $R^7$, a, and m are as defined herein. In one embodiment L is CH. In one embodiment L is N. In one embodiment L is $CR^1$ such as C—OH or C-hydroxy$C_{1-4}$alkyl (e.g. C—OH or C—$CH_2OH$).

In one embodiment, $R^1$ is chloro, nitrile, methyl or methoxy. In one embodiment, $R^1$ is hydroxy or hydroxy$C_{1-4}$ alkyl (e.g. hydroxyl).

In one embodiment, $R^1$ is $O_{0,1}(CR^xR^y)_v$COOH (e.g. —COOH, —$CH_2$COOH, —O$CH_2$COOH or —C($CH_3$)$_2$COOH.

In another embodiment, $R^1$ is chloro or nitrile and the compound of formula (II) is a compound of formula (IIa) or (IIb) or a tautomer or a solvate or a pharmaceutically acceptable salt thereof:

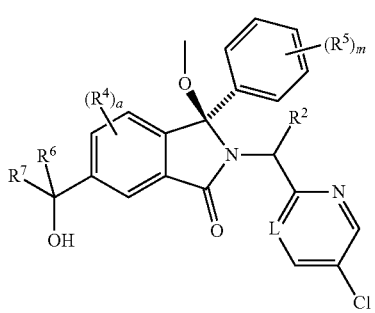
(IIa)

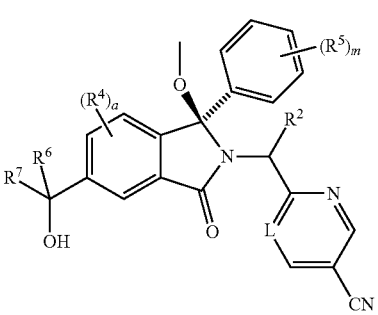
(IIb)

wherein $R^1$, $R^2$, $R^4$, $R^5$, $R^7$, and m are as defined herein.

In one embodiment, $R^6$ is methyl or ethyl, and the compound of formula (II) is a compound of formula (IIIa) or (IIIb) or a tautomer or a solvate or a pharmaceutically acceptable salt thereof:

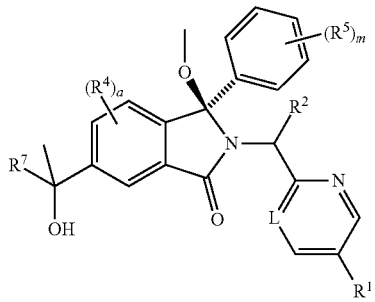
(IIIa)

wherein $R^1$, $R^2$, $R^4$, $R^5$, $R^7$, and m are as defined herein.

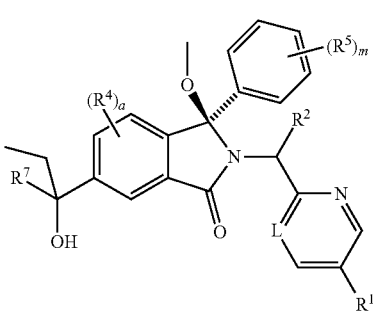
(IIIb)

wherein $R^1$, $R^2$, $R^4$, $R^5$, $R^7$, a, and m are as defined herein.

In one embodiment, a is 1 and the compound of formula (II) is a compound of formula (IVa) or a tautomer or a solvate or a pharmaceutically acceptable salt thereof:

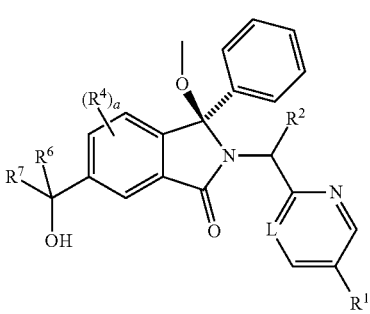
(IVa)

wherein $R^1$, $R^2$, $R^4$, $R^5$, $R^7$, and m are as defined herein.

In one embodiment, and the compound of formula (II) is a compound of formula (IVb) or a tautomer or a solvate or a pharmaceutically acceptable salt thereof:

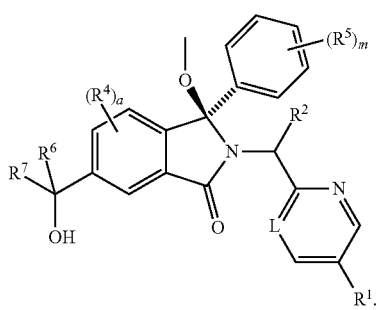

(IVb)

wherein $R^1$, $R^2$, $R^4$, $R^5$, $R^7$, and m are as defined herein.

In one embodiment, $R^4$ is F and the compound of formula (1°) is a compound of formula (V) or a tautomer or a solvate or a pharmaceutically acceptable salt thereof:

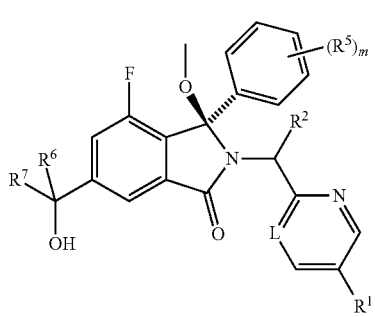

(V)

wherein $R^1$, $R^2$, $R^5$, $R^7$, and m are as defined herein.

In one embodiment, m is 1 and the substituent $R^4$ is at the 4-position of the phenyl group, and the compound of formula (II) is a compound of formula (VI) or a tautomer or a solvate or a pharmaceutically acceptable salt thereof:

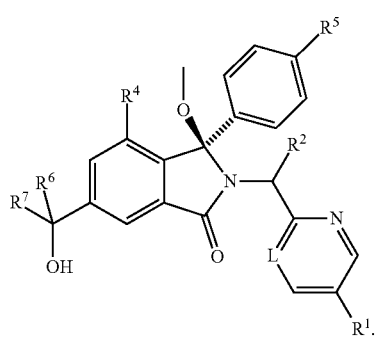

(VI)

In one embodiment, $R^5$ is chloro and the compound of formula (VI) is a compound of formula (VIa) or a tautomer or a solvate or a pharmaceutically acceptable salt thereof:

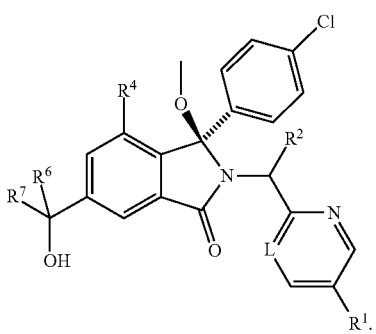

(VIa)

In one embodiment, the invention provides a process for preparing a compound of formula (1°) or a tautomer or a solvate or a pharmaceutically acceptable salt thereof wherein:

Het is pyridinyl, pyrimidinyl, or pyridazinyl, or an N-oxide thereof $R^1$ is attached to a carbon atom and is independently selected from hydroxy, halogen, nitro, nitrile, $C_{1-4}$alkyl, halo$C_{1-4}$alkyl, hydroxy$C_{1-4}$alkyl, $C_{2-6}$alkenyl, $C_{1-4}$alkoxy, halo$C_{1-4}$alkoxy, and $C_{2-4}$alkynyl;

$R^2$ is selected from hydrogen, $C_{1-4}$ alkyl, $C_{2-6}$alkenyl, hydroxy$C_{1-4}$alkyl and —$CH_2CO_2H$;

$R^4$ and $R^5$ are independently selected from halogen, nitrile, $C_{1-4}$alkyl, halo$C_{1-4}$alkyl, $C_{1-4}$alkoxy and halo$C_{1-4}$alkoxy;

$R^6$ and $R^7$ are independently selected from hydrogen, $C_{1-6}$alkyl, halo$C_{1-6}$alkyl, $C_{2-6}$alkenyl, $C_{2-6}$alkynyl, hydroxy, hydroxy$C_{1-6}$alkyl, —COO$C_{1-6}$alkyl, heterocyclic group with 3 to 7 ring members, —$CH_2$-heterocyclic group with 3 to 7 ring members, —$CH_2$—O-heterocyclic group with 3 to 7 ring members, —$CH_2$—NH-heterocyclic group with 3 to 7 ring members, —$CH_2$—N($C_{1-6}$alkyl)-heterocyclic group with 3 to 7 ring members, —C(=O)NH-heterocyclic group with 3 to 7 ring members, $C_{3-8}$cycloalkyl, —$CH_2$—$C_{3-8}$cycloalkyl, —$CH_2$—O—$C_{3-8}$cycloalkyl, and $C_{3-8}$cycloalkenyl, wherein said cycloalkyl, cycloalkenyl or heterocyclic groups may be optionally substituted by one or more $R^z$ groups, and wherein in each instance the heterocyclic group comprises one or more (e.g. 1, 2, or 3) heteroatoms selected from N, O, S and oxidised forms thereof;

$R^z$ is independently selected from halogen, nitro, nitrile, $C_{1-6}$alkyl, halo$C_{1-6}$alkyl, $C_{2-6}$alkenyl, $C_{2-6}$alkynyl, =O, hydroxy, hydroxy$C_{1-6}$alkyl, $C_{1-6}$alkoxy, —$(CH_2)_k$—O—$C_{1-6}$alkyl, hydroxy$C_{1-6}$alkoxy, —C(=O)$C_{1-6}$alkyl, —C(=O)$C_{1-6}$alkyl-OH, —C(=O)$C_{1-6}$alkyl-N(H)$_e$ ($C_{1-4}$alkyl)$_{2-e}$, —C(=O)N(H)$_e$($C_{1-4}$alkyl)$_{2-e}$, —$(CH_2)_r$CO$_2C_{1-6}$alkyl, —$(CH_2)_r$CO$_2$H, —N(H)$_e$($C_{1-4}$alkyl)$_{2-e}$, —$C_{1-6}$alkyl-N(H)$_e$($C_{1-4}$alkyl)$_{2-e}$, heterocyclyl group with 3 to 6 ring members, heterocyclyl group with 3 to 6 ring members substituted by —C(=O)$C_{1-4}$alkyl, heterocyclyl group with 3 to 6 ring members substituted by —C(=O)O$C_{1-4}$alkyl, heterocyclyl group with 3 to 6 ring members substituted by —C(=O)N(H)$_e$($C_{1-4}$alkyl)$_{2-e}$, —C(=O)heterocyclyl group with 3 to 6 ring members, $C_{3-8}$cycloalkyl and $C_{3-8}$cycloalkenyl;

n, e, r and j are independently selected from 0, 1 and 2;

k and m are independently selected from 1 and 2; and v and a are independently selected from 0 and 1.

In one embodiment, the invention provides a process for preparing a compound of formula (1°) or a tautomer or a solvate or a pharmaceutically acceptable salt thereof, wherein:

Het is pyridinyl or pyrimidinyl;
$R^1$ is attached to a carbon atom and is independently selected from hydroxy, halogen, nitro, nitrile and $C_{1-4}$alkyl;
$R^2$ is selected from hydrogen, $C_{1-4}$ alkyl, $C_{2-6}$alkenyl, hydroxy$C_{1-4}$alkyl and —$CH_2CO_2H$;
$R^4$ and $R^5$ are independently selected from halogen, nitrile and $C_{1-4}$ alkyl;
$R^6$ is selected from hydrogen, $C_{1-6}$alkyl, halo$C_{1-6}$alkyl, $C_{2-6}$alkenyl, and $C_{2-6}$alkynyl;
$R^7$ is selected from hydrogen, $C_{1-6}$alkyl, halo$C_{1-6}$alkyl, $C_{2-6}$alkenyl, $C_{2-6}$alkynyl, hydroxy, hydroxy$C_{1-6}$alkyl, —$COOC_{1-6}$alkyl, heterocyclic group with 3 to 7 ring members, —$CH_2$-heterocyclic group with 3 to 7 ring members, —$CH_2$—O-heterocyclic group with 3 to 7 ring members, —$CH_2$—NH-heterocyclic group with 3 to 7 ring members, —$CH_2$—N($C_{1-6}$alkyl)-heterocyclic group with 3 to 7 ring members, —C(=O)NH-heterocyclic group with 3 to 7 ring members, $C_{3-8}$cycloalkyl, —$CH_2$—$C_{3-8}$cycloalkyl, —$CH_2$—O—$C_{3-8}$cycloalkyl, and $C_{3-8}$cycloalkenyl, wherein said cycloalkyl, cycloalkenyl or heterocyclic groups may be optionally substituted by one or more $R^z$ groups, and wherein in each instance the heterocyclic group comprises one or more (e.g. 1, 2, or 3) heteroatoms selected from N, O, S and oxidised forms thereof;
$R^z$ is independently selected from halogen, nitro, nitrile, $C_{1-6}$alkyl, halo$C_{1-6}$alkyl, $C_{2-6}$alkenyl, $C_{2-6}$alkynyl, =O, hydroxy, hydroxy$C_{1-6}$alkyl, $C_{1-6}$alkoxy, —$(CH_2)_k$—O—$C_{1-6}$alkyl, hydroxy$C_{1-6}$alkoxy, —C(=O)$C_{1-6}$alkyl, —C(=O)$C_{1-6}$alkyl-OH, —C(=O)$C_{1-6}$alkyl-N(H)$_e$ ($C_{1-4}$alkyl)$_{2-e}$, —C(=O)N(H)$_e$($C_{1-4}$alkyl)$_{2-e}$, —$(CH_2)_r$CO$_2C_{1-6}$alkyl, —$(CH_2)_r$CO$_2$H, —N(H)$_e$($C_{1-4}$alkyl)$_{2-e}$, —$C_{1-6}$alkyl-N(H)$_e$($C_{1-4}$alkyl)$_{2-e}$, heterocyclyl group with 3 to 6 ring members, heterocyclyl group with 3 to 6 ring members substituted by —C(=O)$C_{1-4}$alkyl, heterocyclyl group with 3 to 6 ring members substituted by —C(=O)O$C_{1-4}$alkyl, heterocyclyl group with 3 to 6 ring members substituted by —C(=O)N(H)$_e$($C_{1-4}$alkyl)$_{2-e}$, —C(=O)heterocyclyl group with 3 to 6 ring members, $C_{3-8}$cycloalkyl and $C_{3-8}$cycloalkenyl;
n, e, r and j are independently selected from 0, 1 and 2;
k and m are independently selected from 1 and 2; and
v and a are independently selected from 0 and 1.

In one embodiment, the invention provides a process for preparing a compound of formula (1°) or a tautomer or a solvate or a pharmaceutically acceptable salt thereof, wherein:

Het is pyridinyl or pyrimidinyl
$R^1$ is attached to a carbon atom and is independently selected from hydroxy, halogen, nitro, nitrile and $C_{1-4}$alkyl;
$R^2$ is selected from hydrogen, $C_{1-4}$ alkyl, $C_{2-6}$alkenyl, hydroxy$C_{1-4}$alkyl and —$CH_2CO_2H$;
$R^4$ and $R^5$ are independently selected from halogen, nitrile and $C_{1-4}$ alkyl;
$R^6$ is selected from hydrogen and $C_{1-6}$alkyl;
$R^7$ is selected from heterocyclic group with 3 to 7 ring members, —$CH_2$-heterocyclic group with 3 to 7 ring members, $C_{3-8}$cycloalkyl, and —$CH_2$—$C_{3-8}$cycloalkyl, wherein said cycloalkyl or heterocyclic groups may be optionally substituted by one or more $R^z$ groups, and wherein in each instance the heterocyclic group comprises one or more (e.g. 1, 2, or 3) heteroatoms selected from N, O, S and oxidised forms thereof;
$R^z$ is independently selected from halogen, nitro, nitrile, $C_{1-6}$alkyl, halo$C_{1-6}$alkyl, $C_{2-6}$alkenyl, hydroxy, hydroxy$C_{1-6}$alkyl, $C_{1-6}$alkoxy, —C(=O)$C_{1-6}$alkyl, and —N(H)$_e$($C_{1-4}$alkyl)$_{2-e}$;
n and e are independently selected from 0, 1 and 2;
m is selected from 1 and 2; and
a is selected from 0 and 1.

In one embodiment, the invention provides a process for preparing a compound of formula (1°) or a tautomer or a solvate or a pharmaceutically acceptable salt thereof, wherein:

Het is pyridinyl or pyrimidinyl
$R^1$ is attached to a carbon atom and is independently selected from halogen, hydroxy and nitrile;
$R^2$ is selected from hydrogen, $C_{1-4}$ alkyl and —$CH_2CO_2H$;
$R^4$ and $R^5$ are independently selected from halogen;
$R^6$ is selected from hydrogen and $C_{1-6}$alkyl;
$R^7$ is selected from heterocyclic group with 3 to 7 ring members, —$CH_2$-heterocyclic group with 3 to 7 ring members, $C_{3-8}$cycloalkyl, and —$CH_2$—$C_{3-8}$cycloalkyl, wherein said cycloalkyl, cycloalkenyl or heterocyclic groups may be optionally substituted by one or more $R^z$ groups, and wherein in each instance the heterocyclic group comprises one or more (e.g. 1, 2, or 3) heteroatoms selected from N, O, S and oxidised forms thereof;
$R^z$ is independently selected from halogen, nitro, nitrile, and $C_{1-6}$alkyl;
n is 1 and m is 1; and
a is selected from 0 and 1.

In one embodiment, the invention provides a process for preparing a compound of formula (1°) or a tautomer or a solvate or a pharmaceutically acceptable salt thereof, wherein:

Het is pyridinyl or pyrimidinyl
$R^1$ is attached to a carbon atom and is independently selected from halogen, hydroxy and nitrile;
$R^2$ is selected from hydrogen, $C_{1-4}$ alkyl and —$CH_2CO_2H$;
$R^4$ and $R^5$ are independently selected from halogen;
$R^6$ is selected from hydrogen and $C_{1-6}$alkyl;
$R^7$ is a heterocyclic group with 3 to 7 ring members optionally substituted by one or more $R^z$ groups;
$R^z$ is independently selected from halogen and $C_{1-6}$alkyl;
n is, 1 and m is 1 and
a is 1.

In one embodiment, the invention provides a process for preparing a compound of formula (1°) or a tautomer or a solvate or a pharmaceutically acceptable salt thereof, wherein:

Het is pyridinyl or pyrimidinyl
$R^1$ is attached to a carbon atom and is independently selected from halogen, hydroxy and nitrile;
$R^2$ is selected from hydrogen, $C_{1-4}$ alkyl and —$CH_2CO_2H$;
$R^4$ and $R^5$ are independently selected from halogen;
$R^6$ is selected from hydrogen and $C_{1-6}$alkyl;
$R^7$ is a heterocyclic group with 3 to 7 ring members optionally substituted by one or more $R^z$ groups;
$R^z$ is independently selected from halogen and $C_{1-6}$alkyl;
n is, 1 and m is 1 and
a is 1.

In one embodiment, the invention provides a process for preparing a compound of formula (1°) or a tautomer or a solvate or a pharmaceutically acceptable salt thereof, wherein:

Het is pyridinyl, pyrimidinyl, or pyridazinyl, or an N-oxide thereof;

$R^1$ is halogen (e.g. Cl), nitrile, hydroxy, $C_{1-4}$alkoxy (e.g. —OCH$_3$), $C_{1-4}$alkyl (e.g. CH$_3$) or —S(O)$_d$—$C_{1-4}$alkyl;

n is 1 or 2;

$R^2$ is selected from hydrogen, $C_{1-4}$ alkyl (e.g. —CH$_3$), hydroxyC$_{1-4}$alkyl (e.g. —CH$_2$OH or —CH(OH)CH$_2$OH), —CH$_2$CO$_2$H and $C_{2-6}$alkenyl (e.g. —CH=CH$_2$);

$R^4$ is $C_{1-4}$ alkyl (e.g. —CH$_3$), or halogen (e.g. F or Cl);

a is 0 or 1;

$R^5$ is halogen (e.g. Cl or F), $C_{1-4}$ alkyl (e.g. —CH$_2$CH$_3$), nitrile, haloC$_{1-4}$alkyl (e.g. —CF$_3$, or —CF$_2$CH$_3$), or haloC$_{1-4}$alkoxy (e.g. —OCF$_3$);

m is 1 or 2;

$R^6$ is hydrogen, $C_{1-6}$alkyl (e.g. —CH$_3$ or —CH$_2$CH$_3$), $C_{2-6}$alkenyl (e.g. —CH=CH$_2$) and haloC$_{1-6}$alkyl (e.g. —CF$_3$ or —CH$_2$F);

$R^7$ is $C_{1-6}$alkyl (e.g. —CH$_3$ or —CH$_2$CH$_3$), $C_{3-8}$cycloalkyl (e.g. cyclopropyl, cyclobutyl or cyclohexyl), $C_{2-6}$alkenyl (e.g. —CH=CH$_2$), haloC$_{1-6}$alkyl (e.g. —CF$_3$), hydroxyC$_{1-6}$alkyl (e.g. —CH$_2$OH or —CH$_2$CH$_2$OH), —C$_{1-6}$alkyl-NR$^x$R$^y$(e.g. —CH$_2$NH$_2$, —CH$_2$N(CH$_3$)$_2$, —CH$_2$NHCH$_3$, or —CH$_2$NH(cyclopropyl)), —(CR$^x$R$^y$)$_p$—CONR$^x$R$^y$(e.g. —C(=O)NHCH$_3$, —(CO)NHCH$_2$CH$_3$, —(CO)NHCH$_2$CH$_2$NH$_2$, —C(=O)NH(CH(CH$_3$)$_2$)), or —(CH$_2$); —O—C$_{1-6}$alkyl (e.g. —CH$_2$OCH$_3$, —CH$_2$OCH$_2$CH$_3$ or —CH$_2$OCD$_3$), —(CR$^x$R$^y$)$_p$—NR$^x$COR$^y$ (e.g. —CH$_2$NHC(=O)CH$_3$), —(CR$^x$R$^y$)$_p$—O—CH$_2$—CONR$^x$R$^y$(e.g. —CH$_2$OCH$_2$C(=O)N(CH$_3$)$_2$), —(CH$_2$); —O-(hydroxyC$_{1-6}$alkyl) (e.g. —CH$_2$OCH$_2$CH$_2$OH), heterocyclic group with 3 to 7 ring members e.g.

(point of attachment represented by dashed bond):

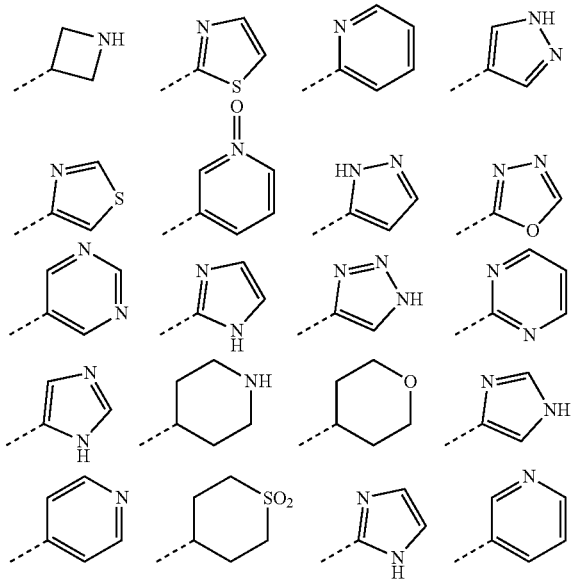

or —CH$_2$-heterocyclic group with 3 to 7 ring members e.g.

(point of attachment represented by dashed bond)

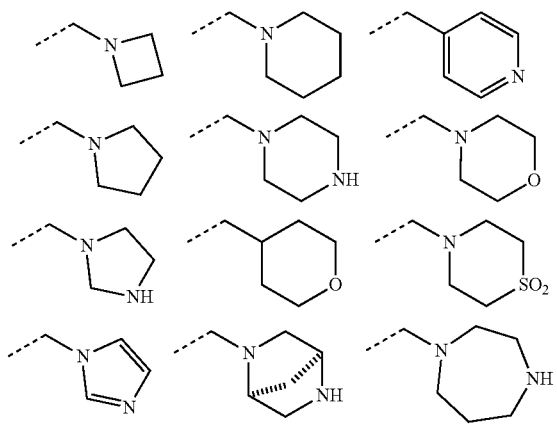

wherein when the moiety $R^7$ comprises a heterocyclic group, the heterocyclic group may be optionally substituted by one or more $R^z$ groups selected from $C_{1-6}$alkyl (e.g. methyl), hydroxyalkyl (e.g. —CH$_2$CH$_2$OH), halogen (e.g. fluoro), =O, $C_{1-6}$alkoxy (e.g. methoxy), —C(=O)$C_{1-6}$alkyl (e.g. —C(=O)CH$_3$), —C(=O)hydroxyC$_{1-6}$alkyl (e.g. —C(=O)CH$_2$OH), heterocyclyl group with 3 to 6 ring members (e.g. oxetanyl or pyrimidinyl), and —S(O)$_d$—$C_{1-4}$alkyl wherein d is selected from 0, 1 and 2 (e.g. —SO$_2$—CH$_3$).

In one embodiment of formula (1°) $R^7$ is a heterocyclic group with 3 to 7 ring members e.g.

(point of attachment represented by dashed bond)

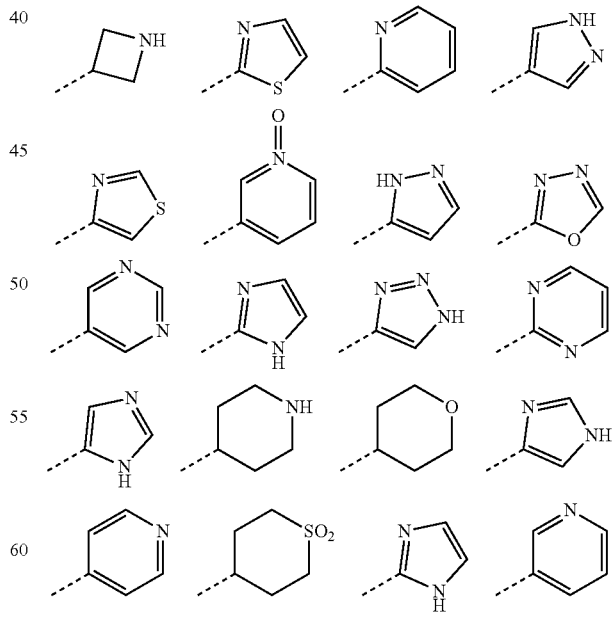

In one embodiment of formula (1°) $R^7$ is a heterocyclic group with 3 to 7 ring members optionally substituted by one or more $R^z$ groups e.g.

99
(point of attachment represented by dashed bond)
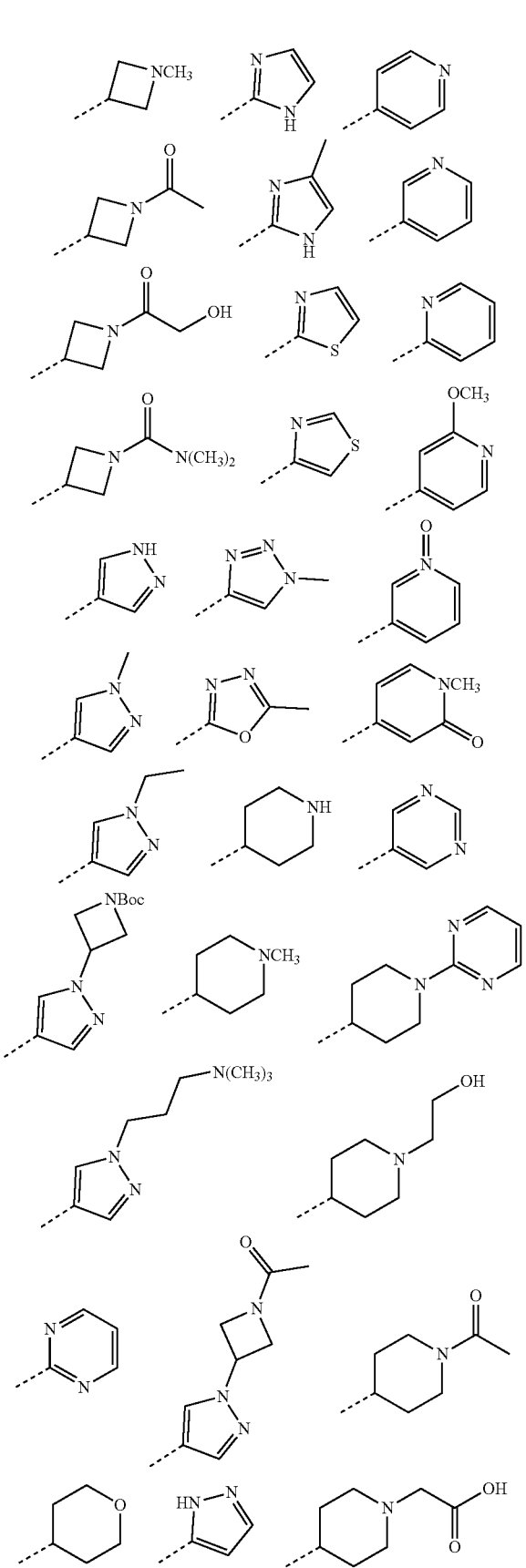
100
-continued
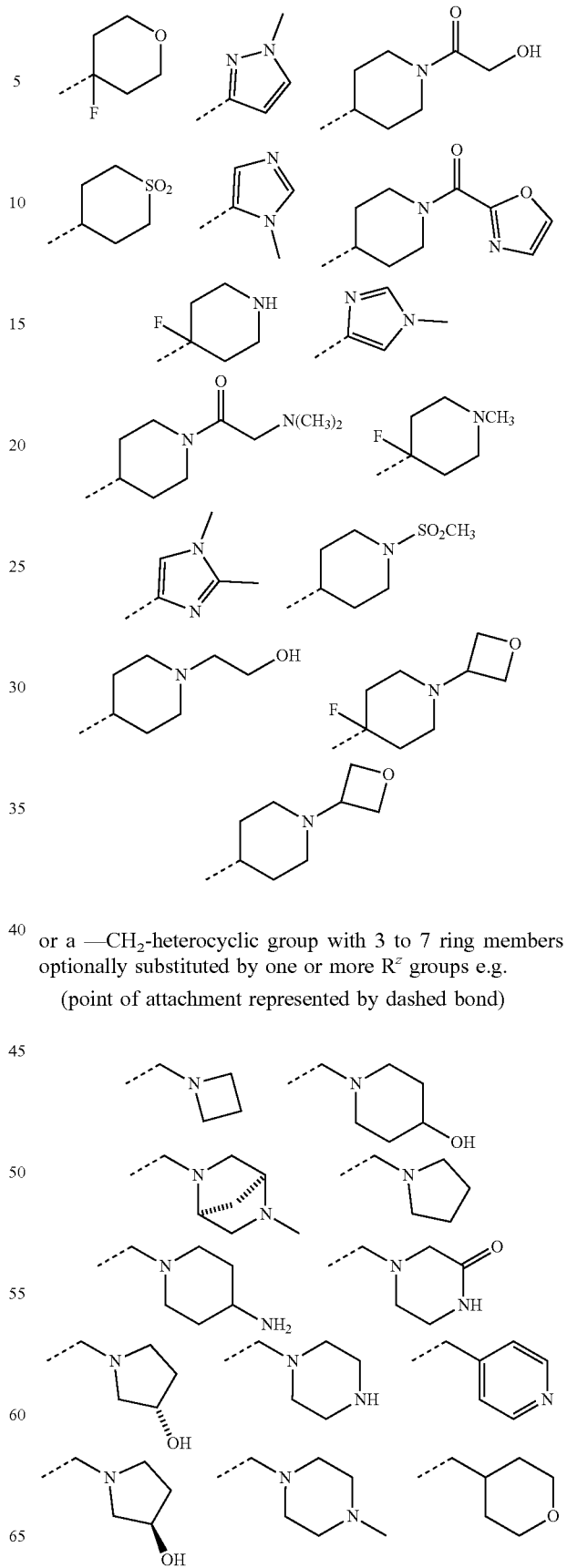
or a —CH$_2$-heterocyclic group with 3 to 7 ring members optionally substituted by one or more R$^z$ groups e.g.
(point of attachment represented by dashed bond)

-continued

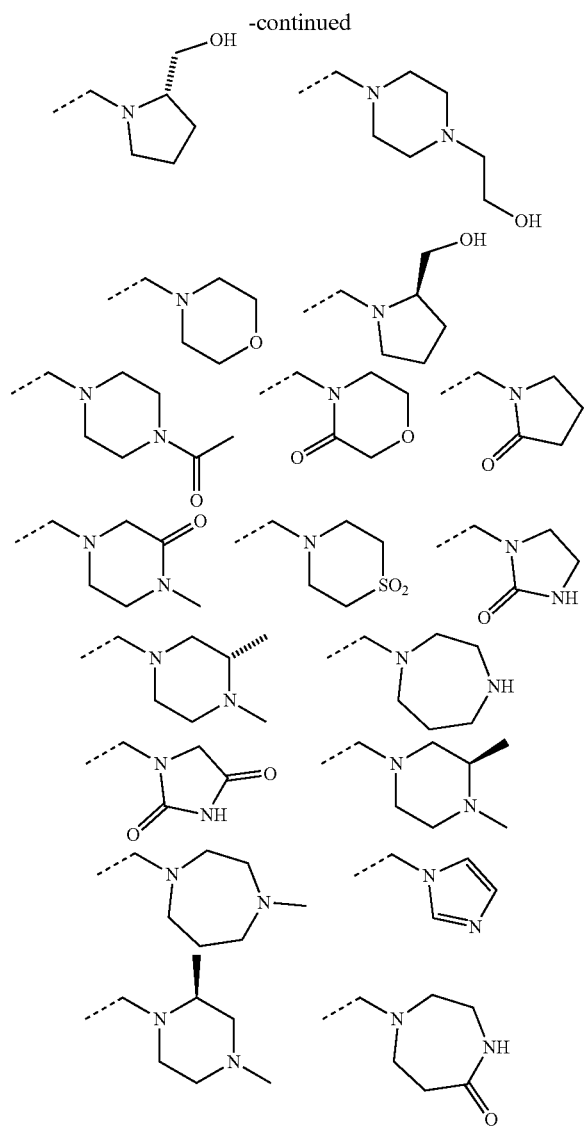

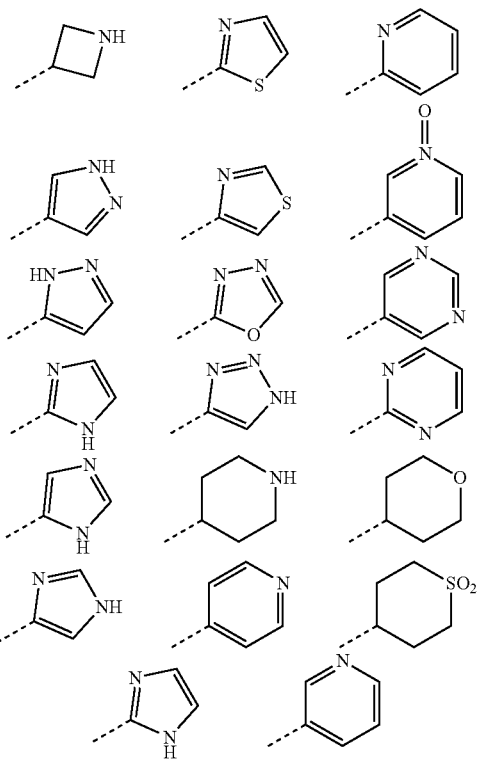

In one embodiment, the invention provides a process for preparing a compound of formula(1°) or a tautomer or a solvate or a pharmaceutically acceptable salt thereof, wherein:
Het is pyridinyl, pyrimidinyl, or pyridazinyl, or an N-oxide thereof;
$R^1$ is halogen (e.g. Cl), nitrile, hydroxy, $C_{1-4}$alkoxy (e.g. —OCH$_3$), $C_{1-4}$alkyl (e.g. CH$_3$) or —S(O)$_d$—$C_{1-4}$alkyl;
n is 1 or 2;
$R^2$ is selected from hydrogen, $C_{1-4}$ alkyl (e.g. —CH$_3$), hydroxyC$_{1-4}$alkyl (e.g. —CH$_2$OH or —CH(OH)CH$_2$OH), —CH$_2$CO$_2$H and $C_{2-6}$ alkenyl (e.g. —CH=CH$_2$);
$R^4$ is $C_{1-4}$ alkyl (e.g. —CH$_3$), or halogen (e.g. F or Cl);
a is 0 or 1;
$R^5$ is halogen (e.g. Cl or F), $C_{1-4}$ alkyl (e.g. —CH$_2$CH$_3$), nitrile, haloC$_{1-4}$alkyl (e.g. —CF$_3$, or —CF$_2$CH$_3$), or haloC$_{1-4}$alkoxy (e.g. —OCF$_3$);
m is 1 or 2;
$R^6$ is hydrogen, $C_{1-6}$alkyl (e.g. —CH$_3$ or —CH$_2$CH$_3$), $C_{2-6}$alkenyl (e.g. —CH=CH$_2$) and haloC$_{1-6}$alkyl (e.g. —CF$_3$ or —CH$_2$F);

$R^7$ is $C_{1-6}$alkyl (e.g. —CH$_3$ or —CH$_2$CH$_3$), $C_{3-8}$cycloalkyl (e.g. cyclopropyl, cyclobutyl or cyclohexyl), $C_{2-6}$alkenyl (e.g. —CH=CH$_2$), haloC$_{1-6}$alkyl (e.g. —CF$_3$), hydroxyC$_{1-6}$alkyl (e.g. —CH$_2$OH or —CH$_2$CH$_2$OH), —C$_{1-6}$alkyl-NR$^x$R$^y$(e.g. —CH$_2$NH$_2$, —CH$_2$N(CH$_3$)$_2$, —CH$_2$NHCH$_3$, or —CH$_2$NH(cyclopropyl)), —(CR$^x$R$^y$)$_p$—CONR$^x$R$^y$(e.g. —C(=O)NHCH$_3$, —(CO)NHCH$_2$CH$_3$, —(CO)NHCH$_2$CH$_2$NH$_2$, —C(=O)NH(CH(CH$_3$)$_2$)), or —(CH$_2$); —O—$C_{1-6}$alkyl (e.g. —CH$_2$OCH$_3$, —CH$_2$OCH$_2$CH$_3$ or —CH$_2$OCD$_3$), —(CR$^x$R$^y$)$_p$—NR$^x$COR$^y$ (e.g. —CH$_2$NHC(=O)CH$_3$), —(CR$^x$R$^y$)$_p$—O—CH$_2$—CONR$^x$R$^y$(e.g. —CH$_2$OCH$_2$C(=O)N(CH$_3$)$_2$), —(CH$_2$); —O-(hydroxyC$_{1-6}$alkyl) (e.g. —CH$_2$OCH$_2$CH$_2$OH), heterocyclic group with 3 to 7 ring members e.g.

(point of attachment represented by dashed bond):

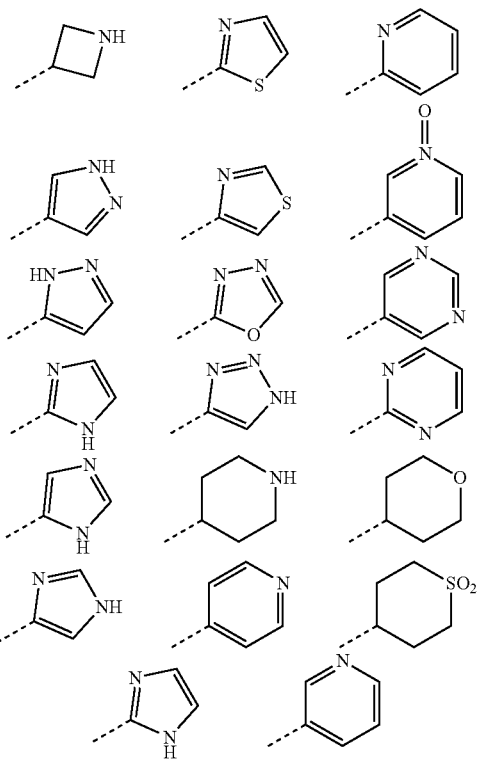

or —CH$_2$-heterocyclic group with 3 to 7 ring members e.g.

(point of attachment represented by dashed bond)

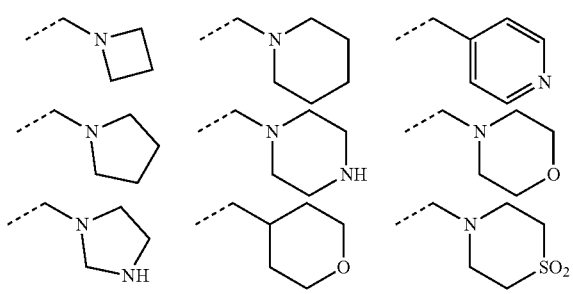

-continued

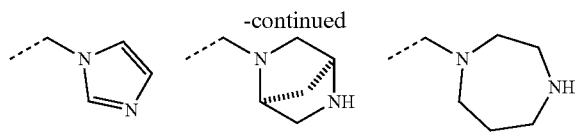

wherein when R⁷ comprises a heterocyclic group, the heterocyclic group may be optionally substituted by one or more R$^z$ groups selected from $C_{1-6}$alkyl (e.g. methyl), halogen (e.g. fluoro), =O, $C_{1-6}$alkoxy (e.g. methoxy), —C(=O)$C_{1-6}$alkyl (e.g. —C(=O)CH$_3$), —C(=O)hydroxy$C_{1-6}$alkyl (e.g. —C(=O)CH$_2$OH), heterocyclyl group with 3 to 6 ring members (e.g. pyrimidinyl), and —S(O)$_d$—$C_{1-4}$alkyl wherein d is selected from 0, 1 and 2 (e.g. —SO$_2$—CH$_3$).

In one embodiment of formula (1°) R⁷ is a heterocyclic group with 3 to 7 ring members e.g.

(point of attachment represented by dashed bond)

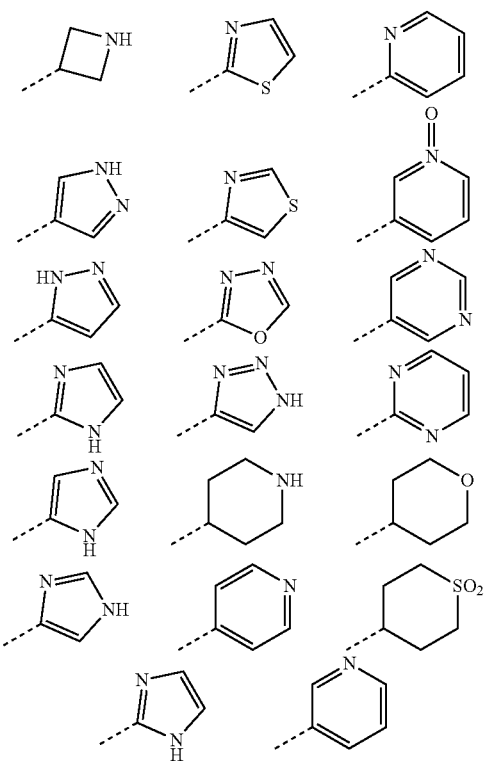

In one embodiment of formula (1°) R⁷ is a heterocyclic group with 3 to 7 ring members optionally substituted by one or more R$^z$ groups e.g.

(point of attachment represented by dashed bond)

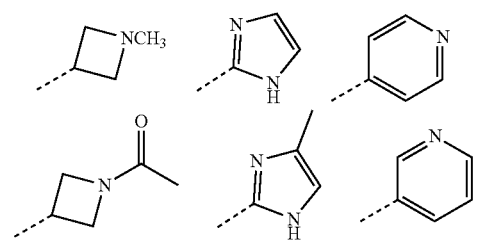

-continued

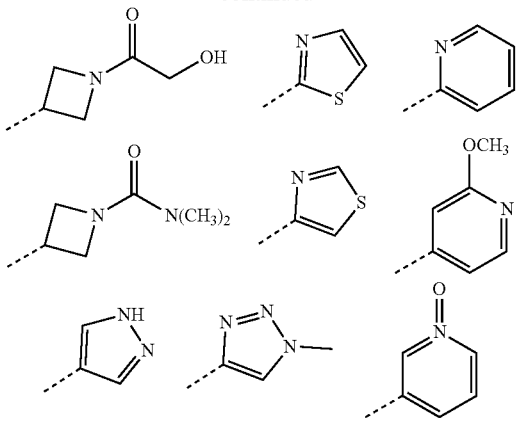

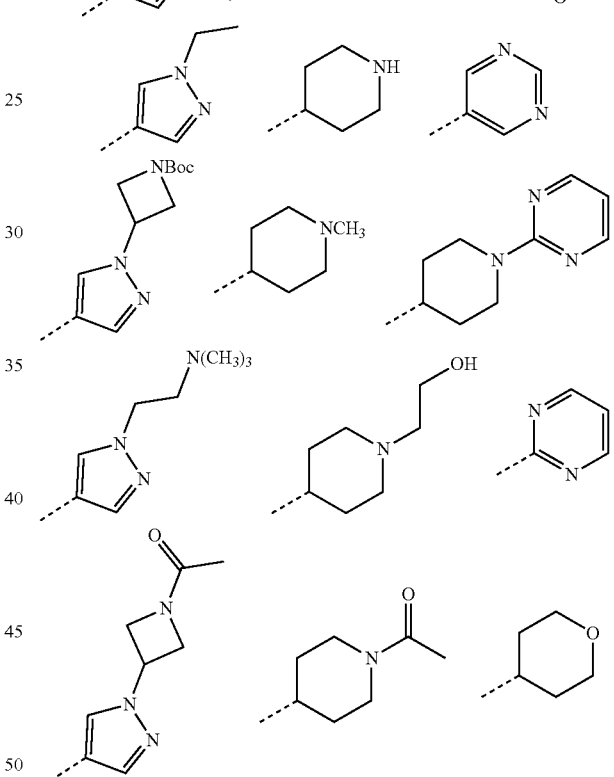

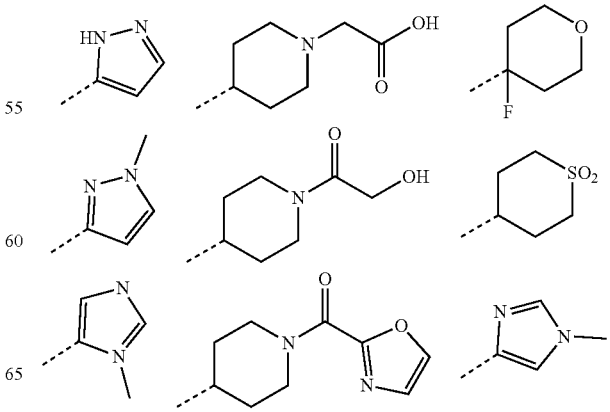

-continued

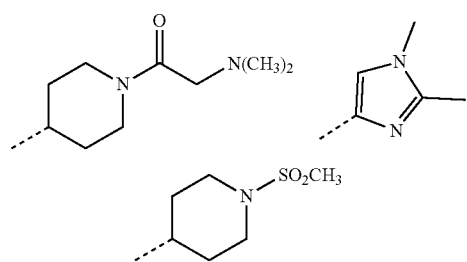

or a —CH$_2$-heterocyclic group with 3 to 7 ring members optionally substituted by one or more R$^z$ groups e.g.

(point of attachment represented by dashed bond)

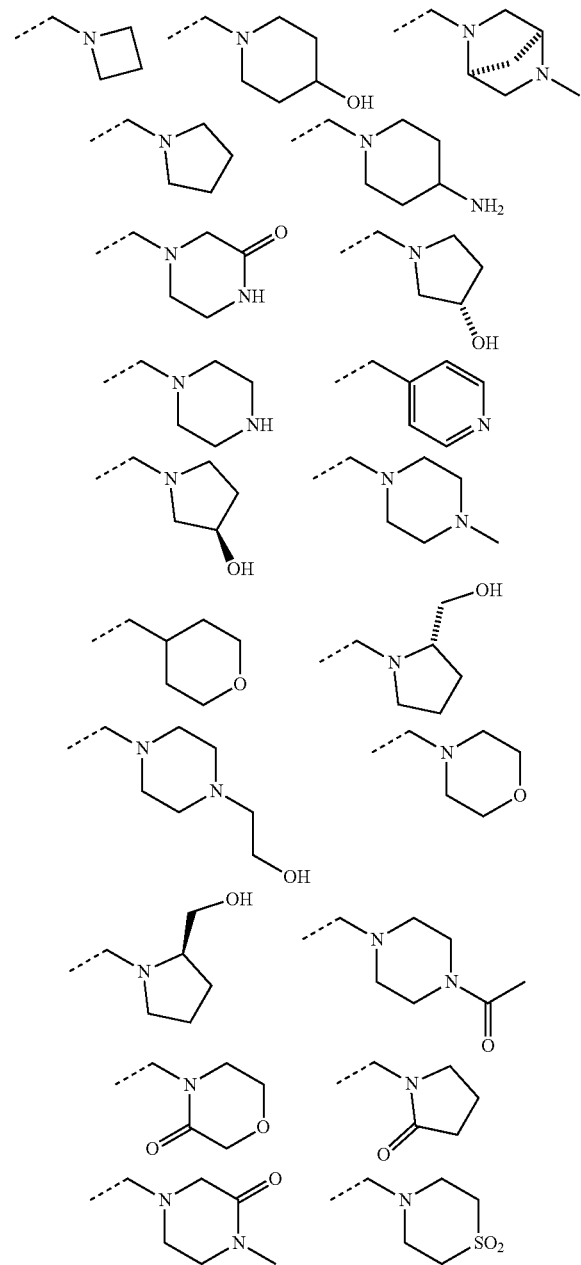

-continued

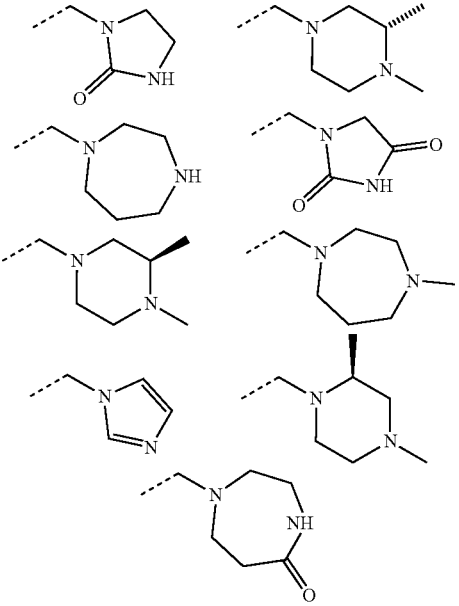

In one embodiment, the invention provides a process for preparing a compound of formula (1°) or a tautomer or a solvate or a pharmaceutically acceptable salt thereof, wherein:
Het is pyridin-2-yl or pyrimidin-2-yl;
R$^1$ is —Cl, —CN, —OH or —OMe;
n is 1;
R$^2$ is hydrogen;
a is 0 or 1 and R$^4$ is halogen (e.g. fluorine);
R$^5$ is halogen (e.g. Cl);
m is 1;
R$^6$ is C$_{1-4}$alkyl (e.g. methyl or ethyl);
R$^7$ is C$_{1-4}$alkyl (e.g. methyl or ethyl), hydroxylC$_{1-4}$alkyl (e.g. hydroxylmethyl or hydroxyethyl), methoxyC$_{1-4}$alkyl (e.g. methoxymethyl), a heterocyclic group with 5 or 6 ring members (e.g. piperidinyl, oxanyl, imidazolyl or pyrazolyl) or C$_{3-6}$cycloalkyl (e.g. cyclobutyl or cyclohexyl) wherein said heterocyclic group with 5 or 6 ring members and C$_{3-6}$cycloalkyl groups may be optionally substituted with one or two R$^z$ groups independently selected from methyl, halogen (such as fluorine), —C(=O)Me, and —OH.

In one embodiment, the invention provides a process for preparing a compound of formula (1°) or a tautomer or a solvate or a pharmaceutically acceptable salt thereof, wherein:
Het is pyridin-2-yl or pyrimidin-2-yl;
R$^1$ is —Cl, —CN, —OH or —OMe;
n is 1;
R$^2$ is hydrogen;
R$^5$ is halogen (e.g. Cl);
m is 1;
R$^6$ is C$_{1-4}$alkyl (e.g. methyl or ethyl);
R$^7$ is C$_{1-4}$alkyl (e.g. methyl or ethyl), hydroxylC$_{1-4}$alkyl (e.g. hydroxylmethyl or hydroxyethyl), methoxyC$_{1-4}$alkyl (e.g. methoxymethyl), a heterocyclic group with 5 or 6 ring members (e.g. piperidinyl, oxanyl, imidazolyl or pyrazolyl) or C$_{3-6}$cycloalkyl (e.g. cyclobutyl or cyclohexyl) wherein said heterocyclic group with 5 or 6 ring members and C$_{3-6}$cycloalkyl groups may be optionally substituted with one or two R$^z$ groups independently selected from methyl, halogen (such as fluorine), —C(=O)Me, and —OH.

THE PROCESS

General Processes

The invention relates to processes for preparing a 1-methoxyisoindoline of formula (1°):

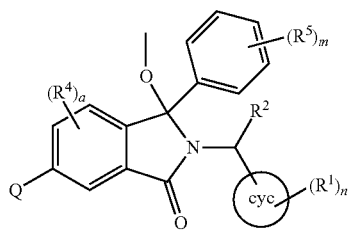

(1°)

or a tautomer or a solvate or a salt thereof,
the process comprising taking a compound of the formula (2°)

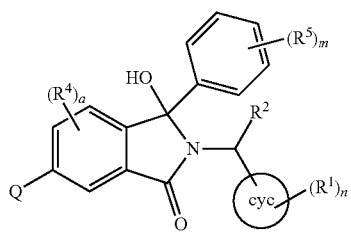

(2°)

wherein cyc is phenyl or a heterocyclic group Het which is pyridinyl, pyrimidinyl, pyrazinyl or pyridazinyl, or an N-oxide thereof;

$R^1$ is independently selected from hydroxy, halogen, nitro, nitrile, $C_{1-4}$alkyl, halo$C_{1-4}$alkyl, hydroxy$C_{1-4}$alkyl, $C_{2-6}$alkenyl, $C_{1-4}$alkoxy, halo$C_{1-4}$alkoxy, $C_{2-4}$alkynyl, —$O_{0,1}$—$(CR^xR^y)_v$—$CO_2H$, —$(CR^xR^y)_v$—$CO_2C_{1-4}$alkyl, —$(CR^xR^y)_v$—$CON(C_{1-4}$alkyl$)_2$, —$P(=O)(R^x)_2$, —$S(O)_d$—$R^x$, —$S(O)_d$-heterocyclic group with 3 to 6 ring members and —$S(O)_d$—$N(R^8)_2$, wherein when cyc is Het then $R^1$ is attached to a carbon atom;

$R^2$ is selected from hydrogen, $C_{1-4}$ alkyl, $C_{2-6}$alkenyl, hydroxy$C_{1-4}$alkyl, —$(CR^xR^y)_u$—$CO_2H$, —$(CR^xR^y)_u$—CONR$^xR^y$, —$(CR^xR^y)_u$—$CO_2R^{10}$ wherein $R^{10}$ is selected from $C_{1-7}$ alkyl, $C_{1-7}$ alkeneyl, $C_{1-7}$ haloalkyl, tri$C_{1-7}$ alkylsilyl-$C_{1-7}$alkyl, $C_{5-20}$ aryl and $C_{5-20}$ aryl-$C_{1-7}$ alkyl.

$R^4$ and $R^5$ are independently selected from halogen, nitrile, $C_{1-4}$ alkyl, halo$C_{1-4}$alkyl, $C_{1-4}$alkoxy and halo$C_{1-4}$alkoxy;

Q is selected from —C(OH)$R^6R^7$, —C(=O)$R^7$, halogen (e.g. —F, —Cl, —Br, —I) and —OTf;

$R^6$ and $R^7$ are independently selected from hydrogen, $C_{1-6}$alkyl, halo$C_{1-6}$alkyl, $C_{2-6}$alkenyl, $C_{2-6}$alkynyl, hydroxy, hydroxy$C_{1-6}$alkyl, —COO$C_{1-6}$alkyl, —(CH$_2$); —O—$C_{1-6}$alkyl, —(CH$_2$); —O-(hydroxy$C_{1-6}$ alkyl), —$C_{1-6}$alkyl-NR$^xR^y$, —$(CR^xR^y)_p$—CONR$^xR^y$, —$(CR^xR^y)_p$—NR$^x$COR$^y$, —$(CR^xR^y)_p$—O—CH$_2$—CONR$^xR^y$, heterocyclic group with 3 to 7 ring members, —CH$_2$-heterocyclic group with 3 to 7 ring members, —CH$_2$—O-heterocyclic group with 3 to 7 ring members, —CH$_2$—NH-heterocyclic group with 3 to 7 ring members, —CH$_2$—N($C_{1-6}$alkyl)-heterocyclic group with 3 to 7 ring members, —C(=O)NH-heterocyclic group with 3 to 7 ring members, $C_{3-8}$cycloalkyl, —CH$_2$—$C_{3-8}$cycloalkyl, —CH$_2$—O—$C_{3-8}$cycloalkyl, and $C_{3-8}$cycloalkenyl, wherein said cycloalkyl, cycloalkenyl or heterocyclic groups may be optionally substituted by one or more $R^z$ groups, and wherein in each instance the heterocyclic group comprises one or more (e.g. 1, 2, or 3) heteroatoms selected from N, O, S and oxidised forms thereof;

or, when Q is —C(OH)$R^6R^7$, the $R^6$ and $R^7$ groups, together with the carbon atom to which they are attached, can join to form a $C_{3-6}$cycloalkyl or heterocyclyl group with 3 to 6 ring members, wherein the heterocyclic group comprises one or more (e.g. 1, 2, or 3) heteroatoms selected from N, O, S and oxidised forms thereof, and wherein said $C_{3-6}$cycloalkyl and heterocyclyl groups may be optionally substituted by one or more $R^z$ groups;

$R^a$ is selected from hydrogen, $C_{1-6}$alkyl, halo$C_{1-6}$alkyl, hydroxy$C_{1-6}$alkyl, —(CH$_2$)$_k$—O—$C_{1-6}$alkyl, —(CH$_2$)$_k$—O-(hydroxy$C_{1-6}$alkyl), hydroxy$C_{1-6}$alkoxy, —(CH$_2$)$_k$—$CO_2C_{1-6}$alkyl, —(CH$_2$)$_k$—$CO_2H$, —$C_{1-6}$alkyl-N(H)$_e$($C_{1-4}$alkyl)$_{2-e}$, —(CH$_2$)$_j$—$C_{3-8}$cycloalkyl and —(CH$_2$)$_j$—$C_{3-8}$cycloalkenyl;

$R^x$ and $R^y$ are independently selected from hydrogen, halogen, nitro, nitrile, $C_{1-6}$alkyl, halo$C_{1-6}$alkyl, $C_{2-6}$alkenyl, $C_{2-6}$alkynyl, hydroxy, hydroxy$C_{1-6}$alkyl, $C_{1-6}$alkoxy, —(CH$_2$)$_k$—O—$C_{1-6}$alkyl, hydroxy$C_{1-6}$ alkoxy, —COO$C_{1-6}$alkyl, —N(H)$_e$($C_{1-4}$alkyl)$_{2-e}$, —$C_{1-6}$ alkyl-N(H)$_e$($C_{1-4}$alkyl)$_{2-e}$, —(CH$_2$)$_k$—C(=O)N(H)$_e$($C_{1-4}$alkyl)$_{2-e}$, $C_{3-8}$cycloalkyl and $C_{3-8}$cycloalkenyl;

or the $R^x$ and $R^y$ groups, together with the carbon or nitrogen atom to which they are attached, can join to form a $C_{3-6}$cycloalkyl or saturated heterocyclyl group with 3 to 6 ring members which may be optionally fused to an aromatic heterocyclyl group of 3 to 5 ring members;

or when on a carbon atom the $R^x$ and $R^y$ groups can join together to form a =CH$_2$ group; $R^z$ is independently selected from halogen, nitro, nitrile, $C_{1-6}$alkyl, halo$C_{1-6}$ alkyl, $C_{2-6}$alkenyl, $C_{2-6}$alkynyl, =O, hydroxy, hydroxy$C_{1-6}$alkyl, $C_{1-6}$alkoxy, —(CH$_2$)$_k$—O—$C_{1-6}$alkyl, hydroxy$C_{1-6}$alkoxy, —C(=O)$C_{1-6}$alkyl, —C(=O)$C_{1-6}$alkyl-OH, —C(=O)$C_{1-6}$alkyl-N(H)$_e$($C_{1-4}$alkyl)$_{2-e}$, —C(=O)N(H)$_e$($C_{1-4}$alkyl)$_{2-e}$, —(CH$_2$)$_r$ $CO_2C_{1-6}$alkyl, —(CH$_2$)$_r$$CO_2H$, —N(H)$_e$($C_{1-4}$alkyl)$_{2-e}$, —$C_{1-6}$alkyl-N(H)$_e$($C_{1-4}$alkyl)$_{2-e}$, heterocyclyl group with 3 to 6 ring members, heterocyclyl group with 3 to 6 ring members substituted by —C(=O)$C_{1-4}$alkyl, heterocyclyl group with 3 to 6 ring members substituted by —C(=O)O$C_{1-4}$alkyl, heterocyclyl group with 3 to 6 ring members substituted by —C(=O)N(H)$_e$($C_{1-4}$alkyl)$_{2-e}$, —C(=O)heterocyclyl group with 3 to 6 ring members, $C_{3-8}$cycloalkyl and $C_{3-8}$cycloalkenyl, wherein if $R^7$ is pyridine then $R^z$ is other then —NH$_2$;

a, j, d, e, n, r and p are independently selected from 0, 1 and 2;

k and m are independently selected from 1 and 2;
u is selected from 0, 1, 2 and 3; and
v and w are independently selected from 0 and 1;
and reacting the compound of formula (2°) with a methylating agent in the presence of a base.

In particular, the invention relates to a process for preparing a 1-methoxyisoindoline according to claim 1, wherein the compound of formula (1°) is a compound of formula (1):

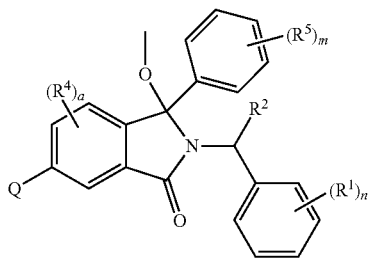

(1)

or a tautomer or a solvate or a salt thereof, and the compound of formula (2°) is a compound of formula (2):

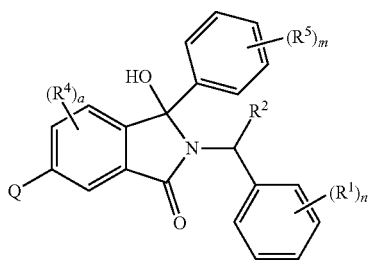

(2)

In other words, the invention provides a process for preparing a compound of formula (1)

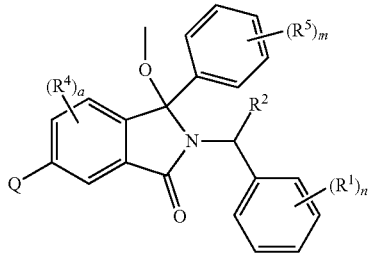

(1)

or a tautomer or a solvate or a salt thereof, the process comprising taking a compound of the formula (2)

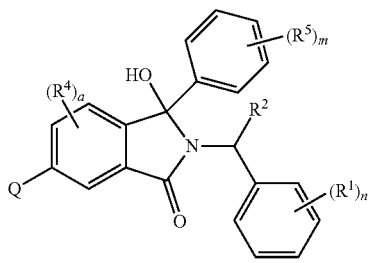

(2)

wherein $R^1$ is independently selected from hydroxy, halogen, nitro, nitrile, $C_{1-4}$alkyl, halo$C_{1-4}$alkyl, hydroxy$C_{1-4}$alkyl, $C_{2-6}$alkenyl, $C_{1-4}$alkoxy, halo$C_{1-4}$alkoxy, $C_{2-4}$alkynyl, $-O_{0,1}-(CR^xR^y)_v-CO_2H$, $-(CR^xR^y)_v-CO_2C_{1-4}$alkyl, $-(CR^xR^y)_v-CON(C_{1-4}$alkyl$)_2$, $-P(=O)(R^x)_2$, $-S(O)_d-R^x$, $-S(O)_d$-heterocyclic group with 3 to 6 ring members and $-S(O)_d-N(R^8)_2$;

$R^2$ is selected from hydrogen, $C_{1-4}$ alkyl, $C_{2-6}$alkenyl, hydroxy$C_{1-4}$alkyl, $-(CR^xR^y)_u-CO_2H$, $-(CR^xR^y)_u-CONR^xR^y$, $-(CR^xR^y)_u-CO_2R^{10}$ wherein $R^{10}$ is selected from $C_{1-7}$ alkyl, $C_{1-7}$ alkeneyl, $C_{1-7}$ haloalkyl, tri$C_{1-7}$ alkylsilyl-$C_{1-7}$alkyl, $C_{5-20}$ aryl and $C_{5-20}$ aryl-$C_{1-7}$ alkyl;

$R^4$ and $R^5$ are independently selected from halogen, nitrile, $C_{1-4}$alkyl, halo$C_{1-4}$alkyl, $C_{1-4}$alkoxy and halo$C_{1-4}$alkoxy;

Q is selected from $-C(OH)R^6R^7$, $-C(=O)R^7$, halogen (e.g. $-F$, $-Cl$, $-Br$, $-I$) and $-OTf$;

$R^6$ and $R^7$ are independently selected from hydrogen, $C_{1-6}$alkyl, halo$C_{1-6}$alkyl, $C_{2-6}$alkenyl, $C_{2-6}$alkynyl, hydroxy, hydroxy$C_{1-6}$alkyl, $-COOC_{1-6}$alkyl, $-(CH_2)$; $-O-C_{1-6}$alkyl, $-(CH_2)_j-O$-(hydroxy$C_{1-6}$ alkyl), $-C_{1-6}$alkyl-$NR^xR^y$, $-(CR^xR^y)_p-CONR^xR^y$, $-(CR^xR^y)_p-NR^xCOR^y$, $-(CR^xR^y)_p-O-CH_2-CONR^xR^y$, heterocyclic group with 3 to 7 ring members, $-CH_2$-heterocyclic group with 3 to 7 ring members, $-CH_2-O$-heterocyclic group with 3 to 7 ring members, $-CH_2-NH$-heterocyclic group with 3 to 7 ring members, $-CH_2-N(C_{1-6}$alkyl)-heterocyclic group with 3 to 7 ring members, $-C(=O)NH$-heterocyclic group with 3 to 7 ring members, $C_{3-8}$cycloalkyl, $-CH_2-C_{3-8}$cycloalkyl, $-CH_2-O-C_{3-8}$cycloalkyl, and $C_{3-8}$cycloalkenyl, wherein said cycloalkyl, cycloalkenyl or heterocyclic groups may be optionally substituted by one or more $R^z$ groups, and wherein in each instance the heterocyclic group comprises one or more (e.g. 1, 2, or 3) heteroatoms selected from N, O, S and oxidised forms thereof;

or, when Q is $-C(OH)R^6R^7$, the $R^6$ and $R^7$ groups, together with the carbon atom to which they are attached, can join to form a $C_{3-6}$cycloalkyl or heterocyclyl group with 3 to 6 ring members, wherein the heterocyclic group comprises one or more (e.g. 1, 2, or 3) heteroatoms selected from N, O, S and oxidised forms thereof, and wherein said $C_{3-6}$cycloalkyl and heterocyclyl groups may be optionally substituted by one or more $R^z$ groups;

$R^8$ is selected from hydrogen, $C_{1-6}$alkyl, halo$C_{1-6}$alkyl, hydroxy$C_{1-6}$alkyl, $-(CH_2)_k-O-C_{1-6}$alkyl, $-(CH_2)_k-O$-(hydroxy$C_{1-6}$alkyl), hydroxy$C_{1-6}$alkoxy, $-(CH_2)_k-CO_2C_{1-6}$alkyl, $-(CH_2)_k-CO_2H$, $-C_{1-6}$alkyl-$N(H)_e(C_{1-4}$alkyl$)_{2-e}$, $-(CH_2)_j-C_{3-8}$cycloalkyl and $-(CH_2)_j-C_{3-8}$cycloalkenyl;

$R^x$ and $R^y$ are independently selected from hydrogen, halogen, nitro, nitrile, $C_{1-6}$alkyl, halo$C_{1-6}$alkyl, $C_2$-6alkenyl, $C_{2-6}$alkynyl, hydroxy, hydroxy$C_{1-6}$alkyl, $C_{1-6}$alkoxy, $-(CH_2)_k-O-C_{1-6}$alkyl, hydroxy$C_{1-6}$ alkoxy, $-COOC_{1-6}$alkyl, $-N(H)_e(C_{1-4}$alkyl$)_{2-e}$, $-C_{1-6}$ alkyl-$N(H)_e(C_{1-4}$alkyl$)_{2-e}$, $-(CH_2)_k-C(=O)N(H)_e(C_{1-4}$alkyl$)_{2-e}$, $C_{3-8}$cycloalkyl and $C_{3-8}$cycloalkenyl;

or the $R^x$ and $R^y$ groups, together with the carbon or nitrogen atom to which they are attached, can join to form a $C_{3-6}$cycloalkyl or saturated heterocyclyl group with 3 to 6 ring members which may be optionally fused to an aromatic heterocyclyl group of 3 to 5 ring members;

or when on a carbon atom the $R^x$ and $R^y$ groups can join together to form a =$CH_2$ group; $R^z$ is independently selected from halogen, nitro, nitrile, $C_{1-6}$alkyl, halo$C_{1-6}$alkyl, $C_{2-6}$alkenyl, $C_{2-6}$alkynyl, =O, hydroxy, hydroxy$C_{1-6}$alkyl, $C_{1-6}$alkoxy, —$(CH_2)_k$—O—$C_{1-6}$alkyl, hydroxy$C_{1-6}$alkoxy, —C(=O)$C_{1-6}$alkyl, —C(=O)$C_{1-6}$alkyl-OH, —C(=O)$C_{1-6}$alkyl-N(H)$_e$(C$_{1-4}$alkyl)$_{2-e}$, —C(=O)N(H)$_e$(C$_{1-4}$alkyl)$_{2-e}$, —$(CH_2)_r$CO$_2$C$_{1-6}$alkyl, —$(CH_2)_r$CO$_2$H, —N(H)$_e$(C$_{1-4}$alkyl)$_{2-e}$, —C$_{1-6}$alkyl-N(H)$_e$(C$_{1-4}$alkyl)$_{2-e}$, heterocyclyl group with 3 to 6 ring members, heterocyclyl group with 3 to 6 ring members substituted by —C(=O)$C_{1-4}$alkyl, heterocyclyl group with 3 to 6 ring members substituted by —C(=O)O$C_{1-4}$alkyl, heterocyclyl group with 3 to 6 ring members substituted by —C(=O)N(H)$_e$(C$_{1-4}$alkyl)$_{2-e}$, —C(=O)heterocyclyl group with 3 to 6 ring members, $C_{3-8}$cycloalkyl and $C_{3-8}$cycloalkenyl, wherein if $R^7$ is pyridine then $R^z$ is other then —$NH_2$;

a, j, d, e, n, r and p are independently selected from 0, 1 and 2;

k and m are independently selected from 1 and 2;

u is selected from 0, 1, 2 and 3; and v and w are independently selected from 0 and 1;

and reacting the compound of formula (2) with a methylating agent in the presence of a base.

The applicant has found that the process of the invention can provide improved diastereocontrol.

In particular, the process of the invention can provide a product in which the proportion of the following desired stereoisomer is increased:

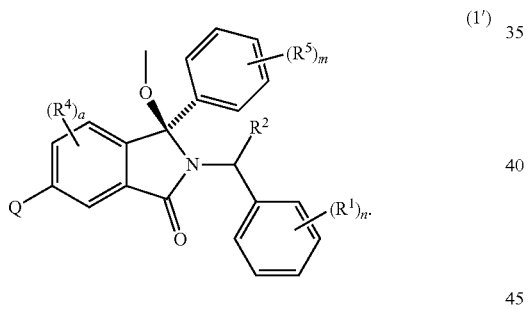
(1')

Q

In one embodiment, the invention provides a process for preparing a 1-methoxyisoindoline wherein Q is —C(OH)R$^6$R$^7$.

In one embodiment, the invention provides a process for preparing a 1-methoxyisoindoline wherein Q is —C(=O)R$^7$.

In the embodiment in which Q is —C(=O)R$^7$, the process may comprise a subsequent step in which Q is converted from a group —C(=O)R$^7$ into a group —C(OH)R$^6$R$^7$ by reaction with an organometallic reagent of the formula R$^6$M where M is a metal (for example a Grignard reagent of the formula R$^6$MgBr or an organozinc reagent of the formula Zn(R$^6$)$_2$).

In one embodiment, the invention provides a process for preparing a 1-methoxyisoindoline wherein Q is halogen (e.g. —F, —Cl, —Br, —I).

In the embodiment in which Q is halogen (e.g. —F, —Cl, —Br, —I) or —OTf the process may comprise subsequent steps in which Q is converted from:

halogen (e.g. —Br) or —OTf into a group

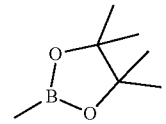

by a boronylation reaction, for example using bis(pinacolato)diboron, potassium acetate and a palladium catalyst (e.g Pd(dppf)Cl$_2$ complexed with dichloromethane);

a group

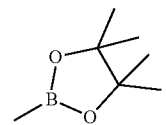

into a group —B(OH)$_2$, for example using NaIO$_4$; then a group —B(OH)$_2$ to a group —C(=CH)R$^7$ by reaction with a electrophile of the formula CH$_2$=CR$^7$-LG, wherein LG is an appropriate leaving group (e.g. —OTf or —Br);

a group —C(=CH)R$^7$ into a group

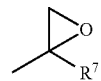

by oxidation (e.g. by a peracid such as mCPBA); and a group

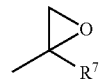

into a group —C(OH)R$^6$R$^7$ by reaction with an organometallic reagent of the formula R$^q$M where M is a metal (for example a Grignard reagent of the formula R$^q$Br or an organolithium reagent of the formula LiR$^q$, in each case in the presence of a Cu(I) salt, such as CuI), wherein R$^6$ Is —CH$_2$R$^q$.

The compounds wherein Q is —OTf, can be prepared from the corresponding compounds in which Q is —OC$_{1-4}$alkyl and —OH.

R$^2$

R$^2$ is selected from hydrogen, C$_{1-4}$ alkyl, C$_{2-6}$alkenyl, hydroxyC$_{1-4}$alkyl, —(CR$^x$R$^y$)$_u$—CO$_2$H, —(CR$^x$R$^y$)$_u$—CONR$^x$R$^y$, —(CR$^x$R$^y$)$_u$—CO$_2$R$^{10}$ wherein R$^{10}$ is selected from C$_{1-7}$ alkyl, C$_{1-7}$ alkeneyl, C$_{1-7}$ haloalkyl, triC$_{1-7}$ alkylsilyl-C$_{1-7}$alkyl, C$_{5-20}$ aryl and C$_{5-20}$ aryl-C$_{1-7}$ alkyl (for example —CHCH$_3$CO$_2$C$_{1-4}$alkyl, —CHCH$_3$CO$_2$CH$_2$CH=CH$_2$, —CHCH$_3$CO$_2$CH$_2$CH$_2$Si(C$_{1-4}$alkyl)$_3$, and —CHCH$_3$—CO$_2$phenyl In one embodiment, R$^2$ is selected from —(CR$^x$R$^y$)$_u$—CO$_2$R$^{10}$, wherein R$^{10}$ is selected from C$_{1-7}$ alkyl, C$_{1-7}$ alkeneyl, C$_{1-7}$ haloalkyl, triC$_{1-7}$ alkylsilyl-C$_{1-7}$alkyl, C$_{5-20}$ aryl and C$_{5-20}$ aryl-C$_{1-7}$ alkyl.

In one embodiment, $R^2$ is selected from

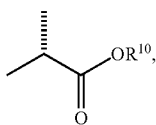

wherein $R^{10}$ is selected from $C_{1-7}$ alkyl, $C_{1-7}$ alkeneyl, $C_{1-7}$ haloalkyl, tri$C_{1-7}$ alkylsilyl-$C_{1-7}$alkyl, $C_{5-20}$ aryl and $C_{5-20}$ aryl-$C_{1-7}$ alkyl.

In particular, $R^2$ is selected from —$(CR^xR^y)_u$—$CO_2R^{10}$ wherein $R^{10}$ is selected from $C_{1-7}$ alkyl, $C_{1-7}$ alkeneyl $C_{1-7}$ haloalkyl, tri$C_{1-7}$ alkylsilyl-$C_{1-7}$alkyl, $C_{5-20}$ aryl and $C_{5-20}$ aryl-$C_{1-7}$ alkyl.

In one embodiment, $R^{10}$ is $C_{1-7}$ alkyl, for example $C_{1-4}$ alkyl (e.g. methyl, t-butyl).

In one embodiment, $R^{10}$ is $C_{1-7}$ alkeneyl, for example $C_{1-4}$ alkeneyl (e.g. —$CH_2CH=CH_2$).

In one embodiment, $R^{10}$ is $C_{1-7}$ trihaloalkyl, for example $C_{1-4}$ trihaloalkyl (e.g. —$CF_3$, —$CCl_3$).

In one embodiment, $R^{10}$ is tri$C_{1-7}$ alkylsilyl-$C_{1-7}$alkyl (e.g —$CH_2CH_2Si(CH_3)_3$).

In one embodiment, $R^{10}$ is selected from $C_{5-20}$ aryl-$C_{1-7}$ alkyl (e.g., benzyl, nitrobenzyl, para-methoxybenzyl).

In one embodiment, $R^{10}$ is selected from $C_{5-20}$ aryl (e.g. phenyl).

In one embodiment, $R^{10}$ is selected from methyl, t-butyl, —$CH_2CH=CH_2$, —$CF_3$, —$CCl_3$, —$CH_2CH_2Si(CH_3)_3$, phenyl, benzyl, nitrobenzyl, para-methoxybenzyl.

In one embodiment, $R^{10}$ is selected from —$CH_2CH=CH_2$, —$CH_2CH_2Si(CH_3)_3$, and phenyl.

In one embodiment, $R^2$ is selected from

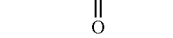

wherein $R^{10}$ is selected from —$CH_2CH=CH_2$, —$CH_2CH_2Si(CH_3)_3$, and phenyl.

In one embodiment u is selected from 0, 1, or 2. In one embodiment u is selected from 0 or 1.

In particular, $R^2$ can be selected from:
(i) —$(CH(CH_3))$—$CO_2C_{1-4}$alkyl, —$(CH(CH_3))$—$CO_2CH_2CH=CH_2$, —$(CH(CH_3))$—$CO_2CH_2CH_2Si(C_{1-4}alkyl)_3$ and —$(CH(CH_3))$—$CO_2$ phenyl;
(ii) —$C(CH_3)_2$—$CO_2C_{1-4}$alkyl, —$C(CH_3)_2$—$CO_2CH_2CH=CH_2$, —$C(CH_3)_2$—$CO_2CH_2CH_2Si(C_{1-4}alkyl)_3$ and —$C(CH_3)_2$—$CO_2C$ phenyl; and (iii)

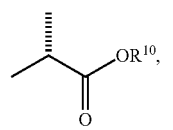

wherein $R^{10}$ is selected from —$C_{1-4}$alkyl, —$CH_2CH=CH_2$, —$CH_2CH_2Si(C_{1-4}alkyl)_3$ and $C_6$phenyl.

In particular, $R^2$ can be selected from —$CH_2CH=CH_2$, —$CH_2CH_2Si(CH_3)_3$ and -Ph e.g. —$CH_2CH=CH_2$.

In one embodiment, the process preferable comprises a subsequent de-esterification step in which $R^{10}$ is converted to hydrogen.

When $R^2$ is selected from —$(CR^xR^y)_u$—$CO_2C_{1-4}$alkyl, —$(CR^xR^y)_u$—$CO_2CH_2CH=CH_2$, —$(CR^xR^y)_u$—$CO_2CH_2CH_2Si(C_{1-4}alkyl)_3$, and —$(CR^xR^y)_u$—$CO_2C_6$ aryl, the de-esterification step provides a group $R^2$ which is —$(CR^xR^y)_u$—$CO_2H$.

When $R^2$ is selected from —$(CH(CH_3))$—$CO_2C_{1-4}$alkyl, —$(CH(CH_3))$—$CO_2CH_2CH=CH_2$, —$(CH(CH_3))$—$CO_2CH_2CH_2Si(C_{1-4}alkyl)_3$ (e.g. $CO_2CH_2CH_2Si(CH_3)_3$) and —$(CH(CH_3))$—$CO_2C_6$ary, the de-esterification step provides a group $R^2$ which is —$(CH(CH_3))$—$CO_2H$.

When $R^2$ is selected from

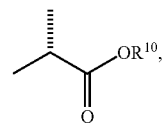

the de-esterification step provides a group $R^2$ which is

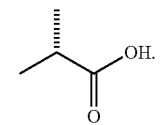

Any conditions can be used for the de-esterification step.

When $R^2$ is —$(CH(CH_3))$—$CO_2CH_2CH=CH_2$ the de-esterification step can be promoted using a Pd catalyst, for example $Pd(Ph_3)_4$.

When $R^2$ is $CO_2CH_2CH_2Si(CH_3)_3$ the de-esterification step can be promoted using a source of fluoride, e.g. TBAF.

When $R^2$ is $CO_2Ph$ the de-esterification step can be promoted by hydrolysis, particularly basic hydrolysis, for example using LiOH or NaOH.

Specific Products

The substituents on the compounds of formula (1°), (2°), (1) and (2) (and any subformulae thereof) can be any of the substituents disclosed in the general disclosure of the compounds hereinabove.

In one embodiment, the invention provides a process for preparing a 1-methoxyisoindoline wherein $R^1$ is p-Cl and n is 1.

In one embodiment, the invention provides a process for preparing a 1-methoxyisoindoline wherein $R^5$ is p-Cl and m is 1.

In one embodiment, the invention provides a process for preparing a 1-methoxyisoindoline wherein $R^4$ is 4-F and a is 1.

In a particular process of the invention, the product is a 1-methoxyisoindoline of formula (3)

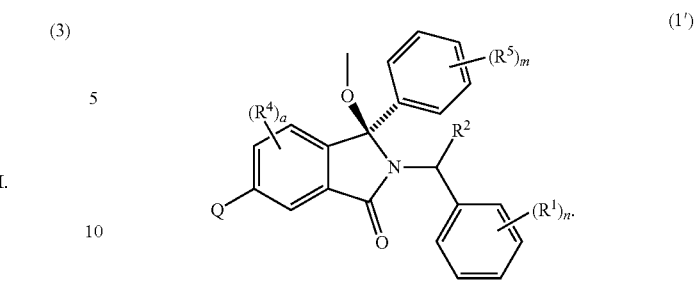

(1')

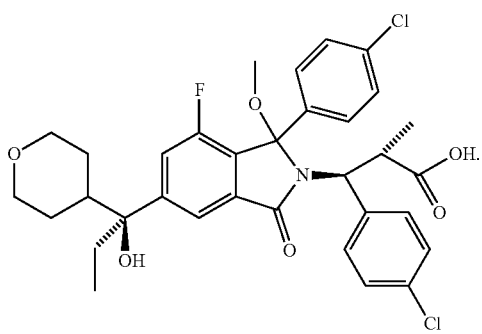

(3)

Stereochemistry

In one embodiment, the product is a 1-methoxyisoindoline which is predominantly the stereoisomer of formula (1°'):

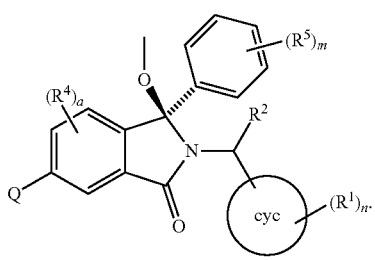

(1°')

For example, the product may be greater than 50%, 60%, 70%, 80%, 90%, 95%, 97%, 98%, or 99% of the desired stereoisomer, and less than 50%, 40%, 30%, 20%, 10%, 5%, 3%, 2%, or 1% of the stereoisomer:

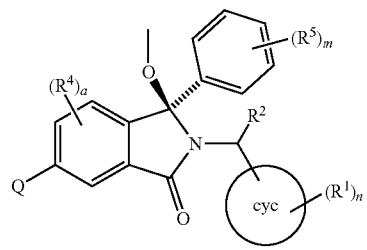

Desired stereoisomer

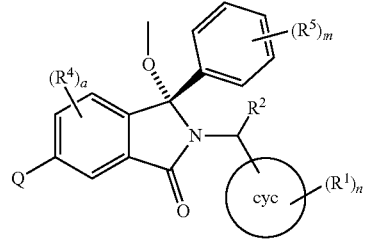

Other stereoisomer

In one embodiment, the product is a 1-methoxyisoindoline which is predominantly the stereoisomer of formula (1'):

For example, the product may be greater than 50%, 60%, 70%, 80%, 90%, 95%, 97%, 98%, or 99% of the desired stereoisomer, and less than 50%, 40%, 30%, 20%, 10%, 5%, 3%, 2%, or 1% of the other stereoisomer:

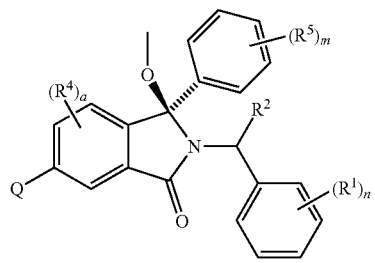

Desired stereoisomer

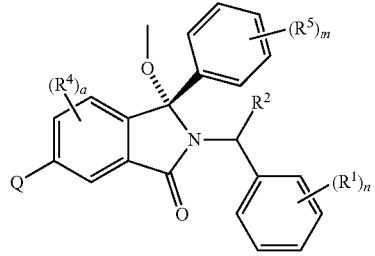

Other stereoisomer

In a particular process, the product is a 1-methoxyisoindoline which is predominantly the stereoisomer of formula (3'):

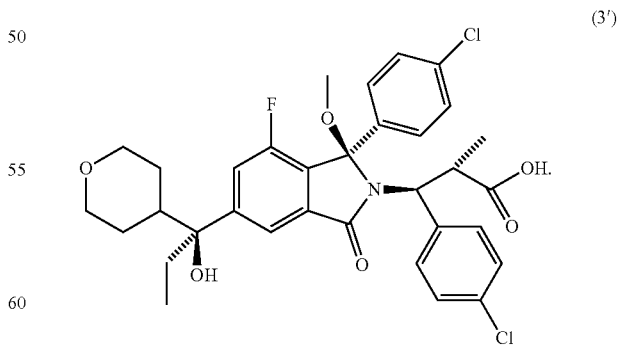

(3')

For example, the product may be greater than 50%, 60%, 70%, 80%, 90%, 95%, 97%, 98%, or 99% of the desired stereoisomer, and less than 50%, 40%, 30%, 20%, 10%, 5%, 3%, 2%, or 1% of the other stereoisomer:

117

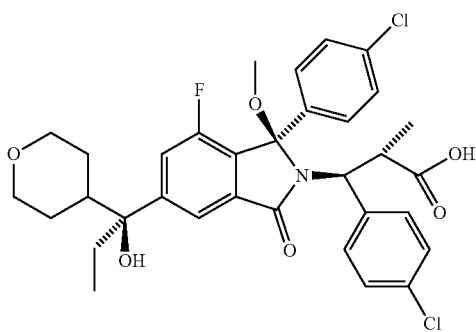

Desired stereoisomer

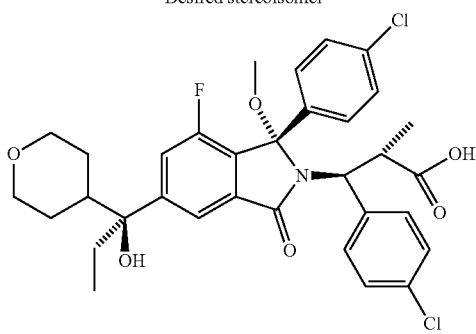

Other stereoisomer

In one embodiment, the product of the process directly obtained following the methylation step is predominantly the stereoisomer of formula (1°'), (1') or (3').

For example, the product may be greater than 50%, 60%, 70%, 80%, 90%, 95%, 97%, 98%, or 99% of the desired stereoisomer (1°'), (1') or (3'), and less than 50%, 40%, 30%, 20%, 10%, 5%, 3%, 2%, or 1% of the other stereoisomer:

In another embodiment, the process comprises an additional step, at any stage, in which the compound of formula 1 is resolved to increase the proportion of the stereoisomer of formula (1°'), (1') or (3').

The compound can be resolved by any standard method known the person skilled in the art. For example, the compound of formula (1°'), (1') or (3') can be resolved by crystallisation (possibly after first forming a derivative of the compound) or chromatography (for example supercritical fluid chromatography).

Accordingly, the invention provides a process, comprising a further step, at any stage, in which the compound of formula (1°), (1) or (3) is resolved to increase the proportion of the stereoisomer of formula (1°'), (1') or (3').

For example, following the resolution step, the product may be greater than 50%, 60%, 70%, 80%, 90%, 95%, 97%, 98%, or 99% of the desired stereoisomer (1°'), (1') or (3'), and less than 50%, 40%, 30%, 20%, 10%, 5%, 3%, 2%, or 1% of the other stereoisomer.

Specific processes for preparing (2S,3S)-3-(4-chlorophenyl)-3-[(1R)-1-(4-chlorophenyl)-7-fluoro-5-[(1S)-1-hydroxy-1-(oxan-4-yl)propyl]-1-methoxy-3-oxo-2,3-dihydro-1H-isoindol-2-yl]-2-methylpropanoic acid In a further embodiment, the invention provides a process for preparing a 1-methoxyisoindoline which is (2S,3S)-3-(4-chlorophenyl)-3-[1-(4-chlorophenyl)-7-fluoro-5-[(1S)-1-

118 hydroxy-1-(oxan-4-yl)propyl]-1-methoxy-3-oxo-2,3-dihydro-1H-isoindol-2-yl]-2-methylpropanoic acid:

(3)

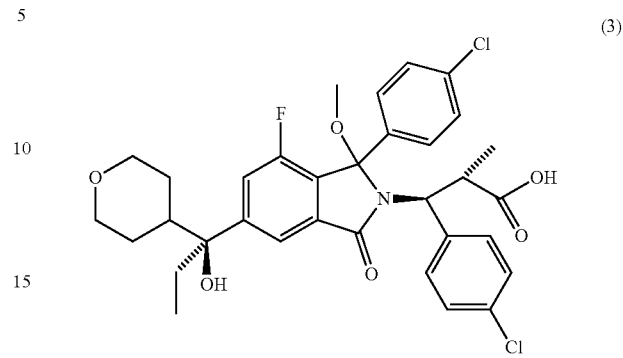

or a tautomer or a solvate or a pharmaceutically acceptable salt thereof, the process comprising:

(i) taking a compound of the formula (4)

(4)

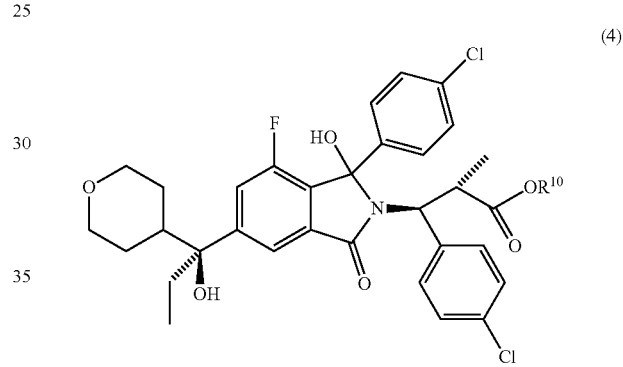

wherein $R^{10}$ is selected from $C_{1-7}$ alkyl, $C_{1-7}$ alkeneyl, $C_{1-7}$ haloalkyl, tri$C_{1-7}$ alkylsilyl-$C_{1-7}$alkyl, $C_{5-20}$ aryl and $C_{5-20}$ aryl-$C_{1-7}$ alkyl;

and reacting the compound of formula (4) with a methylating agent in the presence of a base to give a compound of formula (5):

(5)

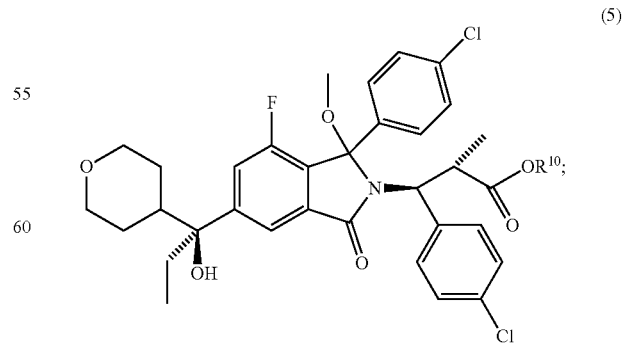

(ii) then a de-esterification step to convert the group $R^{10}$ to hydrogen and provide (2S,3S)-3-(4-chlorophenyl)-3-[(1-(4-chlorophenyl)-7-fluoro-5-[(1S)-1-hydroxy-1-(oxan-4-yl)propyl]-1-methoxy-3-oxo-2,3-dihydro-1H-isoindol-2-yl]-2-methylpropanoic acid (3):

(3)

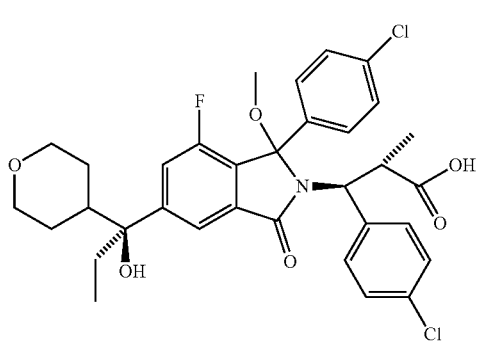

or a tautomer or a solvate or a pharmaceutically acceptable salt thereof; and (iii) optionally, a further step in which the compound of formula (3) is resolved (for example by crystallisation or chromatography e.g supercritical fluid chromatography) to increase the proportion of the stereoisomer which is (2S,3S)-3-(4-chlorophenyl)-3-[(1R)-1-(4-chlorophenyl)-7-fluoro-7-[(1S)-1-hydroxy-1-(oxan-4-yl)propyl]-1-methoxy-3-oxo-2,3-dihydro-1H-isoindol-2-yl]-2-methylpropanoic acid of formula (3')

(3')

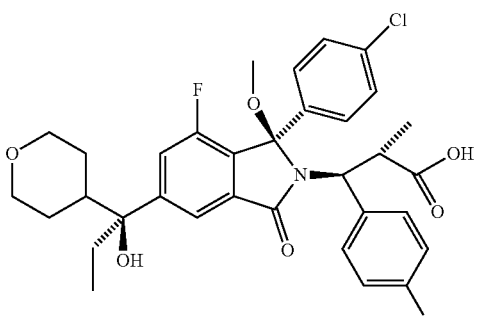

or a tautomer or a solvate or a pharmaceutically acceptable salt thereof.

The skilled person is well aware of conditions to de-esterify simple esters to form an acid. Particular groups $R^{10}$ include —$CH_2CH=CH_2$, —$CH_2CH_2Si(CH_3)_3$, and phenyl.

When $R^{10}$ is —$CH_2CH=CH_2$, the de-esterification may be performed using catalytic Pd (e.g. Pd(PPh$_3$), and K$_2$CO$_3$ in methanol).

When $R^{10}$ is —$CH_2CH_2Si(CH_3)_3$, the de-esterification may be performed using fluoride (e.g. CsF in DMF or TBAF in methanol).

When $R^{10}$ is phenyl, the de-esterification may be performed using basic hydrolysis (e.g. LiOH in THF/water).

In this embodiment, the compound of formula (4) can be prepared by taking a compound of formula (6):

(6)

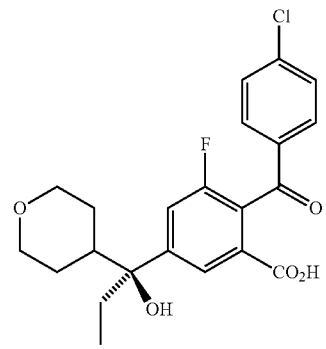

and coupling the compound of formula (6) with an amine of formula (7):

(7)

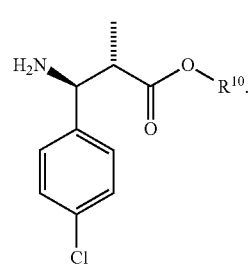

The skilled person is well aware of standard coupling conditions. Certain conditions that can be mentioned include HATU and DIPEA.

In this embodiment, the compound of formula (6) can prepared from a compound of formula (6'):

(6')

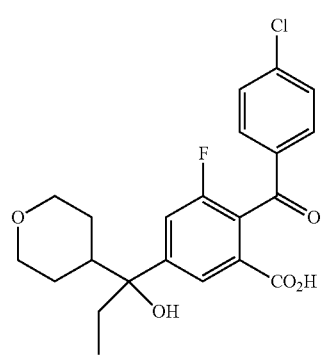

the process comprising the steps of:
(i) esterifying the compound of formula (6') to provide an ester of formula (6"):

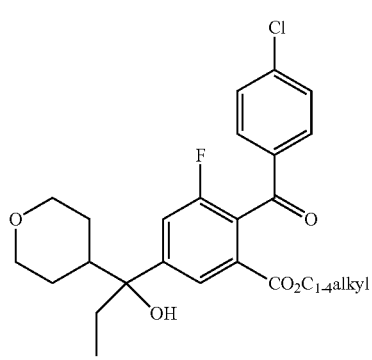
(6")

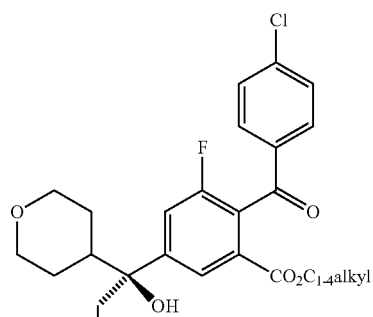
Desired stereoisomer (ii) resolving the compound of formula (6") to provide an ester of formula (6'''), for example resolving by crystallisation or chromatography:

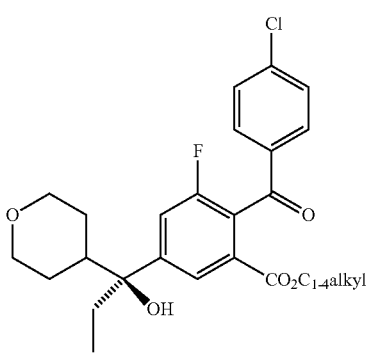
(6''')

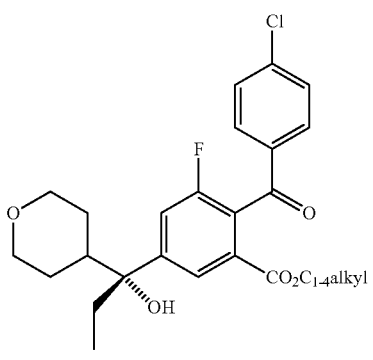
Other stereoisomer

Hydrolysis of the ester to provide the compound of formula (6) can be performed, for example, by basic hydrolysis (e.g. LiOH in THE/methanol/water).

In this embodiment, the compound of formula (6') can be prepared from a compound of formula (8):

(ii) hydrolysing the ester of formula (6''') to provide the compound of formula (6).

The resolution of compound (6") may take place by crystallisation of a pair of diastereomeric salts, for example salts formed by reaction with a chiral non-racemic amine.

The esterification and hydrolysis steps can be performed using conditions known to the skilled person.

In one embodiment, in the compounds of formula (6") and (6''') the $C_{1-4}$ alkyl group is a methyl i.e. the compounds of formula (6") and (6''') are the methyl esters.

The ester of formula (6") can be prepared by reacting the acid of formula (6) with methyl iodide, for example methyl iodide, $K_2CO_3$ in DMF.

The ester of formula (6") can be resolved, for example by chromotography, to provide a product which may be greater than 50%, 60%, 70%, 80%, 90%, 95%, 97%, 98%, or 99% of the desired stereoisomer, and less than 50%, 40%, 30%, 20%, 10%, 5%, 3%, 2%, or 1% of the other stereoisomer:

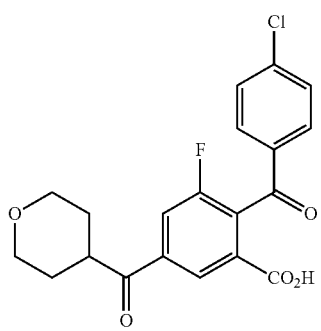
(8)

the process comprising the step of reacting the compound of formula (8) with an organometallic reagent of the formula EtM where M is a metal-containing residue (for example a Grignard reagent of the formula EtMgBr or an organozinc reagent of the formula $ZnEt_2$) for example $ZnEt_2$ and EtLi.

The compound of formula (8) can be prepared starting from a compound of formula (9):

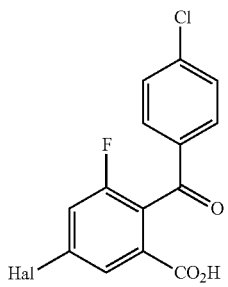

(9)

wherein Hal is a halogen (e.g., —F, —Cl, —Br, —I, for example —Br)

the process comprising the steps of:
(i) esterifying the compound of formula (9) to give a compound of formula (10):

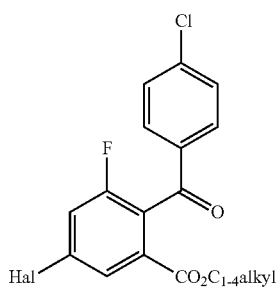

(10)

(ii) borylating the compound of formula (9) to give a compound of formula (11a) or (11b):

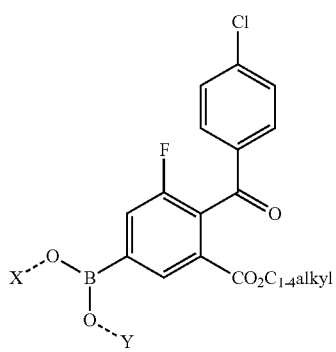

(11a)

wherein X and Y are independently selected from H and $C_{1-4}$ alkyl (e.g. —CH$_3$, —CH$_2$CH$_3$), or X and Y together form a $C_{1-5}$ alkylene chain, optionally substituted by 1-3 $C_{1-4}$ alkyl groups (e.g. —C(CH$_3$)$_2$C(CH$_3$)$_2$— and —CH$_2$C(CH$_3$)$_2$CH$_2$—) or 1-2 oxo groups, and wherein 1-2 carbon atoms of the alkylene chain can be replaced by —NCH$_3$— (e.g. —OC—CH$_2$N(CH$_3$)CH$_2$CO—);

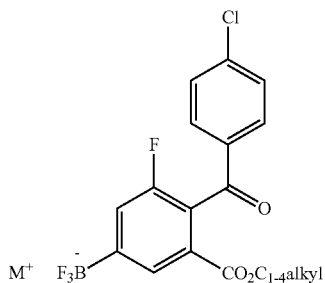

(11b)

where M is a metal, for example Na or K, in particular K,
(iii) coupling the compound of formula (11a) or (11b) with a compound of (11c):

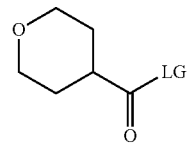

(11c)

wherein LG is a leaving group (for example a benzenethiol optionally substituted by 1 to 3 $C_{1-4}$ alkyl groups e.g. 4-methylbenzenethiol) in the presence of a palladium catalyst (e.g. Pd$_2$(dba)$_3$), a copper (I) salt such as ((thiophene-2-carbonyl)oxy)copper, and a phosphite (e.g. triethylphosphite); to give a compound of formula (8).

The process for preparing the compound of formula (8) is novel, and the invention provides this process for use in a method for preparing (2S,3S)-3-(4-chlorophenyl)-3-[(1R)-1-(4-chlorophenyl)-7-fluoro-5-[(1S)-1-hydroxy-1-(oxan-4-yl)propyl]-1-methoxy-3-oxo-2,3-dihydro-1H-isoindol-2-yl]-2-methylpropanoic acid, and also the invention provides this method per se.

In this embodiment, the amine of formula (7):

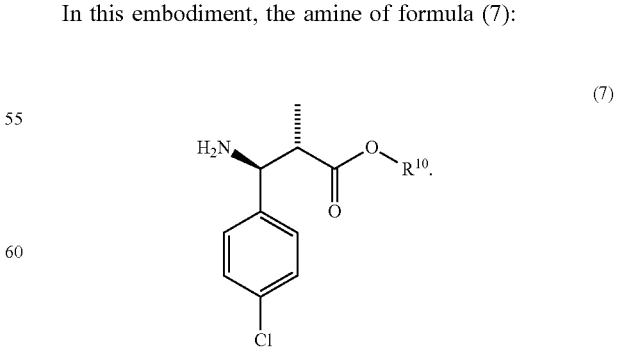

(7)

can be prepared using a process starting from an aldehyde of formula (12):

(12)

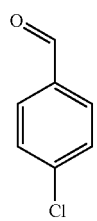

the process comprising the steps of:
(i) reacting the aldehyde of formula (12) with H₂NBoc and PhSO₂Na to give a compound of formula (13):

(13)

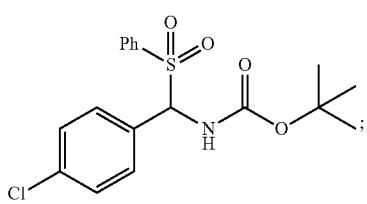

(ii) an elimination reaction on the compound of formula (13) in the presence of a base (e.g. a carbonate, for example potassium carbonate) to give an imine of formula (14):

(14)

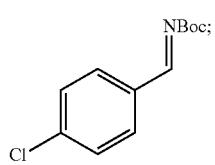

(iii) an imino-aldol reaction catalysed by (S)-proline between imine (14) and propan-2-al to give an aldehyde of formula (15):

(15)

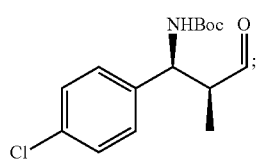

(iii) oxidation of aldehyde (15) to provide acid (16):

(16)

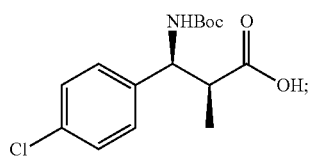

(iii) conversion of acid (16) to provide ester (17):

(17)

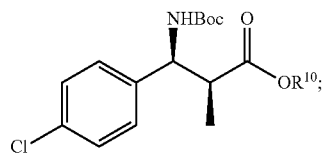

(iv) and then removal of the Boc protecting group to give the amine of formula (7).

In particular, in this process $R^{10}$ is:
—CH₂CH=CH₂;
—CH₂CH₂Si(CH₃)₃; and
-Ph.

When $R^{10}$ is —CH₂CH=CH₂, the ester (17) can be prepared by reacting acid (17) with allyl bromide.

When $R^{10}$ is —CH₂CH₂Si(CH₃)₃ or -Ph, the ester (17) can be prepared by coupling acid (17) with the alcohols HO—CH₂CH₂Si(CH₃)₃ or PhOH, for example using DCC and DMAP.

The Boc group can be removed by hydrolysis e.g. acid hydrolysis.

The process for preparing the amine of formula (7) is novel, and the invention provides this process for use in a method for preparing (2S,3S)-3-(4-chlorophenyl)-3-[(1R)-1-(4-chlorophenyl)-7-fluoro-5-[(1S)-1-hydroxy-1-(oxan-4-yl)propyl]-1-methoxy-3-oxo-2,3-dihydro-1H-isoindol-2-yl]-2-methylpropanoic acid, and the invention also provides this method per se.

In another embodiment, the invention provides a process for preparing a 1-methoxyisoindoline which is (2S,3S)-3-(4-chlorophenyl)-3-[1-(4-chlorophenyl)-7-fluoro-5-[(1S)-1-hydroxy-1-(oxan-4-yl)propyl]-1-methoxy-3-oxo-2,3-dihydro-1H-isoindol-2-yl]-2-methylpropanoic acid (3):

(3)

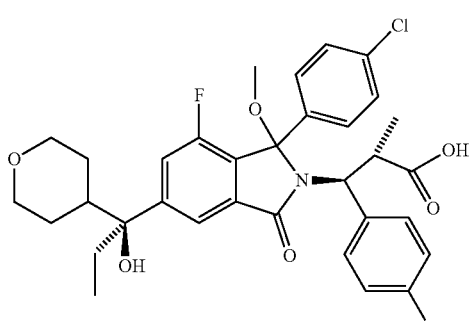

or a tautomer or a solvate or a pharmaceutically acceptable salt thereof,
the process comprising the step of de-esterifying a compound of the formula:

(4')

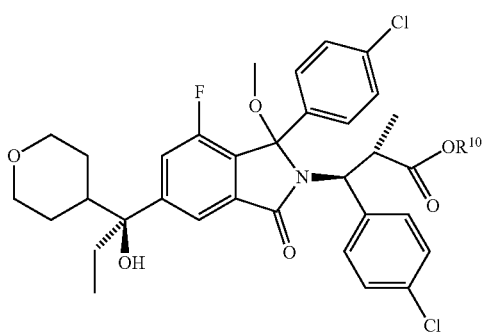

wherein $R^{10}$ is selected from $C_{1-7}$ alkyl, $C_{1-7}$ haloalkyl, triC$_{1-7}$ alkylsilyl-$C_{1-7}$alkyl, $C_{5-20}$ aryl and $C_{5-20}$ aryl-$C_{1-7}$ alkyl;

to provide (2S,3S)-3-(4-chlorophenyl)-3-[(1R)-1-(4-chlorophenyl)-7-fluoro-5-[1-hydroxy-1-(oxan-4-yl)propyl]-1-methoxy-3-oxo-2,3-dihydro-1H-isoindol-2-yl]-2-methylpropanoic acid or a tautomer or a solvate or a pharmaceutically acceptable salt thereof; and optionally, a further step in which the compound of formula (3) is resolved (for example by crystallisation or chromatography e.g supercritical fluid chromatography) to increase the proportion of the stereoisomer which is (2S,3S)-3-(4-chlorophenyl)-3-[(1R)-1-(4-chlorophenyl)-7-fluoro-5-[(1S)-1-hydroxy-1-(oxan-4-yl)propyl]-1-methoxy-3-oxo-2,3-dihydro-1H-isoindol-2-yl]-2-methylpropanoic acid of formula (3')

(3')

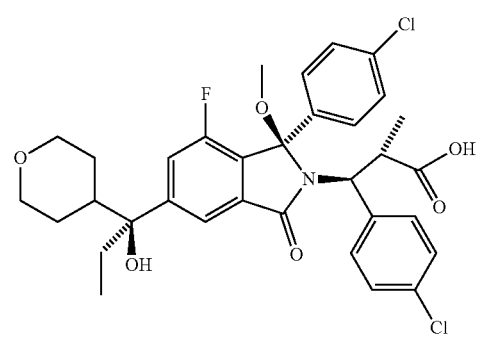

or a tautomer or a solvate or a pharmaceutically acceptable salt thereof.

In this case, the term resolution includes a process which increases the proportion of the epimer or diastereoisomer (3').

In particular, in this embodiment of the invention, $R^{10}$ is selected from —CH$_2$CH$_2$Si(CH$_3$)$_3$ and phenyl, for example —CH$_2$CH$_2$Si(CH$_3$)$_3$.

When $R^{10}$ is a silicon protecting group, it can be removed using a fluoride source. In particular, TBAF in an appropriate organic solvent (DCM, THF, DMF) or CsF in an appropriate solvent (DMF, NMP, DMSO). One set of conditions that can be mentioned are CsF in DMF e.g. at 60° C.

Suitable methods of de-esterification are discussed hereinabove.

In this embodiment, the compound of formula (4') can be prepared by taking a compound of the formula (4):

(4)

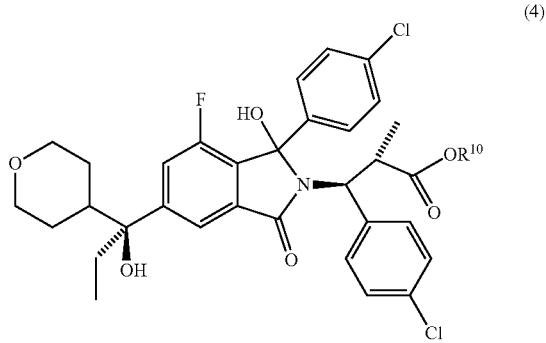

wherein $R^{10}$ is selected from $C_{1-7}$ alkyl, $C_{1-7}$ alkeneyl, $C_{1-7}$ haloalkyl, triC$_{1-7}$ alkylsilyl-$C_{1-7}$alkyl, $C_{5-20}$ aryl and $C_{5-20}$ aryl-$C_{1-7}$ alkyl; and reacting the compound of formula (4) with a methylating agent in the presence of a base.

The process for preparing the compound of formula (4') is novel, and the invention provides this process for use in a method for preparing (2S,3S)-3-(4-chlorophenyl)-3-[(1R)-1-(4-chlorophenyl)-7-fluoro-5-[(1S)-1-hydroxy-1-(oxan-4-yl)propyl]-1-methoxy-3-oxo-2,3-dihydro-1H-isoindol-2-yl]-2-methylpropanoic acid, and the invention also provides this method per se.

We discuss the methylation process hereinbelow under the heading "The methylation step" and the disclosure under that heading applies mutatis mutandis to the above process for preparing the compound of formula (4).

In particular, the methylation takes place using a strong base at a low temperature. Under these conditions, the conversion can take place with retention of stereochemistry and the process involves taking a compound of formula

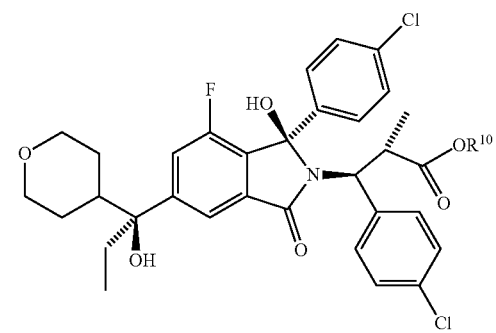

wherein $R^{10}$ is selected from $C_{1-7}$ alkyl, $C_{1-7}$ alkeneyl, $C_{1-7}$ haloalkyl, triC$_{1-7}$ alkylsilyl-$C_{1-7}$alkyl, $C_{5-20}$ aryl and $C_{5-20}$ aryl-$C_{1-7}$ alkyl; and reacting the compound with a methylating agent in the presence of a base to give a compound of the formula:

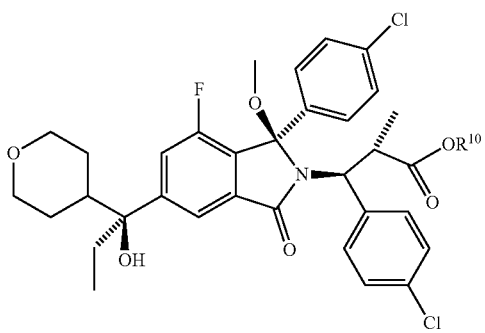

(6)

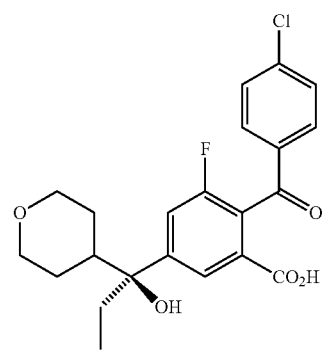

The degree of epimerisation also varies depending on the temperature. The least epimerisation occurs at lower temperatures. Therefore, in one embodiment of the invention, the methylation step takes place at a temperature which is below 0° C., −10° C., −20° C., −30° C., −40° C. or −50° C., preferably between −50° C. and −78° C. e.g. −70° C. In this embodiment, undesired epimerisation is minimised by the use of a low temperature.

This process is highly advantageous, because the diastereomeric purity of the starting material is retained in the product and potentially no subsequent resolution step is required.

In one embodiment, the base is selected from BuLi, tBuLi, sec-BuLi, LDA, LHMDS, NaHMDS, KHMDS, LTMP, LiOtBu and KotBu In one embodiment the base has a lithium counteraction. The diastereoselectivity is improved when using a lithium base relative to a sodium base and a potassium base (Li>Na>K).

In particular, the base is n-BuLi, hexylLi, LiOtBu, e.g. LiOtBu.

In one embodiment, the solvent is an organic solvent e.g. an ethereal solvent.

In one embodiment, the methylating agent is MeOTf or methyl fluorosulfonate.

In particular:

the base is selected from n-BuLi, t-BuLi, sec-BuLi, LDA, LHMDS, NaHMDS, KHMDS, LTMP, LiOtBu or KOtBu;

the methylating agent is selected from MeOTf and methylfluorosulfonate; and the step of reacting with the methylating agent takes place in an ethereal solvent.

In one embodiment, the base is added to a mixture of the compound of the formula (4') and the methylating agent.

In one embodiment of the process, the compound of formula (4) is prepared by taking a compound of formula (6):

and coupling the compound of formula (6) with an amine of formula (7):

(7)

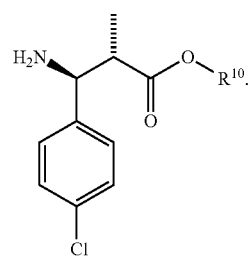

The skilled person is familiar with reactions involving the coupling of an acid and an amine. In particular the coupling step takes place in the presence of HATU and EDC. In one embodiment, the solvent is CH$_2$Cl$_2$ Preferably, the reaction is a crystallisation-induced dynamic resolution which gives a product of formula (4) which is predominantly the shown diastereoisomer:

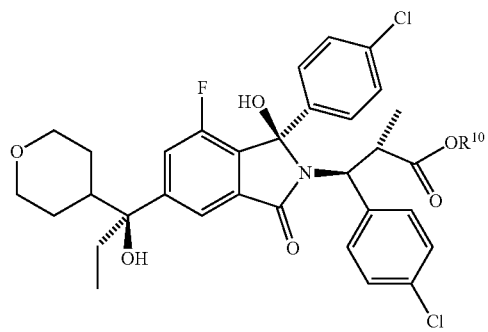

In this embodiment, in particular R$^{10}$ is trimethylsilylethyl.

If necessary, the diastereomeric purity can be increased further by recrystallisation, for example recrystallization from MeOH/water, optionally using seeding.

The process for preparing the compound of formula (4) is novel, and the invention provides this process for use in a method for preparing (2S,3S)-3-(4-chlorophenyl)-3-[(1R)-1-(4-chlorophenyl)-7-fluoro-5-[(1S)-1-hydroxy-1-(oxan-4-yl)propyl]-1-methoxy-3-oxo-2,3-dihydro-1H-isoindol-2-yl]-2-methylpropanoic acid, and the invention also provides this method per se.

In one embodiment, the compound of formula (6) is prepared by taking a compound of formula (6'):

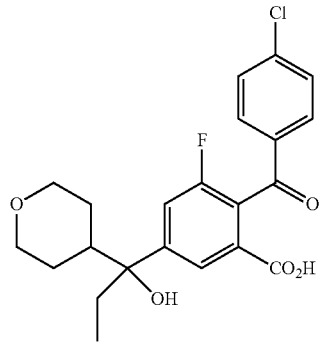

(6')

and resolving the compound of formula (6') using a chiral-non-racemic base.

The chiral non-racemic base reacts with the compound of formula (6') to give a pair of diastereomeric salts:

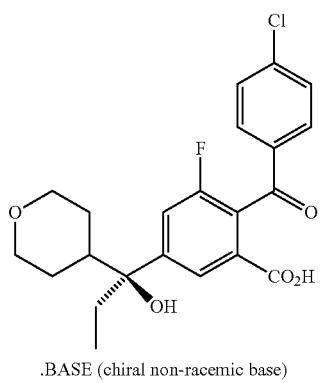

.BASE (chiral non-racemic base)

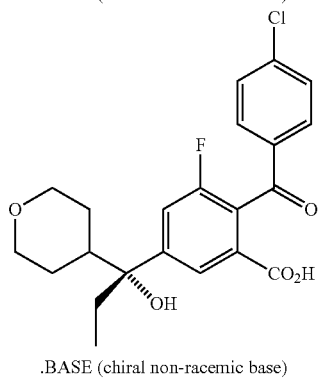

.BASE (chiral non-racemic base)

The desired diastereoisomer can be separated by crystallisation.

In one embodiment, the chiral-non-racemic base is an amine, for example bis[(1S)-1-phenylethyl]amine.

The process for preparing the compound of formula (6) is novel, and the invention provides this process for use in a method for preparing (2S,3S)-3-(4-chlorophenyl)-3-[(1R)-1-(4-chlorophenyl)-7-fluoro-5-[(1S)-1-hydroxy-1-(oxan-4-yl)propyl]-1-methoxy-3-oxo-2,3-dihydro-1H-isoindol-2-yl]-2-methylpropanoic acid, and the invention also provides this method per se.

In one embodiment, the compound of formula (6) is prepared by taking a compound of formula (28):

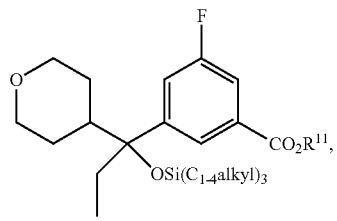

(28)

wherein $R^{11}$ is hydrogen, $C_{1-7}$ alkyl, $C_{1-7}$ alkeneyl, $C_{1-7}$ haloalkyl, tri$C_{1-7}$ alkylsilyl-$C_{1-7}$alkyl, $C_{5-20}$ aryl and $C_{5-20}$ aryl-$C_{1-7}$ alkyl (e.g. —$CH_2CH$=$CH_2$, —$CH_2CH_2Si(CH_3)_3$, and phenyl) and reacting the compound of formula (28) with a compound of the formula (29) in the presence of a base:

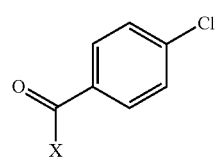

(29)

wherein X=—$OC_{1-4}$alkyl (e.g. —$OCH_3$, —$OCH_2CH_3$), halogen (e.g. —Cl), —$N(OCH_3)CH_3$, —$OC_{1-4}$haloalkyl (e.g. —$OCH_2CF_3$), 2-thiopyridine or 2-pyrrolyl), and then converting the —$OSi(C_{1-4}alkyl)_3$ group to an —OH group by removing the silicon-based protecting group and when $R^{11}$ is other than hydrogen de-esterification to convert $R^{11}$ to hydrogen.

The skilled person is aware of standard methods for removing silicon-based protecting groups. In one embodiment, the step of converting the —$OSi(C_{1-4})_3$ group to an —OH group takes place using an acid, for example HCl, TFA, $H_3PO_4$, or $H_2SO_4$ e.g. $H_3PO_4$. Alternatively, a source of fluoride can be used e.g TBAF or CsF.

In one embodiment $R^{11}$ is hydrogen and the base is added in greater than one equivalent, for example greater than 1.5, 1.7, 1.8 or 1.9 equivalents, relative to the compound of formula (6'), e.g. in two equivalents. When $R^{11}$ is hydrogen the compound has a further acidic hydrogen and so an extra equivalent of base is required.

In one embodiment the base is LDA, LHMDS, LTMP, BuLi, HexLi, sec-BuLi or tBuLi, for example n-BuLi, HexI-Li, sec-BuLi or LiTMP. In one embodiment, an additive is also included, for example TMEDA and LiCl. In one embodiment, the solvent is ethereal.

In one embodiment, the reaction takes place at low temperature, for example between −50° C. and −70° C.

In one embodiment, X is Cl.

In one embodiment, the step of treating the compound of formula (6') with a base takes place by adding the compound of formula (6') to a solution of the base.

In particular, the reaction can be performed using a base which is secBuLi in the presence of TMEDA in THF and wherein the compound of formula (29) is 4-chlorobenzoic acid methyl ester.

In particular, the reaction can be performed using a base which is LiTMP in THF and wherein the compound of formula (29) is 4-chlorobenzoic acid ethyl ester.

In particular, the reaction can be performed using a base which is BuLi, hexyl-Li or sec-BuLi in THF and wherein the compound of formula (29) is 4-chlorobenzoic acid ethyl ester.

In particular, the reaction can be performed using a base which is n-BuLi, hexyl-Li or sec-BuLi in THF and wherein the compound of formula (29) is 4-chlorobenzoyl chloride.

In one embodiment, the reaction can be performed using a base which is n-BuLi or HexLi in THF and wherein the compound of formula (29) is 4-chlorobenzoyl chloride, and the temperature is −50° C. to −70° C.

In one embodiment, the base is n-BuLi or HexLi, the compound of formula (29) is 4-chlorobenzoyl chloride, and $R^{11}$ is H.

In Particular, the Reaction is Performed by Adding the Compound of Formula (28) to a Solution of the Base.

In one embodiment, the compound of formula (6) is prepared by taking a compound of formula (30):

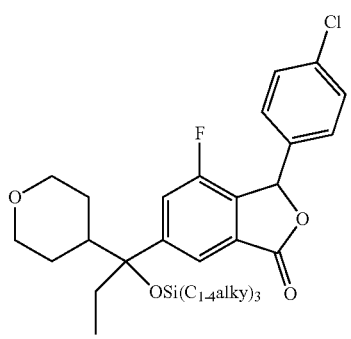
(30)

and treating the compound of formula (30) with an oxidising agent, for example $KMnO_4$, and then converting the —OSi($C_{1-4}$alkyl)$_3$ group to an —OH group by removing the silicon protecting group.

The compound of formula (30) in turn is prepared either by:

(i) taking a compound of formula (28):

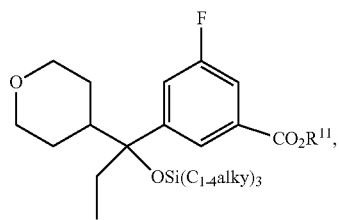
(28)

wherein $R^{11}$ is hydrogen, $C_{1-7}$ alkyl, $C_{1-7}$ alkeneyl, $C_{1-7}$ haloalkyl, tri$C_{1-7}$ alkylsilyl-$C_{1-7}$alkyl, $C_{5-20}$ aryl and $C_{5-20}$ aryl-$C_{1-7}$ alkyl (e.g. —$CH_2CH$=$CH_2$, —$CH_2CH_2Si(CH_3)_3$, and phenyl)
and treating the compound of formula (6) with a base, and then adding a compound of the formula (31):

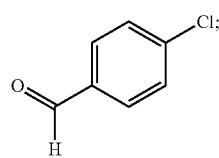
(31)

or (ii) taking a compound of formula (28):

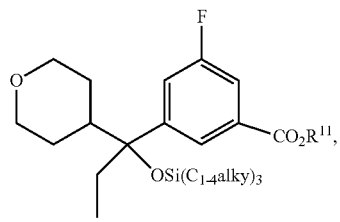
(28)

wherein $R^{11}$ is hydrogen, $C_{1-7}$ alkyl, $C_{1-7}$ alkeneyl, $C_{1-7}$ haloalkyl, tri$C_{1-7}$ alkylsilyl-$C_{1-7}$alkyl, $C_{5-20}$ aryl and $C_{5-20}$ aryl-$C_{1-7}$ alkyl (e.g. —$CH_2CH$=$CH_2$, —$CH_2CH_2Si(CH_3)_3$, and phenyl)
and reacting the compound of formula (28) with iodine in the presence of a base to give a compound of formula (32):

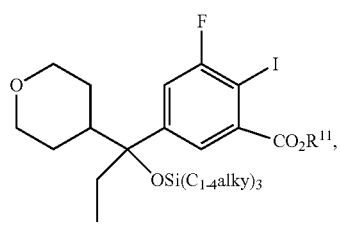
(32)

and treating the compound of formula (32) with a base, and then adding a compound of the formula (31):

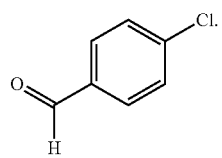
(29)

The processes for preparing the compound of formula (6') are novel, and the invention provides these processes for use in a method for preparing (2S,3S)-3-(4-chlorophenyl)-3-[(1R)-1-(4-chlorophenyl)-7-fluoro-5-[(1S)-1-hydroxy-1-(oxan-4-yl)propyl]-1-methoxy-3-oxo-2,3-dihydro-1H-isoindol-2-yl]-2-methylpropanoic acid, and the invention also provides these methods per se.

In one embodiment, the compound of formula (28) is prepared by reacting a compound of formula (33)

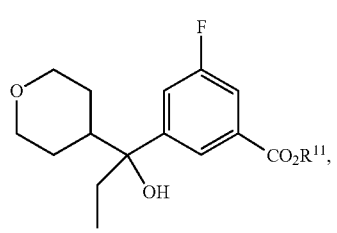
(33)

with (C$_{1-4}$alkyl)$_3$Si-T, wherein T is Cl or —OTf, wherein R$^{11}$ is hydrogen, C$_{1-7}$ alkyl, C$_{1-7}$ alkeneyl, C$_{1-7}$ haloalkyl, triC$_{1-7}$ alkylsilyl-C$_{1-7}$alkyl, C$_{5-20}$ aryl and C$_{5-20}$ aryl-C$_{1-7}$ alkyl (e.g. —CH$_2$CH=CH$_2$, —CH$_2$CH$_2$Si(CH$_3$)$_3$, and phenyl), and when R$^{11}$ is other than hydrogen, optionally de-esterification to convert R$^{11}$ to hydrogen.

This step represents a protection of an alcohol with a silicon-based protecting group, which usual conditions fall within the common general knowledge.

If required, any suitable de-esterification conditions can be used to convert R$^{11}$ to hydrogen, for example an alkyl ester can be hydrolysed using acid e.g., HCl or TFA, for example TFA.

In one embodiment, the compound of formula (33) is prepared by reacting a compound of formula (34) and a compound of formula (35) in the presence of a base:

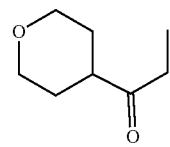

(34)

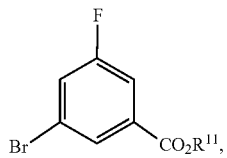

(35)

and when R$^{11}$ is other than hydrogen, optionally de-esterification to convert R$^{11}$ to hydrogen.

In particular, the base is BuLi, HexLi or tBuLi. In particular, the solvent is an ethereal solvent (e.g. 2-MeTHF, THF, or hexane, and when R$^{11}$ is other than hydrogen, optionally de-esterification to convert R$^{11}$ to hydrogen.

An additive, e.g. LiCl (for example at 0.5-1 mol equivalents) can be added.

In particular, the base is added to a mixture of the compounds of formula (34) and (35).

If required, any suitable de-esterification conditions can be used to convert R$^{11}$ to hydrogen, for example an alkyl ester can be hydrolysed using acid e.g. HCl or TFA, for example TFA.

In one embodiment, R$^{11}$ is C$_{1-4}$ alkyl e.g. t-Bu.

In one embodiment, the compound of formula (35) is prepared by reacting a compound of (36)

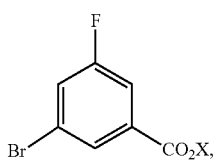

(36)

wherein X=—OC$_{1-4}$alkyl (e.g. —OCH$_3$, —OCH$_2$CH$_3$), halogen (e.g. —Cl), —N(OCH$_3$)CH$_3$, —OC$_{1-4}$haloalkyl (e.g. —OCH$_2$CF$_3$), 2-thiopyridine or 2-pyrrolyl), with an alcohol of formula R$^{11}$OH or an alkoxide of the formula R$^{11}$OM wherein M is Li, Na or Li, wherein in turn the compound of formula (36) is prepared by reacting an acid of formula (37) with a chlorinating agent:

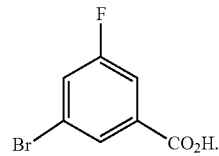

In one embodiment, the chlorinating agent is SO$_2$Cl$_2$ or COCl$_2$, for example COCl$_2$.

The alcohol is chosen to give the desired ester of formula (35). In particular, R$^{11}$ is t-Bu and the compound of formula (36) is reacted with an alkoxide of the formula LiOt-Bu.

In another embodiment, the invention provides a process for preparing a 1-methoxyisoindoline which is (2S,3S)-3-(4-chlorophenyl)-3-[1-(4-chlorophenyl)-7-fluoro-5-[(1S)-1-hydroxy-1-(oxan-4-yl)propyl]-1-methoxy-3-oxo-2,3-dihydro-1H-isoindol-2-yl]-2-methylpropanoic acid (3):

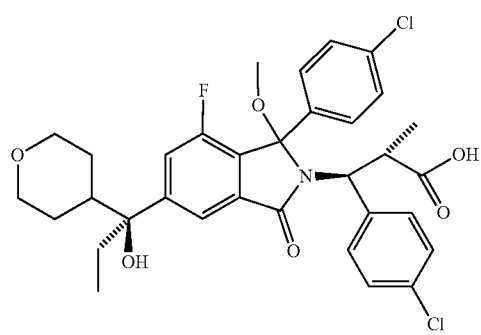

(3)

or a tautomer or a solvate or a pharmaceutically acceptable salt thereof, the process comprising the step of, in any order:
(i) de-esterifying a compound of the formula (4"):

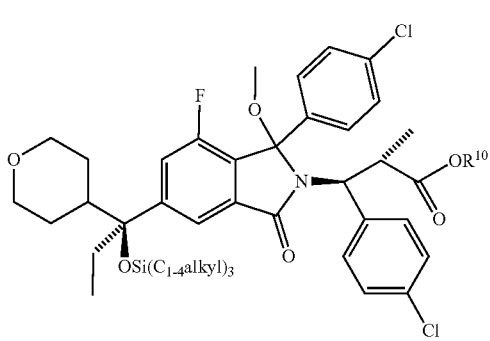

(4")

wherein R$^{10}$ is selected from C$_{1-7}$ alkyl, C$_{1-7}$ haloalkyl, triC$_{1-7}$ alkylsilyl-C$_{1-7}$alkyl, C$_{5-20}$ aryl and C$_{5-20}$ aryl-C$_{1-7}$ alkyl; and
(ii) removing the —Si(C$_{1-4}$alkyl)$_3$ protecting group from the alcohol to provide (2S,3S)-3-(4-chlorophenyl)-3-[(1R)-1-(4-chlorophenyl)-7-fluoro-5-[1-hydroxy-1-(oxan-4-yl)propyl]-1-methoxy-3-oxo-2,3-dihydro-1H-isoindol-2-yl]-2-methylpropanoic acid or a tautomer or a solvate or a pharmaceutically acceptable salt thereof; and optionally, a further step in which the compound of formula (3) is resolved to increase the proportion of the stereoisomer which is (2S,3S)-3-(4-chlorophenyl)-3-[(1R)-1-(4-chlorophenyl)-7-fluoro-5-[(1S)-1-hydroxy-1-(oxan-4-yl)propyl]-1-methoxy-3-oxo-2,3-dihydro-1H-isoindol-2-yl]-2-methylpropanoic acid of formula (3')

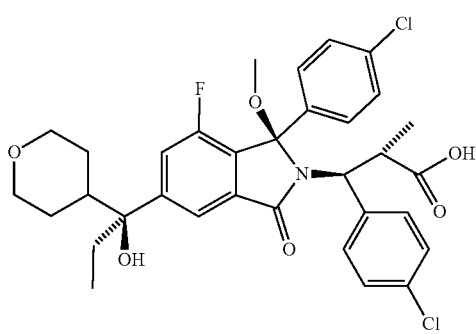
(3')

or a tautomer or a solvate or a pharmaceutically acceptable salt thereof.

Suitable methods of de-esterification are discussed hereinabove.

The removal of the silicon protecting group can be performed using a source of fluoride (e.g. TBAF).

In one embodiment, $R^{10}$ is tri$C_{1-7}$ alkylsilyl-$C_{1-7}$alkyl, for example —$CH_2CH_2Si(CH_3)_3$, and the de-esterification and de-protection can be performed in one step using a source of fluoride (e.g. TBAF).

In another embodiment, the invention provides a process for preparing a 1-methoxyisoindoline which is (2S,3S)-3-(4-chlorophenyl)-3-[1-(4-chlorophenyl)-7-fluoro-5-[1-hydroxy-1-(oxan-4-yl)propyl]-1-methoxy-3-oxo-2,3-dihydro-1H-isoindol-2-yl]-2-methylpropanoic acid (3"):

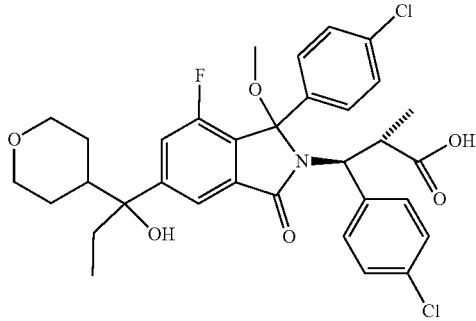
(3")

or a tautomer or a solvate or a pharmaceutically acceptable salt thereof, the process starting from a ketone of formula (18):

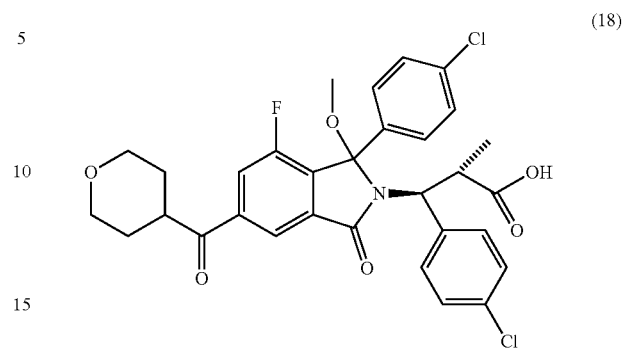
(18)

the process comprising reacting the ketone of formula (18) with an organometallic reagent of the formula EtM where M is a metal-containing residue (for example a Grignard reagent of the formula EtMgBr or an organozinc reagent of the formula $Zn(Et)_2$), to provide (2S,3S)-3-(4-chlorophenyl)-3-[(1R)-1-(4-chlorophenyl)-7-fluoro-5-[1-hydroxy-1-(oxan-4-yl)propyl]-1-methoxy-3-oxo-2,3-dihydro-1H-isoindol-2-yl]-2-methylpropanoic acid or a tautomer or a solvate or a pharmaceutically acceptable salt thereof; and optionally, a further step in which the compound of formula (3) is resolved (for example by crystallisation or chromatography e.g supercritical fluid chromatography) to increase the proportion of the stereoisomer which is (2S,3S)-3-(4-chlorophenyl)-3-[(1R)-1-(4-chlorophenyl)-7-fluoro-5-[(1S)-1-hydroxy-1-(oxan-4-yl)propyl]-1-methoxy-3-oxo-2,3-dihydro-1H-isoindol-2-yl]-2-methylpropanoic acid of formula (3')

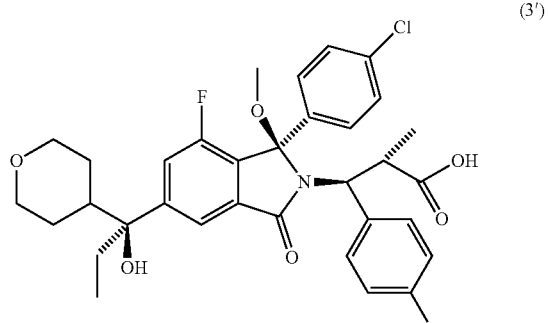
(3')

or a tautomer or a solvate or a pharmaceutically acceptable salt thereof.

In this embodiment, the ketone of formula (18) may be prepared by de-esterifying a compound of the formula (19):

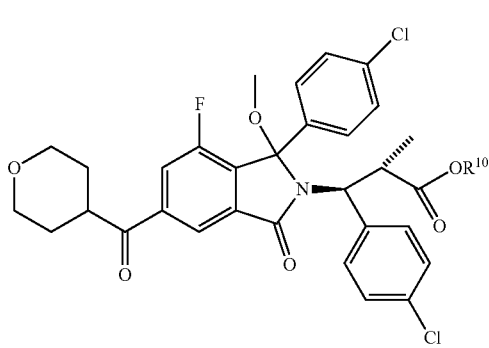

(19)

wherein $R^{10}$ is selected from $C_{1-7}$ alkyl, $C_{1-7}$ alkeneyl, $C_{1-7}$ haloalkyl, $triC_{1-7}$ alkylsilyl-$C_{1-7}$alkyl, $C_{5-20}$ aryl and $C_{5-20}$ aryl-$C_{1-7}$ alkyl (e.g. —CH$_2$CH═CH$_2$, —CH$_2$CH$_2$Si(CH$_3$)$_3$, and phenyl).

Again, suitable methods of de-esterification are discussed hereinabove.

In this embodiment, the compound of the formula (19) may be prepared by:
  (i) taking a compound of the formula (21)

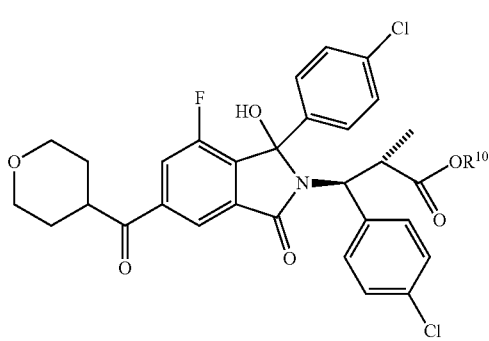

(21)

and reacting the compound of formula (21) with a methylating agent in the presence of a base; and
  (ii) optionally, a further step in which the compound of formula (19) is resolved (for example by crystallisation or chromatography e.g supercritical fluid chromatography) to increase the proportion of the following stereoisomer (19')

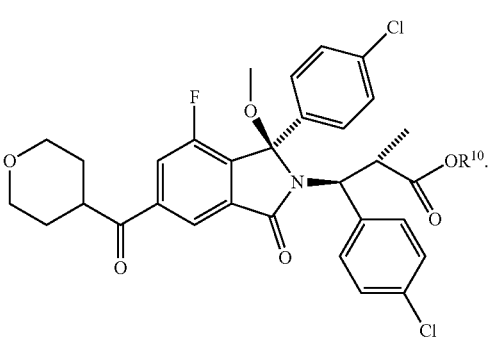

(19')

In this embodiment, the compound of formula (21) may be prepared by taking a compound of formula (8):

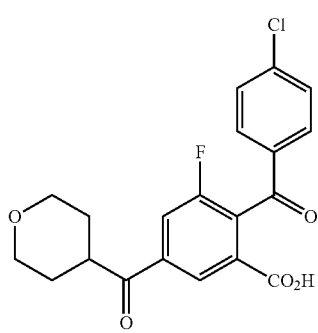

(8)

and coupling the compound of formula (8) with an amine of formula (7):

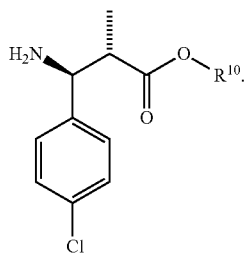

(7)

Suitable coupling conditions are discussed hereinabove. In this embodiment, the compounds of formula (8) and (7) may be prepared by the processes disclosed herein.

In another embodiment, the invention provides a process for preparing a 1-methoxyisoindoline which is (2S,3S)-3-(4-chlorophenyl)-3-[1-(4-chlorophenyl)-7-fluoro-5-[1-hydroxy-1-(oxan-4-yl)propyl]-1-methoxy-3-oxo-2,3-dihydro-1H-isoindol-2-yl]-2-methylpropanoic acid:

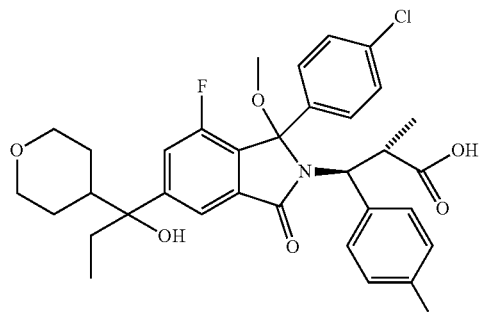

(3″)

or a tautomer or a solvate or a pharmaceutically acceptable salt thereof, the process comprising:

(i) taking an epoxide compound of the formula (22)

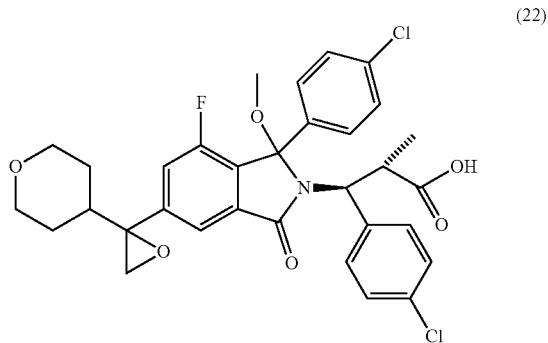 [SMILES: COC1(c2ccc(Cl)cc2)c2c(F)cc(C3(C4CCOCC4)CO3)cc2C(=O)N1[C@H](c1ccc(Cl)cc1)[C@H](C)C(=O)O]

(22)

and reacting the epoxide of formula (22) with an organometallic of the formula MMe, wherein M is a metal (for example CuI/MeLi), to give a compound of formula (3″), and
(ii) optionally, a further step in which the compound of formula (3″) is resolved to increase the proportion of the stereoisomer which is (2S,3S)-3-(4-chlorophenyl)-3-[(1R)-1-(4-chlorophenyl)-7-fluoro-5-[(1S)-1-hydroxy-1-(oxan-4-yl)propyl]-1-methoxy-3-oxo-2,3-dihydro-1H-isoindol-2-yl]-2-methylpropanoic acid of formula (3′)

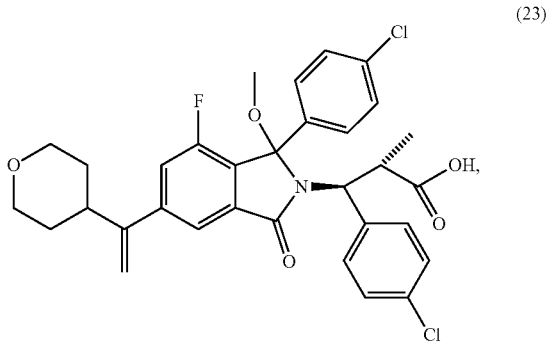 [SMILES: C=C(c1cc(F)c2c(c1)C(=O)N([C@H](c1ccc(Cl)cc1)[C@H](C)C(=O)O)C2(OC)c1ccc(Cl)cc1)C1CCOCC1]

(3′)

or a tautomer or a solvate or a pharmaceutically acceptable salt thereof.

In this embodiment, the compound of formula (22) may be prepared by oxidising a compound of formula (23):

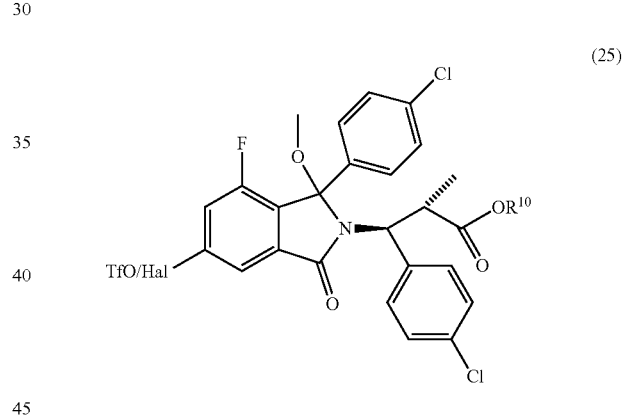

(23)

for example using a peracid such as m-CPBA.

In this embodiment, the compound of formula (23) may be prepared by de-esterifying a compound of the formula (24):

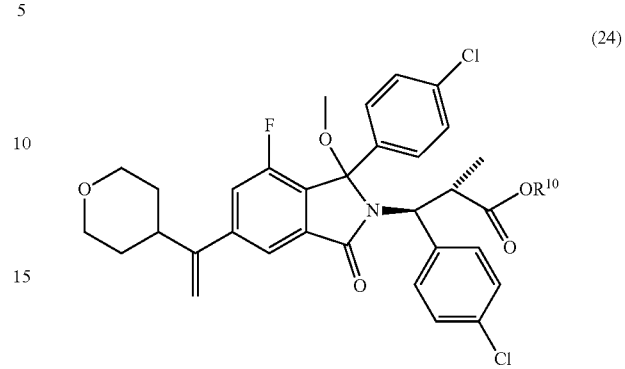

(24)

wherein $R^{10}$ is selected from $C_{1-7}$ alkyl, $C_{1-7}$ alkeneyl, $C_{1-7}$ haloalkyl, tri$C_{1-7}$ alkylsilyl-$C_{1-7}$alkyl, $C_{5-20}$ aryl and $C_{5-20}$ aryl-$C_{1-7}$ alkyl (e.g. —CH$_2$CH=CH$_2$, —CH$_2$CH$_2$Si(CH$_3$)$_3$, and phenyl).

Suitable esterification conditions are discussed hereinabove.

In this embodiment, the compound of formula (24) may be prepared by a process starting from a compound of formula (25):

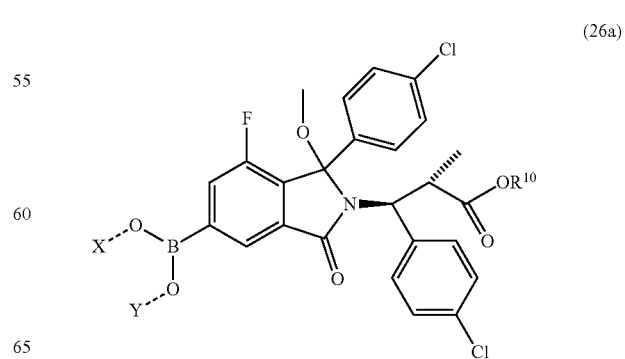

(25)

wherein Hal is a halogen (e.g., —F, —Cl, —Br, —I, for example —Br)
the process comprising the steps of:
(i) borylating the compound of formula (25) to give a compound of formula (26a) or (26b):

(26a)

wherein X and Y are independently selected from H and $C_{1-4}$ alkyl (e.g. —$CH_3$, —$CH_2CH_3$), or X and Y together form a $C_{1-5}$ alkylene chain, optionally substituted by 1-3 $C_{1-4}$ alkyl groups (e.g. —$C(CH_3)_2C(CH_3)_2$— and —$CH_2C(CH_3)_2CH_2$—) or 1-2 oxo groups, and wherein 1-2 carbon atoms of the alkylene chain can be replaced by —$NCH_3$— (e.g. —OC—$CH_2N(CH_3)CH_2$CO—), (26b)

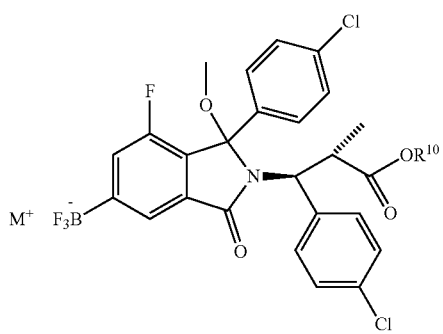

where M is a metal, for example Na or K, in particular K,
(iii) coupling the compound of formula (26a) or (26b) with a compound of (26c):

(26c)

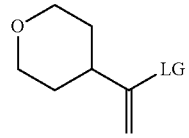

wherein LG is a leaving group (e.g. Hal or triflate) in the presence of a palladium catalyst (e.g. Pd(PPh$_3$)$_4$) and a base (e.g. potassium phosphate);
to give a compound of formula (24).

In this embodiment, the compound of formula (25) may be prepared by a process starting from a compound of formula (27):

(27)

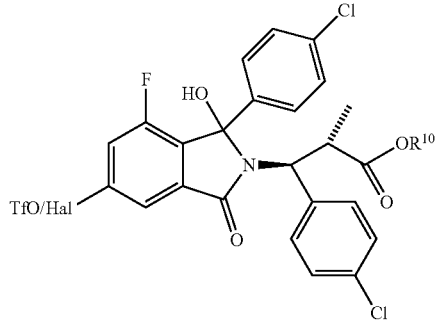

wherein Hal is a halogen (e.g., —F, —Cl, —Br, —I, for example —Br)
and reacting the compound of formula (27) with a methylating agent in the presence of a base,
and, optionally, a further step in which the compound of formula (25) is resolved (for example by crystallisation or chromatography e.g. supercritical fluid chromatography) to increase the proportion of the following stereoisomer (25')

(25')

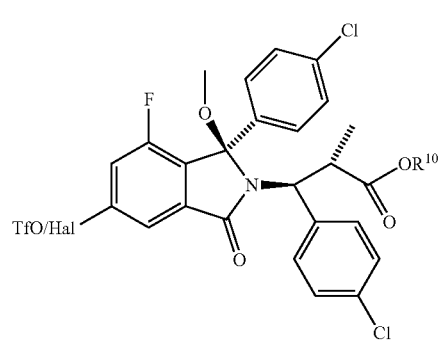

wherein Hal is a halogen (e.g., —F, —Cl, —Br, —I, for example —Br)

In this embodiment, the compound of formula (27) may be prepared by a process starting from a compound of formula (9):

(9)

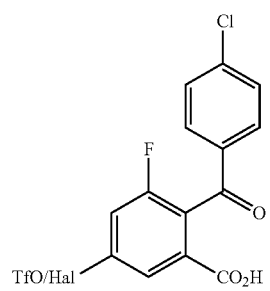

and coupling the compound of formula (9) with an amine of formula (7):

(7)

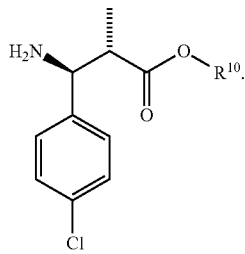

The Methylation Step

The methylation step takes place in the presence of a base e.g. a Bronsted-Lowry base.

In one embodiment, the base is a weak base (one that does not ionize fully in an aqueous solution).

In some embodiments, the base has a pKa of 10 or more in a solvent e.g. DMSO, for example as reported in Bordwell, Acc. Chem. Res. 21:456 1988); Crampton, J. Chem. Res. (S) 22 (1997); Kaljurand et al., J. Org. Chem. 65(19): 6202 (2000); Kaljurand et al, J. Org. Chem. 70(3):1019 (2005).

In some embodiments, the catalyst is a strong base. In some embodiments, the catalyst is a strong base such as a sterically hindered strong base, e.g., a strong base which is a poor nucleophile.

The base may be present in any amount which is effective e.g. 0.5-2 equivalents relative to the amount of the compound of formula (2), preferably 1-2 equivalents, e.g. 1-1.5 equivalents.

In one embodiment of the methylation step of the invention either:
(i) the base is added to a mixture of the compound of the formula (2°) and the methylating agent; or
(ii) the methylating agent is added to a mixture of the compound of the formula (2°) and the base.

In particular, the base is added to a mixture of the compound of the formula (2°) and the methylating agent. For example, the methylating agent is added to the compound of the formula (2°), and then the base is added to a mixture of the compound of the formula (2°) and the methylating agent.

In one embodiment of the methylation step of the invention, the base is selected from n-BuLi, t-BuLi, sec-BuLi, LDA, LHMDS, NaHMDS, KHMDS, LTMP, LiOtBu or KOtBu.

In one embodiment of the methylation step according to the invention, the base is selected from $K_2CO_3$, $Na_2CO_3$, $Cs_2CO_3$, NaOH, LiOH, KOH, $K_2PO_4$, $Et_3N$, DIPEA, 1,8-bis(dimethylamino)naphthalene, N,N,N',N'-tetramethyl-1,8-naphthalenediamine (i.e. proton sponge), KHMDS, lutidine, 2,6-di-tert-butylpyridine and N-methylmorpholine.

In one embodiment of the methylation step according to the invention, the methylating agent is selected from MeI, $Me_2SO_4$, $Me_3OBF_4$, MeOTf and $(MeO)_2CHBF_4$.

In particular, the methylating agent is selected from MeI, $Me_2SO_4$, $Me_3OBF_4$, MeOTf, $(MeO)_2CHBF_4$ and methylfluorosulfonate, for example MeOTf and methylfluorosulfonate e.g. MeOTf.

In one embodiment of the methylation step according to the invention, the solvent is an organic solvent, for example an aprotic solvent e.g. THF, 1,4-dioxane, acetone, acetonitrile, DMF, dichloromethane, or mixtures thereof.

In one embodiment of the methylation step according to the invention, the solvent is an ethereal solvent e.g. THF.

In a first embodiment:
the base is selected from $K_2CO_3$, $Cs_2CO_3$, NaOH, LiOH and KOH;
the methylating agent is selected from MeI and $Me_2SO_4$; and
the step of reacting with the methylating agent takes place in an organic solvent, for example an aprotic solvent e.g. acetone, DMF, dichloromethane, or mixtures thereof.

In particular:
the base is $Cs_2CO_3$;
the methylating agent is MeI; and
the step of reacting with the methylating takes place in an organic solvent, for example an aprotic solvent e.g. acetone, dichloromethane, or mixtures thereof.

In this embodiment, the applicant has surprisingly found that the proportion of the desired stereoisomer is increased.

Without being bound by theory, the applicant believes that the improved stereoselectivity is provided by an epimerisation which occurs under the basic conditions which increase the proportion of the desired alcohol precursor:

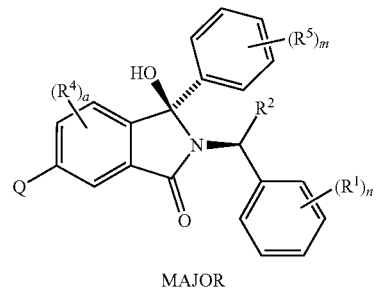

MAJOR

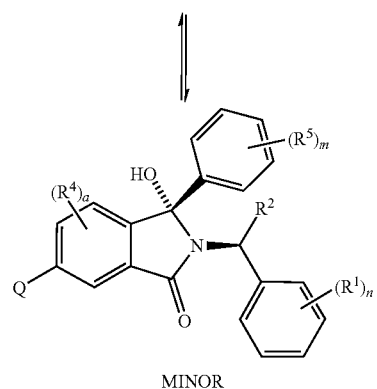

MINOR

Thus, the reaction proceeds predominantly through the major stereoisomer to give the desired stereoisomer of the methylated product:

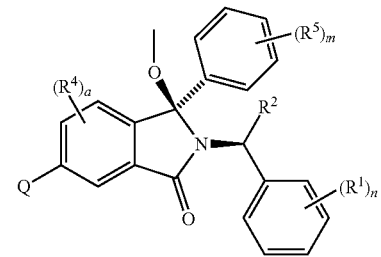

Desired stereoisomer

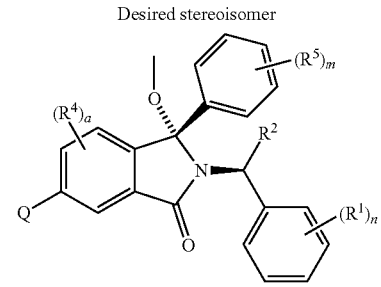

Other stereoisomer

For example, the product may be greater than 50%, 60%, 70%, 80%, 90%, 95%, 97%, 98%, or 99% of the desired stereoisomer, and less than 50%, 40%, 30%, 20%, 10%, 5%, 3%, 2%, or 1% of the other stereoisomer.

In a second embodiment:
the base is selected from 1,8-bis(dimethylamino)naphthalene, N,N,N',N'-tetramethyl-1,8-naphthalenediamine (i.e. proton sponge), lutidine and 2,6-di-tert-butylpyridine;

the methylating agent is selected from Me₃OBF₄, MeOTf and (MeO)₂CHBF₄; and the step of reacting with the methylating agent takes place in an organic solvent, for example an aprotic solvent e.g. THF, 1,4-dioxane, dichloromethane or mixtures thereof.

In particular:

the base is 1,8-bis(dimethylamino)naphthalene,N,N,N',N'-tetramethyl-1,8-naphthalenediamine (i.e. proton sponge);

the methylating agent is Me₃OBF₄; and the step of reacting with the methylating agent takes place in an organic solvent, for example an aprotic solvent e.g. dichloromethane.

Alternatively, in the second embodiment:

the base is selected from n-BuLi, t-BuLi, sec-BuLi, LDA, LHMDS, NaHMDS, KHMDS, LTMP, LiOtBu or KOtBu;

the methylating agent is selected from MeOTf and methylfluorosulfonate; and the step of reacting with the methylating agent takes place in an ethereal solvent.

In this second embodiment, the applicant has surprisingly found that the alcohol does not epimierise. Therefore, if the starting material is predominantly the required stereochemistry, that stereochemistry is retained in the product:

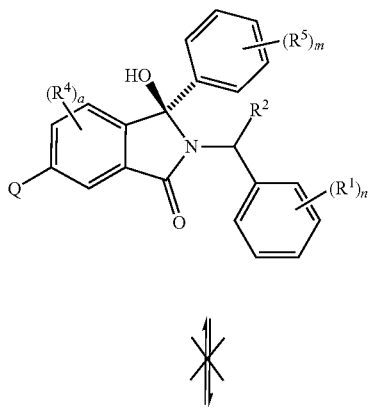

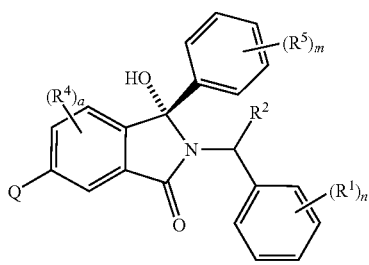

Accordingly, in one embodiment of the invention, the 1-methoxyisoindoline of formula (1°) is a compound of formula (1°'):

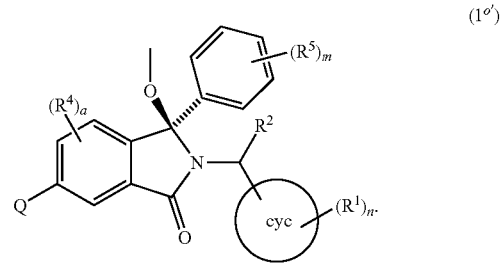

(1°')

or a tautomer or a solvate or a pharmaceutically acceptable salt thereof, and the compound of formula (2°) is a compound of formula (2°'):

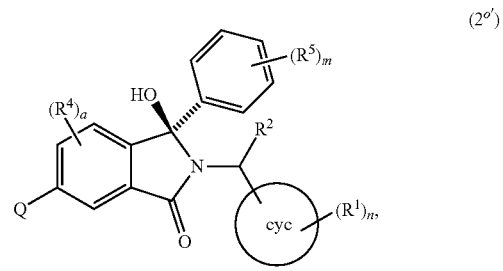

(2°')

and the base is selected from 1,8-bis(dimethylamino)naphthalene,N,N,N',N'-tetramethyl-1,8-naphthalenediamine (i.e. proton sponge), lutidine and 2,6-di-tert-butylpyridine;

the methylating agent is selected from Me₃OBF₄, MeOTf and (MeO)₂CHBF₄; and the step of reacting with the methylating agent takes place in an organic solvent, for example an aprotic solvent e.g. THF, 1,4-dioxane, dichloromethane or mixtures thereof; or the base is selected from n-BuLi, t-BuLi, sec-BuLi, LDA, LHMDS, NaHMDS, KHMDS, LTMP, LiOtBu or KOtBu;

the methylating agent is selected from MeOTf and methylfluorosulfonate; and the step of reacting with the methylating agent takes place in an ethereal solvent.

As discussed, under these conditions the alcohol (2°') does not epimerise. Therefore, in this embodiment, the alcohol may be predominantly the following desired stereoisomer:

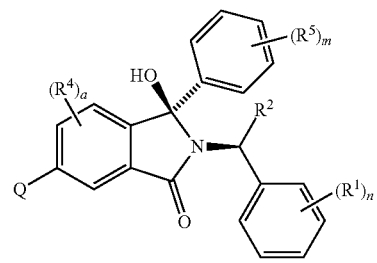

Desired stereoisomer

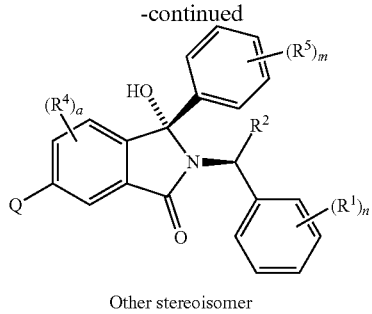

Other stereoisomer

The degree of epimerisation varies depending on the base metal counterion. The least epimerisation occurs when the metal counteranion is Li, then Na and then K. Therefore, in one embodiment of the invention, the base has a metal counteranion, which is Li e.g. n-BuLi, t-BuLi, sec-BuLi, LDA, LHMDS, LTMP or LiOtBu. In particular, the base is LiOtBu.

The degree of epimerisation also varies depending on the temperature. The least epimerisation occurs at lower temperatures. Therefore, in one embodiment of the invention, the methylation step takes place at a temperature which is below 0° C., −10° C., −20° C., −30° C., −40° C. or −50° C., preferably between −50° C. and −78° C. e.g. −70° C. In this embodiment, undesired epimerisation is minimised by the use of a low temperature.

In particular, in one embodiment of the invention, the base is LiOtBu and the methylating agent is MeOTf.

For example, the alcohol may be greater than 50%, 60%, 70%, 80%, 90%, 95%, 97%, 98%, or 99% of the desired stereoisomer, and less than 50%, 40%, 30%, 20%, 10%, 5%, 3%, 2%, or 1% of the other stereoisomer.

The stereoisomerically enriched alcohol (2°') can be prepared for example by resolution (for example by crystallisation or chromatography e.g supercritical fluid chromatography).

This process results in a methylated product that is also predominantly the required stereoisomer, without the need for a further resolution step:

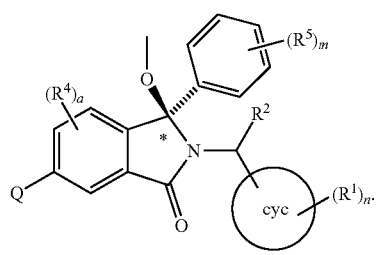

(1°')

The Crystallisation-Induced Dynamic Resolution

In one embodiment, the invention provides a process for preparing a compound of formula (1°):

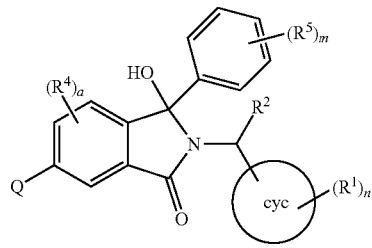

(1°)

or a tautomer or a solvate or a pharmaceutically acceptable salt thereof, wherein $R^1$, $R^2$, $R^4$, $R^5$, Q, a, m and n are as defined herein, wherein a compound of formula (T) is reacted with a compound of formula (U):

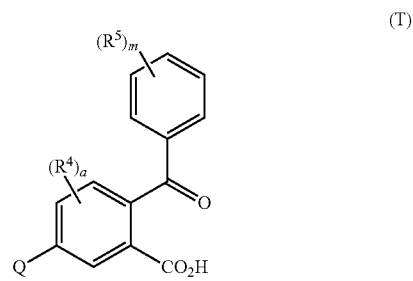

(T)

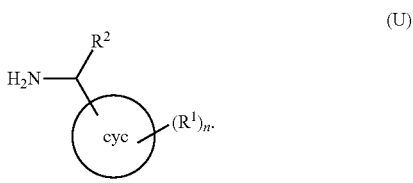

(U)

The skilled person is familiar with reactions involving the coupling of an acid and an amine. Any standard coupling conditions can be used. In particular the coupling step takes place in the presence of HATU and EDC.

In one embodiment, the reaction takes place in a solvent which is $CH_2Cl_2$.

In one embodiment, the compound of formula (U) is a compound of formula (U'):

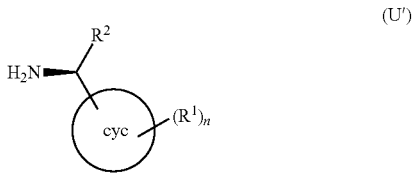

(U')

and the reaction gives a product of formula which is predominantly the shown diastereoisomer:

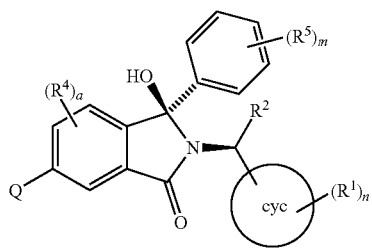

For example, the product can be greater than 50%, 60%, 70%, 80%, 90%, 95%, 97%, 98%, or 99% of the shown diastereoisomer, and less than 50%, 40%, 30%, 20%, 10%, 5%, 3%, 2%, or 1% of the other diastereoisomer.

Preferably, the process is a crystallisation-induced dynamic resolution and the shown diastereoisomer crystallises in the reaction conditions.

If necessary, the diastereomeric purity of the shown diastereoisomer can be increased further by recrystallisation. If necessary, the diastereomeric purity can be increased further by recrystallisation, for example recrystallization from MeOH/water, optionally using seeding.

In one embodiment, cyc is phenyl. In this embodiment, the alcohol may be predominantly the following desired stereoisomer:

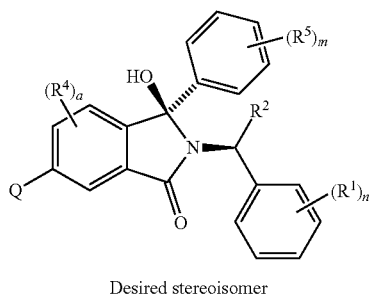

Desired stereoisomer

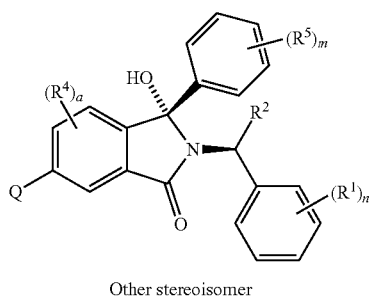

Other stereoisomer

In particular, the compound of formula (U) is a compound of formula (7):

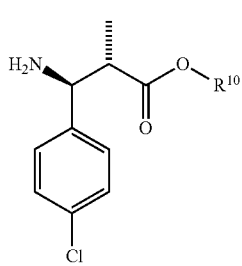

(7)

wherein $R^{10}$ is as defined herein.

In particular, $R^{10}$ is selected from $C_{1-7}$ alkyl, $C_{1-7}$ alkeneyl, $C_{1-7}$ haloalkyl, $triC_{1-7}$ alkylsilyl-$C_{1-7}$alkyl, $C_{5-20}$ aryl and $C_{5-20}$ aryl-$C_{1-7}$ alkyl, for example $C_{1-7}$ alkyl, $C_{1-7}$ haloalkyl, $triC_{1-7}$ alkylsilyl-$C_{1-7}$alkyl, $C_{5-20}$ aryl and $C_{5-20}$ aryl-$C_{1-7}$ alkyl e.g. —$CH_2CH_2Si(CH_3)_3$.

In one embodiment, the compound of formula (T) is a compound of formula (6):

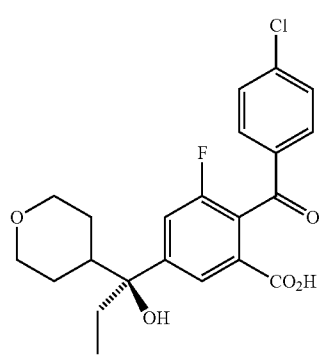

(6)

Salts

In one embodiment, the invention provides any process herein for preparing a 1-methoxyisoindoline, wherein the process comprises an additional step in which the 1-methoxyisoindoline is converted into a pharmaceutically acceptable salt.

In one embodiment, the invention provides any process herein for preparing a 1-methoxyisoindoline which is (2S, 3S)-3-(4-chlorophenyl)-3-[(1R)-1-(4-chlorophenyl)-7-fluoro-5-[(1S)-1-hydroxy-1-(oxan-4-yl)propyl]-1-methoxy-3-oxo-2,3-dihydro-1H-isoindol-2-yl]-2-methylpropanoic acid, wherein the process comprises an additional step in which the 2S,3S)-3-(4-chlorophenyl)-3-[(1R)-1-(4-chlorophenyl)-7-fluoro-5-[(1S)-1-hydroxy-1-(oxan-4-yl)propyl]-1-methoxy-3-oxo-2,3-dihydro-1H-isoindol-2-yl]-2-methylpropanoic acid is converted into a pharmaceutically acceptable salt.

In one embodiment, the pharmaceutically acceptable salt is the (tris(hydroxymethyl)aminomethane salt.

Salts, Solvates, Tautomers, Isomers, N-Oxides, Esters, Prodrugs and Isotopes

A reference to any compound herein e.g. of the formula (1°) or (1), also refers to any sub-groups thereof and any example also includes ionic forms, salts, solvates, isomers (including geometric and stereochemical isomers unless specified), tautomers, N-oxides, esters, prodrugs, isotopes and protected forms thereof, for example, as discussed below; in particular, the salts or tautomers or isomers or N-oxides or solvates thereof; and more particularly the salts or tautomers or N-oxides or solvates thereof.

Salts

Many compounds of the formula (1°) can exist in the form of salts, for example acid addition salts or, in certain cases salts of organic and inorganic bases such as carboxylate, sulfonate and phosphate salts. All such salts are within the scope of this invention, and references to compounds of the formula (1°) include the salt forms of the compounds.

The salts of the present invention can be synthesized from the parent compound that contains a basic or acidic moiety by conventional chemical methods such as methods described in *Pharmaceutical Salts: Properties, Selection, and Use*, P. Heinrich Stahl (Editor), Camille G. Wermuth (Editor), ISBN: 3-90639-026-8, Hardcover, 388 pages, August 2002. Generally, such salts can be prepared by reacting the free acid or base forms of these compounds with the appropriate base or acid in water or in an organic solvent, or in a mixture of the two; generally, nonaqueous media such as ether, ethyl acetate, ethanol, isopropanol, or acetonitrile are used.

Acid addition salts (mono- or di-salts) may be formed with a wide variety of acids, both inorganic and organic. Examples of acid addition salts include mono- or di-salts formed with an acid selected from acetic, 2,2-dichloroacetic, adipic, alginic, ascorbic (e.g. L-ascorbic), L-aspartic, benzenesulfonic, benzoic, 4-acetamidobenzoic, butanoic, (+) camphoric, camphor-sulfonic, (+)-(1S)-camphor-10-sulfonic, capric, caproic, caprylic, cinnamic, citric, cyclamic, dodecylsulfuric, ethane-1,2-disulfonic, ethanesulfonic, 2-hydroxyethanesulfonic, formic, fumaric, galactaric, gentisic, glucoheptonic, D-gluconic, glucuronic (e.g. D-glucuronic), glutamic (e.g. L-glutamic), α-oxoglutaric, glycolic, hippuric, hydrohalic acids (e.g. hydrobromic, hydrochloric, hydriodic), isethionic, lactic (e.g. (+)-L-lactic, (±)-DL-lactic), lactobionic, maleic, malic, (−)-L-malic, malonic, (±)-DL-mandelic, methanesulfonic, naphthalene-2-sulfonic, naphthalene-1,5-disulfonic, 1-hydroxy-2-naphthoic, nicotinic, nitric, oleic, orotic, oxalic, palmitic, pamoic, phosphoric, propionic, pyruvic, L-pyroglutamic, salicylic, 4-amino-salicylic, sebacic, stearic, succinic, sulfuric, tannic, (+)-L-tartaric, thiocyanic, p-toluenesulfonic, undecylenic and valeric acids, as well as acylated amino acids and cation exchange resins.

One particular group of salts consists of salts formed from acetic, hydrochloric, hydriodic, phosphoric, nitric, sulfuric, citric, lactic, succinic, maleic, malic, isethionic, fumaric, benzenesulfonic, toluenesulfonic, methanesulfonic (mesylate), ethanesulfonic, naphthalenesulfonic, valeric, acetic, propanoic, butanoic, malonic, glucuronic and lactobionic acids. One particular salt is the hydrochloride salt.

In one embodiment the compound is the tris(hydroxymethyl)aminomethane (TRIS) salt.

If the compound is anionic, or has a functional group which may be anionic (e.g., —COOH may be —COO⁻), then a salt may be formed with an organic or inorganic base, generating a suitable cation. Examples of suitable inorganic cations include, but are not limited to, alkali metal ions such as $Li^+$, $Na^+$ and $K^+$, alkaline earth metal cations such as $Ca^{2+}$ and $Mg^{2+}$, and other cations such as $Al^{3+}$ or $Zn^+$. Examples of suitable organic cations include, but are not limited to, ammonium ion (i.e., $NH_4^+$) and substituted ammonium ions (e.g., $NH_3R^+$, $NH_2R_2^+$, $NHR_3^+$, $NR_4^+$). Examples of some suitable substituted ammonium ions are those derived from: methylamine, ethylamine, diethylamine, propylamine, dicyclohexylamine, triethylamine, butylamine, ethylenediamine, ethanolamine, diethanolamine, piperazine, benzylamine, phenylbenzylamine, choline, meglumine, and tromethamine, as well as amino acids, such as lysine and arginine. An example of a common quaternary ammonium ion is $N(CH_3)_4^+$.

Where the compounds of the formula (1°) contain an amine function, these may form quaternary ammonium salts, for example by reaction with an alkylating agent according to methods well known to the skilled person. Such quaternary ammonium compounds are within the scope of formula (1°).

The compounds of the invention may exist as mono- or di-salts depending upon the pKa of the acid from which the salt is formed.

The salt forms of the compounds of the invention are typically pharmaceutically acceptable salts, and examples of pharmaceutically acceptable salts are discussed in Berge et al., 1977, "Pharmaceutically Acceptable Salts," *J. Pharm. Sci.*, Vol. 66, pp. 1-19. However, salts that are not pharmaceutically acceptable may also be prepared as intermediate forms which may then be converted into pharmaceutically acceptable salts. Such non-pharmaceutically acceptable salt forms, which may be useful, for example, in the purification or separation of the compounds of the invention, also form part of the invention.

In one embodiment of the invention, there is provided a pharmaceutical composition comprising a solution (e.g. an aqueous solution) containing a compound of the formula (1°) and sub-groups and examples thereof as described herein in the form of a salt in a concentration of greater than 10 mg/ml, typically greater than 15 mg/ml and typically greater than 20 mg/ml.

N-Oxides

Compounds of the formula (1°) containing an amine function may also form N-oxides. A reference herein to a compound of the formula (1°) that contains an amine function also includes the N-oxide.

Where a compound contains several amine functions one, or more than one, nitrogen atom may be oxidised to form an N-oxide. Particular examples of N-oxides are the N-oxides of a tertiary amine or a nitrogen atom of a nitrogen-containing heterocyclic group.

N-Oxides can be formed by treatment of the corresponding amine with an oxidizing agent such as hydrogen peroxide or a per-acid (e.g. a peroxycarboxylic acid), see for example *Advanced Organic Chemistry*, by Jerry March, 4$^{th}$ Edition, Wiley Interscience, pages. More particularly, N-oxides can be made by the procedure of L. W. Deady (*Syn. Comm.* 1977, 7, 509-514) in which the amine compound is reacted with m-chloroperoxybenzoic acid (MCPBA), for example, in an inert solvent such as dichloromethane.

In one embodiment of the invention, the compound is an N-oxide, e.g. from a nitrogen atom on the $R^6$ or $R^7$ group, for example a pyridine N-oxide.

Geometric Isomers and Tautomers

Compounds of the formula (1°) may exist in a number of different geometric isomeric, and tautomeric forms and references to compounds of the formula (1°) include all such forms. For the avoidance of doubt, where a compound can exist in one of several geometric isomeric or tautomeric forms and only one is specifically described or shown, all others are nevertheless embraced by formula (1°).

For example, certain heteroaryl rings can exist in the two tautomeric forms such as A and B shown below. For simplicity, a formula may illustrate one form but the formula is to be taken as embracing both tautomeric forms.

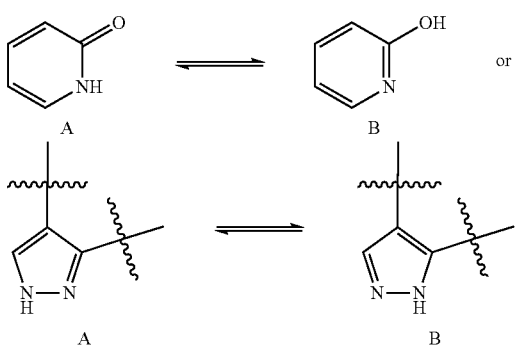

Other examples of tautomeric forms include, for example, keto-, enol-, and enolate-forms, as in, for example, the following tautomeric pairs: keto/enol (illustrated below), imine/enamine, amide/imino alcohol, amidine/enediamines, nitroso/oxime, thioketone/enethiol, and nitro/aci-nitro.

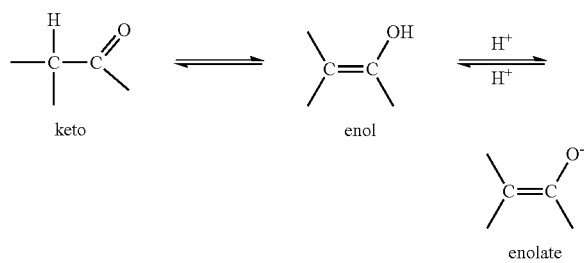

Stereoisomers

Unless otherwise mentioned or indicated, the chemical designation of compounds denotes the mixture of all possible stereochemically isomeric forms.

Stereocentres are illustrated in the usual fashion, using 'hashed' or 'solid' wedged lines. e.g.

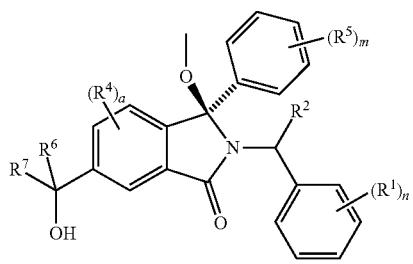

Where a compound is described as a mixture of two diastereoisomers/epimers, the configuration of the stereocentre is not specified and is represented by straight lines.

Where compounds of the formula (1°) contain one or more chiral centres, and can exist in the form of two or more optical isomers, references to compounds of the formula (1°) include all optical isomeric forms thereof (e.g. enantiomers, epimers and diastereoisomers), either as individual optical isomers, or mixtures (e.g. racemic or scalemic mixtures) or two or more optical isomers, unless the context requires otherwise.

The optical isomers may be characterised and identified by their optical activity (i.e. as + and − isomers, or d and/isomers) or they may be characterised in terms of their absolute stereochemistry using the "R and S" nomenclature developed by Cahn, Ingold and Prelog, see *Advanced Organic Chemistry* by Jerry March, 4th Edition, John Wiley & Sons, New York, 1992, pages 109-114, and see also Cahn, Ingold & Prelog, *Angew. Chem. Int. Ed. Engl.*, 1966, 5, 385-415.

Optical isomers can be separated by a number of techniques including chiral chromatography (chromatography on a chiral support) and such techniques are well known to the person skilled in the art.

As an alternative to chiral chromatography, optical isomers can be separated by forming diastereoisomeric salts with chiral acids such as (+)-tartaric acid, (−)-pyroglutamic acid, (−)-di-toluoyl-L-tartaric acid, (+)-mandelic acid, (−)-malic acid, and (−)-camphorsulfonic acid, separating the diastereoisomers by preferential crystallisation, and then dissociating the salts to give the individual enantiomer of the free base.

Additionally enantiomeric separation can be achieved by covalently linking a enantiomerically pure chiral auxiliary onto the compound and then performing diastereoisomer separation using conventional methods such as chromatography. This is then followed by cleavage of the aforementioned covalent linkage to generate the appropriate enantiomerically pure product.

Where compounds of the formula (1°) exist as two or more optical isomeric forms, one enantiomer in a pair of enantiomers may exhibit advantages over the other enantiomer, for example, in terms of biological activity. Thus, in certain circumstances, it may be desirable to use as a therapeutic agent only one of a pair of enantiomers, or only one of a plurality of diastereoisomers.

Accordingly, the invention provides compositions containing a compound of the formula (1°) having one or more chiral centres, wherein at least 55% (e.g. at least 60%, 65%, 70%, 75%, 80%, 85%, 90% or 95%) of the compound of the formula (1°) is present as a single optical isomer (e.g. enantiomer or diastereoisomer). In one general embodiment, 99% or more (e.g. substantially all) of the total amount of the compound of the formula (1°) may be present as a single optical isomer (e.g. enantiomer or diastereoisomer).

Compounds encompassing double bonds can have an E (entgegen) or Z (zusammen) stereochemistry at said double bond. Substituents on bivalent cyclic or (partially) saturated radicals may have either the cis- or trans-configuration. The terms cis and trans when used herein are in accordance with Chemical Abstracts nomenclature (J. Org. Chem. 1970, 35 (9), 2849-2867), and refer to the position of the substituents on a ring moiety.

Of special interest are those compounds of formula (1°) which are stereochemically pure. When a compound of formula (1°) is for instance specified as R, this means that the compound is substantially free of the S isomer. If a compound of formula (1°) is for instance specified as E, this means that the compound is substantially free of the Z isomer. The terms cis, trans, R, S, E and Z are well known to a person skilled in the art.

Isotopic Variations

The present invention includes all pharmaceutically acceptable isotopically-labeled compounds of the invention, i.e. compounds of formula (1°), wherein one or more atoms are replaced by atoms having the same atomic number, but an atomic mass or mass number different from the atomic mass or mass number usually found in nature.

Examples of isotopes suitable for inclusion in the compounds of the invention comprise isotopes of hydrogen, such as $^2H$ (D) and $^3H$ (T), carbon, such as $^{11}C$, $^{13}C$ and $^{14}C$, chlorine, such as $^{36}Cl$, fluorine, such as $^{18}F$, iodine, such as $^{123}I$, $^{125}I$ and $^{131}I$, nitrogen, such as $^{13}N$ and $^{15}N$, oxygen, such as $^{15}O$, $^{17}O$ and $^{18}O$, phosphorus, such as $^{32}P$, and sulfur, such as $^{35}S$.

Certain isotopically-labelled compounds of formula (1°), for example, those incorporating a radioactive isotope, are useful in drug and/or substrate tissue distribution studies. The compounds of formula (1°) can also have valuable diagnostic properties in that they can be used for detecting or identifying the formation of a complex between a labelled compound and other molecules, peptides, proteins, enzymes or receptors. The detecting or identifying methods can use compounds that are labelled with labelling agents such as radioisotopes, enzymes, fluorescent substances, luminous substances (for example, luminol, luminol derivatives, luciferin, aequorin and luciferase), etc. The radioactive isotopes tritium, i.e. $^3H$ (T), and carbon-14, i.e. $^{14}C$, are particularly useful for this purpose in view of their ease of incorporation and ready means of detection.

Substitution with heavier isotopes such as deuterium, i.e. $^2H$ (D), may afford certain therapeutic advantages resulting from greater metabolic stability, for example, increased in vivo half-life or reduced dosage requirements, and hence may be used in some circumstances.

In particular, every reference to hydrogen in the application should be constructed to cover $^1H$ and $^2H$, whether hydrogen is defined explicitly, or hydrogen is present implicitly to satisfy the relevant atom's (in particular carbon's) valency.

Substitution with positron emitting isotopes, such as $^{11}C$, $^{18}F$, $^{15}O$ and $^{13}N$, can be useful in Positron Emission Topography (PET) studies for examining target occupancy.

Isotopically-labeled compounds of formula (1°) can generally be prepared by conventional techniques known to those skilled in the art or by processes analogous to those described in the accompanying Examples and Preparations using an appropriate isotopically-labeled reagents in place of the non-labeled reagent previously employed.

Esters

Esters such as carboxylic acid esters, acyloxy esters and phosphate esters of the compounds of formula (1°) bearing a carboxylic acid group or a hydroxyl group are also embraced by Formula (1°). Examples of esters are compounds containing the group —C(=O)OR, wherein R is an ester substituent, for example, a $C_{1-7}$ alkyl group, a $C_{3-12}$ heterocyclyl group, or a $C_{5-12}$ aryl group, typically a $C_{1-6}$ alkyl group. Particular examples of ester groups include, but are not limited to, —C(=O)OCH$_3$, —C(=O)OCH$_2$CH$_3$, —C(=O)OC(CH$_3$)$_3$, and —C(=O)OPh. Examples of acyloxy (reverse ester) groups are represented by —OC(=O)R, wherein R is an acyloxy substituent, for example, a $C_{1-6}$ alkyl group, a $C_{3-12}$ heterocyclyl group, or a $C_{5-12}$ aryl group, typically a $C_{1-6}$ alkyl group. Particular examples of acyloxy groups include, but are not limited to, —OC(=O)CH$_3$ (acetoxy), —OC(=O)CH$_2$CH$_3$, —OC(=O)C(CH$_3$)$_3$, —OC(=O)Ph, and —OC(=O)CH$_2$Ph. Examples of phosphate esters are those derived from phosphoric acid.

In one embodiment of the invention, formula (1°) includes within its scope esters of compounds of the formula (1°) bearing a carboxylic acid group or a hydroxyl group. In another embodiment of the invention, formula (1°) does not include within its scope esters of compounds of the formula (1°) bearing a carboxylic acid group or a hydroxyl group.

Solvates and Crystalline Forms

Also encompassed by formula (1°) are any polymorphic forms of the compounds, and solvates such as hydrates, alcoholates and the like.

The compounds of the invention may form solvates, for example with water (i.e., hydrates) or common organic solvents. As used herein, the term "solvate" means a physical association of the compounds of the present invention with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. The term "solvate" is intended to encompass both solution-phase and isolatable solvates. Non-limiting examples of suitable solvates include compounds of the invention in combination with water, isopropanol, ethanol, methanol, DMSO, ethyl acetate, acetic acid or ethanolamine and the like. The compounds of the invention may exert their biological effects whilst they are in solution.

Solvates are well known in pharmaceutical chemistry. They can be important to the processes for the preparation of a substance (e.g. in relation to their purification, the storage of the substance (e.g. its stability) and the ease of handling of the substance and are often formed as part of the isolation or purification stages of a chemical synthesis. A person skilled in the art can determine by means of standard and long used techniques whether a hydrate or other solvate has formed by the isolation conditions or purification conditions used to prepare a given compound. Examples of such techniques include thermogravimetric analysis (TGA), differential scanning calorimetry (DSC), X-ray crystallography (e.g. single crystal X-ray crystallography or X-ray powder diffraction) and Solid State NMR (SS-NMR, also known as Magic Angle Spinning NMR or MAS-NMR). Such techniques are as much a part of the standard analytical toolkit of the skilled chemist as NMR, IR, HPLC and MS. Alternatively the skilled person can deliberately form a solvate using crystallisation conditions that include an amount of the solvent required for the particular solvate. Thereafter the standard methods described herein, can be used to establish whether solvates had formed.

Furthermore, the compounds of the present invention may have one or more polymorph or amorphous crystalline forms and as such are intended to be included in the scope of the invention.

The invention also provides certain crystalline forms of (2S,3S)-3-(4-chlorophenyl)-3-[(1R)-1-(4-chlorophenyl)-7-fluoro-5-[(1S)-1-hydroxy-1-(oxan-4-yl)propyl]-1-methoxy-3-oxo-2,3-dihydro-1H-isoindol-2-yl]-2-methylpropanoic acid.

The crystals and their crystal structures can be characterised using a number of techniques including single crystal X-ray crystallography, X-ray powder diffraction (XRPD), differential scanning calorimetry (DSC) and infra red spectroscopy, e.g. Fourier Transform infra-red spectroscopy (FTIR). The behaviour of the crystals under conditions of varying humidity can also be analysed by gravimetric vapour sorption studies and by XRPD.

Determination of the crystal structure of a compound can be performed by X-ray crystallography which can be carried out according to conventional methods, such as those described herein and in Fundamentals of Crystallography, C. Giacovazzo, H. L. Monaco, D. Viterbo, F. Scordari, G. Gilli, G. Zanotti and M. Catti, (International Union of Crystallography/Oxford University Press, 1992 ISBN 0-19-855578-4 (p/b), 0-19-85579-2 (h/b)). This technique involves the analysis and interpretation of the X-ray diffraction of a single crystal.

Alternatively, the crystalline structure of a compound can be analysed by the solid state technique of X-ray Powder Diffraction (XRPD). XRPD can be carried out according to conventional methods such as those described herein (see Example 6) and in Introduction to X-ray Powder Diffraction, Ron Jenkins and Robert L. Snyder (John Wiley & Sons, New York, 1996). The presence of defined peaks (as opposed to random background noise) in an XRPD diffractogram indicates that the compound has a degree of crystallinity.

A compound's X-ray powder pattern is characterised by the diffraction angle (2θ) and interplanar spacing (d) parameters of an X-ray diffraction spectrum. These are related by Bragg's equation, nλ=2d Sin θ, (where n=1; λ=wavelength of the cathode used; d=interplanar spacing; and θ=diffraction angle). Herein, interplanar spacings, diffraction angle and overall pattern are important for identification of crystal in the X-ray powder diffraction, due to the characteristics of the data. The relative intensity should not be strictly interpreted since it may be varied depending on the direction of crystal growth, particle sizes and measurement conditions. In addition, the diffraction angles usually vary within a tolerance of 2θ±0.2°. The peaks mean main peaks and include peaks not larger than medium at diffraction angles other than those stated above.

In one embodiment, the invention provides a crystalline form of (2S,3S)-3-(4-chlorophenyl)-3-[(1R)-1-(4-chlorophenyl)-7-fluoro-5-[(1S)-1-hydroxy-1-(oxan-4-yl)propyl]-1-methoxy-3-oxo-2,3-dihydro-1H-isoindol-2-yl]-2-methylpropanoic acid having:

(a) an X-ray powder diffraction pattern characterised by peaks at diffraction angles 15.1, 15.5, 15.8 and 22.3 degrees 2θ (±0.2 degrees 2θ); or (b) interplanar spacings of 3.99, 5.62, 5.71 and 5.87 Å.

In particular, the crystalline form of (2S,3S)-3-(4-chlorophenyl)-3-[(1R)-1-(4-chlorophenyl)-7-fluoro-5-[(1S)-1-hydroxy-1-(oxan-4-yl)propyl]-1-methoxy-3-oxo-2,3-dihydro-1H-isoindol-2-yl]-2-methylpropanoic acid has:

(a) an X-ray powder diffraction pattern characterised by peaks at diffraction angles 11.3, 15.1, 15.5, 15.8, 17.2, 20.8, 22.3 and 28.6 degrees 2θ (±0.2 degrees 2θ); or (b) interplanar spacings at 3.12, 3.99, 4.27, 5.17, 5.62, 5.71, 5.87 and 7.85 Å.

In particular, the crystalline form of (2S,3S)-3-(4-chlorophenyl)-3-[(1R)-1-(4-chlorophenyl)-7-fluoro-5-[(1S)-1-hydroxy-1-(oxan-4-yl)propyl]-1-methoxy-3-oxo-2,3-dihydro-1H-isoindol-2-yl]-2-methylpropanoic acid has an X-ray powder diffraction pattern characterised by the presence of major peaks at the diffraction angles (2θ), interplanar spacings (d) and intensities set forth in Table 1 herein.

In particular, the crystalline form of (2S,3S)-3-(4-chlorophenyl)-3-[(1R)-1-(4-chlorophenyl)-7-fluoro-5-[(1S)-1-hydroxy-1-(oxan-4-yl)propyl]-1-methoxy-3-oxo-2,3-dihydro-1H-isoindol-2-yl]-2-methylpropanoic acid has an X-ray powder diffraction pattern which exhibits peaks at the same diffraction angles as those of the X-ray powder diffraction pattern shown in FIG. 1, and preferably wherein the peaks have the same relative intensity as the peaks in FIG. 1.

In particular, the crystalline form of (2S,3S)-3-(4-chlorophenyl)-3-[(1R)-1-(4-chlorophenyl)-7-fluoro-5-[(1S)-1-hydroxy-1-(oxan-4-yl)propyl]-1-methoxy-3-oxo-2,3-dihydro-1H-isoindol-2-yl]-2-methylpropanoic acid has an X-ray powder diffraction pattern substantially as shown in FIG. 1.

In one embodiment, the invention provides a crystalline form of (2S,3S)-3-(4-chlorophenyl)-3-[(1R)-1-(4-chlorophenyl)-7-fluoro-5-[(1S)-1-hydroxy-1-(oxan-4-yl)propyl]-1-methoxy-3-oxo-2,3-dihydro-1H-isoindol-2-yl]-2-methylpropanoic acid which exhibits an exothermic peak at 266-267° C. (e.g. 266.61° C.) when subjected to DSC.

The crystalline forms of the invention may be substantially crystalline, which means that one single crystalline form may predominate, although other crystalline forms may be present in minor and preferably negligible amounts.

For example, a crystalline form may contain no more than 5% by weight of any other crystalline form.

Preferably, the crystalline form is a single crystalline form and is accompanied by less than 4%, or less than 3%, or less than 2% of other crystalline forms, and in particular contains less than or equal to about 1% by weight of other crystalline forms. More preferably, the single crystalline form is accompanied by less than 0.9%, or less than 0.8%, or less than 0.7%, or less than 0.6%, or less than 0.5%, or less than 0.4%, or less than 0.3%, or less than 0.2%, or less than 0.1%, or less than 0.05%, or less than 0.01%, by weight of other crystalline forms, for example 0% by weight of other crystalline forms.

The polymorphic forms of the invention will enjoy one or more of the following advantages over other polymorphs in that they:

will be more soluble
will have better stability (e.g. improved shelf life);
will have better thermal stability;
will have advantages for production;
will have improved solubility in aqueous solution;
will have better physicochemical properties;
may have improved anti-cancer activity; and
may have an improved therapeutic index.

In particular the polymorphs may be more stable. The term 'stable' or 'stability' as used herein includes chemical stability and solid state (physical) stability. The term 'chemical stability' means that the polymorph can be stored in an isolated form, or in the form of a formulation in which it is provided in admixture with for example, pharmaceutically acceptable carriers, diluents or adjuvants as described herein, under normal storage conditions, with little or no chemical degradation or decomposition. 'Solid-state stability' means the polymorph can be stored in an isolated solid form, or the form of a solid formulation in which it is provided in admixture with, for example, pharmaceutically acceptable carriers, diluents or adjuvants as described herein, under normal storage conditions, with little or no solid-state transformation (e.g. hydration, dehydration, solvatisation, desolvatisation, crystallisation, recrystallisation or solid-state phase transition).

Complexes

Formula (1°) also includes within its scope complexes (e.g. inclusion complexes or clathrates with compounds such as cyclodextrins, or complexes with metals) of the compounds. Inclusion complexes, clathrates and metal complexes can be formed by means of methods well known to the skilled person.

Prodrugs

Also encompassed by formula (1°) are any pro-drugs of the compounds of the formula (1°). By "prodrugs" is meant for example any compound that is converted in vivo into a biologically active compound of the formula (1°).

For example, some prodrugs are esters of the active compound (e.g., a physiologically acceptable metabolically labile ester). During metabolism, the ester group (—C(=O) OR) is cleaved to yield the active drug. Such esters may be formed by esterification, for example, of any of the carboxylic acid groups (—C(=O)OH) in the parent compound, with, where appropriate, prior protection of any other reactive groups present in the parent compound, followed by deprotection if required.

Examples of such metabolically labile esters include those of the formula —C(=O)OR wherein R is:

$C_{1-7}$alkyl (e.g., -Me, -Et, -nPr, -iPr, -nBu, -sBu, -iBu, -tBu);

$C_{1-7}$aminoalkyl (e.g., aminoethyl; 2-(N,N-diethylamino) ethyl; 2-(4-morpholino)ethyl); and acyloxy-$C_{1-7}$alkyl (e.g., acyloxymethyl; acyloxyethyl; pivaloyloxymethyl; acetoxymethyl; 1-acetoxyethyl; 1-(1-methoxy-1-methyl)ethyl-carbonxyloxyethyl; 1-(benzoyloxy)ethyl; isopropoxy-carbonyloxymethyl; 1-isopropoxy-carbonyloxyethyl; cyclohexyl-carbonyloxymethyl; 1-cyclohexyl-carbonyloxyethyl; cyclohexyloxy-carbonyloxymethyl; 1-cyclohexyloxy-carbonyloxyethyl; (4-oxanyloxy) carbonyloxymethyl; 1-(4-oxanyloxy) carbonyloxyethyl; (4-oxanyl)carbonyloxymethyl; and 1-(4-tetrahydropyranyl)carbonyloxyethyl).

Also, some prodrugs are activated enzymatically to yield the active compound, or a compound which, upon further chemical reaction, yields the active compound (for example, as in antigen-directed enzyme pro-drug therapy (ADEPT), gene-directed enzyme pro-drug therapy (GDEPT), and ligand-directed enzyme pro-drug therapy (LIDEPT), etc.). For example, the prodrug may be a sugar derivative or other glycoside conjugate, or may be an amino acid ester derivative. In one embodiment formula (1°) does not include pro-drugs of the compounds of the formula (1°) within its scope.

Methods for the Preparation of Compounds of Formula (1°)

It will be appreciated that certain compounds can exist in different diastereomeric and/or enantiomeric forms and that processes for their preparation may make use of enantiomerically pure synthetic precursors.

Alternatively racemic precursors may be used and the mixtures of diastereoisomers generated in these process may be separated by methods well known to the person skilled in the art, for example using non-chiral or chiral preparative chromatography or resolution using diastereomeric derivatives: for example crystallisation of a salt formed with an enantiomerically pure acid such as L-tartaric acid (or enantiomerically pure base such as (1R)-1-phenylethan-1-amine); or enantiomer separation of a diastereomeric derivative formed by covalently linking a enantiomerically pure chiral auxiliary onto the compound, followed by separation using conventional methods such as chiral or non-chiral chromatography. The aforementioned covalent linkage is then cleaved to generate the appropriate enantiomerically pure product.

A wide range of well known functional group interconversions are known by a person skilled in the art for converting a precursor compound to a compound of formula I and are described in *Advanced Organic Chemistry* by Jerry March, 4$^{th}$ Edition, John Wiley & Sons, 1992. For example possible metal catalysed functionalisations such as using organo-tin reagents (the Stille reaction), Grignard reagents and reactions with nitrogen nucleophiles are described in 'Palladium Reagents and Catalysts' [Jiro Tsuji, Wiley, ISBN 0-470-85032-9] and Handbook of OrganoPalladium Chemistry for Organic Synthesis [Volume 1, Edited by Ei-ichi Negishi, Wiley, ISBN 0-471-31506-0].

If appropriate, the reactions previously described below are followed or preceded by one or more reactions known to the skilled of the art and are performed in an appropriate order to achieve the requisite substitutions defined above to afford other compounds of formula (1°). Non-limiting examples of such reactions whose conditions can be found in the literature include:

protection of reactive functions,
deprotection of reactive functions,
halogenation,
dehalogenation,
dealkylation,
alkylation or arylation of amine, aniline, alcohol and phenol,
Mitsunobu reaction on hydroxyl groups,
cycloaddition reactions on appropriate groups,
reduction of nitro, esters, cyano, aldehydes,
transition metal-catalyzed coupling reactions,
acylation,
sulfonylation/introduction of sulfonyl groups,
saponification/hydrolysis of ester groups,
amidification or transesterification of ester groups,
esterification or amidification of carboxylic groups,
halogen exchange,
nucleophilic substitution with amine, thiol or alcohol,
reductive amination,
oxime formation on carbonyl and hydroxylamine groups,
S-oxidation,
N-oxidation,
salification.

It will be appreciated that certain compounds e.g. compounds of formulae (1°) and subformulae and specific examples thereof can exist in different diastereomeric and/or enantiomeric forms and that processes for their preparation may make use of enantiomerically pure synthetic precursors.

Alternatively racemic precursors may be used and the mixtures of diastereoisomers generated in these process may be separated by methods well known to the person skilled in the art, for example using non-chiral or chiral preparative chromatography or resolution using diastereomeric derivatives: for example crystallisation of a salt formed with an enantiomerically pure acid such as L-tartaric acid; or enantiomer separation of a diastereomeric derivative formed by covalently linking a enantiomerically pure chiral auxiliary onto the compound, followed by separation using conventional methods such as chiral chromatography. The aforementioned covalent linkage is then cleaved to generate the appropriate enantiomerically pure product.

Certain of the required intermediates, are either commercially available, known in the literature, prepared by methods analogous to those in the literature or prepared by methods analogous to those described in the example procedures below. Other compounds may be prepared by functional group interconversion using methods well known in the art.

In a further embodiment the invention provides a novel intermediate. In one embodiment, the invention provides a novel intermediate which is compound (4'), (5), (13), (15), (16), (18), (19), (21), (22), (23), (24), (25), (26a), (26b) or (27).

Certain other of the compounds described herein are novel, and the invention also relates to those compounds per se.

In particular, the invention provides novel intermediates of the formulae (1°), (1'°), (2°), (2), (3), (3'), (3), (4), (4'), (4"), (5), (6), (6'), (8), (9), (10), (11), (11a), (11b), (11c), (19) and (21).

Protecting Groups

In many of the reactions described herein, it may be necessary to protect one or more groups to prevent reaction from taking place at an undesirable location on the molecule. Examples of protecting groups, and methods of protecting and deprotecting functional groups, can be found in *Protec-* tive Groups in Organic Synthesis (T. Green and P. Wuts; 3rd Edition; John Wiley and Sons, 1999).

In particular the compound may be synthesised in protected forms and the protecting groups removed to generate a compound of formula) (1°).

A hydroxy group may be protected, for example, as an ether (—OR) or an ester (—OC(=O)R), for example, as: a t-butyl ether; a tetrahydropyranyl (THP) ether; a benzyl, benzhydryl (diphenylmethyl), or trityl (triphenylmethyl) ether; a trimethylsilyl or t-butyldimethylsilyl ether; or an acetyl ester (—OC(=O)CH$_3$).

An aldehyde or ketone group may be protected, for example, as an acetal (R—CH(OR)$_2$) or ketal (R$_2$C(OR)$_2$), respectively, in which the carbonyl group (>C=O) is treated with, for example, a primary alcohol. The aldehyde or ketone group is readily regenerated by hydrolysis using a large excess of water in the presence of acid.

An amine group may be protected, for example, as an amide (—NRCO—R) or a carbamate (—NRCO—OR), for example, as: a methyl amide (—NHCO—CH$_3$); a benzyl carbamate (—NHCO—OCH$_2$C$_6$H$_5$, —NH-Cbz or NH—Z); as a t-butyl carbamate (—NHCO—OC(CH$_3$)$_3$, —NH-Boc); a 2-biphenyl-2-propyl carbamate (—NHCO—OC(CH$_3$)$_2$ C$_6$H$_4$C$_6$H$_5$, —NH-Bpoc), as a 9-fluorenylmethyl carbamate (—NH-Fmoc), as a 6-nitroveratryl carbamate (—NH-Nvoc), as a 2-trimethylsilylethyl carbamate (—NH-Teoc), as a 2,2,2-trichloroethyl carbamate (—NH-Troc), as an allyl carbamate (—NH-Alloc), or as a 2(-phenylsulfonyl)ethyl carbamate (—NH—Psec).

Other protecting groups for amines, such as cyclic amines and heterocyclic N—H groups, include toluenesulfonyl (tosyl) and methanesulfonyl (mesyl) groups, benzyl groups such as a para-methoxybenzyl (PMB) group and tetrahydropyranyl (THP) groups.

A carboxylic acid group may be protected as an ester for example, as: an C$_{1-7}$ alkyl ester (e.g., a methyl ester; a t-butyl ester); a C$_{1-7}$ haloalkyl ester (e.g., a C$_{1-7}$ trihaloalkyl ester); a triC$_{1-7}$ alkylsilyl-C$_{1-7}$alkyl ester; or a C$_{5-20}$ aryl-C$_{1-7}$ alkyl ester (e.g., a benzyl ester; a nitrobenzyl ester; para-methoxybenzyl ester. A thiol group may be protected, for example, as a thioether (—SR), for example, as: a benzyl thioether; an acetamidomethyl ether (—S—CH$_2$NHC(=O)CH$_3$).

Isolation and Purification of the Compounds of the Invention

The compounds of the invention can be isolated and purified according to standard techniques well known to the person skilled in the art and examples of such methods include chromatographic techniques such as column chromatography (e.g. flash chromatography) and HPLC. One technique of particular usefulness in purifying the compounds is preparative liquid chromatography using mass spectrometry as a means of detecting the purified compounds emerging from the chromatography column.

Preparative LC-MS is a standard and effective method used for the purification of small organic molecules such as the compounds described herein. The methods for the liquid chromatography (LC) and mass spectrometry (MS) can be varied to provide better separation of the crude materials and improved detection of the samples by MS. Optimisation of the preparative gradient LC method will involve varying columns, volatile eluents and modifiers, and gradients. Methods are well known in the art for optimising preparative LC-MS methods and then using them to purify compounds. Such methods are described in Rosentreter U, Huber U.; Optimal fraction collecting in preparative LC/MS; *J Comb Chem.;* 2004; 6(2), 159-64 and Leister W, Strauss K, Wisnoski D, Zhao Z, Lindsley C., Development of a custom high-throughput preparative liquid chromatography/mass spectrometer platform for the preparative purification and analytical analysis of compound libraries; *J Comb Chem.;* 2003; 5(3); 322-9. An example of such a system for purifying compounds via preparative LC-MS is described below in the Examples section of this application (under the heading "Mass Directed Purification LC-MS System").

Methods of recrystallisation of compounds of formula (1°) and salt thereof can be carried out by methods well known to the skilled person—see for example (P. Heinrich Stahl (Editor), Camille G. Wermuth (Editor), ISBN: 3-90639-026-8, Handbook of Pharmaceutical Salts: Properties, Selection, and Use, Chapter 8, Publisher Wiley-VCH). Products obtained from an organic reaction are seldom pure when isolated directly from the reaction mixture. If the compound (or a salt thereof) is solid, it may be purified and/or crystallized by recrystallisation from a suitable solvent. A good recrystallisation solvent should dissolve a moderate quantity of the substance to be purified at elevated temperatures but only a small quantity of the substance at lower temperature. It should dissolve impurities readily at low temperatures or not at all. Finally, the solvent should be readily removed from the purified product. This usually means that it has a relatively low boiling point and a person skilled in the art will know recrystallising solvents for a particular substance, or if that information is not available, test several solvents. To get a good yield of purified material, the minimum amount of hot solvent to dissolve all the impure material is used. In practice, 3-5% more solvent than necessary is used so the solution is not saturated. If the impure compound contains an impurity which is insoluble in the solvent it may then be removed by filtration and then allowing the solution to crystallize. In addition, if the impure compound contains traces of coloured material that are not native to the compound, it may be removed by adding a small amount of decolorizing agent e.g. activating charcoal to the hot solution, filtering it and then allowing it to crystallize. Usually crystallization spontaneously occurs upon cooling the solution. If it is not, crystallization may be induced by cooling the solution below room temperature or by adding a single crystal of pure material (a seed crystal). Recrystallisation can also be carried out and/or the yield optimized by the use of an anti-solvent or co-solvent. In this case, the compound is dissolved in a suitable solvent at elevated temperature, filtered and then an additional solvent in which the required compound has low solubility is added to aid crystallization. The crystals are then typically isolated using vacuum filtration, washed and then dried, for example, in an oven or via desiccation.

Other examples of methods for purification include sublimation, which includes an heating step under vacuum for example using a cold finger, and crystallization from melt (Crystallization Technology Handbook 2nd Edition, edited by A. Mersmann, 2001).

Biological Effects

It is envisaged that the compound of the invention will be useful in medicine or therapy. The compounds of the invention, subgroups and examples thereof, have been shown to inhibit the interaction of p53 with MDM2. Such inhibition leads to cell proliferative arrest and apoptosis, which may be useful in preventing or treating disease states or conditions described herein, for example the diseases and conditions discussed below and the diseases and conditions described in the "Background of the Invention" section above in which p53 and MDM2 play a role. Thus, for example, it is envisaged that the compounds of the invention may be useful in alleviating or reducing the incidence of cancer.

The compounds of the present invention may be useful for the treatment of the adult population. The compounds of the present invention may be useful for the treatment of the pediatric population.

The compounds of the present invention have been shown to be good inhibitors of the formation of MDM2-p53 complex. The antagonist compounds of formula (1°) are capable of binding to MDM2 and exhibiting potency for MDM2. The efficacies of the compounds of the present invention have been determined against MDM2/p53 using the assay protocol described herein and other methods known in the art. More particularly, the compounds of the formula (1°) and sub-groups thereof have affinity for MDM2/p53.

Certain compounds of the invention are those having $IC_{50}$ values of less than 0.1 µM in particular less than 0.01 or 0.001 µM.

MDM2/p53 function has been implicated in many diseases due to its role in a variety of process for example vascular remodelling and antiangiogenic processes and regulation of metabolic pathways, as well as in oncogenesis. As a consequence of their affinity for MDM2 it is anticipated that the compounds may prove useful in treating or preventing a range of diseases or conditions including autoimmune conditions; diabetes mellitus; chronic inflammatory diseases, for example lupus nephritis, systemic lupus erythematosus (SLE), autoimmune mediated glomerulonephritis, rheumatoid arthritis, psoriasis, inflammatory bowel disease, autoimmune diabetes mellitus, Eczema hypersensitivity reactions, asthma, COPD, rhinitis, and upper respiratory tract disease; hyperkeratotic diseases such as autosomal recessive congenital ichthyosis (ARCI); kidney diseases including glomerular disorders, chronic kidney disease (CKD) renal inflammation, podocyte loss, glomerulosclerosis, proteinuria, and progressive kidney disease; cardiovascular diseases for example cardiac hypertrophy, restenosis, arrhythmia, atherosclerosis; ischemic injury associated myocardial infarctions, vascular injury, stroke and reperfusion injury; vascular proliferative diseases; ocular diseases such as age-related macular degeneration in particular wet form of age-related macular degeneration, ischemic proliferative retinopathies such as retinopathy of prematurity (ROP) and diabetic retinopathy, and hemangioma.

As a consequence of their affinity for MDM2 it is anticipated that the compounds may prove useful in treating or preventing proliferative disorders such as cancers.

Examples of cancers (and their benign counterparts) which may be treated (or inhibited) include, but are not limited to tumours of epithelial origin (adenomas and carcinomas of various types including adenocarcinomas, squamous carcinomas, transitional cell carcinomas and other carcinomas) such as carcinomas of the bladder and urinary tract, breast, gastrointestinal tract (including the esophagus, stomach (gastric), small intestine, colon, bowel, colorectal, rectum and anus), liver (hepatocellular carcinoma), gall bladder and biliary system, exocrine pancreas, kidney (for example renal cell carcinoma), lung (for example adenocarcinomas, small cell lung carcinomas, non-small cell lung carcinomas, bronchioalveolar carcinomas and mesotheliomas), head and neck (for example cancers of the tongue, buccal cavity, larynx, pharynx, nasopharynx, tonsil, salivary glands, nasal cavity and paranasal sinuses), ovary, fallopian tubes, peritoneum, vagina, vulva, penis, testes, cervix, myometrium, endometrium, thyroid (for example thyroid follicular carcinoma), brain, adrenal, prostate, skin and adnexae (for example melanoma, basal cell carcinoma, squamous cell carcinoma, keratoacanthoma, dysplastic naevus); haematological malignancies (i.e. leukemias, lymphomas) and premalignant haematological disorders and disorders of borderline malignancy including haematological malignancies and related conditions of lymphoid lineage (for example acute lymphocytic leukemia [ALL], chronic lymphocytic leukemia [CLL], B-cell lymphomas such as diffuse large B-cell lymphoma [DLBCL], follicular lymphoma, Burkitt's lymphoma, mantle cell lymphoma, T-cell lymphomas and leukaemias, natural killer [NK] cell lymphomas, Hodgkin's lymphomas, hairy cell leukaemia, monoclonal gammopathy of uncertain significance, plasmacytoma, multiple myeloma, and post-transplant lymphoproliferative disorders), and haematological malignancies and related conditions of myeloid lineage (for example acute myelogenous leukemia [AML], chronic myelogenous leukemia [CML], chronic myelomonocytic leukemia [CMML], hypereosinophilic syndrome, myeloproliferative disorders such as polycythaemia vera, essential thrombocythaemia and primary myelofibrosis, myeloproliferative syndrome, myelodysplastic syndrome, and promyelocytic leukemia); tumours of mesenchymal origin, for example sarcomas of soft tissue, bone or cartilage such as osteosarcomas, fibrosarcomas, chondrosarcomas, rhabdomyosarcomas, leiomyosarcomas, liposarcomas, angiosarcomas, Kaposi's sarcoma, Ewing's sarcoma, synovial sarcomas, epithelioid sarcomas, gastrointestinal stromal tumours, benign and malignant histiocytomas, and dermatofibrosarcoma protuberans; tumours of the central or peripheral nervous system (for example astrocytomas (e.g. gliomas), neuromas and glioblastomas, meningiomas, ependymomas, pineal tumours and schwannomas); endocrine tumours (for example pituitary tumours, adrenal tumours, islet cell tumours, parathyroid tumours, carcinoid tumours and medullary carcinoma of the thyroid); ocular and adnexal tumours (for example retinoblastoma); germ cell and trophoblastic tumours (for example teratomas, seminomas, dysgerminomas, hydatidiform moles and choriocarcinomas); and paediatric and embryonal tumours (for example medulloblastoma, neuroblastoma, Wilms tumour, and primitive neuroectodermal tumours); or syndromes, congenital or otherwise, which leave the patient susceptible to malignancy (for example Xeroderma Pigmentosum).

Growth of cells is a closely controlled function. Cancer, a condition of abnormal cell growth, results when cells replicate in an uncontrolled manner (increasing in number), uncontrollably grow (getting larger) and/or experience reduced cell death by apoptosis (programmed cell death), necrosis, or annoikis. In one embodiment abnormal cell growth is selected from uncontrolled cell proliferation, excessive cell growth or reduced programmed cell death. In particular, the condition or disease of abnormal cell growth is a cancer.

Thus, in the pharmaceutical compositions, uses or methods of this invention for treating a disease or condition comprising abnormal cell growth (i.e. uncontrolled and/or rapid cell growth), the disease or condition comprising abnormal cell growth in one embodiment is a cancer.

Many diseases are characterized by persistent and unregulated angiogenesis. Chronic proliferative diseases are often accompanied by profound angiogenesis, which can contribute to or maintain an inflammatory and/or proliferative state, or which leads to tissue destruction through the invasive proliferation of blood vessels. Tumour growth and metastasis have been found to be angiogenesis-dependent. Compounds of the invention may therefore be useful in preventing and disrupting initiation of tumour angiogenesis.

Angiogenesis is generally used to describe the development of new or replacement blood vessels, or neovascularisation. It is a necessary and physiological normal process by which vasculature is established in the embryo. Angiogenesis does not occur, in general, in most normal adult tissues, exceptions being sites of ovulation, menses and wound healing. Many diseases, however, are characterized by persistent and unregulated angiogenesis. For instance, in arthritis, new capillary blood vessels invade the joint and destroy cartilage. In diabetes (and in many different eye diseases), new vessels invade the macula or retina or other ocular structures, and may cause blindness. The process of atherosclerosis has been linked to angiogenesis. Tumor growth and metastasis have been found to be angiogenesis-dependent. The compounds may be beneficial in the treatment of diseases such as cancer and metastasis, ocular diseases, arthritis and hemangioma.

Therefore, the compounds of the invention may be useful in the treatment of metastasis and metastatic cancers. Metastasis or metastatic disease is the spread of a disease from one organ or part to another non-adjacent organ or part. The cancers which can be treated by the compounds of the invention include primary tumours (i.e. cancer cells at the originating site), local invasion (cancer cells which penetrate and infiltrate surrounding normal tissues in the local area), and metastatic (or secondary) tumours ie. tumours that have formed from malignant cells which have circulated through the bloodstream (haematogenous spread) or via lymphatics or across body cavities (trans-coelomic) to other sites and tissues in the body. In particular, the compounds of the invention may be useful in the treatment of metastasis and metastatic cancers.

In one embodiment the haematological malignancies is a leukaemia. In another embodiment the haematological malignancies is a lymphoma. In one embodiment the cancer is AML. In another embodiment the cancer is CLL.

In one embodiment the compound of the invention is for use in the prophylaxis or treatment of leukemia, such as acute or chronic leukaemia, in particular acute myeloid leukaemia (AML), acute lymphocytic leukaemia (ALL), chronic lymphocytic leukaemia (CLL), or chronic myeloid leukemia (CML). In one embodiment the compound of the invention is for use in the prophylaxis or treatment of lymphoma, such as acute or chronic lymphoma, in particular Burkitt lymphoma, Hodgkin lymphoma, non-Hodgkin lymphoma or diffuse large B-cell lymphoma.

In one embodiment the compound of the invention is for use in the prophylaxis or treatment of acute myeloid leukaemia (AML) or acute lymphocytic leukaemia (ALL).

One embodiment includes a compound of the invention for use in the prophylaxis or treatment of cancer in a patient selected from a sub-population possessing cancers which are p53 wild-type or have an MDM2 amplification The cancers may be cancers which are sensitive to treatment with MDM2 inhibitors. The cancers may be cancers which overexpress MDM2. The cancer may be cancers which are p53 wild-type.

Particular cancers include those with an MDM2 amplification and/or MDM2 overexpression, for example, hepatocellular carcinoma, lung, sarcomas, osteosarcomas, and Hodgkin disease.

Particular cancers include those with wild-type p53. Particulars cancers include those cancer cells with wild-type p53, particularly but not exclusively, if MDM2 is highly expressed.

In one embodiment the cancer is a p53 functional tumours. In one embodiment this disease to be treated is p53 functional solid and haematological malignancies. In another embodiment the patient to be treated has p53 mutant tumour for example AML patients with p53 mutant tumour.

In one embodiment the cancer is a tumour of the brain, for example glioma, or neuroblastoma.

In one embodiment the cancer is a cancer of the skin, for example melanoma.

In one embodiment the cancer is a cancer of the lung, for example mesothelioma. In one embodiment the mesothelioma is malignant peritoneal mesothelioma or malignant pleural mesothelioma.

In one embodiment the cancer is a cancer of the gastrointestinal tract, for example GIST, gastric, colorectal or bowel.

In one embodiment the cancer is osteosarcoma.

In one embodiment the cancer is liposarcoma.

In one embodiment the cancer is Ewing's sarcoma.

In one embodiment, the cancer is liposarcoma, soft tissue sarcoma, osteosarcoma, oesophageal cancer, and certain paediatric malignancies including B-cell malignancies.

In one embodiment, the cancer is colorectal, breast, lung and brain

In one embodiment, the cancer is a paediatric cancer.

Whether a particular cancer is one which is sensitive to MDM2 inhibitors, may be determined by a method as set out in the section headed "Methods of Diagnosis".

A further aspect provides the use of a compound for the manufacture of a medicament for the treatment of a disease or condition as described herein, in particular cancer.

Certain cancers are resistant to treatment with particular drugs. This can be due to the type of the tumour (most common epithelial malignancies are inherently chemoresistant and prostate is relatively resistant to currently available regimens of chemotherapy or radiation therapy) or resistance can arise spontaneously as the disease progresses or as a result of treatment. In this regard, references to prostate includes prostate with resistance towards anti-androgen therapy, in particular abiraterone or enzalutamide, or castrate-resistant prostate. Similarly references to multiple myeloma includes bortezomib-insensitive multiple myeloma or refractory multiple myeloma and references to chronic myelogenous leukemia includes imitanib-insensitive chronic myelogenous leukemia and refractory chronic myelogenous leukemia. In this regard, references to mesothelioma includes mesothelioma with resistance towards topoisomerase poisons, alkylating agents, antitubulines, antifolates, platinum compounds and radiation therapy, in particular cisplatin-resistant mesothelioma.

The compounds may also be useful in the treatment of tumour growth, pathogenesis, resistance to chemo- and radio-therapy by sensitising cells to chemotherapy and as an anti-metastatic agent.

Therapeutic anticancer interventions of all types necessarily increase the stresses imposed on the target tumour cells. Inhibitors of MDM2/p53 represent a class of chemotherapeutics with the potential for: (i) sensitizing malignant cells to anticancer drugs and/or treatments; (ii) alleviating or reducing the incidence of resistance to anticancer drugs and/or treatments; (iii) reversing resistance to anticancer drugs and/or treatments; (iv) potentiating the activity of anticancer drugs and/or treatments; (v) delaying or preventing the onset of resistance to anticancer drugs and/or treatments.

In one embodiment the invention provides a compound for use in the treatment of a disease or condition which is mediated by MDM2. In a further embodiment the disease or condition which is mediated by MDM2 is a cancer which is characterised by overexpression and/or increased activity of MDM2, or high copy number MDM2 and/or wildtype p53.

A further aspect provides the use of a compound for the manufacture of a medicament for the treatment of a disease or condition as described herein, in particular cancer.

In one embodiment there is provided a compound for use in the prophylaxis or treatment of a disease or condition mediated by MDM2/p53. In one embodiment there is provided a compound for inhibiting the interaction between of MDM2 protein with p53.

In one embodiment there is provided a pharmaceutical composition comprising an effective amount of at least one compound as defined. In a further aspect of the present invention, there is provided a compound as defined in the present In one embodiment there is provided a method for the prophylaxis or treatment of cancer comprising the steps of administering to a mammal a medicament comprising at least one compound as defined.

Methods of Diagnosis

Prior to administration of a compound of the formula (1°), a patient may be screened to determine whether a disease or condition from which the patient is or may be suffering is one which would be susceptible to treatment with a compound which inhibits Mdm2/p53. The term 'patient' includes human and veterinary subjects such as primates, in particular human patients.

For example, a biological sample taken from a patient may be analysed to determine whether a condition or disease, such as cancer, that the patient is or may be suffering from is one which is characterised by a genetic abnormality or abnormal protein expression which leads to up-regulation of the levels of MDM2 or to upregulation of a biochemical pathway downstream of MDM2/p53.

Examples of such abnormalities that result in activation or sensitisation of MDM2, loss of, or inhibition of regulatory pathways impacting on MDM2 expression, up-regulation of receptors or their ligands, cytogenetic aberrations or presence of mutant variants of the receptors or ligands. Tumours with up-regulation of MDM2/p53, in particular over-expression of MDM2 or exhibit wild-type p53, may be particularly sensitive to inhibitors of MDM2/p53. For example, amplification of MDM2 and/or deletion of its negative regulator such as p14ARF has been identified in a range of cancers as discussion in the Introduction section.

The term up-regulation includes elevated expression or over-expression, including gene amplification (i.e. multiple gene copies), cytogenetic aberration and increased expression by a transcriptional or post-translational effect. Thus, the patient may be subjected to a diagnostic test to detect a marker characteristic of up-regulation of MDM2. The term diagnosis includes screening. By marker we include genetic markers including, for example, the measurement of DNA composition to identify presence of mutations in p53 or amplification MDM2 or deletion (loss) of p14ARF. The term marker also includes markers which are characteristic of up regulation of MDM2/p53, including protein levels, protein state and mRNA levels of the aforementioned proteins. Gene amplification includes greater than 7 copies, as well as gains of between 2 and 7 copies.

The diagnostic tests and screens are typically conducted on a biological sample (i.e. body tissue or body fluids) selected from tumour biopsy samples, blood samples (isolation and enrichment of shed tumour cells), cerebrospinal fluid, plasma, serum, saliva, stool biopsies, sputum, chromosome analysis, pleural fluid, peritoneal fluid, buccal smears, skin biopsy or urine.

Methods of identification and analysis of cytogenetic aberration, genetic amplification, mutations and up-regulation of proteins are known to a person skilled in the art. Screening methods could include, but are not limited to, standard methods such as DNA sequence analysis by conventional Sanger or next-generation sequencing methods, reverse-transcriptase polymerase chain reaction (RT-PCR), RNA sequencing (RNAseq), nanostring hybridisation proximity RNA nCounter assays, or in-situ hybridization such as fluorescence in situ hybridization (FISH) or allele-specific polymerase chain reaction (PCR).

In screening by RT-PCR, the level of mRNA in the tumour is assessed by creating a cDNA copy of the mRNA followed by amplification of the cDNA by PCR. Methods of PCR amplification, the selection of primers, and conditions for amplification, are known to a person skilled in the art. Nucleic acid manipulations and PCR are carried out by standard methods, as described for example in Ausubel, F. M. et al., eds. (2004) Current Protocols in Molecular Biology, John Wiley & Sons Inc., or Innis, M. A. et al., eds. (1990) PCR Protocols: a guide to methods and applications, Academic Press, San Diego. Reactions and manipulations involving nucleic acid techniques are also described in Sambrook et al., (2001), $3^{rd}$ Ed, Molecular Cloning: A Laboratory Manual, Cold Spring Harbor Laboratory Press. Alternatively a commercially available kit for RT-PCR (for example Roche Molecular Biochemicals) may be used, or methodology as set forth in U.S. Pat. Nos. 4,666,828; 4,683,202; 4,801,531; 5,192,659, 5,272,057, 5,882,864, and 6,218,529 and incorporated herein by reference. An example of an in-situ hybridisation technique for assessing mRNA expression would be fluorescence in-situ hybridisation (FISH) (see Angerer (1987) Meth. Enzymol., 152: 649).

Generally, in situ hybridization comprises the following major steps: (1) fixation of tissue to be analyzed; (2) prehybridization treatment of the sample to increase accessibility of target nucleic acid, and to reduce nonspecific binding; (3) hybridization of the mixture of nucleic acids to the nucleic acid in the biological structure or tissue; (4) post-hybridization washes to remove nucleic acid fragments not bound in the hybridization, and (5) detection of the hybridized nucleic acid fragments. The probes used in such applications are typically labelled, for example, with radio-isotopes or fluorescent reporters. Certain probes are sufficiently long, for example, from about 50, 100, or 200 nucleotides to about 1000 or more nucleotides, to enable specific hybridization with the target nucleic acid(s) under stringent conditions. Standard methods for carrying out FISH are described in Ausubel, F. M. et al., eds. (2004) Current Protocols in Molecular Biology, John Wiley & Sons Inc and Fluorescence In Situ Hybridization: Technical Overview by John M. S. Bartlett in Molecular Diagnosis of Cancer, Methods and Protocols, 2nd ed.; ISBN: 1-59259-760-2; March 2004, pps. 077-088; Series: Methods in Molecular Medicine.

Methods for gene expression profiling are described by (DePrimo et al. (2003), BMC Cancer, 3:3). Briefly, the protocol is as follows: double-stranded cDNA is synthesized from total RNA using a (dT)24 oligomer for priming first-strand cDNA synthesis from polyadenylated mRNA, followed by second strand cDNA synthesis with random hexamer primers. The double-stranded cDNA is used as a template for in vitro transcription of cRNA using biotinylated ribonucleotides. cRNA is chemically fragmented according to protocols described by Affymetrix (Santa Clara, CA, USA), and then hybridized overnight to gene-specific oligonucleotide probes on Human Genome Arrays.

Alternatively, single nucleotide polymorphism (SNP) arrays, a type of DNA microarray, can be used to detect polymorphisms within a population.

Alternatively, the protein products expressed from the mRNAs may be assayed by immunohistochemistry of tumour samples, solid phase immunoassay with microtitre plates, Western blotting, 2-dimensional SDS-polyacrylamide gel electrophoresis, ELISA, flow cytometry and other methods known in the art for detection of specific proteins e.g. capillary electrophoresis. Detection methods would include the use of site specific antibodies. The skilled person will recognize that all such well-known techniques can be used for detection of upregulation of MDM2 and p53, detection of MDM2 or p53 variants or mutants, or loss of negative regulators of MDM2 in the present case.

Abnormal levels of proteins such as MDM2 or p53 can be measured using standard protein assays, for example, those assays described herein. Elevated levels or overexpression could also be detected in a tissue sample, for example, a tumour tissue by measuring the protein levels with an assay such as that from Chemicon International. The protein of interest would be immunoprecipitated from the sample lysate and its levels measured. Assay methods also include the use of markers.

In other words, p53 and MDM2 overexpression can be measured by tumour biopsy.

Methods for assessing gene copy changes include techniques commonly used in cytogenetic laboratories such as MLPA (Multiplex Ligation-dependent Probe Amplification) a multiplex PCR method detecting abnormal copy numbers, or other PCR techniques which can detect gene amplification, gain and deletion.

Ex-functional assays could also be utilised where appropriate, for example measurement of circulating leukemia cells in a cancer patient, to assess the response to challenge with an MDM2/p53 inhibitor.

Therefore all of these techniques could also be used to identify tumours particularly suitable for treatment with the compounds of the invention.

Therefore in a further aspect of the invention includes use of a compound according to the invention for the manufacture of a medicament for the treatment or prophylaxis of a disease state or condition in a patient who has been screened and has been determined as suffering from, or being at risk of suffering from, a disease or condition which would be susceptible to treatment with an MDM2/p53 inhibitor.

Another aspect of the invention includes a compound of the invention for use in the prophylaxis or treatment of cancer in a patient selected from a sub-population possessing amplification of MDM2.

Another aspect of the invention includes a compound of the invention for use in the prophylaxis or treatment of cancer in a patient selected from a sub-population possessing p53 wild-type.

Another aspect of the invention includes a compound of the invention for use in the prophylaxis or treatment of cancer in a patient possessing loss of a MDM2 negative regulator such as p14ARF.

MRI determination of vessel normalization (e.g. using MRI gradient echo, spin echo, and contrast enhancement to measure blood volume, relative vessel size, and vascular permeability) in combination with circulating biomarkers may also be used to identify patients suitable for treatment with a compound of the invention.

Thus a further aspect of the invention is a method for the diagnosis and treatment of a disease state or condition mediated by MDM2/p53, which method comprises (i) screening a patient to determine whether a disease or condition from which the patient is or may be suffering is one which would be susceptible to treatment with MDM2/p53 inhibitor; and (ii) where it is indicated that the disease or condition from which the patient is thus susceptible, thereafter administering to the patient a compound of formula (1°) and sub-groups or examples thereof as defined herein.

Advantages of Compounds of the Invention

The compounds of the formula (1°) have a number of advantages over prior art compounds.

Compounds of the invention may have particular advantage in one or more of the following aspects:
 (i) Superior potency;
 (ii) Superior in vivo efficacy
 (iii) Superior PK;
 (iv) Superior metabolic stability;
 (v) Superior oral bioavailability; and
 (vi) Superior physiochemical properties.

Superior Potency and In Vivo Efficacy

The compounds of the formula (1°) have increased affinity for MDM2 and in particular increased cell potency against cell lines known to be sensitive to MDM2 antagonists.

Enhanced target engagement is a highly desirable property in a pharmaceutical compound as it allows for a reduced dosage of drug and a good separation ('therapeutic window') between MDM2 activity and toxic effects.

The compounds of the formula (1°) have improved cell potency and/or improved selectivity for p53 WT vs mutant p53 cell lines. As a result of increased potency against MDM2 compounds of the invention may have increased in vivo efficacy in cancer cell lines and in vivo models. In addition the compounds show selectivity for MDM2 over MDMX, despite the close sequence, structural and functional similarity between these genetic paralogues.

Superior PK and Metabolic Stability

The compounds of the formula (1°) may have advantageous ADMET properties for example better metabolic stability (for example as determined with mouse liver microsomes), a better P450 profile, short half-life and/or beneficial clearance (e.g. low or high clearance). It has also been found that many compounds of the formula (1°) have an improved PK profile.

These features could confer the advantage of having more drug available in the systemic circulation to reach the appropriate site of action to exert its therapeutic effect. Increased drug concentrations to exert pharmacological action in tumours potentially leads to improved efficacy which thereby allows reduced dosages to be administered. Thus, the compounds of formula (1°) should exhibit reduced dosage requirements and should be more readily formulated and administered.

This results in a good separation ('therapeutic window') between MDM2 activity and toxic effects. Many compounds of the formula (1°) have a reduction in Cmax required for efficacy (due to better MDM2 potency and/or PK).

Superior Oral Bioavailability

Potentially the compounds of the invention have physiochemical properties suitable for oral exposure (oral exposure or AUC). In particular, compounds of the formula (1°) may exhibit improved oral bioavailability or improved reproducibility of oral absorption. Oral bioavailability can be defined as the ratio (F) of the plasma exposure of a compound when dosed by the oral route to the plasma exposure of the compound when dosed by the intravenous (i.v.) route, expressed as a percentage.

Compounds having an oral bioavailability (F value) of greater than 10%, 20% or 30%, more particularly greater than 40%, are particularly advantageous in that they may be administered orally rather than, or as well as, by parenteral administration.

Superior Physiochemical Properties

The compounds of the formula (1°) may have advantageous physiochemical properties in particular chemical stability in acidic conditions and reduced lipophilicity.

Lipophilicity can be measured using a partition-coefficient (log P) or a distribution-coefficient (log D).

The partition coefficient is a ratio of concentrations of un-ionized compound between two immiscible phases (n-octanol and water) at equilibrium whereas the distribution coefficient is the ratio of the sum of the concentrations of all forms of the compound (ionized plus un-ionized) in each of the two phases.

High lipophilicity is associated with poor drug like properties such us low aqueous solubility, poor pharmacokinetics properties (low oral bioavailability), undesired drug metabolism and high promiscuity. Compounds with optimal lipophilicity might have greater chances of success in drug development. However reduced log P (or calculated log P, c log P) can be challenging to achieve whilst retaining an acceptable level of potency for inhibition of protein-protein interactions (PPIs) due to the lipophilic nature of the targets involved.

PHARMACEUTICAL FORMULATIONS

While it is possible for the active compound to be administered alone, it is generally presented as a pharmaceutical composition (e.g. formulation).

Thus, the present invention further provides pharmaceutical compositions, as defined above, and methods of making a pharmaceutical composition comprising (e.g admixing) at least one compound of formula (1°) (and sub-groups thereof as defined herein), together with one or more pharmaceutically acceptable excipients and optionally other therapeutic or prophylactic agents as described herein.

The pharmaceutically acceptable excipient(s) can be selected from, for example, carriers (e.g. a solid, liquid or semi-solid carrier), adjuvants, diluents, fillers or bulking agents, granulating agents, coating agents, release-controlling agents, binding agents, disintegrants, lubricating agents, preservatives, antioxidants, buffering agents, suspending agents, thickening agents, flavouring agents, sweeteners, taste masking agents, stabilisers or any other excipients conventionally used in pharmaceutical compositions. Examples of excipients for various types of pharmaceutical compositions are set out in more detail below.

The term "pharmaceutically acceptable" as used herein pertains to compounds, materials, compositions, and/or dosage forms which are, within the scope of sound medical judgment, suitable for use in contact with the tissues of a subject (e.g. a human subject) without excessive toxicity, irritation, allergic response, or other problem or complication, commensurate with a reasonable benefit/risk ratio. Each excipient must also be "acceptable" in the sense of being compatible with the other ingredients of the formulation.

Pharmaceutical compositions containing compounds of the formula (1°) can be formulated in accordance with known techniques, see for example, Remington's Pharmaceutical Sciences, Mack Publishing Company, Easton, PA, USA.

The pharmaceutical compositions can be in any form suitable for oral, parenteral, topical, intranasal, intrabronchial, sublingual, ophthalmic, otic, rectal, intra-vaginal, or transdermal administration. Where the compositions are intended for parenteral administration, they can be formulated for intravenous, intramuscular, intraperitoneal, subcutaneous administration or for direct delivery into a target organ or tissue by injection, infusion or other means of delivery. The delivery can be by bolus injection, short-term infusion or longer term infusion and can be via passive delivery or through the utilisation of a suitable infusion pump or syringe driver.

Pharmaceutical formulations adapted for parenteral administration include aqueous and non-aqueous sterile injection solutions which may contain anti-oxidants, buffers, bacteriostats, co-solvents, surface active agents, organic solvent mixtures, cyclodextrin complexation agents, emulsifying agents (for forming and stabilizing emulsion formulations), liposome components for forming liposomes, gellable polymers for forming polymeric gels, lyophilisation protectants and combinations of agents for, inter alia, stabilising the active ingredient in a soluble form and rendering the formulation isotonic with the blood of the intended recipient. Pharmaceutical formulations for parenteral administration may also take the form of aqueous and non-aqueous sterile suspensions which may include suspending agents and thickening agents (R. G. Strickly, Solubilizing Excipients in oral and injectable formulations, Pharmaceutical Research, Vol 21(2) 2004, p 201-230).

The formulations may be presented in unit-dose or multi-dose containers, for example sealed ampoules, vials and prefilled syringes, and may be stored in a freeze-dried (lyophilised) condition requiring only the addition of the sterile liquid carrier, for example water for injections, immediately prior to use. In one embodiment, the formulation is provided as an active pharmaceutical ingredient in a bottle for subsequent reconstitution using an appropriate diluent.

The pharmaceutical formulation can be prepared by lyophilising a compound of formula (1°), or sub-groups thereof. Lyophilisation refers to the procedure of freeze-drying a composition. Freeze-drying and lyophilisation are therefore used herein as synonyms.

Extemporaneous injection solutions and suspensions may be prepared from sterile powders, granules and tablets.

Pharmaceutical compositions of the present invention for parenteral injection can also comprise pharmaceutically acceptable sterile aqueous or non-aqueous solutions, dispersions, suspensions or emulsions as well as sterile powders for reconstitution into sterile injectable solutions or dispersions just prior to use. Examples of suitable aqueous and nonaqueous carriers, diluents, solvents or vehicles include water, ethanol, polyols (such as glycerol, propylene glycol, polyethylene glycol, and the like), carboxymethylcellulose and suitable mixtures thereof, vegetable oils (such as sunflower oil, safflower oil, corn oil or olive oil), and injectable organic esters such as ethyl oleate. Proper fluidity can be maintained, for example, by the use of thickening materials such as lecithin, by the maintenance of the required particle size in the case of dispersions, and by the use of surfactants.

The compositions of the present invention may also contain adjuvants such as preservatives, wetting agents, emulsifying agents, and dispersing agents. Prevention of the action of microorganisms may be ensured by the inclusion of various antibacterial and antifungal agents, for example, paraben, chlorobutanol, phenol, sorbic acid, and the like. It may also be desirable to include agents to adjust tonicity such as sugars, sodium chloride, and the like. Prolonged absorption of the injectable pharmaceutical form may be brought about by the inclusion of agents which delay absorption such as aluminum monostearate and gelatin.

In one typical embodiment of the invention, the pharmaceutical composition is in a form suitable for iv. administration, for example by injection or infusion. For intravenous administration, the solution can be dosed as is, or can be injected into an infusion bag (containing a pharmaceutically acceptable excipient, such as 0.9% saline or 5% dextrose), before administration.

In another typical embodiment, the pharmaceutical composition is in a form suitable for sub-cutaneous (s.c.) administration.

Pharmaceutical dosage forms suitable for oral administration include tablets (coated or uncoated), capsules (hard or soft shell), caplets, pills, lozenges, syrups, solutions, powders, granules, elixirs and suspensions, sublingual tablets, wafers or patches such as buccal patches.

Thus, tablet compositions can contain a unit dosage of active compound together with an inert diluent or carrier such as a sugar or sugar alcohol, eg; lactose, sucrose, sorbitol or mannitol; and/or a non-sugar derived diluent such as sodium carbonate, calcium phosphate, calcium carbonate, or a cellulose or derivative thereof such as microcrystalline cellulose (MCC), methyl cellulose, ethyl cellulose, hydroxypropyl methyl cellulose, and starches such as corn starch. Tablets may also contain such standard ingredients as binding and granulating agents such as polyvinylpyrrolidone, disintegrants (e.g. swellable crosslinked polymers such as crosslinked carboxymethylcellulose), lubricating agents (e.g. stearates), preservatives (e.g. parabens), antioxidants (e.g. BHT), buffering agents (for example phosphate or citrate buffers), and effervescent agents such as citrate/bicarbonate mixtures. Such excipients are well known and do not need to be discussed in detail here.

Tablets may be designed to release the drug either upon contact with stomach fluids (immediate release tablets) or to release in a controlled manner (controlled release tablets) over a prolonged period of time or with a specific region of the GI tract.

Capsule formulations may be of the hard gelatin or soft gelatin variety and can contain the active component in solid, semi-solid, or liquid form. Gelatin capsules can be formed from animal gelatin or synthetic or plant derived equivalents thereof.

The solid dosage forms (eg; tablets, capsules etc.) can be coated or un-coated. Coatings may act either as a protective film (e.g. a polymer, wax or varnish) or as a mechanism for controlling drug release or for aesthetic or identification purposes. The coating (e.g. a Eudragit™ type polymer) can be designed to release the active component at a desired location within the gastro-intestinal tract. Thus, the coating can be selected so as to degrade under certain pH conditions within the gastrointestinal tract, thereby selectively release the compound in the stomach or in the ileum, duodenum, jejenum or colon.

Instead of, or in addition to, a coating, the drug can be presented in a solid matrix comprising a release controlling agent, for example a release delaying agent which may be adapted to release the compound in a controlled manner in the gastrointestinal tract. Alternatively the drug can be presented in a polymer coating e.g. a polymethacrylate polymer coating, which may be adapted to selectively release the compound under conditions of varying acidity or alkalinity in the gastrointestinal tract.

Alternatively, the matrix material or release retarding coating can take the form of an erodible polymer (e.g. a maleic anhydride polymer) which is substantially continuously eroded as the dosage form passes through the gastrointestinal tract. In another alternative, the coating can be designed to disintegrate under microbial action in the gut. As a further alternative, the active compound can be formulated in a delivery system that provides osmotic control of the release of the compound. Osmotic release and other delayed release or sustained release formulations (for example formulations based on ion exchange resins) may be prepared in accordance with methods well known to those skilled in the art.

The compound of formula (1°) may be formulated with a carrier and administered in the form of nanoparticles, the increased surface area of the nanoparticles assisting their absorption. In addition, nanoparticles offer the possibility of direct penetration into the cell. Nanoparticle drug delivery systems are described in "Nanoparticle Technology for Drug Delivery", edited by Ram B Gupta and Uday B. Kompella, Informa Healthcare, ISBN 9781574448573, published $13^{th}$ March 2006. Nanoparticles for drug delivery are also described in J. Control. Release, 2003, 91 (1-2), 167-172, and in Sinha et al., Mol. Cancer Ther. August 1, (2006) 5, 1909.

The pharmaceutical compositions typically comprise from approximately 1% (w/w) to approximately 95% active ingredient and from 99% (w/w) to 5% (w/w) of a pharmaceutically acceptable excipient or combination of excipients. Typically, the compositions comprise from approximately 20% (w/w) to approximately 90%,% (w/w) active ingredient and from 80% (w/w) to 10% of a pharmaceutically acceptable excipient or combination of excipients. The pharmaceutical compositions comprise from approximately 1% to approximately 95%, typically from approximately 20% to approximately 90%, active ingredient. Pharmaceutical compositions according to the invention may be, for example, in unit dose form, such as in the form of ampoules, vials, suppositories, pre-filled syringes, dragées, tablets or capsules.

The pharmaceutically acceptable excipient(s) can be selected according to the desired physical form of the formulation and can, for example, be selected from diluents (e.g solid diluents such as fillers or bulking agents; and liquid diluents such as solvents and co-solvents), disintegrants, buffering agents, lubricants, flow aids, release controlling (e.g. release retarding or delaying polymers or waxes) agents, binders, granulating agents, pigments, plasticizers, antioxidants, preservatives, flavouring agents, taste masking agents, tonicity adjusting agents and coating agents.

The skilled person will have the expertise to select the appropriate amounts of ingredients for use in the formulations. For example tablets and capsules typically contain 0-20% disintegrants, 0-5% lubricants, 0-5% flow aids and/or 0-99% (w/w) fillers/or bulking agents (depending on drug dose).

They may also contain 0-10% (w/w) polymer binders, 0-5% (w/w) antioxidants, 0-5% (w/w) pigments. Slow release tablets would in addition contain 0-99% (w/w) polymers (depending on dose). The film coats of the tablet or capsule typically contain 0-10% (w/w) release-controlling (e.g. delaying) polymers, 0-3% (w/w) pigments, and/or 0-2% (w/w) plasticizers.

Parenteral formulations typically contain 0-20% (w/w) buffers, 0-50% (w/w) cosolvents, and/or 0-99% (w/w) Water for Injection (WFI) (depending on dose and if freeze dried). Formulations for intramuscular depots may also contain 0-99% (w/w) oils.

Pharmaceutical compositions for oral administration can be obtained by combining the active ingredient with solid carriers, if desired granulating a resulting mixture, and processing the mixture, if desired or necessary, after the addition of appropriate excipients, into tablets, dragee cores or capsules. It is also possible for them to be incorporated into a polymer or waxy matrix that allow the active ingredients to diffuse or be released in measured amounts.

The compounds of the invention can also be formulated as solid dispersions. Solid dispersions are homogeneous extremely fine disperse phases of two or more solids. Solid solutions (molecularly disperse systems), one type of solid dispersion, are well known for use in pharmaceutical technology (see (Chiou and Riegelman, J. Pharm. Sci., 60, 1281-1300 (1971)) and are useful in increasing dissolution rates and increasing the bioavailability of poorly water-soluble drugs.

This invention also provides solid dosage forms comprising the solid solution described herein. Solid dosage forms include tablets, capsules, chewable tablets and dispersible or effervescent tablets. Known excipients can be blended with the solid solution to provide the desired dosage form. For example, a capsule can contain the solid solution blended with (a) a disintegrant and a lubricant, or (b) a disintegrant, a lubricant and a surfactant. In addition a capsule can contain a bulking agent, such as lactose or microcrystalline cellulose. A tablet can contain the solid solution blended with at least one disintegrant, a lubricant, a surfactant, a bulking agent and a glidant. A chewable tablet can contain the solid solution blended with a bulking agent, a lubricant, and if desired an additional sweetening agent (such as an artificial sweetener), and suitable flavours. Solid solutions may also be formed by spraying solutions of drug and a suitable polymer onto the surface of inert carriers such as sugar beads ('non-pareils'). These beads can subsequently be filled into capsules or compressed into tablets.

The pharmaceutical formulations may be presented to a patient in "patient packs" containing an entire course of treatment in a single package, usually a blister pack. Patient packs have an advantage over traditional prescriptions, where a pharmacist divides a patient's supply of a pharmaceutical from a bulk supply, in that the patient always has access to the package insert contained in the patient pack, normally missing in patient prescriptions. The inclusion of a package insert has been shown to improve patient compliance with the physician's instructions.

Compositions for topical use and nasal delivery include ointments, creams, sprays, patches, gels, liquid drops and inserts (for example intraocular inserts). Such compositions can be formulated in accordance with known methods.

Examples of formulations for rectal or intra-vaginal administration include pessaries and suppositories which may be, for example, formed from a shaped moldable or waxy material containing the active compound. Solutions of the active compound may also be used for rectal administration.

Compositions for administration by inhalation may take the form of inhalable powder compositions or liquid or powder sprays, and can be administered in standard form using powder inhaler devices or aerosol dispensing devices. Such devices are well known. For administration by inhalation, the powdered formulations typically comprise the active compound together with an inert solid powdered diluent such as lactose.

The compounds of the formula (1°) will generally be presented in unit dosage form and, as such, will typically contain sufficient compound to provide a desired level of biological activity. For example, a formulation may contain from 1 nanogram to 2 grams of active ingredient, e.g. from 1 nanogram to 2 milligrams of active ingredient. Within these ranges, particular sub-ranges of compound are 0.1 milligrams to 2 grams of active ingredient (more usually from 10 milligrams to 1 gram, e.g. 50 milligrams to 500 milligrams), or 1 microgram to 20 milligrams (for example 1 microgram to 10 milligrams, e.g. 0.1 milligrams to 2 milligrams of active ingredient).

For oral compositions, a unit dosage form may contain from 1 milligram to 2 grams, more typically 10 milligrams to 1 gram, for example 50 milligrams to 1 gram, e.g. 100 milligrams to 1 gram, of active compound.

The active compound will be administered to a patient in need thereof (for example a human or animal patient) in an amount sufficient to achieve the desired therapeutic effect.

Methods of Treatment

The compounds of the formula (1°) and sub-groups as defined herein may be useful in the prophylaxis or treatment of a range of disease states or conditions mediated by MDM2/p53. Examples of such disease states and conditions are set out above.

The compounds are generally administered to a subject in need of such administration, for example a human or animal patient, typically a human.

The compounds will typically be administered in amounts that are therapeutically or prophylactically useful and which generally are non-toxic. However, in certain situations (for example in the case of life threatening diseases), the benefits of administering a compound of the formula (1°) may outweigh the disadvantages of any toxic effects or side effects, in which case it may be considered desirable to administer compounds in amounts that are associated with a degree of toxicity.

The compounds may be administered over a prolonged term to maintain beneficial therapeutic effects or may be administered for a short period only. Alternatively they may be administered in a continuous manner or in a manner that provides intermittent dosing (e.g. a pulsatile manner).

A typical daily dose of the compound of formula (1°) can be in the range from 100 picograms to 100 milligrams per kilogram of body weight, more typically 5 nanograms to 25 milligrams per kilogram of bodyweight, and more usually 10 nanograms to 15 milligrams per kilogram (e.g. 10 nanograms to 10 milligrams, and more typically 1 microgram per kilogram to 20 milligrams per kilogram, for example 1 microgram to 10 milligrams per kilogram) per kilogram of bodyweight although higher or lower doses may be administered where required. The compound of the formula (1°) can be administered on a daily basis or on a repeat basis every 2, or 3, or 4, or 5, or 6, or 7, or 10 or 14, or 21, or 28 days for example.

Dosages may also be expressed as the amount of drug administered relative to the body surface area of the patient (mg/m$^2$). A typical daily dose of the compound of formula (1°) can be in the range from 3700 pg/m$^2$ to 3700 mg/m$^2$, more typically 185 ng/m$^2$ to 925 mg/m$^2$, and more usually 370 ng/m$^2$ to 555 mg/m$^2$ (e.g. 370 ng/m$^2$ to 370 mg/m$^2$, and more typically 37 mg/m$^2$ to 740 mg/m$^2$, for example 37 mg/m$^2$ to 370 mg/m$^2$) although higher or lower doses may be administered where required. The compound of the formula (1°) can be administered on a daily basis or on a repeat basis every 2, or 3, or 4, or 5, or 6, or 7, or 10 or 14, or 21, or 28 days for example.

The compounds of the invention may be administered orally in a range of doses, for example 0.1 to 5000 mg, or 1 to 1500 mg, 2 to 800 mg, or 5 to 500 mg, e.g. 2 to 200 mg or 10 to 1000 mg, particular examples of doses including 10, 20, 50 and 80 mg. The compound may be administered once or more than once each day. The compound can be administered continuously (i.e. taken every day without a break for the duration of the treatment regimen). Alternatively, the compound can be administered intermittently (i.e. taken continuously for a given period such as a week, then discontinued for a period such as a week and then taken continuously for another period such as a week and so on throughout the duration of the treatment regimen). Examples of treatment regimens involving intermittent administration include regimens wherein administration is in cycles of one week on, one week off; or two weeks on, one week off; or three weeks on, one week off; or two weeks on, two weeks off; or four weeks on two weeks off; or one week on three weeks off—for one or more cycles, e.g. 2, 3, 4, 5, 6, 7, 8, 9 or 10 or more cycles. This discontinuous treatment can also be based upon numbers of days rather than a full week. For example, the treatment can comprise daily dosing for 1 to 6 days, no dosing for 1 to 6 days with this pattern repeating during the treatment protocol. The number of days (or weeks) wherein the compounds of the invention are not dosed do not necessarily have to equal the number of days (or weeks) wherein the compounds of the invention are dosed.

In one embodiment, the compounds of the invention can be administered in amounts from 3 mg/m$^2$ to 125 mg/m$^2$ daily. Treatment can be by continuous daily dosing or more usually consist of multiple cycles of treatment separated by treatment breaks. One example of a single treatment cycle is 5 consecutive daily doses followed by 3 weeks without treatment.

One particular dosing regimen is once a day (e.g. orally) for a week (e.g. 5 days of treatment), followed by a treatment break of 1, 2, or 3 weeks. An alternative dosing regimen is once a week (e.g. orally), for 1, 2, 3 or 4 weeks.

In one particular dosing schedule, a patient will be given an infusion of a compound of the formula (1°) for periods of one hour daily for up to ten days in particular up to five days for one week, and the treatment repeated at a desired interval such as two to four weeks, in particular every three weeks.

More particularly, a patient may be given an infusion of a compound of the formula (1°) for periods of one hour daily for 5 days and the treatment repeated every three weeks.

In another particular dosing schedule, a patient is given an infusion over 30 minutes to 1 hour followed by maintenance infusions of variable duration, for example 1 to 5 hours, e.g. 3 hours.

The compounds of the invention can also be administered by bolus or continuous infusion. The compound of the invention can be given daily to once every week, or once every two weeks, or once every three weeks, or once every four weeks during the treatment cycle. If administered daily during a treatment cycle, this daily dosing can be discontinuous over the number of weeks of the treatment cycle: for example, dosed for a week (or a number of days), no dosing for a week (or a number of days, with the pattern repeating during the treatment cycle.

In a further particular dosing schedule, a patient is given a continuous infusion for a period of 12 hours to 5 days, and in particular a continuous infusion of 24 hours to 72 hours.

Ultimately, however, the quantity of compound administered and the type of composition used will be commensurate with the nature of the disease or physiological condition being treated and will be at the discretion of the physician.

It may be beneficial to use a compound of the invention as a single agent or to combine the compound of the invention with another agent which acts via a different mechanism to regulate cell growth thus treating two of the characteristic features of cancer development. Combination experiments can be performed, for example, as described in Chou T C, Talalay P. Quantitative analysis of dose-effect relationships: the combined effects of multiple drugs or enzyme inhibitors. Adv Enzyme Regulat 1984; 22: 27-55.

The compounds as defined herein can be administered as the sole therapeutic agent or they can be administered in combination therapy with one of more other compounds (or therapies) for treatment of a particular disease state, for example a neoplastic disease such as a cancer as hereinbefore defined. For the treatment of the above conditions, the compounds of the invention may be advantageously employed in combination with one or more other medicinal agents, more particularly, with other anti-cancer agents or adjuvants (supporting agents in the therapy) in cancer therapy. Examples of other therapeutic agents or treatments that may be administered together (whether concurrently or at different time intervals) with the compounds of the formula (1°) include but are not limited to:
Topoisomerase I inhibitors
Antimetabolites
Tubulin targeting agents
DNA binder and topoisomerase II inhibitors
Alkylating Agents
Monoclonal Antibodies.
Anti-Hormones
Signal Transduction Inhibitors
Proteasome Inhibitors
DNA methyl transferase inhibitors
Cytokines and retinoids
Chromatin targeted therapies
Radiotherapy, and,
Other therapeutic or prophylactic agents.

Particular examples of anti-cancer agents or adjuvants (or salts thereof), include but are not limited to any of the agents selected from groups (i)-(xlviii), and optionally group (xlix), below:
(i) Platinum compounds, for example cisplatin (optionally combined with amifostine), carboplatin or oxaliplatin;
(ii) Taxane compounds, for example paclitaxel, paclitaxel protein bound particles (Abraxane™) docetaxel, cabazitaxel or larotaxel;
(iii) Topoisomerase I inhibitors, for example camptothecin compounds, for example camptothecin, irinotecan (CPT11), SN-38, or topotecan;
(iv) Topoisomerase II inhibitors, for example anti-tumour epipodophyllotoxins or podophyllotoxin derivatives for example etoposide, or teniposide;
(v) Vinca alkaloids, for example vinblastine, vincristine, liposomal vincristine (Onco-TCS), vinorelbine, vindesine, vinflunine or vinvesir;
(vi) Nucleoside derivatives, for example 5-fluorouracil (5-FU, optionally in combination with leucovorin), gemcitabine, capecitabine, tegafur, UFT, S1, cladribine, cytarabine (Ara-C, cytosine arabinoside), fludarabine, clofarabine, or nelarabine;
(vii) Antimetabolites, for example clofarabine, aminopterin, or methotrexate, azacitidine, cytarabine, floxuridine, pentostatin, thioguanine, thiopurine, 6-mercaptopurine, or hydroxyurea (hydroxycarbamide);
(viii) Alkylating agents, such as nitrogen mustards or nitrosourea, for example cyclophosphamide, chlorambucil, carmustine (BCNU), bendamustine, thiotepa, melphalan, treosulfan, lomustine (CCNU), altretamine, busulfan, dacarbazine, estramustine, fotemustine, ifosfamide (optionally in combination with mesna), pipobroman, procarbazine, streptozocin, temozolomide, uracil, mechlorethamine, methylcyclohexylchloroethylnitrosurea, or nimustine (ACNU);

(ix) Anthracyclines, anthracenediones and related drugs, for example daunorubicin, doxorubicin (optionally in combination with dexrazoxane), liposomal formulations of doxorubicin (eg. Caelyx™, Myocet™, Doxil™), idarubicin, mitoxantrone, epirubicin, amsacrine, or valrubicin;

(x) Epothilones, for example ixabepilone, patupilone, BMS-310705, KOS-862 and ZK-EPO, epothilone A, epothilone B, desoxyepothilone B (also known as epothilone D or KOS-862), aza-epothilone B (also known as BMS-247550), aulimalide, isolaulimalide, or luetherobin;

(xi) DNA methyl transferase inhibitors, for example temozolomide, azacytidine, or decitabine;

(xii) Antifolates, for example methotrexate, pemetrexed disodium, or raltitrexed;

(xiii) Cytotoxic antibiotics, for example antinomycin D, bleomycin, mitomycin C, dactinomycin, carminomycin, daunomycin, levamisole, plicamycin, or mithramycin;

(xiv) Tubulin-binding agents, for example combrestatin, colchicines or nocodazole;

(xv) Signal Transduction inhibitors such as Kinase inhibitors for example receptor tyrosine kinase inhibitors (e.g. EGFR (epithelial growth factor receptor) inhibitors, VEGFR (vascular endothelial growth factor receptor) inhibitors, PDGFR (platelet-derived growth factor receptor) inhibitors, Axl inhibitors, MTKI (multi target kinase inhibitors), Raf inhibitors, ROCK inhibitors, mTOR inhibitors, MEK inhibitors or PI3K Inhibitors) for example imatinib mesylate, erlotinib, gefitinib, dasatinib, lapatinib, dovotinib, axitinib, nilotinib, vandetanib, vatalinib, pazopanib, sorafenib, sunitinib, temsirolimus, everolimus (RAD 001), vemurafenib (PLX4032 or RG7204), dabrafenib, encorafenib, selumetinib (AZD6244), trametinib (GSK121120212), dactolisib (BEZ235), buparlisib (BKM-120; NVP-BKM-120), BYL719, copanlisib (BAY-80-6946), ZSTK-474, CUDC-907, apitolisib (GDC-0980; RG-7422), pictilisib (pictrelisib, GDC-0941, RG-7321), GDC-0032, GDC-0068, GSK-2636771, idelalisib (formerly CAL-101, GS 1101, GS-1101), MLN1117 (INK1117), MLN0128 (INK128), IPI-145 (INK1197), LY-3023414, ipatasertib, afuresertib, MK-2206, MK-8156, LY-3023414, LY294002, SF1126 or PI-103, sonolisib (PX-866), or AT13148.

(xvi) Aurora kinase inhibitors for example AT9283, barasertib (AZD1152), TAK-901, MK0457 (VX680), cenisertib (R-763), danusertib (PHA-739358), alisertib (MLN-8237), or MP-470; (xvii) CDK inhibitors for example AT7519, roscovitine, seliciclib, alvocidib (flavopiridol), dinaciclib (SCH-727965), 7-hydroxy-staurosporine (UCN-01), JNJ-7706621, BMS-387032 (a.k.a. SNS-032), PHA533533, ZK-304709, or AZD-5438 and including CDK4 inhibitors such as palbociclib (PD332991) and ribociclib (LEE-011);

(xviii) PKA/B inhibitors and PKB (akt) pathway inhibitors for example AT13148, AZ-5363, Semaphore, SF1126 and MTOR inhibitors such as rapamycin analogues, AP23841 and AP23573, calmodulin inhibitors (forkhead translocation inhibitors), API-2/TCN (triciribine), RX-0201, enzastaurin HCl (LY317615), NL-71-101, SR-13668, PX-316, or KRX-0401 (perifosine/NSC 639966);

(xix) Hsp90 inhibitors for example onalespib (AT13387), herbimycin, geldanamycin (GA), 17-allylamino-17-desmethoxygeldanamycin (17-AAG) e.g. NSC-330507, Kos-953 and CNF-1010, 17-dimethylaminoethylamino-17-demethoxygeldanamycin hydrochloride (17-DMAG) e.g. NSC-707545 and Kos-1022, NVP-AUY922 (VER-52296), NVP-BEP800, CNF-2024 (B11B-021 an oral purine), ganetespib (STA-9090), SNX-5422 (SC-102112) or IPI-504;

(xx) Monoclonal Antibodies (unconjugated or conjugated to radioisotopes, toxins or other agents), antibody derivatives and related agents, such as anti-CD, anti-VEGFR, anti-HER2 or anti-EGFR antibodies, for example rituximab (CD20), ofatumumab (CD20), ibritumomab tiuxetan (CD20), GA101 (CD20), tositumomab (CD20), epratuzumab (CD22), lintuzumab (CD33), gemtuzumab ozogamicin (CD33), alemtuzumab (CD52), galiximab (CD80), trastuzumab (HER2 antibody), pertuzumab (HER2), trastuzumab-DM1 (HER2), ertumaxomab (HER2 and CD3), cetuximab (EGFR), panitumumab (EGFR), necitumumab (EGFR), nimotuzumab (EGFR), bevacizumab (VEGF), catumaxumab (EpCAM and CD3), abagovomab (CA125), farletuzumab (folate receptor), elotuzumab (CS1), denosumab (RANK ligand), figitumumab (IGF1R), CP751,871 (IGF1R), mapatumumab (TRAIL receptor), metMAB (met), mitumomab (GD3 ganglioside), naptumomab estafenatox (5T4), or siltuximab (IL6) or immunomodulating agents such as CTLA-4 blocking antibodies and/or antibodies against PD-1 and PD-L1 and/or PD-L2 for example ipilimumab (CTLA4), MK-3475 (pembrolizumab, formerly lambrolizumab, anti-PD-1), nivolumab (a anti-PD-1), BMS-936559 (anti-PD-L1), MPDL320A, AMP-514 or MED14736 (anti-PD-L1), or tremelimumab (formerly ticilimumab, CP-675,206, anti-CTLA-4);

(xxi) Estrogen receptor antagonists or selective estrogen receptor modulators (SERMs) or inhibitors of estrogen synthesis, for example tamoxifen, fulvestrant, toremifene, droloxifene, faslodex, or raloxifene;

(xxii) Aromatase inhibitors and related drugs, such as exemestane, anastrozole, letrazole, testolactone aminoglutethimide, mitotane or vorozole;

(xxiii) Antiandrogens (i.e. androgen receptor antagonists) and related agents for example bicalutamide, nilutamide, flutamide, cyproterone, or ketoconazole;

(xxiv) Hormones and analogues thereof such as medroxyprogesterone, diethylstilbestrol (a.k.a. diethylstilboestrol) or octreotide;

(xxv) Steroids for example dromostanolone propionate, megestrol acetate, nandrolone (decanoate, phenpropionate), fluoxymestrone or gossypol, (xxvi) Steroidal cytochrome P450 17alpha-hydroxylase-17,20-lyase inhibitor (CYP17), e.g. abiraterone;

(xxvii) Gonadotropin releasing hormone agonists or antagonists (GnRAs) for example abarelix, goserelin acetate, histrelin acetate, leuprolide acetate, triptorelin, buserelin, or deslorelin; (xxviii) Glucocorticoids, for example prednisone, prednisolone, dexamethasone;

(xxix) Differentiating agents, such as retinoids, rexinoids, vitamin D or retinoic acid and retinoic acid metabolism blocking agents (RAMBA) for example accutane, alitretinoin, bexarotene, or tretinoin;

(xxx) Farnesyltransferase inhibitors for example tipifarnib;
(xxxi) Chromatin targeted therapies such as histone deacetylase (HDAC) inhibitors for example sodium butyrate, suberoylanilide hydroxamide acid (SAHA), depsipeptide (FR 901228), dacinostat (NVP-LAQ824), R306465/JNJ-16241199, JNJ-26481585, trichostatin A, vorinostat, chlamydocin, A-173, JNJ-MGCD-0103, PXD-101, or apicidin;
(xxxii) Drugs targeting the ubiquitin-proteasome pathway including proteasome Inhibitors for example bortezomib, carfilzomib, CEP-18770, MLN-9708, or ONX-0912; NEDD8 inhibitors; HDM2 antagonist and deubiquitinases (DUBs);
(xxxiii) Photodynamic drugs for example porfimer sodium or temoporfin;
(xxxiv) Marine organism-derived anticancer agents such as trabectidin;
(xxxv) Radiolabelled drugs for radioimmunotherapy for example with a beta particle-emitting isotope (e.g., Iodine-131, Yittrium-90) or an alpha particle-emitting isotope (e.g., Bismuth-213 or Actinium-225) for example ibritumomab or Iodine tositumomab or alpha radium 223;
(xxxvi) Telomerase inhibitors for example telomestatin;
(xxxvii) Matrix metalloproteinase inhibitors for example batimastat, marimastat, prinostat or metastat;
(xxxviii) Recombinant interferons (such as interferon-γ and interferon α) and interleukins (e.g. interleukin 2), for example aldesleukin, denileukin diftitox, interferon alfa 2a, interferon alfa 2b, or peginterferon alfa 2b;
(xxxix) Selective immunoresponse modulators for example thalidomide, or lenalidomide;
(xl) Therapeutic Vaccines such as sipuleucel-T (Provenge) or OncoVex;
(xli) Cytokine-activating agents include Picibanil, Romurtide, Sizofiran, Virulizin, or Thymosin;
(xlii) Arsenic trioxide;
(xliii) Inhibitors of G-protein coupled receptors (GPCR) for example atrasentan;
(xliv) Enzymes such as L-asparaginase, pegaspargase, rasburicase, or pegademase;
(xlv) DNA repair inhibitors such as PARP inhibitors for example, olaparib, velaparib, iniparib, INO-1001, AG-014699, or ONO-2231;
(xlvi) Agonists of Death receptor (e.g. TNF-related apoptosis inducing ligand (TRAIL) receptor), such as mapatumumab (formerly HGS-ETR1), conatumumab (formerly AMG 655), PR095780, lexatumumab, dulanermin, CS-1008, apomab or recombinant TRAIL ligands such as recombinant Human TRAIL/Apo2 Ligand;
(xlvii) Immunotherapies such as immune checkpoint inhibitors; cancer vaccines and CAR-T cell therapy;
(xlviii) Regulators of Cell death (apoptosis) including Bcl-2 (B-cell lymphoma 2) antagonists such as venetoclax (ABT-199 or GDC-0199), ABT-737, ABT-263, TW-37, sabutoclax, obatoclax, and MIM1 and IAP antagonists including LCL-161 (Novartis), Debio-1143 (Debiopharma/Ascenta), AZD5582, Birinapant/TL-32711 (TetraLogic), CUDC-427/GDC-0917/RG-7459 (Genentech), JP1201 (Joyant), T-3256336 (Takeda), GDC-0152 (Genentech) or HGS-1029/AEG-40826 (HGS/Aegera);
(xlix) Prophylactic agents (adjuncts); i.e. agents that reduce or alleviate some of the side effects associated with chemotherapy agents, for example anti-emetic agents,
agents that prevent or decrease the duration of chemotherapy-associated neutropenia and prevent complications that arise from reduced levels of platelets, red blood cells or white blood cells, for example interleukin-11 (e.g. oprelvekin), erythropoietin (EPO) and analogues thereof (e.g. darbepoetin alfa), colony-stimulating factor analogs such as granulocyte macrophage-colony stimulating factor (GM-CSF) (e.g. sargramostim), and granulocyte-colony stimulating factor (G-CSF) and analogues thereof (e.g. filgrastim, pegfilgrastim),
agents that inhibit bone resorption such as denosumab or bisphosphonates e.g. zoledronate, zoledronic acid, pamidronate and ibandronate,
agents that suppress inflammatory responses such as dexamethasone, prednisone, and prednisolone,
agents used to reduce blood levels of growth hormone and IGF-I (and other hormones) in patients with acromegaly or other rare hormone-producing tumours, such as synthetic forms of the hormone somatostatin e.g. octreotide acetate,
antidote to drugs that decrease levels of folic acid such as leucovorin, or folinic acid,
agents for pain e.g. opiates such as morphine, diamorphine and fentanyl,
non-steroidal anti-inflammatory drugs (NSAID) such as COX-2 inhibitors for example celecoxib, etoricoxib and lumiracoxib,
agents for mucositis e.g. palifermin,
agents for the treatment of side-effects including anorexia, cachexia, oedema or thromoembolic episodes, such as megestrol acetate.

Each of the compounds present in the combinations of the invention may be given in individually varying dose schedules and via different routes. As such, the posology of each of the two or more agents may differ: each may be administered at the same time or at different times. A person skilled in the art would know through his or her common general knowledge the dosing regimes and combination therapies to use. For example, the compound of the invention may be using in combination with one or more other agents which are administered according to their existing combination regimen. Examples of standard combination regimens are provided below.

The taxane compound is advantageously administered in a dosage of 50 to 400 mg per square meter (mg/m$^2$) of body surface area, for example 75 to 250 mg/m$^2$, particularly for paclitaxel in a dosage of about 175 to 250 mg/m$^2$ and for docetaxel in about 75 to 150 mg/m$^2$ per course of treatment.

The camptothecin compound is advantageously administered in a dosage of 0.1 to 400 mg per square meter (mg/m$^2$) of body surface area, for example 1 to 300 mg/m$^2$, particularly for irinotecan in a dosage of about 100 to 350 mg/m$^2$ and for topotecan in about 1 to 2 mg/m$^2$ per course of treatment.

The anti-tumour podophyllotoxin derivative is advantageously administered in a dosage of 30 to 300 mg per square meter (mg/m$^2$) of body surface area, for example 50 to 250 mg/m$^2$, particularly for etoposide in a dosage of about 35 to 100 mg/m$^2$ and for teniposide in about 50 to 250 mg/m$^2$ per course of treatment.

The anti-tumour vinca alkaloid is advantageously administered in a dosage of 2 to 30 mg per square meter (mg/m$^2$) of body surface area, particularly for vinblastine in a dosage of about 3 to 12 mg/m$^2$, for vincristine in a dosage of about 1 to 2 mg/m², and for vinorelbine in dosage of about 10 to 30 mg/m² per course of treatment.

The anti-tumour nucleoside derivative is advantageously administered in a dosage of 200 to 2500 mg per square meter (mg/m²) of body surface area, for example 700 to 1500 mg/m², particularly for 5-FU in a dosage of 200 to 500 mg/m², for gemcitabine in a dosage of about 800 to 1200 mg/m² and for capecitabine in about 1000 to 2500 mg/m² per course of treatment.

The alkylating agents such as nitrogen mustard or nitrosourea is advantageously administered in a dosage of 100 to 500 mg per square meter (mg/m²) of body surface area, for example 120 to 200 mg/m², particularly for cyclophosphamide in a dosage of about 100 to 500 mg/m², for chlorambucil in a dosage of about 0.1 to 0.2 mg/kg, for carmustine in a dosage of about 150 to 200 mg/m², and for lomustine in a dosage of about 100 to 150 mg/m² per course of treatment.

The anti-tumour anthracycline derivative is advantageously administered in a dosage of 10 to 75 mg per square meter (mg/m²) of body surface area, for example 15 to 60 mg/m², particularly for doxorubicin in a dosage of about 40 to 75 mg/m², for daunorubicin in a dosage of about 25 to 45 mg/m², and for idarubicin in a dosage of about 10 to 15 mg/m² per course of treatment.

The antiestrogen agent is advantageously administered in a dosage of about 1 to 100 mg daily depending on the particular agent and the condition being treated. Tamoxifen is advantageously administered orally in a dosage of 5 to 50 mg, typically 10 to 20 mg twice a day, continuing the therapy for sufficient time to achieve and maintain a therapeutic effect. Toremifene is advantageously administered orally in a dosage of about 60 mg once a day, continuing the therapy for sufficient time to achieve and maintain a therapeutic effect. Anastrozole is advantageously administered orally in a dosage of about 1 mg once a day. Droloxifene is advantageously administered orally in a dosage of about 20-100 mg once a day. Raloxifene is advantageously administered orally in a dosage of about 60 mg once a day. Exemestane is advantageously administered orally in a dosage of about 25 mg once a day.

Antibodies are advantageously administered in a dosage of about 1 to 5 mg per square meter (mg/m²) of body surface area, or as known in the art, if different. Trastuzumab is advantageously administered in a dosage of 1 to 5 mg per square meter (mg/m²) of body surface area, particularly 2 to 4 mg/m² per course of treatment.

Where the compound of the formula (1°) is administered in combination therapy with one, two, three, four or more other therapeutic agents (typically one or two, more typically one), the compounds can be administered simultaneously or sequentially. In the latter case, the two or more compounds will be administered within a period and in an amount and manner that is sufficient to ensure that an advantageous or synergistic effect is achieved. When administered sequentially, they can be administered at closely spaced intervals (for example over a period of 5-10 minutes) or at longer intervals (for example 1, 2, 3, 4 or more hours apart, or even longer periods apart where required), the precise dosage regimen being commensurate with the properties of the therapeutic agent(s). These dosages may be administered for example once, twice or more per course of treatment, which may be repeated for example every 7, 14, 21 or 28 days.

It will be appreciated that the typical method and order of administration and the respective dosage amounts and regimes for each component of the combination will depend on the particular other medicinal agent and compound of the present invention being administered, their route of administration, the particular tumour being treated and the particular host being treated. The optimum method and order of administration and the dosage amounts and regime can be readily determined by those skilled in the art using conventional methods and in view of the information set out herein.

The weight ratio of the compound according to the present invention and the one or more other anticancer agent(s) when given as a combination may be determined by the person skilled in the art.

Said ratio and the exact dosage and frequency of administration depends on the particular compound according to the invention and the other anticancer agent(s) used, the particular condition being treated, the severity of the condition being treated, the age, weight, gender, diet, time of administration and general physical condition of the particular patient, the mode of administration as well as other medication the individual may be taking, as is well known to those skilled in the art. Furthermore, it is evident that the effective daily amount may be lowered or increased depending on the response of the treated subject and/or depending on the evaluation of the physician prescribing the compounds of the instant invention. A particular weight ratio for the present compound of formula (1°) and another anticancer agent may range from 1/10 to 10/1, more in particular from 1/5 to 5/1, even more in particular from 1/3 to 3/1.

The compounds of the invention may also be administered in conjunction with non-chemotherapeutic treatments such as radiotherapy, photodynamic therapy, gene therapy; surgery and controlled diets. Radiotherapy may be for radical, palliative, adjuvant, neoadjuvant or prophylactic purposes.

The compounds of the present invention also have therapeutic applications in sensitising tumour cells for radiotherapy and chemotherapy. Hence the compounds of the present invention can be used as "radiosensitizer" and/or "chemosensitizer" or can be given in combination with another "radiosensitizer" and/or "chemosensitizer". In one embodiment the compound of the invention is for use as chemosensitiser.

The term "radiosensitizer" is defined as a molecule administered to patients in therapeutically effective amounts to increase the sensitivity of the cells to ionizing radiation and/or to promote the treatment of diseases which are treatable with ionizing radiation.

The term "chemosensitizer" is defined as a molecule administered to patients in therapeutically effective amounts to increase the sensitivity of cells to chemotherapy and/or promote the treatment of diseases which are treatable with chemotherapeutics.

Many cancer treatment protocols currently employ radiosensitizers in conjunction with radiation of x-rays. Examples of x-ray activated radiosensitizers include, but are not limited to, the following: metronidazole, misonidazole, desmethylmisonidazole, pimonidazole, etanidazole, nimorazole, mitomycin C, RSU 1069, SR 4233, E09, RB 6145, nicotinamide, 5-bromodeoxyuridine (BUdR), 5-iododeoxyuridine (IUdR), bromodeoxycytidine, fluorodeoxyuridine (FudR), hydroxyurea, cisplatin, and therapeutically effective analogs and derivatives of the same.

Photodynamic therapy (PDT) of cancers employs visible light as the radiation activator of the sensitizing agent. Examples of photodynamic radiosensitizers include the following, but are not limited to: hematoporphyrin derivatives, Photofrin, benzoporphyrin derivatives, tin etioporphyrin, pheoborbide-a, bacteriochlorophyll-a, naphthalocyanines, phthalocyanines, zinc phthalocyanine, and therapeutically effective analogs and derivatives of the same.

Radiosensitizers may be administered in conjunction with a therapeutically effective amount of one or more other compounds, including but not limited to: compounds which promote the incorporation of radiosensitizers to the target cells; compounds which control the flow of therapeutics, nutrients, and/or oxygen to the target cells; chemotherapeutic agents which act on the tumour with or without additional radiation; or other therapeutically effective compounds for treating cancer or other diseases.

Chemosensitizers may be administered in conjunction with a therapeutically effective amount of one or more other compounds, including but not limited to: compounds which promote the incorporation of chemosensitizers to the target cells; compounds which control the flow of therapeutics, nutrients, and/or oxygen to the target cells; chemotherapeutic agents which act on the tumour or other therapeutically effective compounds for treating cancer or other disease. Calcium antagonists, for example verapamil, are found useful in combination with antineoplastic agents to establish chemosensitivity in tumor cells resistant to accepted chemotherapeutic agents and to potentiate the efficacy of such compounds in drug-sensitive malignancies.

For use in combination therapy with another chemotherapeutic agent, the compound of the formula (1°) and one, two, three, four or more other therapeutic agents can be, for example, formulated together in a dosage form containing two, three, four or more therapeutic agents i.e. in a unitary pharmaceutical composition containing all components. In an alternative, the individual therapeutic agents may be formulated separately and presented together in the form of a kit, optionally with instructions for their use.

In one embodiment the pharmaceutical composition comprises a compound of formula I together with a pharmaceutically acceptable carrier and optionally one or more therapeutic agent(s)

In another embodiment the invention relates to the use of a combination according to the invention in the manufacture of a pharmaceutical composition for inhibiting the growth of tumour cells.

In a further embodiment the invention relates to a product containing a compound of formula I and one or more anticancer agent, as a combined preparation for simultaneous, separate or sequential use in the treatment of patients suffering from cancer.

EXAMPLES

Figure 1:
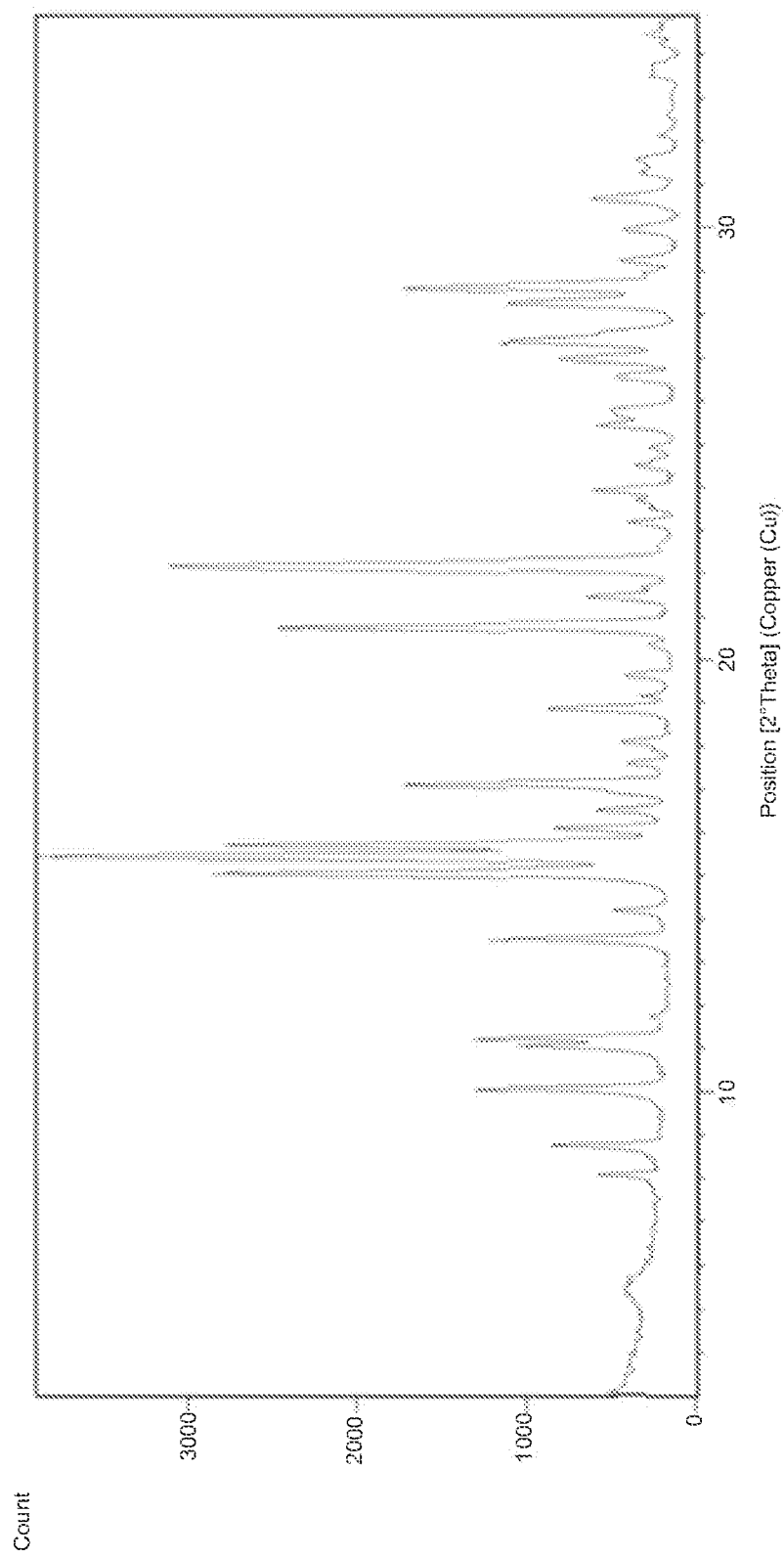
FIG. 1 is an X-ray powder diffractogram of (2S,3S)-3-(4-chlorophenyl)-3-[(1R)-1-(4-chlorophenyl)-7-fluoro-5-[(1S)-1-hydroxy-1-(oxan-4-yl)propyl]-1-methoxy-3-oxo-2,3-dihydro-1H-isoindol-2-yl]-2-methylpropanoic acid.

The invention will now be illustrated, but not limited, by reference to the specific embodiments described in the following examples. Compounds are named using an automated naming package such as AutoNom (MDL) or ChemAxon Structure to Name or are as named by the chemical supplier.

In the examples, the following abbreviations are used:
AcOH acetic acid
Boc tert-butyloxycarbonyl
BuLi butyllithium
DAST diethylaminosulfur trifluoride
DCM dichloromethane
DMF N,N-dimethylformamide
DMSO dimethyl sulfoxide
EDC 1-ethyl-3-(3-dimethylaminopropyl)carbodiimide
$Et_3N$ trimethylamine
EtOAc ethyl acetate
EtOH ethanol
$Et_2O$ diethyl ether
HATU 2-(7-aza-1H-benzotriazole-1-yl)-1,1,3,3-tetramethyluronium hexafluorophosphate)
HCl hydrochloric acid
HOAc acetic acid
HOAt 1-hydroxyazabenzotriazole
HOBt 1-hydroxybenzotriazole
HPLC high pressure liquid chromatography
IPA isopropyl alcohol
LiOtBu lithium tert-butoxide
MeCN acetonitrile
MTBE methyl ter-butylether
MeOH methanol
MeOTf methyl trifluoromethanesulfonate
mins. minutes
MS mass spectrometry
MW microwave
NMP N-methyl-2-pyrrolidinone
NMR nuclear magnetic resonance spectroscopy
$Pd_2(dba)_3$ tris(dibenzylideneacetone)dipalladium (o)
$Pd(OAc)_2$ palladium (2) acetate
$Pd(PPh_3)_4$ tetrakis(triphenylphosphine)palladium (0)
petrol petroleum ether fraction with boiling point range 40-60° C.
RT room temperature
$SiO_2$ silica
TBME methyl tert-butyl ether
TEA triethylamine
TFA trifluoroacetic acid
THE tetrahydrofuran
TMSOTf trimethylsilyl trifluoromethanesulfonate
UV ultraviolet Column Chromatography Purification using column chromatography can be achieved, for example using a Biotage automated flash purification system with UV monitoring at 298 nm and collection at 254 nm. Biotage automated chromatography pre-packed silica cartridges were used in most cases. Where stated, the purification of some compounds was performed using Biotage C18 reversed phase silica columns, which have octadecyl (end-capped) functionalised silica or Biotage KP-NH cartridges were used for the separation of highly polar compounds, which uses primary amine bonded silica.

Where necessary, semi-preparative HPLC can be carried out, for example using one of the following machines: (i) Varian Prostar Modular HPLC system with a binary pumping system, UV detector and fraction collector and controlled by Varian Star software. (ii) Agilent 1200 HPLC system with a binary pump, autosampler, fraction collector and diode array detector and controlled by Agilent ChemStation software.

Analytical LC-MS System Description

In the following examples, many of the compounds prepared were characterised by mass spectroscopy using the systems and suitable operating conditions set out below. Where atoms with different isotopes are present and a single mass quoted, the mass quoted for the compound is the monoisotopic mass (i.e. $^{35}$Cl; $^{79}$Br etc.). Several systems can be used, as described below, and these can be equipped with, and can be set up to run under, closely similar operating conditions. Possible operating conditions are also described below.

Aqilent 1200SL-6140 LC-MS System—RAPID:
  HPLC System: Agilent 1200 series SL
  Mass Spec Detector: Agilent 6140 single quadrupole
  Second Detector: Agilent 1200 MWD SL
Agilent MS Running Conditions:
  Capillary voltage: 3000V on ES pos (2700V on ES Neg)
  Fragmentor/Gain: 190 on ES pos (160 on ES neg)
  Gain: 1
  Drying gas flow: 12.0 L/min
  Gas Temperature: 345° C.
  Nebuliser Pressure: 60 psig
  Scan Range: 125-800 amu
  Ionisation Mode: ElectroSpray Positive-Negative switching
Shimadzu Nexera LC-MS System
  HPLC System: Shimadzu SIL-30AC autosampler/2× Shimadzu LC-30AD pumps
  Mass Spec Detector: Shimadzu LCMS-2020 single quadrupole MS
  Second Detector: Shimadzu SPD-M20A diode array detector
Shimadzu MS Running Conditions:
  Qarray DC voltage: 20V on ES Pos (—20V on ES Neg)
  Drying gas flow: 20.0 L/min
  DL Temperature: 300° C.
  Heat Block Temperature: 350° C.
  Nebulising Gas Flow: 1.5 L/min
  Scan Range: 100-750 amu
  Ionisation Mode: ElectroSpray Positive-Negative switching Mass Directed Purification LC-MS System Preparative LC-MS is a standard and effective method used for the purification of small organic molecules such as the compounds described herein. The methods for the liquid chromatography (LC) and mass spectrometry (MS) can be varied to provide better separation of the crude materials and improved detection of the samples by MS. Optimisation of the preparative gradient LC method will involve varying columns, volatile eluents and modifiers, and gradients. Methods are well known in the art for optimising preparative LC-MS methods and then using them to purify compounds. Such methods are described in Rosentreter U, Huber U.; Optimal fraction collecting in preparative LC/MS; *J Comb Chem.;* 2004; 6(2), 159-64 and Leister W, Strauss K, Wisnoski D, Zhao Z, Lindsley C., Development of a custom high-throughput preparative liquid chromatography/mass spectrometer platform for the preparative purification and analytical analysis of compound libraries; *J Comb Chem.;* 2003; 5(3); 322-9.

Several systems for purifying compounds via preparative LC-MS are described below although a person skilled in the art will appreciate that alternative systems and methods to those described could be used. In particular, normal phase preparative LC based methods might be used in place of the reverse phase methods described here. Most preparative LC-MS systems utilise reverse phase LC and volatile acidic modifiers, since the approach is very effective for the purification of small molecules and because the eluents are compatible with positive ion electrospray mass spectrometry. Employing other chromatographic solutions e.g. normal phase LC, alternatively buffered mobile phase, basic modifiers etc as outlined in the analytical methods described above could alternatively be used to purify the compounds.

Preparative LC-MS System Description:
Waters Fractionlynx System:
Hardware:
  2767 Dual Loop Autosampler/Fraction Collector
  2525 preparative pump
  CFO (column fluidic organiser) for column selection
  RMA (Waters reagent manager) as make up pump
  Waters ZQ Mass Spectrometer
  Waters 2996 Photo Diode Array detector
  Waters ZQ Mass Spectrometer
Software:
  Masslynx 4.1
Waters MS Running Conditions:
  Capillary voltage: 3.5 kV (3.2 kV on ES Negative)
  Cone voltage: 25 V
  Source Temperature: 120° C.
  Multiplier: 500 V
  Scan Range: 125-800 amu
  Ionisation Mode: ElectroSpray Positive or ElectroSpray Negative Aqilent 1100 LC-MS Preparative System:
Hardware:
  Autosampler: 1100 series "prepALS"
  Pump: 1100 series "PrepPump" for preparative flow gradient and 1100 series "QuatPump" for pumping modifier in prep flow
  UV detector: 1100 series "MWD" Multi Wavelength Detector
  MS detector: 1100 series "LC-MSD VL"
  Fraction Collector: 2×"Prep-FC"
  Make Up pump: "Waters RMA"
  Agilent Active Splitter
Software:
  Chemstation: Chem32
Agilent MS Running Conditions:
  Capillary voltage: 4000 V (3500 V on ES Negative)
  Fragmentor/Gain: 150/1
  Drying gas flow: 13.0 L/min
  Gas Temperature: 350° C.
  Nebuliser Pressure: 50 psig
  Scan Range: 125-800 amu
  Ionisation Mode: ElectroSpray Positive or ElectroSpray Negative Columns: A range of commercially available columns—both achiral and chiral—may be used such that, in conjunction with the changes in mobile phase, organic modifier and pH, they enabled the greatest cover in terms of a broad range of selectivity. All columns were used in accordance with the manufacturers recommended operating conditions. Typically 5 micron particle sized columns were used where available. For example, columns from Waters (including but not limited to XBridge Prep Phenyl 5µ OBD 100×19 mm, XBridge Prep C18 5µ OBD 100×19 mm, Waters Atlantis Prep T3 OBD 5µ 100×19 mm and SunFire Prep C18 OBD 5µ 100×19 mm), Phenomenex (including but not limited to Synergy MAX-RP and LUX™ Cellulose-2), Astec (Chirobiotic™ columns including but not limited to V, V2 and T2) and Diacel® (including but not limited to Chiralpak® AD-H) were available for screening.

Eluents: Mobile phase eluent was chosen in conjunction with column manufacturers recommended stationary phase limitations in order to optimise a columns separation performance.

Methods: According to the analytical trace the most appropriate preparative chromatography type was chosen. A typical routine was to run an analytical LC-MS using the type of chromatography (low or high pH) most suited for compound structure. Once the analytical trace showed good chromatography a suitable preparative method of the same type was chosen.

Solvent: All compounds were usually dissolved in 100% MeOH or 100% DMSO or 90:10 Methanol:Water+0.2% Formic Acid.

Supercritical Fluid Chromatography (SFC)

In some cases, final compounds were purified by Supercritcal Fluid Chromatography (SFC) using a Waters Thar Prep100 preparative SFC system (P200 CO2 pump, 2545 modifier pump, 2998 UV/VIS detector, 2767 liquid handler with Stacked Injection Module). The Waters 2767 liquid handler acted as both auto-sampler and fraction collector.

The column used for the preparative purification of the compounds was a Diacel Chiralpak IA/IB/IC, YMC Amylose/Cellulose C or Phenomenex Lux Cellulose-4 at 5 um 20-21.2×250 mm unless otherwise stated.

Appropriate isocratic methods were selected based on methanol, ethanol or isopropanol solvent systems under un-modified or basic conditions. The standard method used was typically 5-55% modifier/CO2, 100 ml/min, 120 Bar backpressure, 40° C. column temperature.

All compounds were screened analytically prior to the purification step. Each sample was run under both un-modified and basic conditions (5.0 ul injection, 5/95 gradient for 5 minutes) across ethanol, methanol and isopropanol. If necessary, secondary screen across extended solvents such as acetonitrile, ethyl acetate and THF may also be considered. A decision was then made by the analyst as to what pH and which isocratic condition to use depending on where the desired product elutes and the separation achieved.

The modifier used under basic conditions was diethyl amine (0.1% V/V). Occasionally formic acid (0.1% V/V) may be used as an acidic modifier.

The purification was controlled by Waters Fractionlynx software through monitoring at 210-400 nm and triggered a threshold collection value at 260 nm unless otherwise started. Collected fractions were analysed by SFC (Waters/Thar SFC systems with Waters SQD). The fractions that contained the desired product were concentrated by vacuum centrifugation.

From the information provided someone skilled in the art could purify the compounds described herein by preparative LC-MS.

Synthetic Methods

By following methods similar and/or analogous to general procedures below, the compounds set out below were prepared.

The following synthetic procedures are provided for illustration of the methods used; for a given preparation or step the precursor used may not necessarily derive from the individual batch synthesised according to the step in the description given.

As understood by a person skilled in the art, compounds synthesised using the protocols as indicated may exist as a solvate e.g. hydrate, and/or contain residual solvent or minor impurities. Compounds isolated as a salt form, may be integer stoichiometric i.e. mono- or di-salts, or of intermediate stoichiometry.

Some of the compounds below are isolated as the salt, for example some compounds are acidic and can be isolated as a TRIS salt.

Introduction: Stereochemistry (dr)*

In some cases, compound exists as a mixture of diastereoisomers at the 1-position of the isoindolinone. In such cases, the diastereoisomeric ration (dr) is quoted as a ratio of the R to S isomers at the 1-position of the isoindolinone ring.

For example, in the case below, the product consists of

Prop-2-en-1-yl (2S,3S)-3-(4-chlorophenyl)-3-[(1R)-1-(4-chlorophenyl)-7-fluoro-1-hydroxy-5-[(1S)-1-hydroxy-1-(oxan-4-yl)propyl]-3-oxo-2,3-dihydro-1H-isoindol-2-yl]-2-methylpropanoate (75%)

Prop-2-en-1-yl (2S,3S)-3-(4-chlorophenyl)-3-[(1S)-1-(4-chlorophenyl)-7-fluoro-1-hydroxy-5-[(1S)-1-hydroxy-1-(oxan-4-yl)propyl]-3-oxo-2,3-dihydro-1H-isoindol-2-yl]-2-methylpropanoate (25%)

Making a diastereoisomeric ration (dr)=3:1.

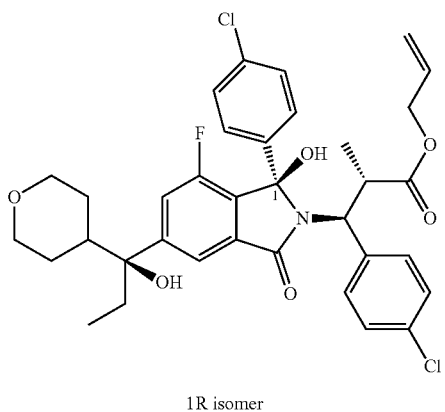

1R isomer

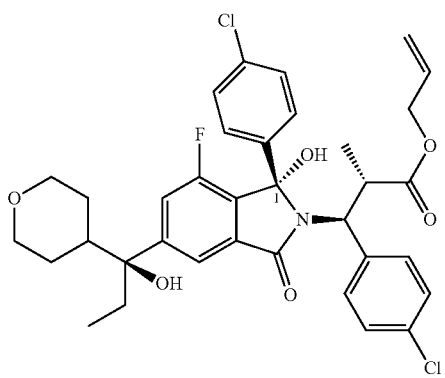

1S isomer

3:1

Where the 1R isomer represents the major component, this is written as:

Prop-2-en-1-yl (2S,3S)-3-(4-chlorophenyl)-3-[(1R)-1-(4-chlorophenyl)-7-fluoro-1-hydroxy-5-[(1S)-1-hydroxy-1-(oxan-4-yl)propyl]-3-oxo-2,3-dihydro-1H-isoindol-2-yl]-2-methylpropanoate [dr (1R:1S)=3:1]

Intermediates

S-p-Tolyl tetrahydro-2H-pyran-4-carbothioate

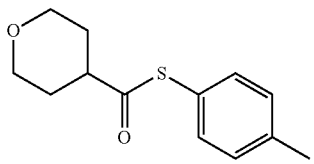 [SMILES: Cc1ccc(SC(=O)C2CCOCC2)cc1]

A stirred of solution 4-methylbenzenethiol (18.63 g, 150 mmol) and tetrahydro-2H-pyran-4-carbonyl chloride (22.29 g, 150 mmol) in isohexane (300 mL) was cooled in an ice-bath and treated dropwise over 30 mins with triethylamine (23.00 ml, 165 mmol) to give a thick white paste which was stirred at room temperature overnight. The mixture was filtered and the solids were washed twice with a mixture of methyl t-butyl ether (70 mL) and isohexane (140 mL) followed by methyl t-butyl ether (200 mL). The combined filtrates were evaporated to give S-p-tolyl tetrahydro-2H-pyran-4-carbothioate (32.452 g, 130 mmol, 87% yield) as a white crystalline solid. 1H NMR (CDCl$_3$, 400 MHz) δ 7.31-7.26 (2H, m), 7.25-7.19 (2H, m), 4.11-3.95 (2H, m), 3.61-3.35 (2H, m), 2.93-2.76 (1H, m), 2.37 (3H, s), 1.98-1.79 (4H, m), m/z 237.1 (M+H)$^+$ (ES$^+$);

(2S,3S)-3-(tert-Butoxycarbonylamino)-3-(4-chlorophenyl)-2-methyl-propanoic acid

The synthesis of (2S,3S)-3-(tert-Butoxycarbonylamino)-3-(4-chlorophenyl)-2-methyl-propanoic acid was performed using conditions similar to those described in Org. Synth, 2009, 86, 11-17.

Step 1: tert-Butyl N-[(benzenesulfonyl)(4-chlorophenyl)methyl]carbamate

To a 10 L flange flask equipped with a stirrer bar, N$_2$ inlet, bubbler and thermoprobe, a solution of t-butyl carbamate (660 g, 5.64 mol, 1.0 eq.) in THF (2 L) was added. Sodium benzenesulfinate (927.0 g, 5.64 mol, 1.0 eq) was added portion-wise and slurried as a white cloudy solution. Water (3 L) and 4-chlorobenzaldehyde (810 g, 5.76 mol, 1.02 eq.) were then added in one portion along with formic acid (97%, 1.25 L, 33.4 mol, 5.8 eq.). The reaction was stirred for 2 days. The resulting white solid was filtered and washed with water (2×1 L) and placed in a 20 L bucket equipped with an overhead stirrer and ice bath. The white solid was triturated in ice-cold diethyl ether (3 L) for 1 hour. The solid was filtered, washed with ice-cold petrol (2×1 L) and dried overnight in the vacuum oven at 40° C. to yield a free-flowing white solid.

Step 2: tert-Butyl N-[(4-chlorophenyl)methylidene]carbamate

To a 5 L RBF equipped with a stirrer bar, N$_2$ inlet, bubbler, thermoprobe, and condenser, THF (2.4 L) and step 1 product (138 g, 0.363 mol, 1.0 eq.) was added to yield a cloudy suspension. Anhydrous potassium carbonate (300.0 g, 2.177 mol, 6.0 eq) was then added and the reaction was heated at reflux for 24 hours (oil bath 73° C.). The mixture was filtered and the pad was washed with THF (1 L). The filtrate was concentrated and the remaining solid dried under high-vacuum to yield a beige solid/wax (90 g) which was used immediately in the next step.

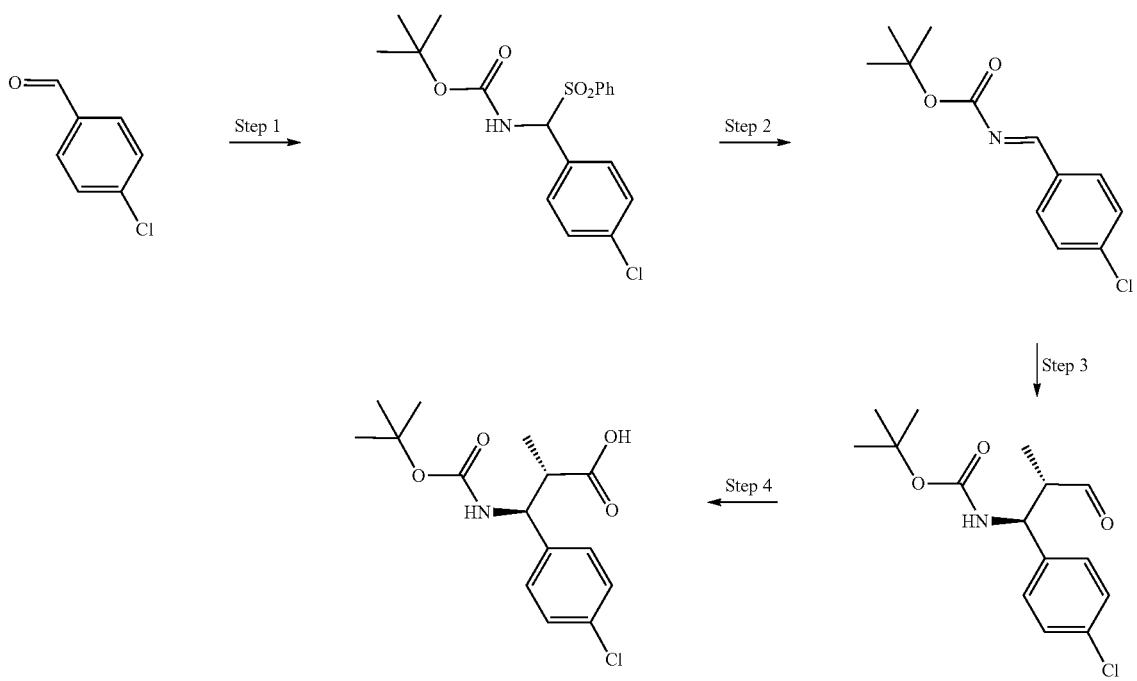

Step 3: tert-Butyl N-[(1S,2S)-1-(4-chlorophenyl)-2-methyl-3-oxopropyl]carbamate To a 10 L flange flask equipped with a stirrer bar, N₂ inlet, bubbler and thermoprobe, was added tert-butyl N-[(4-chlorophenyl)methylidene]carbamate (90 g, 0.375 mol, 1.0 eq.) in HPLC grade acetonitrile (4.5 L). This resulted in a murky white solution. Propionaldehyde (43.5 g, 54 mL, 0.854 mol, 2.0 eq.) was added portion-wise and the reaction was cooled to 0° C. using an acetone/cardice bath. S-proline (8.6 g, 0.075, 20 mol %) was then added and the reaction was stirred overnight at RT. This process was run in duplicate and the two batches were then combined in a 20 L separating funnel and water (1.6 L) was added (endotherm 17-10° C.) and the reaction was stirred vigorously for 20 minutes. Diethyl ether (4.5 L) and brine (2 L) was added, stirred and the organic layer was separated and dried with MgSO₄. This was filtered and concentrated in vacuo at 30° C. on a rotary evaporator to yield a beige wax which was dissolved in diethyl ether (1 L) to remove residual acetonitrile. This was then triturated in hexane (500 mL) at RT overnight. The off-white solid was filtered and dried under high-vacuum to yield a white solid (75 g) of aldehyde.

Step 4: (2S,3S)-3-(tert-Butoxycarbonylamino)-3-(4-chlorophenyl)-2-methyl-propanoic acid To a 10 L flange flask equipped with a stirrer bar, N₂ inlet, bubbler, dropping funnel and thermoprobe, step 3 aldehyde (187.5 g, 0.63 mol, 1.0 eq.) in acetonitrile (2 L) was added and cooled to 0° C. using an acetone/cardice bath. Sodium chlorite (156.7 g, 1.73 mol, 2.75 eq.) in water (1.7 L) was added drop-wise over 10 minutes. The solution became an intense yellow. Keeping the reaction at 0° C., sulfamic acid (177.4 g, 1.83 mol, 2.90 eq.) in water (1.8 L) was added drop-wise over 30 minutes (care: very large exotherm if added too quickly, cool acetone/cardice bath to −40° C.). The reaction became a very intense yellow solution (chlorine produced) and a white precipitate was observed. The reaction was stirred overnight at RT. The solid was filtered, washed with water (2×1 L) and dried in a vacuum oven at 50° C. to yield a white free-flowing powder (130 g). 1H NMR (400 MHz, DMSO-d6): 12.13 (1H, s), 7.43 (1H, d), 7.40-7.22 (4H, m), 4.63 (1H, t), 2.77-2.65 (1H, m), 1.36 (9H, s), 1.12 (4H, d). MS: m/z=312 [M−H⁺]⁻, [α]$_D^{20}$=−54 (c 1.15, MeOH).

Allyl-Protected β-Aminoacid

Allyl (2S,3S)-3-amino-3-(4-chlorophenyl)-2-methyl-propanoate hydrochloride

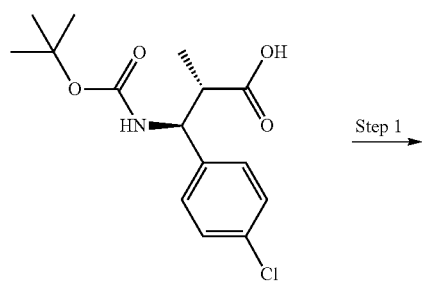

Step 1

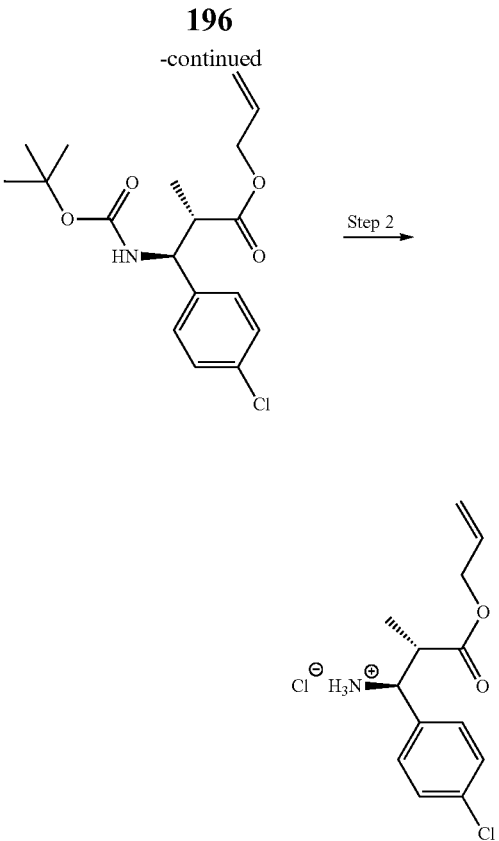

Step 1: Allyl (2S,3S)-3-((tert-butoxycarbonyl)amino)-3-(4-chlorophenyl)-2-methylpropanoate Allyl bromide (3.9 mL, 45.10 mmol) was added drop-wise to a stirred mixture of (2S,3S)-3-(tert-butoxycarbonylamino)-3-(4-chlorophenyl)-2-methyl-propanoic acid (12 g, 38.24 mmol) in anhydrous DMF (120 mL) and stirred for 2 h at RT under N₂. The mixture was poured into water (1000 mL) and extracted with ethyl acetate (3×500 mL). Combined organics were washed with water (500 mL), 4% aq. LiCl (2×250 mL), dried (MgSO₄) and evaporated. The resulting crude solid was purified by silica column chromatography (330 g) using a 0-100% ethyl acetate in isohexane gradient (15 CVs) to afford the title product as a colourless solid (12.1 g, 89.6%). ¹H NMR (400 MHz, CDCl3) 7.27 (2H, d), 7.18 (2H, d), 5.85-5.73 (1H, m), 5.33-5.32 (1H, m), 5.25-5.17 (2H, m), 4.94-4.90 (1H, m), 4.50-4.48 (2H, m), 2.90 (1H, dd), 1.40 (9H, s), 1.16 (3H, d).

Step 2: Allyl (2S,3S)-3-amino-3-(4-chlorophenyl)-2-methylpropanoate hydrochloride salt Allyl (2S,3S)-3-((tert-butoxycarbonyl)amino)-3-(4-chlorophenyl)-2-methylpropanoate (12 g, 33.9 mmol) was stirred in 4N HCl in dioxane (120 mL) for 1 h at RT. The mixture was evaporated to dryness. Toluene (2×50 mL) was added and the crude solid was further evaporated to afford a cream solid (9.8 g, 100%). ¹H NMR (400 MHz, CDCl3) 9.00-8.95 (3H, s, br), 7.37 (2H, d, J=8.7 Hz), 7.31 (2H, d, J=8.5 Hz), 5.75-5.65 (1H, m), 5.18-5.12 (2H, m), 4.45-4.38 (3H, m), 3.25-3.16 (1H, m), 1.34 (3H, d). MS: [M+H]+= 254.1, [α]$_D^{20}$=−60.09 (c 1.0, MeOH).

SEM-Protected β-Amino acid 2-(Trimethylsilyl)ethyl (2S,3S)-3-((tert-butoxycarbonyl)amino)-3-(4-chlorophenyl)-2-methylpropanoate

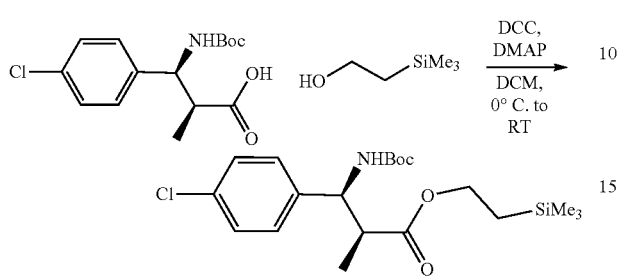

DCC (13.81 g, 66.9 mmol) was added portion-wise to an ice-cooled stirred suspension of (2S,3S)-3-(tert-butoxycarbonylamino)-3-(4-chlorophenyl)-2-methyl-propanoic acid (20.0 g, 63.7 mmol), 2-(trimethylsilyl)ethanol (10.96 ml, 76 mmol) and DMAP (0.779 g, 6.37 mmol) in DCM (320 mL). The mixture was allowed to warm slowly to RT and stirred for 18 h. The reaction mixture was filtered to remove DCU, washing with DCM (300 mL). The filtrate was washed with 1 M HCl (400 mL), dried (MgSO$_4$), filtered and concentrated in vacuo to give 2-(trimethylsilyl)ethyl (2S,3S)-3-((tert-butoxycarbonyl)amino)-3-(4-chlorophenyl)-2-methylpropanoate (29.0 g, 59.5 mmol, 93% yield) as a pale yellow oil, which solidified on standing. $^1$H NMR in CDCl$_3$ $^1$H NMR (CDCl$_3$, 400 MHz) δ 7.30-7.24 (2H, m), 7.22-7.14 (2H, m), 5.48-5.34 (1H, m), 5.02-4.78 (1H, m), 4.24-3.94 (2H, m), 2.98-2.64 (1H, m), 1.40 (9H, s), 1.12 (3H, d), 0.91-0.77 (2H, m), 0.00 (9H, s). The crude product was used in the next step without further purification.

2-(Trimethylsilyl)ethyl (2S,3S)-3-amino-3-(4-chlorophenyl)-2-methylpropanoate

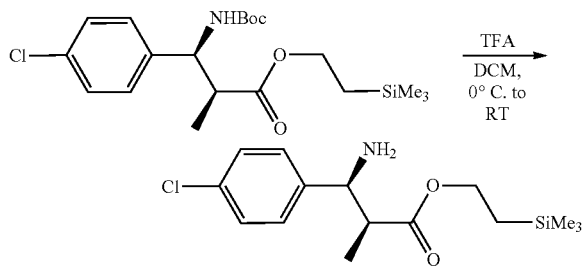

TFA (22.94 ml, 298 mmol) was added to an ice-cooled stirred solution of 2-(trimethylsilyl)ethyl (2S,3S)-3-((tert-butoxycarbonyl)amino)-3-(4-chlorophenyl)-2-methylpropanoate (29.0 g, 59.5 mmol) in DCM (120 mL). The mixture was stirred at 0° C. for 1 h. A further portion of TFA (22.94 ml, 298 mmol) was added and the mixture was stirred at 0° C. for 4 h then warmed slowly to RT and stirred for 1.5 h. The mixture was re-cooled to 0° C. and quenched carefully and slowly with sat. NaHCO$_3$ (aq.) (~300 mL) (caution: effervescence). The layers were separated and the organic phase was washed with sat. NaHCO$_3$ (3×200 mL), brine (200 mL), dried and concentrated in vacuo to give an orange oil (19.72 g). The crude product was loaded onto a column of SCX (100 g) in MeOH (~20 mL). The column was washed with MeOH (500 mL) and then the product was eluted with 0.7 M ammonia in MeOH (~1,000 mL). The resultant mixture was concentrated in vacuo to afford 2-(trimethylsilyl)ethyl (2S,3S)-3-amino-3-(4-chlorophenyl)-2-methylpropanoate (14.60 g, 44.2 mmol, 74.2% yield) as a pale orange oil. $^1$H NMR (DMSO-d$_6$, 400 MHz) δ 7.39-7.26 (4H, m), 3.97-3.85 (3H, m), 2.62-2.49 (1H, m), 1.94 (2H, br s), 1.07 (3H, d), 0.76-0.61 (2H, m), −0.03 (9H, s).

Phenyl-Protected β-Aminoacid

Phenyl (2S,3S)-3-amino-3-(4-chlorophenyl)-2-methylpropanoate hydrochloride

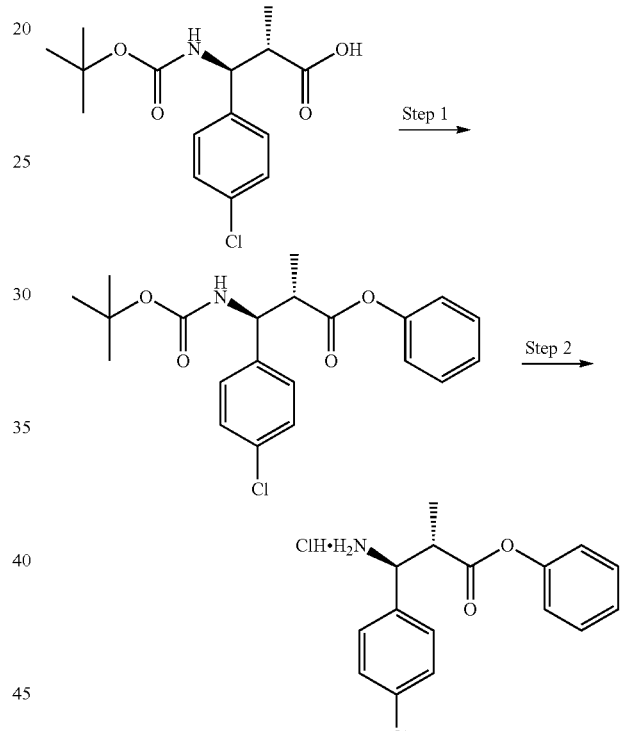

Step 1: Phenyl (2S,3S)-3-((tert-butoxycarbonyl)amino)-3-(4-chlorophenyl)-2-methylpropanoate To a solution of (2S,3S)-3-(tert-butoxycarbonylamino)-3-(4-chlorophenyl)-2-methyl-propanoic acid (5 g, 15.93 mmol), N,N-dicyclohexylcarbodiimide (3.62 g, 17.52 mmol) and 4-dimethylaminopyridine (194 mg, 1.59 mmol) in anhydrous dichloromethane (100 mL) at room temperature was added phenol (6.96 g, 31.86 mmol) in one portion. The reaction was stirred for 3 h at room temperature, after which point LCMS indicated full conversion to product. The mixture was diluted with water (50 mL) and separated. The water was washed with dichloromethane (3×50 mL) and organics combined. The organics were washed with saturated sodium bicarbonate (100 mL×2), brine (100 mL×2), passed through a phase separator cartridge and concentrated under reduced pressure. The crude product was dissolved in ethyl acetate (200 mL) and stirred for five minutes, and the resulting precipitate filtered off. The filtrate was concentrated and purified by silica chromatography (gradient elution 0 to 5% ethyl acetate in dichloromethane). Fractions containing product were combined and concentrated. Crude material was triturated using 10% diethyl ether in iso-hexane (2×50 mL) to give the title compound as a colourless solid (4.2 g, 68%). $^1$H NMR (400 MHz, CDCl3) 7.36-7.26 (6H, m), 7.21 (1H, dd), 6.88 (2H, d), 5.29 (1H, s, br), 5.14 (1H, s), 3.16-3.10 (1H, m), 1.41 (9H, s), 1.30 (3H, d).

Step 2: Phenyl (2S,3S)-3-amino-3-(4-chlorophenyl)-2-methylpropanoate hydrochloride To a round bottom flask was added phenyl (2S,3S)-3-((tert-butoxycarbonyl)amino)-3-(4-chlorophenyl)-2-methyl-propanoate (4.1 g, 10.52 mmol) and anhydrous HCl in ethyl acetate (1M solution, 60 mL) and the resulting mixture stirred at room temperature for 16 h. The mixture was concentrated under reduced pressure. The resulting solid was triturated in diethyl ether (25 mL) to give the title compound as an off-white solid (3.05 g, quant.). $^1$H NMR (400 MHz, DMSO) 8.91 (3H, s), 7.65 (2H, d), 7.58 (2H, d), 7.36 (2H, dd), 7.24 (1H, dd), 6.76 (2H, d), 4.54 (1H, d), 3.47 (1H, m), 1.49 (3H, d).

Synthesis of: 2-(4-chlorobenzoyl)-3-fluoro-5-(tetrahydro-2H-pyran-4-carbonyl)benzoic acid

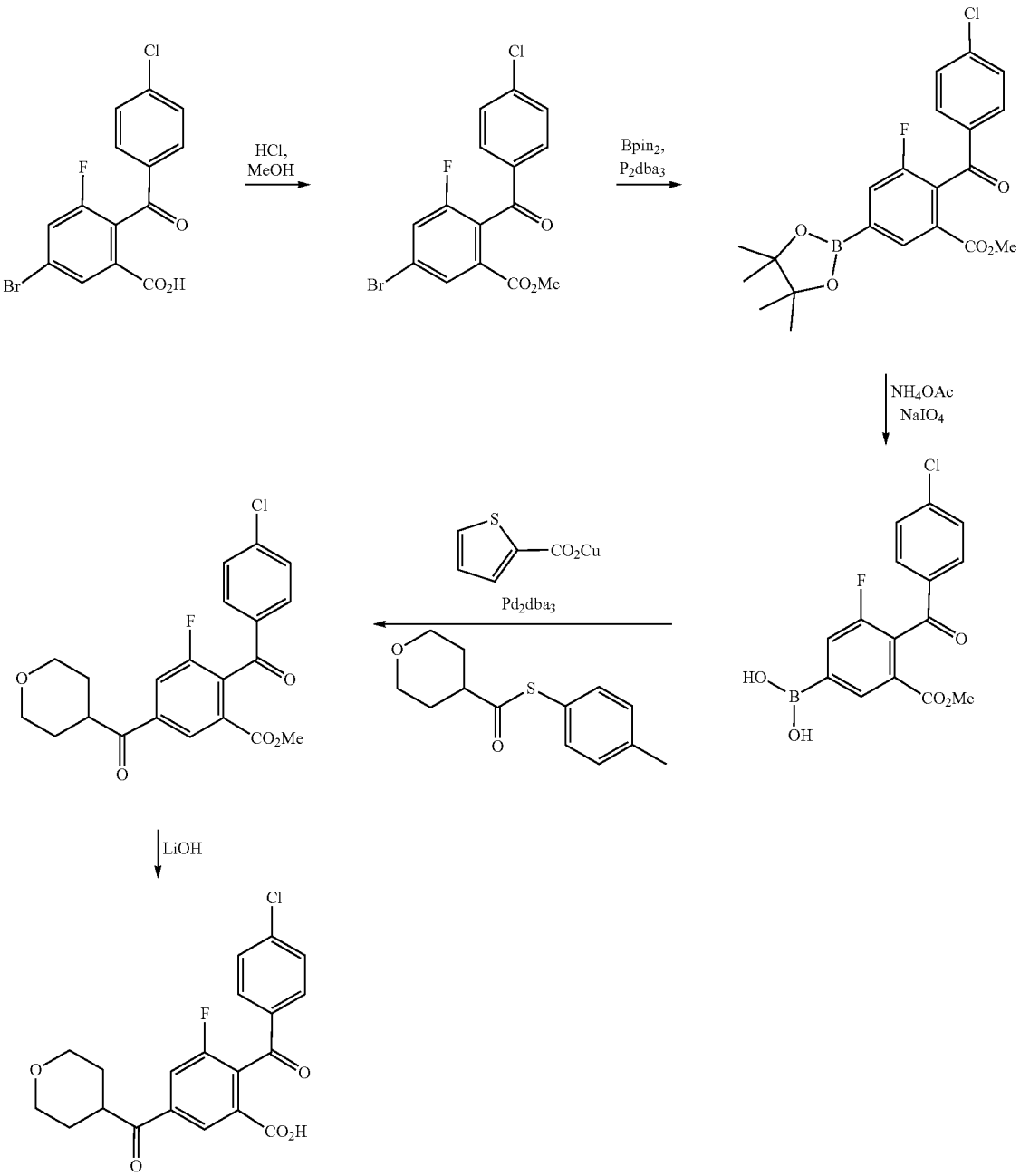

Step 1: Methyl 5-bromo-2-(4-chlorobenzoyl)-3-fluorobenzoate

To a solution of 5-bromo-2-(4-chlorobenzoyl)-3-fluorobenzoic acid (625 gm 1.751 mol), in MeOH (6.25 L), was added conc. HCl (62 mL) and the mixture heated at reflux for 48 hours. The reaction was allowed to cool to room temperature where the product precipitated out. This was filtered and dried in a vacuum oven overnight at 40° C. Mother liquors were concentrated to half their volume and allowed to stir overnight. Additional solid had precipitated out of the solution which was collected by filtration and dried in a vacuum oven at 40° C. These were combined with previous crops to give methyl 5-bromo-2-(4-chlorobenzoyl)-3-fluorobenzoate as a white solid (1256.9 g, 96.7%).

Step 2: Methyl 2-(4-chlorobenzoyl)-3-fluoro-5-(4,4,5,5-tetramethyl-1,3,2-dioxaborolan-2-yl)benzoate To a stirred solution of methyl 5-bromo-2-(4-chlorobenzoyl)-3-fluorobenzoate (264.5 g, 0.713 mol, 1.0 eq) in dioxane (2 L), was added bispinacolato diboron (217.3 g, 0.856 mol, 1.2 eq) and potassium acetate (139.7 g, 1.426, 2.0 eq). This was de-gassed with $N_2$ for 20 mins before adding Pd(dppf)$Cl_2$·DCM (17.47 g, 0.021 mol, 0.03 eq) and de-gassed for a further 10 mins before being heated to 90° C. overnight. The reaction was cooled to room temperature before being transferred to the large separator. Ethyl acetate (2 L) was added and the organics were washed with water (3×1 L). The organics were combined, dried (MgSO$_4$) and concentrated to a brown oil (468.6 g).

The crude material was taken up in toluene and placed upon a silica column (4 L sinter, 20 cm thick) and eluted with toluene (15 L). The material was concentrated and combined with all other runs before being slurried in petrol 40-60 (4 L) for 3 hours to give the title compound as an off white solid (908.2 g, 66.3%). $^1$H NMR (CDCl$_3$): 8.32 (1H, s, Ar—H), 7.72-7.79 (5H, m, 5×Ar-H), 3.75 (3H, s, O-Me), 1.39 (12H, s, C—CH$_3$)

Step 3: (4-(4-Chlorobenzoyl)-3-fluoro-5-(methoxycarbonyl)phenyl)boronic acid To a suspension of methyl 2-(4-chlorobenzoyl)-3-fluoro-5-(4,4,5,5-tetramethyl-1,3,2-dioxaborolan-2-yl)benzoate (50 g, 107 mmol) in acetone (340 mL) and water (170 mL) was added ammonium acetate (20.71 g, 269 mmol) and sodium periodate (57.5 g, 269 mmol). The suspension was stirred at RT for 48 h. The reaction mixture was diluted with EtOAc (100 mL) and filtered. The filter cake was washed with EtOAc (4×100 mL). The filtrate was part-concentrated in vacuo to approx. half volume. The mixture was diluted with 1 M HCl (aq.) (200 mL) and the layers separated. The aqueous phase was extracted with EtOAc (200 mL) and the combined organic extracts were washed with brine (400 mL), dried (MgSO$_4$) and concentrated in vacuo to give the crude product as a white solid (~42 g).

The crude product was triturated with isohexane (300 mL), filtered, washed with isohexane (3×200 mL) and dried to give (4-(4-chlorobenzoyl)-3-fluoro-5-(methoxycarbonyl)phenyl)boronic acid (38.9 g, 104 mmol, 97% yield) as a white solid. $^1$H NMR (DMSO-d6, 400 MHz) δ 8.64 (2H, br s), 8.34 (1H, d), 7.95 (1H, dd), 7.80-7.68 (2H, m), 7.65-7.55 (2H, m), 3.69 (3H, s). m/z 336.9 (M+H)$^+$ (ES$^+$);

Step 4: Methyl-2-(4-chlorobenzoyl)-3-fluoro-5-(tetrahydro-2H-pyran-4-carbonyl)benzoate A mixture of (4-(4-chlorobenzoyl)-3-fluoro-5-(methoxycarbonyl)phenyl)boronic acid (25 g, 74.3 mmol) and S-p-tolyl tetrahydro-2H-pyran-4-carbothioate (36.0 g, 152 mmol) in dry THF (350 mL) was evacuated and back-filled with nitrogen (×3). Pd$_2$(dba)$_3$ (0.340 g, 0.371 mmol), ((thiophene-2-carbonyl)oxy)copper (29.0 g, 152 mmol) and triethyl phosphite (0.260 ml, 1.486 mmol) in dry THF (20 mL) were added and the mixture was evacuated and back-filled with nitrogen (×3). The reaction was stirred at RT for 72 h. The mixture was diluted with MTBE (300 mL) and filtered through a pad of Celite, washing with MTBE (1000 mL). The filtrate was concentrated in vacuo and the residue re-dissolved in MTBE (500 mL) and washed with 1 M NaOH (aq.) (2×300 mL). The aqueous phase was extracted with MTBE (400 mL) and the combined organic phases were washed with brine (300 mL), dried (MgSO$_4$), filtered and partially concentrated in vacuo to approx. 300 mL.

The solution was stirred with decolourising charcoal (~5 g) for 2 h then filtered over Celite. The filtrate was concentrated in vacuo to give dark orange oil (47.5 g). The crude product was co-evaporated with isohexane (250 mL) to give a yellow/orange solid. The solid was suspended in isohexane (550 mL), heated to reflux and stirred vigorously for 3 h. The suspension was filtered and the collected solid washed with isohexane (3×100 mL) and dried to give methyl-2-(4-chlorobenzoyl)-3-fluoro-5-(tetrahydro-2H-pyran-4-carbonyl) benzoate (26.4 g, 63.9 mmol, 86% yield) as a pale yellow solid. $^1$H NMR (CDCl$_3$, 400 MHz) δ 8.41 (1H, d), 7.91 (1H, dd), 7.78-7.69 (2H, m), 7.49-7.41 (2H, m), 4.16-4.02 (2H, m), 3.77 (3H, s), 3.66-3.55 (2H, m), 3.55-3.46 (1H, m), 1.99-1.76 (4H, m). m/z 404.9 (M+H)$^+$ for 35Cl (ES$^+$);

Step 5: 2-(4-Chlorobenzoyl)-3-fluoro-5-(tetrahydro-2H-pyran-4-carbonyl)benzoic acid 1N LiOH (4.40 ml, 4.40 mmol) was added to a solution of methyl-2-(4-chlorobenzoyl)-3-fluoro-5-(tetrahydro-2H-pyran-4-carbonyl)benzoate (0.89 g, 2.199 mmol) in dioxane (15 mL) and the resulting suspension was stirred for 1 h. The mixture was diluted with EtOAc and water and 1 N HCl (20 mL) was added. The crude product was extracted with EtOAc and the combined organic extracts were washed with brine, dried (MgSO$_4$) and concentrated under vacuum to afford the title compound (0.78 g) as a white solid. $^1$H NMR (CDCl$_3$, 400 MHz) δ 13.92 (s, 1H), 8.36 (d, 1H), 8.28 (dd, 1H), 7.76 (d, 1H), 7.66-7.57 (m, 2H), 3.95-3.87 (m, 2H), 3.85-3.73 (m, 1H), 3.53 (ddd, 2H), 1.81-1.73 (m, 3H), 1.69-1.53 (m, 2H). LCMS m/z 391/393 (M+H)$^+$ Alternative Synthesis of 2-(4-chlorobenzoyl)-3-fluoro-5-(tetrahydro-2H-pyran-4-carbonyl)benzoic Acid Derivatives: Ethyl 2-(4-chlorobenzoyl)-3-fluoro-5-(tetrahydro-2H-pyran-4-carbonyl)benzoate

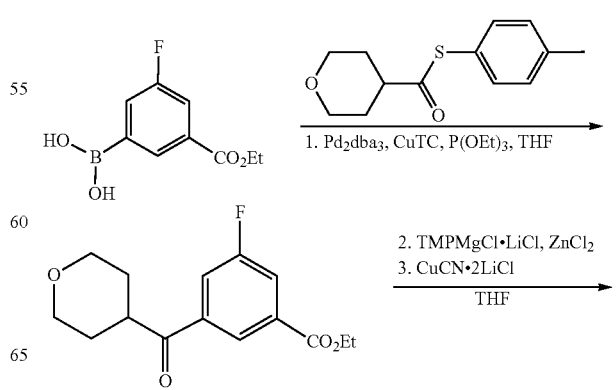

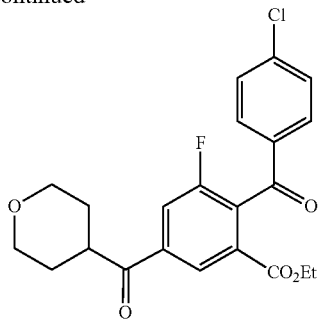

Step 1: 3-Fluoro-5-(tetrahydro-2H-pyran-4-carbonyl)benzoate

A mixture of (3-(ethoxycarbonyl)-5-fluorophenyl)boronic acid (2.00 g, 9.43 mmol) and S-p-tolyl tetrahydro-2H-pyran-4-carbothioate (4.91 g, 20.76 mmol) in THF (47 mL) was evacuated and back-filled with nitrogen (×3). The mixture was then treated with tris(dibenzylideneacetone)dipalladium (O) (0.173 g, 0.189 mmol), ((thiophene-2-carbonyl)oxy) copper (3.96 g, 20.76 mmol) and triethyl phosphite (0.132 ml, 0.755 mmol) and the mixture was evacuated and back-filled with nitrogen (×3). The mixture was stirred at room temperature for 3 days, then diluted with MTBE (20 ml) and filtered through celite. The pad was washed with MTBE (2×50 ml) and the combined filtrates were evaporated. The residue was taken up in MTBE (50 ml), washed with cold 1N aqueous sodium hydroxide solution (2×25 ml) followed by water (2×25 ml) and then brine (25 ml), dried (MgSO$_4$) and evaporated. The residue was purified by chromatography (SiO$_2$, 80 g column, 0-50% MTBE/isohexane) to give a yellow oil (2.618 g, 99%) which was further purified by chromatography (SiO$_2$, 80 g column, 0-25% EtOAc/isohexane) to give ethyl 3-fluoro-5-(tetrahydro-2H-pyran-4-carbonyl)benzoate (2.336 g, 8.21 mmol, 87% yield) as a pale yellow oil. $^1$H NMR (CDCl$_3$) δ: 8.36 (t, 1H), 7.92 (ddd, 1H), 7.82 (ddd, 1H), 4.43 (q, 2H), 4.11-3.99 (m, 2H), 3.58 (ddd, 2H), 3.54-3.45 (m, 1H), 1.94-1.72 (m, 4H), 1.42 (t, 3H). LCMS m/z 281 (M+H)$^+$

Step 2-3: Ethyl 2-(4-chlorobenzoyl)-3-fluoro-5-(tetrahydro-2H-pyran-4-carbonyl)benzoate Zinc chloride (1.362 g, 9.99 mmol) and a stirring bar were placed in a flask, sealed with a septum, evacuated and heated at 140° C. (block) for 3 h. The zinc chloride was allowed to cool, purged with nitrogen and dissolved in THF (10 ml) to give a 1.0 M solution.

A stirred solution of ethyl 3-fluoro-5-(tetrahydro-2H-pyran-4-carbonyl)benzoate (280 mg, 0.999 mmol) in THF (0.5 ml) was treated with zinc chloride (1.0 M in THF) (0.5 mL, 0.500 mmol) and stirred for 10 minutes. The solution was then treated with 2,2,6,6-tetramethylpiperidinemagnesium chloride lithium chloride complex (1.0 M in THF/toluene) (1.1 mL, 1.100 mmol) and stirred at room temperature overnight. The solution was then treated at −40° C. with copper cyanide·2LiCl (1 M solution in THF) (1.1 mL, 1.100 mmol) followed immediately by a solution of 4-chlorobenzoyl chloride (0.154 mL, 1.199 mmol) in THF (0.5 mL) and stirred at room temperature for 3 days. The mixture was quenched with saturated aqueous NaHCO$_3$ (10 ml) and extracted with MTBE (3×10 mL). The combined extracts were washed with brine (10 mL), dried (MgSO$_4$) and evaporated to give a brown oil (526 mg). The oil was purified by chromatography (SiO$_2$, 24 g column, 0-50% MTBE/isohexane) to give ethyl 2-(4-chlorobenzoyl)-3-fluoro-5-(tetrahydro-2H-pyran-4-carbonyl)benzoate (183 mg, 0.415 mmol, 41.6% yield) as a yellow solid. $^1$H NMR (CDCl$_3$, 400 MHz) δ 8.43 (d, 1H), 7.90 (dd, 1H), 7.78-7.69 (m, 2H), 7.48-7.41 (m, 2H), 4.21 (q, 2H), 4.14-4.01 (m, 2H), 3.59 (ddd, 2H), 3.55-3.46 (m, 1H), 1.98-1.78 (m, 4H), 1.17-1.07 (m, 3H). LCMS m/z 419 (M+H)$^+$

Step 4: 2-(4-Chlorobenzoyl)-3-fluoro-5-(tetrahydro-2H-pyran-4-carbonyl)benzoic acid A stirred solution of ethyl 2-(4-chlorobenzoyl)-3-fluoro-5-(tetrahydro-2H-pyran-4-carbonyl)benzoate (100 mg, 0.239 mmol) in THF (1 ml) and methanol (0.5 ml) was treated with a solution of lithium hydroxide (10 mg, 0.418 mmol) in water (0.24 ml) and stirred at room temperature for 3 h. The solution was concentrated to remove most of the organic solvents and the residue was diluted with water (10 ml), washed with methyl t-butyl ether (3×5 ml) and acidified to pH1 with 1N hydrochloric acid. The aqueous layer was extracted with methyl t-butyl ether (3×5 ml) and the combined organic layers were washed with brine (10 ml), dried (MgSO$_4$) and evaporated to give 2-(4-chlorobenzoyl)-3-fluoro-5-(tetrahydro-2H-pyran-4-carbonyl)benzoic acid (97 mg, 0.199 mmol, 83% yield) as a cream solid. $^1$H NMR (CDCl$_3$, 400 MHz) δ 13.92 (s, 1H), 8.36 (d, 1H), 8.28 (dd, 1H), 7.79-7.70 (m, 2H), 7.65-7.60 (m, 2H), 3.94-3.87 (m, 2H), 3.83-3.74 (m, 1H), 3.53 (ddd, 2H), 1.83-1.72 (m, 2H), 1.69-1.53 (m, 2H). LCMS m/z 391 (M+H)$^+$

Synthesis 1a (Allyl Ester)

(2S,3S)-3-(4-Chlorophenyl)-3-[(1R)-1-(4-chlorophenyl)-7-fluoro-5-[(1S)-1-hydroxy-1-(oxan-4-yl)propyl]-1-methoxy-3-oxo-2,3-dihydro-1H-isoindol-2-yl]-2-methylpropanoic acid

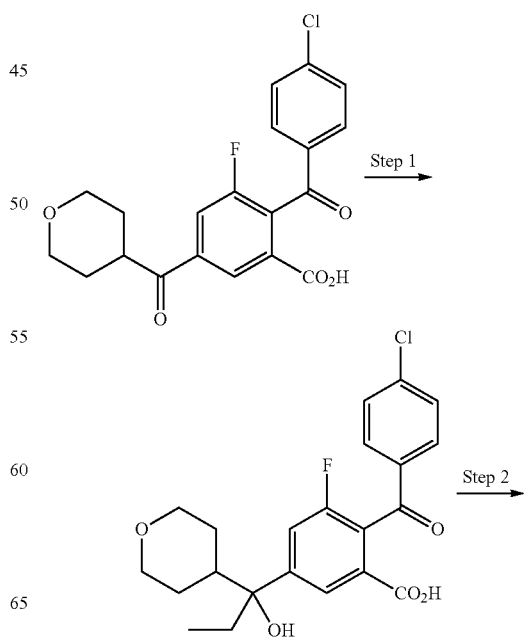

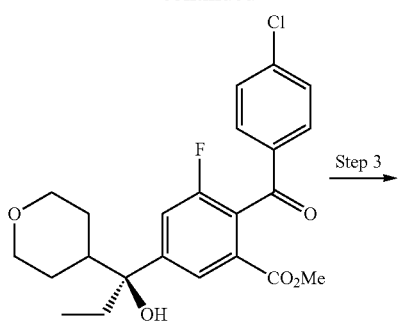

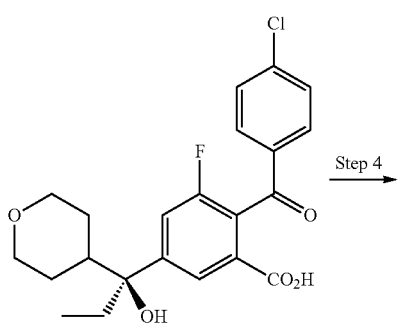

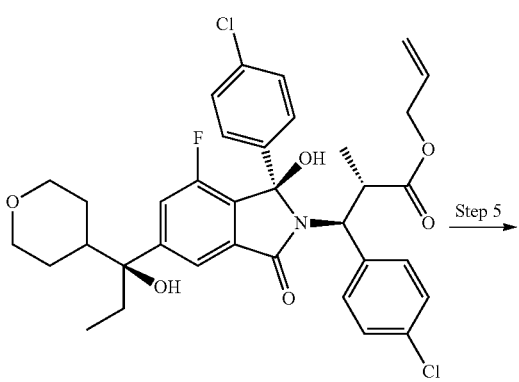

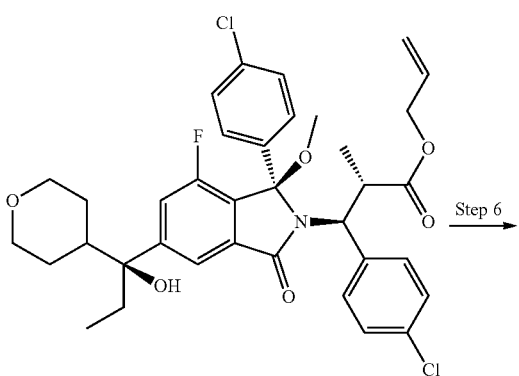

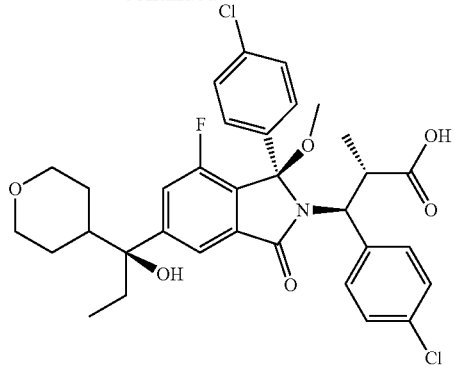

Step 1: 2-(4-Chlorobenzoyl)-3-fluoro-5-(1-hydroxy-1-(tetrahydro-2H-pyran-4-yl)propyl)benzoic acid To 50 mL of THF at −50° C. under nitrogen atmosphere was added diethylzinc (62 mL, 1 M solution in hexanes, 62.0 mmol) and ethyl lithium (36 mL, 1.72 M solution in dibutyl ether, 62.0 mmol). The mixture was stirred at −50° C. for 1 h and then 2-(4-chlorobenzoyl)-3-fluoro-5-(tetrahydro-2H-pyran-4-carbonyl)benzoic acid (9.7 g, 24.0 mmol) was added as a THF (100 mL) solution. The mixture turned dark orange immediately and the internal temperature reached −22° C. The mixture was stirred at −50° C. for 20 min before being quenched by slow addition of 2N HCl (500 mL) (Caution). After stirring for 1 h, the pH was adjusted to 1-2 with 2M HCl and the aqueous was extracted with ethyl acetate (200 mL), washed with 2M HCl (75 mL), dried over magnesium sulfate, filtered and concentrated. The crude product was purified by silica column chromatography (gradient elution 0 to 100% EtOAc in iso-hexane) to give the title compound (9.03 g, 90%) as a colourless foam.

$^1$H NMR (400 MHz, DMSO) 7.89 (1H, s), 7.70 (2H, d), 7.64-7.55 (3H, m), 4.96 (1H, s), 3.91 (1H, dd), 3.79 (1H, dd), 3.30-3.17 (2H, m), 1.92-1.85 (3H, m), 1.69 (1H, d), 1.42-1.28 (2H, m), 1.03 (1H, d), 0.65 (3H, dd) 1 exchangeable proton not observed. MS: [M+H]$^+$=421

Step 2: Methyl (S)-2-(4-chlorobenzoyl)-3-fluoro-5-(1-hydroxy-1-(tetrahydro-2H-pyran-4-yl)propyl)benzoate To a round bottom flask containing crude 2-(4-chlorobenzoyl)-3-fluoro-5-(1-hydroxy-1-(tetrahydro-2H-pyran-4-yl)propyl)benzoic acid (6.32 g, 15 mmol), K$_2$CO$_3$ (2.69 g, 19 mmol) and DMF (50 mL) was added methyl iodide (0.934 mL, 16 mmol). The reaction was stirred for 1.5 h at room temperature, after which point LCMS showed complete conversion to the desired product. The mixture was concentrated under reduced pressure and the residue dissolved in ethyl acetate (150 mL) and washed with water (100 mL), then a 4% aqueous LiCl solution (2×100 mL). The organic layer was dried over magnesium sulfate, filtered and concentrated to give a pale yellow foam. The enantiomers were separated using chiral SFC to give the title compound as a colourless solid.

Methyl (S)-2-(4-chlorobenzoyl)-3-fluoro-5-(1-hydroxy-1-(tetrahydro-2H-pyran-4-yl)propyl)benzoate: Fast running isomer MS: [M+H]$^+$=435. [α]$_D^{20}$=−1.83 (c 1.0, MeOH). $^1$H NMR (400 MHz, CDCl3) 7.84 (1H, d), 7.75-7.72 (2H, m), 7.47-7.42 (3H, m), 4.05 (1H, dd), 3.95 (1H, dd), 3.72 (3H, s), 3.44-3.27 (2H, m), 1.99-1.88 (3H, m), 1.78 (2H, s), 1.55-1.41 (2H, m), 1.18 (1H, d), 0.77 (3H, dd); MS: [M+H]$^+$= 435

Methyl (R)-2-(4-chlorobenzoyl)-3-fluoro-5-(1-hydroxy-1-(tetrahydro-2H-pyran-4-yl)propyl)benzoate: Slow running isomer MS: [M+H]$^+$=435. $[\alpha]_D^{20}$=+1.48 (c 1.0, MeOH).

Step 3: (S)-2-(4-Chlorobenzoyl)-3-fluoro-5-(1-hydroxy-1-(tetrahydro-2H-pyran-4-yl)propyl)benzoic acid Methyl (S)-2-(4-chlorobenzoyl)-3-fluoro-5-(1-hydroxy-1-(tetrahydro-2H-pyran-4-yl)propyl)benzoate (8.2 g, 18.86 mmol) was dissolved in THF (250 mL), methanol (30 mL) and water (50 mL). Anhydrous LiOH (2.26 g, 94.3 mmol) was added and the mixture was stirred at room temperature for 2 h. The resultant solution was concentrated to approximately 60 mL volume, diluted with water (500 mL) and washed with diethyl ether (400 mL). The aqueous layer was then acidified with 2N HCl and extracted with DCM (3×200 mL). Combined extracts were dried (MgSO$_4$) and evaporated to afford the title compound (8.1 g, quant.) as a colourless foam. $^1$H NMR (400 MHz, CDCl$_3$) 7.86 (1H, s), 7.71 (2H, d), 7.49-7.41 (3H, m), 4.05 (1H, dd), 3.98-3.93 (1H, m), 3.43-3.28 (2H, m), 1.97-1.89 (2H, m), 1.77-1.74 (1H, m), 1.52-1.40 (2H, m), 1.20-1.13 (1H, m), 0.75 (3H, dd), OH and COOH not observed. MS: [M−H$^+$]$^-$=419. $[\alpha]_D^{20}$=−2.3 (c 1.0, MeOH).

Step 4: Prop-2-en-1-yl (2S,3S)-3-(4-chlorophenyl)-3-[(1R)-1-(4-chlorophenyl)-7-fluoro-1-hydroxy-5-[(1S)-1-hydroxy-1-(oxan-4-yl)propyl]-3-oxo-2,3-dihydro-1H-isoindol-2-yl]-2-methylpropanoate To a stirred solution of (S)-2-(4-chlorobenzoyl)-3-fluoro-5-(1-hydroxy-1-(tetrahydro-2H-pyran-4-yl)propyl)benzoic acid (1.0 µg, 2.37 mmol), allyl (2S,3S)-3-amino-3-(4-chlorophenyl)-2-methylpropanoate hydrochloride (0.69 g, 2.37 mmol) and DIPEA (1.23 mL, 7.11 mmol) in anhydrous DMF (10 mL) was added HATU (1.35 g, 3.55 mmol) in one portion. After stirring for 3 h, the reaction was diluted with water (100 mL) and 2N HCl (25 mL) added. The mixture was stirred for 10 minutes and the precipitated solid filtered, washed with 0.5M HCl, water and air dried. This solid was dissolved in EtOAc (100 mL), dried with MgSO$_4$ and evaporated to afford a pale cream solid. The crude solid was dissolved in the minimum of DCM (approx. 8 mL in total) and applied to the top of a dry silica cartridge (40 g, Isochim spherical particle cartridge) and was chromatographed eluting with 100% isohexane (2CV's) then 0-100% EtOAc in isohexane gradient over 20CV's. Fractions 5-18 (eluting from approx. 40-60% EtOAc) were pooled and evaporated to afford a colourless foam.

The colourless foam was dissolved in DCM (10 mL), diluted with MeOH (30 mL) and the solution evaporated. Methanol (10 mL) was added to the residue and the mixture evaporated and held under vacuum on the rotary (vac pump) for 10 minutes to afford the title compound as a colourless solid. (1.36 g, 90%) [dr (1R:1S)=24:1*]. $^1$H NMR (400 MHz, CDCl3) 7.70 (1H, s), 7.18 (1H, d), 7.03 (4H, s), 6.96 (4H, s), 5.61-5.50 (1H, m), 5.08-4.99 (2H, m), 4.38 (1H, d), 4.30-4.20 (3H, m), 4.09 (1H, s), 3.93 (1H, dd), 3.61 (1H, dd), 3.35-3.28 (1H, m), 3.15 (1H, dd), 2.03 (1H, s), 1.93-1.68 (4H, m), 1.34-1.22 (5H, m), 0.9 (1H, d), 0.68 (3H, t). MS: [M−H]$^-$=654.

Step 5 [Method 1 Using Me$_3$OBF$_4$]

Prop-2-en-1-yl (2S,3S)-3-(4-chlorophenyl)-3-[(1R)-1-(4-chlorophenyl)-7-fluoro-5-[(1S)-1-hydroxy-1-(oxan-4-yl)propyl]-1-methoxy-3-oxo-2,3-dihydro-1H-isoindol-2-yl]-2-methylpropanoate To an oven dried round bottom flask containing prop-2-en-1-yl (2S,3S)-3-(4-chlorophenyl)-3-[(1R)-1-(4-chlorophenyl)-7-fluoro-1-hydroxy-5-[(1S)-1-hydroxy-1-(oxan-4-yl)propyl]-3-oxo-2,3-dihydro-1H-isoindol-2-yl]-2-methylpropanoate (0.53 g, 0.8 mmol), was added fresh anhydrous DCM at room temperature (15 mL). After stirring the fine white suspension for 5 min at room temperature a freshly prepared solution of proton sponge (0.57 g, 2.6 mmol in 5 mL anhydrous DCM) was added and the reaction mixture stirred for a further 5 min at room temperature (still a very fine white suspension). Fresh Me$_3$OBF$_4$ (0.36 g, 2.4 mmol) was added at once to the white fine suspension at room temperature. After stirring for 6 hours the yellow, heterogeneous, reaction mixture was filtered and the yellow filtrate solution was concentrated under reduced pressure to afford a yellow solid. The crude solid was washed with a mixture of diethyl ether/DCM (25 mL, 9:1) and the pale yellow solid filtered. The filtrate, a pale off-white solution, was concentrated under reduced pressure and the residue was washed with a mixture of iso-hexane/diethyl ether (10 mL, 1:1). The resulting crude product was purified by silica column chromatography (gradient elution 0 to 20% of EtOAc in DCM) to give the desired product as an off-white foam solid (0.225 g, 41%) and desired product contaminated with some proton sponge (0.288 g, 1:1 mixture by LC-MS). The contaminated material was then taken in DCM (1 mL) and loaded onto a 1 g MP-TsOH cartridge (Bioatage) and eluted with one column reservoir volume of DCM, (process repeated twice). The collected fractions were concentrated under reduced pressure to afford pure product as a white foam solid (0.19 g, 35%). The two collected solids were combined and dried on high vacuum to afford the title compound (0.373 g, 70%), [dr (1R:1S)=24:1]*, $^1$H NMR (400 MHz, CDCl3) 7.66 (1H, d), 7.29 (1H, d), 6.94-6.86 (8H, m), 5.60-5.49 (1H, m), 5.06-4.96 (2H, m), 4.34-4.26 (4H, m), 4.03 (1H, dd), 3.91 (1H, dd), 3.42-3.27 (2H, m), 3.24 (3H, s), 1.98-1.87 (3H, m), 1.75 (1H, d), 1.70 (1H, s), 1.50-1.37 (5H, m), 1.08 (1H, d), 0.70 (3H, dd). MS: [M+H]$^+$=670.

Step 5 [Method 2 Using Cs$_2$CO$_3$/MeI]

Prop-2-en-1-yl (2S,3S)-3-(4-chlorophenyl)-3-[(1R)-1-(4-chlorophenyl)-7-fluoro-5-[(1S)-1-hydroxy-1-(oxan-4-yl)propyl]-1-methoxy-3-oxo-2,3-dihydro-1H-isoindol-2-yl]-2-methylpropanoate Prop-2-en-1-yl (2S,3S)-3-(4-chlorophenyl)-3-[1-(4-chlorophenyl)-7-fluoro-1-hydroxy-5-[(1S)-1-hydroxy-1-(oxan-4-yl)propyl]-3-oxo-2,3-dihydro-1H-isoindol-2-yl]-2-methylpropanoate (7.10 g, 10.80 mmol) [dr (1R:1S)=3:1*), Cs$_2$CO$_3$ (7.05 g, 20 mmol) and MeI (0.8 mL, 12.9 mmol) were stirred in 1:1 acetone: dichloromethane (250 ml) for 48 h at RT. The reaction mixture was evaporated to dryness and the residue dissolved in ethyl acetate (500 mL) and washed with water (500 mL). The aqueous layer was back extracted with ethyl acetate (300 mL), the organic extracts combined, dried (MgSO$_4$) and evaporated to afford prop-2-en-1-yl (2S,3S)-3-(4-chlorophenyl)-3-[(1R)-1-(4-chlorophenyl)-7-fluoro-5-[(1S)-1-hydroxy-1-(oxan-4-yl)propyl]-1-methoxy- 3-oxo-2,3-dihydro-1H-isoindol-2-yl]-2-methylpropanoate [dr (1R:1S)=3:1]+ (7.6 g, 100%).

The diastereoisomers can be separated by SFC [(LUX CELLULOSE-4 column, 10/90 MeOH/CO₂, 100 ml/min, 120 bar, 40 C, GLS 40 PSI, SYSTEM 3150 PSI, DROP 100 bar, STACKER, 225 nm, sample prepared as 4400 mg in 300 mL MeOH/CAN (1:1), 500 µl/inj, approx. 7.4 mg/imj, CT 3.9/1.0 min. Total INJ 611) to give the title compound:

Prop-2-en-1-yl (2S,3S)-3-(4-chlorophenyl)-3-[(1R)-1-(4-chlorophenyl)-7-fluoro-5-[(1S)-1-hydroxy-1-(oxan-4-yl)propyl]-1-methoxy-3-oxo-2,3-dihydro-1H-isoindol-2-yl]-2-methylpropanoate As the fast eluting isomer: and Prop-2-en-1-yl (2S,3S)-3-(4-chlorophenyl)-3-[(1S)-1-(4-chlorophenyl)-7-fluoro-5-[(1S)-1-hydroxy-1-(oxan-4-yl)propyl]-1-methoxy-3-oxo-2,3-dihydro-1H-isoindol-2-yl]-2-methylpropanoateS (as the slow eluting isomer: ¹H NMR (400 MHz, CDCl₃) 7.66-7.62 (3H, m), 7.37 (3H, s), 7.34 (1H, s), 7.32-7.29 (1H, m), 7.26 (2H, m, overlapping with CHCl₃), 5.61-5.50 (1H, m), 5.08-4.97 (2H, m), 4.31-4.24 (3H, m), 4.17 (1H, d), 4.03 (1H, dd), 3.90 (1H, dd), 3.41-3.23 (2H, m), 2.33 (3H, s), 1.98-1.87 (3H, m), 1.76 (1H, d), 1.72 (1H, s), 1.50-1.37 (2H, m), 1.05 (1H, d), 0.79-0.69 (6H, m); MS: [M+H]⁺=670

Step 6 (Method 1): (2S,3S)-3-(4-chlorophenyl)-3-[(1R)-1-(4-chlorophenyl)-7-fluoro-5-[(1S)-1-hydroxy-1-(oxan-4-yl)propyl]-1-methoxy-3-oxo-2,3-dihydro-1H-isoindol-2-yl]-2-methylpropanoic acid Prop-2-en-1-yl (2S,3S)-3-(4-chlorophenyl)-3-[(1R)-1-(4-chlorophenyl)-7-fluoro-5-[(1S)-1-hydroxy-1-(oxan-4-yl) propyl]-1-methoxy-3-oxo-2,3-dihydro-1H-isoindol-2-yl]-2-methylpropanoate (0.35 g, 0.52 mmol; from Step 5, method 1), Pd(PPh₃)₄ (0.060 g, 0.05 mmol) and K₂CO₃ (0.14 g, 1.05 mmol) were stirred in methanol (10 mL) for 1.5 h at RT. The reaction mixture was concentrated to 5 mL then diluted with 5% aq. citric acid (75 mL). The precipitated solid was extracted with ethyl acetate (3×50 mL). The organic layers were combined, dried (MgSO₄) and evaporated to afford a white solid. Crude material was purified by silica chromatography using 0-100% ethyl acetate: iso-hexane gradient to give product. (0.19 g, 58%).

This material was dissolved in 5 mL of diethyl ether and a few drops of iso-hexane was added to give a turbid solution. The flask was stoppered and the solution left to stand for 18 h. The resulting crystals were filtered and washed with 1:1 diethyl ether: iso-hexane to yield the title compound as a white solid (0.164 g, 49%). 1H NMR (400 MHz, DMSO-d₆): 12.56-12.00 (1H, m), 7.71 (1H, s), 7.42 (1H, d), 7.02 (4H, d), 6.88 (3H, d), 4.91 (1H, s), 4.23 (1H, d), 3.99-3.85 (2H, m), 3.75 (1H, dd), 3.25-3.10 (5H, m), 2.02-1.90 (1H, m), 1.90-1.78 (2H, m), 1.67 (1H, d), 1.43-1.17 (6H, m), 0.95 (1H, d), 0.58 (3H, t). MS: m/z=630 [M+H]⁺. MS: m/z=628 [M−H⁺]⁻

Step 6 (Method 2): (2S,3S)-3-(4-Chlorophenyl)-3-[(1R)-1-(4-chlorophenyl)-7-fluoro-5-[(1S)-1-hydroxy-1-(oxan-4-yl)propyl]-1-methoxy-3-oxo-2,3-dihydro-1H-isoindol-2-yl]-2-methylpropanoic acid Starting from the product from Step 5 (method 2), and using procedures similar to those described in Step 6 (Method 1), (2S,3S)-3-(4-chlorophenyl)-3-[1-(4-chlorophenyl)-7-fluoro-5-[(1S)-1-hydroxy-1-(oxan-4-yl)propyl]-1-methoxy-3-oxo-2,3-dihydro-1H-isoindol-2-yl]-2-methyl-propanoic acid was obtained as a white solid [dr (1R:1S)= 3:1]. 300 mg of this material was purified by SFC using a Lux C2 (21.2 mm×250 nn, 5 um) column and eluting with 32:68 MeOH:CO₂ (0.1% v/v NH₃) to give the title compound (175 mg).

The title compound can also be differentiated form the other epimer (at the isoindolinone 1-position) using chiral HPLC:

Analysis was performed on a Shimadzu Prominence HPLC-UV using a Chiralpak IA column (250×4.6 mm, 5µ), maintained at 27° C. The mobile phase consisted of 85:15 Heptane:IPA+0.1% Trifluoroacetic Acid, run isocratically for 25 minutes at 1 mL/min, and UV detection was performed at a wavelength of 254 nm.

(2S,3S)-3-(4-Chlorophenyl)-3-[(1R)-1-(4-chlorophenyl)-7-fluoro-5-[(1S)-1-hydroxy-1-(oxan-4-yl)propyl]-1-methoxy-3-oxo-2,3-dihydro-1H-isoindol-2-yl]-2-methylpropanoic acid (title compound) [retention time=9.85].

(2S,3S)-3-(4-Chlorophenyl)-3-[(1S)-1-(4-chlorophenyl)-7-fluoro-5-[(1S)-1-hydroxy-1-(oxan-4-yl)propyl]-1-methoxy-3-oxo-2,3-dihydro-1H-isoindol-2-yl]-2-methylpropanoic acid (retention time=8.0)

Synthesis 1b (SEM Ester)

(2S,3S)-3-(4-Chlorophenyl)-3-[(1R)-1-(4-chlorophenyl)-7-fluoro-5-[(1S)-1-hydroxy-1-(oxan-4-yl)propyl]-1-methoxy-3-oxo-2,3-dihydro-1H-isoindol-2-yl]-2-methylpropanoic acid

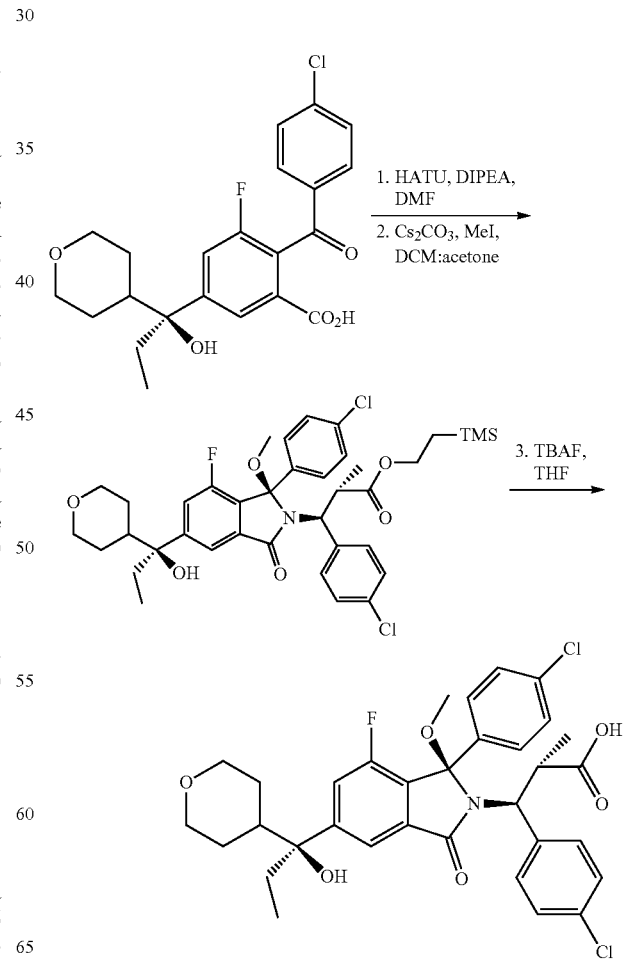

Step 1: 2-(Trimethylsilyl)ethyl (2S,3S)-3-(4-chlorophenyl)-3-[(1R)-(4-chlorophenyl)-7-fluoro-1-hydroxy-5-[(1S)-1-hydroxy-1-(oxan-4-yl)propyl]-3-oxo-2,3-dihydro-1H-isoindol-2-yl]-2-methylpropanoate HATU (0.095 g, 0.249 mmol) was added to a mixture of (S)-2-(4-chlorobenzoyl)-3-fluoro-5-(1-hydroxy-1-(tetrahydro-2H-pyran-4-yl)propyl)benzoic acid (0.1 g, 0.238 mmol), 2-(trimethylsilyl)ethyl (2S,3S)-3-amino-3-(4-chlorophenyl)-2-methylpropanoate (0.093 g, 0.297 mmol) and DIPEA (0.083 ml, 0.475 mmol) in DMF (1 mL) and the mixture was stirred for 3 h. Sat. NH$_4$Cl was added and the crude product extracted with EtOAc. The combined organic extracts were washed with water, NaHCO$_3$, brine, dried (MgSO$_4$) and concentrated to afford the title compound [dr (1R:1S)=3:1)$^+$ (0.17 g) as a pale yellow sticky glass/foam. The product was used without further purification in the next step.

Step 2: 2-(Trimethylsilyl)ethyl (2S,3S)-3-(4-chlorophenyl)-3-[(1R)-1-(4-chlorophenyl)-7-fluoro-5-[(1S)-1-hydroxy-1-(oxan-4-yl)propyl]-1-methoxy-3-oxo-2,3-dihydro-1H-isoindol-2-yl]-2-methylpropanoate Iodomethane (0.016 ml, 0.261 mmol) was added to a suspension 2-(trimethylsilyl)ethyl (2S,3S)-3-(4-chlorophenyl)-3-[1-(4-chlorophenyl)-7-fluoro-1-hydroxy-5-[(1S)-1-hydroxy-1-(oxan-4-yl)propyl]-3-oxo-2,3-dihydro-1H-isoindol-2-yl]-2-methylpropanoate [dr (1R:1S)=3:1)$^+$ (0.17 g, 0.237 mmol) and cesium carbonate (0.155 g, 0.474 mmol) in 1:1 acetone:DCM (0.75 mL) and the mixture was stirred overnight. Further iodomethane (4.45 µl, 0.071 mmol) was added and the mixture stirred for 5 h. Saturated NH$_4$Cl was added and the crude product was extracted with DCM. The combined organic extracts were washed with brine, dried (MgSO$_4$) and absorbed on silica. The crude product was purified by chromatography (SiO$_2$, 24 g column, 0-50% EtOAc/isohexane) to afford 2-(trimethylsilyl)ethyl (2S,3S)-3-(4-chlorophenyl)-3-[(1R)-1-(4-chlorophenyl)-7-fluoro-5-[(1S)-1-hydroxy-1-(oxan-4-yl)propyl]-1-methoxy-3-oxo-2,3-dihydro-1H-isoindol-2-yl]-2-methylpropanoate (0.057 g, 0.074 mmol, 31.2% yield). 1H NMR (Chloroform-d) δ: 7.73 (d, 1H), 7.38-7.34 (m, 1H), 6.99 (m (br), 8H), 4.42-4.27 (m, 2H), 4.09 (td, 1H), 4.02-3.82 (m, 3H), 3.44 (ddd, 1H), 3.38 (ddd, 1H), 3.30 (s, 3H), 1.98 (dq, 1H), 1.89-1.74 (m, 1H), 1.50 (ddd, 2H), 1.44 (d, 3H), 1.20-1.12 (m, 1H), 0.78 (q, 3H), 0.72-0.61 (m, 2H), −0.00 (s, 9H). LCMS [M+Na$^+$]: 752/754/756

Step 3: (2S,3S)-3-(4-Chlorophenyl)-3-[(1R)-1-(4-chlorophenyl)-7-fluoro-5-[(1S)-1-hydroxy-1-(oxan-4-yl)propyl]-1-methoxy-3-oxo-2,3-dihydro-1H-isoindol-2-yl]-2-methylpropanoic acid TBAF (0.082 ml, 0.082 mmol) was added to a solution of 2-(trimethylsilyl)ethyl (2S,3S)-3-(4-chlorophenyl)-3-[(1R)-1-(4-chlorophenyl)-7-fluoro-5-[(1S)-1-hydroxy-1-(oxan-4-yl)propyl]-1-methoxy-3-oxo-2,3-dihydro-1H-isoindol-2-yl]-2-methylpropanoate (0.050 g, 0.068 mmol) in THF (0.684 ml, 0.068 mmol) and the mixture was stirred at room temperature for 16 h. A second portion of TBAF (0.082 ml, 0.082 mmol) was added and reaction stirred for further 16 h. The reaction was concentrated under reduced pressure and the residue diluted with EtOAc (10 mL), then transferred into a separating funnel. Saturated NH$_4$Cl (10 mL) was added and the phase separated. The organic layer was washed with water (10 mL), brine (10 mL), dried (MgSO$_4$), filtered and concentrated under reduced pressure. The crude product was purified by chromatography (SiO$_2$, 12 g column, 0-10% MeOH/DCM) to afford a white solid. The solid was dissolved in EtOAc and washed with saturated NH$_4$Cl (3×20 mL). The organic layer was then washed with brine, dried (MgSO$_4$) and concentrated under vacuum to afford the title compound (0.028 g, 0.044 mmol, 63.6% yield) as a white solid.

Alternative End to Synthesis 1b (2S,3S)-3-(4-Chlorophenyl)-3-[(1R)-1-(4-chlorophenyl)-7-fluoro-5-[(1S)-1-hydroxy-1-(oxan-4-yl)propyl]-1-methoxy-3-oxo-2,3-dihydro-1H-isoindol-2-yl]-2-methylpropanoic acid

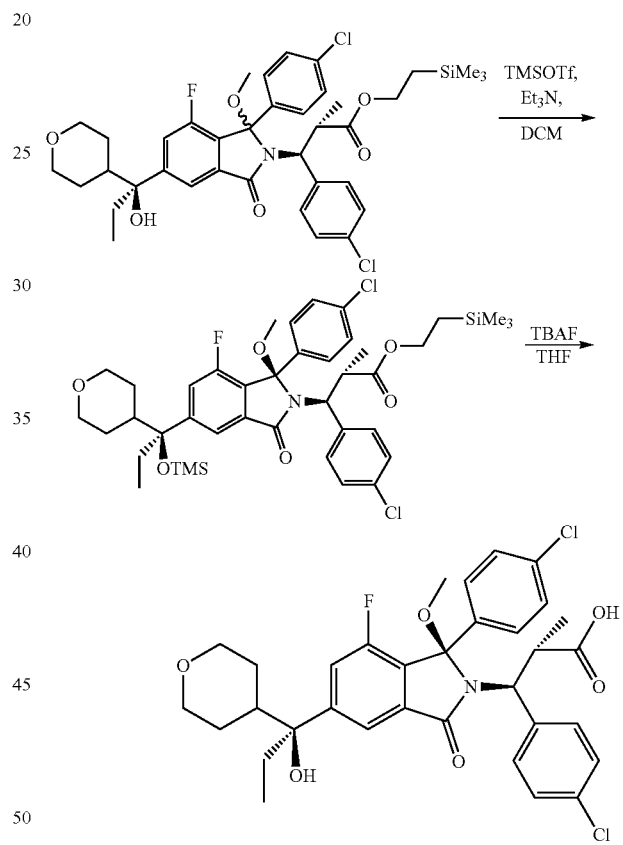

Step 1: 2-(Trimethylsilyl)ethyl (2S,3S)-3-(4-chlorophenyl)-3-[(1R)-1-(4-chlorophenyl)-7-fluoro-1-methoxy-5-[(1S)-1-(oxan-4-yl)-1-[(trimethylsilyl)oxy]propyl]-3-oxo-2,3-dihydro-1H-isoindol-2-yl]-2-methylpropanoate Trimethylsilyl trifluoromethanesulfonate (0.179 ml, 0.992 mmol) was added dropwise to a solution of 2-(trimethylsilyl)ethyl (2S,3S)-3-(4-chlorophenyl)-3-[1-(4-chlorophenyl)-7-fluoro-5-[(1S)-1-hydroxy-1-(oxan-4-yl)propyl]-1-methoxy-3-oxo-2,3-dihydro-1H-isoindol-2-yl]-2-methylpropanoate [dr (1R:1S)=3:1] (0.29 g, 0.397 mmol) in DCM (3 mL) under nitrogen at 0° C. and the mixture was stirred for 1.2 h. Saturated NaHCO$_3$ was added at 0° C. and the crude product was extracted with DCM. The combined organic extracts were washed with brine, dried (MgSO₄) and absorbed on silica. The crude product was purified by chromatography (SiO₂, 12 g column, 0-10% EtOAc/isohexane) to afford a 2-(trimethylsilyl)ethyl (2S,3S)-3-(4-chlorophenyl)-3-[1-(4-chlorophenyl)-7-fluoro-1-methoxy-5-[(1S)-1-(oxan-4-yl)-1-[(trimethylsilyl)oxy]propyl]-3-oxo-2,3-dihydro-1H-isoindol-2-yl]-2-methylpropanoate [dr (1R:1S)-3:1] as a white solid. 1 mL of EtOH was added to 100 mg of this mixture to give a solution. The solution was concentrated shortly under vacuum during which a precipitate formed. ~0.5 mL of EtOH was added giving a very thick suspension. Further ~0.5 mL EtOH were added and the suspension was heated with heat gun until dissolution. A precipitate appeared quickly and suspension was left to stir for 45 minutes. The precipitate was filtered through a phase separating cartridge, washed with EtOH and air-dried. The solid was taken up in DCM and the solution concentrated under vacuum to afford 2-(trimethylsilyl)ethyl (2S,3S)-3-(4-chlorophenyl)-3-[(1R)-1-(4-chlorophenyl)-7-fluoro-1-methoxy-5-[(1S)-1-(oxan-4-yl)-1-[(trimethylsilyl)oxy]propyl]-3-oxo-2,3-dihydro-1H-isoindol-2-yl]-2-methylpropanoate (0.059 g, 0.072 mmol, 58.5% yield) as a white solid. LCMS [M+Na]⁺: 824/826/828

Step 2: (2S,3S)-3-(4-chlorophenyl)-3-[(1R)-1-(4-chlorophenyl)-7-fluoro-5-[(1S)-1-hydroxy-1-(oxan-4-yl)propyl]-1-methoxy-3-oxo-2,3-dihydro-1H-isoindol-2-yl]-2-methylpropanoic acid TBAF (1M in THF) (0.156 ml, 0.156 mmol) was added to a solution of 2-(trimethylsilyl)ethyl (2S,3S)-3-(4-chlorophenyl)-3-[(1R)-1-(4-chlorophenyl)-7-fluoro-1-methoxy-5-[(1S)-1-(oxan-4-yl)-1-[(trimethylsilyl)oxy]propyl]-3-oxo-2,3-dihydro-1H-isoindol-2-yl]-2-methylpropanoate (0.05 g, 0.062 mmol) in THF (0.3 mL) and the mixture was stirred overnight. Sat. NH₄Cl was added and the crude product extracted with EtOAc. The combined organic extracts were washed with water, 1 N HCl, water, brine, dried (MgSO₄) and concentrated under vacuum to afford (2S,3S)-3-(4-chlorophenyl)-3-[(1R)-1-(4-chlorophenyl)-7-fluoro-5-[(1S)-1-hydroxy-1-(oxan-4-yl)propyl]-1-methoxy-3-oxo-2,3-dihydro-1H-isoindol-2-yl]-2-methylpropanoic acid (0.037 g, 0.053 mmol, 85% yield) as a white solid.

Synthesis 1c (Phenyl Ester)

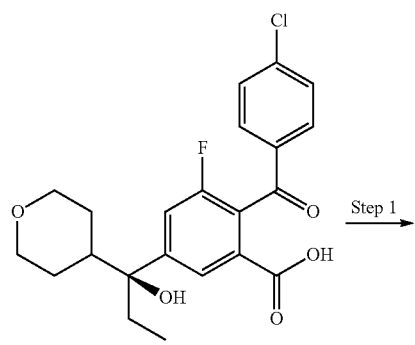

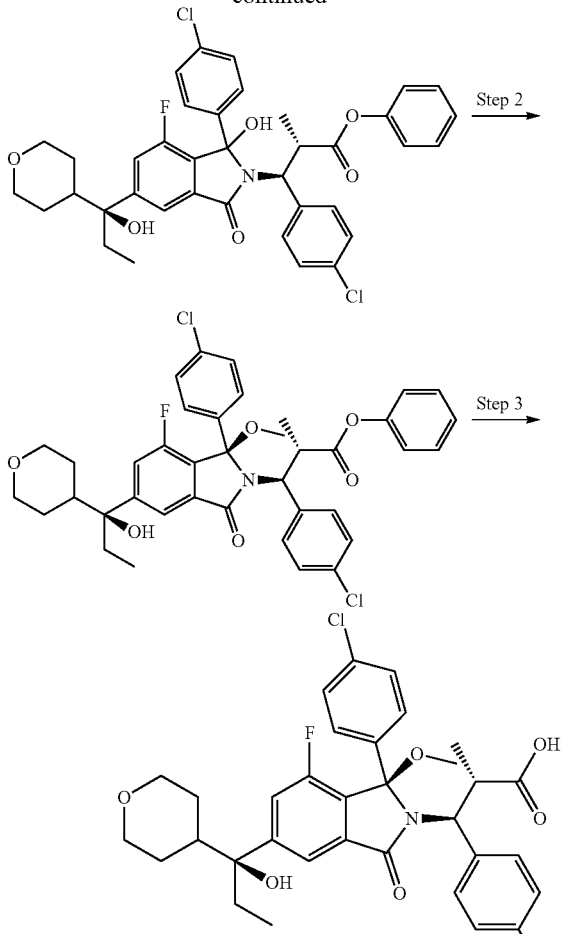

Step 1: Phenyl (2S,3S)-3-(4-chlorophenyl)-3-[(1R)-1-(4-chlorophenyl)-7-fluoro-1-hydroxy-5-[(1S)-1-hydroxy-1-(oxan-4-yl)propyl]-3-oxo-2,3-dihydro-1H-isoindol-2-yl]-2-methylpropanoate To a stirred solution of (S)-2-(4-chlorobenzoyl)-3-fluoro-5-(1-hydroxy-1-(tetrahydro-2H-pyran-4-yl)propyl)benzoic acid (0.649 g, 1.54 mmol), phenyl (2S,3S)-3-amino-3-(4-chlorophenyl)-2-methylpropanoate hydrochloride (0.5 g, 1.54 mmol) and DIPEA (0.805 mL, 4.62 mmol) in anhydrous DMF (10 mL) at room temperature was added HATU (0.875 g, 2.30 mmol) in one portion. The reaction was stirred at room temperature for 1.5 h. The reaction was diluted with water and 2N HCl added. The resulting solid for was filtered and air dried. This solid was dissolved in the minimum of DCM and applied to the top of a dry silica cartridge (80 g) and was chromatographed eluting with 0%-90% EtOAc in isohexane gradient. Fractions containing product were pooled and evaporated to afford a colourless solid. The colourless foam was dissolved in DCM/MeOH and the solution evaporated. Methanol (10 mL) was added to the residue and the mixture evaporated and held under vacuum on the rotary (vac pump) for 10 minutes to afford the title compound [dr (1R:1S)=3:1] as a cream solid. (0.752 g, 71%). ¹H NMR (400 MHz, CDCl3) 7.74-7.69 (2H, m), 7.38 (1H, dd), 7.29 (1H, dd), 7.26-7.21 (1H, m, overlapping with CHCl3), 7.18-7.11 (2H, m), 7.06-7.03 (6H, m), 6.58-6.53

(2H, m), 4.58-4.44 (2H, m), 3.96-3.76 (1H, m), 3.47 (3H, d), 3.34-3.07 (2H, m), 2.09-1.65 (5H, m), 1.47 (2H, d), 1.06-0.78 (3H, m), 0.70 (3H, dd).

Step 2: Phenyl (2S,3S)-3-(4-chlorophenyl)-3-[(1R)-1-(4-chlorophenyl)-7-fluoro-5-[(1S)-1-hydroxy-1-(oxan-4-yl)propyl]-1-methoxy-3-oxo-2,3-dihydro-1H-isoindol-2-yl]-2-methylpropanoate To a round bottom flask was added freshly opened anhydrous DCM (10 mL) and 1,8-bis(dimethylamino)naphthalene (proton sponge) (0.69 g, 3.26 mmol) and the mixture was stirred until dissolved. Then was added the product from Step 1 (0.75 g, 1.09 mmol) and trimethyloxonium tetrafluoroborate (0.483 g, 3.26 mmol). The mixture was stirred for 18 h at RT. The mixture was diluted with DCM (40 mL) and water (40 mL), layers shaken and separated, and aqueous back extracted with DCM (3×50 mL). Organics were pooled, washed with water (100 mL), brine (100 mL), dried over MgSO$_4$ and concentrated under reduced pressure. The resulting crude residue was triturated with diethyl ether (50 mL) and filtered. Filtrate was concentrated and purified by silica chromatography (gradient elution 0 to 100% ethyl acetate in iso-hexane). Fractions containing product were combined and concentrated to give the title compound as an off-pink foam (0.385 g) [dr (1R:1S)=2:1]. Purification by SFC gave phenyl (2S,3S)-3-(4-chlorophenyl)-3-[(1R)-1-(4-chlorophenyl)-7-fluoro-5-[(1S)-1-hydroxy-1-(oxan-4-yl)propyl]-1-methoxy-3-oxo-2,3-dihydro-1H-isoindol-2-yl]-2-methylpropanoate (0.096 g, 12%) (as the slower eluting isomer). MS:[M+H]$^+$=706.3, 708.3

Step 3: (2S,3S)-3-(4-Chlorophenyl)-3-[(1R)-1-(4-chlorophenyl)-7-fluoro-5-[(1S)-1-hydroxy-1-(oxan-4-yl)propyl]-1-methoxy-3-oxo-2,3-dihydro-1H-isoindol-2-yl]-2-methylpropanoic acid To a stirred solution of phenyl (2S,3S)-3-(4-chlorophenyl)-3-[(1R)-1-(4-chlorophenyl)-7-fluoro-5-[(1S)-1-hydroxy-1-(oxan-4-yl)propyl]-1-methoxy-3-oxo-2,3-dihydro-1H-isoindol-2-yl]-2-methylpropanoate (slower running isomer, 50 mg, 0.071 mmol) in THF (2 mL) and water (1 mL) at room temperature was added LiOH·H$_2$O (20 mg) in one portion and the mixture stirred for 16 h. The reaction mixture was concentrated under reduced pressure. The resulting residue was diluted with water (2 mL), washed with diethyl ether (2 mL) and ethyl acetate (3 mL) was added. The mixture was acidified with 2M HCl and back extracted with ethyl acetate (3×3 mL). Organics were pooled, washed with brine (2×3 mL), dried over MgSO$_4$ and concentrated under reduced pressure to afford the title compound as a crude off-white solid (0.044 g).

Synthesis 2a (Allyl Ester)

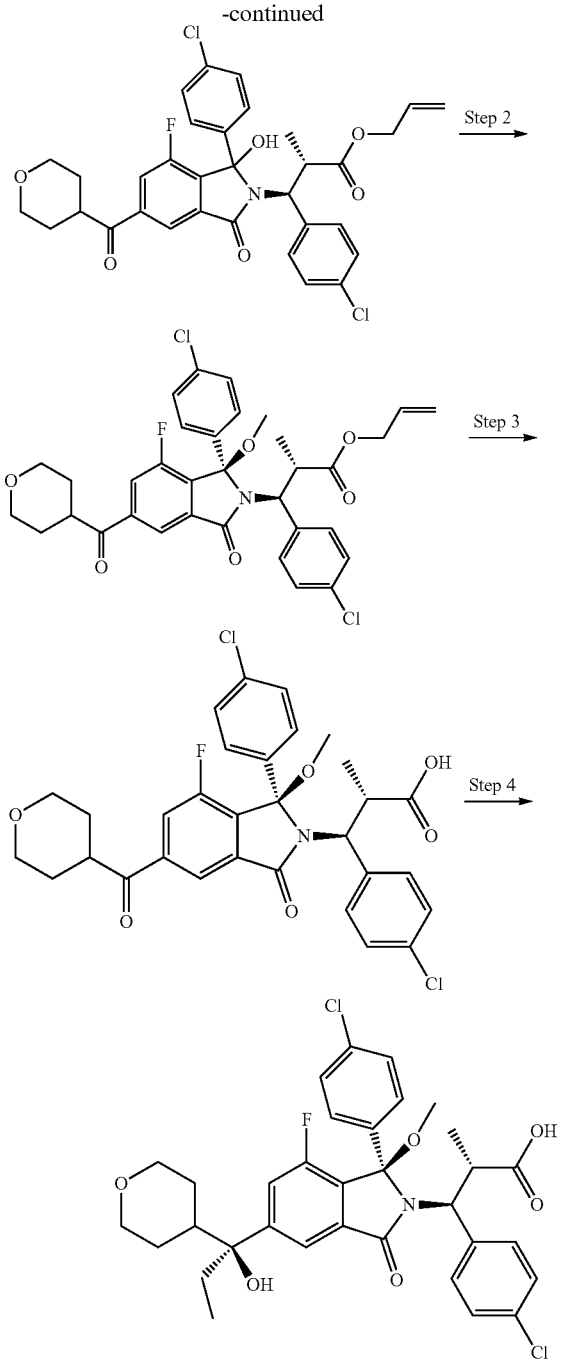

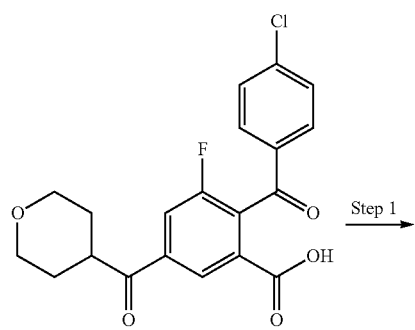

Step 1: Prop-2-en-1-yl (2S,3S)-3-(4-chlorophenyl)-3-[1-(4-chlorophenyl)-7-fluoro-1-hydroxy-5-(oxane-4-carbonyl)-3-oxo-2,3-dihydro-1H-isoindol-2-yl]-2-methylpropanoate To a stirred solution of 2-(4-chlorobenzoyl)-3-fluoro-5-(tetrahydro-2H-pyran-4-carbonyl)benzoic acid (18.53 g; 47.4 mmol), allyl (2S,3S)-3-amino-3-(4-chlorophenyl)-2-methylpropanoate hydrochloride (13.73 g; 47.5 mmol) and DIPEA (36.6 mL; 211 mmol) in anhydrous DCM (500 mL) at room temperature was added HATU (27 g; 71 mmol) in one portion. The reaction was stirred at room temperature for 2 h, washed with 1 N HCl (500 mL), a 2:1 saturated NaHCO$_3$: brine mixture (500 mL), dried (MgSO$_4$) and evaporated. The residue was chromatographed on silica (330 g) eluting with 0-100% EtOAc in isohexane gradient over 15 column volumes to afford the title compound as a mixture of diastereoisomers (30.9 g). MS: [M+H]$^+$=626. This was used in the next step without further purification.

Step 2: Prop-2-en-1-yl (2S,3S)-3-(4-chlorophenyl)-3-[(1R)-1-(4-chlorophenyl)-7-fluoro-1-methoxy-5-(oxane-4-carbonyl)-3-oxo-2,3-dihydro-1H-isoindol-2-yl]-2-methylpropanoate Iodomethane (3.54 mL; 56.9 mmol) was added to a stirred mixture of the crude prop-2-en-1-yl (2S,3S)-3-(4-chlorophenyl)-3-[1-(4-chlorophenyl)-7-fluoro-1-hydroxy-5-(oxane-4-carbonyl)-3-oxo-2,3-dihydro-1H-isoindol-2-yl]-2-methylpropanoate derived from step 1 (30.9 g) and anhydrous cesium carbonate (33.6 g; 94.8 mmol) in 1:1 acetone:DCM (1000 mL) and the mixture stirred at room temperature for 18 h. The reaction was concentrated and the residue partitioned between EtOAc (1000 mL) and water (1000 mL). The layers were separated and the aqueous extracted with EtOAc (1000 mL). Pooled organics were washed with water (750 mL), dried (MgSO$_4$) and evaporated to afford the title compound as a mixture of diastereoisomers as a pale orange foam (28.7 g, 94.7% over 2 steps). This was separated using chiral SFC to afford:—
Fast running isomer: (2S,3S)-3-(4-chlorophenyl)-3-[(1S)-1-(4-chlorophenyl)-7-fluoro-1-methoxy-5-(oxane-4-carbonyl)-3-oxo-2,3-dihydro-1H-isoindol-2-yl]-2-methylpropanoate (6.6 g; 21.7%) $^1$H NMR (400 MHz, CDCl3) 8.20 (1H, s), 7.79 (1H, d), 7.63 (2H, d), 7.42-7.35 (4H, m), 7.27 (2H, d), 5.61-5.50 (1H, m), 5.09-4.97 (2H, m), 4.28-4.25 (3H, m), 4.18 (1H, d), 4.11-4.04 (2H, m), 3.62-3.48 (3H, m), 2.35 (3H, s), 1.95-1.79 (4H, m), 0.78 (3H, d).
Slow Running Isomer:
prop-2-en-1-yl (2S,3S)-3-(4-chlorophenyl)-3-[(1R)-1-(4-chlorophenyl)-7-fluoro-1-methoxy-5-(oxane-4-carbonyl)-3-oxo-2,3-dihydro-1H-isoindol-2-yl]-2-methylpropanoate (14.22 g; 46.9%). $^1$H NMR (400 MHz, CDCl3) 8.23 (1H, d), 7.77 (1H, dd), 6.92 (8H, s), 5.60-5.49 (1H, m), 5.07-4.96 (2H, m), 4.34-4.27 (4H, m), 4.11-4.04 (2H, m), 3.61-3.48 (3H, m), 3.27 (3H, s), 1.94-1.76 (4H, m), 1.40 (3H, dd). MS: [M+H]$^+$=640.2. [α]$_D^{20}$=+71.57 (c 1.0, MeOH).
The slow running isomer was used in the following steps.

Step 3: (2S,3S)-3-(4-Chlorophenyl)-3-[(1R)-1-(4-chlorophenyl)-7-fluoro-1-methoxy-5-(oxane-4-carbonyl)-3-oxo-2,3-dihydro-1H-isoindol-2-yl]-2-methylpropanoic acid To a stirred solution of prop-2-en-1-yl (2S,3S)-3-(4-chlorophenyl)-3-[(1R)-1-(4-chlorophenyl)-7-fluoro-1-methoxy-5-(oxane-4-carbonyl)-3-oxo-2,3-dihydro-1H-isoindol-2-yl]-2-methylpropanoate (30.5 g, 47.65 mmol) in anhydrous MeOH (1500 mL) at room temperature under nitrogen was added K$_2$CO$_3$ (13.22 g, 95.6 mmol) followed by Pd(PPh$_3$)$_4$ (5.5 g, 4.76 mmol). After stirring for 1.5 h, the reaction was concentrated to approximately 50 mL and 5% citric acid (1000 mL) added. The mixture was extracted with EtOAc (3×500 mL) and the pooled extracts dried (MgSO$_4$) and evaporated. Chromatography on SiO$_2$ (330 g) eluting with 0-20% acetone in DCM gradient over 15 CV's afforded the title compound as a pale orange solid which contained approximately 10 mol % of triphenylphosphine oxide. (27.8 g). $^1$H NMR (400 MHz, CDCl3) 8.23 (1H, d), 7.77 (1H, d), 6.90 (8H, s), 4.28 (2H, dd), 4.10-4.03 (2H, m), 3.61-3.47 (3H, m), 3.26 (3H, s), 1.95-1.78 (4H, m), 1.40 (3H, d). Exchangeable proton not observed.

Step 4: (2S,3S)-3-(4-chlorophenyl)-3-[(1R)-1-(4-chlorophenyl)-7-fluoro-5-[(1S)-1-hydroxy-1-(oxan-4-yl)propyl]-1-methoxy-3-oxo-2,3-dihydro-1H-isoindol-2-yl]-2-methylpropanoic acid This reaction was run in duplicate on the same scale. A 1.65M solution of ethyllithium in di-n-butylether (35.1 mL, 58 mmol) was added over 1 minute to a solution of 1M diethylzinc in hexanes (58 mL) in anhydrous THF (58 mL) at −50° C. under nitrogen and the mixture stirred at −50° C. under nitrogen for a further 1 h. A solution of (2S,3S)-3-(4-chlorophenyl)-3-[(1R)-1-(4-chlorophenyl)-7-fluoro-1-methoxy-5-(oxane-4-carbonyl)-3-oxo-2,3-dihydro-1H-isoindol-2-yl]-2-methylpropanoic acid (13.9 g, 23.2 mmol) in anhydrous THF (100 mL) was added in a rapid stream over 30-45 seconds. On complete addition the reaction was stirred in a −50° C. cooling bath for 10 minutes then carefully quenched with 1N HCl (150 mL) and allowed to reach room temperature. The mixture was extracted with EtOAc (2×750 mL) and the pooled extracts from both reactions dried (MgSO$_4$) and evaporated to afford a pale orange foam (32 g). This material was combined with 8 g of material prepared in an identical manner and chromatographed on SiO$_2$ (330 g) eluting with 0-20% acetone in DCM gradient over 15 CV's to afford the title compound, as a mixture of diastereoisomers as a pale yellow foam (33 g). Purification by chiral SFC [YMC AMYLOSE-C column, 20/80 EtOH/CO$_2$, 100 mL/min, 120 bar, 40 C, GLS 40 PSI, SYSTEM 3750PSI, DROP 131 bar, STACKER, 230 nm). The title compound was isolated as the faster eluting isomer (13.8 g). This material was dissolved in diethyl ether (30 mL) and left to stand at room temperature for 18 h. The resulting solid was isolated by decanting the mother liquors and washing the solid with 1:1 diethyl ether: isohexane. The solid was then dissolved in 200 mL methanol: dichloromethane (1:2) and filtered through a short pad of cotton wool. The solvent was removed by evaporation to afford the title compound as a white solid (9.36 g, 25%).

The title compound can be differentiated from the other epimer by using analytical HPLC: This was performed on a Shimadzu Prominence HPLC-UV using a Chiralpak IA column (250×4.6 mm, 5p), maintained at 27° C. The mobile phase consisted of 70:30 Heptane:Ethanol+0.1% Trifluoroacetic Acid, run isocratically for 25 minutes at 1 mL/min, and UV detection was performed at a wavelength of 254 nm.
(2S,3S)-3-(4-chlorophenyl)-3-[(1R)-1-(4-chlorophenyl)-7-fluoro-5-[(1S)-1-hydroxy-1-(oxan-4-yl)propyl]-1-methoxy-3-oxo-2,3-dihydro-1H-isoindol-2-yl]-2-methylpropanoic acid (title compound) [retention time=6.45 minutes].
(2S,3S)-3-(4-chlorophenyl)-3-[(1R)-1-(4-chlorophenyl)-7-fluoro-5-[(1R)-1-hydroxy-1-(oxan-4-yl)propyl]-1-methoxy-3-oxo-2,3-dihydro-1H-isoindol-2-yl]-2-methylpropanoic acid (retention time=9.06 minutes)
(2S,3S)-3-(4-chlorophenyl)-3-[(1R)-1-(4-chlorophenyl)-7-fluoro-5-[(1S)-1-hydroxy-1-(oxan-4-yl)propyl]-1-methoxy-3-oxo-2,3-dihydro-1H-isoindol-2-yl]-2-methylpropanoic acid (9.36 g) was dissolved in anhydrous MeOH (300 mL) and tris(hydroxymethyl)aminomethane (1.8 g; 1 equivalent) added. The mixture was agitated until all solid had dissolved then evaporated under reduced pressure to afford the title compound as the Tris salt (11.3 g). 1H NMR (500 MHz, DMSO-d6) δ 7.69 (s, 1H), 7.39 (d, J=10.7 Hz, 1H), 7.01 (broad s, 4H), 6.96-6.88 (m, 4H), 4.92 (broad s, 1H), 4.34-4.22 (m, 1H), 3.88 (dd, J=10.9, 4.2 Hz, 1H), 3.74 (dd, J=11.1, 4.2 Hz, 1H), 3.71-3.61 (m, 1H), 3.29 (s, 6H), 3.33-3.22 (m, 1H), 3.21-3.14 (m, 1H), 3.13 (s, 3H), 1.94 (tt, J=12.2, 3.6 Hz, 1H), 1.89-1.78 (m, 2H), 1.66 (d, J=12.8 Hz, 1H), 1.41-1.24 (m, 2H), 1.19 (d, J=6.8 Hz, 3H), 0.93 (d, J=13.2 Hz, 1H), 0.57 (t, J=7.3 Hz, 3H). MS:[M+H]+=630.

Synthesis 2b (SEM Ester)

2-(Trimethylsilyl)ethyl (2S,3S)-3-(4-chlorophenyl)-3-[(1R)-1-(4-chlorophenyl)-7-fluoro-1-hydroxy-5-(oxane-4-carbonyl)-3-oxo-2,3-dihydro-1H-isoindol-2-yl]-2-methylpropanoate

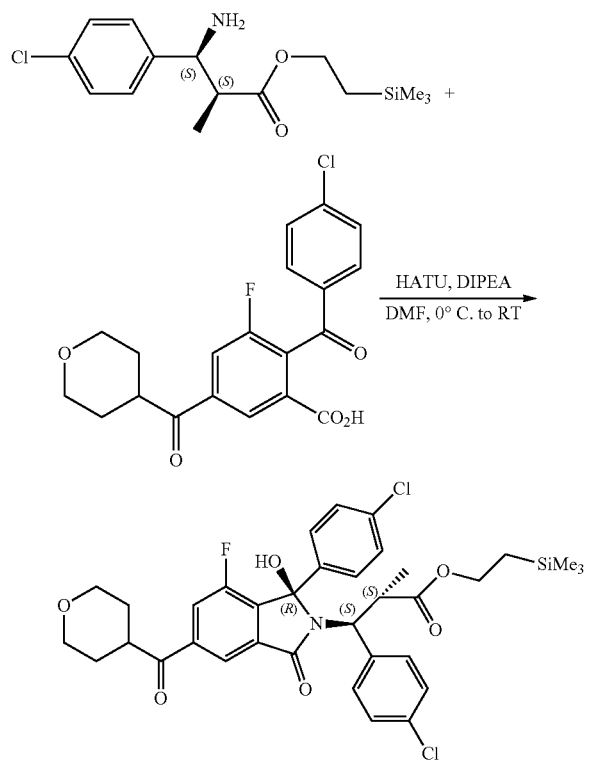

HATU (10.22 g, 26.9 mmol) was added portion-wise to a stirred solution of 2-(trimethylsilyl)ethyl (2S,3S)-3-amino-3-(4-chlorophenyl)-2-methylpropanoate (10.15 g, 30.7 mmol), 2-(4-chlorobenzoyl)-3-fluoro-5-(tetrahydro-2H-pyran-4-carbonyl)benzoic acid (10.0 g, 25.6 mmol) and DIPEA (8.94 ml, 51.2 mmol) in DMF (130 mL) at RT. The mixture was stirred at RT for 3.5 h. The reaction mixture was diluted with water (200 mL) and extracted with EtOAc (200 mL). The organic phase was washed with brine (3×200 mL), dried (MgSO4), filtered and concentrated in vacuo to give the title compound (19.99 g, 23.29 mmol, 91% yield) [dr (1R:1S)=2.5:1] as a foamy pale yellow solid. ¹H NMR (CDCl₃, 400 MHz) δ 8.17-8.07 (1H, m), 7.78-7.68 (1H, m), 7.60 (1H, d), 7.43-7.35 (2H, m), 7.22 (1H, d), 7.09-7.01 (2H, m), 7.00-6.93 (2H, m), 4.38 (1H, d), 4.21-4.05 (2H, m), 4.05-3.95 (2H, m), 3.94-3.77 (2H, m), 3.64-3.40 (3H, m), 1.89-1.63 (4H, m), 1.28 (3H, d, major ds), 0.77 (3H, d, minor ds), 0.70-0.53 (2H, m), −0.06 (9H, s). m/z 708.2 (M+Na)+

2-(Trimethylsilyl)ethyl (2S,3S)-3-(4-chlorophenyl)-3-[(1R)-1-(4-chlorophenyl)-7-fluoro-1-methoxy-5-(oxane-4-carbonyl)-3-oxo-2,3-dihydro-1H-isoindol-2-yl]-2-methylpropanoate

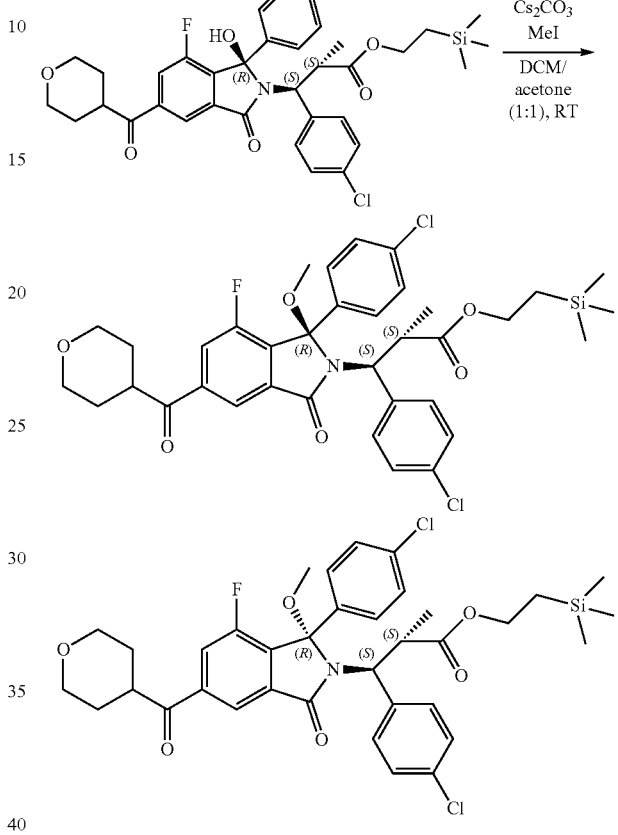

Methyl iodide (1.202 ml, 19.22 mmol) was added to a stirred suspension of 2-(trimethylsilyl)ethyl (2S,3S)-3-(4-chlorophenyl)-3-[(1R)-1-(4-chlorophenyl)-7-fluoro-1-hydroxy-5-(oxane-4-carbonyl)-3-oxo-2,3-dihydro-1H-isoindol-2-yl]-2-methylpropanoate (15 g, 17.48 mmol)) [dr (1R:1S)=2.5:1] and Cs₂CO₃ (11.39 g, 35.0 mmol) in acetone (90 mL) and DCM (90 mL). The mixture was stirred at RT for 18 h. The mixture was washed with sat. NH₄Cl (aq.) (200 mL). The aqueous phase was extracted with DCM (2×200 mL). The combined organic phases were washed with 1 M HCl (aq.) (400 mL) and brine (400 mL), dried (MgSO₄), filtered and concentrated in vacuo to give the crude product as a pale orange foamy solid (15.3 g). The crude product was purified by chromatography (SiO₂, 330 g column, 5-40% EtOAc/isohexane) to afford the title compound (9.678 g, 13.54 mmol, 77% yield) [dr (1R:1S~3:1) as a pale yellow solid. m/z 639.9 (M-MeOH-2×Me)+ (ES+);

5.1 g of the product was purified by chiral SFC to give:
The major diastereoisomer, 2-(trimethylsilyl)ethyl (2S,3S)-3-(4-chlorophenyl)-3-[(1R)-1-(4-chlorophenyl)-7-fluoro-1-methoxy-5-(oxane-4-carbonyl)-3-oxo-2,3-dihydro-1H-isoindol-2-yl]-2-methylpropanoate (3.295 g, 4.66 mmol, 64.0% yield) as an off-white solid. ¹H NMR (CDCl₃, 400 MHz) δ 8.23 (1H, d), 7.76 (1H, dd), 7.05-6.78 (8H, br m), 4.31 (1H, d), 4.28-4.20 (1H, m), 4.13-4.02 (2H, m), 3.92-3.77 (2H, m), 3.63-3.52 (2H, m), 3.53-3.46 (1H, m), 3.27 (3H, s), 1.97-1.73 (4H, m), 1.37 (3H, d), 0.70-0.52 (2H, m), −0.07 (9H, s). m/z 721.8 (M+Na)⁺

The minor diastereoisomer, 2-(trimethylsilyl)ethyl (2S,3S)-3-(4-chlorophenyl)-3-[(1S)-1-(4-chlorophenyl)-7-fluoro-1-methoxy-5-(oxane-4-carbonyl)-3-oxo-2,3-dihydro-1H-isoindol-2-yl]-2-methylpropanoate (1.219 g, 1.722 mmol, 23.66% yield) as an off-white solid. ¹H NMR (CDCl₃, 400 MHz) δ 8.20 (1H, d), 7.78 (1H, dd), 7.66-7.59 (2H, m), 7.45-7.30 (4H, br m), 7.30-7.22 (2H, m), 4.26-4.12 (2H, m), 4.12-4.02 (2H, m), 3.91-3.75 (2H, m), 3.66-3.43 (3H, m), 2.34 (3H, s), 1.98-1.74 (4H, m), 0.76 (3H, d), 0.68-0.53 (2H, m), −0.07 (9H, s).

Alternatively 2-(trimethylsilyl)ethyl (2S,3S)-3-(4-chlorophenyl)-3-[1-(4-chlorophenyl)-7-fluoro-1-methoxy-5-(oxane-4-carbonyl)-3-oxo-2,3-dihydro-1H-isoindol-2-yl]-2-methylpropanoate (4.35 g, 6.21 mmol) [dr (1R:1S~3:1] was suspended in EtOH (150 mL) and stirred at 50° C. for 1.5 h. The solid was filtered, washed with EtOH (2×25 mL) and dried to give 2-(trimethylsilyl)ethyl (2S,3S)-3-(4-chlorophenyl)-3-[(1R)-1-(4-chlorophenyl)-7-fluoro-1-methoxy-5-(oxane-4-carbonyl)-3-oxo-2,3-dihydro-1H-isoindol-2-yl]-2-methylpropanoate (2.186 g, 3.06 mmol, 49.2% yield) as an off white solid.

The mother liquor was part concentrated in vacuo to ~20 mL when more solid started to crash out. This mixture was heated to reflux and more EtOH added until the entire solid had dissolved (~20-30 mL). The mixture was allowed to cool to RT overnight, resulting in the crystallisation of a white solid. The solid was filtered, washed with EtOH (2×10 mL) and dried to give a second crop of give 2-(trimethylsilyl)ethyl (2S,3S)-3-(4-chlorophenyl)-3-[(1R)-1-(4-chlorophenyl)-7-fluoro-1-methoxy-5-(oxane-4-carbonyl)-3-oxo-2,3-dihydro-1H-isoindol-2-yl]-2-methylpropanoate (0.429 g, 0.600 mmol, 9.66% yield) as a pale yellow solid. m/z 721.8 (M+Na)⁺

(2S,3S)-3-(4-chlorophenyl)-3-[(1R)-1-(4-chlorophenyl)-7-fluoro-1-methoxy-5-(oxane-4-carbonyl)-3-oxo-2,3-dihydro-1H-isoindol-2-yl]-2-methylpropanoic acid

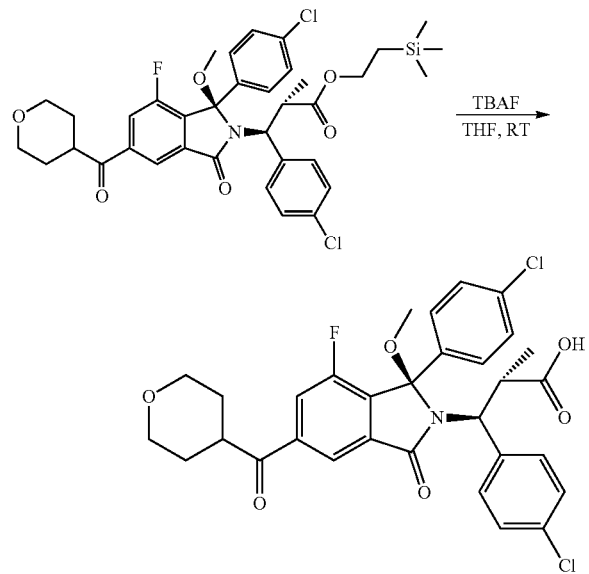

TBAF (1.0 M in THF) (5.52 ml, 5.52 mmol) was added to a stirred solution of (2S,3S)-2-(trimethylsilyl)ethyl (2S,3S)-3-(4-chlorophenyl)-3-[(1R)-1-(4-chlorophenyl)-7-fluoro-1-methoxy-5-(oxane-4-carbonyl)-3-oxo-2,3-dihydro-1H-isoindol-2-yl]-2-methylpropanoate (3.224 g, 4.60 mmol) in THF (46 mL). The mixture was stirred at RT for 20 h. A further portion of TBAF (1.0 M in THF) (0.920 ml, 0.920 mmol) was added and the mixture was stirred at RT for a further 72 h. The solvent was removed in vacuo and the residue re-dissolved in EtOAc (100 mL) and washed with sat. NH₄Cl (aq.) (4×75 mL), water (75 mL) and brine (75 mL). The organic phase was dried (MgSO₄), filtered and concentrated in vacuo to give a foamy pale yellow solid (3.183 g).

The crude product was re-dissolved in EtOAc (100 mL) and washed with 1 M HCl (aq.) (3×100 mL) and water (100 mL). The organic phase was dried (MgSO₄), filtered and concentrated in vacuo to give (2S,3S)-3-(4-chlorophenyl)-3-[(1R)-1-(4-chlorophenyl)-7-fluoro-1-methoxy-5-(oxane-4-carbonyl)-3-oxo-2,3-dihydro-1H-isoindol-2-yl]-2-methylpropanoic acid (2.941 g, 4.31 mmol, 94% yield) as a pale yellow solid. ¹H NMR (DMSO-d6, 400 MHz) δ 12.28 (1H, s), 8.27 (1H, d), 8.03 (1H, dd), 7.25-6.95 (4H, m), 6.96-6.73 (4H, m), 4.24 (1H, d), 3.99-3.93 (1H, m), 3.89 (2H, ddd), 3.86-3.76 (1H, m), 3.59-3.46 (2H, m), 3.22 (3H, s), 1.79-1.67 (2H, m), 1.67-1.50 (2H, m), 1.30 (3H, d). m/z 599.9 (M+H)⁺

(2S,3S)-3-(4-Chlorophenyl)-3-[(1R)-1-(4-chlorophenyl)-7-fluoro-5-[(1S)-1-hydroxy-1-(oxan-4-yl)propyl]-1-methoxy-3-oxo-2,3-dihydro-1H-isoindol-2-yl]-2-methylpropanoic acid

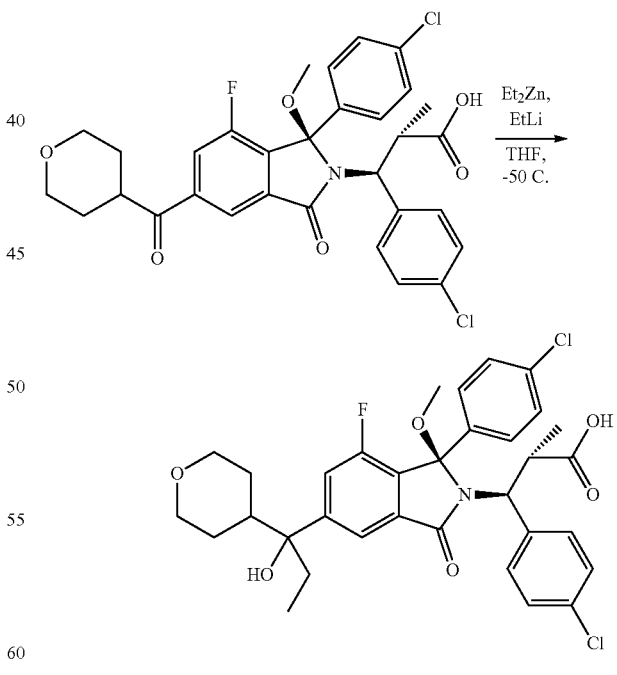

A three-neck flask fitted with a thermometer and under nitrogen was charged with THF (40 mL) and cooled to −50° C. (dry ice/acetone). Et₂Zn (1.0 M in hexanes) (5.62 ml, 5.62 mmol) was added followed by EtLi (8 wt % in dibutyl ether) (3.33 ml, 5.62 mmol) drop-wise. The mixture was stirred at −50° C. for 45 min before (2S,3S)-3-(4-chlorophenyl)-3-

[(1R)-1-(4-chlorophenyl)-7-fluoro-1-methoxy-5-(oxane-4-carbonyl)-3-oxo-2,3-dihydro-1H-isoindol-2-yl]-2-methylpropanoic acid (1.5 g, 2.248 mmol) in THF (20 mL) was added drop-wise. The mixture was stirred at −50° C. for 2 h. The reaction was quenched carefully with sat. NH$_4$Cl (30 mL) and allowed to warm to RT. The mixture was acidified to pH ~1-2 with 1 M HCl (aq.) and extracted with EtOAc (2×100 mL). The combined organic extracts were washed with brine (200 mL), dried (MgSO$_4$), filtered and concentrated in vacuo to give a yellow gummy solid (2.1 g). The crude product was purified by chromatography (SiO$_2$, 80 g column, 0-5% MeOH/DCM) to afford (2S,3S)-3-(4-chlorophenyl)-3-[1-(4-chlorophenyl)-7-fluoro-5-[1-hydroxy-1-(oxan-4-yl)propyl]-1-methoxy-3-oxo-2,3-dihydro-1H-isoindol-2-yl]-2-methylpropanoic acid (1.212 g, 1.903 mmol, 85% yield) as an off white solid. (1:1 mixture of epimers at the tertiary alcohol).

$^1$H NMR (DMSO-d6, 400 MHz) δ 12.24 (1H, br s), 7.71 (1H, s), 7.41 (1H, dd), 7.21-6.94 (4H, br m), 6.94-6.83 (4H, br m), 4.92 (1H, br s), 4.21 (1H, d), 3.95 (1H, dd), 3.92-3.84 (1H, m), 3.79-3.69 (1H, m), 3.27-3.19 (1H, m), 3.19-3.10 (4H, m), 2.02-1.78 (3H, m), 1.76-1.56 (1H, m), 1.45-1.22 (2H, m), 1.28 (3H, d), 1.01-0.86 (1H, m), 0.63-0.51 (3H, m). m/z 630.0 (M+H)$^+$ 1.1 g diastereomer mixture was separated by chiral SFC [AmyC (20 mm×250 mm, 5 um) column using the following conditions: Column Temperature 40° C.; Flow Rate 50 mL/min; BPR 125 BarG; Detector Wavelength 210 nm; Injection Volume 200 uL (10 mg); Isocratic Conditions 20:80 MeOH:CO$_2$ (0.1% v/v TFA)] to afford (2S,3S)-3-(4-chlorophenyl)-3-[(1R)-1-(4-chlorophenyl)-7-fluoro-5-[(1S)-1-hydroxy-1-(oxan-4-yl)propyl]-1-methoxy-3-oxo-2,3-dihydro-1H-isoindol-2-yl]-2-methylpropanoic acid (491 mg, 0.740 mmol, 42.8% yield)

Alternatively, EtLi/Et$_2$Zn can be Reacted with 2-(trimethylsilyl)ethyl (2S,3S)-3-(4-chlorophenyl)-3-[(1R)-1-(4-chlorophenyl)-7-fluoro-5-[1-hydroxy-1-(oxan-4-yl)propyl]-1-methoxy-3-oxo-2,3-dihydro-1H-isoindol-2-yl]-2-methylpropanoate

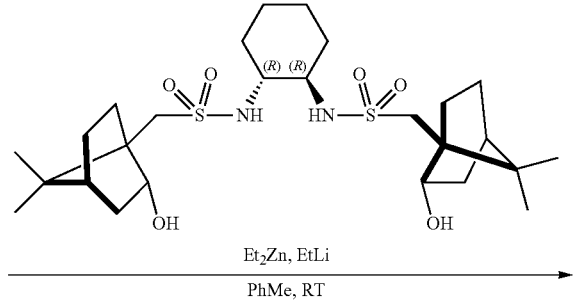

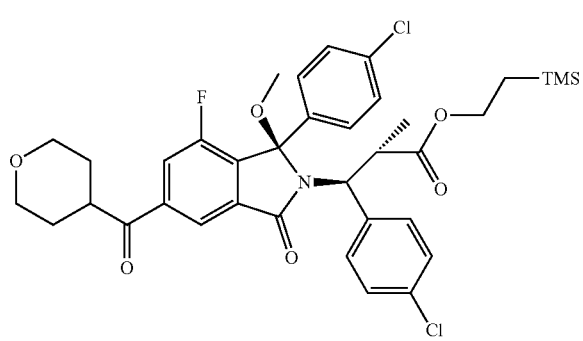

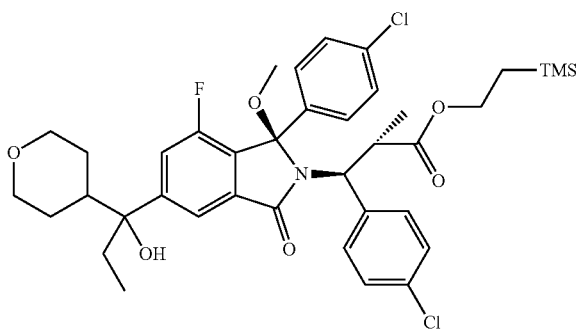

Et$_2$Zn (1.0 M in hexanes) (1.070 mL, 1.070 mmol) and EtLi (8 wt % in dibutyl ether) (0.634 mL, 1.070 mmol) were added to a stirred solution of 1-((2R,4R)-2-hydroxy-7,7-dimethylbicyclo[2.2.1]heptan-1-yl)-N-((1R,2R)-2-(((2S)-2-hydroxy-7,7-dimethylbicyclo[2.2.1]heptan-1-yl)methyl-sulfonamido)cyclohexyl)methanesulfonamide (23.40 mg, 0.043 mmol) in PhMe (1.5 mL). The mixture was stirred at RT for 15 min, 2-(trimethylsilyl)ethyl (2S,3S)-3-(4-chlorophenyl)-3-[(1R)-1-(4-chlorophenyl)-7-fluoro-1-methoxy-5-(oxane-4-carbonyl)-3-oxo-2,3-dihydro-1H-isoindol-2-yl]-2-methylpropanoate (300 mg, 0.428 mmol) was added in PhMe (9.0 mL) The mixture was stirred at RT for 3 h. The reaction mixture was quenched with sat. NH$_4$Cl (aq.) (15 mL), diluted with water (20 mL) and extracted with EtOAc (2×30 mL). The combined organic phases were washed with brine (50 mL), dried (MgSO$_4$), filtered and concentrated in vacuo to give the crude product as a yellow oil/gum (~350 mg). The crude product was purified by chromatography (SiO$_2$, 80 g column, 40 g column, 0-30% EtOAc/PhMe) to afford 2-(trimethylsilyl)ethyl (2S,3S)-3-(4-chlorophenyl)-3-[(1R)-1-(4-chlorophenyl)-7-fluoro-5-[1-hydroxy-1-(oxan-4-yl)propyl]-1-methoxy-3-oxo-2,3-dihydro-1H-isoindol-2-yl]-2-methylpropanoate (230 mg, 0.290 mmol, 67.7% yield; 1:1 mixture of diastereoisomers) as a pale yellow foamy solid.

$^1$H NMR (CDCl3, 400 MHz) δ 7.68-7.61 (1H, m), 7.33-7.27 (1H, m), 7.00-6.66 (8H, br m), 4.33-4.19 (2H, m), 4.08-3.99 (1H, m), 3.98-3.74 (3H, m), 3.47-3.26 (2H, m), 3.24 (3H, s, diastereomer a), 3.23 (3H, s, diastereomer b), 2.00-1.84 (3H, m), 1.80-1.64 (2H, m), 1.51-1.39 (2H, m), 1.37 (3H, d), 1.13-1.04 (1H, m), 0.75-0.66 (3H, m), 0.65-0.55 (2H, m), −0.07 (9H, s). m/z 752.2 (M+Na)$^+$ The diastereoisomeric mixture (219 mg) was separated by SFC [Lux C4 (21.2 mm×250 mm, 5 um) column using the following conditions: Column Temperature 40° C.; Flow Rate 50 mL/min; BPR 125 BarG; Detector Wavelength 210 nm; Injection Volume 400 uL (9 mg); Isocratic Conditions 20:80 MeOH:CO$_2$)] to the give the desired isomer 2-(trimethylsilyl)ethyl (2S,3S)-3-(4-chlorophenyl)-3-[(1R)-1-(4-chlorophenyl)-7-fluoro-5-[(1S)-1-hydroxy-1-(oxan-4-yl)propyl]-1-methoxy-3-oxo-2,3-dihydro-1H-isoindol-2-yl]-2-methylpropanoate (95 mg, 0.127 mmol, 29.8% yield) as an off white solid. $^1$H NMR (CDCl$_3$, 400 MHz) δ 7.66 (1H, d), 7.29 (1H, dd), 7.08-6.64 (8H, br m), 4.33-4.19 (2H, m), 4.03 (1H, dd), 3.97-3.75 (3H, m), 3.45-3.26 (2H, m), 3.23 (3H, s), 2.01-1.84 (3H, m), 1.74 (1H, d), 1.70 (1H, s), 1.50-1.39 (2H, m), 1.37 (3H, d), 1.14-1.03 (1H, m), 0.70 (3H, t), 0.64-0.54 (2H, m), −0.07 (9H, s).

And 2-(trimethylsilyl)ethyl (2S,3S)-3-(4-chlorophenyl)-3-[(1R)-1-(4-chlorophenyl)-7-fluoro-5-[(1R)-1-hydroxy-1-(oxan-4-yl)propyl]-1-methoxy-3-oxo-2,3-dihydro-1H-isoindol-2-yl]-2-methylpropanoate (98 mg, 0.131 mmol, 30.7% yield) as a white solid. $^1$H NMR (CDCl$_3$, 400 MHz) δ 1H NMR (CDCl3, 400 MHz) δ 7.65 (1H, d), 7.29 (1H, dd), 7.07-6.62 (8H, br m), 4.38-4.17 (2H, m), 4.04 (1H, dd), 3.96-3.75 (3H, m), 3.46-3.26 (2H, m), 3.24 (3H, s), 2.00-1.85 (3H, m), 1.82-1.71 (1H, m), 1.68 (1H, s), 1.51-1.39 (2H, m), 1.37 (3H, d), 1.17-1.01 (1H, m), 0.70 (3H, t), 0.60 (2H, ddd), −0.07 (9H, s).

The two isomers can also be characterised by analytical chiral SFC [Lux C4 (4.6 mm×250 mm, 5 um) column using the following conditions: Column Temperature 40° C.; Flow Rate 4 mL/min; Detector Wavelength 210-400 nm; Injection Volume 1.0 uL; BPR 125 BarG; Isocratic Conditions 15:85 MeOH:CO$_2$]:

2-(trimethylsilyl)ethyl (2S,3S)-3-(4-chlorophenyl)-3-[(1R)-1-(4-chlorophenyl)-7-fluoro-5-[(1S)-1-hydroxy-1-(oxan-4-yl)propyl]-1-methoxy-3-oxo-2,3-dihydro-1H-isoindol-2-yl]-2-methylpropanoate (retention time=3.09 min)

2-(trimethylsilyl)ethyl (2S,3S)-3-(4-chlorophenyl)-3-[(1R)-1-(4-chlorophenyl)-7-fluoro-5-[(1R)-1-hydroxy-1-(oxan-4-yl)propyl]-1-methoxy-3-oxo-2,3-dihydro-1H-isoindol-2-yl]-2-methylpropanoate (retention time=3.63 min)

2-(trimethylsilyl)ethyl (2S,3S)-3-(4-chlorophenyl)-3-[(1R)-1-(4-chlorophenyl)-7-fluoro-5-[(1S)-1-hydroxy-1-(oxan-4-yl)propyl]-1-methoxy-3-oxo-2,3-dihydro-1H-isoindol-2-yl]-2-methylpropanoate can then be deprotected to give (2S,3S)-3-(4-chlorophenyl)-3-[(1R)-1-(4-chlorophenyl)-7-fluoro-5-[(1S)-1-hydroxy-1-(oxan-4-yl)propyl]-1-methoxy-3-oxo-2,3-dihydro-1H-isoindol-2-yl]-2-methylpropanoic acid using procedures similar to those for, described above.

Synthesis 3a (Epoxide)

2-(Trimethylsilyl)ethyl (2S,3S)-3-(4-chlorophenyl)-3-[(1R)-1-(4-chlorophenyl)-7-fluoro-1-methoxy-5-[1-(oxan-4-yl)ethenyl]-3-oxo-2,3-dihydro-1H-isoindol-2-yl]-2-methylpropanoate Route A:

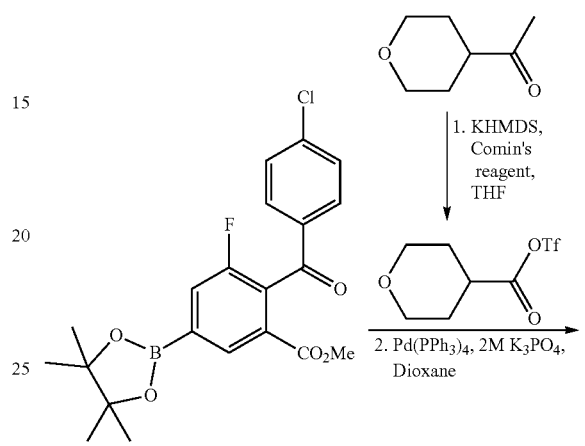

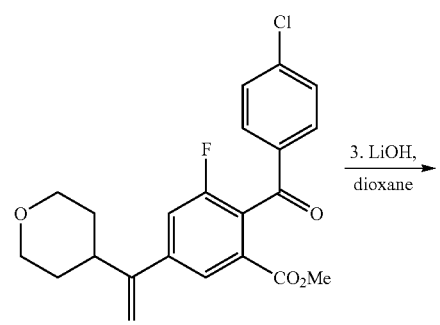

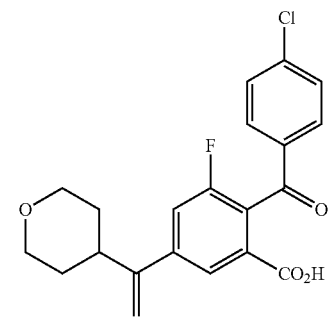

-continued

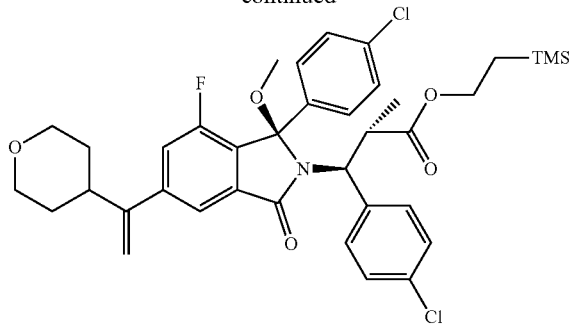

Step 1: 1-(Tetrahydro-2H-pyran-4-yl)vinyl trifluoromethanesulfonate

KHMDS (1M in THF) (39.0 mL, 39.0 mmol) was added to THF (150 mL) at −78° C. under nitrogen. A solution of 1-(tetrahydro-2H-pyran-4-yl)ethanone (5 g, 39.0 mmol) in THF (20 mL) was added and the mixture was stirred at −78° C. under nitrogen for 1.5 h, giving a pale yellow solution. A solution of N-(5-chloropyridin-2-yl)-1,1,1-trifluoro-N-((trifluoromethyl)sulfonyl)methanesulfonamide (15.32 g, 39.0 mmol) in THF (25 mL) was added over 20 minutes and the resulting orange, then colourless mixture was allowed to warm slowly to room temperature and stirred overnight. The reaction was quenched with NaHCO$_3$ and the crude product extracted with MTBE (300 mL). The combined organic extracts were washed with brine, dried (MgSO$_4$) and concentrated under vacuum. The residue was dissolved in a small amount of 10% EtOAc:Isohexane and loaded on a 40 g column. The crude product was purified by chromatography (SiO$_2$, 40 g column, 0-10% EtOAc/isohexane). Fractions containing product were combined, filtered, washing with 10% EtOAc:Isohexane, then concentrated. A solid formed in the residue, which was then taken up in 10% EtOAc:Isohexane, filtered through cotton wool. The filtrate was then loaded on a 40 g column and the crude product was purified by chromatography (SiO$_2$, 40 g column, 0-10% EtOAc/isohexane) to afford 1-(tetrahydro-2H-pyran-4-yl) vinyl trifluoromethanesulfonate (6.17 g, 20.15 mmol, 51.7% yield) as a colourless oil. $^1$H NMR (CDCl$_3$) δ: 5.14 (dd, 1H), 4.94 (dd, 1H), 4.06-3.98 (m, 2H), 3.41 (td, 2H), 2.54-2.41 (m, 1H), 1.89-1.79 (m, 2H), 1.66-1.50 (m, 2H).

Step 2: Methyl 2-(4-chlorobenzoyl)-3-fluoro-5-(1-(tetrahydro-2H-pyran-4-yl)vinyl)benzoate Pd(PPh$_3$)$_4$ (0.552 g, 0.478 mmol) was added to a degassed mixture of methyl 2-(4-chlorobenzoyl)-3-fluoro-5-(4,4,5,5-tetramethyl-1,3,2-dioxaborolan-2-yl)benzoate (4 g, 9.55 mmol), 1-(tetrahydro-2H-pyran-4-yl)vinyl trifluoromethanesulfonate (3.66 g, 11.94 mmol) and 2M K$_3$PO$_4$ (9.55 ml, 19.11 mmol) in dioxane (45 mL) and the mixture was purged and put under nitrogen atmosphere. The mixture was then stirred at 90° C. for 1.5 h and allowed to cool to room temperature. The mixture was diluted with EtOAc and filtered through Celite, washing with EtOAc and water. The crude product was extracted with EtOAc and the combined organic extracts were washed with brine, dried (MgSO$_4$) and absorbed on silica. The crude product was purified by chromatography (SiO$_2$, 80 g column, 0-20% EtOAc/isohexane) to afford methyl 2-(4-chlorobenzoyl)-3-fluoro-5-(1-(tetrahydro-2H-pyran-4-yl)vinyl)benzoate (2.79 g, 6.86 mmol, 71.8% yield) as a white solid. LCMS: [M+H]$^+$: 403/405

Step 3: 2-(4-Chlorobenzoyl)-3-fluoro-5-(1-(tetrahydro-2H-pyran-4-yl)vinyl)benzoic acid 1N LiOH (4.96 ml, 4.96 mmol) was added to a solution of methyl 2-(4-chlorobenzoyl)-3-fluoro-5-(1-(tetrahydro-2H-pyran-4-yl)vinyl)benzoate (1 g, 2.482 mmol) in dioxane (20 mL) and the resulting suspension was stirred for 3.5 h. The mixture was diluted with 1N HCl and water and the crude product extracted with EtOAc. The combined organic extracts were washed with brine, dried (MgSO$_4$) and concentrated under vacuum to afford 2-(4-chlorobenzoyl)-3-fluoro-5-(1-(tetrahydro-2H-pyran-4-yl)vinyl)benzoic acid (0.936 g, 2.335 mmol, 94% yield) as a white solid. LCMS [M+H]$^+$: 389/391

Step 4: 2-(Trimethylsilyl)ethyl (2S,3S)-3-(4-chlorophenyl)-3-[(1R)-1-(4-chlorophenyl)-7-fluoro-1-hydroxy-5-[1-(oxan-4-yl)ethenyl]-3-oxo-2,3-dihydro-1H-isoindol-2-yl]-2-methylpropanoate (2:1)

HATU (0.513 g, 1.350 mmol) was added to a mixture of 2-(4-chlorobenzoyl)-3-fluoro-5-(1-(tetrahydro-2H-pyran-4-yl)vinyl)benzoic acid (0.5 g, 1.286 mmol), (2-(trimethylsilyl)ethyl (2S,3S)-3-amino-3-(4-chlorophenyl)-2-methylpropanoate (0.505 g, 1.607 mmol) and DIPEA (0.448 ml, 2.57 mmol) in DMF (6 mL) and the mixture was stirred overnight. Sat. NH$_4$Cl was added and the crude product extracted with EtOAc. The combined organic extracts were washed with water, NaHCO$_3$, brine, dried (MgSO$_4$) and concentrated to afford the 2:1 mixture of the title compounds) (0.88 g, 1.285 mmol, 100% yield) as a colourless sticky glass/foam [dr (1R:1S)=2:1]. The product was used without further purification in the next step.

Step 5: 2-(Trimethylsilyl)ethyl (2S,3S)-3-(4-chlorophenyl)-3-[(1R)-1-(4-chlorophenyl)-7-fluoro-1-methoxy-5-[1-(oxan-4-yl)ethenyl]-3-oxo-2,3-dihydro-1H-isoindol-2-yl]-2-methylpropanoate Iodomethane (0.059 ml, 0.948 mmol) was added to a suspension the product from Step 4 (0.59 g, 0.862 mmol) and cesium carbonate (0.562 g, 1.723 mmol) in 1:1 acetone:DCM (3 mL) and the mixture was stirred overnight. Sat. NH$_4$Cl was added and the crude product was extracted with DCM. The combined organic extracts were washed with brine, dried (MgSO$_4$). The crude product from a separate experiment (0.255 g) was combined and the mixture absorbed on silica. The crude product was purified by chromatography (SiO$_2$, 80 g column, 0-25% EtOAc/isohexane) to afford 2-(trimethylsilyl)ethyl (2S,3S)-3-(4-chlorophenyl)-3-[(1R)-1-(4-chlorophenyl)-7-fluoro-1-methoxy-5-[1-(oxan-4-yl)ethenyl]-3-oxo-2,3-dihydro-1H-isoindol-2-yl]-2-methylpropanoate (0.437 g, 0.525 mmol, 48.0% yield). 1H NMR (CDCl3, 400 MHz) δ 7.68 (d, 1H), 7.12 (dd, 1H), 7.02-6.80 (m, 8H), 5.31 (s, 1H), 5.17 (d, 1H), 4.34-4.21 (m, 2H), 4.06-3.98 (m, 2H), 3.92-3.74 (m, 2H), 3.55-3.40 (m, 2H), 3.26 (s, 3H), 2.72-2.61 (m, 1H), 1.79-1.65 (m, 2H), 1.64-1.50 (m, 2H), 1.36 (d, 3H), 0.64-0.52 (m, 2H), −0.07 (s, 9H). LCMS [M+H]+: 720/722/724. (M+Na)+

Synthesis 3b (Epoxide)

2-(Trimethylsilyl)ethyl (2S,3S)-3-(4-chlorophenyl)-3-[(1R)-1-(4-chlorophenyl)-7-fluoro-1-methoxy-5-[1-(oxan-4-yl)ethenyl]-3-oxo-2,3-dihydro-1H-isoindol-2-yl]-2-methylpropanoate

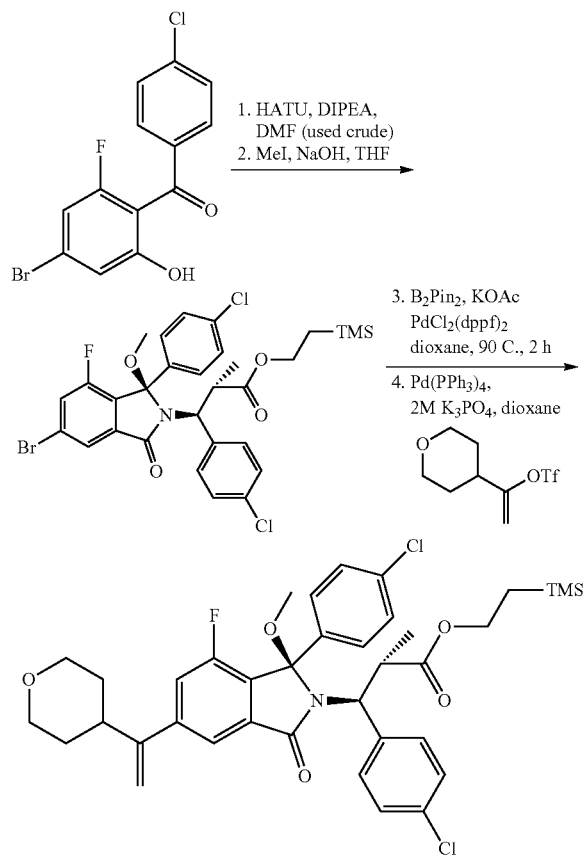

Step 1-2: 2-(Trimethylsilyl)ethyl (2S,3S)-3-[(1R)-5-bromo-1-(4-chlorophenyl)-7-fluoro-1-methoxy-3-oxo-2,3-dihydro-1H-isoindol-2-yl]-3-(4-chlorophenyl)-2-methylpropanoate HATU (6.83 g, 17.96 mmol) was added to a solution of 5-bromo-2-(4-chlorobenzoyl)-3-fluorobenzoic acid (4.28 µg, 11.98 mmol), 2-(trimethylsilyl)ethyl (2S,3S)-3-amino-3-(4-chlorophenyl)-2-methylpropanoate (5.00 g, 15.93 mmol) and DIPEA (6.28 ml, 35.9 mmol) in DMF (114 ml, 11.98 mmol) and the reaction mixture was stirred for 4 h. Water (50 mL) was added and the crude product was extracted with ethyl acetate (50 mL). The organic phase was washed with saturated $NaHCO_3$ (50 mL), water (4×50 mL), brine (50 mL), dried ($MgSO_4$), filtered and concentrated under vacuum. The crude product was used in the next step without further purification.

A solution of 2-(trimethylsilyl)ethyl (2S,3S)-3-[5-bromo-1-(4-chlorophenyl)-7-fluoro-1-hydroxy-3-oxo-2,3-dihydro-1H-isoindol-2-yl]-3-(4-chlorophenyl)-2-methylpropanoate (8.02 g, 11.91 mmol) and NaOH (0.476 g, 11.91 mmol) in THF (21.84 ml, 11.91 mmol) was stirred at room temperature for 30 minutes before addition of MeI (0.893 ml, 14.29 mmol). The reaction mixture was stirred for further 3 h and a second portion of NaOH (200 mg) was added and the mixture stirred for further 16 h. Sat·$NH_4Cl$ (10 mL) was added and the organic phase separated, washed with water (20 mL), dried ($MgSO_4$), filtered and concentrated under reduced pressure. The crude product was purified by chromatography ($SiO_2$, 80 g column, 0-30% EtOAc/isohexane) to afford 2-(trimethylsilyl)ethyl (2S,3S)-3-[(1S)-5-bromo-1-(4-chlorophenyl)-7-fluoro-1-methoxy-3-oxo-2,3-dihydro-1H-isoindol-2-yl]-3-(4-chlorophenyl)-2-methylpropanoate (0.203 g, 0.301 mmol, 2.53% yield) and 2-(trimethylsilyl)ethyl (2S,3S)-3-[(1R)-5-bromo-1-(4-chlorophenyl)-7-fluoro-1-methoxy-3-oxo-2,3-dihydro-1H-isoindol-2-yl]-3-(4-chlorophenyl)-2-methylpropanoate (4.27 g, 6.33 mmol, 53.2% yield) as white solids. LCMS m/z 667 $(M+H)^+$ Step 3-4: 2-(Trimethylsilyl)ethyl (2S,3S)-3-(4-chlorophenyl)-3-[(1R)-1-(4-chlorophenyl)-7-fluoro-1-methoxy-5-[1-(oxan-4-yl)ethenyl]-3-oxo-2,3-dihydro-1H-isoindol-2-yl]-2-methylpropanoate A flask was charged with 2-(trimethylsilyl)ethyl (2S,3S)-3-[(1R)-5-bromo-1-(4-chlorophenyl)-7-fluoro-1-methoxy-3-oxo-2,3-dihydro-1H-isoindol-2-yl]-3-(4-chlorophenyl)-2-methylpropanoate (1 µg, 1.498 mmol), bis(pinacolato)diboron (0.571 g, 2.247 mmol), potassium acetate (0.441 g, 4.49 mmol) and $PdCl_2(dppf)_2$ (0.055 g, 0.075 mmol). The system was evacuated and back-filled with nitrogen (×3). 1,4-Dioxane (3 mL) was added and the system was evacuated and back-filled with nitrogen (×3). The mixture was heated to 90° C. and stirred for 2 h. The reaction mixture was diluted with EtOAc (50 mL) and filtered through a pad of Celite, eluting with EtOAc (200 mL). The filtrate was concentrated in vacuo to give the crude product as a viscous brown oil. The crude product was used in the next step without further purification.

$Pd(PPh_3)_4$ (0.086 g, 0.074 mmol) was added to a degassed mixture of 2-(trimethylsilyl)ethyl (2S,3S)-3-(4-chlorophenyl)-3-[(1R)-1-(4-chlorophenyl)-7-fluoro-1-methoxy-3-oxo-5-(4,4,5,5-tetramethyl-1,3,2-dioxaborolan-2-yl)-2,3-dihydro-1H-isoindol-2-yl]-2-methylpropanoate (1.06 g, 1.483 mmol), 1-(tetrahydro-2H-pyran-4-yl)vinyl trifluoromethanesulfonate (0.483 g, 1.854 mmol) and 2M $K_3PO_4$ (1.483 ml, 2.97 mmol) in dioxane (7 mL) and the mixture was purged and put under nitrogen atmosphere.

The mixture was then stirred at 90° C. for 1.5 h and allowed to cool to room temperature and stirred overnight. The mixture was diluted with EtOAc and filtered through Celite, washing with EtOAc and water. The crude product was extracted with EtOAc and the combined organic extracts were washed with brine, dried ($MgSO_4$) and absorbed on silica. The crude product was purified by chromatography ($SiO_2$, 40 g column, 0-20% EtOAc/isohexane) to afford 2-(trimethylsilyl)ethyl (2S,3S)-3-(4-chlorophenyl)-3-[(1R)-1-(4-chlorophenyl)-7-fluoro-1-methoxy-5-[1-(oxan-4-yl)ethenyl]-3-oxo-2,3-dihydro-1H-isoindol-2-yl]-2-methylpropanoate (0.538 g, 0.755 mmol, 50.9% yield) as a white solid. 1H NMR (DMSO-d6, 400 MHz) δ 7.71 (d, 1H), 7.54 (dd, 1H), 7.30-6.50 (m (br), 4H), 7.00 (d, 2H), 6.86 (d, 2H), 5.46 (s, 1H), 5.20 (s, 1H), 4.18 (d, 1H), 4.12-3.99 (m, 1H), 3.89 (dd, 2H), 3.84-3.72 (m, 2H), 3.53-3.37 (m, 2H), 3.19 (d, 3H), 2.90-2.79 (m, 1H), 1.71-1.57 (m, 2H), 1.48-1.31 (m, 2H), 1.28 (d, 3H), 0.59-0.47 (m, 2H), −0.10 (s, 9H)

(2S,3S)-3-(4-Chlorophenyl)-3-[(1R)-1-(4-chlorophenyl)-7-fluoro-5-[1-hydroxy-1-(oxan-4-yl)propyl]-1-methoxy-3-oxo-2,3-dihydro-1H-isoindol-2-yl]-2-methylpropanoic acid

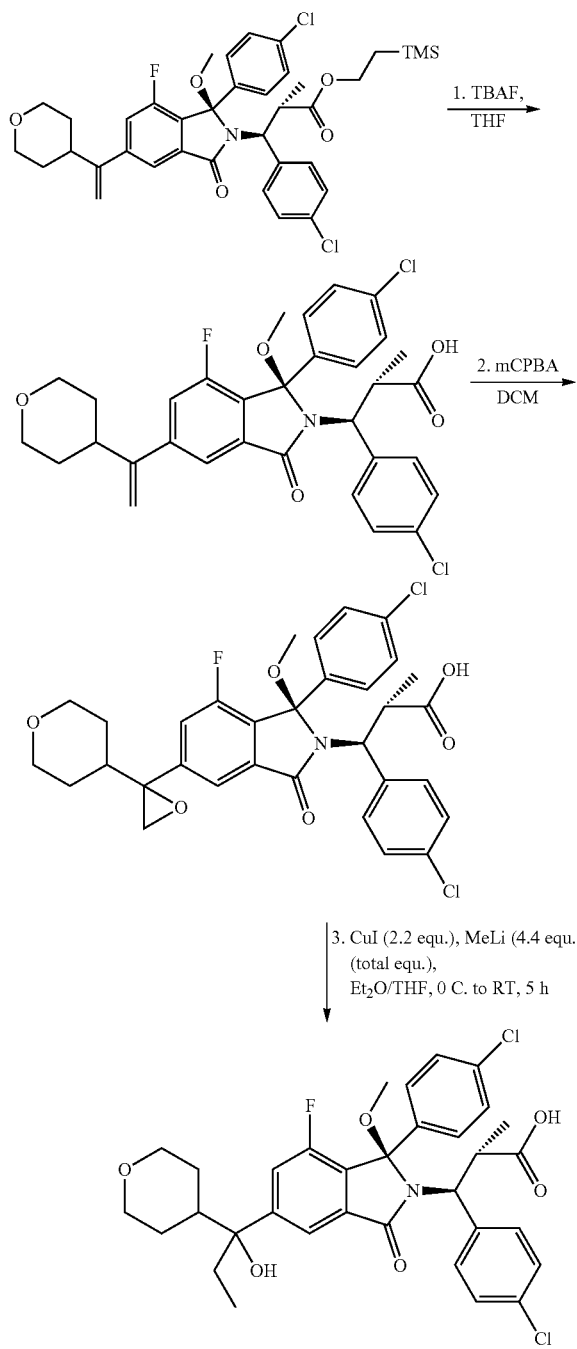

Step 1: (2S,3S)-3-(4-Chlorophenyl)-3-[(1R)-1-(4-chlorophenyl)-7-fluoro-1-methoxy-5-[1-(oxan-4-yl)ethenyl]-3-oxo-2,3-dihydro-1H-isoindol-2-yl]-2-methylpropanoic acid TBAF (1M in THF) (0.385 ml, 0.385 mmol) was added to a solution (2S,3S)-3-(4-chlorophenyl)-3-[(1R)-1-(4-chlorophenyl)-7-fluoro-1-methoxy-5-[1-(oxan-4-yl)ethenyl]-3-oxo-2,3-dihydro-1H-isoindol-2-yl]-2-methylpropanoate (0.224 g, 0.321 mmol) in THF (1 mL) and the mixture was stirred under nitrogen overnight. A second portion of TBAF (1 M in THF) (0.064 ml, 0.064 mmol) was added and the mixture stirred for a further 24 h. Saturated NH$_4$Cl was added and the crude product was extracted with EtOAc. The combined organic extracts were washed with water, 1N HCl, water, brine, dried (MgSO$_4$) and concentrated under vacuum to afford the title compound (0.172 g, 0.273 mmol, 85% yield) as a white solid. 1H NMR (DMSO-d6) δ: 12.25 (s, 1H), 7.71 (d, 1H), 7.52 (dd, 1H), 7.25-6.54 (m (br), 4H), 7.00 (d, 2H), 6.89 (d, 2H), 5.46 (s, 1H), 5.20 (s, 1H), 4.22 (d, 1H), 3.99-3.81 (m, 3H), 3.54-3.36 (m, 2H), 3.20 (s, 3H), 2.92-2.79 (m, 1H), 1.71-1.59 (m, 2H), 1.48-1.32 (m, 2H), 1.28 (d, 3H). LCMS [M+H]$^+$: 598/600/602.

Step 2: (2S,3S)-3-(4-Chlorophenyl)-3-[(1R)-1-(4-chlorophenyl)-7-fluoro-1-methoxy-5-[2-(oxan-4-yl)oxiran-2-yl]-3-oxo-2,3-dihydro-1H-isoindol-2-yl]-2-methylpropanoic acid mCPBA (0.069 g, 0.302 mmol) was added to a (2S,3S)-3-(4-chlorophenyl)-3-[(1R)-1-(4-chlorophenyl)-7-fluoro-1-methoxy-5-[1-(oxan-4-yl)ethenyl]-3-oxo-2,3-dihydro-1H-isoindol-2-yl]-2-methylpropanoic acid (0.17 g, 0.241 mmol) in DCM (1 mL) and the mixture was stirred for 3 days. The reaction was quenched with 10% aqueous solution of sodium metabisulfite and the layers were separated. The crude product was extracted with DCM and the combined organic extracts were washed with saturated NH$_4$Cl, brine, dried (MgSO$_4$), then absorbed on silica. The crude product was purified by chromatography (SiO$_2$, 12 g column, 0-50% EtOAc/isohexane) to afford (2S,3S)-3-(4-chlorophenyl)-3 the title compound (0.097 g, 0.142 mmol, 58.8% yield) as a white solid. 1H NMR (DMSO-d6) δ: 12.26 (s, 1H), 7.69 (s, 1H), 7.47 (d, 1H), 7-10-6.90 (m (br), 4H), 7.00 (d, 2H), 6.88 (d, 2H), 4.21 (d, 1H), 3.99-3.77 (m, 3H), 3.18 (s, 1.5H), 3.18 (s, 1H), 3.16 (dd, 1H), 2.77-2.70 (m, 1H), 2.41-2.34 (m, 1H), 1.53 (d, 1H), 1.44 (d, 1H), 1.28 (d, 3H), 1.26-1.13 (m, 3H). LCMS [M+H]$^+$: 614/616/618

Step 3: (2S,3S)-3-(4-Chlorophenyl)-3-[(1R)-1-(4-chlorophenyl)-7-fluoro-5-[1-hydroxy-1-(oxan-4-yl)propyl]-1-methoxy-3-oxo-2,3-dihydro-1H-isoindol-2-yl]-2-methylpropanoic acid MeLi (1.6M in DME) (0.140 ml, 0.223 mmol) was added to a suspension of copper(I) iodide (0.021 g, 0.111 mmol) in THF (0.5 mL) at 0° C. under nitrogen and the mixture was stirred for 10 minutes. A solution of (2S,3S)-3-(4-chlorophenyl)-3-[(1R)-1-(4-chlorophenyl)-7-fluoro-1-methoxy-5-[2-(oxan-4-yl)oxiran-2-yl]-3-oxo-2,3-dihydro-1H-isoindol-2-yl]-2-methylpropanoic acid (0.055 g, 0.072 mmol) in THF (1 mL) was added and the resulting yellow suspension was allowed to warm slowly to room temperature and stirred for 4 h. A second portion of Me$_2$CuLi (generated from addition of MeLi (1.6M in DME) (0.056 ml, 0.090 mmol) to copper (I) iodide (8.52 mg, 0.045 mmol) in THF (250 μL) under nitrogen at 0° C., stirring for 5 minutes) was added at room temperature and the mixture was stirred for a further 1 h. The reaction was quenched with saturated NH$_4$Cl followed by 1N HCl and the crude product was extracted with EtOAc. The combined organic extracts were washed with brine, dried (MgSO$_4$) and absorbed on silica. The crude product was purified by chromatography (SiO$_2$, 4 g column, 0-5% MeOH/DCM) to afford (2S,3S)-3-(4-chlorophenyl)-3-

[(1R)-1-(4-chlorophenyl)-7-fluoro-5-[1-hydroxy-1-(oxan-4-yl)propyl]-1-methoxy-3-oxo-2,3-dihydro-1H-isoindol-2-yl]-2-methylpropanoic acid (0.022 g, 0.033 mmol, 46.3% yield) as a white solid. LCMS [M+H]+: 630/632/634

Synthesis 4

Stage 1: tert-butyl 3-bromo-5-fluorobenzoate

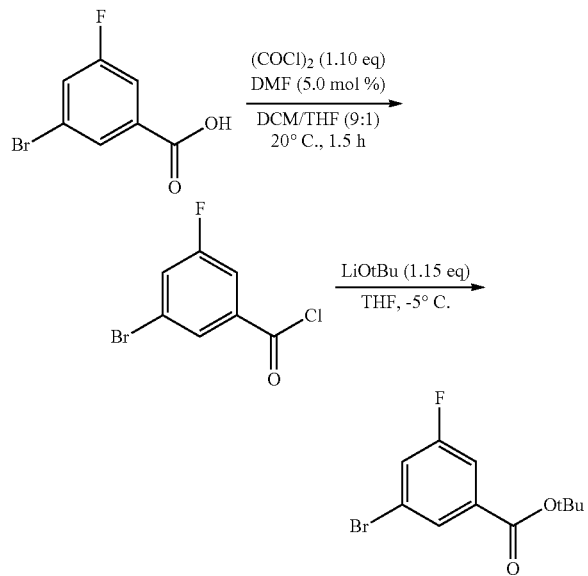

3-bromo-5-fluorobenzoic acid (32.0 g, 1.0 equiv) was stirred in a mixture of DCM (288 mL, 9 vol) and THF (32 mL, 1 vol) until the majority of the solid dissolved. DMF (0.57 mL, 5 mol %) was added, and the flask placed in an ambient temperature water bath. Oxalyl chloride (13.7 mL, 1.10 equiv) was added over 1 h via syringe pump; 30 minute after the end of addition the reaction was complete by HPLC (sample quenched into MeOH to form methyl ester prior to analysis). The resulting thin slurry was aged overnight, concentrated to 100 mL volume, diluted with THF (160 mL, 5 vol) and again concentrated to 100 mL. The resulting thin slurry of acid chloride was diluted to 160 mL total volume with THF. A solution of LiOtBu in THF (20 wt %, 67.3 g, 77 mL, 1.15 equiv) was diluted with THF (243 mL), then this solution was cooled to an internal temperature of −9° C. with an ice/salt bath. To this was added the slurry containing acid chloride over 55 min, while the internal temperature remained below −3° C. The reaction was complete 15 min following the end of addition. The solution was aged overnight as it warmed to ambient temperature, diluted with heptane (320 mL, 10 vol), and washed with water (160 mL, 5 vol). The aqueous layer was removed to the insoluble rag at the interface, then the organic layer was filtered through a pad of solka-floc. The pad was rinsed with heptane (10 mL), then the combined organic layer was washed 2× with water (2×80 mL, 2.5 vol). The resulting organic layer was distilled under reduced pressure to a 100 mL final volume, diluted with heptane (160 mL, 5 vol), and concentrated again to 100 mL total volume. The solution of tert-butyl 3-bromo-5-fluorobenzoate was used directly in the next step. NMR $^1$H (400 MHz; CDCl$_3$): 7.89-7.88 (1H, m), 7.60-7.57 (1H, m), 7.40-7.37 (1H, m), 1.57 (9H, s).

Stage 2: 3-fluoro-5-[1-hydroxy-1-(oxan-4-yl)propyl]benzoic acid

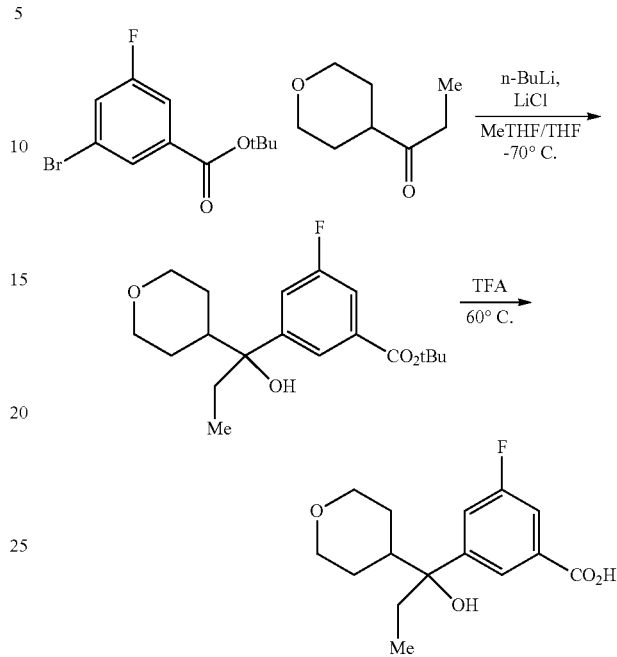

A solution of tert-butyl 3-bromo-5-fluorobenzoate (20.0 g, 1.0 equiv) and 1-(oxan-4-yl)propan-1-one (10.85 g, 1.05 equiv) in 2-MeTHF (200 mL, 10 vol) was treated with a 0.5 M solution of LiCl in THF (72.7 mL, 0.5 equiv) and cooled to −70° C. A solution of n-butyllithium in hexanes (2.2 M, 39.0 mL, 1.1 equiv) was added dropwise over 1 h; the reaction was complete upon end of addition. The mixture was warmed to −20° C., quenched with half-saturated aq. NH$_4$Cl solution (200 mL) and agitated for 10 minutes. The mixture was allowed to settle and the layers were separated. The organic phase was washed with water (50 mL, 2.5 vol). The solution assayed by HPLC for 20.6 g tert-butyl 3-fluoro-5-[1-hydroxy-1-(oxan-4-yl)propyl]benzoate (84% assay yield). LCMS (M−H)$^-$; m/z=337.2. The organic solution was concentrated to ca 40 mL total volume (~2 vol) by distillation under reduced pressure. The concentrated solution of tert-butyl 3-fluoro-5-[1-hydroxy-1-(oxan-4-yl)propyl]benzoate was treated with TFA (28.0 mL, 6.0 equiv) at 20° C. and the solution warmed to 60° C. and aged for 2 hours when HPLC analysis showed the reaction was 98% complete; the mixture was cooled to 20° C. then diluted with MTBE (40 mL, 2 vol) and heptane (80 mL, 4 vol). The solution was seeded with authentic tert-butyl 3-fluoro-5-[1-hydroxy-1-(oxan-4-yl)propyl]benzoate and aged for 30 min while a seed bed grew. The slurry was diluted over 1 h by addition of heptane (120 mL), filtered, and the cake washed with heptane (40 mL) to give the title compound as an off-white solid (14.89 g, 87% yield). NMR $^1$H (400 MHz; DMSO): 13.23 (1H, s), 7.79 (1H, t), 7.50-7.47 (1H, m), 7.43-7.39 (1H, m), 4.79 (1H, s, broad), 3.79 (2H, ddd), 3.18 (2H, dt), 1.86-1.79 (3H, m), 1.64 (1H, d), 1.36-1.09 (2H, m), 0.93 (1H, d), 0.58 (3H, t); LCMS (M+H)$^+$: m/z=283.1

Stage 3: 3-fluoro-5-[1-(oxan-4-yl)-1-[(trimethylsi-lyl)oxy]propyl]benzoic acid

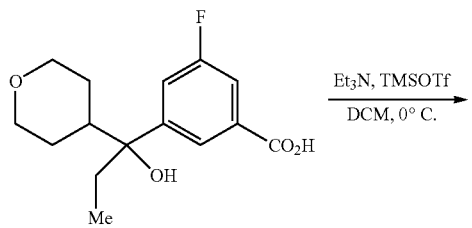

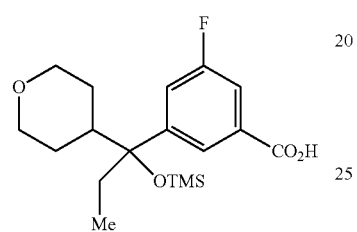

To a suspension of 3-fluoro-5-[1-hydroxy-1-(oxan-4-yl)propyl]benzoic acid (7.06 g, 1.0 equiv) in DCM (40 mL) at 0° C. was added Et₃N (7.08 g, 2.6 equiv) over 30 mins (maintaining a temperature below 5° C.). The resulting clear solution was treated with a solution of TMSOTf (13.34 g, 2.4 equiv) in DCM (40 mL) over 60 mins (maintaining a temperature below 5° C.). The reaction mixture was stirred for a further 1 h at 0° C. Water (88 mL) was added to the cold reaction mixture over 15 mins and the phases were separated. The organic phase was washed with 0.2M KHSO₄ solution (53 mL) and water (2×88 mL). The solution was dried over Na₂SO₄ and concentrated in vacuo. The crude product (an oil) was crystallized from DCM/heptane to afford the titled compound (8.24 g, 93%) as an off-white solid. NMR ¹H (400 MHz; DMSO): 7.79 (1H, t), 7.65-8.62 (1H, m), 7.35-7.31 (1H, m), 3.98 (2H, ddd), 3.33 (2H, dtd), 2.04-1.84 (3H, m), 1.75 (1H, d), 1.37 (1 h, qd), 1.26-1.20 (2H, m), 0.72 (3H, t), 0.25 (9H, s); LCMS (M+H)⁺: m/z=355.2

Stage 4: 2-(4-chlorobenzoyl)-3-fluoro-5-[1-hydroxy-1-(oxan-4-yl)propyl]benzoic acid

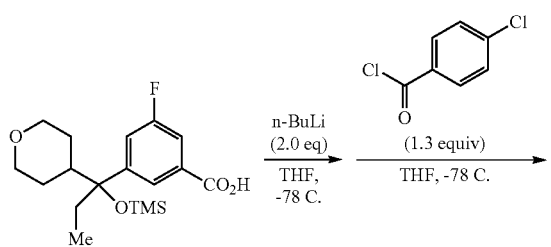

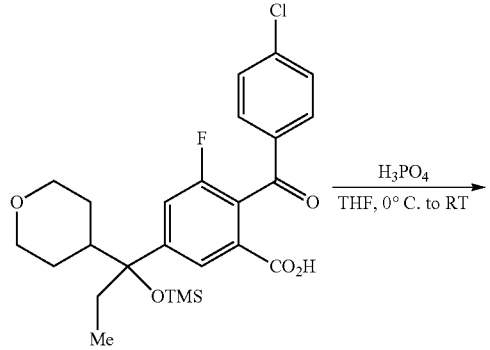

To THF (60 mL, 15 vol) at −70 C internal temp was added n-BuLi (9.8 mL, 2.0 equiv, 2.3M solution in hexanes). A solution of 3-fluoro-5-[1-(oxan-4-yl)-1-[(trimethylsilyl)oxy]propyl]benzoic acid (4.0 g, 1.0 equiv) in THF (20.0 mL, 5 vol) was added dropwise over 60 min while the internal temperature was kept below −65 C. The resulting pale red solution was stirred for 30 min after the end of addition, and 4-chlorobenzoyl chloride (1.6 mL, 1.15 equiv) in THF (2 vol, 8.0 mL) was added over 10 min while the internal temperature was kept below ~60 C—the reaction is complete at the end of addition; this solution was warmed to 0° C. to give 2-(4-chlorobenzoyl)-3-fluoro-5-[1-(oxan-4-yl)-1-[(trimethylsilyl)oxy]propyl]benzoic acid as a solution in THF. LCMS (M+H)⁺: m/z=493.2

To the solution was added conc. H₃PO₄ (3.8 mL, 5.0 equiv) and the mixture was stirred at 50° C. for 18 h. The mixture was diluted with toluene (40 mL, 10 vol) and 4% aq. NaCl (20 mL, 5 vol). The phases were separated, and the top organic layer was washed with 4% aq. NaCl (20 mL) and water (10 mL).

The organic layer was concentrated to ~1/3 volume, then diluted with toluene (60 mL, 15 vol). The solution was concentrated to ~35 mL total volume (~9 vol, 50° C. bath temp, 80 mbar pressure), over which time a while solid precipitated. The slurry was aged at 50° C. for 1 h, then cooled to ambient temperature and aged for 3 h. The slurry was filtered, and the cake washed with 2×8 mL (2×2 vol) toluene before being dried in a vacuum oven (50° C. oven temp) to a constant mass. The title compound was obtained as a white solid in 81% corr. yield (4.04 g, 95 wt %). LCMS (M+H)⁺: m/z=421.1

Stage 5: 2-(4-chlorobenzoyl)-3-fluoro-5-[(1S)-1-hydroxy-1-(oxan-4-yl)propyl]benzoic acid-bis[(1S)-1-phenylethyl]amine salt

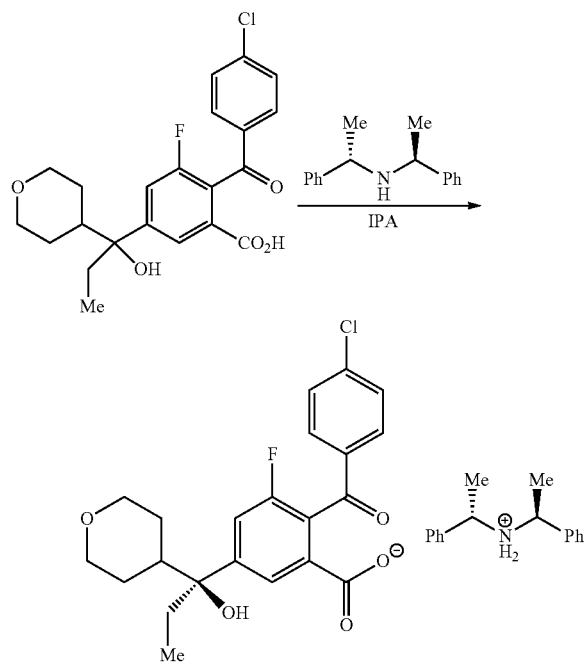

2-(4-chlorobenzoyl)-3-fluoro-5-[1-hydroxy-1-(oxan-4-yl)propyl]benzoic acid (racemate, 300 g, 85 wt %, 255 g 6, 1.0 equiv) was dissolved in Isopropanol (4000 mL) by stirring at 55° C. for 10 min to give a homogeneous solution before cooling to 25° C. To the solution was added bis[(1S)-1-phenylethyl]amine (136.52 g; 1.0 equiv) in IPA (300 ml) over 2 minutes followed by an IPA rinse (200 mL). The solution was stirred at ambient temperature (22-23°) for 15 minutes and then seeded with authentic sample of the title compound (0.50 g); a solid crystallized readily and a slight endotherm (ca −0.4°) was observed. The suspension was stirred at an internal temperature of 19° C. for 20 h, filtered, and the cake washed with IPA (450 mL). The solid was dried under vacuum aspiration for 2 h then in a vacuum oven at 50° C. for 20 h to give a beige solid; 175.5 g (41% yield as IPA solvate)—by HPLC, the mixture is 95:5 e.r.
Chiral HPLC Conditions:
  Column: ChiralPak IC-3 3 μcolumn 4.6×150 mm
  Column Temp: 270
  Eluent: Heptane/IPA 80: 20 with 0.1% TFA
  Flow rate: 1.0 mL/min@254 nm
  Retention Desired (S) enantiomer; RT=4.60 mins. Undesired (R) enantiomer), RT=5.83 mins The material (250 g, 1.0 equiv, 95:5 e.r.) was dissolved in IPA (4000 mL, 16 vol) by warming to 800 and stirring at this temperature for 15 min until a homogeneous solution formed. The solution was cooled over ~1 h to 52° C., seeded with an authentic sample of the title compound (0.50 g) and the suspension was cooled to 20° C. over 4 hours and then stirred at ambient temperature this temperature overnight (total 24 h). The solid was isolated by filtration under vacuum, the filter cake washed with IPA (2×450 mL) and the filter cake sucked dry for 5 mins before further drying in a 50° C. vacuum oven. 2-(4-chlorobenzoyl)-3-fluoro-5-[(1S)-1-hydroxy-1-(oxan-4-yl)propyl]benzoic acid-bis[(1S)-1-phenylethyl]amine salt was obtained as a beige solid (219.2 g; 88% recovery); by HPLC the e.r. was 99.6:0.4. NMR $^1$H (400 MHz; DMSO): 7.84 (1H, d), 7.67 (1H, t), 7.65 (1H, t), 7.58 (1H, t), 7.56 (1H, t), 7.47 (1H, dd), 7.34-7.30 (4H, m), 7.28-7.20 (6H, m), 4.90 (1H, s), 3.90 (1H, dd), 3.80-3.72 (1H, m), 3.51-3.46 (1H, m), 3.30-3.15 (1H, m), 1.93-1.83 (3H, m), 1.68 (1H, d), 1.41-1.28 (1H, m), 1.26 (3H, s), 1.24 (3H, s), 1.04 (3H, s), 1.03 (3H, s), 0.65 (3H, t)

Stage 6: 2-(trimethylsilyl)ethyl (2S,3S)-3-amino-3-(4-chlorophenyl)-2-methylpropanoate-hydrochloride salt

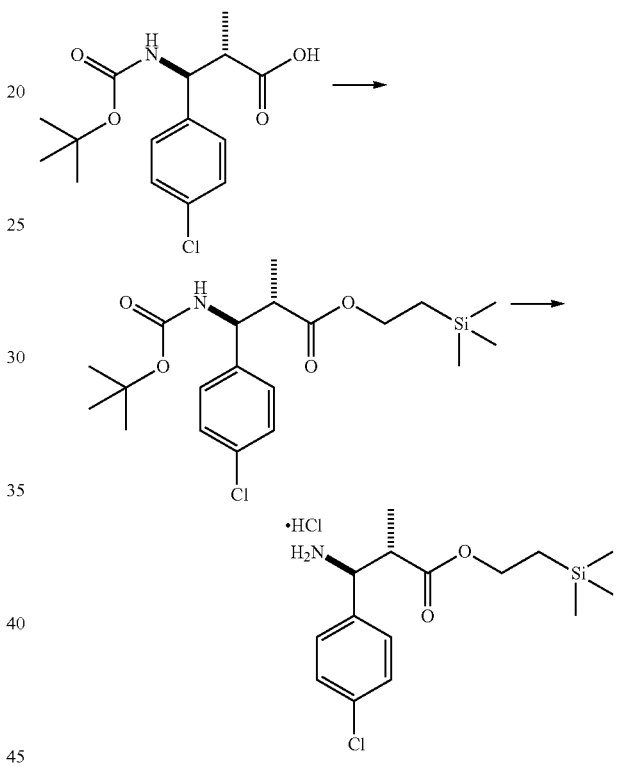

To a suspension of (2S,3S)-3-{[(tert-butoxy)carbonyl]amino}-3-(4-chlorophenyl)-2-methylpropanoic acid (109.82 g, 1.0 equiv), 2-trimethylsilylmethanol (49.66 g, 1.2 equiv) and DMAP (4.28 g, 0.05 mol %) in DCM (1100 mL, 10 vol) at −10° C. was added EDC·HCl (100.65 g, 1.5 equiv) in five equal portions over 75 mins (maintaining a temperature below 0° C.). The resulting clear solution was slowly allowed to warm to room temperature and stirred for 16 h. 1N HCl solution (1000 mL) was slowly added to the reaction mixture over 15 mins and the phases were separated. The organic phase was washed with 5% NaHCO$_3$ solution (500 mL) and water (2×500 mL). The organic phase was concentrated in vacuo to give a 2-(trimethylsilyl)ethyl (2S,3S)-3-{[(tert-butoxy)carbonyl]amino}-3-(4-chlorophenyl)-2-methylpropanoate, which was used directly in the next step. LCMS (M+H)$^+$: m/z=414.2

The crude material (a waxy white solid) was redissolved into DCM (200 mL)/heptane (1500 mL) and a 4N solution of HCl in dioxane (350 mL, 4.0 equiv) was added dropwise to the heptane solution over 2 hrs. During this addition HCl salt begins to precipitate and the suspension gradually thickens as the reaction is aged at ambient temperature for 24 h. The suspension was diluted with MTBE (800 mL), filtered and the filter cake washed with MTBE (2×200 mL) to afford the title compound as a white flaky solid (108.22 g, 88%) after drying in a vacuum oven at 50° C. to a constant weight. NMR $^1$H (400 MHz; CDCl$_3$): 8.93 (3H, bs), 7.39-7.29 (4H, m), 4.3 (1H, bd), 4.06-3.92 (2H, m), 3.17-3.08 (1H, m), 1.32 (3H, d), 0.80-0.71 (2H, m), −0.02 (9H, s); LCMS (M+H)$^+$: m/z=314.1

Stage 7: 2-(trimethylsilyl)ethyl (2S,3S)-3-(4-chlorophenyl)-3-[(1R)-1-(4-chlorophenyl)-7-fluoro-1-hydroxy-5-[(1S)-1-hydroxy-1-(oxan-4-yl)propyl]-3-oxo-2,3-dihydro-1H-isoindol-2-yl]-2-methylpropanoate

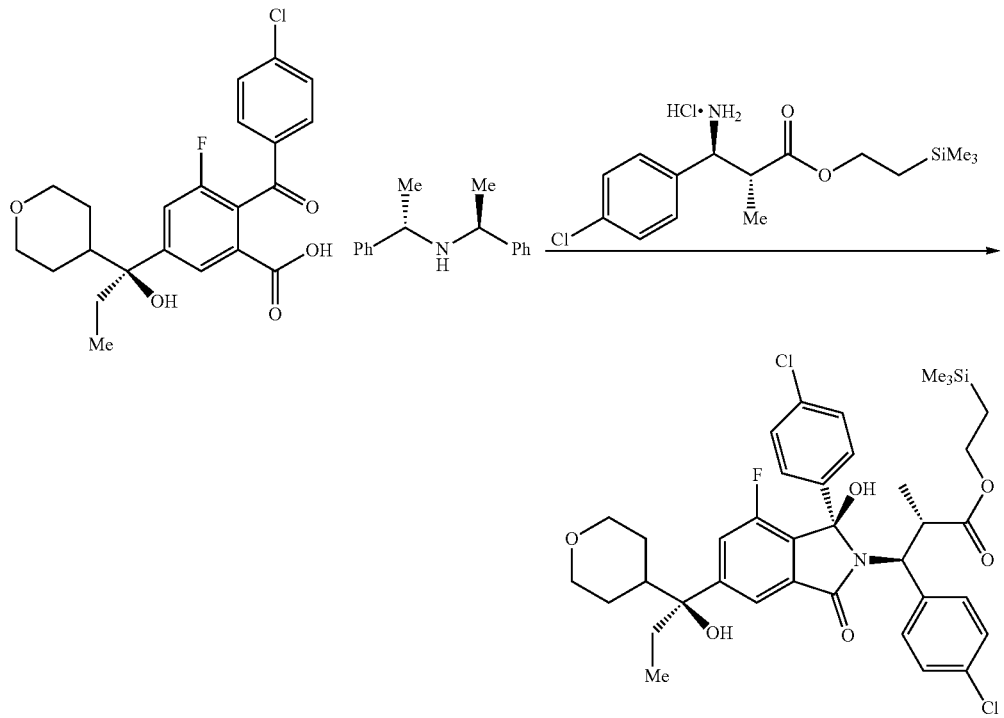

Dichloromethane (150 mL, 10 vol) was added to a mixture of 2-(4-chlorobenzoyl)-3-fluoro-5-[(1S)-1-hydroxy-1-(oxan-4-yl)propyl]benzoic acid-bis[(1S)-1-phenylethyl] amine salt (15.0 g, 1.0 equiv), 2-(trimethylsilyl)ethyl (2S, 3S)-3-amino-3-(4-chlorophenyl)-2-methylpropanoate-hydrochloride salt (8.2 g, 1.1 equiv), EDC hydrochloride (4.7 g, 1.15 equiv), DMAP (260 mg, 0.1 equiv), and 2-hydroxypyridine-N-oxide (230 mg, 0.1 equiv). The mixture was stirred for 18 h, then quenched by addition of aq. NaHCO$_3$ (4.5 g, 2.5 equiv in 60 mL H$_2$O). The layers were separated and the DCM phase concentrated to 30 mL (2 vol). MTBE (150 mL, 10 vol) was added, and the organic layer washed sequentially with 2×aq. H$_3$PO$_4$ (3.5 mL, 2.5 equiv in 60 mL water), aq. NaHCO$_3$(4.5 g, 2.5 equiv in 60 mL H$_2$O), and water (60 mL). The organic layer was concentrated to 60 mL (2 vol), diluted with MeOH (300 mL, 20 vol), and concentrated to 150 mL (10 vol). The MeOH solution was diluted with water (15 mL), seeded with authentic sample (15 mg, 0.1 wt %), and aged at ambient temperature for 30 min while a seed bed grew. The slurry was diluted with water (45 mL) added over 2 h, aged for 1 h, then filtered. The cake was washed with 2.5/1 MeOH:H$_2$O (45 mL) and water (45 mL), and dried in a vacuum oven at 50° C. for 18 h to give the title compound as a white solid (13.5 g, 89% yield, d.r.>99:1 by 19F NMR). NMR $^1$H (400 MHz; CDCl$_3$): 7.80 (1H, s), 7.15 (1H, d), 7.01-6.99 (4H, m), 6.97-6.92 (4H, m), 4.77 (1H, s), 4.36 (1H, d), 4.16-4.08 (1H, m), 3.94-3.90 (1H, m), 3.89-3.79 (2H, m), 3.47 (1H, d), 3.31 (1H, t), 3.08 (1H, t), 2.55 (1H, s), 1.91 (1H, sep), 1.86-1.77 (2H, m), 1.74-1.71 (1H, m), 1.41-1.22 (5H, m), 0.94 (1H, d), 0.68-0.54 (5H, m), 0.10 (9H, s), NMR $^{19}$F (376 MHz, CDCl$_3$) δ: −119.1 and LCMS (M+H)$^+$: m/z=716.2

Stage 8: 2-(trimethylsilyl)ethyl (2S,3S)-3-(4-chlorophenyl)-3-[(1R)-1-(4-chlorophenyl)-7-fluoro-5-[(1S)-1-hydroxy-1-(oxan-4-yl)propyl]-1-methoxy-3-oxo-2,3-dihydro-1H-isoindol-2-yl]-2-methylpropanoate

Stage 9: (2S,3S)-3-(4-chlorophenyl)-3-[(1R)-1-(4-chlorophenyl)-7-fluoro-5-[(1S)-1-hydroxy-1-(oxan-4-yl)propyl]-1-methoxy-3-oxo-2,3-dihydro-1H-isoindol-2-yl]-2-methylpropanoic acid

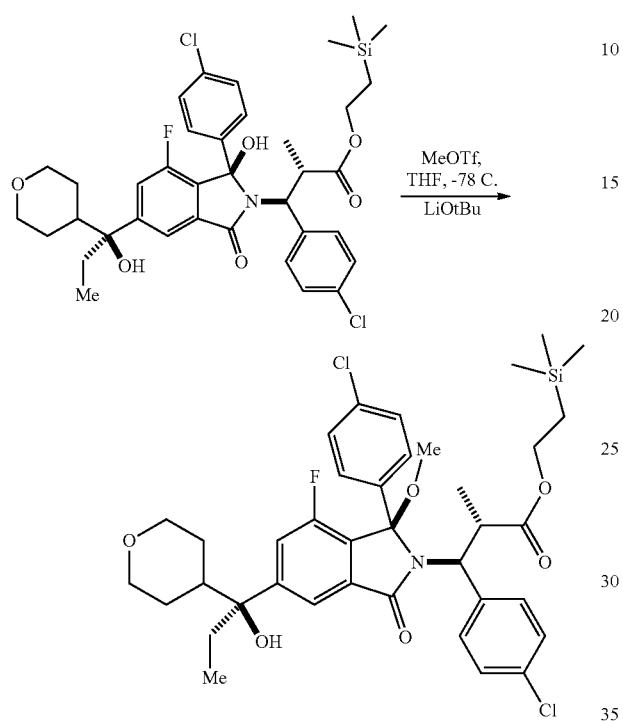

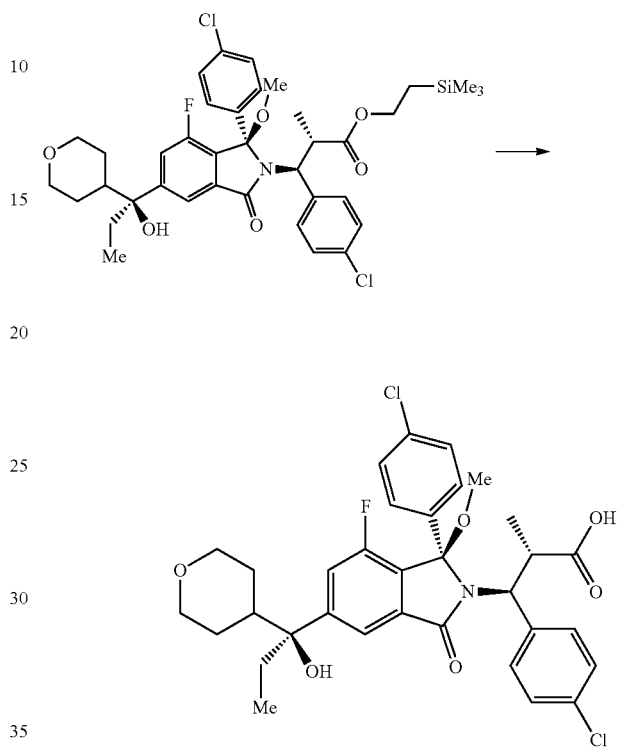

Solid 2-(trimethylsilyl)ethyl (2S,3S)-3-(4-chlorophenyl)-3-[(1R)-1-(4-chlorophenyl)-7-fluoro-1-hydroxy-5-[(1S)-1-hydroxy-1-(oxan-4-yl)propyl]-3-oxo-2,3-dihydro-1H-isoindol-2-yl]-2-methylpropanoate (2.5 g, 1.0 equiv) was dissolved in anhydrous THF (12.5 mL, 5 vol) in a 100 mL 3-neck flask at room temperature. The solution was cooled to −70° C. internal temperature, and MeOTf (methyl trifluoromethanesulfonate) (0.46 mL, 1.2 equiv) was added. The resulting clear solution was held at internal temperature of −70° C. LiOtBu (20 wt % in THF, 1.9 mL, 1.2 equiv) was added dropwise over a period of 1 h by syringe pump. The mixture was held at −70° C. for 18 h then warmed to −15° C. over 2 h at which point conversion was >98%. The reaction mixture was diluted with IPA (12.5 mL) and then water (12.5 mL). The solution was seeded with product 10, and stirred at ambient temperature for 30 minutes while a seed bed formed. Additional water (25 mL) was added slowly via a syringe pump over 1.5 h and the slurry aged for 1 h at ambient temperature before being filtered. The cake was washed with 1:1 IPA/water (20 mL) and dried in a vacuum oven at 50° C. to give the title compound (2.4 g) (94% uncorrected yield, 100:0.5 d.r by 19F NMR). NMR $^{1}$H (400 MHz; CDCl$_3$): 7.67 (1H, d), 7.28 (1H, dd), 6.93-6.88 (8H, m), 4.30-4.19 (m, 2H), 4.01 (dd, 1H), 3.92-3.77 (m, 3H), 3.40-3.26 (m, 2H), 3.22 (s, 3H), 1.97-1.84 (m, 4H), 1.72 (bs, 3H), 1.49-1.38 (m, 2H), 1.36 (d, 3H), 1.07 (bd, 1H), 0.69 (t, 3H), 0.61-0.52 (m, 2H), −0.08 (s, 9H); NMR $^{19}$F (376 MHz, CDCl$_3$) δ: −118.8 and LCMS (M+H)$^{+}$: m/z=730.3

2-(trimethylsilyl)ethyl (2S,3S)-3-(4-chlorophenyl)-3-[(1R)-1-(4-chlorophenyl)-7-fluoro-5-[(1S)-1-hydroxy-1-(oxan-4-yl)propyl]-1-methoxy-3-oxo-2,3-dihydro-1H-isoindol-2-yl]-2-methylpropanoate (170.0 g, 1.0 equiv) and CsF (70.7 g, 2.0 equiv) were charged to a 5 L fixed vessel and DMF (510 mL, 3 vol) was added at ambient temperature. The mixture was warmed to 60° C. and aged for 7 h at this temperature at which point the reaction was complete. The mixture was cooled to 20° C. and stirred overnight. The DMF was diluted with EtOAc (1700 mL, 10 mL) and 1 M HCl (510 mL, 3 vol). The layers were separated, and the organic layer was washed sequentially with 5% aq. LiCl (4×680 mL, 4 vol) and water (2×680 mL, 4 vol) before being concentrated. The resulting oil was concentrated twice from EtOAc (250 mL each time) to give the title compound as a pale yellow foam (141 g corr., 92 wt %, 96% yield). The solid was suspended in EtOAc (684 mL, 4 vol) and heated to 70° C., held at this temperature for 1 h, then cooled to 20° C. over 2 h. Heptane (1370 mL, 8 vol) was added over 70 min and the slurry aged overnight. The solid was filtered, washed with EtOAc/heptane 1:2 (2×300 mL), and dried to a constant weight in a vacuum oven at 50° C. to give 133 g (86% yield).

The product was isolated in stable anhydrous crystalline form. This has been designated as free acid 'Form F' and is a stable crystalline polymorph.

Figure 2:
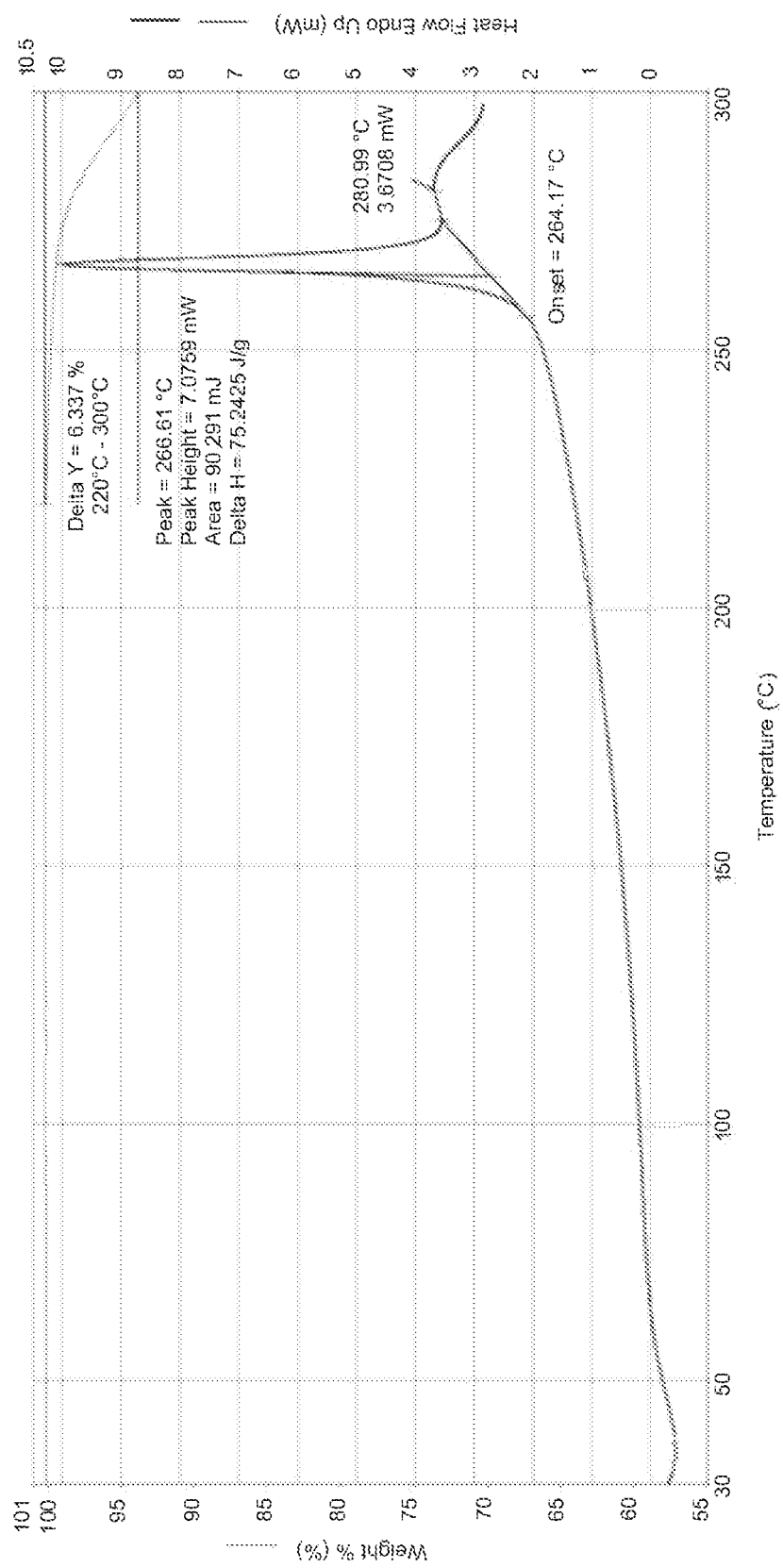
FIG. 2 is a DSC scan of (2S,3S)-3-(4-chlorophenyl)-3-[(1R)-1-(4-chlorophenyl)-7-fluoro-5-[(1S)-1-hydroxy-1-(oxan-4-yl)propyl]-1-methoxy-3-oxo-2,3-dihydro-1H-isoindol-2-yl]-2-methylpropanoic acid.

The XRPD of Form F is shown at FIG. 1 and the DSC is shown at FIG. 2.

The XRPD has peaks at the following resonances (Table 1):

TABLE 1

| Pos. [°2Th.] | Height [cts] | FWHM [°2Th.] | d-spacing [Å] | Rel. Int. [%] |
|---|---|---|---|---|
| 5.5324 | 119.60 | 0.4093 | 15.97459 | 3.19 |
| 8.0939 | 363.89 | 0.0768 | 10.92389 | 9.72 |
| 8.7670 | 654.55 | 0.0768 | 10.08658 | 17.48 |
| 10.0983 | 1123.93 | 0.0768 | 8.75963 | 30.02 |
| 11.0597 | 867.75 | 0.0768 | 8.00021 | 23.18 |
| 11.2706 | 1141.77 | 0.1023 | 7.85102 | 30.50 |
| 11.7674 | 80.69 | 0.1535 | 7.52066 | 2.16 |
| 13.5705 | 1039.22 | 0.1023 | 6.52514 | 27.76 |
| 14.2250 | 333.44 | 0.0768 | 6.22639 | 8.91 |
| 15.1034 | 2704.30 | 0.1279 | 5.86616 | 72.24 |
| 15.5082 | 3743.65 | 0.1279 | 5.71395 | 100.00 |
| 15.7699 | 2649.88 | 0.1023 | 5.61973 | 70.78 |
| 16.1290 | 684.97 | 0.1023 | 5.49539 | 18.30 |
| 16.5503 | 413.16 | 0.1023 | 5.35644 | 11.04 |
| 17.1682 | 1577.31 | 0.1279 | 5.16504 | 42.13 |
| 17.6278 | 246.51 | 0.1023 | 5.03138 | 6.58 |
| 18.1385 | 279.01 | 0.1023 | 4.89085 | 7.45 |
| 18.8833 | 723.33 | 0.1279 | 4.69961 | 19.32 |
| 19.1793 | 179.94 | 0.0768 | 4.62773 | 4.81 |
| 19.6727 | 256.37 | 0.1279 | 4.51276 | 6.85 |
| 20.3698 | 132.83 | 0.1023 | 4.35988 | 3.55 |
| 20.8132 | 2330.35 | 0.1279 | 4.26799 | 62.25 |
| 21.4724 | 496.23 | 0.1279 | 4.13844 | 13.26 |
| 22.2644 | 2823.66 | 0.2303 | 3.99297 | 75.43 |
| 23.2042 | 254.87 | 0.1023 | 3.83333 | 6.81 |
| 23.9443 | 465.26 | 0.1279 | 3.71650 | 12.43 |
| 24.5109 | 196.57 | 0.1023 | 3.63186 | 5.25 |
| 24.9654 | 105.69 | 0.1279 | 3.56676 | 2.82 |
| 25.4394 | 438.68 | 0.1023 | 3.50137 | 11.72 |
| 25.8370 | 351.04 | 0.1023 | 3.44839 | 9.38 |
| 26.5691 | 327.59 | 0.1535 | 3.35500 | 8.75 |
| 26.9367 | 637.86 | 0.1791 | 3.31004 | 17.04 |
| 27.3570 | 1012.15 | 0.1279 | 3.26015 | 27.04 |
| 28.2316 | 985.61 | 0.1535 | 3.16110 | 26.33 |
| 28.6372 | 1599.45 | 0.1535 | 3.11725 | 42.72 |
| 29.2407 | 315.65 | 0.1535 | 3.05427 | 8.43 |
| 29.9430 | 289.99 | 0.1791 | 2.98422 | 7.75 |
| 30.6433 | 463.31 | 0.1535 | 2.91759 | 12.38 |
| 31.2365 | 165.53 | 0.1279 | 2.86353 | 4.42 |
| 31.5627 | 201.49 | 0.1279 | 2.83467 | 5.38 |
| 32.1380 | 66.90 | 0.1535 | 2.78523 | 1.79 |
| 33.5238 | 129.51 | 0.2047 | 2.67320 | 3.46 |
| 33.7620 | 120.56 | 0.1535 | 2.65488 | 3.22 |
| 34.4905 | 171.78 | 0.1279 | 2.60045 | 4.59 |

Step 10a: (2S,3S)-3-(4-Chlorophenyl)-3-[(1R)-1-(4-chlorophenyl)-7-fluoro-5-[(1S)-1-hydroxy-1-(oxan-4-yl)propyl]-1-methoxy-3-oxo-2,3-dihydro-1H-isoindol-2-yl]-2-methylpropanoic acid tris(hydroxymethyl)aminomethane salt

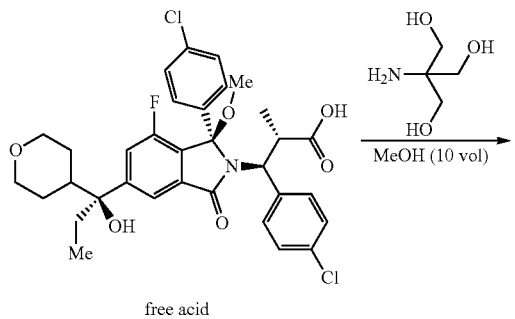

free acid

MeOH (10 vol) →

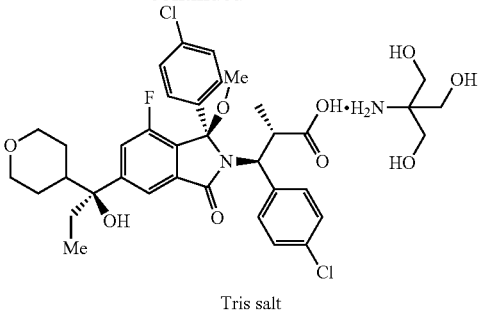

Tris salt (2S,3S)-3-(4-chlorophenyl)-3-[(1R)-1-(4-chlorophenyl)-7-fluoro-5-[(1S)-1-hydroxy-1-(oxan-4-yl)propyl]-1-methoxy-3-oxo-2,3-dihydro-1H-isoindol-2-yl]-2-methylpropanoic acid (113.0 g, 1.0 equiv) and tris(hydroxymethyl)aminomethane (21.95 g, 1.01 equiv) were charged as solids to a 2 L vessel. Methanol (1130 mL) was added with stirring under nitrogen to give a mobile suspension. The solids were dissolved by warming to 38-40° over 30 mins to give a clear solution. This was cooled to 20-22° and then concentrated under reduced pressure on a Buchi rotavapor to give a white foam. The foam was transferred to a crystallization dish and dried under vacuum (ca 20 mmHg) at 600 over a weekend (60 h) to give the title compound as a crisp white foam (134.1 g; 99.5).

Synthesis 5: Preparation of Other Intermediates 2-(4-chlorobenzoyl)-3-fluoro-5-(1-(tetrahydro-2H-pyran-4-yl)-1((trimethylsilyl)oxy)propyl)benzoic acid Sec-butyllithium (1.28 M in cyclohexane/hexane 92/8) (9.70 ml, 12.41 mmol) was added to a stirred solution of TMEDA (1.873 ml, 12.41 mmol) in THF (20 mL) at −70° C. under nitrogen. The mixture was stirred at −70° C. for 10 minutes before a solution of 3-fluoro-5-(1-(tetrahydro-2H-pyran-4-yl)-1-((trimethylsilyl)oxy)propyl)benzoic acid (2.0 g, 5.64 mmol) in THF (20 mL) was added dropwise over ca. 30 minutes. The mixture was stirred at −70° C. for 1 h before a solution of methyl 4-chlorobenzoate (3.85 g, 22.57 mmol) in THF (15 mL) was added dropwise over ca. 15 minutes. The mixture was stirred at −70° C. for 10 minutes then allowed to warm to room temperature and stirred overnight (18 h). The reaction mixture was quenched with sat. NH$_4$Cl (aq.) (50 mL) and acidified to ~pH 3 with 1 M KHSO$_4$ (aq.) (50 mL). The aqueous phase was extracted with TBME (3×200 mL) and the combined organic extracts were washed with brine (300 mL), dried (MgSO$_4$), filtered and concentrated in vacuo to give a pale yellow solid (5.97 g). The crude product was adsorbed onto silica and purified by chromatography (SiO$_2$, 80 g column, 5-40% [(1% AcOH in EtOAc)/isohexane]) to afford 2-(4-chlorobenzoyl)-3-fluoro-5-(1-(tetrahydro-2H-pyran-4-yl)-1-((trimethylsilyl)oxy)propyl)benzoic acid (1.957 g, 68.9% yield) as an off-white solid.

3-(4-chlorophenyl)-4-fluoro-6-(1-(tetrahydro-2H-pyran-4-yl)-1-((trimethylsilyl)oxy)propyl)isobenzofuran-1(3H)-one

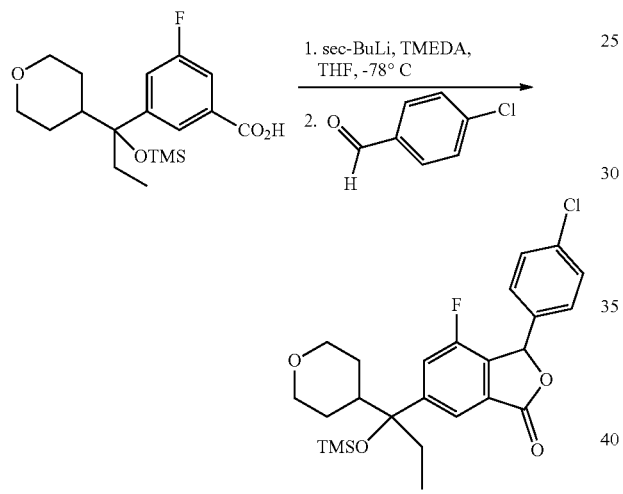

Sec-butyllithium (1.28M in cyclohexane/hexane, 92/8) (4.85 ml, 6.21 mmol) was added dropwise to a stirred solution of TMEDA (0.937 ml, 6.21 mmol) in THF (15 mL) at −70° C. under nitrogen over 2 minutes. The mixture was stirred for 10 minutes then a solution of 3-fluoro-5-(1-(tetrahydro-2H-pyran-4-yl)-1-((trimethylsilyl)oxy)propyl) benzoic acid (1.0 g, 2.82 mmol) in THF (10 mL) was added in portions over 25 minutes. After stirring for 60 minutes at −70° C., a solution of 4-chlorobenzaldehyde (0.991 g, 7.05 mmol) in THF (10 mL) was added in portions over 15 minutes. The reaction was allowed to warm to room temperature slowly and was stirred overnight. Water (25 mL) was cautiously added followed by sat. NH$_4$Cl (aq, sat, 25 mL). The mixture was acidified to pH<3 with 1M KHSO$_4$ then extracted with TBME (3×25 mL). The combined organic layers were washed with brine (25 mL) then dried (MgSO$_4$), filtered then concentrated in vacuo to leave a pale yellow gum (1.91 g). The crude product was dissolved in minimum amount of DCM, filtered, loaded on a 40 g column and purified by chromatography (SiO$_2$, 40 g column, 0-50% EtOAc in iso-hexane) to afford 3-(4-chlorophenyl)-4-fluoro-6-(1-(tetrahydro-2H-pyran-4-yl)-1-((trimethylsilyl)oxy)propyl)isobenzofuran-1 (3H)-one (1.04 g, 71.9% yield) as a sticky white gum. 1H NMR (DMSO-d6) δ: 7.70-7.67 (m, 1H), 7.55-7.47 (m, 3H), 7.42-7.36 (m, 2H), 6.87 (s, 1H), 3.92-3.84 (m, 1H), 3.80-3.71 (m, 1H), 3.29-3.13 (m, 2H), 2.22-2.09 (m, 1H), 2.04-1.83 (m, 2H), 1.77-1.64 (m, 1H), 1.23-0.96 (m, 3H), 0.62 (t, 1.5H), 0.61 (t, 1.5H), 0.24 (s, 4.5H), 0.24 (s, 4.5H). LCMS m/z 499/501 (M+Na)+.

2-(4-chlorobenzoyl)-3-fluoro-5-(1-hydroxy-1-(tetrahydro-2H-pyran-4-yl)propyl)benzoic acid

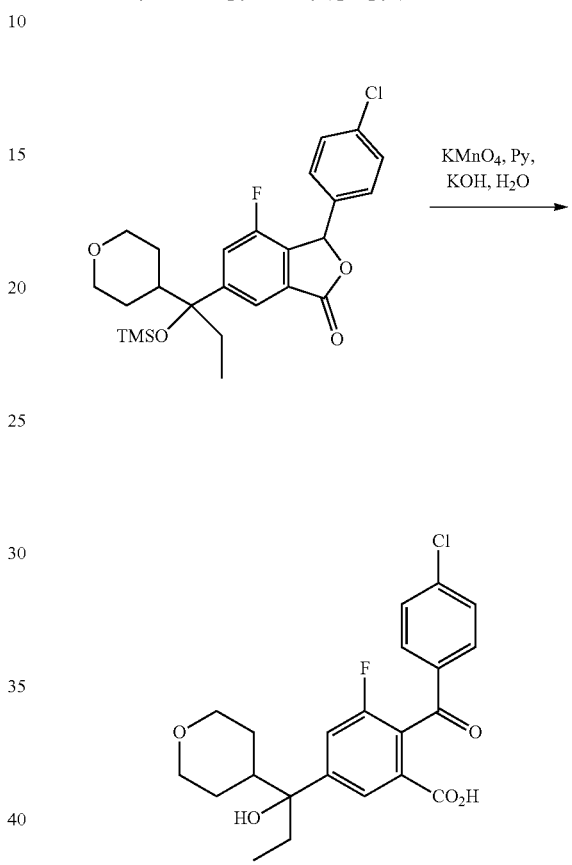

KMnO$_4$ (226 mg, 1.431 mmol) was added to a stirred mixture of 3-(4-chlorophenyl)-4-fluoro-6-(1-(tetrahydro-2H-pyran-4-yl)-1-((trimethylsilyl)oxy)propyl)isobenzofuran-1(3H)-one (455 mg, 0.954 mmol), pyridine (2 mL, 24.73 mmol) and KOH (395 mg, 5.98 mmol) in WATER (3 mL, 167 mmol). The reaction was placed under nitrogen then stirred at 60° C. for 19 h. The reaction was allowed to cool to RT then filtered through a pad of Celite which was washed with water (25 mL). The filtrate was acidified to pH 1 with 1 M HCl (aq.) then the white solid collected by filtration in vacuo then washed with water (15 mL). The white solid was dried in vacuo and the crude product (340 mg) was purified by chromatography on the Companion (12 g column, using a 0-60% mixture of 1% AcOH in EtOAc: iso-hexane as eluant) to afford 2-(4-chlorobenzoyl)-3-fluoro-5-(1-hydroxy-1-(tetrahydro-2H-pyran-4-yl)propyl) benzoic acid as a white solid (246 mg, 58%). $^1$H NMR (400 MHz, DMSO-d6) δ 13.55 (br s, 1H), 7.88 (d, 1H), 7.75-7.65 (m, 2H), 7.65-7.59 (m, 2H), 7.56 (dd, 1H), 4.95 (s, 1H), 4.00-3.83 (m, 1H), 3.78 (dd, 1H), 3.29-3.23 (m, 1H), 3.23-3.13 (m, 1H), 1.99-1.78 (m, 3H), 1.76-1.59 (m, 1H), 1.48-1.23 (m, 2H), 1.08-0.95 (m, 1H), 0.64 (t, 3H). LCMS m/z 421 (M+H)+.

247 tert-butyl 2-(4-chlorobenzoyl)-3-fluoro-5-(1-(tetra-hydro-2H-pyran-4-yl)-1-((trimethylsilyl)oxy)propyl) benzoate

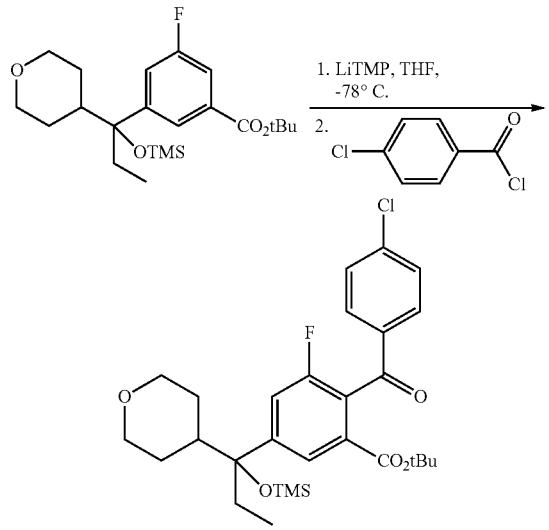

nBuLi (2.3 M in hexane) (0.582 ml, 1.340 mmol) was added to a solution of 2,2,6,6-tetramethylpiperidine (0.247 ml, 1.461 mmol) in THF (3.69 ml, 1.218 mmol) at −78° C. under nitrogen and the mixture was stirred for 30 minutes. A solution of tert-butyl 3-fluoro-5-(1-(tetrahydro-2H-pyran-4-yl)-1-((trimethylsilyl)oxy)propyl)benzoate (0.500 g, 1.218 mmol) in THF (0.3 mL) was added dropwise and the mixture stirred for a further 45 minutes. 4-chlorobenzoyl chloride (0.187 ml, 1.461 mmol) was then added and reaction stirred for a further 1 h. Sat. NH₄Cl was added (3 mL) followed by EtOAc (5 mL). The layers were separated and the organic extract washed with water (10 mL), brine (10 mL), dried (MgSO₄), filtered and concentrated under reduced pressure to give the crude product (735.8 mg). Purification by chromatography (SiO₂, 40 g column, 0-30% EtOAc in iso-hexane) to afford tert-butyl 2-(4-chlorobenzoyl)-3-fluoro-5-(1-(tetrahydro-2H-pyran-4-yl)-1-((trimethylsilyl)oxy)propyl)benzoate (0.250 g, 0.451 mmol, 37.0% yield) as a viscous colourless oil. 1H NMR (MeOD) δ: 7.88 (d, 1H), 7.79-7.72 (m, 2H), 7.57-7.51 (m, 2H), 7.43 (dd, 1H), 4.04-3.97 (m, 1H), 3.95-3.86 (m, 1H), 3.46-3.33 (m, 2H), 2.16-2.02 (m, 3H), 1.92-1.78 (m, 1H), 1.45-1.25 (m, 3H), 1.28 (s, 9H), 0.78 (t, 3H), 0.30 (s, 9H). LCMS m/z 403/405 (M-tBu-HOTMS+H)+.

2-(4-chlorobenzoyl)-3-fluoro-5-(1-(tetrahydro-2H-pyran-4-yl)-1-((trimethylsilyl)oxy)propyl)benzoic acid

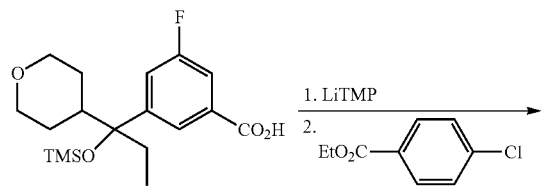

248

-continued

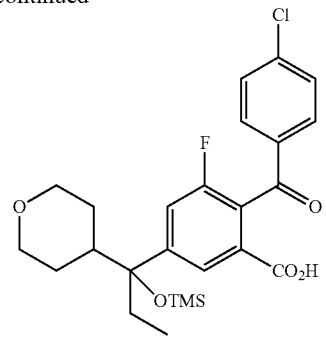

A stirred solution of 2,2,6,6-tetramethylpiperidine (0.081 ml, 0.480 mmol) in THF (0.4 ml) was treated dropwise at −78° C. (bath) under nitrogen with n-butyllithium, 2.5M in hexane (0.18 ml, 0.450 mmol) and stirred at −78° C. (bath) for 20 minutes. The solution was then treated with a solution of 3-fluoro-5-(1-(tetrahydro-2H-pyran-4-yl)-1-((trimethylsilyl)oxy)propyl)benzoic acid (0.050 g, 0.141 mmol) in THF (0.4 ml) and stirred at −78° C. (bath) for 1 h. The mixture was treated with ethyl 4-chlorobenzoate (0.099 ml, 0.635 mmol) and allowed to reach room temp. The mixture was quenched sat. NH₄Cl (10 ml), acidified with 1 M KHSO₄ (2 ml) and extracted MTBE (3×5 ml). The combined extracts were washed with brine (10 ml), were dried (MgSO₄) and evaporated to give a brown oil (137 mg).

The oil was purified by chromatography (SiO₂, 12 g column, 0-40% EtOAc in iso-hexane, both containing 1% of acetic acid). The clean fractions were pooled, diluted with toluene (10 ml) and evaporated. The residue was taken up in toluene (2×10 ml) and evaporated. The residue was transferred into a vial with a few drops of ethyl acetate and evaporated. The residue was dried under vacuum at 40° C. for 4 h to give 2-(4-chlorobenzoyl)-3-fluoro-5-(1-(tetrahydro-2H-pyran-4-yl)-1-((trimethylsilyl)oxy)propyl)benzoic acid (29 mg, 0.056 mmol, 39.6% yield) as a yellow foam.

tert-butyl 3-fluoro-2-iodo-5-(1-(tetrahydro-2H-pyran-4-yl)-1-((trimethylsilyl)oxy)propyl)benzoate

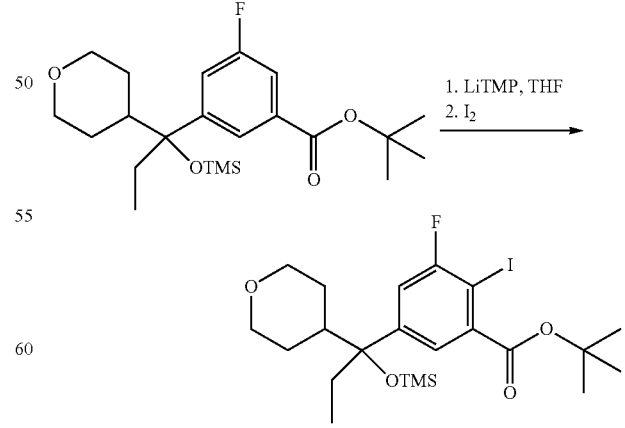

n-BuLi (2.5 M in hexanes) (5.85 ml, 14.61 mmol) was added dropwise to a solution of 2,2,6,6-tetramethylpiperidine (2.466 ml, 14.61 mmol) in THF (20 ml) at 0° C. (bath)

under nitrogen and the mixture was stirred for 1 hour. The mixture was cooled to −78° C. (bath) and a solution of tert-butyl 3-fluoro-5-(1-(tetrahydro-2H-pyran-4-yl)-1-((trimethylsilyl)oxy)propyl)benzoate (4.00 g, 9.74 mmol) in THF (20 ml) was added dropwise and the mixture stirred at −78° C. (bath) for 1 hour. A solution of iodine (3.71 g, 14.61 mmol) in THF (20 ml) was added dropwise and the mixture stirred at −78° C. (bath) for 3.5 h. The reaction was quenched with sat. aq. $NH_4Cl$ (80 ml) and the mixture was allowed to warm to room temperature and stirred overnight. EtOAc (80 ml) and 1 M aq. sodium thiosulfate (80 ml) were added and the layers separated. The aqueous layer was extracted with EtOAc (2×60 ml) and the combined organic extracts were washed with brine (80 ml), dried ($MgSO_4$) and concentrated in vacuo. The crude product was purified by chromatography ($SiO_2$, 120 g column, 0-50% EtOAc in iso-hexane) to afford tert-butyl 3-fluoro-2-iodo-5-(1-(tetrahydro-2H-pyran-4-yl)-1-((trimethylsilyl)oxy)propyl)benzoate (3.59 g, 67.3% yield) as a sticky yellow oil. 1H NMR ($CDCl_3$) δ: 7.38 (dd, 1H), 7.09 (dd, 1H), 4.04-3.95 (m, 1H), 3.93-3.84 (m, 1H), 3.34 (ddd, 1H), 3.26 (ddd, 1H), 2.01-1.84 (m, 2H), 1.88-1.74 (m, 1H), 1.74-1.66 (m, 1H), 1.63 (s, 9H), 1.40-1.28 (m, 1H), 1.22-1.14 (m, 2H), 0.72 (t, 3H), 0.23 (s, 9H). LCMS m/z 559 (M+Na)+

3-(4-chlorophenyl)-4-fluoro-6-(1-(tetrahydro-2H-pyran-4-yl)-1-((trimethylsilyl)oxy)propyl)isobenzofuran-1(3H)-one

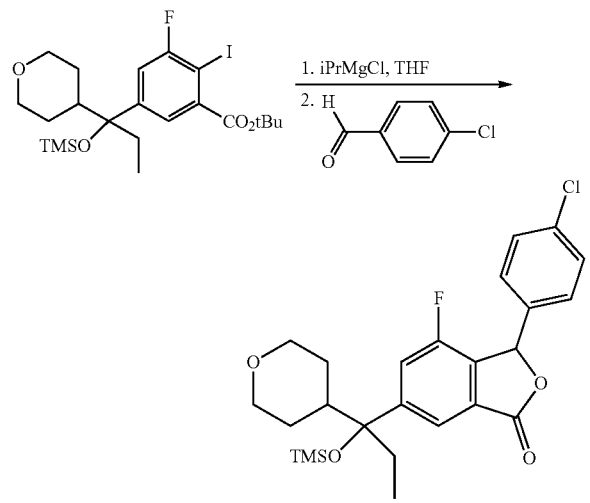

A solution of tert-butyl 3-fluoro-2-iodo-5-(1-(tetrahydro-2H-pyran-4-yl)-1-((trimethylsilyl)oxy)propyl)benzoate (1.00 g, 1.864 mmol) in THF (7 ml) was cooled to −30° C. under nitrogen and isopropylmagnesium chloride (1.398 ml, 2.80 mmol) was added dropwise. The mixture was stirred at −30° C. for 15 minutes then a solution of 4-chlorobenzaldehyde (1.048 g, 7.46 mmol) in THF (7 ml) was added and the mixture stirred at −30° C. for 30 minutes, then allowed to warm slowly to room temperature before stirring overnight. Sat. aq. $NH_4Cl$ (40 ml) was added and the reaction mixture was extracted with EtOAc (2×100 ml). The combined organic layers were washed with brine (80 ml), dried ($MgSO_4$) and concentrated in vacuo. The crude product was purified by chromatography ($SiO_2$, 120 g column, 0-50% EtOAc in iso-hexane) to afford 3-(4-chlorophenyl)-4-fluoro-6-(1-(tetrahydro-2H-pyran-4-yl)-1-((trimethylsilyl)oxy)propyl)isobenzofuran-1(3H)-one (702 mg, 1.472 mmol, 79% yield) as a pale yellow foam.

Biological Assays

MDM2-p53 Interaction Using a 96-Well Plate Binding Assay (ELISA)

The ELISA assay was performed in streptavidin coated plates which were preincubated with 200 μl per well of 1 μg $ml^{-1}$ biotinylated IP3 peptide. The plates were ready to use for MDM2 binding after washing the plate with PBS.

Compounds and control solutions in DMSO aliquoted in 96-well plates were pre-incubated in a final 2.5-5% (v/v) DMSO concentration at room temperature (for example 20° C.) for 20 min with 190 μl aliquots of optimized concentrations of in vitro translated MDM2, before transfer of the MDM2-compound mixture to the b-IP3 streptavidin plates, and incubation at 4° C. for 90 min. After washing three times with PBS to remove unbound MDM2, each well was incubated at 20° C. for 1 hour with a TBS-Tween (50 mM Tris pH7.5; 150 mM NaCl; 0.05% Tween 20 nonionic detergent) buffered solution of primary mouse monoclonal anti-MDM2 antibody (Ab-5, Calbiochem, used at a 1/10000 or 1/200 dilution depending on the antibody stock solution used), then washed three times with TBS-Tween before incubation for 45 mins at 20° C. with a TBS-Tween buffered solution of a goat-anti-mouse horseradish peroxidase (HRP) conjugated secondary antibody (used at 1/20000 or 1/2000 depending on the antibody stock solution). The unbound secondary antibody was removed by washing three times with TBS-Tween. The bound HRP activity was measured by enhanced chemiluminesence (ECL™, Amersham Biosciences) using the oxidation of the diacylhydrazide substrate, luminol, to generate a quantifiable light signal. The percentage of MDM2 inhibition at a given concentration is calculated as the [1−(RLU detected in the compound treated sample−RLU negative DMSO control)÷(RLU of DMSO positive and negative controls)]×100 or as the (RLU detected in the compound treated sample÷RLU of DMSO controls)×100. The $IC_{50}$ was calculated using a plot of % MDM2 inhibition vs concentration and is the average of two or three independent experiments.

Western Blot Analysis

SJSA cells were treated for 6 hours with 5, 10 and 20 μM of compounds in 0.5% DMSO. The cells together with 0.5% DMSO only controls were washed with ice-cold phosphate buffered saline (PBS) and protein extracts prepared by lysing the cells in SDS buffer (62.5 mM Tris pH 6.8; 2% sodium dodecyl sulphate(SDS); 10% glycerol) with sonication for 2×5 seconds (Soniprep 150ME) to break down high molecular weight DNA and reduce the viscosity of the samples. The protein concentration of the samples was estimated using the Pierce BCA assay system (Pierce, Rockford, IL) and 50 pg aliquots of protein analysed using standard SDS-polyacrylamide gel electrophoresis (SDS-PAGE) and Western immunoblotting procedures. p-mercaptoethanol (5%) and bromophenol blue (0.05%) were added and the samples, which were then boiled for 5 minutes, followed by brief centrifugation, before loading onto a pre-cast 4-20% gradient Tris-Glycine buffered SDS-polyacrylamide gel (Invitrogen).

Molecular weight standards (SeeBlue™, Invitrogen) were included on every gel and electrophoresis was carried out in a Novex XL tank (Invitrogen) at 180 volts for 90 minutes. The separated proteins were transferred electrophoretically overnight from the gel onto a Hybond C nitrocellulose membrane (Amersham) using a BioRad electrophoresis tank and 25 mM Tris, 190 mM glycine and 20% methanol transfer buffer at 30 volts or two hours at 70 volts. Primary antibodies used for immunodetection of the transferred proteins were: mouse monoclonal NCL-p53DO-7 (Novocastra) at 1:1000; MDM2(Ab-1, clone IF2) (Oncogene) at 1:500; WAF1 (Ab-1, clone 4D10) (Oncogene) at 1:100; Actin (AC40) (Sigma) at 1:1000. The secondary antibody used was peroxidase conjugated, affinity purified, goat anti-mouse (Dako) at 1:1000. Protein detection and visualisation was performed by enhanced chemiluminescence (ECL™, Amersham) with light detection by exposure to blue-sensitive autoradiography film (Super RX, Fuji).

Protocol A: SJSA-1 and SN40R2 Assays

The MDM2 amplified cell lines tested were an isogenic matched pair of p53 wild-type and mutated osteosarcoma (SJSA-1 and SN40R2, respectively). All cell cultures were grown in RPMI 1640 medium (Gibco, Paisley, UK) supplemented with 10% fetal calf serum and routinely tested and confirmed negative for mycoplasma infection. The growth of cells and its inhibition was measured using the sulphorhodamine B (SRB) method as previously outlined. 100 µl of 3×10$^4$/ml and 2×10$^4$/ml SJSA-1 and SN40R2 cells, respectively, were seeded into 96-well tissue culture plates and incubated at 37° C. in a 5% CO$_2$ humidified incubator for 24 hrs, after which the medium was replaced with 100 µl of test medium containing a range of MDM2-p53 antagonist concentrations and incubated for a further 72 hrs to allow cell growth before adding 25 µL of 50% trichloroacetic acid (TCA) to fix the cells for 1 h at 4° C. The TCA was washed off with distilled water and 100 µL of SRB dye (0.4% w/v in 1% acetic acid) (Sigma-Aldrich, Poole, Dorset) added to each well of the plate. Following incubation with the SRB dye at room temperature for 30 min, the plates were washed with 1% acetic acid and left to dry. The SRB stained protein, which is a measure of the number of cells in a well, was then resuspended in 100 µL of 10 mM Tris-HCl (pH 10.5) and the absorbance at λ=570 nm measured in each well using a FluoStar Omega Plate reader. The GI$_{50}$ was calculated by non-linear regression analysis of the data using Prism v4.0 statistical software.

Protocol B: SJSA-1 and SN40R2 Assays

The CellTiter-Glo® Luminescent Cell Viability Assay is a homogeneous method to determine the number of viable cells in culture based on quantitation of the ATP present, which signals the presence of metabolically active cells. Both SJSA-1 and SN40R2 were grown in RPMI 1640 (Life Technologies #61870) supplemented with 10% FBS (PAA #A15-204) and 10 U/ml penicillin/streptomycin. 2000 cells in 75 µl were seeded in each well of a 96 well plate and left at 37° C. in a 5% CO$_2$ humidified incubator for 24 hrs. A range of MDM2-p53 antagonist concentrations in DMSO was then added to the cells to a final DMSO concentration of 0.3%, and incubated for a further 72 hrs to allow cell growth. 100 µl of CTG reagent (Promega #G7573) was added to all wells and luminescence was measured on the topcount. The EC$_{50}$ values were determined from a sigmoidal 4 parameter curve fit using XLfit in conjunction with Activity Base (IDBS; Guildford, Surrey, UK).

Anti-Proliferative Activity

Inhibition of cell growth is measured using the Alamar Blue assay (Nociari, M. M, Shalev, A., Benias, P., Russo, C. Journal of Immunological Methods 1998, 213, 157-167). The method is based on the ability of viable cells to reduce resazurin to its fluorescent product resorufin. For each proliferation assay cells are plated onto 96 well plates and allowed to recover for 16 hours prior to the addition of inhibitor compounds (in 0.1% DMSO v/v) for a further 72 hours. At the end of the incubation period 10% (v/v) Alamar Blue is added and incubated for a further 6 hours prior to determination of fluorescent product at 535 nM ex/590 nM em. The anti-proliferative activities of compounds of the invention can be determined by measuring the ability of the compounds to inhibit growth in cancer cell lines for example as available from DSMZ, ECACC or ATCC.

Results

TABLE 3 biological data obtained from assays as described herein for (2S,3S)-3-(4-chlorophenyl)-3-[(1R)-1-(4-chlorophenyl)-7-fluoro-5-[(1S)-1-hydroxy-1-(oxan-4-yl)propyl]-1-methoxy-3-oxo-2,3-dihydro-1H-isoindol-2-yl]-2-methylpropanoic acid

| Patent Example | MDM2 IC50 (µM) | SJSA-1 IC50 (µM) (ProtocolA) | SJSA1 IC50 (µM) (Protocol B) | SN40R2 IC50 (µM) (Protocol A) | SN40R2 IC50 (µM) (Protocol B) |
| --- | --- | --- | --- | --- | --- |
| 1 | 80%@0.0010 | 0.023 | 0.027 | 23 | 55% at 10 |

Where more than one data point has been obtained, the table above shows an average (e.g. geometric or arithmetic mean) of these data points.

It is of course to be understood that the invention is not intended to be restricted to the details of the above embodiments which are described by way of example only.

Combination Protocol for Cell Proliferation

The effect of a compound of formula (1°) (Compound I) in combination with an anticancer agent (Compound II) can be assessed using the following technique. Cells from human cells lines (e.g. SJSA-1) were seeded onto 96-well tissue culture plates at a concentration of 2.5×10$^3$, 6.0×10$^3$, or 4.0×10$^3$ cells/well respectively. Cells were allowed to recover for 24-48 hours prior to addition of compound(s) or vehicle control (0.35-0.5% DMSO) as follows:

Compounds were added concurrent for 72-96 hours. Following a total of 72-96 hours compound incubation, cells were fixed with ice-cold 10% (w/v) trichloroacetic acid for 1 hour on ice and then washed four times with dH$_2$O using a plate washer (Labsystems Wellwash Ascent) and air-dried. Cells were then stained with 0.4% (w/v) Sulforhodamine B (Sigma) in 1% acetic acid for 20 min at room temperature and then washed four times with 1% (v/v) acetic acid and air-dried before the addition of 10 mM Tris buffer to solubilise the dye. Colourmetric product was quantified by reading at Abs490 nm or Abs570 nm on a Wallac Victor$^2$ plate reader (1420 multilabel counter, Perkin Elmer Life Sciences). The IC$_{50}$ for Compound II in the presence of varying doses of Compound I was determined. Synergy was determined when the IC$_{50}$ shifted down in the presence of sub-effective doses of Compound I. Additivity was determined when the response to Compound II and Compound I together resulted in an effect equivalent to the sum of the two compounds individually. Antagonistic effects were defined as those causing the $IC_{50}$ to shift upwards, i.e. those where the response to the two compounds was less than the sum of the effect of the two compounds individually.

PHARMACEUTICAL FORMULATION EXAMPLES (i) Tablet Formulation

A tablet composition containing a compound of the formula (1°) is prepared by mixing an appropriate amount of the compound (for example 50-250 mg) with an appropriate diluent, disintegrant, compression agent and/or glidant. One possible tablet comprises 50 mg of the compound with 197 mg of lactose (BP) as diluent, and 3 mg magnesium stearate as a lubricant and compressing to form a tablet in known manner. The compressed tablet may be optionally film coated.

(ii) Capsule Formulation

A capsule formulation is prepared by mixing 100-250 mg of a compound of the formula (1°) with an equivalent amount of lactose and filling the resulting mixture into standard hard gelatin capsules. An appropriate disintegrant and/or glidant can be included in appropriate amounts as required.

(iii) Injectable Formulation I

A parenteral composition for administration by injection can be prepared by dissolving a compound of the formula (1°) (e.g. in a salt form) in water containing 10% propylene glycol to give a concentration of active compound of 1.5% by weight. The solution is then made isotonic, sterilised by filtration or by terminal sterilisation, filled into an ampoule or vial or pre-filled syringe, and sealed.

(iv) Injectable Formulation II

A parenteral composition for injection is prepared by dissolving in water a compound of the formula (1°) (e.g. in salt form) (2 mg/ml) and mannitol (50 mg/ml), sterile filtering the solution or by terminal sterilisation, and filling into sealable 1 ml vials or ampoules or pre-filled syringe.

(v) Injectable Formulation III

A formulation for i.v. delivery by injection or infusion can be prepared by dissolving the compound of formula (1°) (e.g. in a salt form) in water at 20 mg/ml and then adjusted for isotonicity. The vial is then sealed and sterilised by autoclaving or filled into an ampoule or vial or pre-filled syringe, sterilised by filtration and sealed.

(vi) Injectable Formulation IV

A formulation for i.v. delivery by injection or infusion can be prepared by dissolving the compound of formula (1°) (e.g. in a salt form) in water containing a buffer (e.g. 0.2 M acetate pH 4.6) at 20 mg/ml. The vial, ampoule or pre-filled syringe is then sealed and sterilised by autoclaving or sterilized by filtration and sealed.

(vii) Subcutaneous or Intramuscular Injection Formulation

A composition for sub-cutaneous or intramuscular administration is prepared by mixing a compound of the formula (1°) with pharmaceutical grade corn oil to give a concentration of 5-50 mg/ml. The composition is sterilised and filled into a suitable container.

(viii) Lyophilised Formulation I

Aliquots of formulated compound of formula (1°) are put into 50 ml vials and lyophilized. During lyophilisation, the compositions are frozen using a one-step freezing protocol at (−45° C.). The temperature is raised to −10° C. for annealing, then lowered to freezing at −45° C., followed by primary drying at +25° C. for approximately 3400 minutes, followed by a secondary drying with increased steps if temperature to 50° C. The pressure during primary and secondary drying is set at 80 millitor.

(ix) Lyophilised Formulation II

Aliquots of formulated compound of formula (1°) or a salt thereof as defined herein are put into 50 mL vials and lyophilized. During lyophilisation, the compositions are frozen using a one-step freezing protocol at (−45° C.). The temperature is raised to −10° C. for annealing, then lowered to freezing at −45° C., followed by primary drying at +25° C. for approximately 3400 minutes, followed by a secondary drying with increased steps if temperature to 50° C. The pressure during primary and secondary drying is set at 80 millitor.

(x) Lyophilised Formulation for Use in i.v. Administration III

An aqueous buffered solution is prepared by dissolving a compound of formula I in a buffer. The buffered solution is filled, with filtration to remove particulate matter, into a container (such as a Type 1 glass vial) which is then partially sealed (e.g. by means of a Fluorotec stopper). If the compound and formulation are sufficiently stable, the formulation is sterilised by autoclaving at 121° C. for a suitable period of time. If the formulation is not stable to autoclaving, it can be sterilised using a suitable filter and filled under sterile conditions into sterile vials. The solution is freeze dried using a suitable cycle.

On completion of the freeze drying cycle the vials are back filled with nitrogen to atmospheric pressure, stoppered and secured (e.g. with an aluminium crimp). For intravenous administration, the freeze dried solid can be reconstituted with a pharmaceutically acceptable diluent, such as 0.9% saline or 5% dextrose. The solution can be dosed as is, or can be diluted further into an infusion bag (containing a pharmaceutically acceptable diluent, such as 0.9% saline or 5% dextrose), before administration.

(xii) Powder in a Bottle

A composition for oral administration is prepared by filling a bottle or vial with a compound of the formula (1°). The composition is then reconstituted with a suitable diluent for example water, fruit juice, or commercially available vehicle such as OraSweet or Syrspend. The reconstituted solution may be dispensed into dosing cups or oral syringes for administration.

The invention claimed is:

1. A process for preparing a 1-methoxyisoindoline of formula (1°):

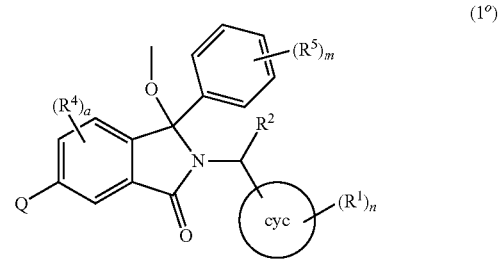

or a tautomer or a solvate or a salt thereof, the process comprising taking a compound of the formula (2°)

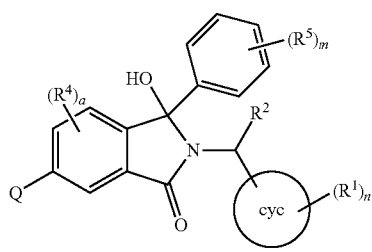

(2°)

wherein cyc is phenyl or a heterocyclic group Het which is pyridinyl, pyrimidinyl, pyrazinyl or pyridazinyl, or an N-oxide thereof;

$R^1$ is independently selected from hydroxy, halogen, nitro, nitrile, $C_{1-4}$alkyl, halo$C_{1-4}$alkyl, hydroxy$C_{1-4}$alkyl, $C_{2-6}$alkenyl, $C_{1-4}$alkoxy, halo$C_{1-4}$alkoxy, $C_{2-4}$alkynyl, —$O_{0,1}$—$(CR^xR^y)_v$—$CO_2H$, —$(CR^xR^y)_v$—$CO_2C_{1-4}$alkyl, —$(CR^xR^y)_v$—$CON(C_{1-4}$alkyl$)_2$, —$P(=O)(R^x)_2$, —$S(O)_d$—$R^x$, —$S(O)_d$-heterocyclic group with 3 to 6 ring members and —$S(O)_d$—$N(R^8)_2$, wherein when cyc is Het then $R^1$ is attached to a carbon atom;

$R^2$ is selected from hydrogen, $C_{1-4}$alkyl, $C_{2-6}$alkenyl, hydroxy$C_{1-4}$alkyl, —$(CR^xR^y)_u$—$CO_2H$, —$(CR^xR^y)_u$—$CONR^xR^y$, —$(CR^xR^y)_u$—$CO_2R^{10}$ wherein $R^{10}$ is selected from $C_{1-7}$ alkyl, $C_{1-7}$ alkeneyl, $C_{1-7}$ haloalkyl, tri$C_{1-7}$ alkylsilyl-$C_{1-7}$alkyl, $C_{5-20}$ aryl and $C_{5-20}$ aryl-$C_{1-7}$ alkyl;

$R^4$ and $R^5$ are independently selected from halogen, nitrile, $C_{1-4}$alkyl, halo$C_{1-4}$alkyl, $C_{1-4}$alkoxy and halo$C_{1-4}$alkoxy;

Q is selected from —$C(OH)R^6R^7$, —$C(=O)R^7$, halogen and —OTf;

$R^6$ and $R^7$ are independently selected from hydrogen, $C_{1-6}$alkyl, halo$C_{1-6}$alkyl, $C_{2-6}$alkenyl, $C_{2-6}$alkynyl, hydroxy, hydroxy$C_{1-6}$alkyl, —$COOC_{1-6}$alkyl, —$(CH_2)_j$—$O$—$C_{1-6}$alkyl, —$(CH_2)_j$—$O$-(hydroxy$C_{1-6}$alkyl), —$C_{1-6}$alkyl-$NR^xR^y$, —$(CR^xR^y)_p$—$CONR^xR^y$, —$(CR^xR^y)_p$—$NR^xCOR^y$, —$(CR^xR^y)_p$—$O$—$CH_2$—$CONR^xR^y$, heterocyclic group with 3 to 7 ring members, —$CH_2$-heterocyclic group with 3 to 7 ring members, —$CH_2$—$O$-heterocyclic group with 3 to 7 ring members, —$CH_2$—NH-heterocyclic group with 3 to 7 ring members, —$CH_2$—$N(C_{1-6}$alkyl)-heterocyclic group with 3 to 7 ring members, —$C(=O)$NH-heterocyclic group with 3 to 7 ring members, $C_{3-8}$cycloalkyl, —$CH_2$—$C_{3-8}$cycloalkyl, —$CH_2$—$O$—$C_{3-8}$cycloalkyl, and $C_{3-8}$cycloalkenyl, wherein said cycloalkyl, cycloalkenyl or heterocyclic groups may be optionally substituted by one or more $R^z$ groups, and wherein in each instance the heterocyclic group comprises one or more heteroatoms selected from N, O, S and oxidised forms thereof;

or, when Q is —$C(OH)R^6R^7$, the $R^6$ and $R^7$ groups, together with the carbon atom to which they are attached, can join to form a $C_{3-6}$cycloalkyl or heterocyclyl group with 3 to 6 ring members, wherein the heterocyclic group comprises one or more heteroatoms selected from N, O, S and oxidised forms thereof, and wherein said $C_{3-6}$cycloalkyl and heterocyclyl groups may be optionally substituted by one or more $R^z$ groups;

$R^8$ is selected from hydrogen, $C_{1-6}$alkyl, halo$C_{1-6}$alkyl, hydroxy$C_{1-6}$alkyl, —$(CH_2)_k$—$O$—$C_{1-6}$alkyl, —$(CH_2)_k$—$O$-(hydroxy$C_{1-6}$alkyl), hydroxy$C_{1-6}$alkoxy, —$(CH_2)_k$—$CO_2C_{1-6}$alkyl, —$(CH_2)_k$—$CO_2H$, —$C_{1-6}$alkyl-$N(H)_e(C_{1-4}$alkyl$)_{2-e}$, —$(CH_2)_j$—$C_{3-8}$cycloalkyl and —$(CH_2)_j$—$C_{3-8}$cycloalkenyl;

$R^x$ and $R^y$ are independently selected from hydrogen, halogen, nitro, nitrile, $C_{1-6}$alkyl, halo$C_{1-6}$alkyl, $C_{2-6}$alkenyl, $C_{2-6}$alkynyl, hydroxy, hydroxy$C_{1-6}$alkyl, $C_{1-6}$alkoxy, —$(CH_2)_k$—$O$—$C_{1-6}$alkyl, hydroxy$C_{1-6}$ alkoxy, —$COOC_{1-6}$alkyl, —$N(H)_e(C_{1-4}$alkyl$)_{2-e}$, —$C_{1-6}$alkyl-$N(H)_e(C_{1-4}$alkyl$)_{2-e}$, —$(CH_2)_k$—$C(=O)N(H)_e(C_{1-4}$alkyl$)_{2-e}$, $C_{3-8}$cycloalkyl and $C_{3-8}$cycloalkenyl;

or the $R^x$ and $R^y$ groups, together with the carbon or nitrogen atom to which they are attached, can join to form a $C_{3-6}$cycloalkyl or saturated heterocyclyl group with 3 to 6 ring members which may be optionally fused to an aromatic heterocyclyl group of 3 to 5 ring members;

or when on a carbon atom the $R^x$ and $R^y$ groups can join together to form a =$CH_2$ group; $R^z$ is independently selected from halogen, nitro, nitrile, $C_{1-6}$alkyl, halo$C_{1-6}$alkyl, $C_{2-6}$alkenyl, $C_{2-6}$alkynyl, =O, hydroxy, hydroxy$C_{1-6}$alkyl, $C_{1-6}$alkoxy, —$(CH_2)$—$O$—$C_{1-6}$alkyl, hydroxy$C_{1-6}$alkoxy, —$C(=O)C_{1-6}$alkyl, $C(=O)$ $C_{1-6}$alkyl-OH, —$C(=O)C_{1-6}$alkyl-$N(H)_e(C_{1-4}$alkyl$)_{2-e}$, —$C(=O)N(H)_e(C_{1-4}$alkyl$)_{2-e}$, —$(CH_2)_r$—$CO_2C_{1-6}$alkyl, —$(CH_2)_r$—$CO_2H$, —$N(H)_e(C_{1-4}$alkyl$)_{2-e}$, —$C_{1-6}$alkyl-$N(H)_e(C_{1-4}$alkyl$)_{2-e}$, heterocyclyl group with 3 to 6 ring members, heterocyclyl group with 3 to 6 ring members substituted by —$C(=O)C_{1-4}$alkyl, heterocyclyl group with 3 to 6 ring members substituted by —$C(=O)OC_{1-4}$alkyl, heterocyclyl group with 3 to 6 ring members substituted by —$C(=O)N(H)_e(C_{1-4}$alkyl$)_{2-e}$, —$C(=O)$heterocyclyl group with 3 to 6 ring members, $C_{3-8}$cycloalkyl and $C_{3-8}$cycloalkenyl, wherein if $R^7$ is pyridine then $R^z$ is other than —$NH_2$;

a, j, d, e, n, r and p are independently selected from 0, 1 and 2;

k and m are independently selected from 1 and 2;

u is selected from 0, 1, 2 and 3; and v is selected from 0 and 1;

and reacting the compound of formula (2°) with a methylating agent in the presence of a base.

2. A process for preparing a 1-methoxyisoindoline according to claim 1, wherein the compound of formula (1°) is a compound of formula (1):

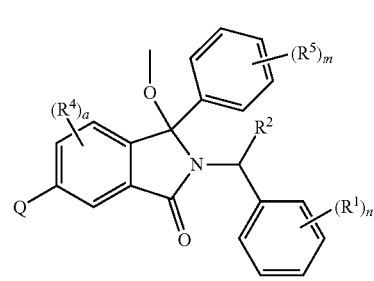

(1)

or a tautomer or a solvate or a salt thereof, and the compound of formula (2°) is a compound of formula (2):

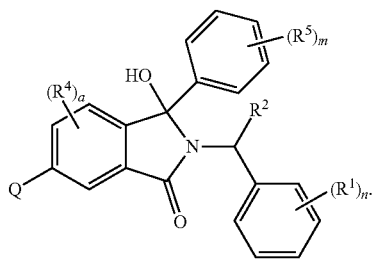

(2)

3. A process for preparing a 1-methoxyisoindoline according to claim 2, wherein:
$R^1$ is p-Cl and n is 1; and/or
$R^5$ is p-C and m is 1; and/or
$R^4$ is 4-F and a is 1; and/or
Q is —C(OH)$R^6R^7$.

4. A process for preparing a 1-methoxyisoindoline according to claim 1, comprising a further step, at any stage, in which the compound of formula (1°) is resolved to increase the proportion of the stereoisomer of formula (1°'):

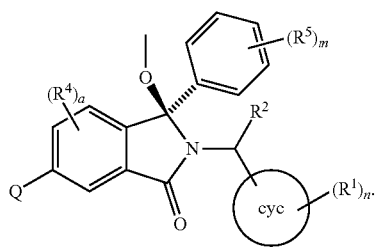

(1°')

5. A process for preparing a 1-methoxyisoindoline according to claim 1, comprising a further step, at any stage, in which the compound of formula (2°) is resolved to increase the stereoisomer (2°'):

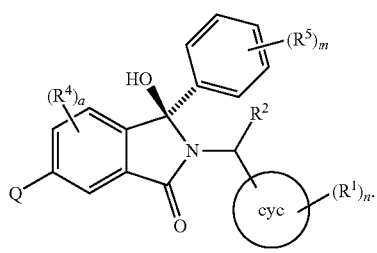

(2°')

6. A process for preparing a 1-methoxyisoindoline according to claim 5 wherein:
the base is selected from 1,8-bis(dimethylamino)naphthalene,N,N,N',N'-tetramethyl-1,8naphthalenediamine, lutidine and 2,6-di-tert-butylpyridine;
the methylating agent is selected from Me$_3$OBF$_4$, MeOTf and (MeO)$_2$CHBF$_4$; and
the step of reacting with the methylating agent takes place in an organic solvent; or
the base is selected from n-BuLi, t-BuLi, sec-BuLi, LDA, LHMDS, NaHMDS, KHMDS, LTMP, LiOtBu or KOtBu;

the methylating agent is selected from MeOTf and methylfluorosulfonate; and
the step of reacting with the methylating agent takes place in an ethereal solvent.

7. A process for preparing a 1-methoxyisoindoline according to claim 1, wherein the 1-methoxyisoindoline is (2S,3S)-3-(4-chlorophenyl)-3-[(1R)-1-(4-chlorophenyl)-7-fluoro-5-[(1S)-1-hydroxy-1-(oxan-4-yl)propyl]-1-methoxy-3-oxo-2,3-dihydro-1H-isoindol-2-yl]-2-methylpropanoic acid (3'):

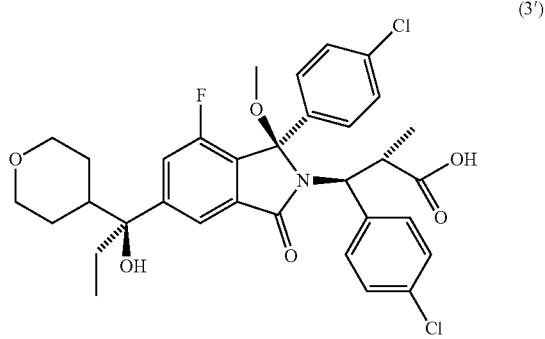 [SMILES: CC[C@@](O)(c1cc(F)c2c(c1)C(=O)N([C@H](c1ccc(Cl)cc1)[C@H](C)C(=O)O)[C@@]2(OC)c1ccc(Cl)cc1)C1CCOCC1]

(3')

or a tautomer or a solvate or a pharmaceutically acceptable salt thereof.

8. A process for preparing a 1-methoxyisoindoline according to claim 1, wherein:
the base is selected from n-BuLi, t-BuLi, sec-BuLi, LDA, LHMDS, NaHMDS, KHMDS, LTMP, LiOtBu or KOtBu; or
the base is selected from K$_2$CO$_3$, Na$_2$CO$_3$, Cs$_2$CO$_3$, NaOH, LiOH, KOH, K$_2$PO$_4$, Et$_3$N, DIPEA, 1,8-bis(dimethylamino)naphthalene,N,N,N',N'-tetramethyl-1,8-naphthalenediamine, KHMDS, lutidine, 2,6-di-tert-butylpyridine and N-methylmorpholine; or
the methylating agent is selected from MeI, Me$_2$SO$_4$, Me$_3$OBF$_4$, MeOTf, (MeO)$_2$CHBF$_4$ and methylfluorosulfonate; or
the methylating agent is selected from MeI, Me$_2$SO$_4$, Me$_3$OBF$_4$, MeOTf and (MeO)$_2$CHBF$_4$; or
the step of reacting with the methylating agent takes place in an organic solvent; or
the step of reacting with the methylating agent takes place in an ethereal solvent; or
the base is selected from K$_2$CO$_3$, Cs$_2$CO$_3$, NaOH, LiOH and KOH; the methylating agent is selected from MeI and Me$_2$SO$_4$; and the step of reacting with the methylating agent takes place in an organic solvent; or
the base is Cs$_2$CO$_3$; the methylating agent is MeI; and the step of reacting with the methylating agent takes place in an organic solvent; or
the base is selected from 1,8-bis(dimethylamino)naphthalene,N,N,N',N'-tetramethyl-1,8-naphthalenediamine, lutidine and 2,6-di-tert-butylpyridine; the methylating agent is selected from Me$_3$OBF$_4$, MeOTf and (MeO)$_2$CHBF$_4$; and the step of reacting with the methylating agent takes place in an organic solvent; or
the base is 1,8-bis(dimethylamino)naphthalene,N,N,N',N'-tetramethyl-1,8-naphthalenediamine; the methylating agent is Me$_3$OBF$_4$; and the step of reacting with the methylating agent takes place in an organic solvent; or
the base is selected from n-BuLi, t-BuLi, sec-BuLi, LDA, LHMDS, NaHMDS, KHMDS, LTMP, LiOtBu or KOtBu; the methylating agent is selected from MeOTf and methylfluorosulfonate; and the step of reacting with the methylating agent takes place in an ethereal solvent.

9. A process for preparing a 1-methoxyisoindoline according to claim 1, wherein either:
   (i) the base is added to a mixture of the compound of the formula (2°) and the methylating agent; or
   (ii) the methylating agent is added to a mixture of the compound of the formula (2°) and the base.

10. A process for preparing a 1-methoxyisoindoline according to claim 1, wherein the step of reacting with the methylating agent takes place at a temperature which is below 0° C.

11. A process for preparing a 1-methoxyisoindoline according to claim 1, wherein the process comprises an additional step in which the 1-methoxyisoindoline is converted into a pharmaceutically acceptable salt.

12. A process for preparing a 1-methoxyisoindoline which is (2S,3S)-3-(4-chlorophenyl)-3-[(1R)-1-(4-chlorophenyl)-7-fluoro-5-[(1S)-1-hydroxy-1-(oxan-4-yl)propyl]-1-methoxy-3-oxo-2,3-dihydro-1H-isoindol-2-yl]-2-methylpropanoic acid according to claim 1, wherein the process comprises an additional step in which the 2S,3S)-3-(4-chlorophenyl)-3-[(1R)-1-(4-chlorophenyl)-7-fluoro-5-[(1S)-1-hydroxy-1-(oxan-4-yl)propyl]-1-methoxy-3-oxo-2,3-dihydro-1H-isoindol-2-yl]-2-methylpropanoic acid is converted into a pharmaceutically acceptable salt.

13. A process for preparing a 1-methoxyisoindoline according to claim 4, wherein the compound of formula (1°) is resolved to increase the proportion of the stereoisomer of formula (1°') by crystallization or chromatography.

14. A process for preparing a 1-methoxyisoindoline according to claim 13, wherein the compound of formula (1°) is resolved to increase the proportion of the stereoisomer of formula (1°') by supercritical fluid chromatography.

15. A process for preparing a 1-methoxyisoindoline according to claim 5, wherein the compound of formula (2°) is resolved to increase the stereoisomer (2°') by crystallization or chromatography.

16. A process for preparing a 1-methoxyisoindoline according to claim 15, wherein the compound of formula (2°) is resolved to increase the stereoisomer (2°') by supercritical fluid chromatography.

17. A process for preparing a 1-methoxyisoindoline according to claim 8, wherein:
   the methylating agent is selected from MeOTf and methylfluorosulfonate; or
   the step of reacting with the methylating agent takes place in an organic solvent that is an aprotic solvent selected from THF, 1,4-dioxane, acetone, acetonitrile, DMF, dichloromethane, or mixtures thereof; or
   the step of reacting with the methylating agent takes place in an ethereal solvent that is THF; or
   l the base is selected from $K_2CO_3$, $Cs_2CO_3$, NaOH, LiOH and KOH; the methylating agent is selected from MeI and $Me_2SO_4$; and the step of reacting with the methylating agent takes place in an organic solvent that is an aprotic solvent selected from acetone, DMF, dichloromethane, or mixtures thereof; or
   the base is $Cs_2CO_3$; the methylating agent is MeI; and the step of reacting with the methylating agent takes place in an organic solvent that is an aprotic solvent selected from acetone, dichloromethane, or mixtures thereof; or
   the base is selected from 1,8-bis(dimethylamino)naphthalene,N,N,N',N'-tetramethyl-1,8-naphthalenediamine, lutidine and 2,6-di-tert-butylpyridine; the methylating agent is selected from $Me_3OBF_4$, MeOTf and (MeO)$_2CHBF_4$; and the step of reacting with the methylating agent takes place in an organic solvent that is an aprotic solvent selected from THF, 1,4-dioxane, dichloromethane or mixtures thereof; or
   the base is 1,8-bis(dimethylamino)naphthalene,N,N,N',N'-tetramethyl-1,8-naphthalenediamine; the methylating agent is $Me_3OBF_4$; and the step of reacting with the methylating agent takes place in an organic solvent that is dichloromethane.

18. A process for preparing a 1-methoxyisoindoline according to claim 10, wherein the step of reacting with the methylating agent takes place at a temperature which is below −10° C.

19. A process for preparing a 1-methoxyisoindoline according to claim 10, wherein the step of reacting with the methylating agent takes place at a temperature which is below −40° C.

20. A process for preparing a 1-methoxyisoindoline according to claim 10, wherein the step of reacting with the methylating agent takes place at a temperature which is below −50° C.

21. A process for preparing a 1-methoxyisoindoline according to claim 11, wherein the 1-methoxyisoindoline is converted into a pharmaceutically acceptable salt which is a tris(hydroxymethyl)aminomethane salt.

22. A process for preparing a 1-methoxyisoindoline which is (2S,3S)-3-(4-chlorophenyl)-3-[(1R)-1-(4-chlorophenyl)-7-fluoro-5-[(1S)-1-hydroxy-1-(oxan-4-yl)propyl]-1-methoxy-3-oxo-2,3-dihydro-1H-isoindol-2-yl]-2-methylpropanoic acid according to claim 12, wherein the 2S,3S)-3-(4-chlorophenyl)-3-[(1R)-1-(4-chlorophenyl)-7-fluoro-5-[(1S)-1-hydroxy-1-(oxan-4-yl)propyl]-1-methoxy-3-oxo-2,3-dihydro-1H-isoindol-2-yl]-2-methylpropanoic acid is converted into a pharmaceutically acceptable salt which is a tris(hydroxymethyl)aminomethane salt.

* * * * *

UNITED STATES PATENT AND TRADEMARK OFFICE
CERTIFICATE OF CORRECTION

PATENT NO. : 12,077,526 B2
APPLICATION NO. : 18/159452
DATED : September 3, 2024
INVENTOR(S) : Howard et al.

It is certified that error appears in the above-identified patent and that said Letters Patent is hereby corrected as shown below:

In the Claims

Column 255, Line 1, Claim 1: Delete "(2°)" and insert -- (2°) --

Column 256, Lines 24-25, Claim 1: Delete "-(CH$_2$)-O-C$_{1-6}$alkyl" and insert -- -(CH$_2$)$_k$-O-C$_{1-6}$alkyl --

Column 260, Line 3, Claim 17: Delete "1 the base" and insert -- the base --

Column 257, Line 17, Claim 3: Delete "R$^5$ is p-C and" and insert -- R$^5$ is p-Cl and --

Signed and Sealed this
Eleventh Day of March, 2025

Coke Morgan Stewart
*Acting Director of the United States Patent and Trademark Office*